United States Patent
Tweardy et al.

(10) Patent No.: US 11,161,831 B2
(45) Date of Patent: *Nov. 2, 2021

(54) METHODS AND COMPOSITIONS FOR TREATMENT OF MUSCLE WASTING, MUSCLE WEAKNESS, AND/OR CACHEXIA

(71) Applicant: Baylor College of Medicine, Houston, TX (US)

(72) Inventors: David J. Tweardy, Houston, TX (US); Moses M. Kasembeli, Houston, TX (US); Marvin X. Xu, Kaifeng (CN); Thomas Kristian Eckols, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,661

(22) Filed: Apr. 14, 2020

(65) Prior Publication Data

US 2020/0331880 A1  Oct. 22, 2020

Related U.S. Application Data

(63) Continuation of application No. 14/335,853, filed on Jul. 18, 2014, now Pat. No. 10,676,455.

(60) Provisional application No. 61/847,778, filed on Jul. 18, 2013.

(51) Int. Cl.

| | |
|---|---|
| *C07D 333/34* | (2006.01) |
| *A61K 31/47* | (2006.01) |
| *A61K 31/4406* | (2006.01) |
| *A61K 31/415* | (2006.01) |
| *A61K 31/381* | (2006.01) |
| *A61K 31/357* | (2006.01) |
| *A61K 31/145* | (2006.01) |
| *C07D 215/36* | (2006.01) |

(Continued)

(52) U.S. Cl.

CPC .......... *C07D 333/34* (2013.01); *A61K 31/145* (2013.01); *A61K 31/18* (2013.01); *A61K 31/357* (2013.01); *A61K 31/381* (2013.01); *A61K 31/404* (2013.01); *A61K 31/4035* (2013.01); *A61K 31/415* (2013.01); *A61K 31/4164* (2013.01); *A61K 31/4196* (2013.01); *A61K 31/42* (2013.01); *A61K 31/428* (2013.01); *A61K 31/4406* (2013.01); *A61K 31/45* (2013.01); *A61K 31/454* (2013.01); *A61K 31/47* (2013.01); *A61K 31/4704* (2013.01); *A61K 31/4709* (2013.01); *A61K 31/513* (2013.01); *A61K 45/06* (2013.01); *C07C 311/08* (2013.01); *C07C 311/10* (2013.01); *C07C 311/13* (2013.01); *C07C 311/21* (2013.01); *C07C 311/24* (2013.01); *C07C 311/29* (2013.01); *C07C 311/44* (2013.01); *C07C 323/49* (2013.01); *C07C 381/06* (2013.01); *C07D 213/71* (2013.01); *C07D 215/36* (2013.01); *C07D 231/18* (2013.01); *C07D 319/18* (2013.01); *C07C 2101/14* (2013.01); *C07C 2102/10* (2013.01); *C07C 2601/14* (2017.05); *C07C 2602/10* (2017.05); *Y02A 50/30* (2018.01)

(58) Field of Classification Search

CPC .. A61K 31/145; A61K 31/404; A61K 31/454; A61K 31/4035; A61K 31/381; A61K 31/4709; A61K 31/513; A61K 31/4196; A61K 31/42; A61K 31/4164; A61K 31/47; A61K 31/4704; A61K 31/18; A61K 31/428; A61K 31/4406; A61K 31/45; A61K 31/415; C07C 311/29; C07C 311/13; C07C 311/08; C07C 323/49; C07C 381/06; C07C 311/10; C07C 311/44; C07C 311/21; C07C 2601/14; C07C 2102/10; C07C 2101/14; C07C 2602/10; C07D 319/18; C07D 215/36; C07D 213/71; C07D 333/34; C07D 231/18; A61P 21/06; A61P 21/00; Y02A 50/30

See application file for complete search history.

(56) References Cited

U.S. PATENT DOCUMENTS

| | | | |
|---|---|---|---|
| 4,279,909 A | 7/1981 | Takashima | |
| 10,112,933 B2 * | 10/2018 | Tweardy | ............ A61K 31/4196 |

(Continued)

FOREIGN PATENT DOCUMENTS

| | | | |
|---|---|---|---|
| EP | 3021841 A1 | 5/2016 | |
| WO | 2009/149192 A1 | 12/2009 | |

(Continued)

OTHER PUBLICATIONS

Morley et al: "Cachexia: pathophysiology and clinical relevance", The American Journal of Clinical Nutrition, American Society for Nutrition, US, vol. 83, No. 4, Apr. 1, 2006 (Apr. 1, 2006), pp. 735-743.

(Continued)

*Primary Examiner* — Blessing M Fubara
(74) *Attorney, Agent, or Firm* — Norton Rose Fulbright US LLP

(57) ABSTRACT

Embodiments of the invention include methods of treating, preventing, and/or reduce the risk or severity of a condition selected from the group consisting of muscle wasting, muscle weakness, cachexia, and a combination thereof in an individual in need thereof. In some embodiments, particular small molecules are employed for treatment, prevention, and/or reduction in the risk of muscle wasting. In at least particular cases, the small molecules are inhibitors of STAT3.

15 Claims, 106 Drawing Sheets

Specification includes a Sequence Listing.

(51) Int. Cl.

| | | |
|---|---|---|
| C07D 213/71 | (2006.01) | |
| C07D 231/18 | (2006.01) | |
| C07D 319/18 | (2006.01) | |
| C07C 311/08 | (2006.01) | |
| C07C 311/10 | (2006.01) | |
| C07C 311/13 | (2006.01) | |
| C07C 311/31 | (2006.01) | |
| C07C 311/24 | (2006.01) | |
| C07C 311/29 | (2006.01) | |
| C07C 311/44 | (2006.01) | |
| C07C 311/49 | (2006.01) | |
| C07C 311/06 | (2006.01) | |
| A61K 31/06 | (2006.01) | |
| A61K 31/18 | (2006.01) | |
| A61K 31/4035 | (2006.01) | |
| A61K 31/404 | (2006.01) | |
| A61K 31/4164 | (2006.01) | |
| A61K 31/4196 | (2006.01) | |
| A61K 31/42 | (2006.01) | |
| A61K 31/428 | (2006.01) | |
| A61K 31/45 | (2006.01) | |
| A61K 31/454 | (2006.01) | |
| A61K 31/4704 | (2006.01) | |
| A61K 31/4709 | (2006.01) | |
| A61K 31/513 | (2006.01) | |
| C07C 311/21 | (2006.01) | |
| C07C 323/49 | (2006.01) | |
| C07C 381/06 | (2006.01) | |
| A61K 45/06 | (2006.01) | |

(56) References Cited

U.S. PATENT DOCUMENTS

| | | | | |
|---|---|---|---|---|
| 10,676,455 | B2* | 6/2020 | Tweardy | A61K 31/18 |
| 2005/0239886 | A1 | 10/2005 | Hamuro et al. | |
| 2010/0041685 | A1 | 2/2010 | Tweardy et al. | |
| 2010/0209950 | A1 | 8/2010 | Gernez et al. | |
| 2011/0312984 | A1 | 12/2011 | Tweardy et al. | |
| 2012/0003191 | A1* | 1/2012 | Burkin | A61K 38/39 |
| | | | | 424/93.7 |
| 2012/0035163 | A1* | 2/2012 | Yasuma | C07D 417/14 |
| | | | | 514/228.2 |
| 2012/0040917 | A1* | 2/2012 | Orum | A61P 29/00 |
| | | | | 514/21.2 |
| 2012/0178718 | A1* | 7/2012 | Nique | A61P 3/00 |
| | | | | 514/94 |
| 2013/0123266 | A1* | 5/2013 | Zagury | A61K 31/352 |
| | | | | 514/248 |
| 2014/0088171 | A1 | 3/2014 | Yan et al. | |
| 2015/0024032 | A1 | 1/2015 | Tweardy et al. | |
| 2015/0031714 | A1 | 1/2015 | Tweardy et al. | |
| 2015/0051233 | A1 | 2/2015 | Tweardy et al. | |

FOREIGN PATENT DOCUMENTS

| | | | | |
|---|---|---|---|---|
| WO | WO-2009149192 | A1 * | 12/2009 | A61P 11/00 |
| WO | 2012/017166 | A2 | 2/2012 | |
| WO | WO-2012017166 | A2 * | 2/2012 | A61K 31/403 |
| WO | 2012/159107 | A1 | 11/2012 | |
| WO | 2013/078372 | A1 | 5/2013 | |
| WO | WO-2013078372 | A1 * | 5/2013 | A61K 31/56 |
| WO | 2015/010107 | A1 | 1/2015 | |

OTHER PUBLICATIONS

Aoyagi, Tomoyoshi et al; "Cancer Cachexia, Mechanism and Treatment"; World Journal of Gastrointestinal Onocolgy, Apr. 15, 2015; 7(4): 17-29.

Avery et al. "STAT3 is required for IL-21-induced secretion of IgE from human naive B cells", Blood, Sep. 1, 2008, vol. 112, No. 5, pp. 1784-1793.

Bharadwaj et al., "Drug-repositioning screening identified piperlongumine as a direct STAT3 inhibitor with potent activity against breast cancer," Oncogene, 34(100):1341-1353, (2015).

Bharadwaj et al., "Small-molecule inhibition of STAT3 in radioresistant head and neck squamous cell carcinoma," Oncotarget, 7(18):26307-26330, (2016).

Bharadwaj et al., Cancer Drug Discovery and Development, "STAT Inhibitors in Cancer", Springer, in press.

Bonetto et al., "STAT3 Activation in Skeletal Muscle Links Muscle Wasting and the Acute Phase Response in Cancer Cachexia", Plos One, Jul. 20, 2011, vol. 6, No. 7, p. e22538.

Braun, et al.: "Muscle Atrophy in Response to Cytotoxic Chemotherapy is Dependent on Intact Glucocorticoid Signaling in Skeletal Muscle"; PLOS One; www.plosone.org; vol. 9, Issue 9; Sep. 2014.

Damrauer, et al,: "Chemotherapy-Induced Muscle Wasting: Association iwth NF-kB and Cancer Cachexia": Basic Applied Myology 18 (5): 139-148; 2008.

Garcia, et al.; "Ghrelin Prevents Cisplatin-Induced Mechanical Hyperalgesia and Cachexia"; Endocrinology, Feb. 2008; 149(2); 455-460; published online Oct. 25, 2007.

Gilliam, et al; "Chemotherpy-Induced Weakness and Fatigue in Skeletal Muscle: The Role of Oxidative Stress"; Antioxidants & Redox Signaling; vol. 15, No. 9, 2011.

Gueta, I. et al, "The Effect of Blocking TNF-Alpha in Patients with Cancer-Related Cachexia and Anorexia"; Harefuah, Aug. 2010: 149 (8): 512-4, 551, 550.

Kleiton Augusto Santos Silva et al., "A new therapeuthical approach to block cancer cachexia: focusing inhibition of STAT3", Apr. 1, 2013. XP055337620, Retrieved from the Internet: URL: http://www.fasebj.org/content/30/1_Supplement/lb312.short.

Lerouge, S. "Sterilisation and cleaning of metallic biomaterials (chapter 13)", Metals for Biomedical Devices. Edited by M. Niinomi, CRC Press, Boca Raton, p. 320.

Ma, Jie-Qiong et al "Ursolic Acid Ameliorates Carbon Tetrachloride-Induced Oxicative FNA damage and inflammation in Mouse Kidney by Inhibiting the STAT3 and NF-kB Activities" International Ummuno 21 (2014) 389-395.

McMurray, ("Structural Basis for the Binding of High Affinity Phosphopeptides to STAT3" in Peptide Science vol. 90, No. 1, pp. 69-79, Nov. 2007).

Wang, Xiaonan H. et al; "Muscle Wasting from Kidney Failure—A Model for Catabolic Conditions"; Int. J. Biochem Cell Biol. Oct. 2013: 45 (10): 2230-2238.

Choi, Il-Whan, et al; Platelet-Activating Factor-Mediated NF-kB Dependency of a Late Anaphylactic Reaction; J. Exp. Med. vol. 198, No. 1, Jul. 7, 2003; 145-151.

Galli et al., "The development of allergic inflammation", Nature, Jul. 24, 2008, vol. 454, p. 445-454.

Gavino et al: "Small-Molecule Inhibition Of Stat3 Prevents House-Dust-Mite (HDM)-Induced Airway Inflammation By Blocking Lung Production Of Th17 and Th2 Cytokines", Mar. 1, 2014, Annual Meeting AAAA&I, San Diego, California.

Holgate et al., "The mechanisms, diagnosis, and management of severe asthma in adults", www.thelancet.com, Aug. 26, 2006, vol. 368, pp. 780-793.

Hox Valerie et al: "Diminution of signal transducer and activator of transcription 3 signaling inhibits vascular permeability and anaphylaxis", Journal of Allergy and Clinical Immunology, Mar. 2, 2016, vol. 138, No. 1, pp. 187-199, Elsevier. Amsterdam. NL.

Humira "Highlights of Prescribing Information",. Reference ID: 3196923; Abbott Laboratories; Content revised Sep. 2012.

Kang, Nam-In, et al; Tumor Necrosis Factor-a Develos Late Anaphylactic Reaction through Cytosolic Phospholipase A2 Activation; Inc Arch Allergy and Immunology 2008; 147: 315-322.

Kim et al. "Anaphylaxis", Allergy, Asthma & Clinical Immunology 2011, 7(Suppl 1):S6.

Kim, Sung Hoon, et al; Paeonol Inhibits Anaphylactic Reaction by Regulating Histamine and TNF-a; Elsevier, International Immunopharmacology 4 (2004) 2789-287.

(56) References Cited

OTHER PUBLICATIONS

Kishimoto et al., "Contaminated Heparin Associated with Adverse Clinical Events and Activation of the Contact System", N Engl J Med, Jun. 5, 2008; vol. 358, pp. 2457-2467.
Krzysztof Lis, et al; "Tumor Necrosis Factor Inhibitors—State of Knowledge"; Arch Med Sci 6; Dec. 2014; 1175-1185.
Lerouge, S. "Sterilisation and cleaning of metallic biomaterials (chapter 13)", Metals for Biomedical Devices. Edited by M. Niinomi, CRC Press, Boca Raton, p. 320, 2010.
Lew et al., "Lung Remodeling in Asthma", ACI Intenational, 2003, vol. 15, No. 1, pp. 4-10.
Lieberman et al., "The diagnosis and management of anaphylaxis: An updated practice parameter", J Allergy Clin Immunol, Mar. 2005, vol. 115, No. 3, pp. S483-S523.
Lieberman et al., "Pulmondary Remodeling in Asthma", J Invest Aller Clin Immun, 2001, vol. 11, No. 4, pp. 220-234.
Lieberman, "Anaphylaxis and Anaphylactoid Reactions" Clinical Science, 2003, Chapter 83, Section E, pp. 1497-1522.
Lieberman, "Biphasic Anaphylaxis", Research Trends, Allergy Clin Immunol Int—J World Allergy Org, 16/6 (2004), pp. 241-248.
Yamada, Masato, et al; Passive Anaphylaxis and IgE Antibody Production are Compromised in Tumor Necrosis Factor—and in Granulocyte-macrophage Colony Stimulating Factor-Deficient Mice; Allergology International (2001) 59: 163-169.
Medic, Nevenka, et al; Knockout of the Trpc1 gene reveals that TRPC1 can promote recovery from anaphylaxis by negativityly regulating mast cell TNF-a production; Elsevier, SciVerse Science Direct; Cell Calcium 53 (2013) 315-326.
Metcalfe, Dean D., et al; Mechanisms of Mast Cell Signaling in Anaphylaxis; Mechanisms of Allergic Diseases, 2009;, 639-646.
National Heart, Lung, and Blood Institute. "National Asthma Education and Prevention Program / Expert Panel Report 3: Guidelines for the Diagnosis and Management of Asthma Full Report 2007".
Pumphrey RS, "Fatal anaphylaxis in the UK, 1992-2001", Novartis Found Symp. 2004; 257:116-28; discussion 128-32, 157-60, 276-85.
Ramirez Jr. et al., "Food hypersensitivity by inhalation", Clinical and Molecular Allergy, 2009, 7:4, pp. 1-6.
Schwartz et al., "Heparin Comes Clean", N Engl J Med, Jun. 5, 2008, 358:23, pp. 2505-2509.
Simeone-Penney et al: "Airway Epithelial STAT3 Is Required for Allergic Inflammation in a Murine Model of Asthma", The Journal of Immunology, May 2, 2007, vol. 178, No. 10, pp. 6191-6199.
Smith et al., "Physiologic Manifestations of Human Anaphylaxis" J. Clin. Invest., Nov. 1980, vol. 66, pp. 1072-1080.
Tole et al., "Biphasic Anaphylaxis: Review of Incidence, Clinical Predictors, and Observation Recommendations", Immunol Allergy Clin N Am, 2007, vol. 27, pp. 309-326.

\* cited by examiner

Cpd3

4-[3-(2,3-dihydro-1,4-benzodioxin-6-yl)-3-oxo-1-propen-1-yl] benzoic acid

Cpd30  
4-{5-[(3-ethyl-4-oxo-2-thioxo-1,3-thiazolidin-5-ylidene)methyl]-2-furyl}benzoic acid Cpd188

4-[({3-[(carboxymethyl)thio]-4-hydroxy-1-naphthyl}amino)sulfonyl]benzoic acid

Cpd30-12

4-chloro-3-{5-[((1,3-diethyl-4,6-dioxo-2-thioxotetrahydro-5(2H)-pyrimidinylidene)methyl]-2-furyl}benzoic acid

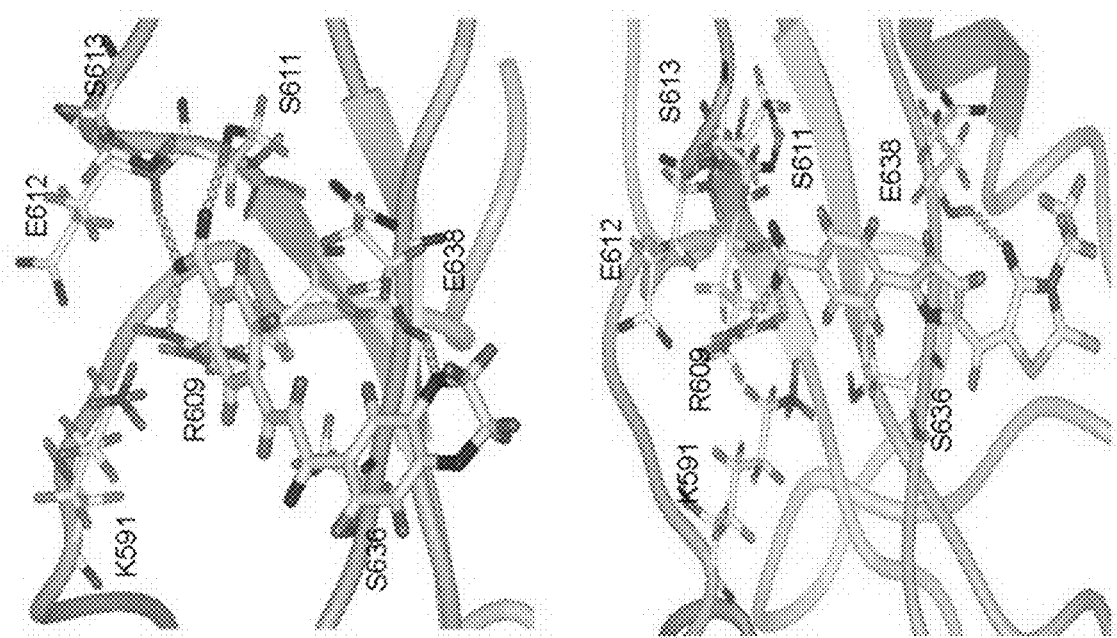
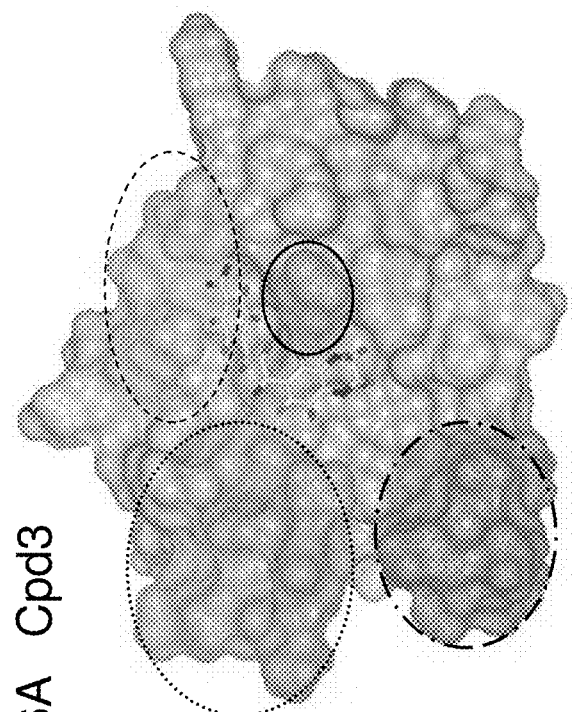
FIG. 6A Cpd3
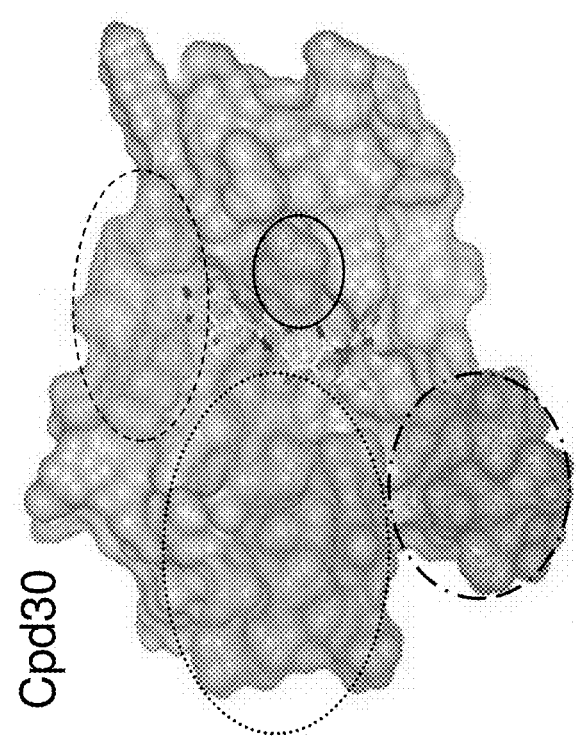
FIG. 6B Cpd30

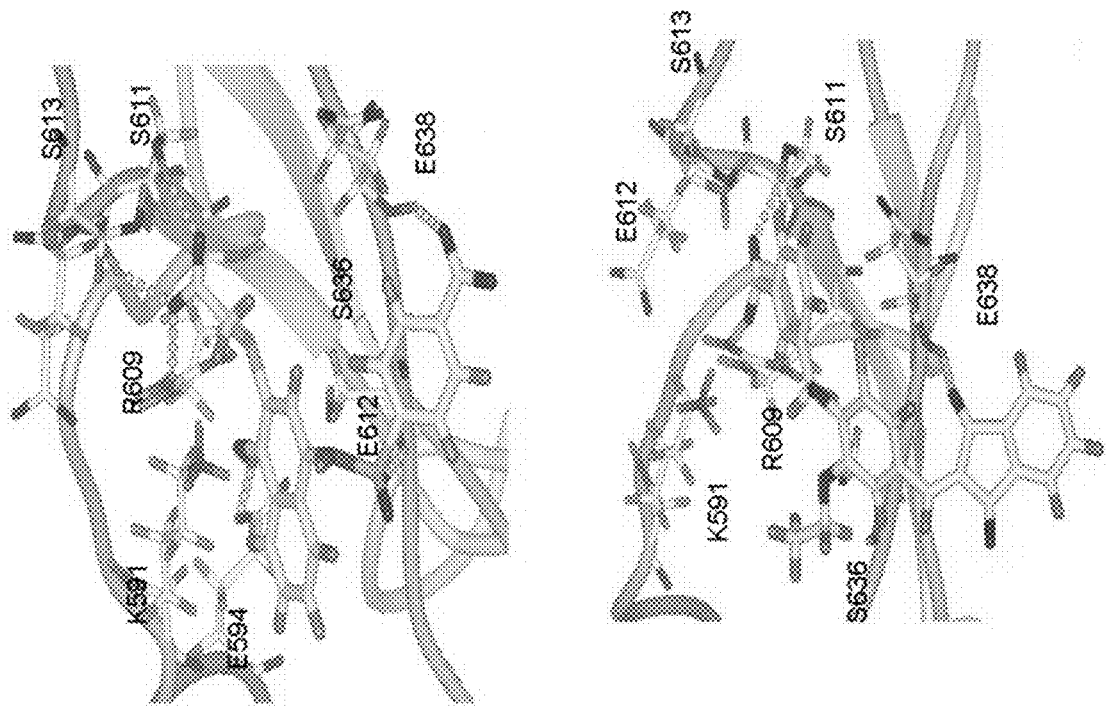
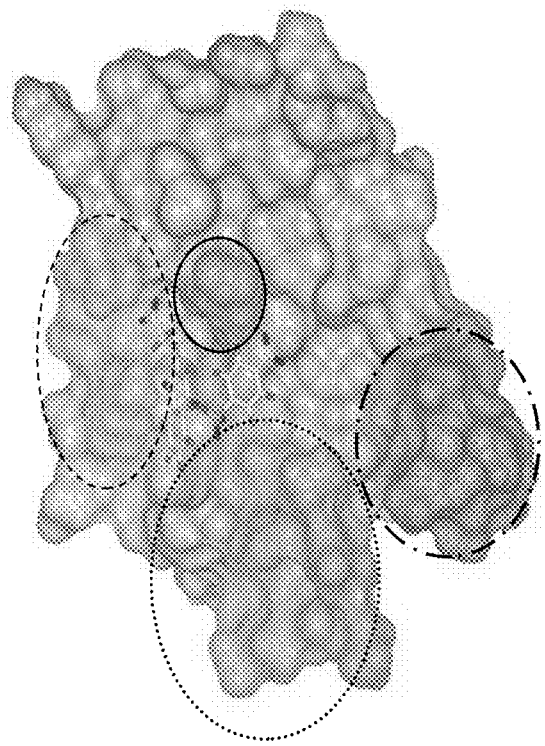
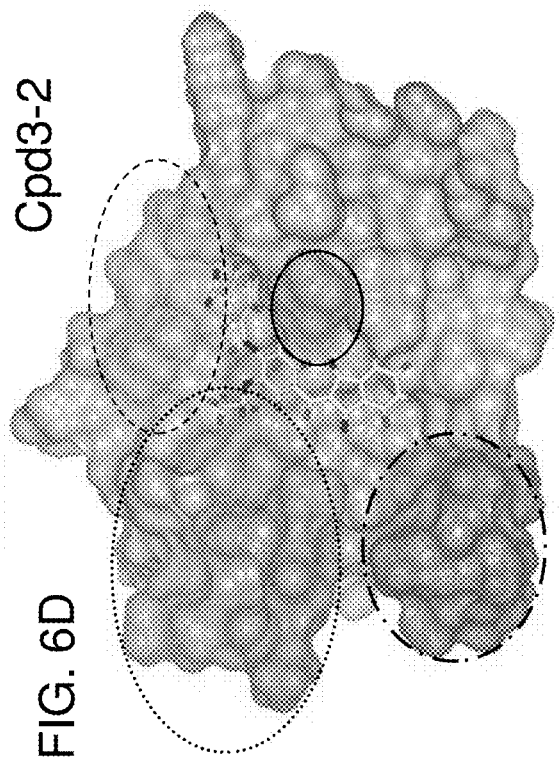
FIG. 6C
FIG. 6D

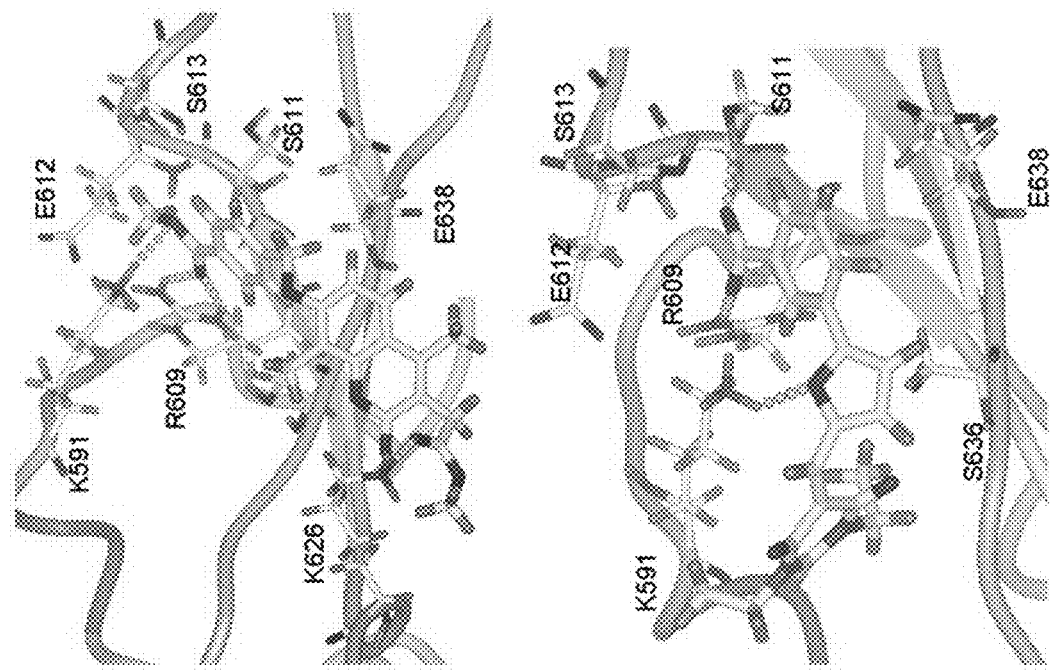
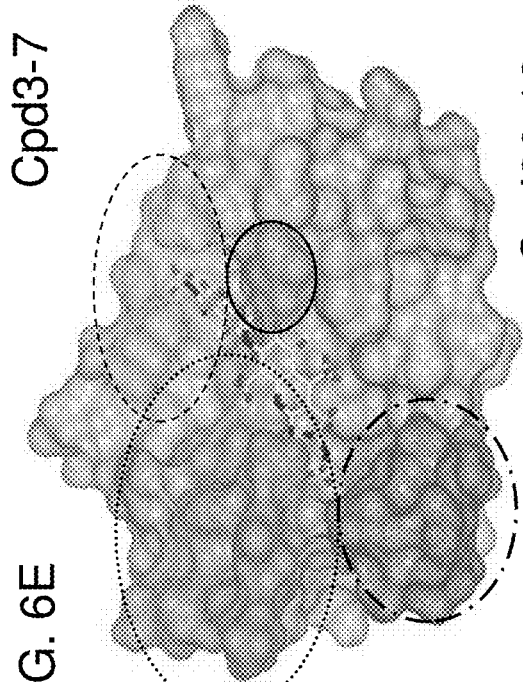
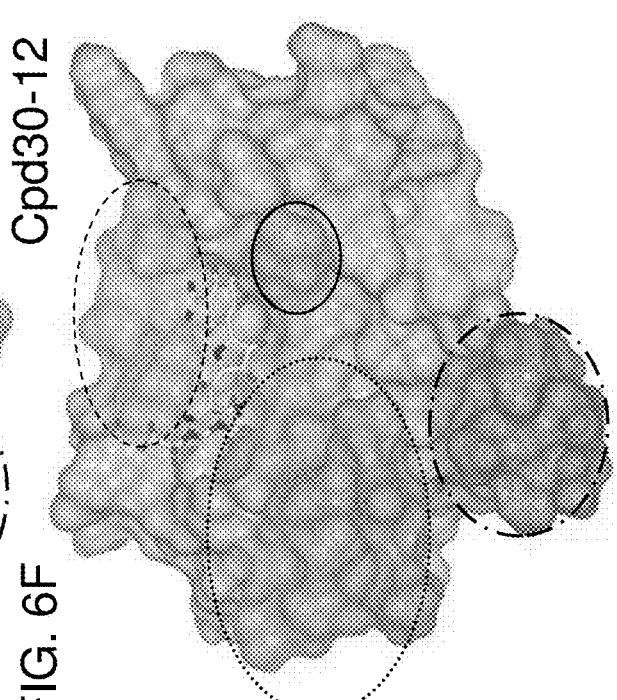
FIG. 6E
FIG. 6F

Cpd3

4-[3-(2,3-dihydro-1,4-benzodioxin-6-yl)-3-oxo-1-propen-1-yl] benzoic acid

Cpd30

4-{5-[(3-ethyl-4-oxo-2-thioxo-1,3-thiazolidin-5-ylidene)methyl]-2-furyl} benzoic acid Cpd188

4-[({3-[(carboxymethyl)thio]-4-hydroxy-1-naphthyl}amino)sulfonyl] benzoic acid 188-15

SPR IC$_{50}$ = 1.5 µM 188-9

SPR IC$_{50}$ = 2.5 µM

AMLAPOPTOSIS
EC$_{50}$ = 12 µM

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
tctacatctt actcctgttg at                                                  22

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer

<400> SEQUENCE: 2
caaatgctgc tttattctta caa                                                 23

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
caacctgaat ccaactta                                                       18

<210> SEQ ID NO 4
<211> LENGTH: 18
<212> TYPE: DNA
<213> ORGANISM: Artificial Sequence
<220> FEATURE:
<223> OTHER INFORMATION: Synthetic Primer

<400> SEQUENCE: 4
tgttaccttg acctctaa                                                       18

<210> SEQ ID NO 5
<211> LENGTH: 18
<212> TYPE: DNA
<213> ORGANISM: Artificial Sequence
<220> FEATURE:
<223> OTHER INFORMATION: Synthetic Primer

<400> SEQUENCE: 5
ttacaatctg cctcaatc                                                       18
```

```
<210> SEQ ID NO 6
<211> LENGTH: 18
<212> TYPE: DNA
<213> ORGANISM: Artificial Sequence
<220> FEATURE:
<223> OTHER INFORMATION: Synthetic Primer

<400> SEQUENCE: 6
atctcctaat agcctcaa                                                 18

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7
ctctggtaaa gtggatattg t                                             21

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
ggtggaatca tattggaaca                                               20

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9
caacctcttc tggctcaa                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic Primer

<400> SEQUENCE: 10
tggtggtctt gttgctta                                                 18

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
ctccagggtc taaatacata gc                                            22

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer
```

<400> SEQUENCE: 12
ctcacagcag tccacaag                                                    18

<210> SEQ ID NO 13
<211> LENGTH: 21
<212> TYPE: DNA
<213> ORGANISM: Artificial Sequence
<220> FEATURE:
<223> OTHER INFORMATION: Synthetic Primer

<400> SEQUENCE: 13
cacagcaagt ttcccgccgc c                                                21

<210> SEQ ID NO 14
<211> LENGTH: 21
<212> TYPE: DNA
<213> ORGANISM: Artificial Sequence
<220> FEATURE:
<223> OTHER INFORMATION: Synthetic Primer

<400> SEQUENCE: 14
gtgcaccagc ttgagtacac a                                                21

<210> SEQ ID NO 15
<211> LENGTH: 19
<212> TYPE: DNA
<213> ORGANISM: Artificial Sequence
<220> FEATURE:
<223> OTHER INFORMATION: Synthetic Primer

<400> SEQUENCE: 15
ctccagaata gaagccata                                                   19

<210> SEQ ID NO 16
<211> LENGTH: 19
<212> TYPE: DNA
<213> ORGANISM: Artificial Sequence
<220> FEATURE:
<223> OTHER INFORMATION: Synthetic Primer

<400> SEQUENCE: 16
gcagaagttg tcttatagc                                                   19

<210> SEQ ID NO 17
<211> LENGTH: 24
<212> TYPE: DNA
<213> ORGANISM: Artificial Sequence
<220> FEATURE:
<223> OTHER INFORMATION: Synthetic Primer

<400> SEQUENCE: 17
gaggcagatt cgcaagcgtt tgat                                             24

<210> SEQ ID NO 18
<211> LENGTH: 24
<212> TYPE: DNA
<213> ORGANISM: Artificial Sequence
<220> FEATURE:
<223> OTHER INFORMATION: Synthetic Primer

<400> SEQUENCE: 18
tccaggagag aatgtggcag tgtt                                             24

<210> SEQ ID NO 19

```
<211> LENGTH: 24
<212> TYPE: DNA
<213> ORGANISM: Artificial Sequence
<220> FEATURE:
<223> OTHER INFORMATION: Synthetic Primer

<400> SEQUENCE: 19
agtgtccatg tctggaggtc gttt                                          24

<210> SEQ ID NO 20
<211> LENGTH: 24
<212> TYPE: DNA
<213> ORGANISM: Artificial Sequence
<220> FEATURE:
<223> OTHER INFORMATION: Synthetic Primer

<400> SEQUENCE: 20
actggagcac tcctgcttgt agat                                          24

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
accaccatgg agaaggccgg                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
ctcagtgtag cccaagatgc                                               20
```

METHODS AND COMPOSITIONS FOR TREATMENT OF MUSCLE WASTING, MUSCLE WEAKNESS, AND/OR CACHEXIA

This application is a continuation application of U.S. Non-Provisional application Ser. No. 14/335,853 filed Jul. 18, 2014 which claims priority to U.S. Provisional Patent Application Ser. No. 61/847,778 filed Jul. 18, 2013, both of which are incorporated by reference herein in their entirety.

STATEMENT REGARDING FEDERALLY SPONSORED RESEARCH OR DEVELOPMENT

This invention was made with government support under P50 CA058183, K08 HL085018-01A2, P50 CA097007, R21 CA149783, and R41 CA153658, awarded by National Institutes of Health. The United States Government has certain rights in the invention.

INCORPORATION OF SEQUENCE LISTING

The instant application contains a Sequence Listing, named "SeqLst_BAYM_P0112USC1_1001121419_BLG_14_005.txt" (4,602 bytes) which has been submitted electronically in ASCII format and is hereby incorporated by reference in its entirety.

TECHNICAL FIELD

The present invention generally concerns at least the fields of cell biology, molecular biology, and medicine.

BACKGROUND OF THE INVENTION

Muscle wasting is a debilitating complication of catabolic conditions including chronic kidney disease (CKD), diabetes, cancer or serious infections. Unfortunately, there are few reliable strategies that block the loss of muscle protein initiated by these conditions. Previously, it was found that myostatin, a negative regulator of muscle growth, is increased in muscles of mice with CKD and when myostatin is inhibited with a "humanized" myostatin peptibody, CKD-induced muscle wasting was blocked (Zhang et al., 2011a). A similar conclusion was reached in studies of mouse models of cancer cachexia (Zhou et al., 2010). In the mice with CKD, inhibition of myostatin reduced circulating levels of IL-6 and TNFα suggesting a link between inflammation and muscle wasting as reported in clinical studies (Carrero et al., 2008; Hung et al., 2011). The evidence that inflammation stimulates muscle wasting includes reports that infusion of TNFα, IL-6, IL-10 or IFN-γ into rodents results in muscle wasting while neutralization of cytokines using genetic or pharmacological approaches attenuates muscle wasting (Cheung et al., 2010). For example, rodents were treated with a constant infusion of angiotensin II (AngII) and found there was muscle wasting plus increased circulating levels of IL-6 and increased expression of SOCS3 with suppressed insulin/IGF-1 signaling; knockout IL-6 from mice suppressed Ang II induced muscle wasting (Zhang et al., 2009; Rui et al., 2004; Rui et al., 2002).

Responses to IL-6 or INFγ involve stimulation of intracellular signaling pathways including activation of Janus protein tyrosine kinases (JAKs). Subsequently, JAKs mediate tyrosine phosphorylation of Signal Transducer and Activator of Transcription (STAT) factors followed by their dimerization, nuclear translocation and activation of target genes (Horvath, 2004). Among the seven members of the Stat family, Stat3 is the major member that is activated by the IL-6 family of cytokines (Hirano et al., 1997; Kishimoto et al., 1994). Recently, Bonetto et al reported the results of a microarray analysis of muscles from mice with cancer-induced cachexia. Components of 20 signaling pathways were upregulated, including IL-6, Stat3, JAK-STAT, SOCS3, complement and coagulation pathways. Therefore, the Stat3 pathway could be linked to loss of muscle mass but the pathway from Stat3 to muscle wasting is unknown.

A potential target of activated Stat3 is C/EBPδ. The C/EBP transcription factors (C/EBP-α, -β, -γ, -δ, -ω, and -ζ) are expressed in several tissues and act to regulate inflammatory and metabolic processes (Ramji and Foka, 2002). C/EBP-β or -δ can stimulate intracellular signaling in hepatocytes or inflammatory cells (Poli, 1998; Akira et al., 1990; Alonzi et al., 1997) and in mice responding to an excess of glucocorticoids, the expression and binding activity of C/EBP-β and -δ in muscle are increased (Penner et al., 2002; Yang et al., 2005).

One embodiment that includes C/EBPδ involves increased myostatin expression because the myostatin promoter contains recognition sites for glucocorticoid receptors, forkhead transcription factors as well as members of the C/EBP family of transcription factors (Ma et al., 2003; Allen and Unterman, 2007). In the present disclosure, an intracellular signaling pathway in cultured myotubes is identified that bridges the gaps between p-Stat3 and myostatin and loss of muscle mass. To examine if the pathway was operative in vivo, it was studied how two catabolic conditions, CKD or acute, streptozotocin-induced diabetes affect muscle metabolism in a muscle-specific Stat3 knockout (KO) mouse. It was also tested whether a small molecule inhibitor of Stat3 phosphorylation would correct muscle wasting. Interruption of Stat3 improved muscle metabolism and strength in mice with CKD and evidence was gathered for the pathway in muscle biopsies from patients with CKD.

The present disclosure satisfies a need in the art to provide novel compounds and methods for treating and/or preventing muscle wasting or cachexia in individuals.

SUMMARY OF THE INVENTION

Embodiments of the invention include methods and/or compositions for the treatment of at least muscle wasting (which may occur as weakening, shrinking, and/or loss of muscle caused by disease, age, or lack of use) and/or muscle weakness and/or cachexia. The muscle wasting and/or weakness may be related to any underlying medical condition and be the result of any cause. The underlying condition may or may not be known. In specific embodiments, the muscle wasting and/or muscle weakness may be part of cachexia, and cachexia may also be treated with methods and compositions of the invention.

Embodiments of the invention include methods and/or compositions for the treatment of muscle weakness and/or muscle wasting and/or cachexia in an individual known to have the muscle weakness and/or muscle wasting and/or cachexia, suspected of having muscle weakness and/or muscle wasting and/or cachexia, or at risk for having muscle weakness and/or muscle wasting and/or cachexia. The compositions include small molecules and functional derivatives as described herein. In some embodiments, the individual is receiving an additional therapy for an underlying condition that is related to (and may be the direct or indirect cause of) the muscle weakness and/or muscle wasting and/or cachexia and/or the individual is receiving an additional therapy for the muscle weakness and/or muscle wasting and/or cachexia itself.

In embodiments of the invention, an individual is given more than one dose of one or more compositions described herein or functional derivatives thereof. The dosing regimen may be separated in time by minutes, hours, days, months or years.

An individual in need thereof is an individual that has at least one symptom of a condition selected from muscle weakness, muscle wasting and cachexia or any combination thereof or is susceptible to having a condition selected from muscle weakness, muscle wasting and cachexia or any combination thereof by having an underlying condition that can have a condition selected from muscle weakness, muscle wasting and cachexia or any combination thereof as part of the underlying condition or as a secondary component of the underlying condition, for example.

Delivery of the composition of the invention may occur by any suitable route, including systemic or local, although in specific embodiments, the delivery route is oral, intravenous, topical, subcutaneous, intraarterial, intraperitoneal, buccal, by aerosol, by inhalation, and so forth, for example.

In some embodiments of the invention, the methods and/or compositions of the invention are useful for treating and/or preventing and/or reducing the risk of a condition selected from muscle weakness, muscle wasting and cachexia or any combination thereof, and in specific cases such treatment occurs by inhibiting Stat3 and/or Stat1 activity. In certain embodiments, the compositions inhibit Stat3 but fail to inhibit Stat1. In particular embodiments, the compositions do not inhibit Stat3 or Stat1. In some embodiments, compounds of the invention interact with the Stat3 SH2 domain, competitively inhibit recombinant Stat3 binding to its immobilized pY-peptide ligand, and/or inhibit IL-6-mediated tyrosine phosphorylation of Stat3, for example. In particular embodiments, the compositions of the invention fulfills the criteria of interaction analysis (CIA): 1) global minimum energy score ≤−30; 2) formation of a salt-bridge and/or H-bond network within the pY-residue binding site of Stat3; and/or 3) formation of a H-bond with or blocking access to the amide hydrogen of E638 of Stat3, for example. In some embodiments, the composition(s) interacts with a hydrophobic binding pocket with the Stat3 SH2 domain.

In a specific embodiment of the invention, there is a method of treating, preventing, and/or reducing the risk of a condition selected from muscle weakness, muscle wasting and cachexia or any combination thereof in an individual comprising delivering to the individual a therapeutically effective amount of a compound selected from the group consisting of N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, a functionally active derivative thereof, and a mixture thereof.

In a specific embodiment, there is a method of treating, preventing, and/or reducing the risk of a condition selected from muscle weakness, muscle wasting and cachexia or any combination thereof in an individual comprising delivering to the individual a therapeutically effective amount of a compound selected from the group consisting of 4-[3-(2,3-dihydro-1,4-benzodioxin-6-yl)-3-oxo-1-propen-1-yl] benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl] benzoic acid; 3-({2-chloro-4-[(1,3-dioxo-1,3-dihydro-2H-inden-2-ylidene)methyl]-6-ethoxyphenoxy}methyl)benzoic acid; methyl 4-({[3-(2-methyoxy-2-oxoethyl)-4,8-dimethyl-2-oxo-2H-chromen-7-yl]oxy}methyl) benzoate; 4-chloro-3-{5-[(1,3-diethyl-4,6-dioxo-2-thioxo-tetrahydro-5(2H)-pyrimidinylidene)methyl]-2-furyl}benzoic acid; a functionally active derivative thereof; and a mixture thereof. In a specific embodiment, any of the compounds disclosed herein are suitable to treat and/or prevent cachexia, for example.

In another embodiment, the inhibitor comprises the general formula:

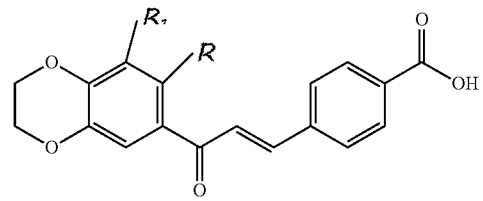

wherein $R_1$ and $R_2$ may be the same or different and are selected from the group consisting of hydrogen, carbon, sulfur, nitrogen, oxygen, flourine, chlorine, bromine, iodine, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the composition comprises the general formula:

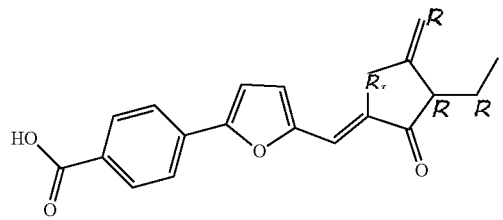

wherein $R_1$, and $R_3$ may be the same or different and are selected from the group consisting of hydrogen, carbon, nitrogen, sulfur, oxygen, flouring, chlorine, bromine, iodine, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives; and $R_2$ and $R_4$ may be the same or different and are selected from the group consisting of hydrogen, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the composition comprises the general formula:

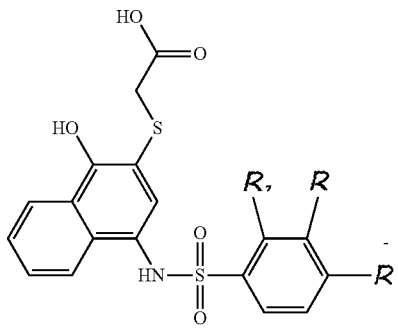

wherein $R_1$, $R_2$, and $R_3$ may be the same or different and are selected from the group consisting of hydrogen, carbon, nitrogen, sulfur, oxygen, fluorine, chlorine, bromine, iodine, carboxyl, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In specific embodiments, the condition selected from muscle weakness, muscle wasting and cachexia or any combination thereof treated by the composition may be in an individual with any type of cancer. In some cases, the cancer may be of the lung, breast, skin, liver, kidney, testes, ovary, cervix, bone, spleen, gall bladder, brain, pancreas, stomach, anus, prostate, colon, blood, head and neck, or lymphoid organs. For example; the composition may inhibit Stat3 in a cell of the muscles or other tissues of individuals with any of these cancers. Mammals may be treated with the methods and/or compositions of the invention, including humans, dogs, cats, horses, cows, pigs, sheep, and goats, for example.

In other embodiments of the invention, there are methods of treating a condition selected from muscle weakness, muscle wasting and cachexia or any combination thereof in an individual wherein the composition(s) is an inhibitor of any members of the STAT protein family, including STAT1, STAT2, STAT3, STAT4, STAT5 (STAT5A and STAT5B), or STAT6, for example.

In embodiments of the invention, there is a composition selected from the group consisting of N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, and 4-Bromo-N-(1,6'-dihydroxy-[2,2']binaphthalenyl-4-yl)-benzenesulfonamide. The composition may be comprised in a pharmaceutical formulation. The composition may be comprised with a carrier. The composition may be comprised with another therapeutic composition, such as a therapeutic composition for a condition selected from muscle weakness, muscle wasting and cachexia or any combination thereof. The composition may be comprised in a suitable solvent. The composition may be comprised in a solvent and/or polyethylene glycol (PEG). In specific embodiments, the solvent is Labrasol® (Caprylocaproyl macrogol-8 glycerides EP; Caprylocaproyl polyoxyl-8 glycerides NF; PEG-8 Caprylic/Capric Glycerides (USA FDA IIG), water, ethanol, glycerin, propylene glycol, isopropyl alcohol, methanol, acetone, isopropanol, acetonitrile, t-butanol, n-hexane, cyclohexane, and so forth. In specific embodiments, the PEG is PEG-200, PEG-300, or PEG-400. In particular cases, the composition is formulated in 60% Labrasol® and 40% PEG-400. The composition may be comprised in a tablet, soft gel cap, and so forth.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

Figure 1A:
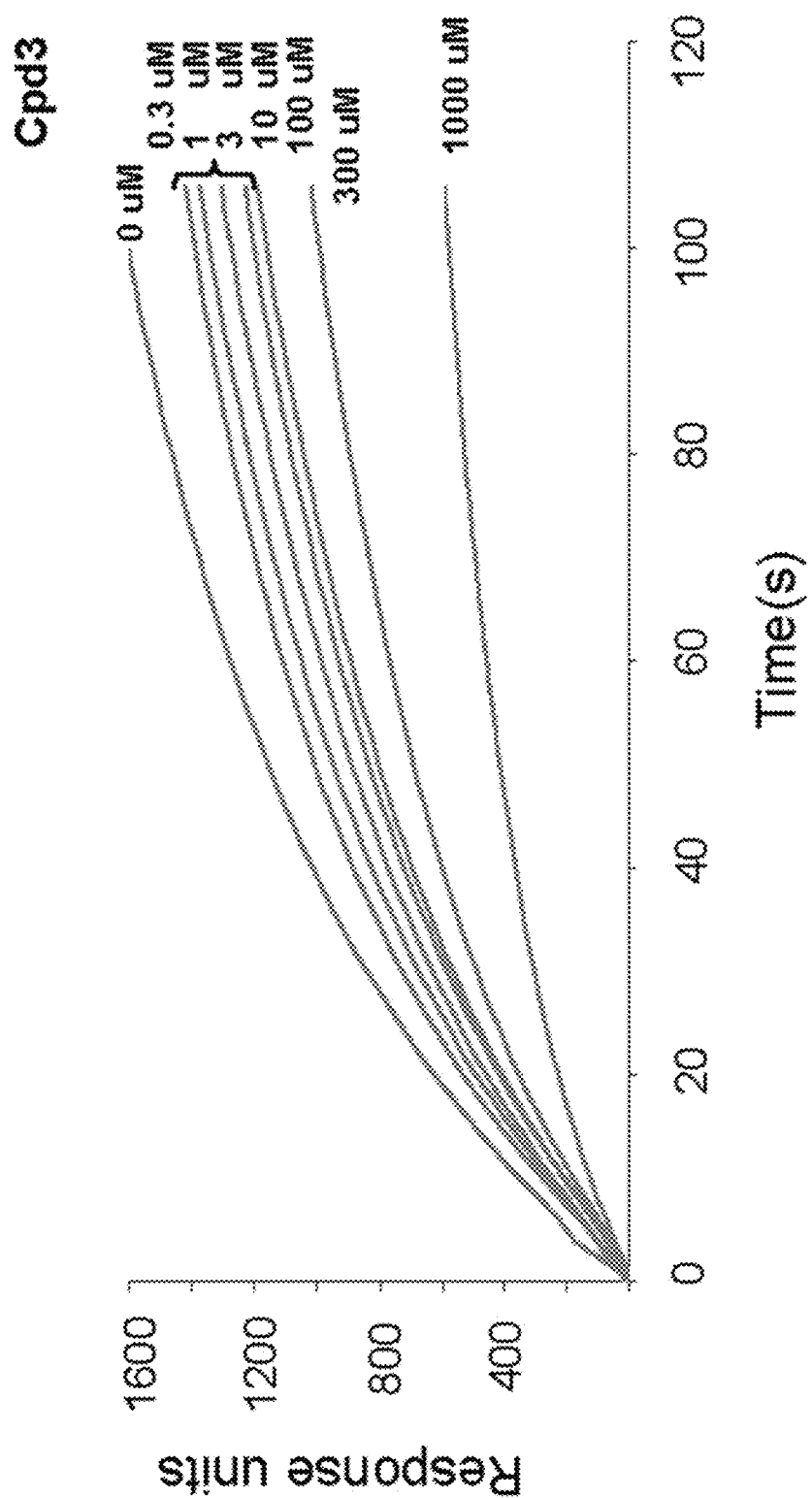
FIGS. 1A-1G demonstrates inhibition of Stat3 binding to immobilized phosphopeptide ligand by compounds. Binding of recombinant Stat3 (500 nM) to a BiaCore sensor chip coated with a phosphododecapeptide based on the amino acid sequence surrounding Y1068 within the EGFR was measured in real time by SPR (Response Units) in the absence (0 μM) or presence of increasing concentrations (0.1 to 1,000 μM) of Cpd3 (FIG. 1A), Cpd30 (FIG. 1B), Cpd188 (FIG. 1C), Cpd3-2 (FIG. 1D), Cpd3-7 (FIG. 1E) and Cpd30-
Figure 1B:
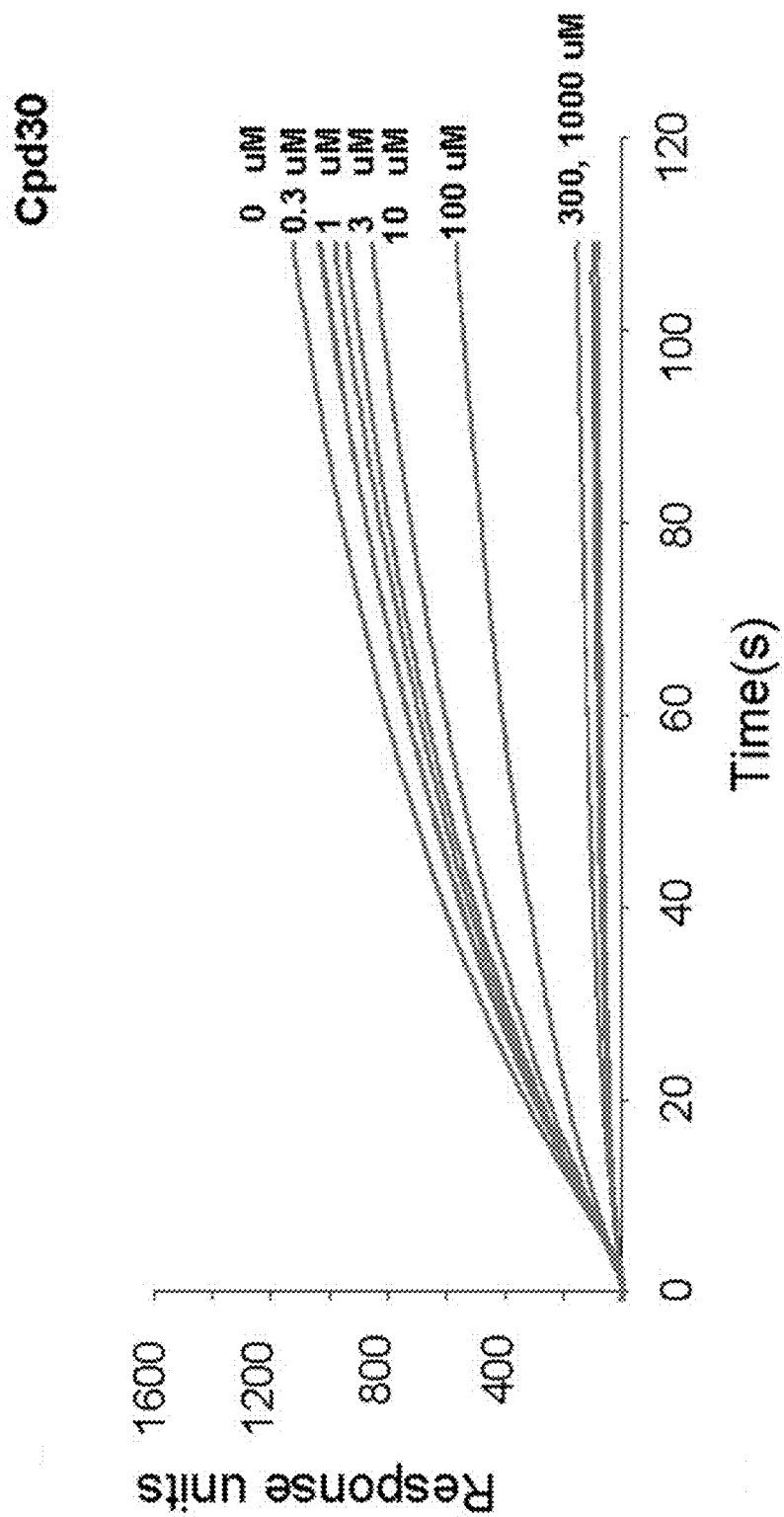
Figure 1C:
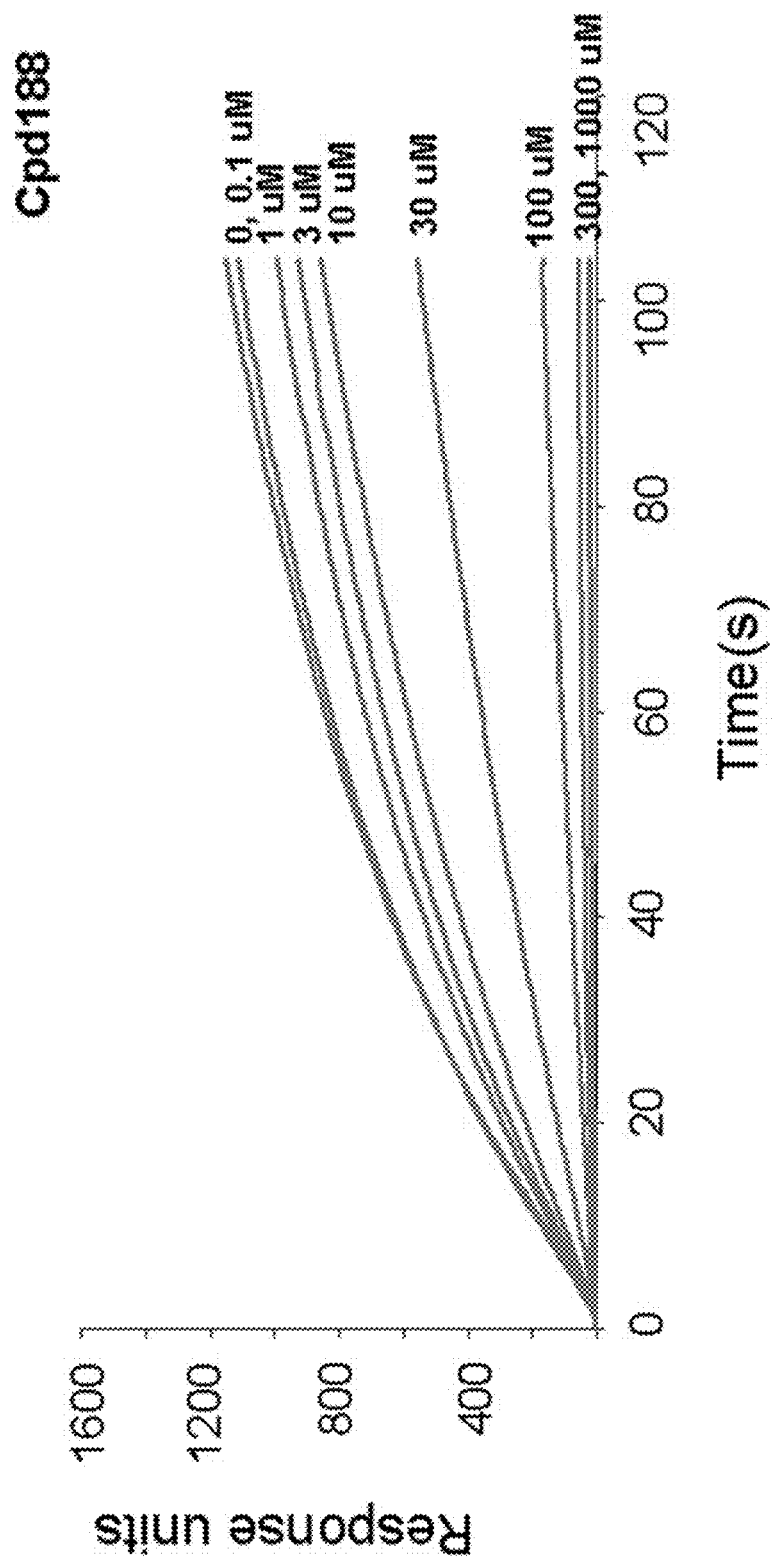
Figure 1D:
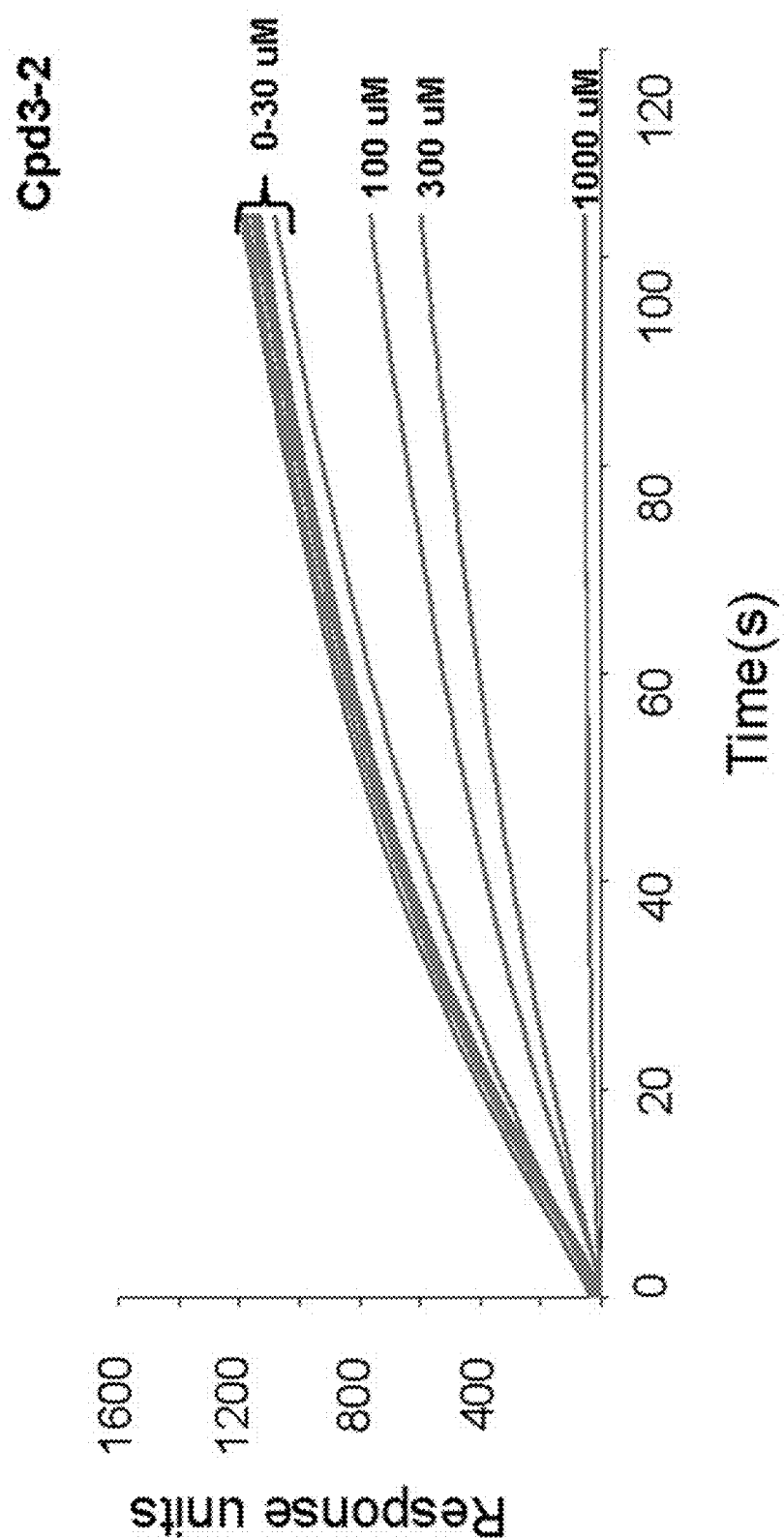
Figure 1E:
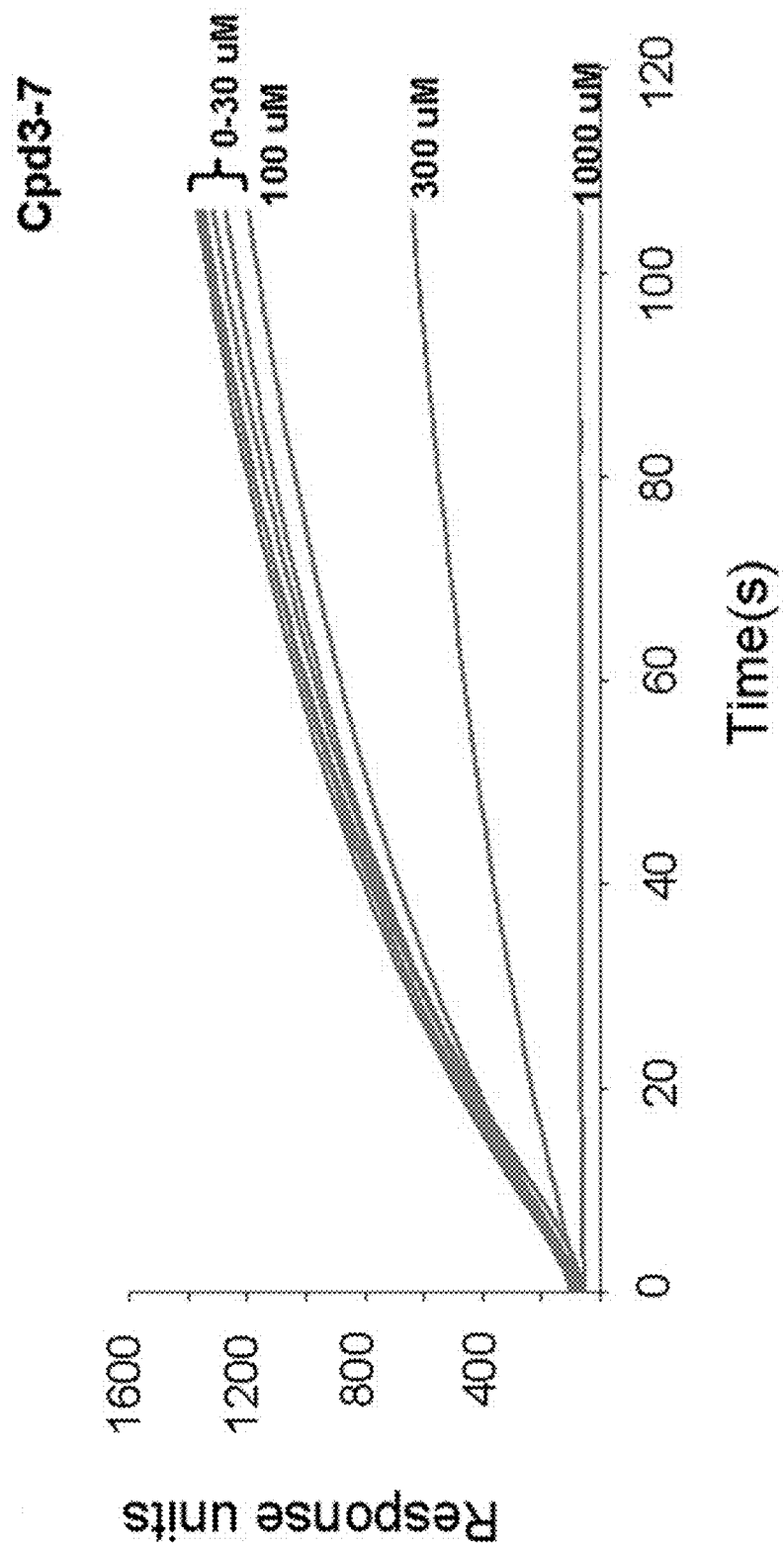
Figure 1F:
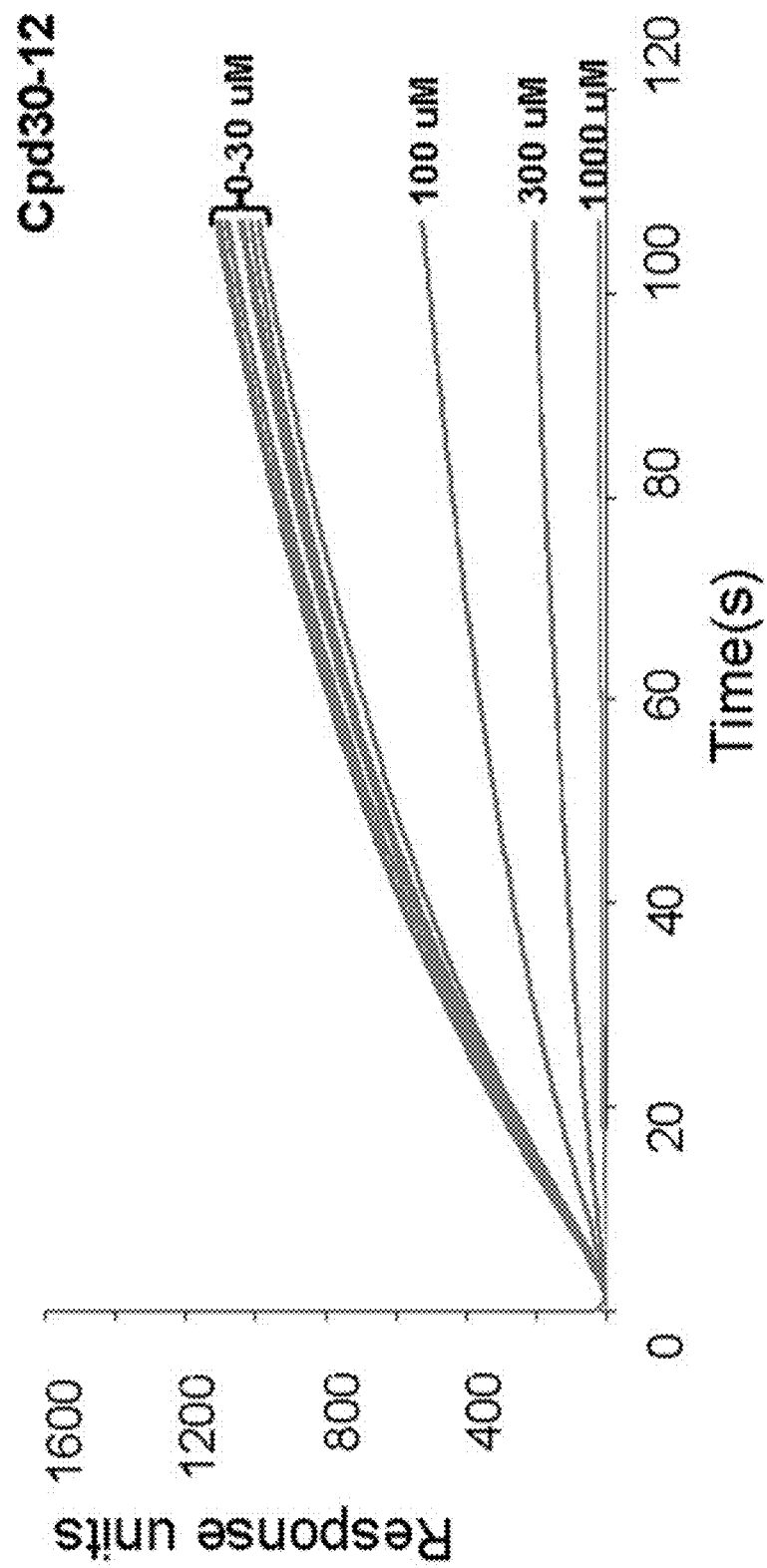
Figure 1G:
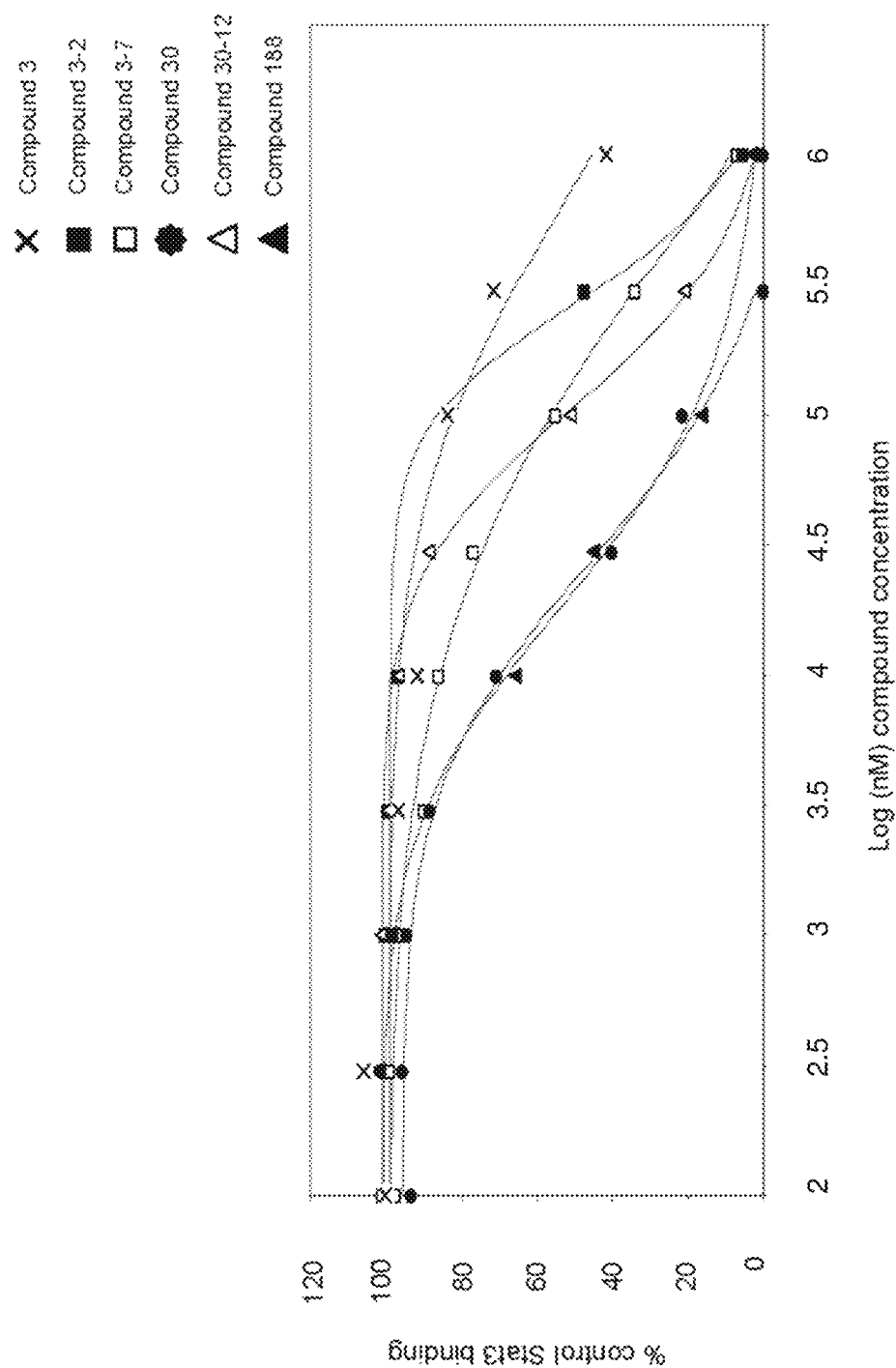
Figure 2A:
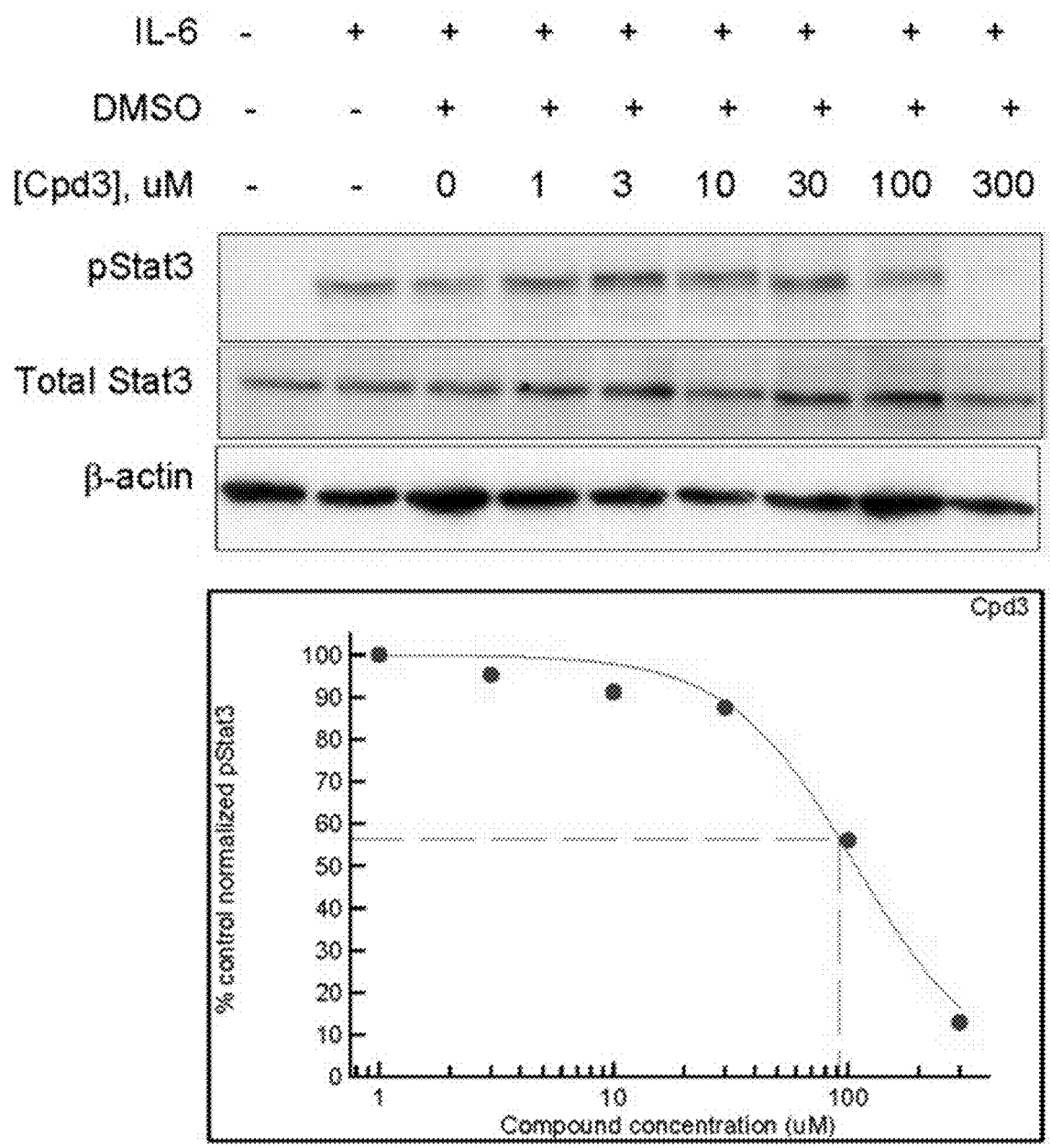
Figure 2B:
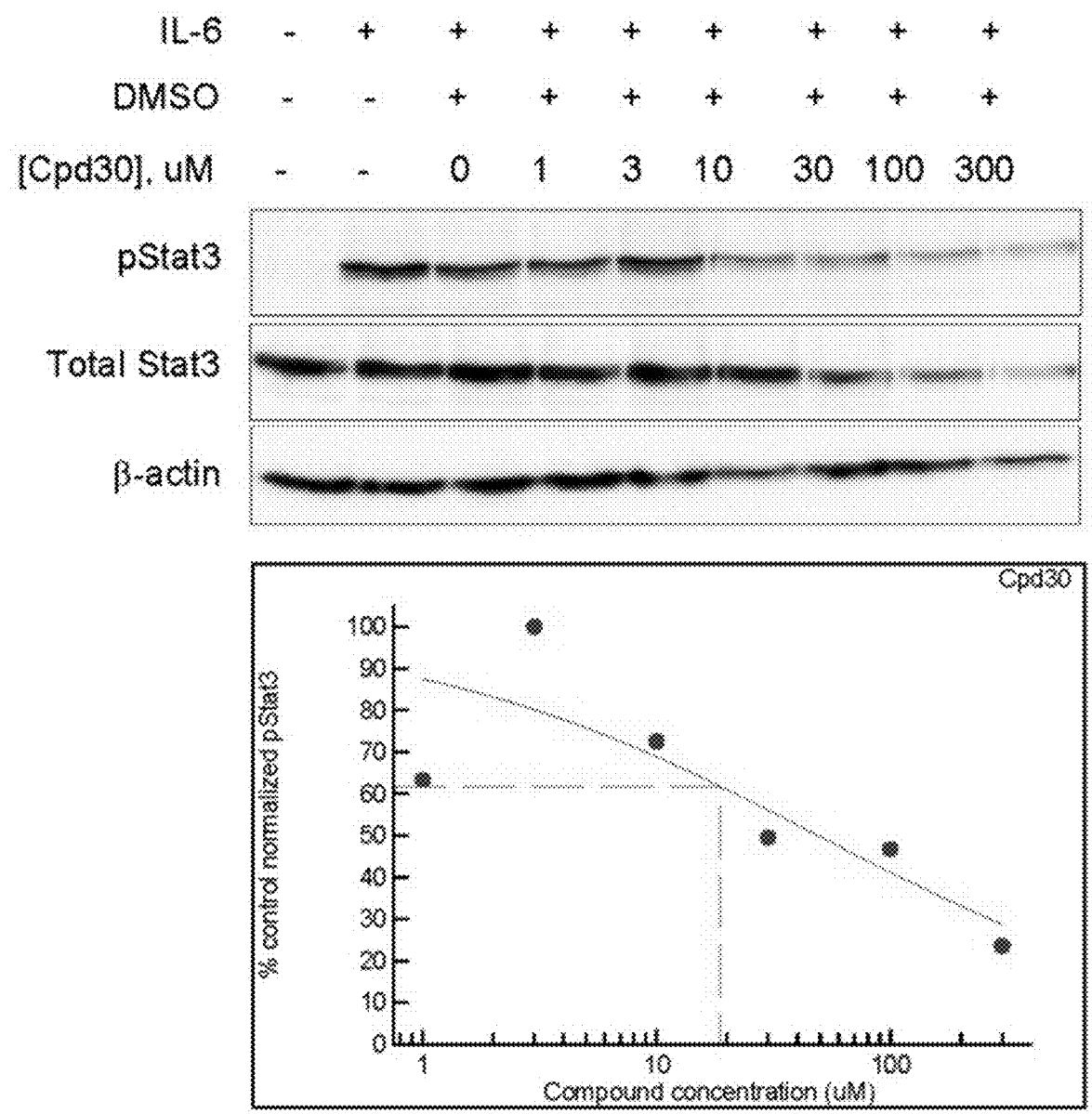
Figure 2C:
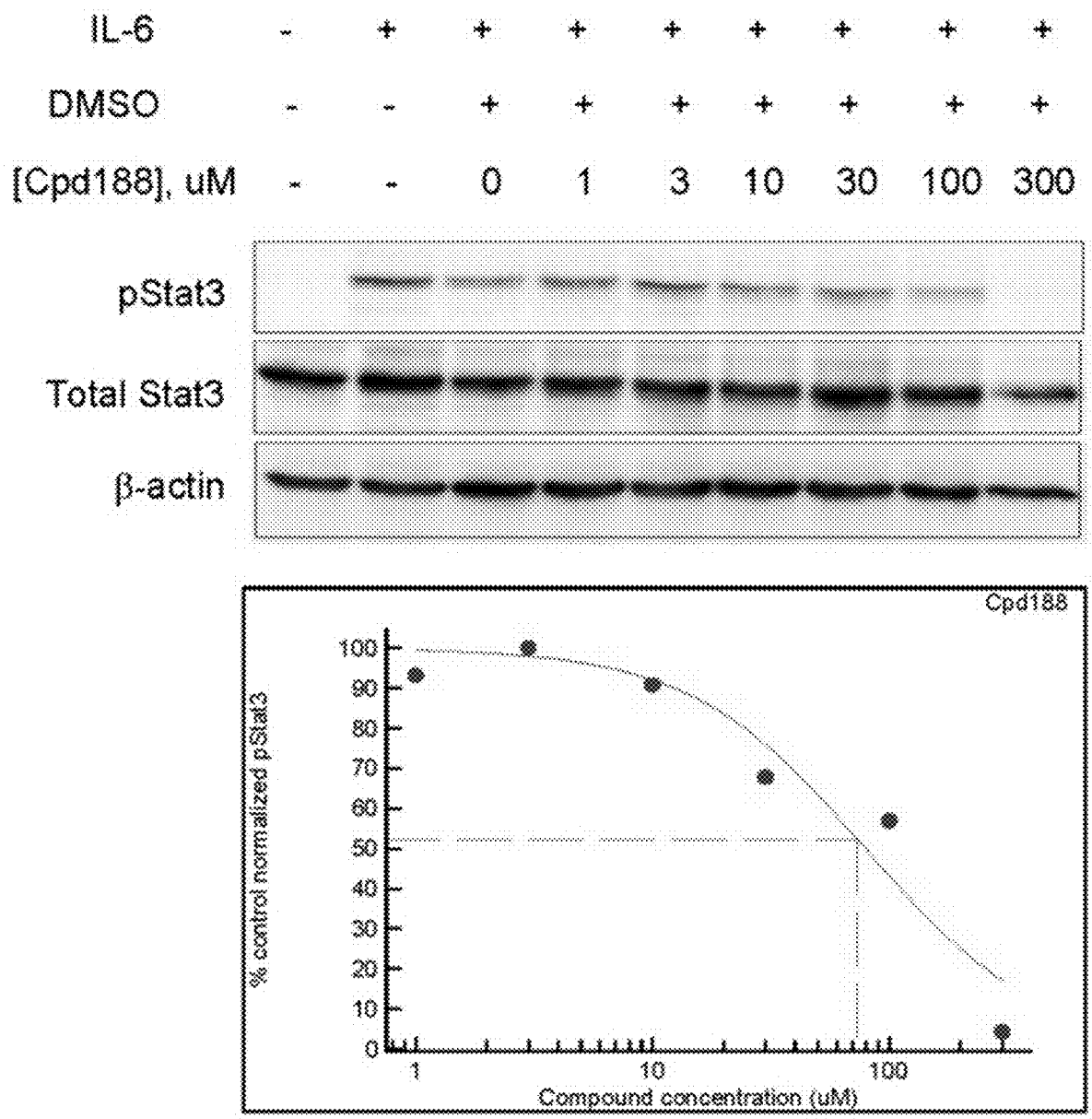
Figure 2D:
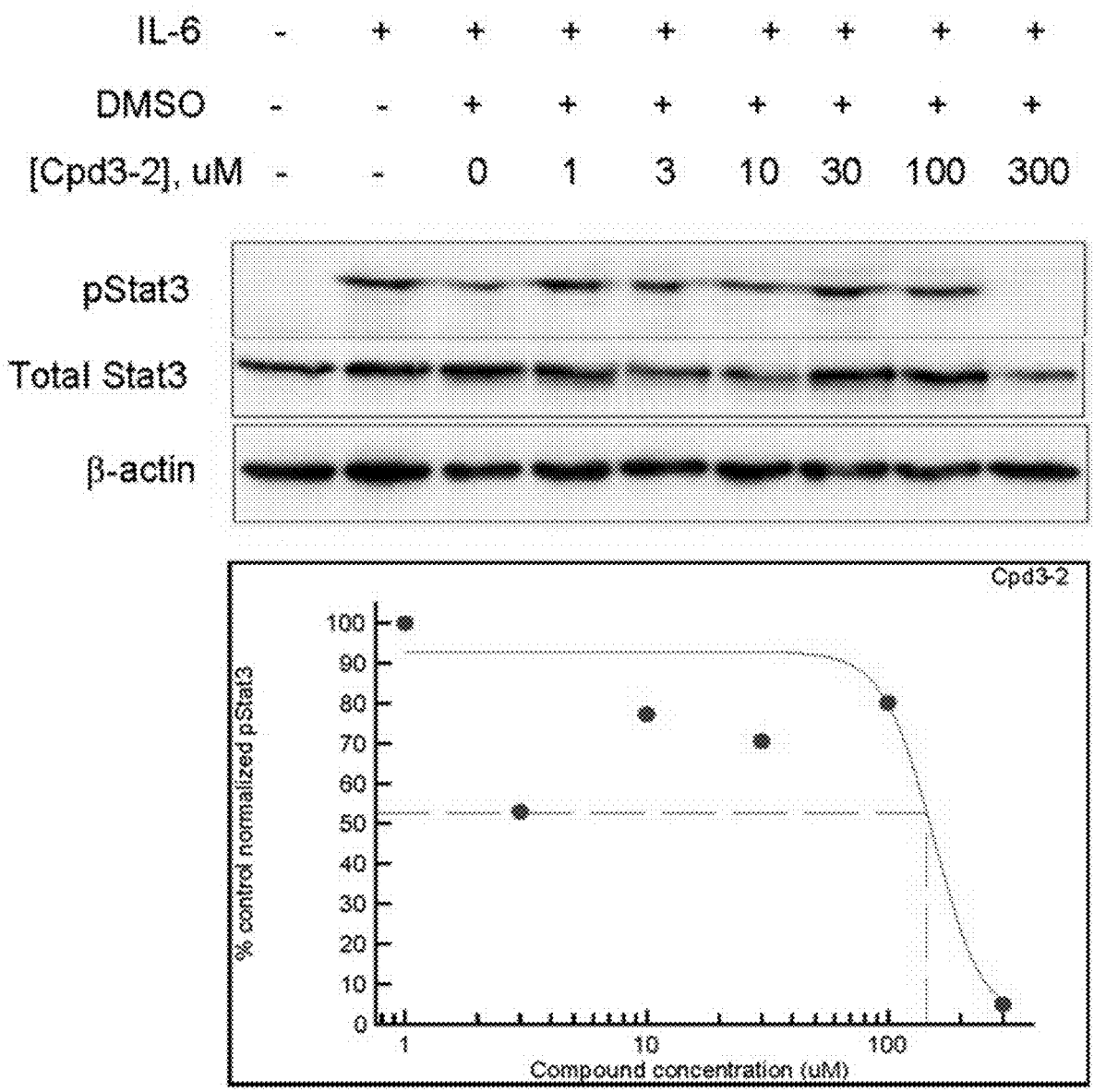
Figure 2E:
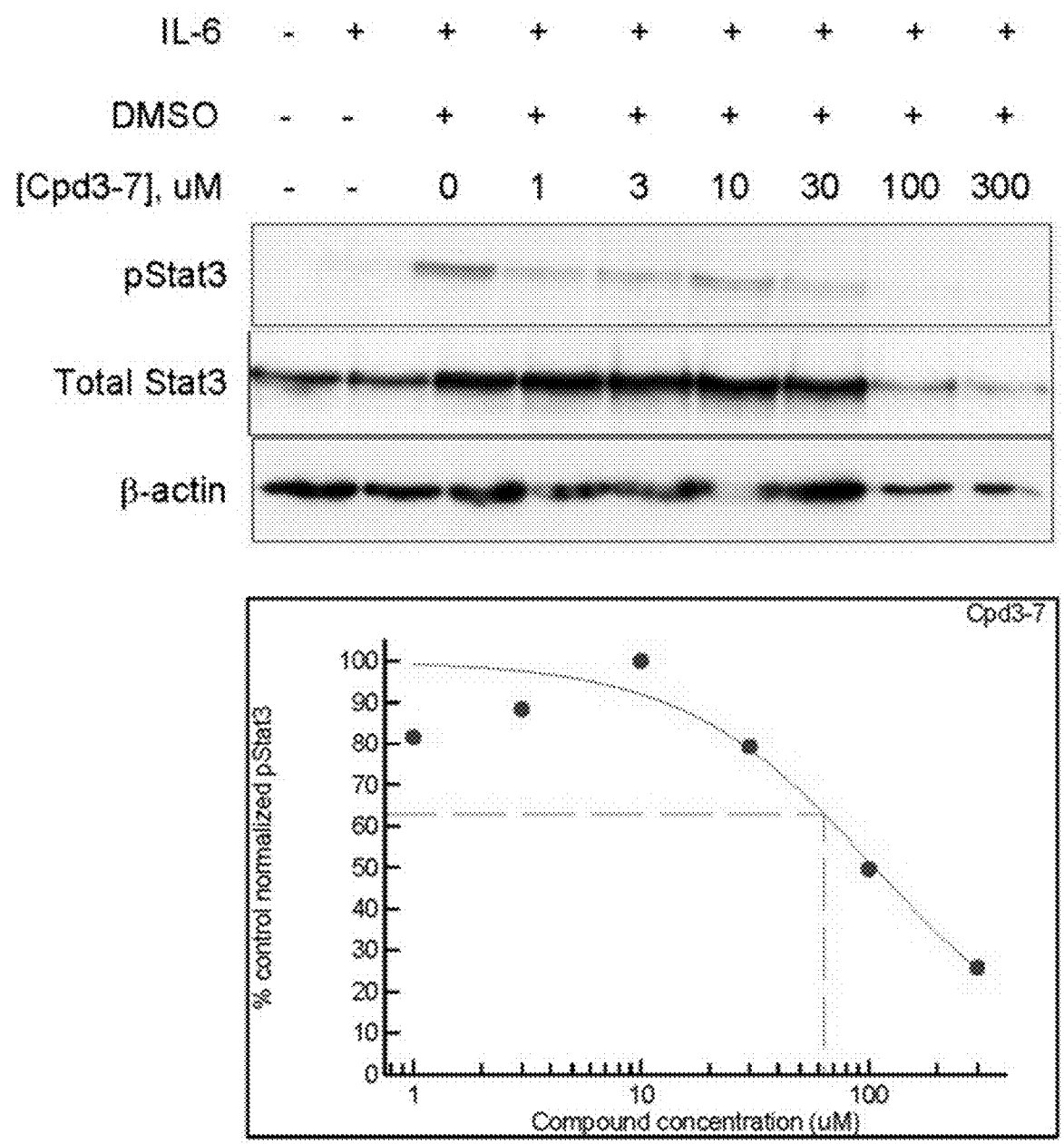
Figure 2F:
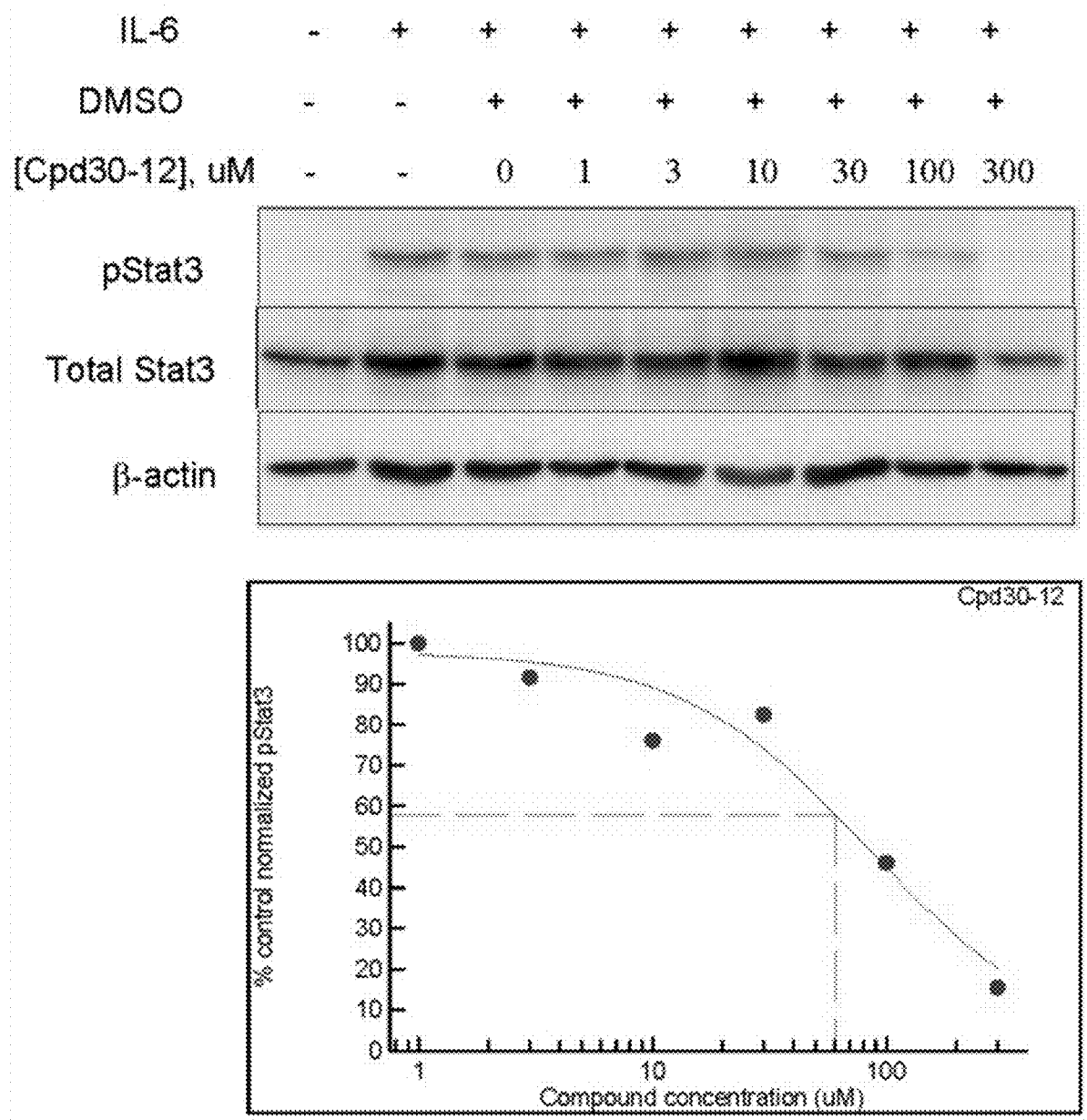

12 (FIG. 1F). Data shown are representative of 2 or more experiments. The equilibrium binding levels obtained in the absence or presence of compounds were normalized (response obtained in the presence of compound÷the response obtained in the absence of compound×100), plotted against the log concentration (nM) of the compounds (FIG. 1G). The experimental points fit to a competitive binding curve that uses a four-parameter logistic equation (see exemplary methods for details). These curves were used to calculate $IC_{50}$ (Table 1).

FIGS. 2A-2F demonstrates inhibition of IL-6-mediated activation of Stat3 by compounds. HepG2 cells were pretreated with DMSO alone or DMSO containing Cpd3 (FIG. 2A), Cpd188 (FIG. 2B), Cpd30 (FIG. 2C), Cpd3-2 (FIG. 2D), Cpd3-7 (FIG. 2E) or Cpd30-12 (FIG. 2F) at the indicated concentration for 60 min. Cells were then stimulated with IL-6 (30 ng/ml) for 30 min. Protein extracts of cells were separated by SDS-PAGE, blotted and developed serially with antibodies to pStat3, total Stat3 and β-actin. Blots were stripped between each antibody probing. The bands intensities of immunoblot were quantified by densitometry. The value of each pStat3 band's intensity was divided by each corresponding value of total Stat3 band intensity and the results normalized to the DMSO-treated control value and plotted as a function of the log compound concentration. The best-fit curves were generated based on 4 Parameter Logistic Model/Dose Response One Site/XLfit 4.2, IDBS. Each panel is representative of 3 or more experiments.

Figure 3A:
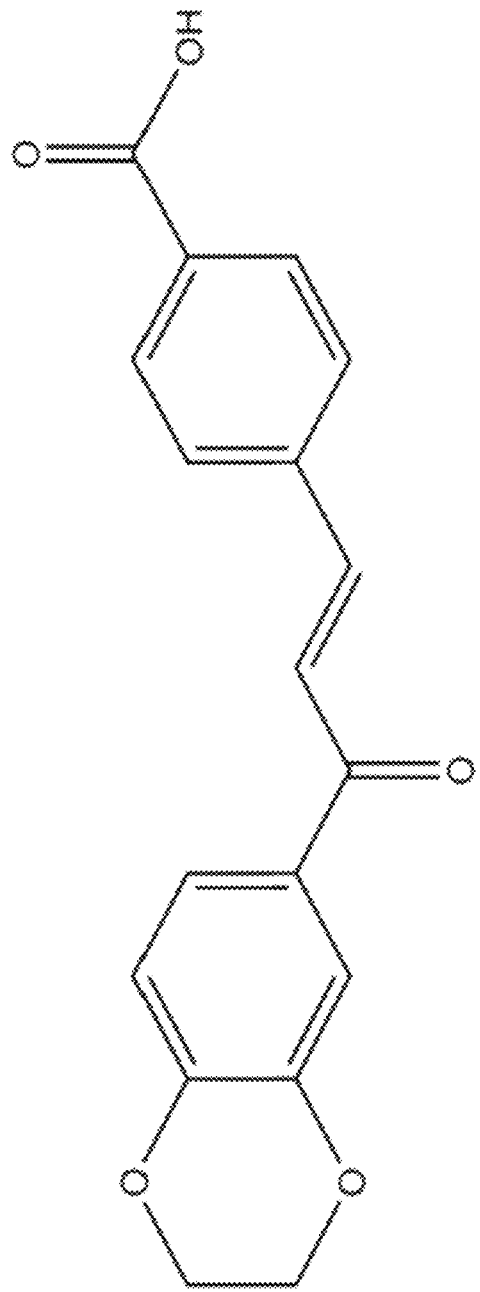
Figure 3B:
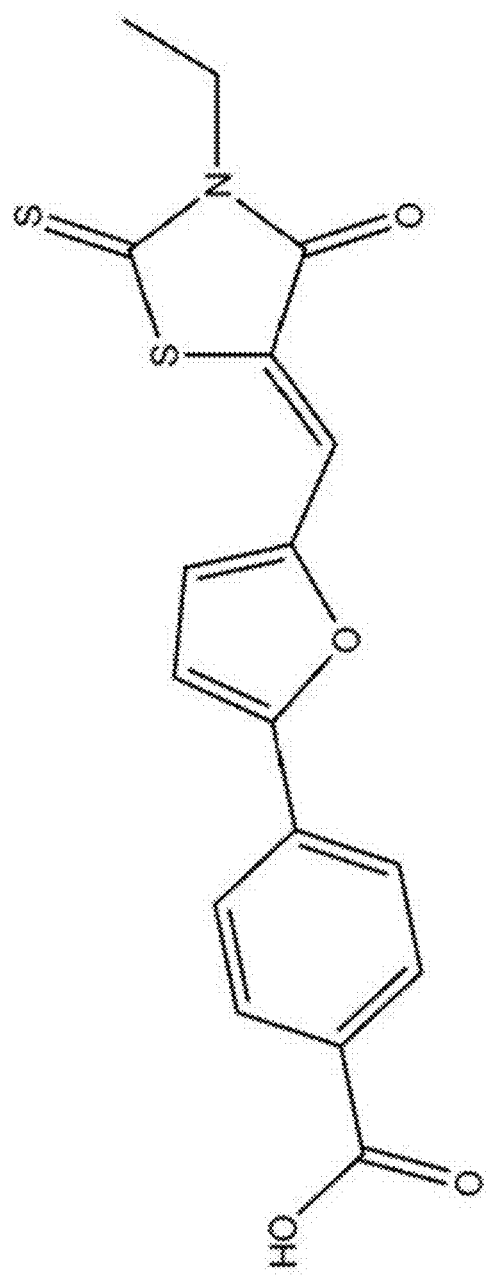
Figure 3C:
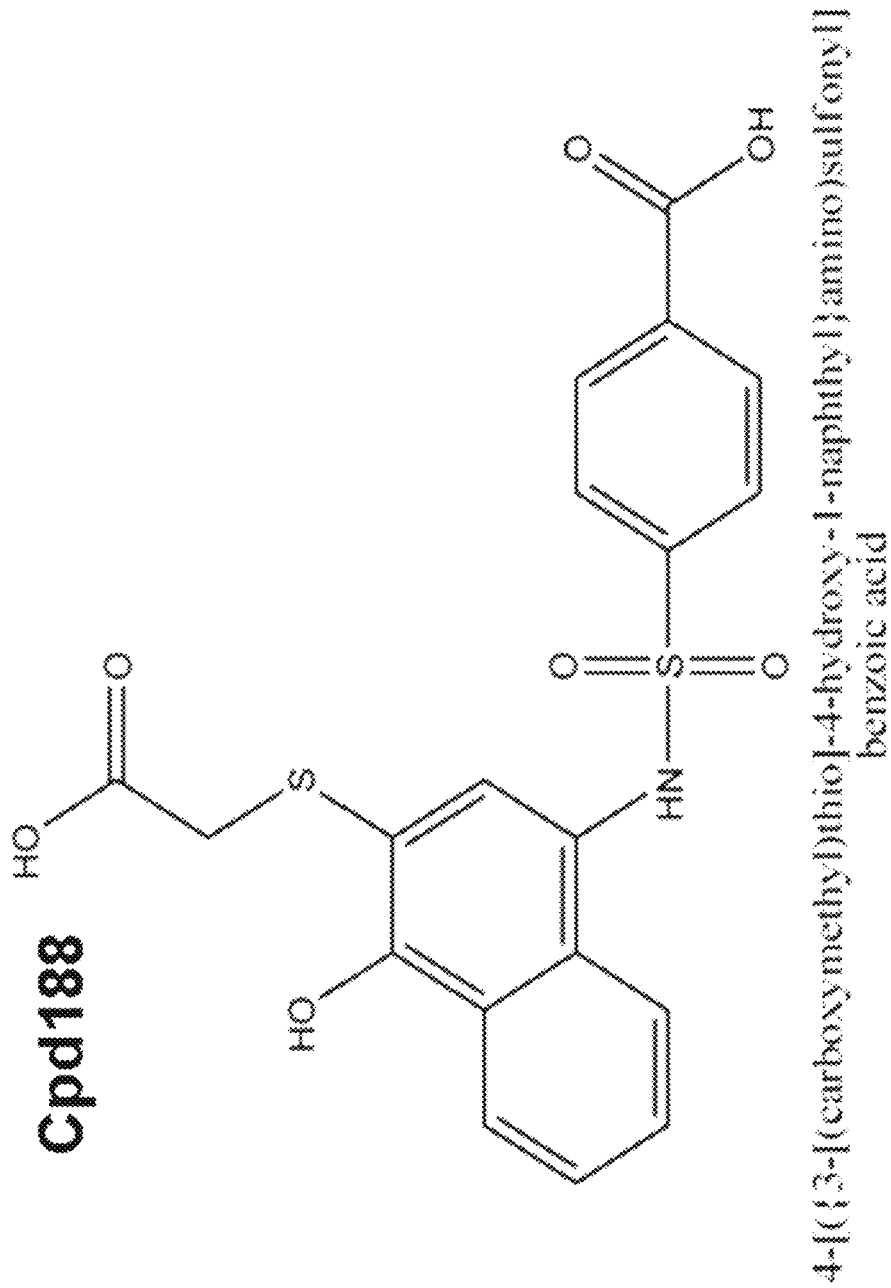
Figure 3D:
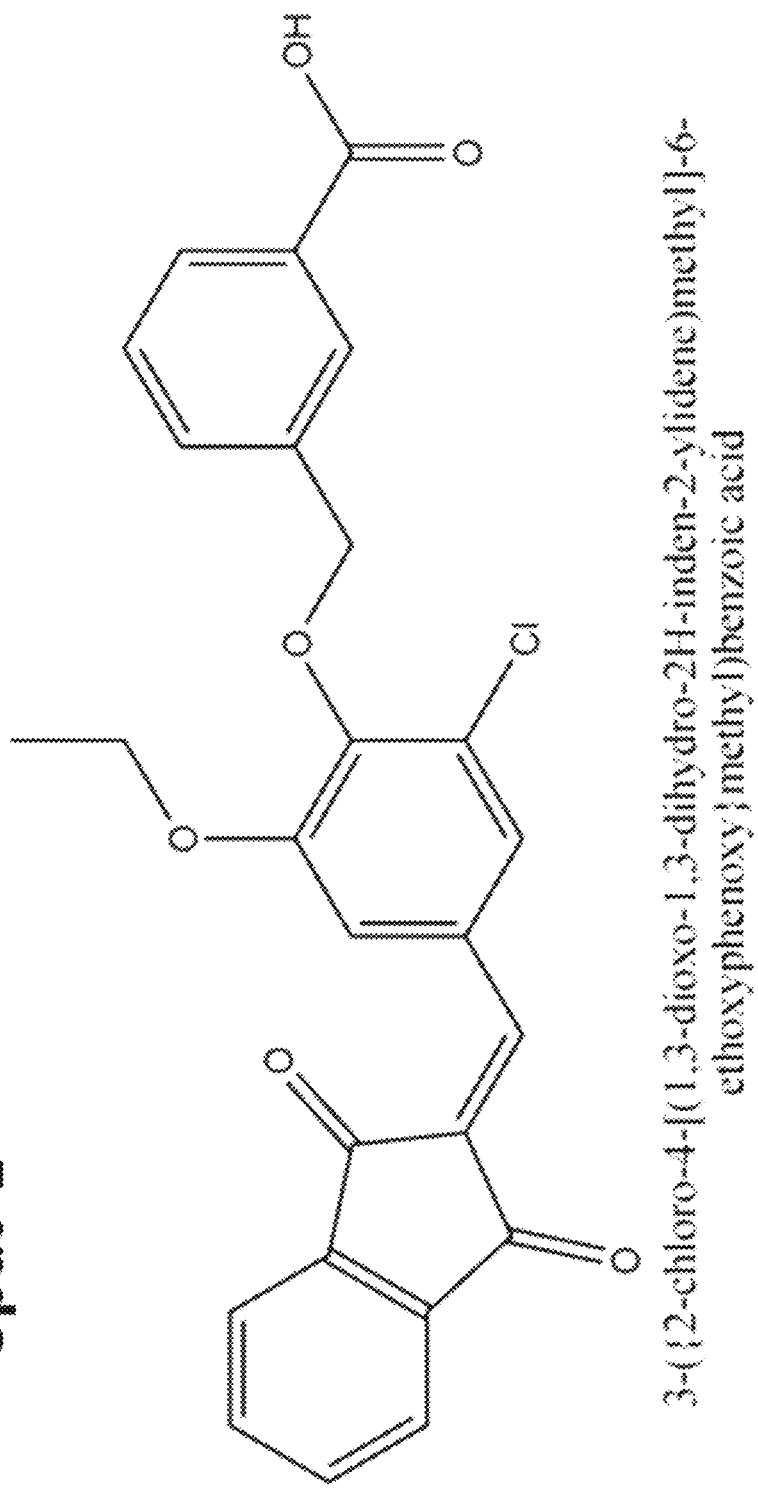
Figure 3E:
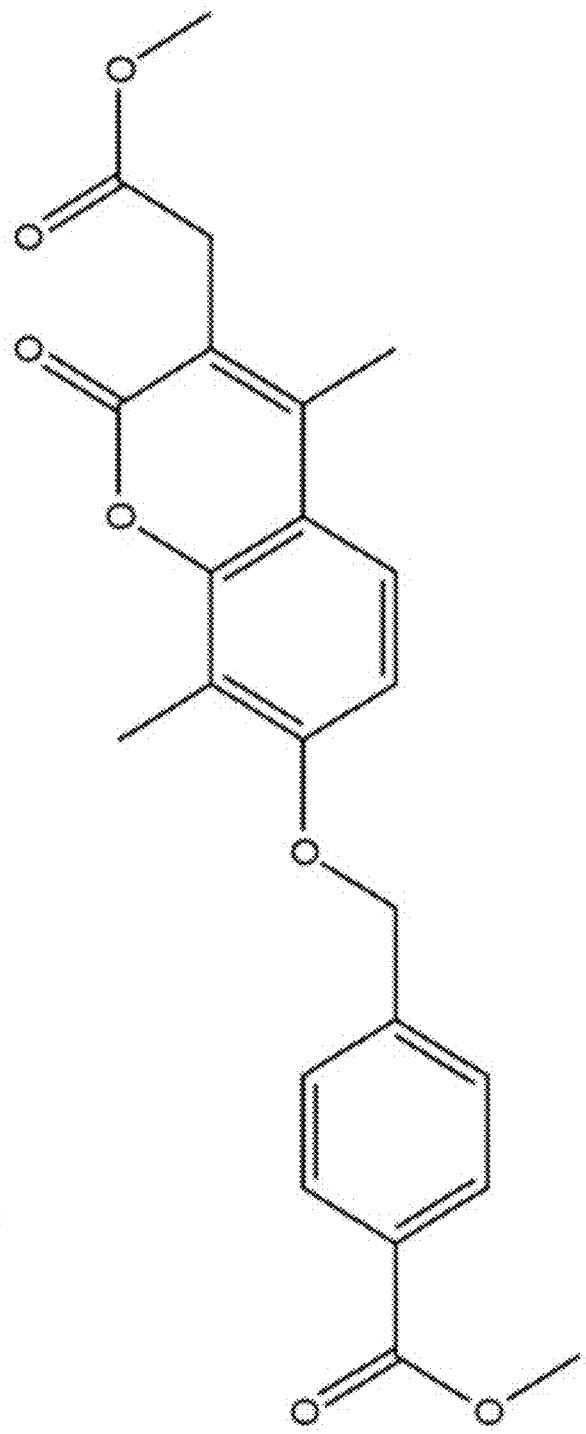
Figure 3F:
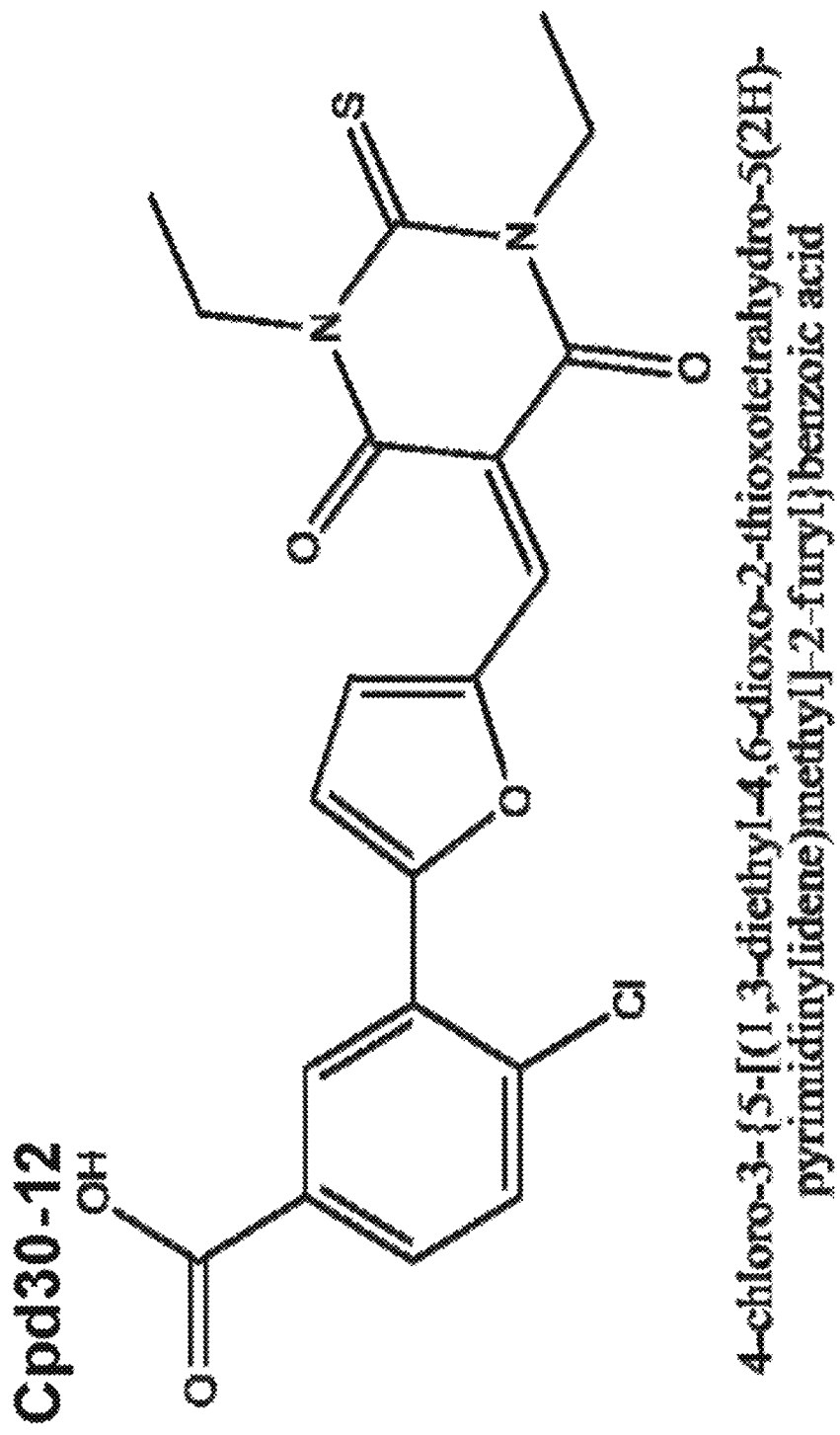

FIGS. 3A-3F provides exemplary chemical formulas and names of compounds. The chemical formulas and names are indicated for Cpd3 (FIG. 3A), Cpd30 (FIG. 3B), Cpd188 (FIG. 3C), Cpd3-2 (FIG. 3D), Cpd3-7 (FIG. 3E) and Cpd30-12 (FIG. 3F).

Figure 4:
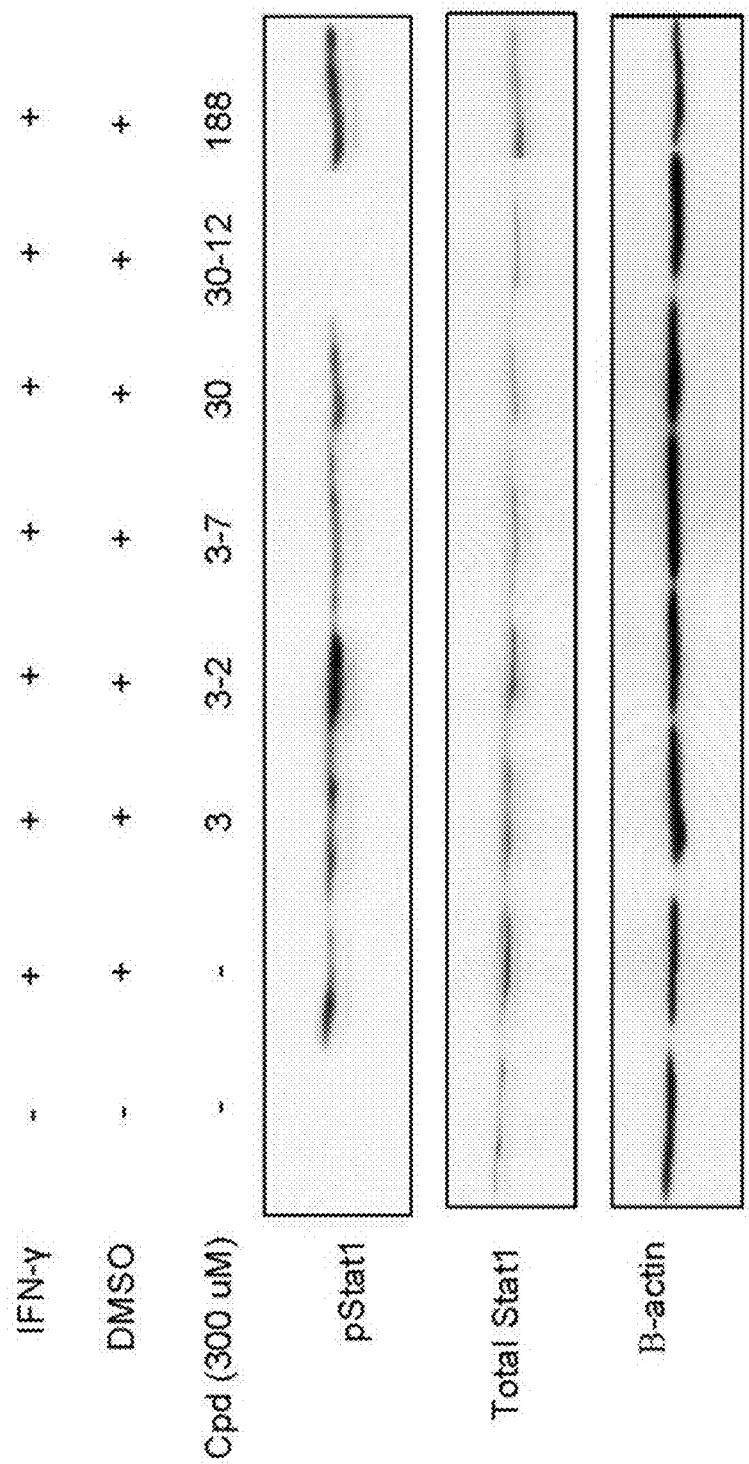

FIG. 4 shows effect of compounds on Stat1 activation. HepG2 cells were pretreated with DMSO alone or DMSO containing each of the compounds at a concentration of 300 μM for 60 min. Cells were then stimulated with IFN-γ (30 ng/ml) for 30 min. Protein extracts of cells were separated by SDS-PAGE and immunoblotted serially with antibodies to pStat1, total Stat1 and β-actin. Blots were stripped between each immunoblotting. The results shown are representative of 2 or more experiments.

Figure 5A:
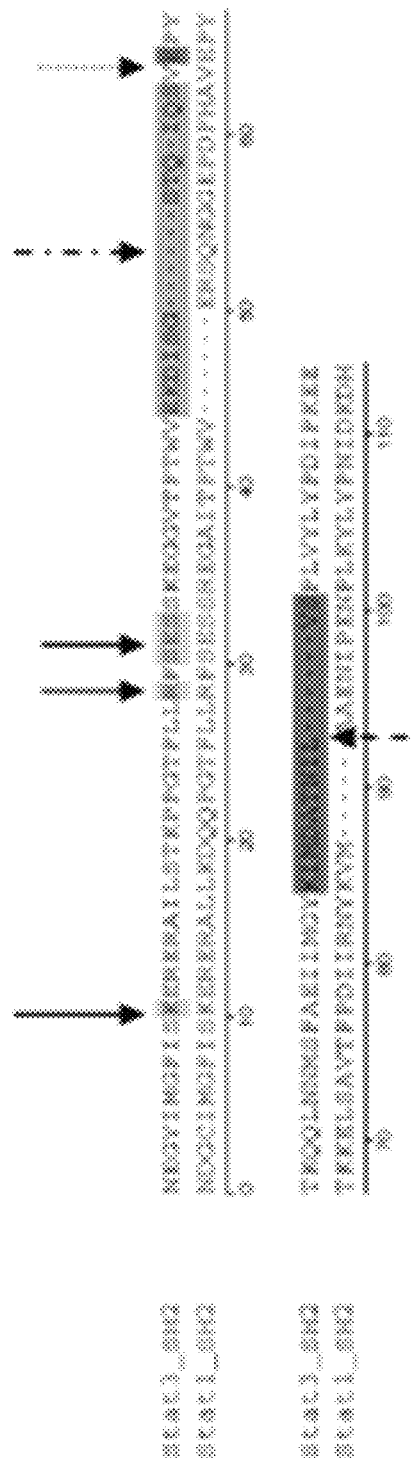
Figure 5B:
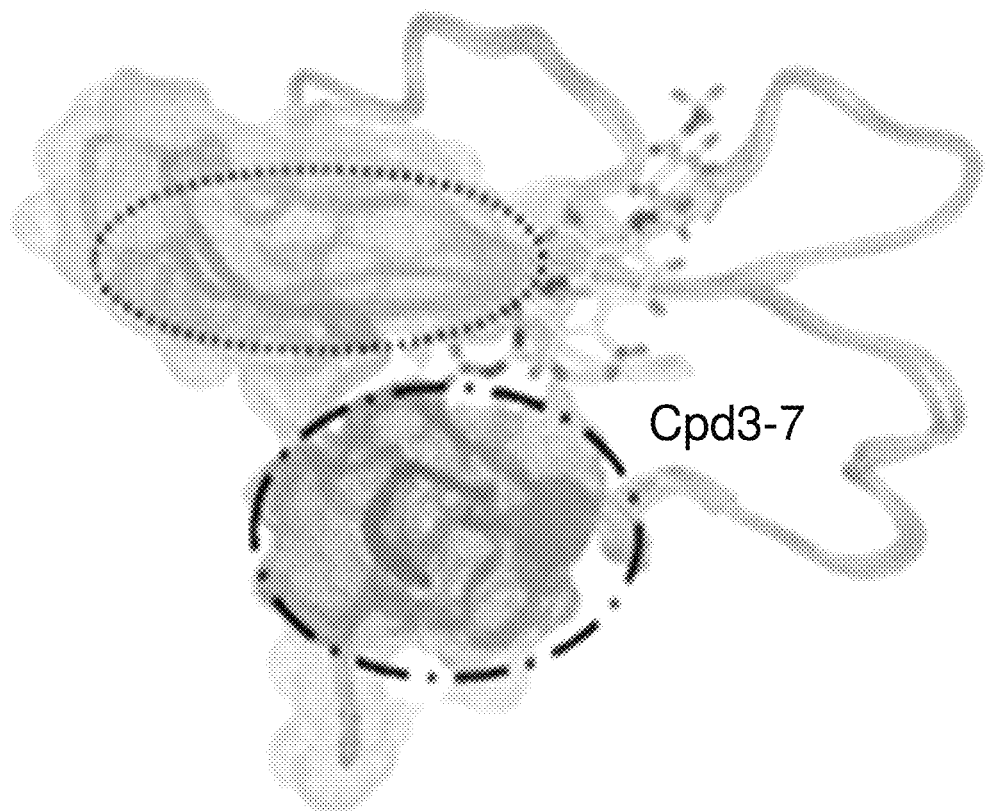
Figure 5C:
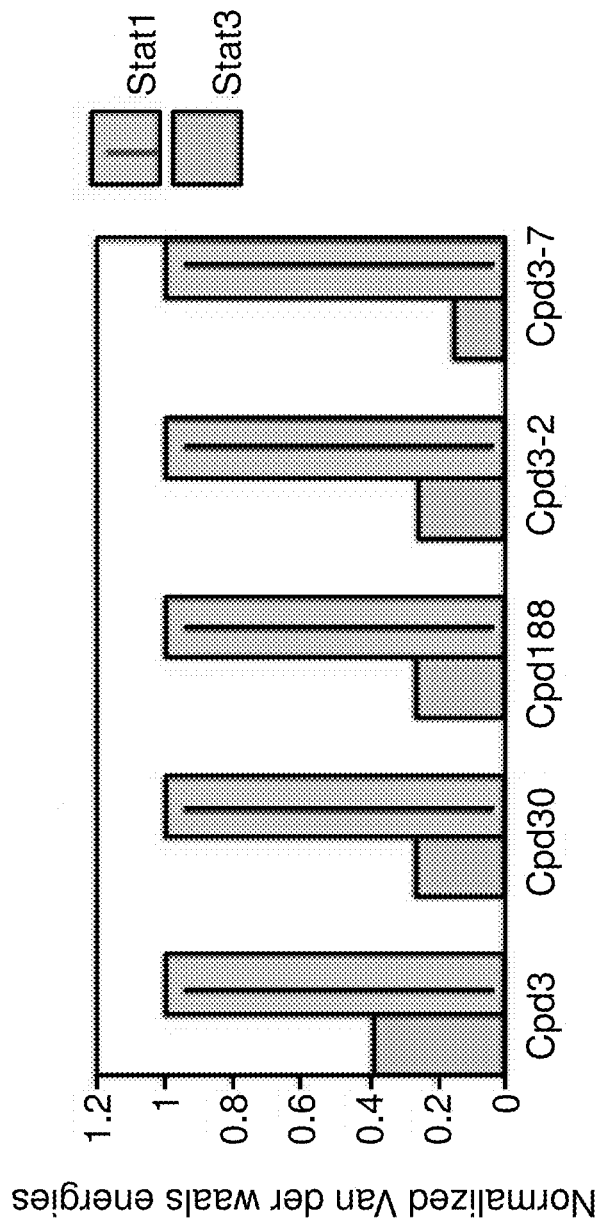

FIGS. 5A-5C provides comparisons of the Stat3 and Stat1 SH2 domain sequences, 3-D structures and van der Waals energies of compound binding. Sequence alignment of Stat3 and Stat1 SH2 domains is shown in FIG. 5A. The residues that bind the pY residue are highlighted in and pointed to by a solid arrow, the residue (E638) that binds to the +3 residue highlighted and pointed to by a dotted arrow and $Loop_{\beta C-\beta D}$ and $Loop_{\alpha B-\alpha C}$, which comprise the hydrophobic binding site consisting, are highlighted and pointed to by dot-dashed and dashed arrows, respectively. FIG. 5B shows an overlay of a tube-and-fog van der Waals surface model of the Stat3 SH2 domain and a tube-and-fog van der Waals surface model of the Stat1 SH2. The residues of the Stat3 SH2 domain represents $Loop_{\beta C-\beta D}$ are highlighted and shown by dotted circles and the residues represent $Loop_{\alpha B-\alpha C}$ are highlighted and shown by a dotted-dashed circle; the corresponding loop residues within the Stat1 SH2 domain are shown in a light fog surrounding the circles. This overlay is shown bound by Cpd3-7 as it would bind to the Stat3 SH2 domain. The van der Waals energy of each compound bound to the Stat1 SH2 domain or the Stat3 SH2 domain was calculated, normalized to the value for Stat1 and depicted in FIG. 5C.

FIGS. 6A-6F shows a computer model of each compound bound by the Stat3 SH2 domain. The results of computer docking to the Stat3 SH2 domain is shown for Cpd3 (FIG. 6A), Cpd30 (FIG. 6B), Cpd188 (FIG. 6C), Cpd3-2 (FIG. 6D), Cpd3-7 (FIG. 6E) and Cpd30-12 (FIG. 6F). The image on the left of each panel shows the compound binding to a spacefilling model of the Stat3 SH2 domain. The pY-residue binding site is represented by dashed circle, the +3 residue binding site is represented by a solid circle, loop $Loop_{\beta C-\beta D}$ is represented by dotted circle and loop $Loop_{\alpha B-\alpha C}$ is represented by dot-dashed circle. Residues R609 and K591 critical for binding pY are shown within a dashed circle, residue E638 that binds the +3 residue shown within a solid circle and the hydrophobic binding site consisting of $Loop_{\beta C-\beta D}$ and $Loop_{\alpha B-\alpha C}$ is shown within a dash-dot and dotted circle, respectively. The image on the right side of each panel is a closer view of this interaction with hydrogen bonds indicated by dotted lines. In FIG. 6A the negatively charged benzoic acid moiety of Cpd3 has electrostatic interactions with the positively-charge pY residue binding site consisting mainly of the guanidinium cation group of R609 and the basic ammonium group of K591. The benzoic acid group also forms a hydrogen-bond network consisting of double H-bonds between the carboxylic oxygen and the ammonium hydrogen of R609 and the amide hydrogen of E612. H-bond formation also occurs between the benzoic acid carbonyl oxygen and the side chain hydroxyl hydrogen of Serine 611. Within the +3 residue-binding site, the oxygen atom of 1,4-benzodioxin forms a hydrogen bond with the amide hydrogen of E638. In addition, the 2,3-dihydro-1,4-benzodioxin of Cpd3 interacts with the loops forming the hydrophobic binding site. In FIG. 6B the carboxylic terminus of the benzoic acid moiety of Cpd30, which is negatively charged under physiological conditions, forms a salt bridge with the guanidinium group of R609 within the pY residue binding site. Within the +3 residue-binding site, the oxygen of the thiazolidin group forms a H-bond with the peptide backbone amide hydrogen of E638. In addition, the thiazolidin moiety plunges into the hydrophobic binding site. In FIG. 6C there is an electrostatic interaction between the (carboxymethyl) thio moiety of Cpd188 carrying a negative charge and the pY-residue binding site consisting of R609 and K591 carrying positive charge under physiological conditions. There are H-bonds between the hydroxyloxygen of the (carboxymethyl) thio group of Cpd188 and the guanidinium hydrogen of R609, between the hydroxyloxygen of the (carboxymethyl) thio group and the backbone amide hydrogen of E612, and between the carboxyl-oxygen of the (carboxymethyl) thio group of Cpd188 and the hydroxyl-hydrogen of S611. Within the +3 residue-binding site, there is a H-bond between the hydroxyl-oxygen of benzoic acid group of Cpd188 and the amide-hydrogen of E638. In addition, the benzoic acid group extends and interacts with the hydrophobic binding site. In FIG. 6D the benzoic acid group of Cpd3-2 has significant electrostatic interactions with the pY-residue binding site pocket, mainly contributed by R609 and K591, and forms two H bonds; the carboxylic oxygen of the benzoic acid group binds the guanidinium hydrogen of R609, and the carbonyl oxygen of the benzoic acid group binds to the carbonyl hydrogen of S611. Within the +3 residue-binding site, oxygen within the 1,3-dihydro-2H-inden-2-ylidene group forms an H bond to the backbone amide-hydrogen of E638. In addition, the 1,3-dihydro-2H-inden-2-ylidene group plunges into the hydrophobic binding site. In FIG. 6E H-bonds are formed between the carbonyl-oxygen of the methyl 4-benzoate moiety of Cpd 3-7 and the side chain guanidinium of R609 and between the methoxy-oxygen and the hydrogen of the ammonium terminus of K591. The (2-methoxy-2-oxoethyl)-4,8-dimethyl-2-oxo-2H-chromen group of Cpd3-7 blocks access to the amide hydrogen of E638 within the +3 residue-binding site. In addition, this group plunges into the hydrophobic binding site. In FIG. 6F there are electrostatic interactions between the benzoic acid derivative group of Cpd30-12 and R609 and 591 within the pY-residue binding site. Also, H-bonds are formed between the hydroxyl-oxygen of Cpd30-12 and the guanidinium-hydrogen of R609, between the carboxyl-oxygen of Cpd30-12 and the hydroxyl-hydrogen of S611 and between the furyl group of Cpd30-12 and the hydrogen of ammonium of K591. The 1,3-diethyl-4, 6-dioxo-2-thioxotetrahydro-5(2H)-pyrimidinylidene groups blocks access to the +3 residue binding site; however, it extends into the groove between the pY-residue binding site and LoopβC-βD, while sparing the hydrophobic binding site.

Figure 7A:
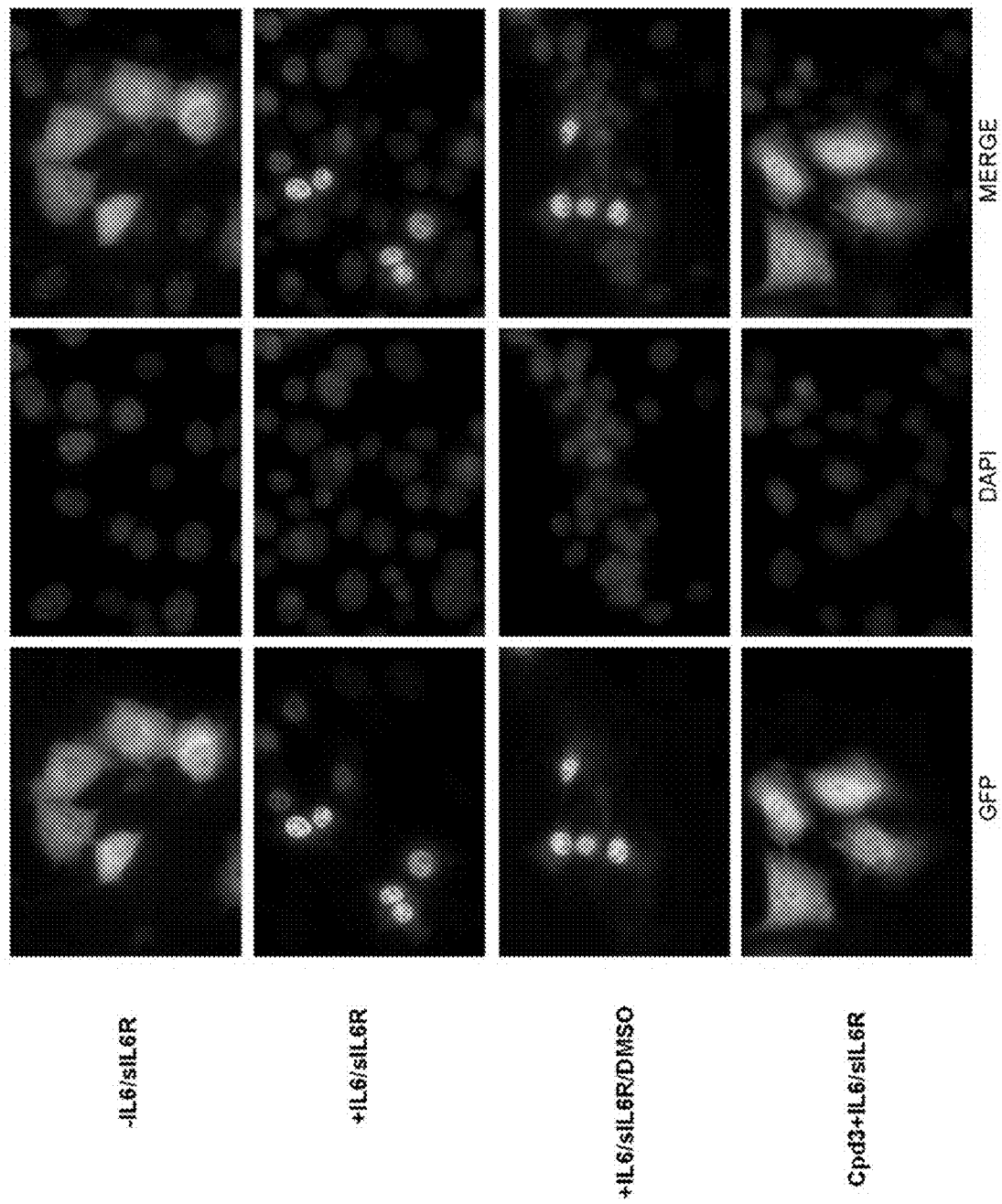
Figure 7B:
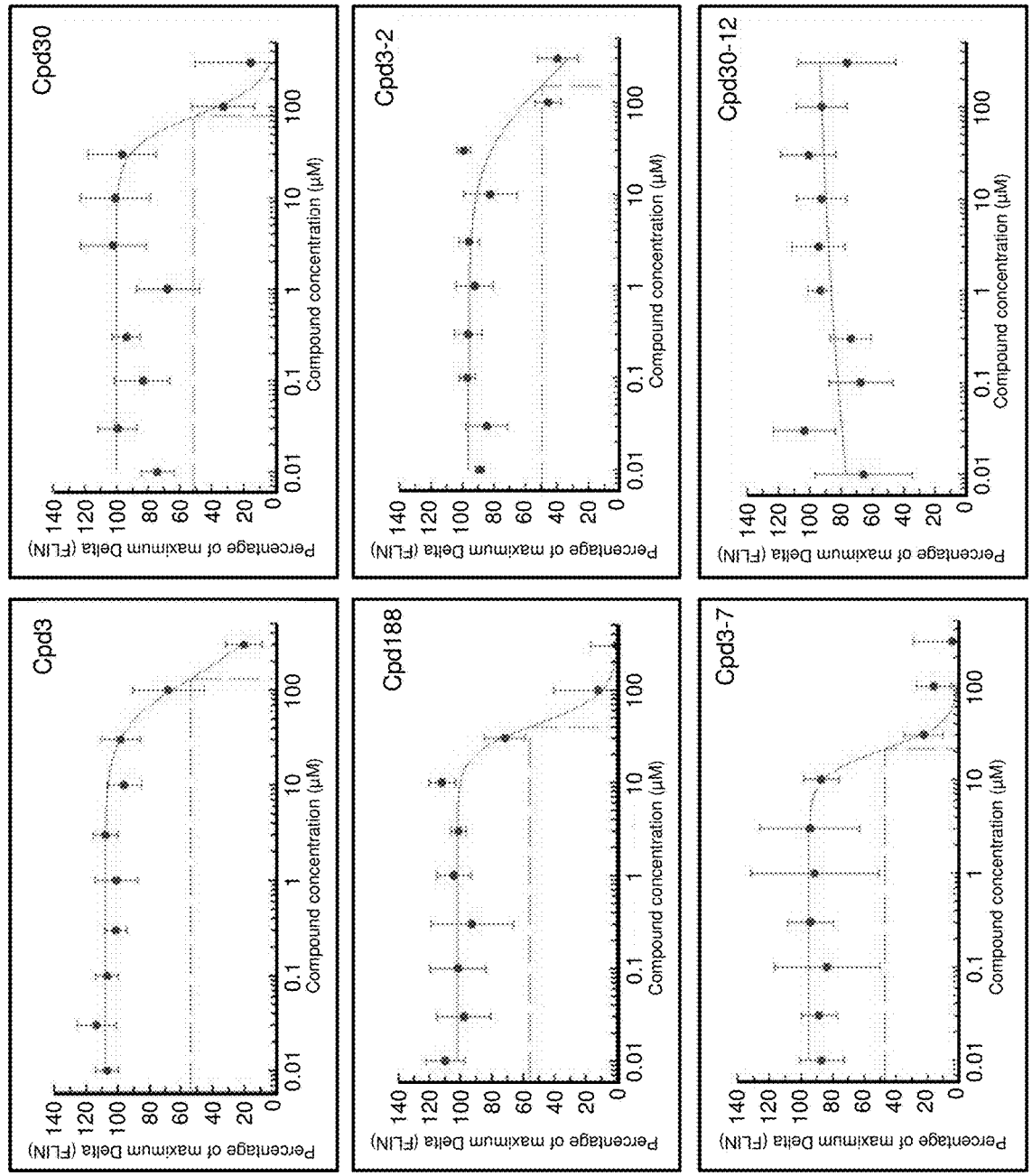

FIGS. 7A-7B shows inhibition of cytoplasmic-to-nuclear translocation of Stat3 assessed by confocal and high-throughput fluorescence microscopy. In FIG. 7A, MEF/GFP-Stat3 cells grown on coverslips were pretreated with DMSO that either contained (row four) or did not contain (row three) Cpd3 (300 μM) for 60 min before being stimulated without (row one) or with IL-6 (200 ng/ml) and IL-6sR (250 ng/ml) for 30 minutes (rows two, three and four). Coverslips were examined by confocal fluorescent microscopy using filters to detect GFP (column one), DAPI (column two) or both (merge; column three). In FIG. 7B, MEF-GFP-Stat3 cells were grown in 96-well plates with optical glass bottoms and pretreated with the indicated compound at the indicated concentrations in quadruplicate for 1 hour then stimulated with IL-6 (200 ng/ml) and IL-6sR (250 ng/ml) for 30 minutes. Cells were fixed and the plates were examined by high-throughput microscopy to determine the fluorescence intensity in the nucleus (FLIN) and the % ΔFLIN$_{Max}$ was calculated as described in Example 1. Data shown are mean±SD and are representative of 2 or more studies. Best-fit curves were generated based on 4 Parameter Logistic Model/Dose Response One Site/XLfit 4.2, IDBS and were used to calculate IC$_{50}$ (Table 1).

Figure 8:
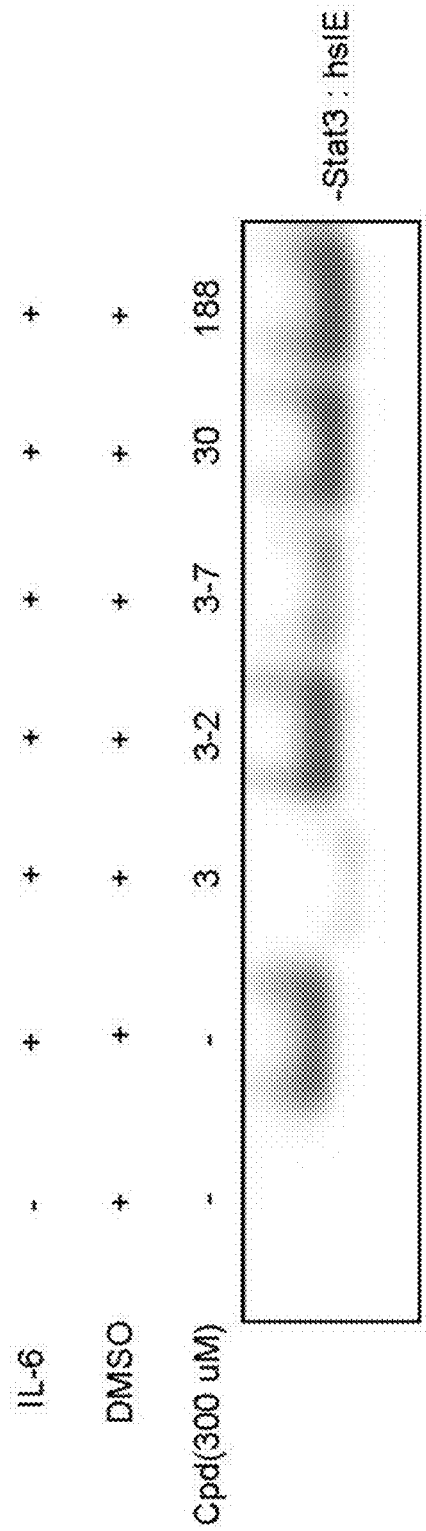

FIG. 8 demonstrates inhibition of Stat3 DNA binding by compounds. Electrophoretic mobility shift assays were performed using whole-cell extracts prepared from HepG2 cells without and with stimulation with IL-6 (30 ng/ml) for 30 min. Protein (20 μg) was incubated with radiolabeled duplex oligonucleotide (hSIE) and DMSO without or with the indicated compounds (300 uM) for 60 minutes at 37° C. then separated by PAGE. The gel was dried and autoradiographed; the portion of the gel corresponding to the Stat3-bound hSIE band is shown. Data shown are representative of 2 studies.

Figure 9:
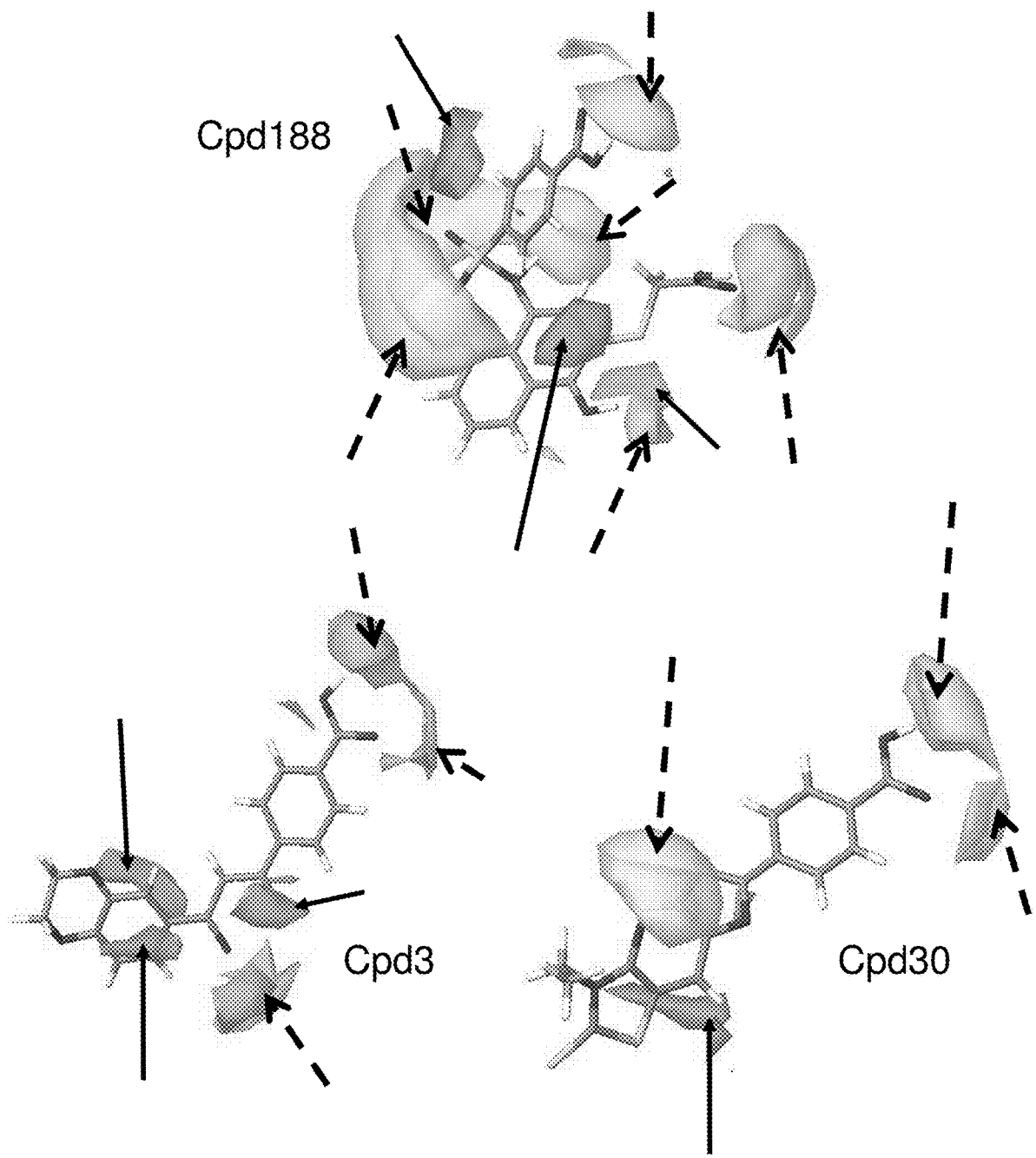

FIG. 9 shows Cpd3, Cpd30 and Cpd188 and the hydrophobicity or hydrophilicity of the surface of the molecule. The dashed arrows point to hydrophilic surfaces, and the solid arrows point to hydrophobic surfaces.

Figure 10:
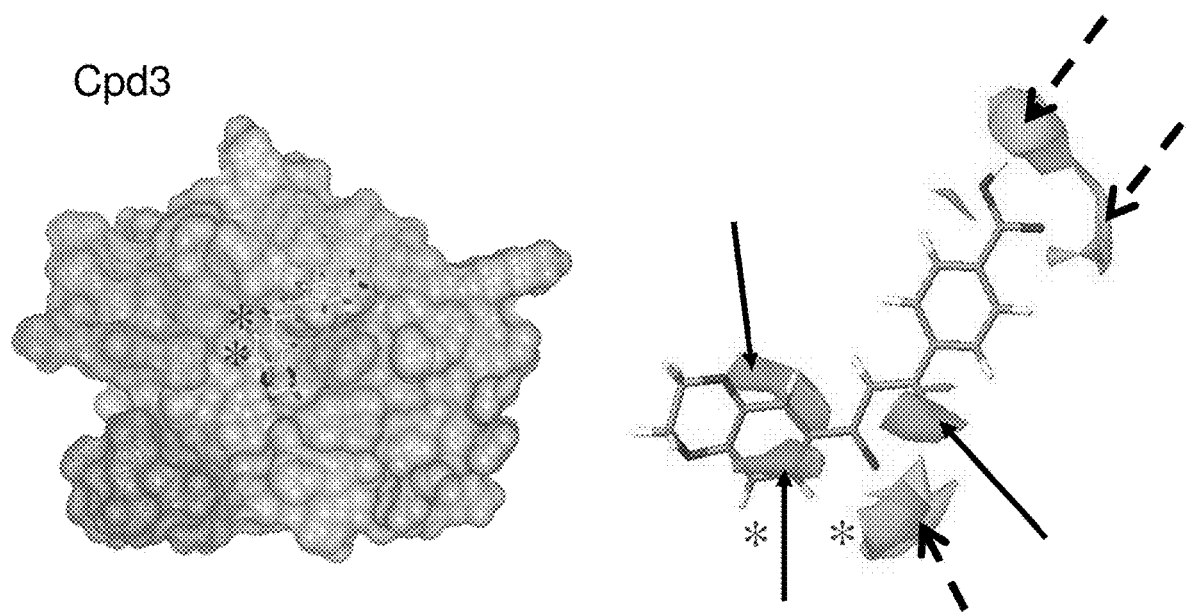
Figure 10:
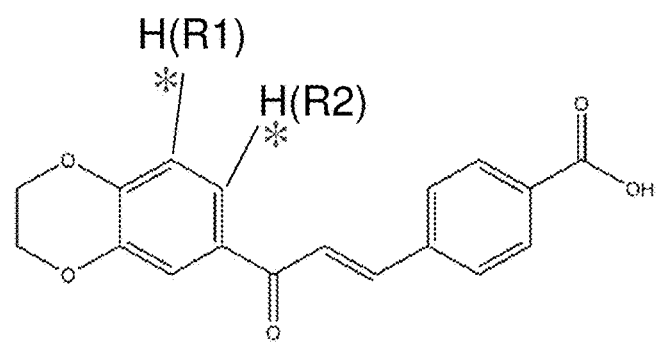
Figure 11:
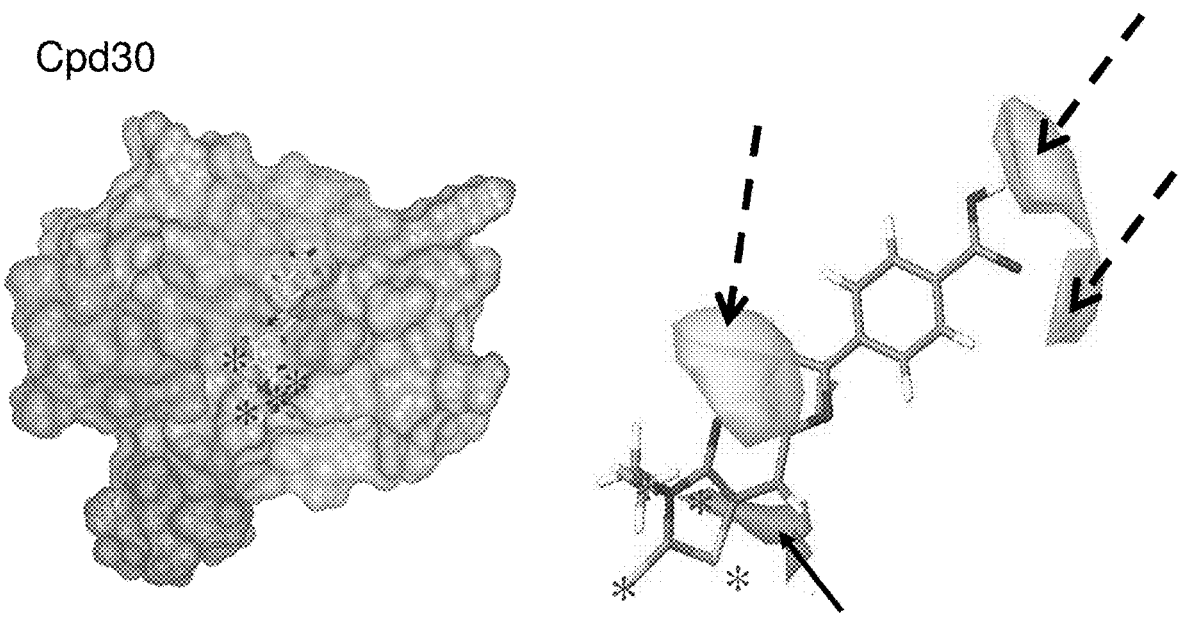
Figure 11:
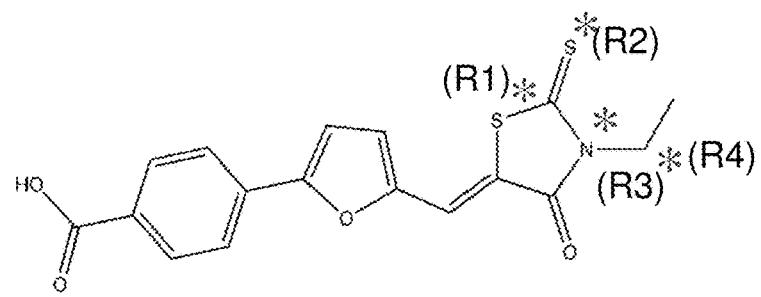

FIG. 10 illustrates exemplary compound 3 (Cpd3). The top-left picture of FIG. 11 shows Cpd3 docked into Stat3 and the interaction between Cpd3 and the surface of the protein and derivatives of Cpd3 that can fit into the surface of the protein. Stars represent atoms and chemical groups that can be replaced with other atoms or chemical groups to create one or more functional derivatives. The hydrophobic/hydrophilic surfaces of Cpd3 are also demonstrated on the top-right picture. The dashed arrows point to hydrophilic surfaces, and the solid arrows point to hydrophobic surfaces. R$_1$ and R$_2$ could be identical or different and may comprise hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, or benzoic acid-based derivatives.

Figure 12:
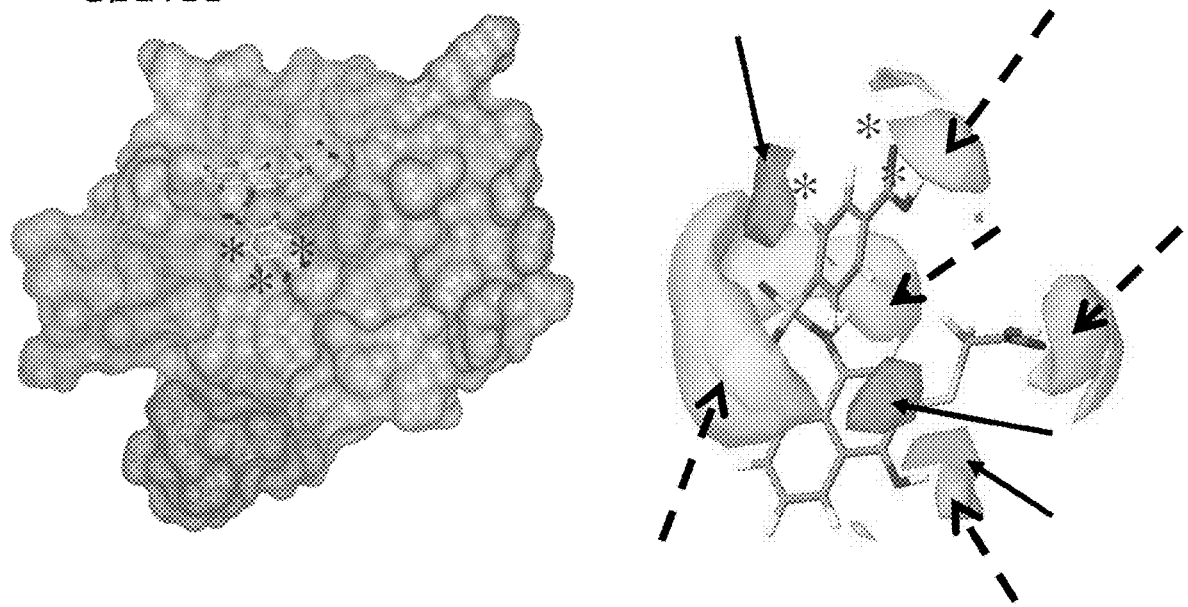
Figure 12:
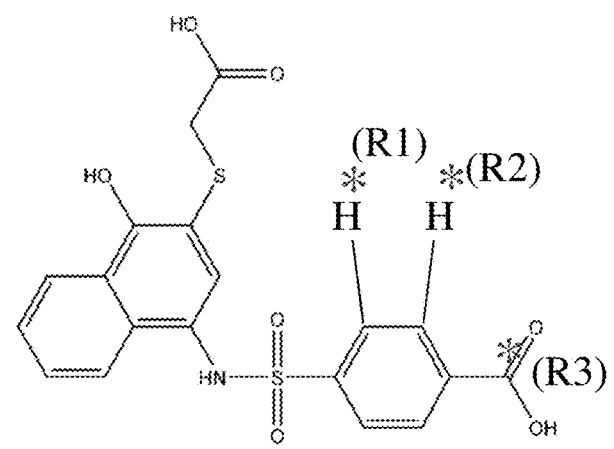

FIG. 11 illustrates exemplary compound 30 (Cpd30). The top-left picture of FIG. 12 shows Cpd30 docked into Stat3 and the interaction between Cpd30 and the surface of the protein, and derivatives of Cpd30 that fit into the surface of the protein. Stars represent atoms and chemical groups that can be replaced with other atoms or chemical groups to create one or more functional derivatives. The hydrophobic/hydrophilic surfaces of Cpd30 are also demonstrated on the top-right picture. The dashed arrows point to hydrophilic surfaces, and the solid arrows point to hydrophobic surfaces. 2-D structure of Cpd30 shown on the bottom picture, R$_1$, R$_2$ R$_3$ and R$_4$ could identical or different and may comprise be hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, aor benzoic acid-based derivatives.

FIG. 12 illustrates exemplary compound 188 (Cpd188). The top picture of FIG. 12 shows Cpd188 docked into Stat3 SH2 domain and the interaction between Cpd188 and the surface of the protein, and derivatives of Cpd188 that fit into the surface of the protein. Stars represent atoms and chemical groups that can be replaced with other atoms or chemical groups to create one ore more functional derivative. The hydrophobic/hydrophilic surfaces of Cpd188 are also demonstrated on the left picture on the bottom. The dashed arrows point to hydrophilic surfaces, and the solid arrows point to hydrophobic surfaces. Shown on the right bottom picture, R$_1$ and R$_2$ could be identical or different and may comprise hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, or benzoic acid-based derivatives.

Figure 13:
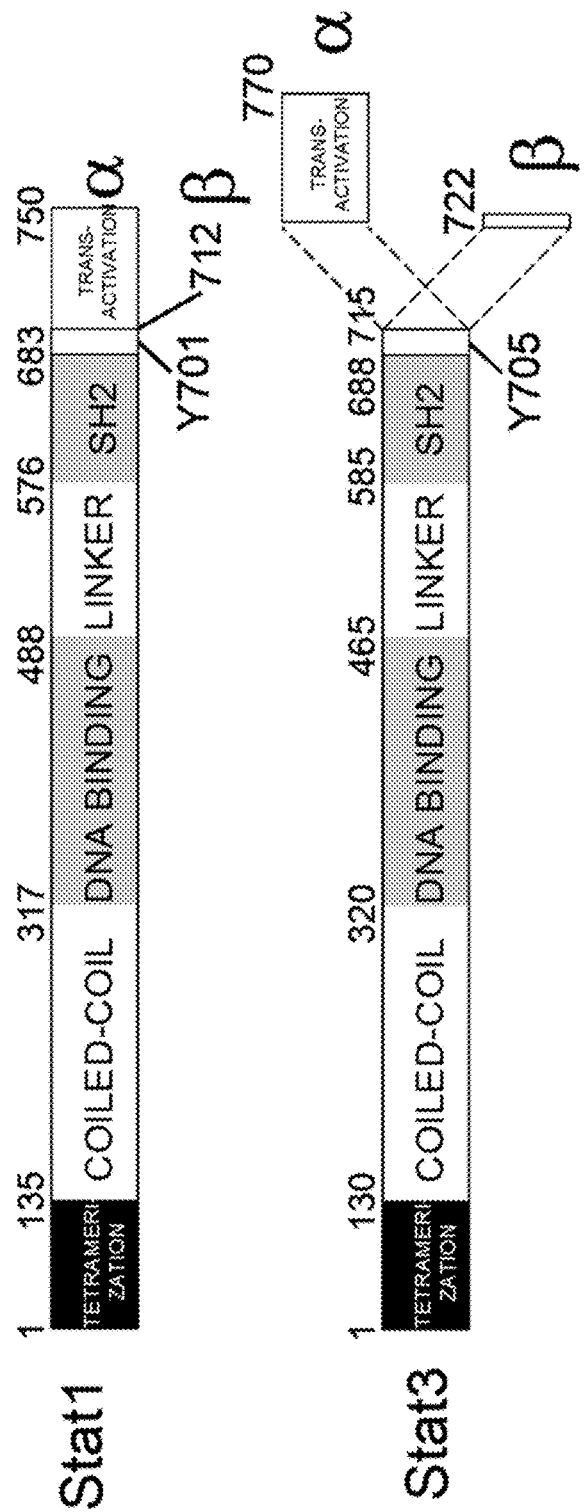

FIG. 13 illustrates schematic diagrams of Stat1 and Stat3.

Figure 14:
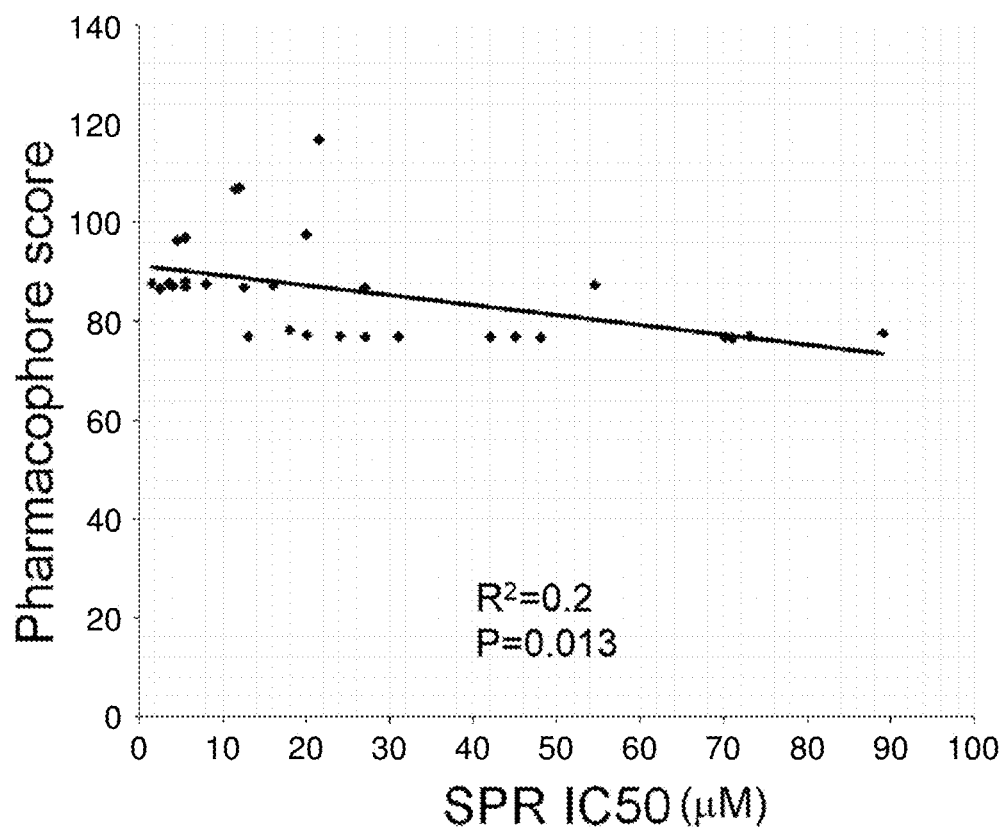

FIG. 14 demonstrates that SPR IC$_{50}$ of 2nd generation Stat3 chemical probes is inversely correlated with 3-D pharmacophore score.

Figure 15:
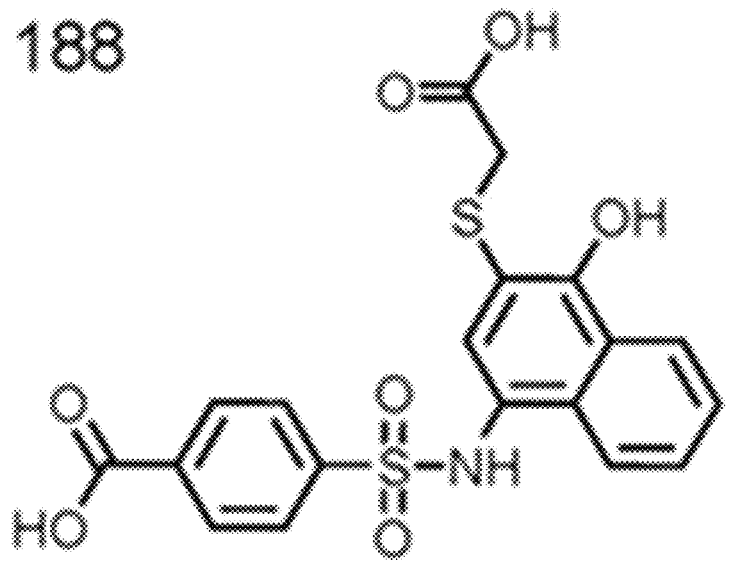
Figure 15:
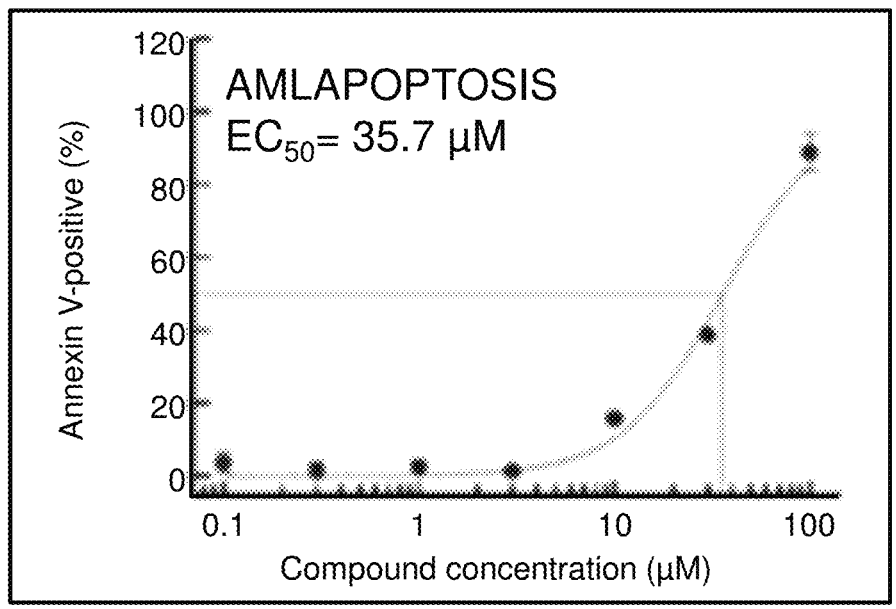
Figure 15:
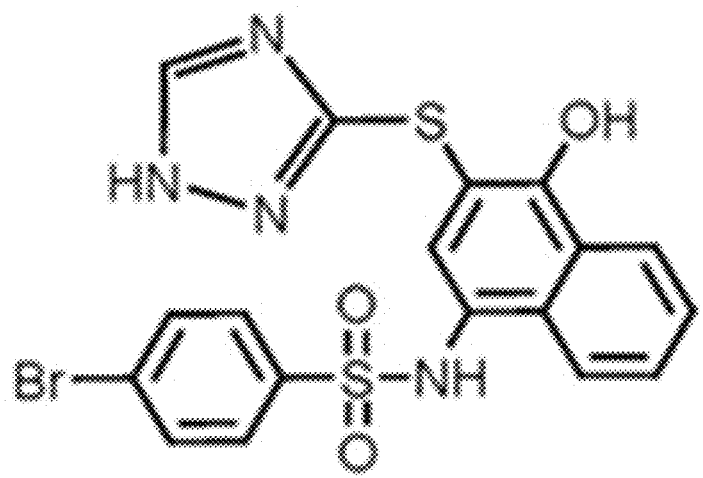
Figure 15:
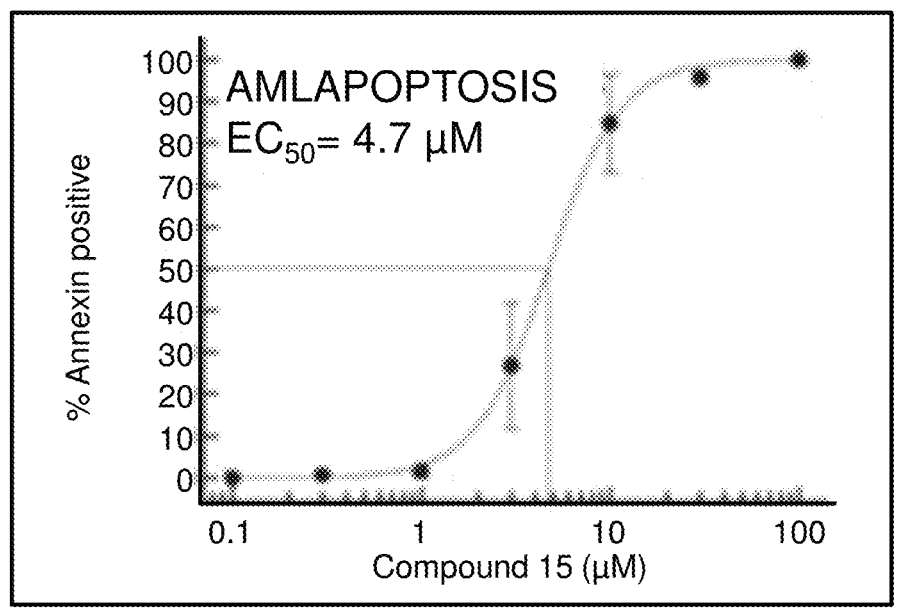
Figure 15:
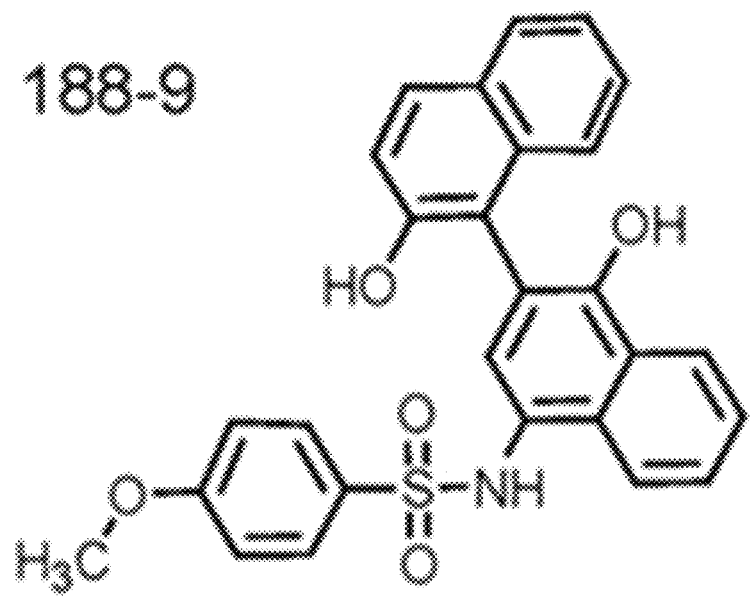
Figure 15:
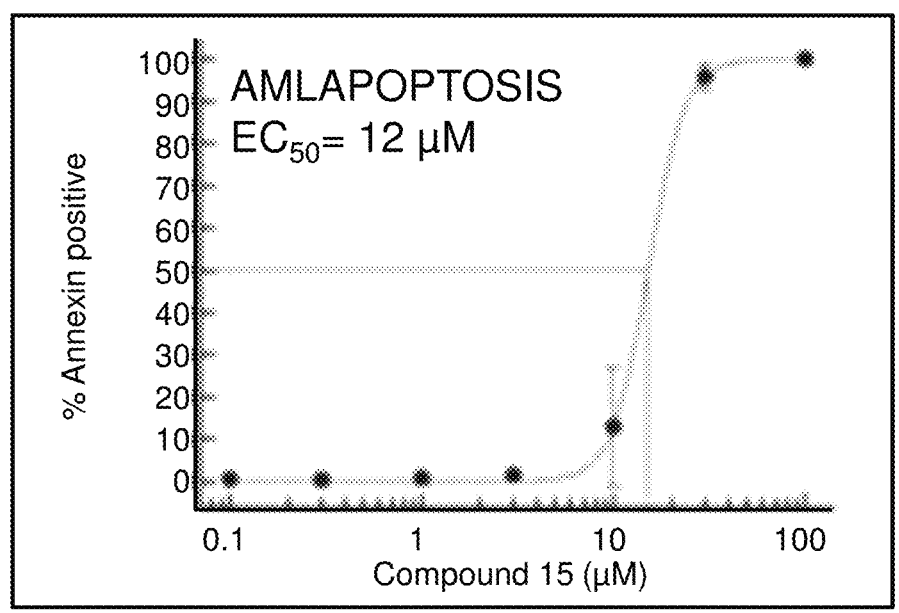

FIG. 15 shows SPR IC$_{50}$ and AML apoptosis EC$_{50}$ of parent Cpd188 and two 2nd generation 188-like Stat3 chemical probes.

Figure 16:
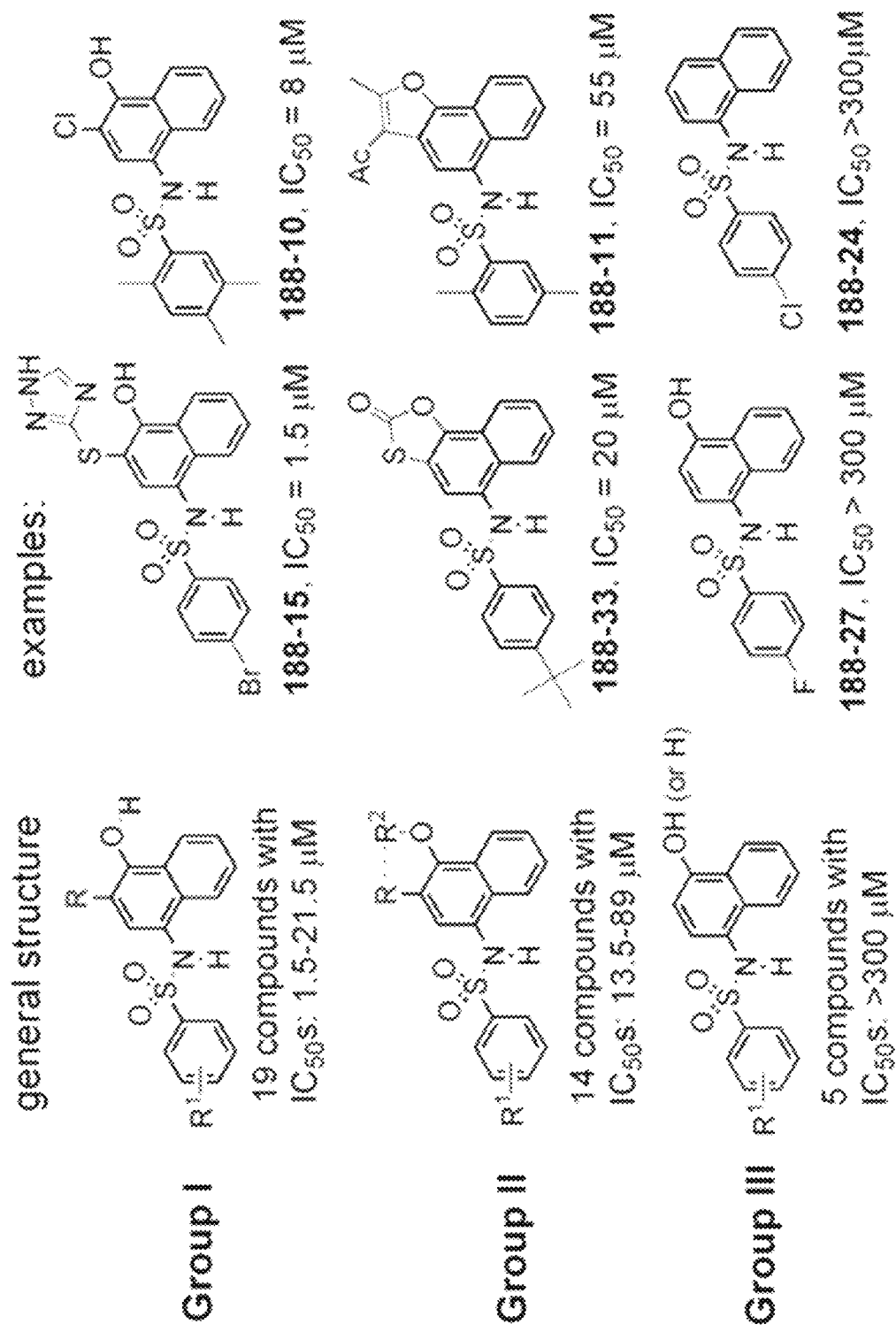

FIG. 16 provides an illustration of structure-activity relationships of 38 Cpd188-like, 2nd generation Stat3 probes.

Figure 17:
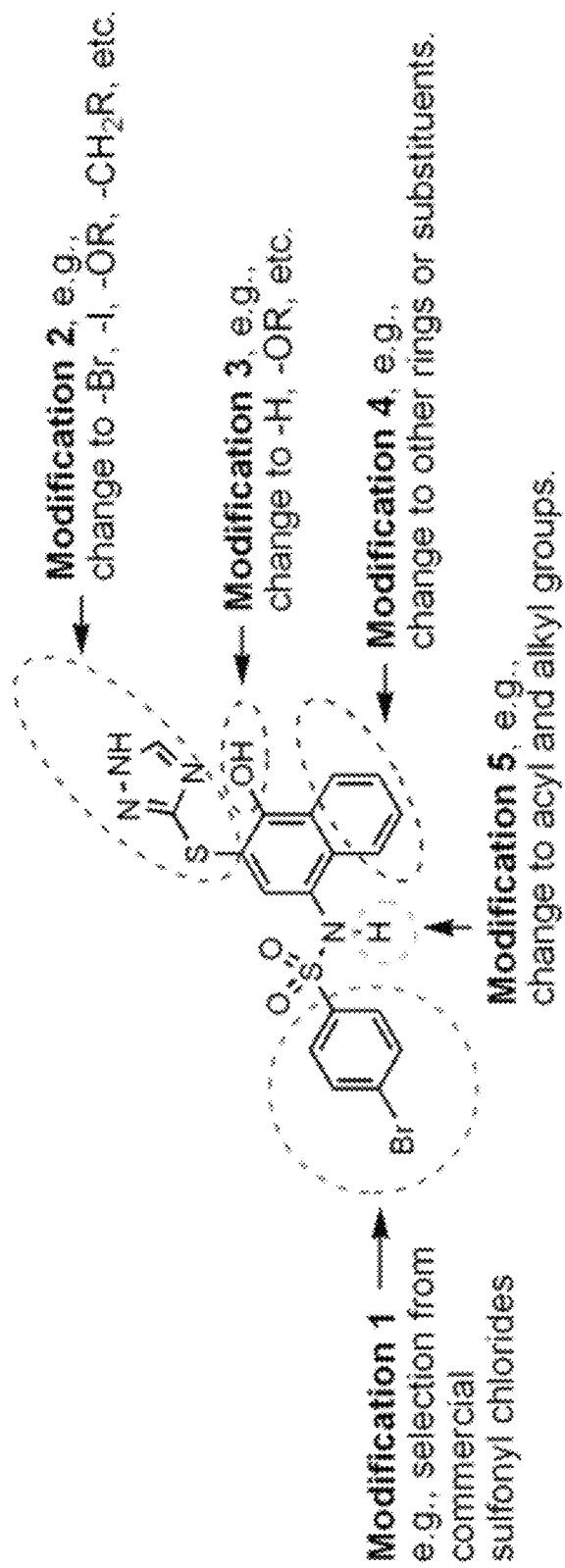

FIG. 17 shows an exemplary modification scheme for 3rd generation Stat3 probe development using Cpd188-15 as a scaffold.

Figure 18:
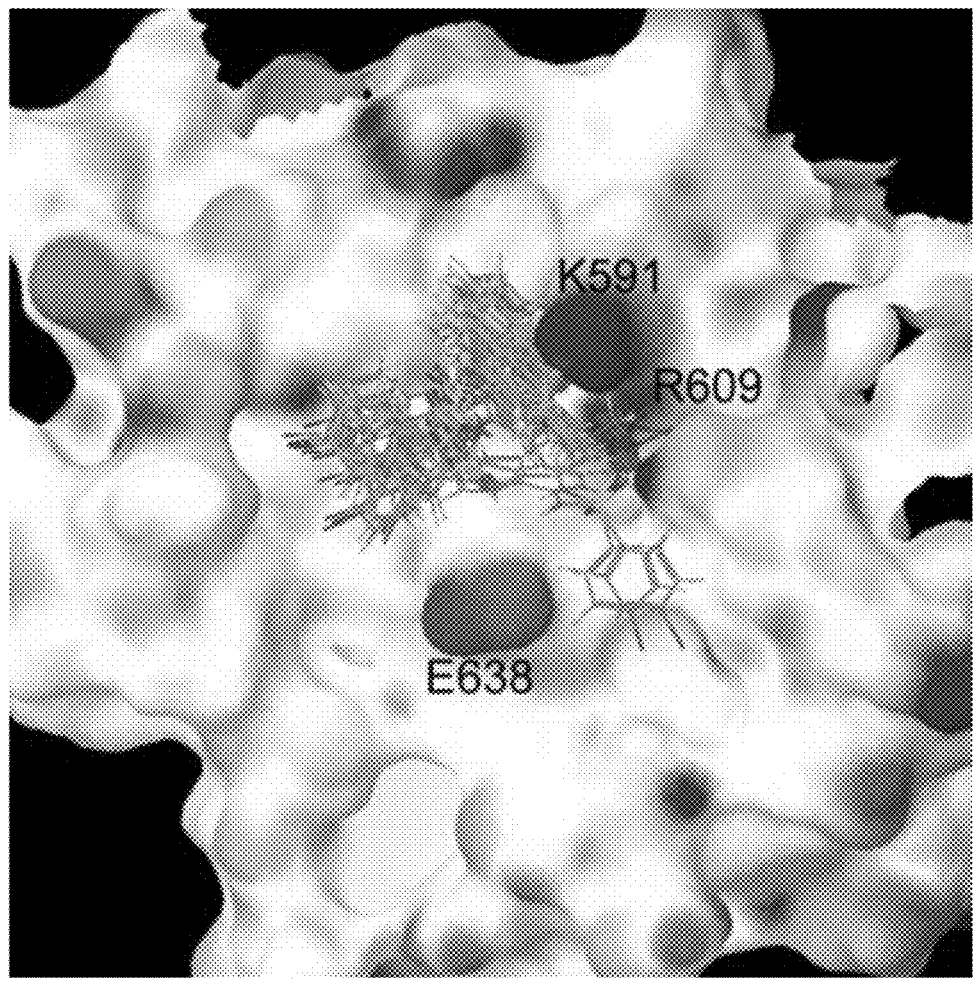

FIG. 18 provides illustration of the electrostatic surface of Stat3 SH2 domain (positive area in blue, neutral in white and negative in red in a color figure) and 20 docking poses of 5 (R=CH$_2$PO$_3$ 2-), showing strong interactions between phosphonate groups (in purple and red) and K591/R609.

Figure 19A:
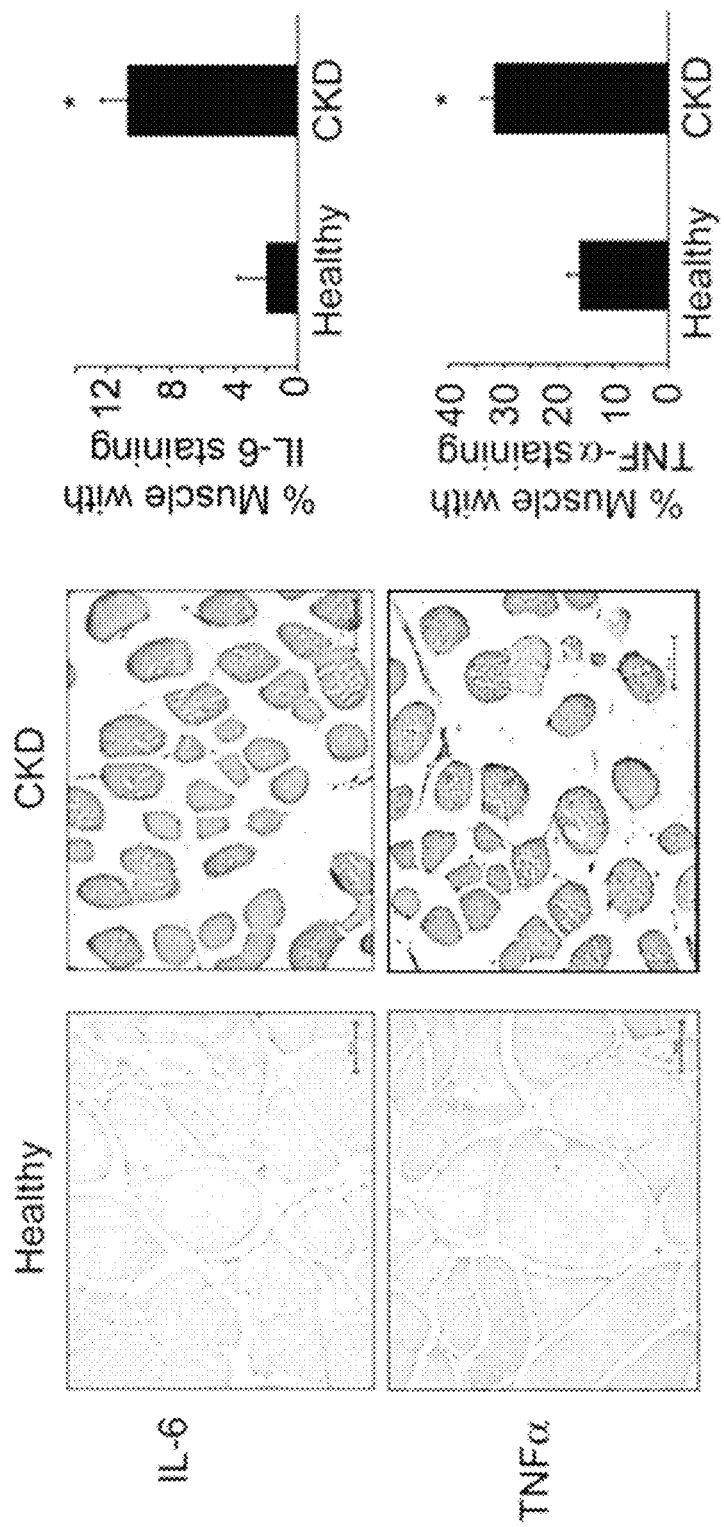
Figure 19B:
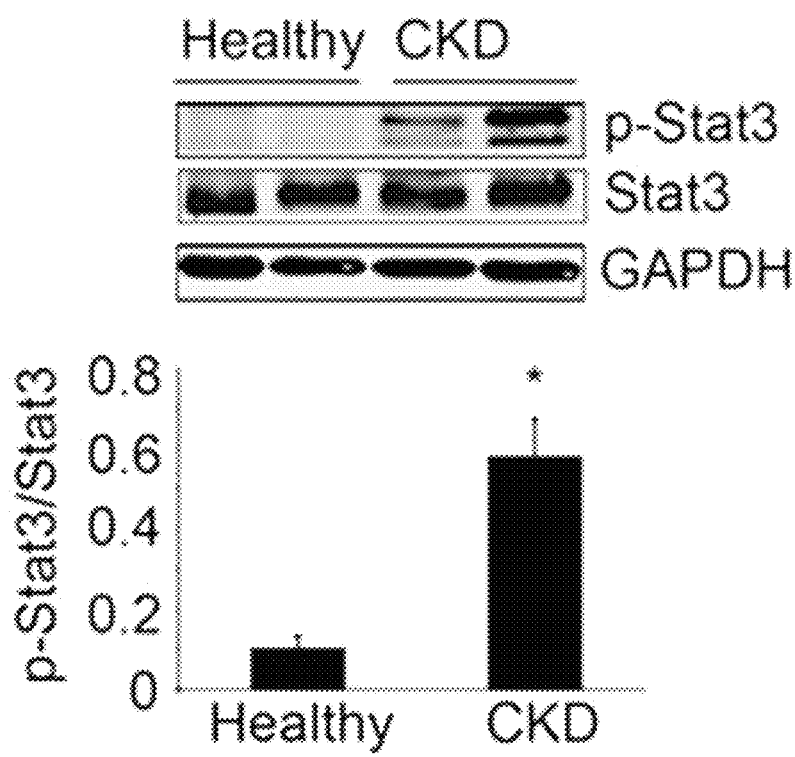
Figure 19C:
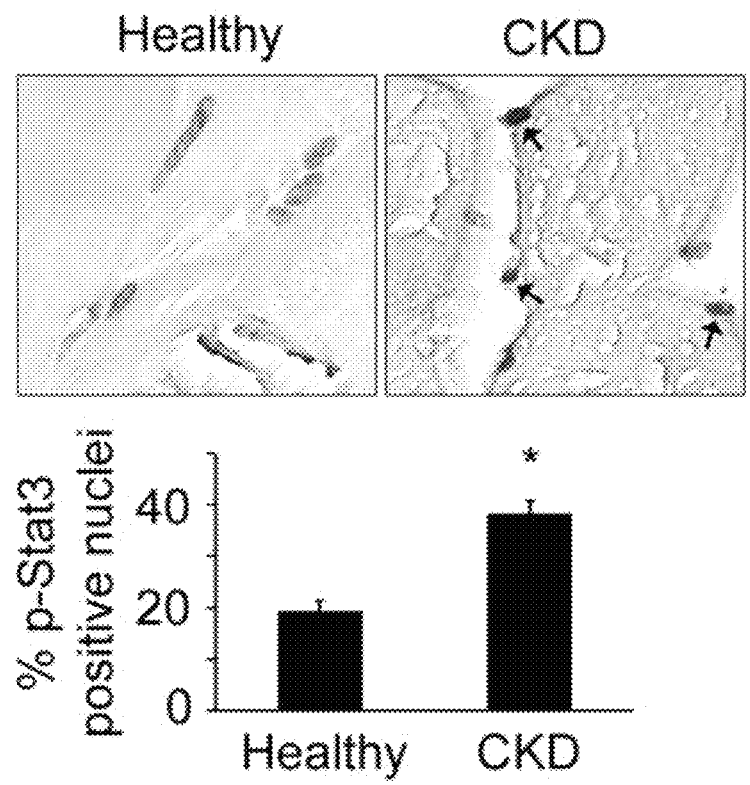

FIGS. 19A-19C shows inflammatory cytokines and p-Stat3 are elevated in muscles of patients with CKD. FIG. 19A. Immunostaining of muscle sections for IL-6 and TNFα (brown color) from biopsies of age- and gender-matched, healthy control subjects (left panel) and CKD patients (middle panel). Staining quantification is calculated as the percentage of muscle fibers that are immunostained (right panel; n=3 control subjects; n=4 CKD patients; ruler=50 µm). FIG. 19B. Representative western blots for p-Stat3 in control subjects and CKD patients (upper panel) and the ratio of the intensity of p-Stat3 to total Stat3 (lower panel) (n=6 control subjects; n=6 CKD patients). FIG. 19C. Muscle sections from control subjects and CKD patients were immunostained for p-Stat3 (upper panel). Brown nuclei are p-Stat3 positive (arrows). Percentage of p-Stat3 positive nuclei in a total of 550 nuclei (lower panel; n=4 control subjects; n=6 CKD patients). Values are means±SEM. *p<0.05 vs. control subjects.

Figure 20A:
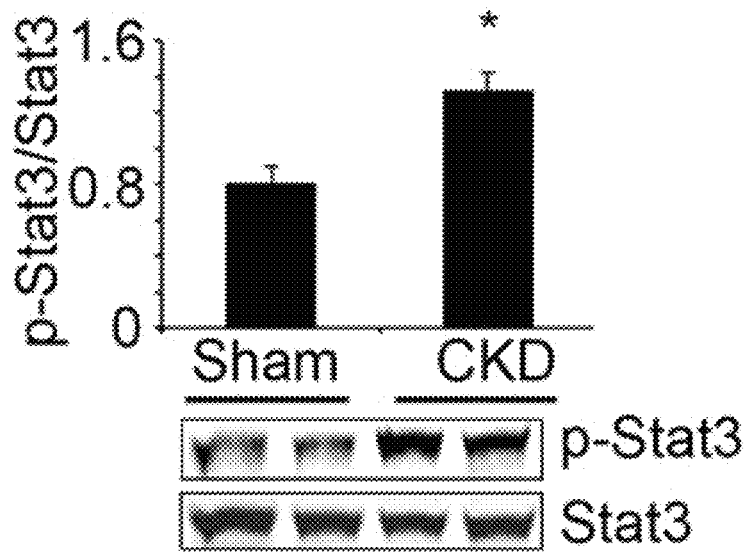
Figure 20B:
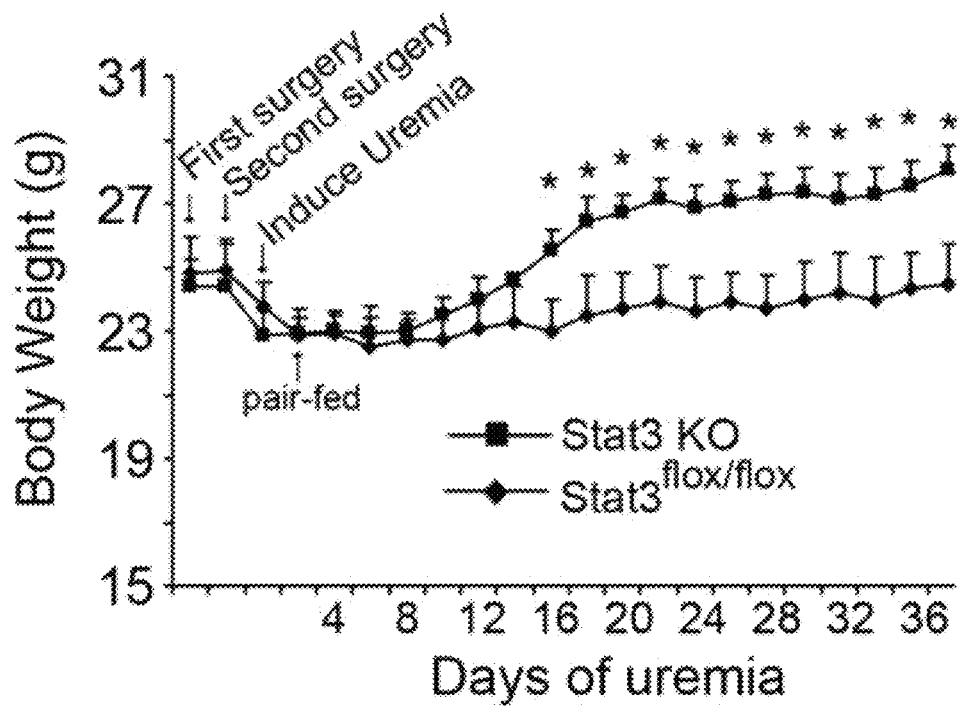
Figure 20C:
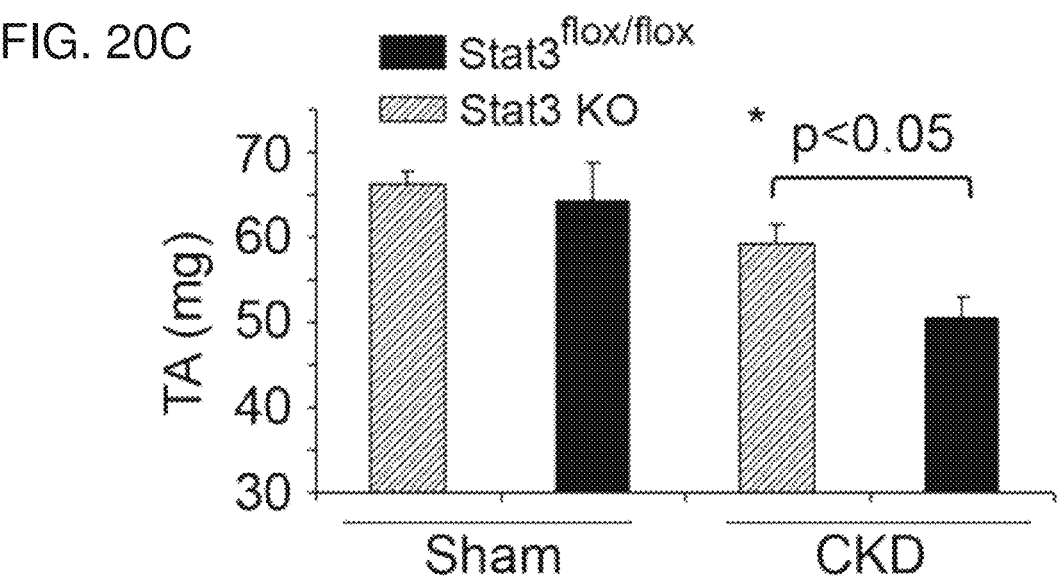
Figure 20D:
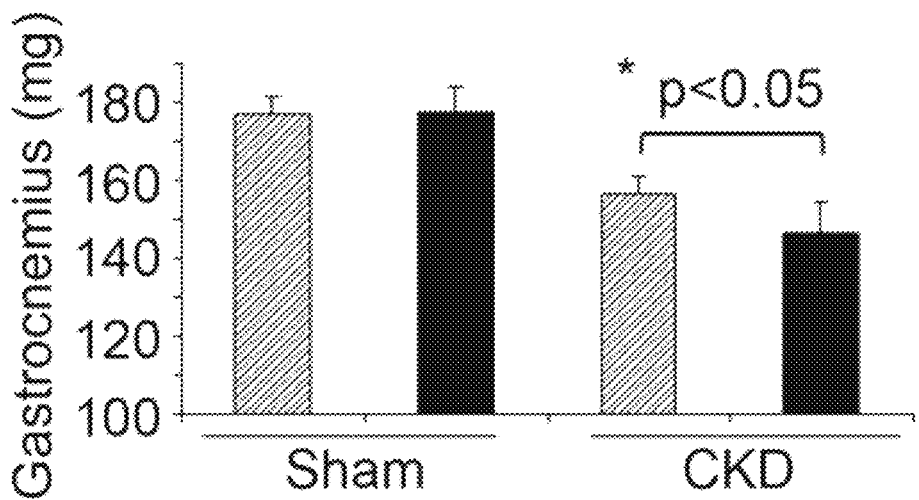
Figure 20E:
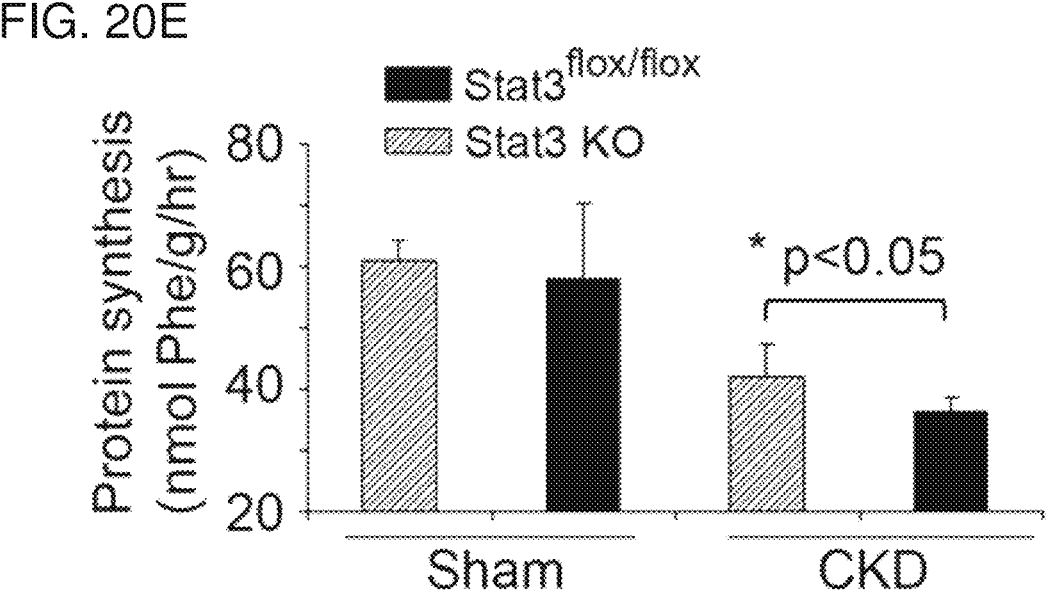
Figure 20F:
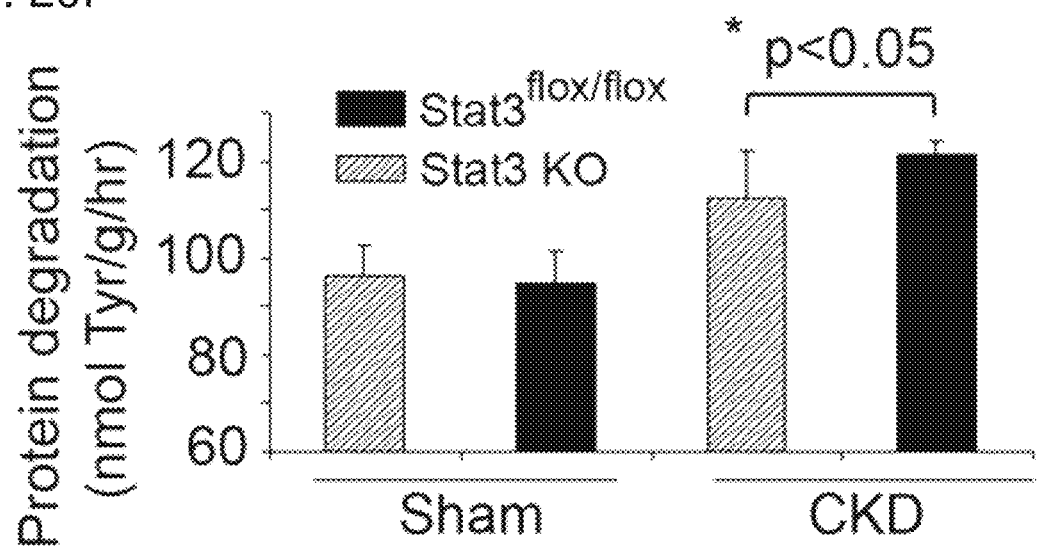
Figure 20G:
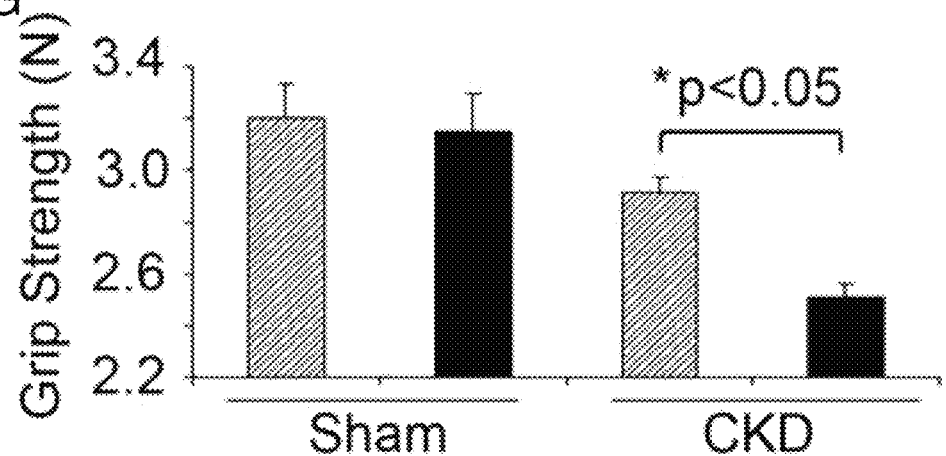
Figure 20H:
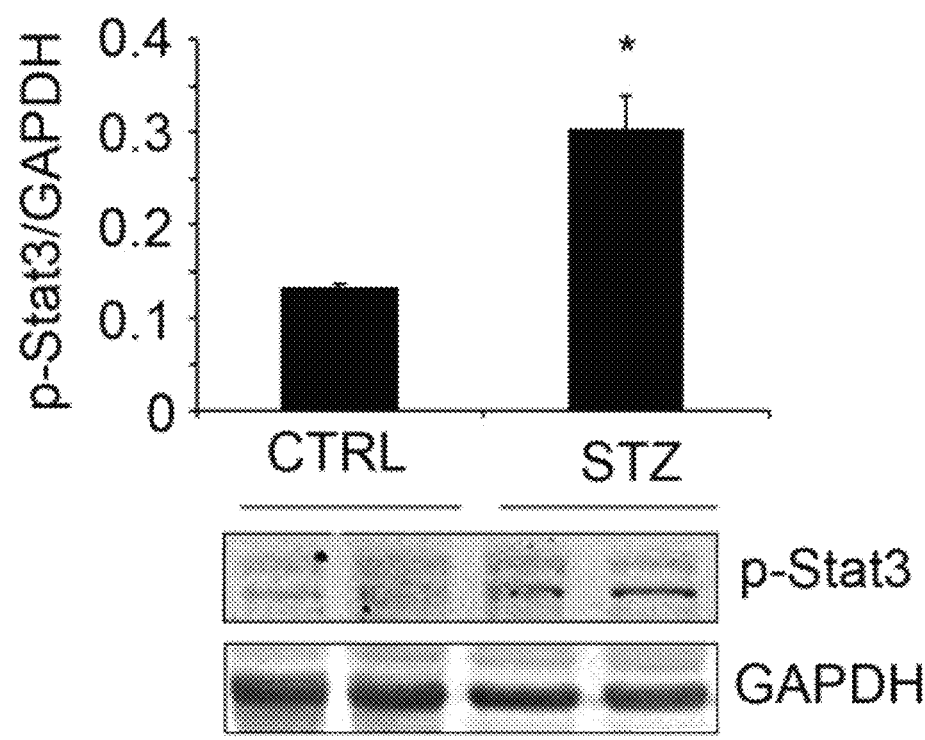
Figure 20I:
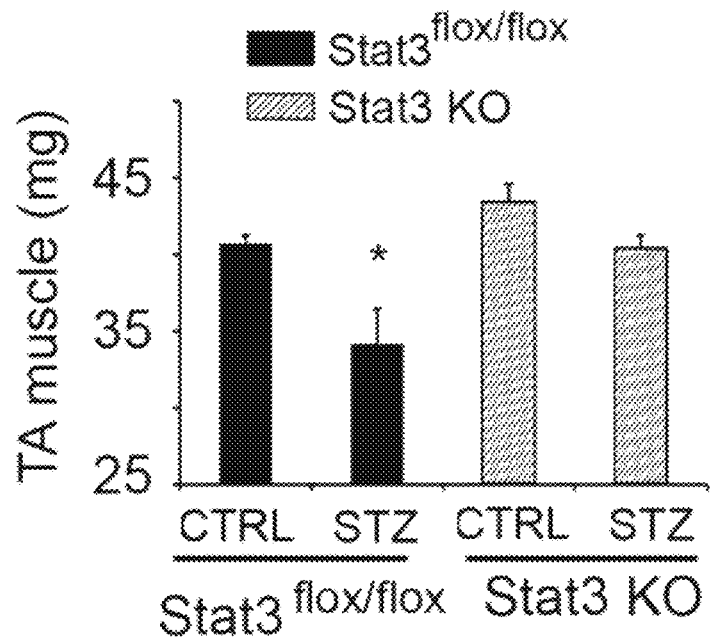
Figure 20J:
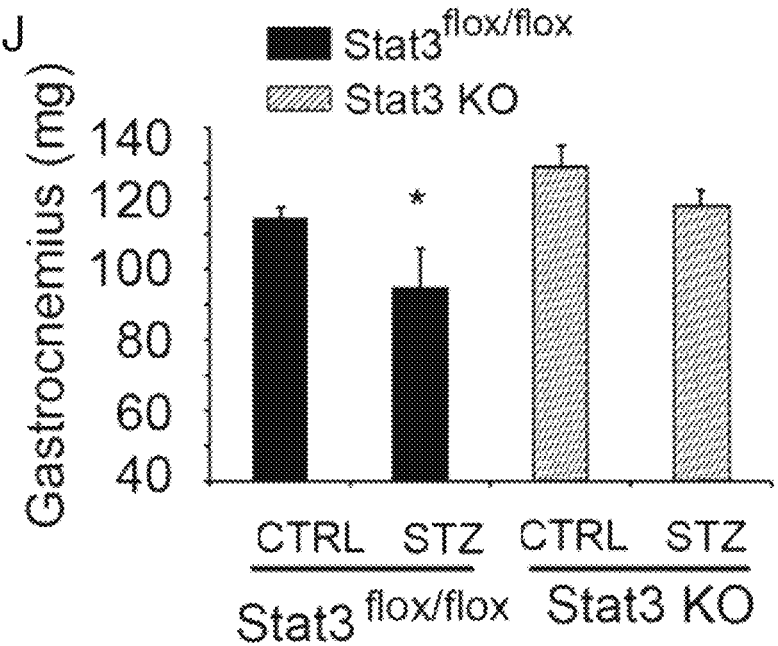

FIGS. 20A-20J shows muscle-specific Stat3 knockout in mice suppresses CKD or streptozotocin-induced muscle wasting. FIG. 20A. Density of p-Stat3 corrected for total Stat3 in lysates of gastrocnemius muscles (upper panel; n=5 mice/group; *p<0.05 vs. sham control mice). Also shown are representative western blots of p-Stat3 (lower panel). FIG. 20B. Changes in body weights of Stat3 KO and Stat3flox/flox, control mice over 5 weeks following creation of CKD (n=10 pairs of mice; *p<0.05 vs. Stat3flox/flox). FIGS. 20C & 20D. Average weights of mixed fiber gastrocnemius and tibialis anterior (TA) muscles (n=10 mice/group). FIGS. 20E & 20F. EDL muscles from sham or CKD mice and either Stat3flox/flox or Stat3 KO were isolated. Rates of protein synthesis (FIG. 20E) and protein degradation (FIG. 20F) were measured (n=20 EDL muscles from 10 mice/group). FIG. 20G. Muscle force of each mouse used in FIG. 2B was measured on four consecutive days. The average muscle force (in Newtons) is shown (n=10 mice/group). FIG. 20H. Representative western blots of p-Stat3 in lysates of gastrocnemius muscles of acutely diabetic (STZ) and control mice. Bar graph shows the densities of p-Stat3 corrected for GAPDH (n=10 mice/group; *p<0.05 vs. CTRL mice). FIGS. 20I & 20J. Average weights of the mixed fiber tibialis anterior (TA) and gastrocnemius muscles from both legs (n=10 mice/group; *p<0.05 vs. control Stat3$^{flox/flox}$). Values are means±SEM.

Figure 21A:
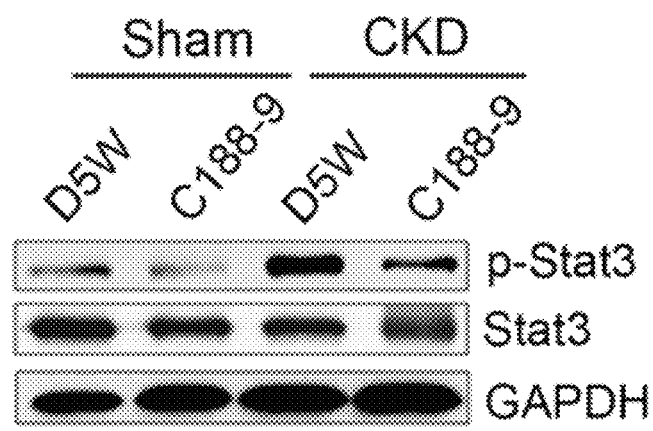
Figure 21B:
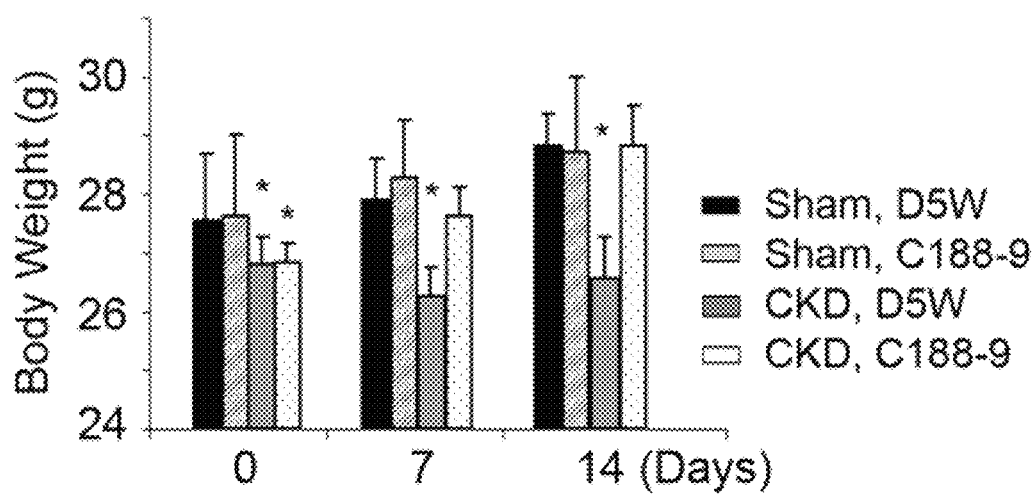
Figure 21C:
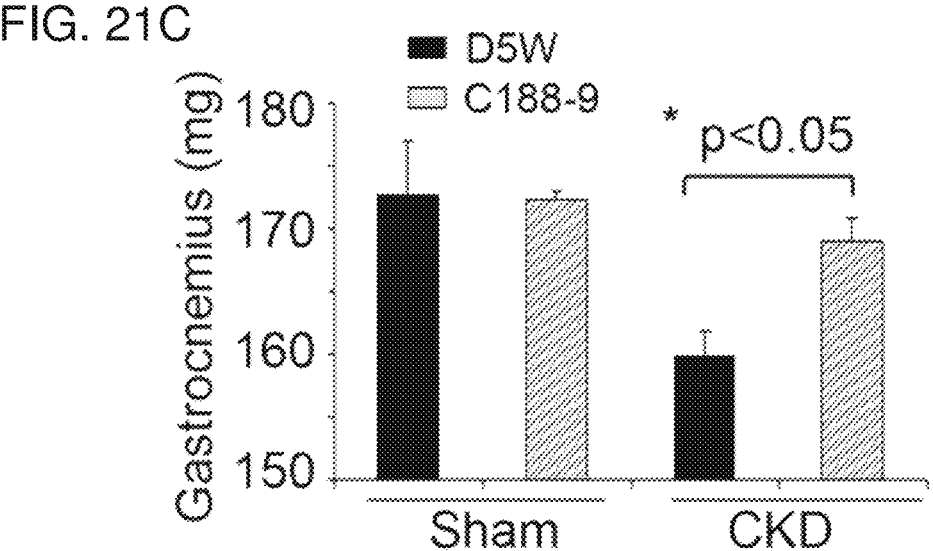
Figure 21D:
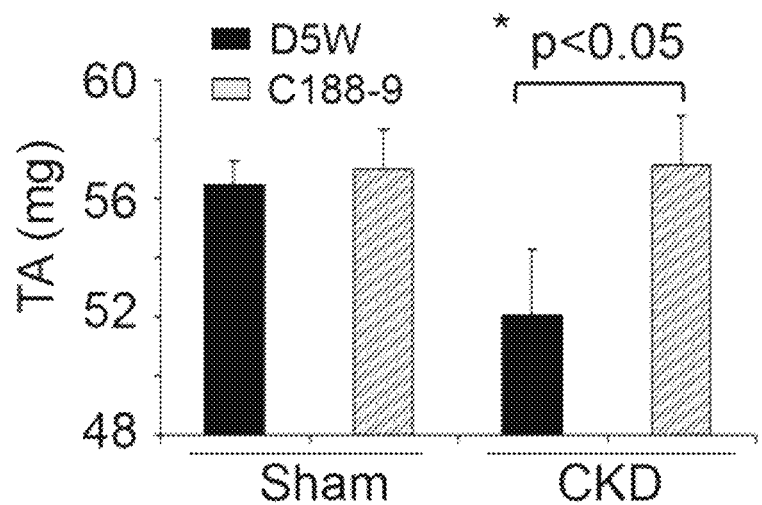
Figure 21E:
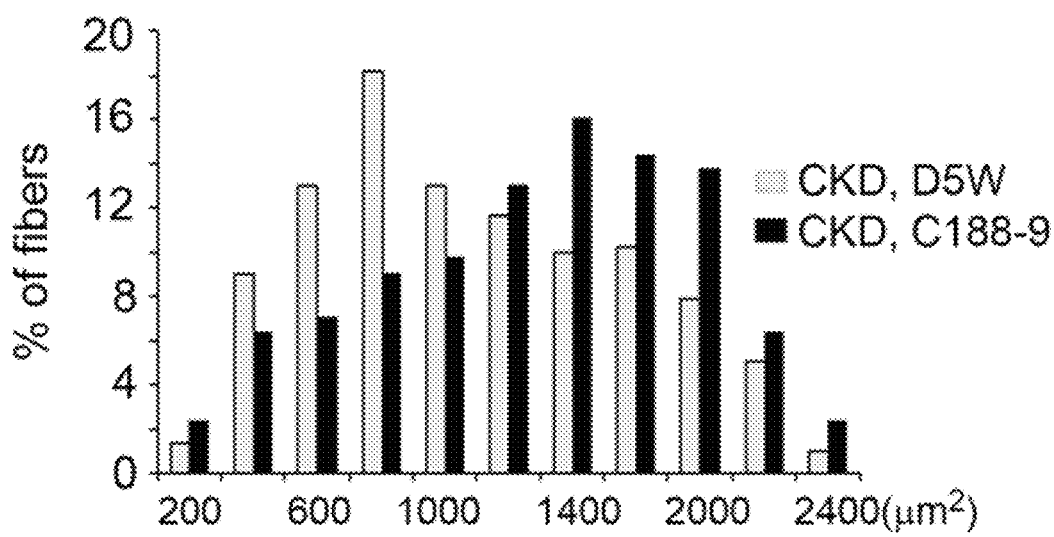
Figure 21F:
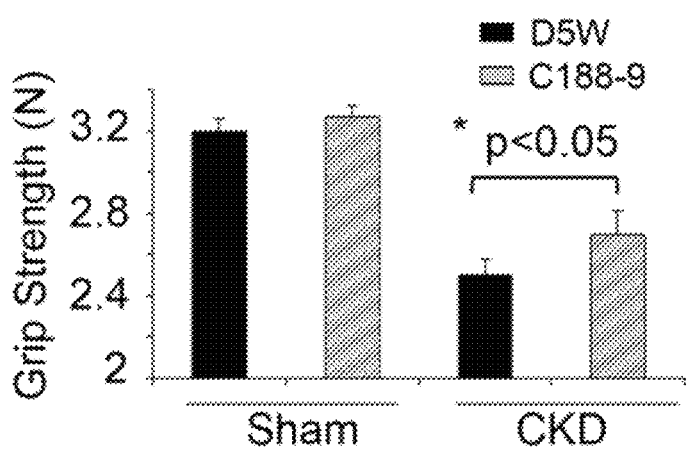

FIGS. 21A-21G provides a small molecule inhibitor of Stat3 activation, C188-9, that blocks CKD-induced muscle wasting. FIG. 21A. Sham or CKD mice were treated with C188-9 or D5W (diluent) for 14 days. Representative western blots of p-Stat3, Stat3 and GAPDH from lysates of gastrocnemius muscles are shown (n=8 mice/group). FIG. 21B. Differences in body weights of pair-fed, sham or CKD mice treated with C188-9 or D5W at baseline and after 7 or 14 days of treatment (*p<0.05 vs. D5W sham). FIGS. 21C & 21D. Average weights of mixed fiber gastrocnemius and tibialis anterior (TA) muscles from both legs (n=7 mice/group). FIG. 21E. Cryosections of TA muscles were immunostained with anti-laminin to identify the muscle basement membrane. The myofiber areas were measured and the myofiber size distribution was calculated from the areas of ~500 myofibers assessed by an observer blinded to treatment group (n=4 pairs of mice). FIG. 21F. Muscle force of each mouse studied in FIG. 3C was measured on four consecutive days (Experimental Procedures; n=7 mice/group). G&H. At 2 weeks of C188-9 or D5W treatment, protein synthesis (FIG. 21G) and degradation (FIG. 21H) were measured (n=8 pairs of mice; *p<0.05 vs. D5W). Values are means±SEM.

Figure 22A:
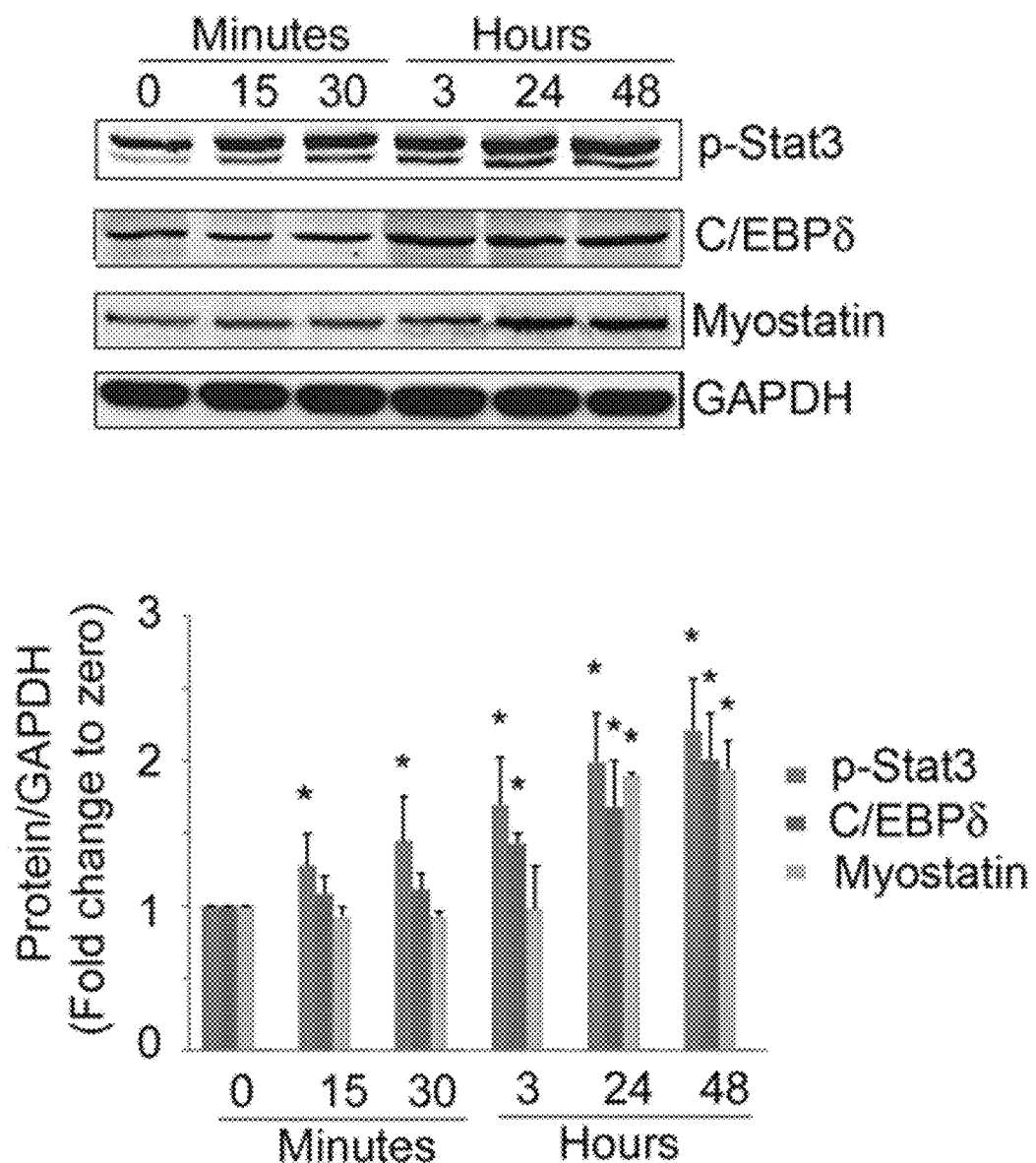
Figure 22B:
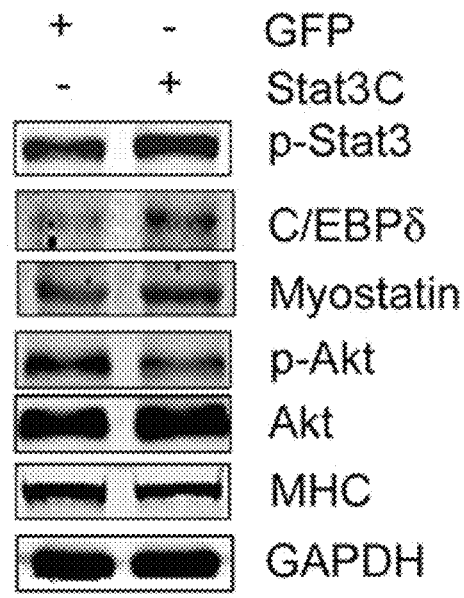
Figure 22C:
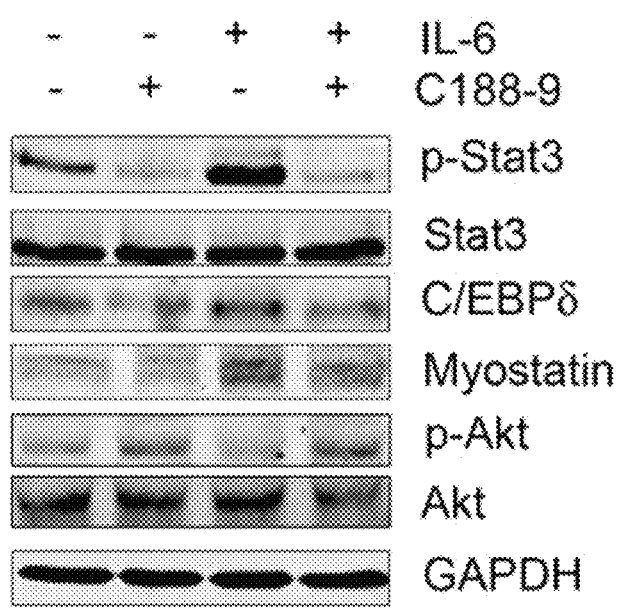
Figure 22D:
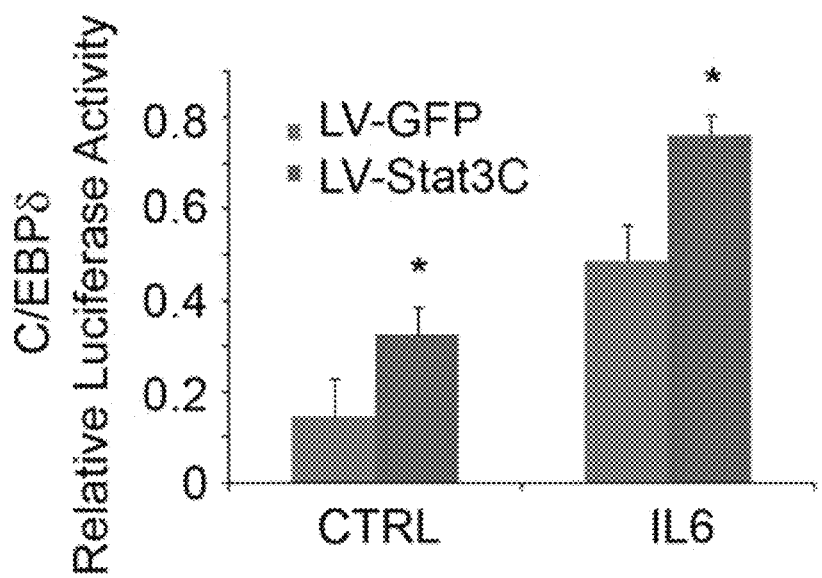
Figure 22E:
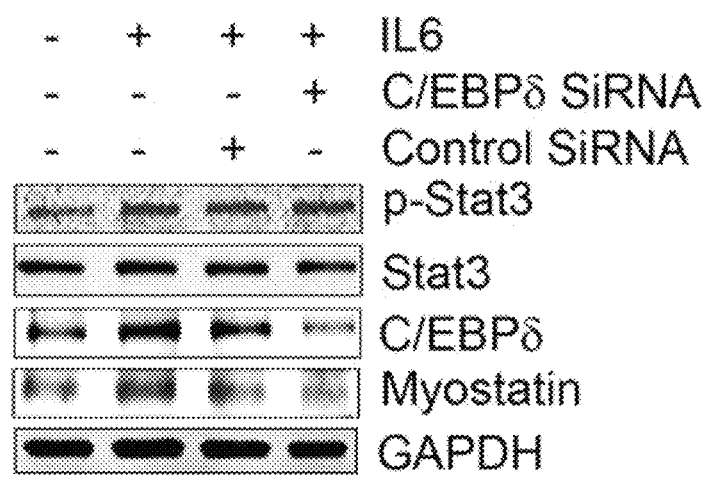
Figure 22F:
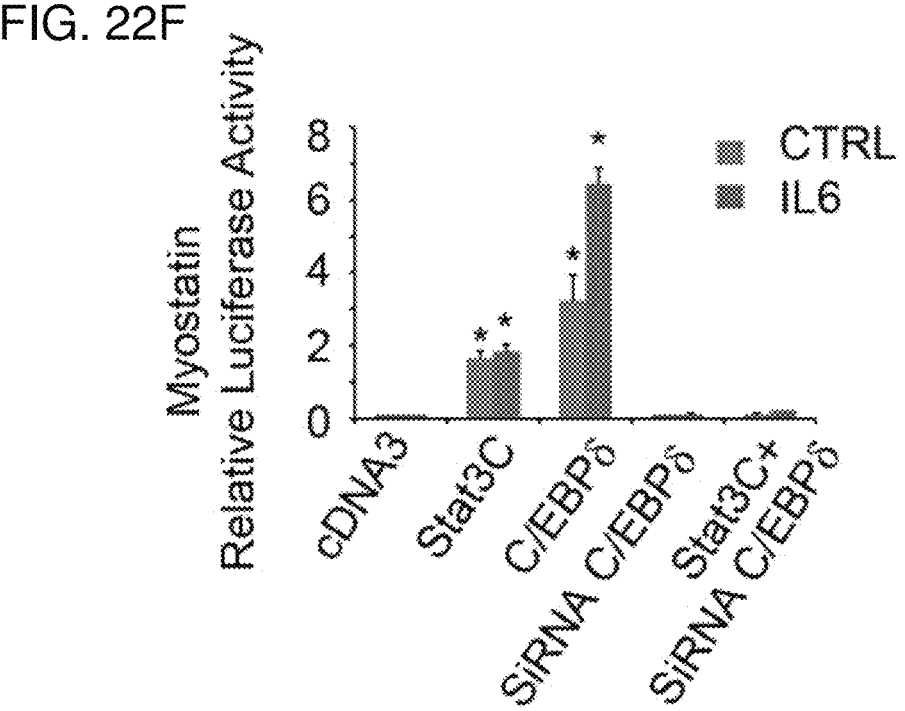
Figure 22G:
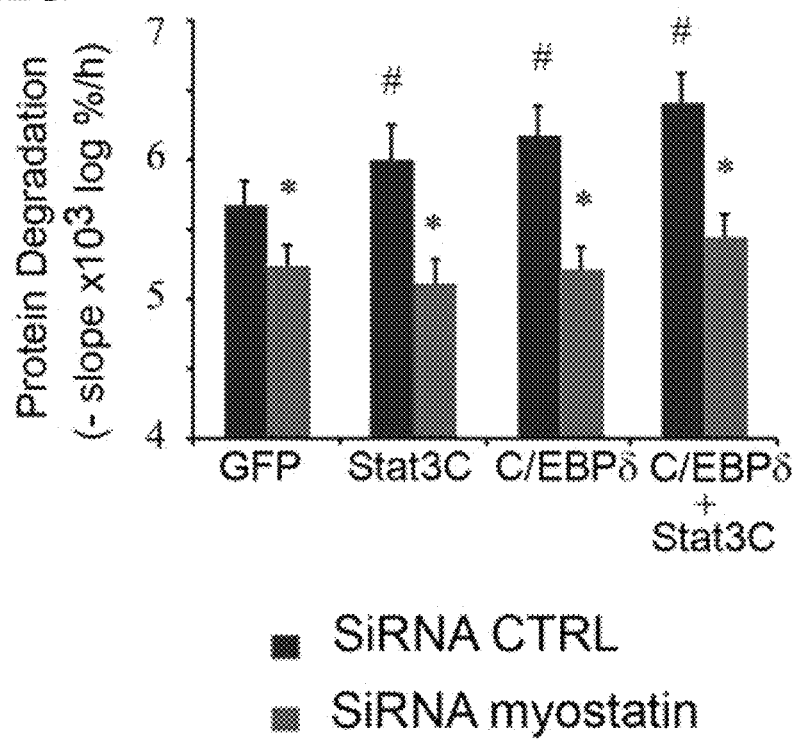

FIGS. 22A-22G demonstrates that Stat3 activation in C2Cl2 myotubes increases the expression of C/EBPδ and myostatin. FIG. 22A. Representative western blots from C2Cl2 myotubes treated with IL-6 (100 ng/ml) for different times (left panel). Fold-changes in the densities of proteins corrected for GAPDH at different times calculated from values at time zero (right panel), n=3 repeats; *p<0.05 vs. time zero. FIG. 22B. C2Cl2 myotubes were infected with a lentivirus expressing constitutively active Stat3 (Stat3C-GFP). A representative western blot for the indicated proteins is shown. FIG. 22C. C2Cl2 myotubes were treated with or without C188-9 for 2 h before adding IL-6 (100 ng/ml) for 24 h. A representative western blot for the indicated proteins is shown. FIG. 22D. C2Cl2 myoblasts were co-transfected with a plasmid expressing C/EBPδ promoter-driven luciferase, Renila plus a lentivirus expressing Stat3C-GFP and treated with or without IL-6. Dual luciferase activity was measured (n=3 repeats; *p<0.05 vs respective GFP control). FIG. 22E. C2Cl2 myoblasts were transfected with control siRNA or C/EBPδ siRNA and after differentiation to myotubes were treated with or without IL-6. Representative western blots of Stat3, C/EBPδ and myostatin are shown. FIG. 22F. C2Cl2 myoblasts were co-transfected with a plasmid expressing the myostatin promoter-driven luciferase plus plasmids (cDNA3 control, Stat3C, C/EBPδ, C/EBPδ siRNA or Stat3C plus C/EBPδ siRNA) and treated with or without IL6. Luciferase activity was measured (n=3 repeats; *p<0.05 vs. cDNA3 CTRL). FIG. 22G. C2Cl2 myoblasts were transfected with lentivirus expressing a siRNA to myostatin. Myoblasts exhibiting suppression of myostatin were selected and then differentiated after they had been transfected with plasmids expressing Stat3C, C/EBPδ or Stat3C plus C/EBPδ. In these cells, protein degradation (upper panel; n=6 repeats, #p<0.05 vs GFP control, *p<0.05 vs siRNA CTRL) was measured. Western blots of proteins expressed in response to tranfections was shown in FIG. 32.

Figure 23A:
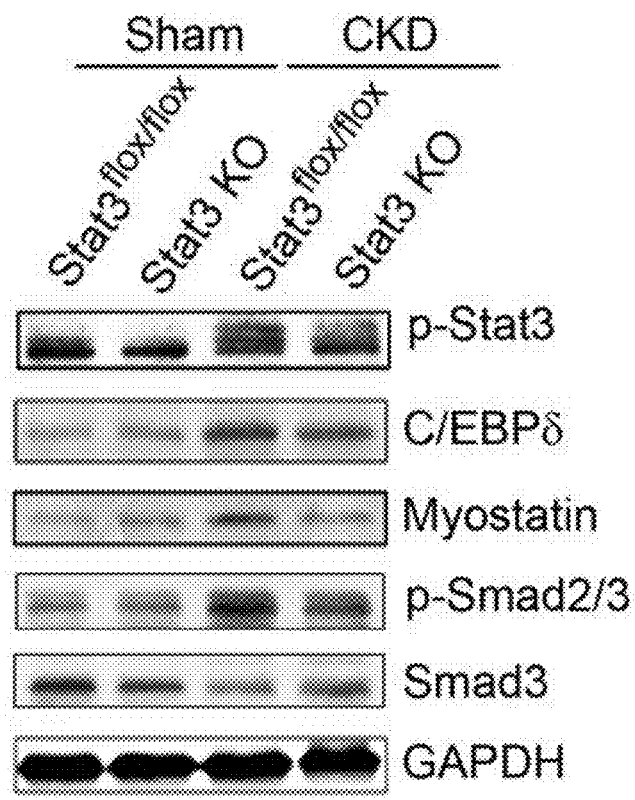
Figure 23B:
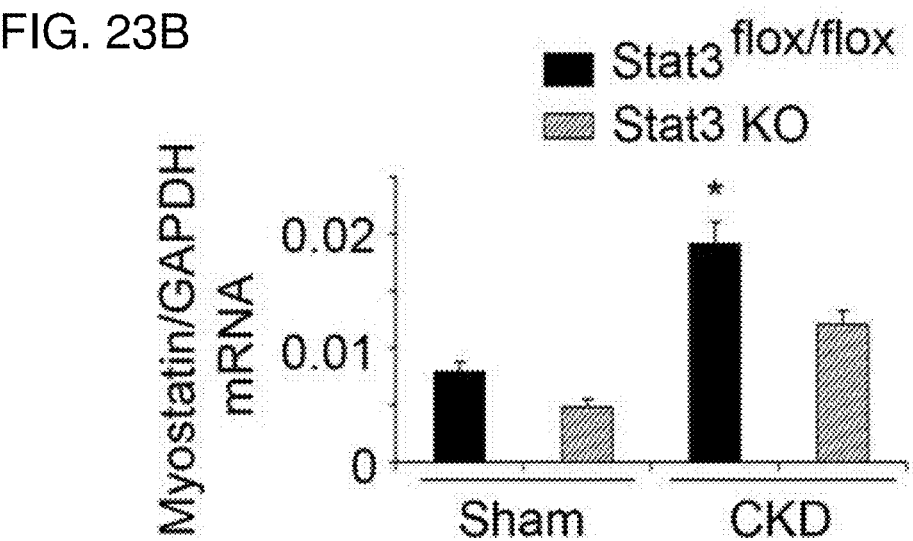
Figure 23C:
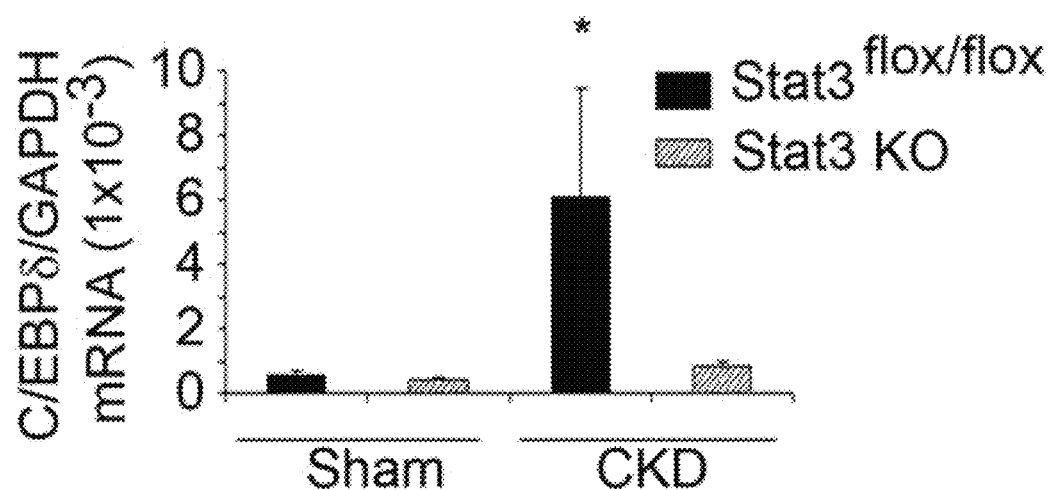
Figure 23D:
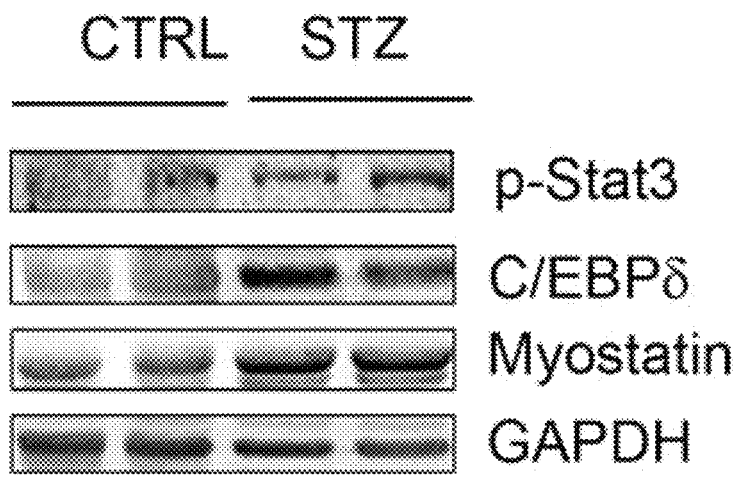
Figure 23E:
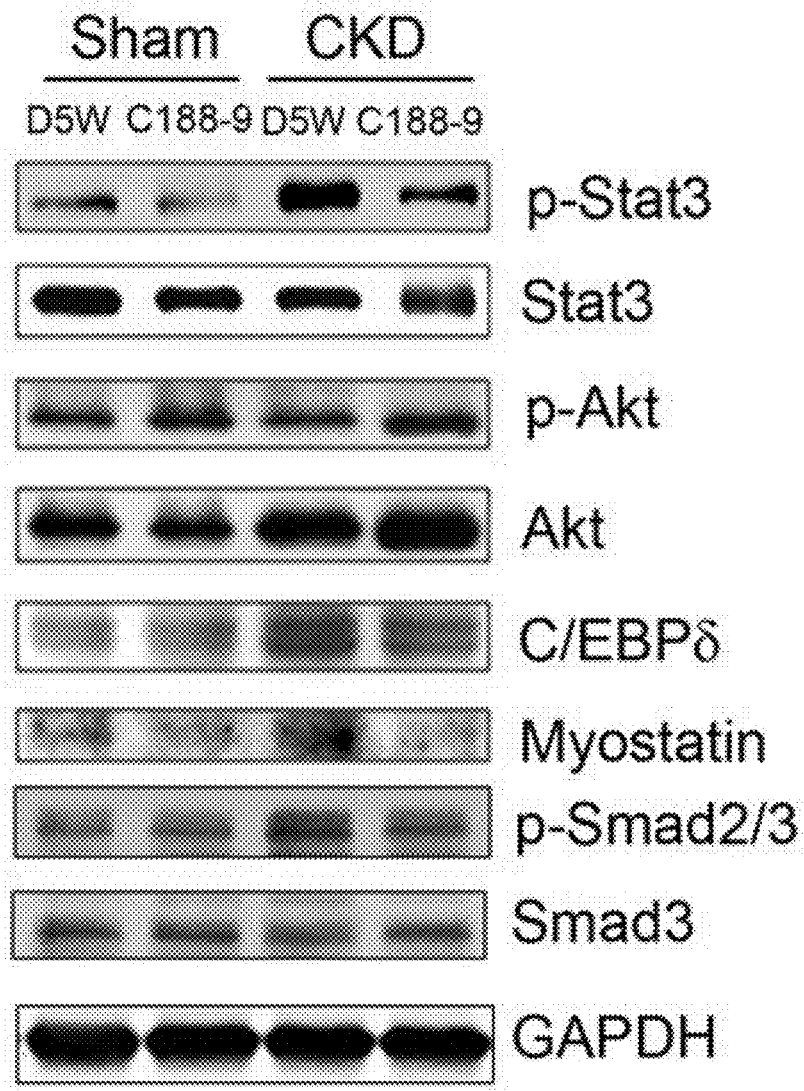
Figure 23F:
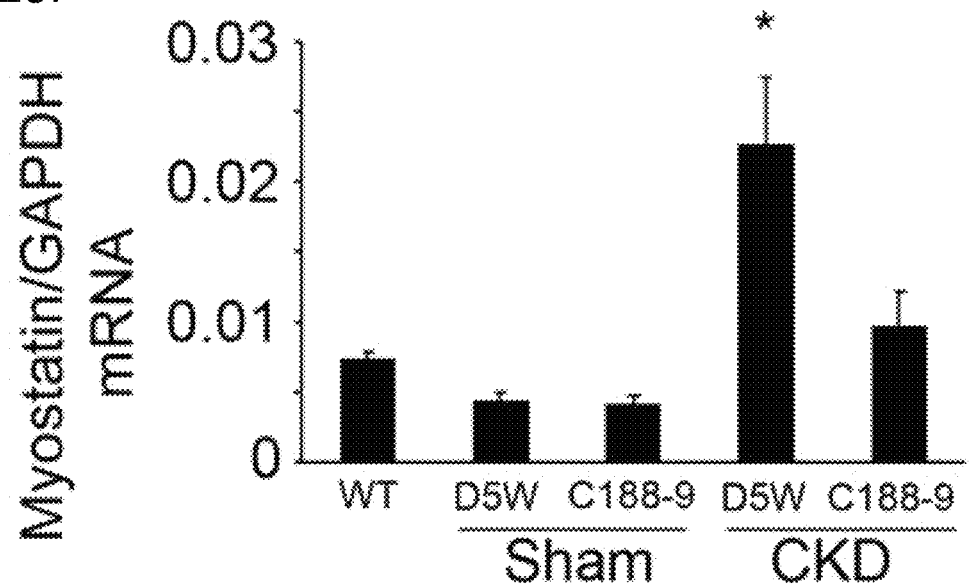
Figure 23G:
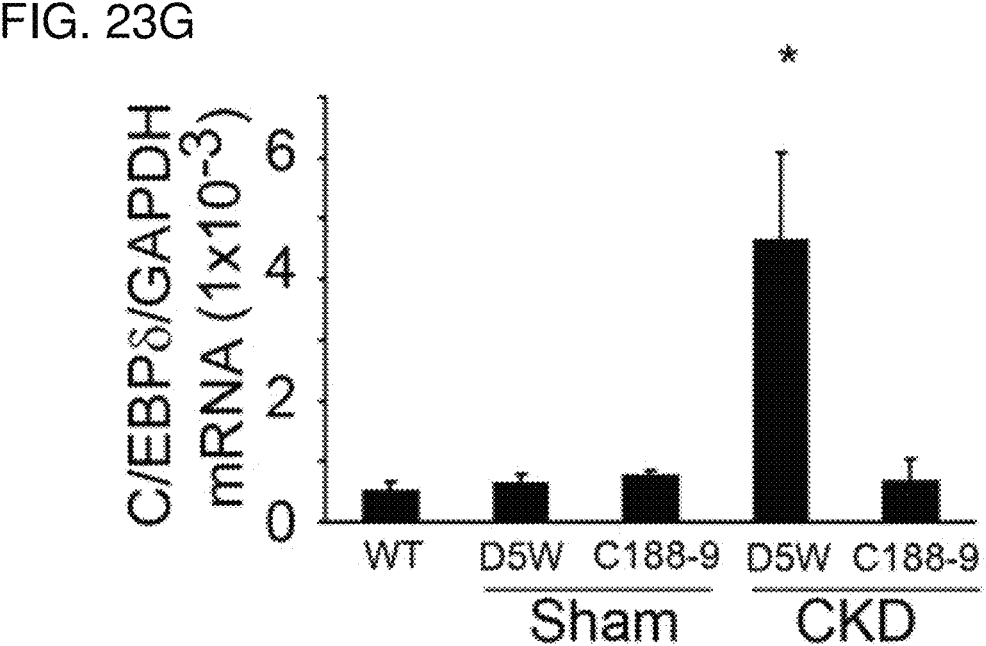

FIGS. 23A-23G demonstrates that Stat3 activation in mouse muscles increases C/EBPδ and myostatin expression. FIG. 23A. Representative western blots of the indicated proteins from lysates of gastrocnemius muscles of control (Stat3flox/flox) or Stat3 KO sham or CKD mice. FIGS. 23B & 23C. mRNAs of myostatin (FIG. 23B) and C/EBPδ in muscles of sham or CKD mice analyzed by RT-PCR (n=4 mice/group; *p<0.05 vs. Stat3flox/flox sham). FIG. 23D. Representative western blots of the indicated proteins in lysates of gastrocnemius muscles of STZ vs. WT control mice (n=5 pairs). FIG. 23E. Sham or CKD mice were treated with C188-9 or D5W (diluent) for 14 days. Representative western blots of indicated proteins from lysates of gastrocnemius muscles are shown (n=8 mice/group). FIGS. 23F & 23G. mRNA levels of myostatin (FIG. 23F) and C/EBPδ (FIG. 23G) analyzed by RT-PCR and corrected for GAPDH (n=3 mice/group: wild-type mice without CKD; sham mice treated with C188-9 or D5W; mice with CKD treated with C188-9 or D5W; *p<0.05 vs. WT non-CKD). Values are means±SEM. FIG. 6. C/EBPδ and myostatin mediate CKD or Stat3-induced muscle wasting. A. Body weights of wild type or homo- or hetero-C/EBPδ KO mice following creation of CKD. Values are expressed as a percentage of basal body weight (mean±SEM; n=9 for WT mice; n=11 for C/EBPδ−/−; n=11 for C/EBPδ+/− mice; *p<0.05 vs. WT CKD). FIG. 23B. Survival was calculated as the percentage of mice surviving at 3 weeks after CKD or after sham surgery (n=20 for WT; n=25 for C/EBPδ−/−; n=21 for C/EBPδ+/−; *p<0.05 vs. C/EBPδ−/− CKD). FIG. 23C. Average weights from both legs of red fiber (soleus) or white fiber (EDL) muscles (mean±SEM; n=10 mice/group; *p<0.05 vs. WT CKD). FIG. 23D. Representative western blots of p-Stat3 and myostatin from muscles of CKD or sham-operated mice of the following groups: C/EBPδ−/−, C/EBPδ+/− or control (WT). FIG. 23E. Cryosections of gastrocnemius muscles from mice that were transfected with lentivirus expressing Stat3C-GPF or GFP and treated with anti-myostatin inhibitor or PBS. The sections were immunostained with p-Smad2/3 (red, lower panel). The upper panel, overlap picture shows GFP-positive myofibers (green) that expressed p-Smad2/3. FIG. 23F. GFP-positive areas in myofibers were measured and the mean myofiber sizes of each group are shown (left panel). The percentage of p-Smad2/3 positive nuclei to total nuclei was calculated (right panel; mean±SEM, *p<0.05 vs. GFP/PBS).

Figure 24A:
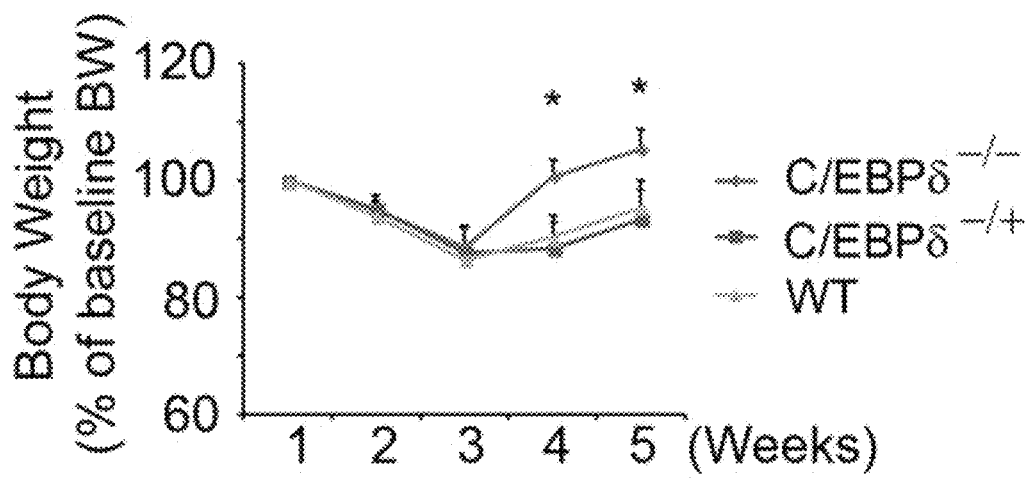
Figure 24B:
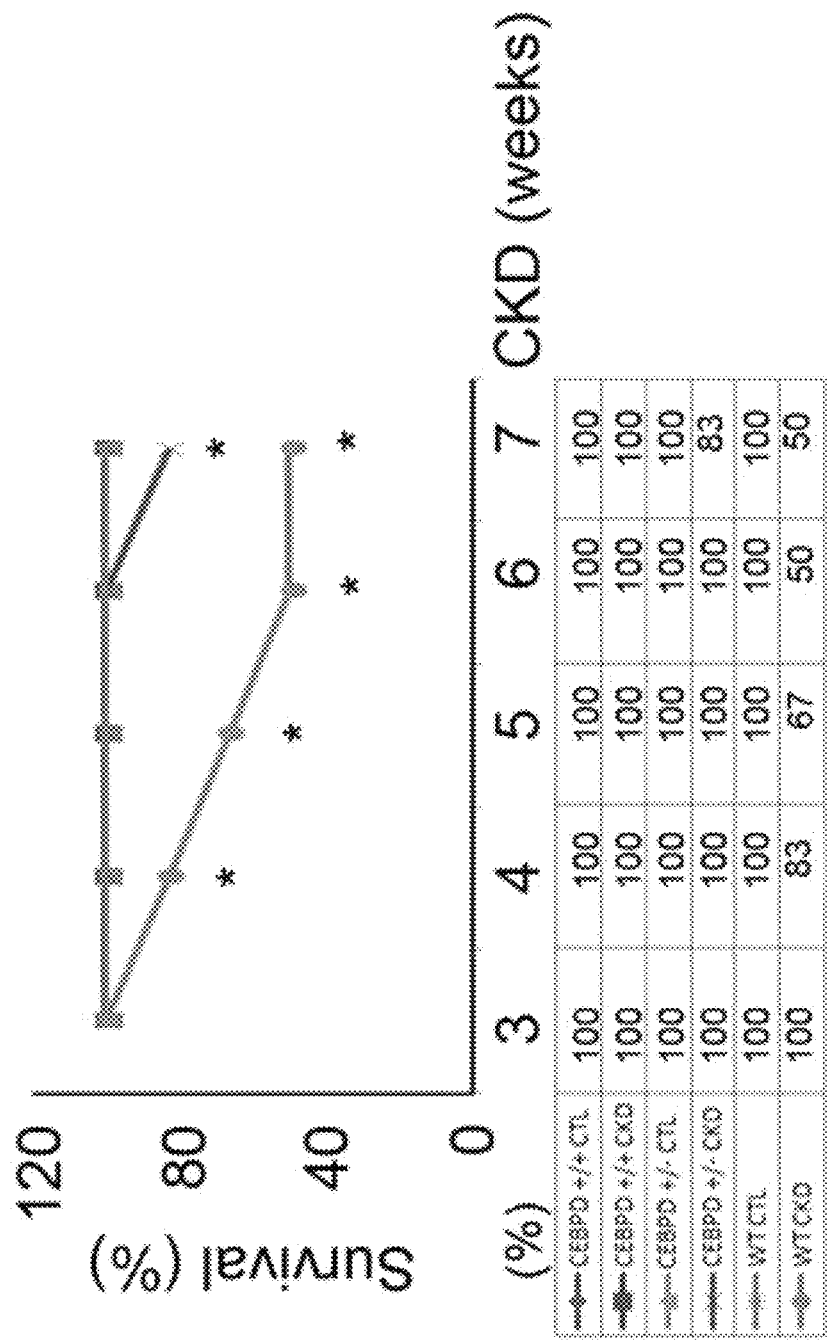
Figure 24C:
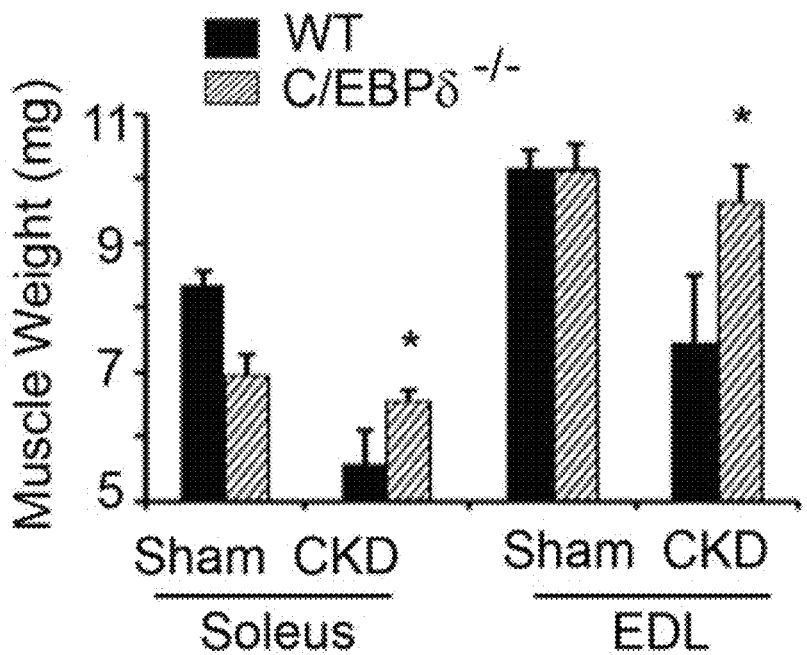
Figure 24D:
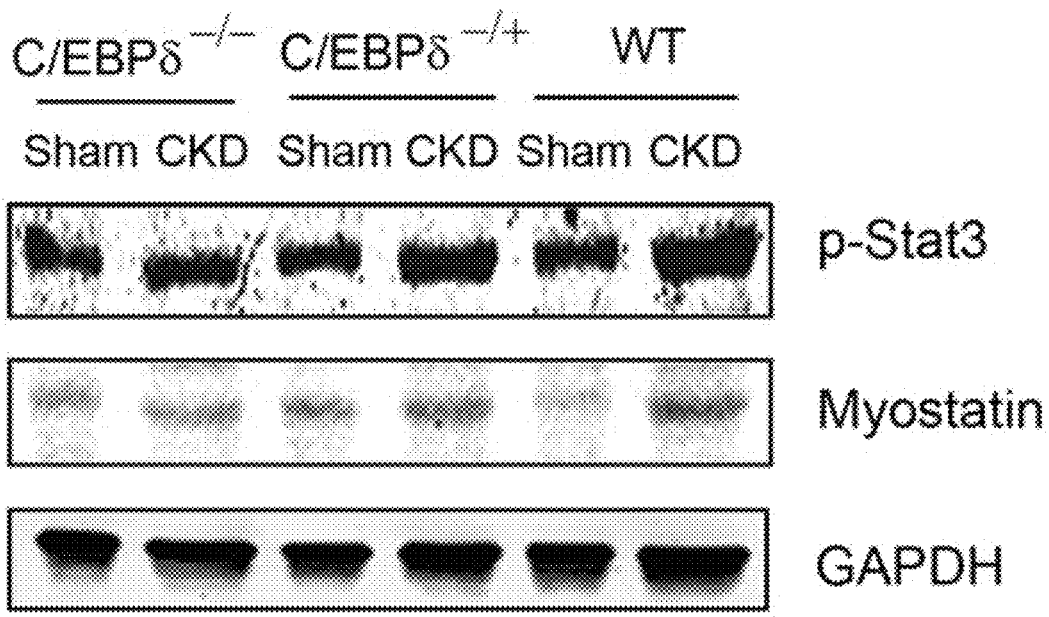
Figure 24E:
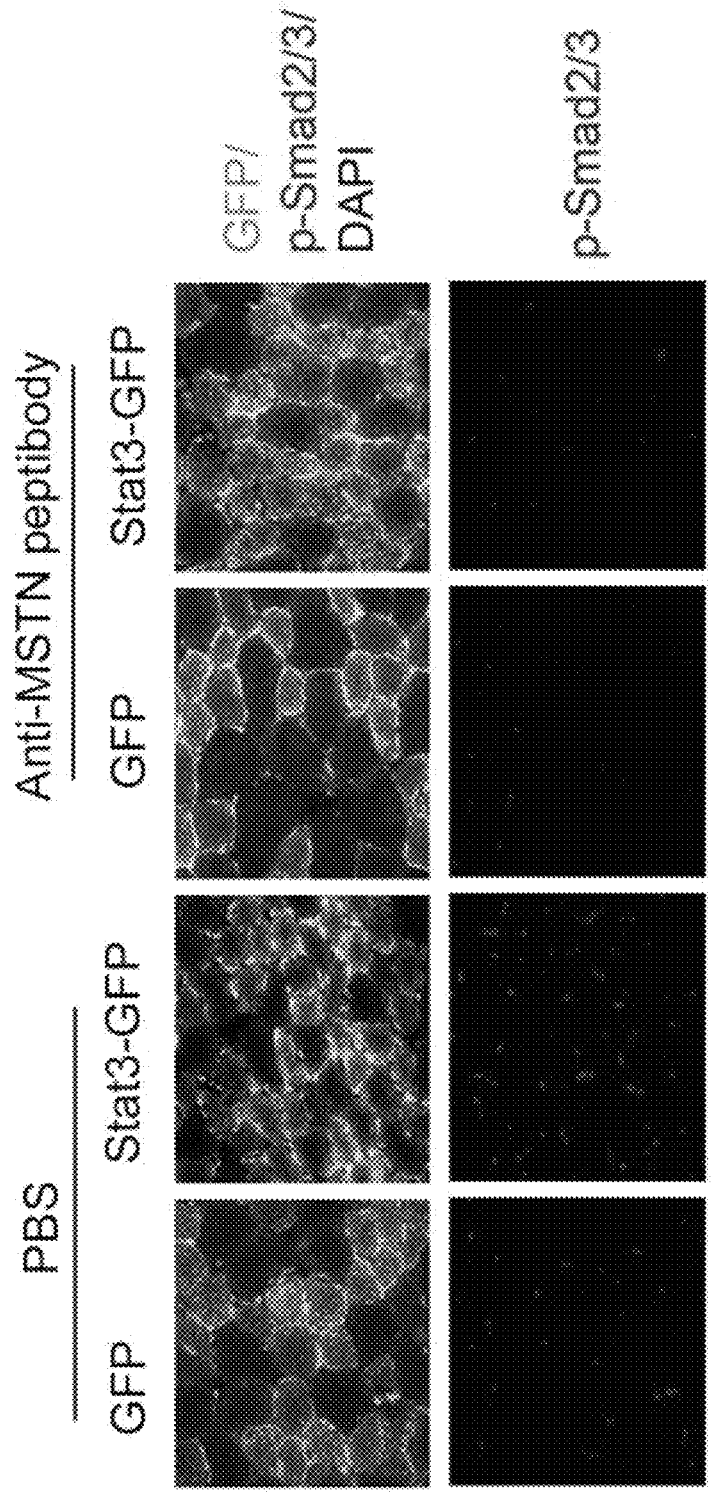
Figure 24F:
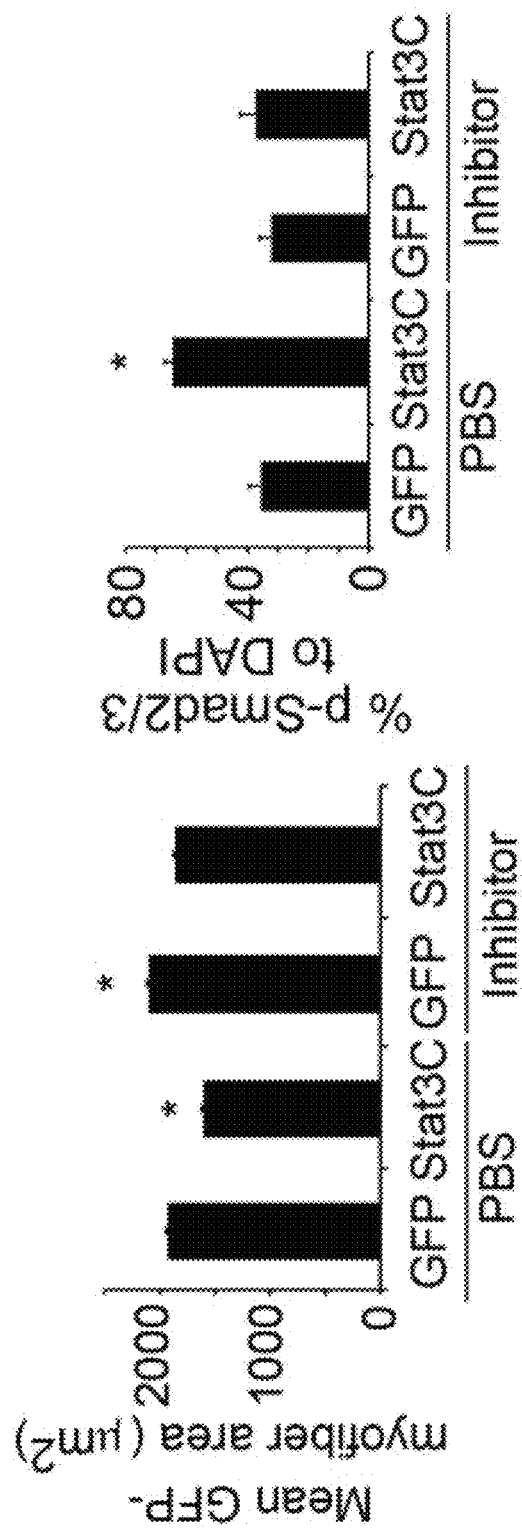

FIGS. 24A-24F demonstrates a link from Stat3 to C/EBPδ to myostatin in vivo. FIG. 24A. Body weight as a function of time for pair fed, homozygous C/EBPδ KO mice with CKD compared to control. FIG. 24B. Survival percentages over time in C/EBPδ KO mice with CKD compared to various controls. FIG. 24C. Muscle weight in C/EBPδ KO mice with CKD compared to wild type. FIG. 24D. Expression levels of myostatin in mice with homozygous C/EBPδ KO. FIG. 24E demonstrates immunostaining with anti-MSTN peptibody in mice expressing constitutively active Stat3-GFP (Stat3C-GFP), and FIG. 24F. Quantification of GFP in a myofiber area.

Figure 25A:
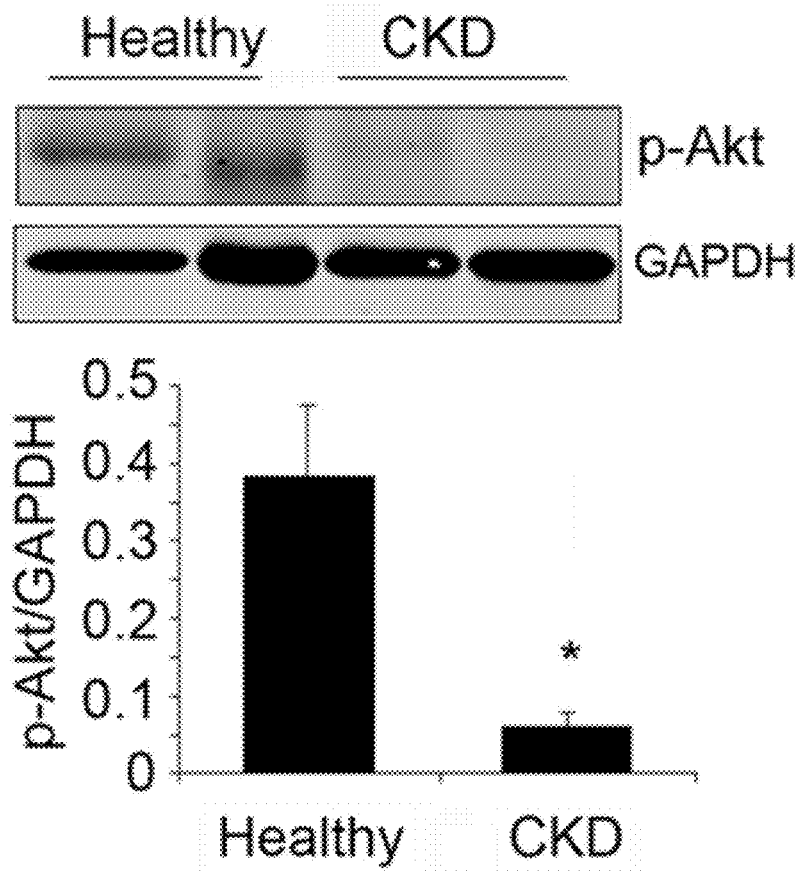
Figure 25B:
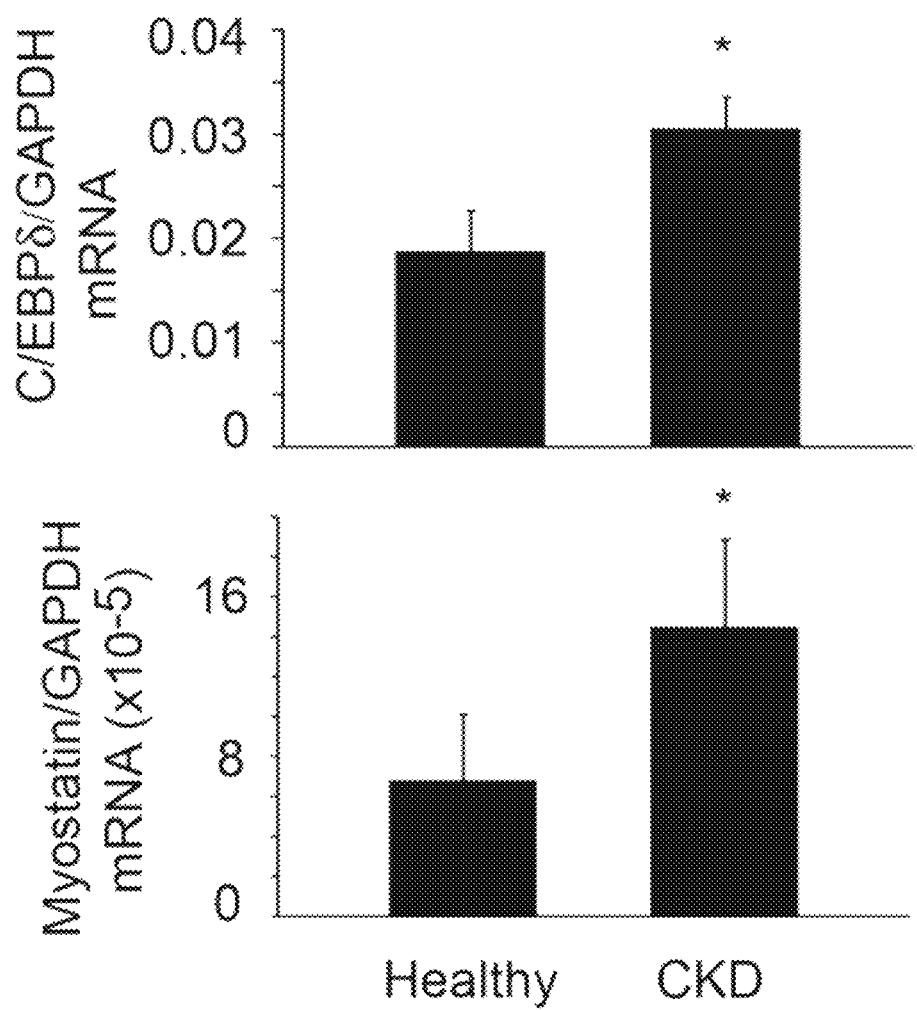
Figure 25C:
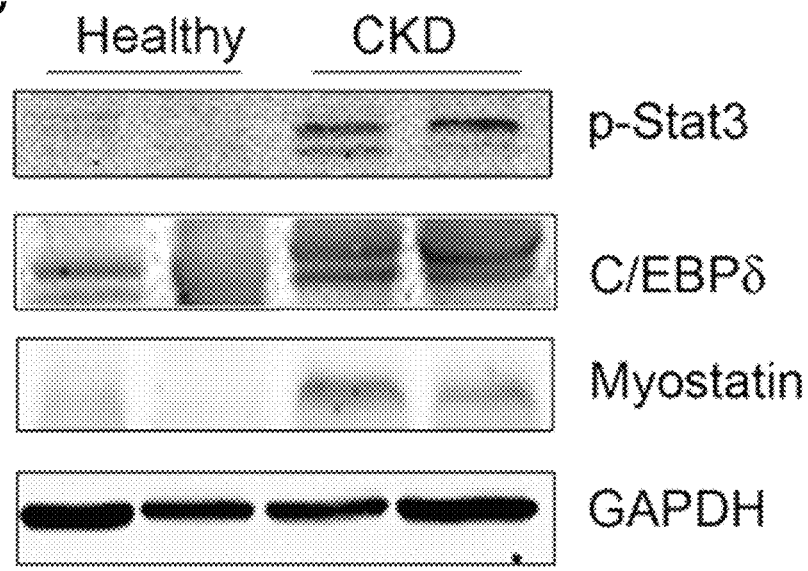
Figure 25D:
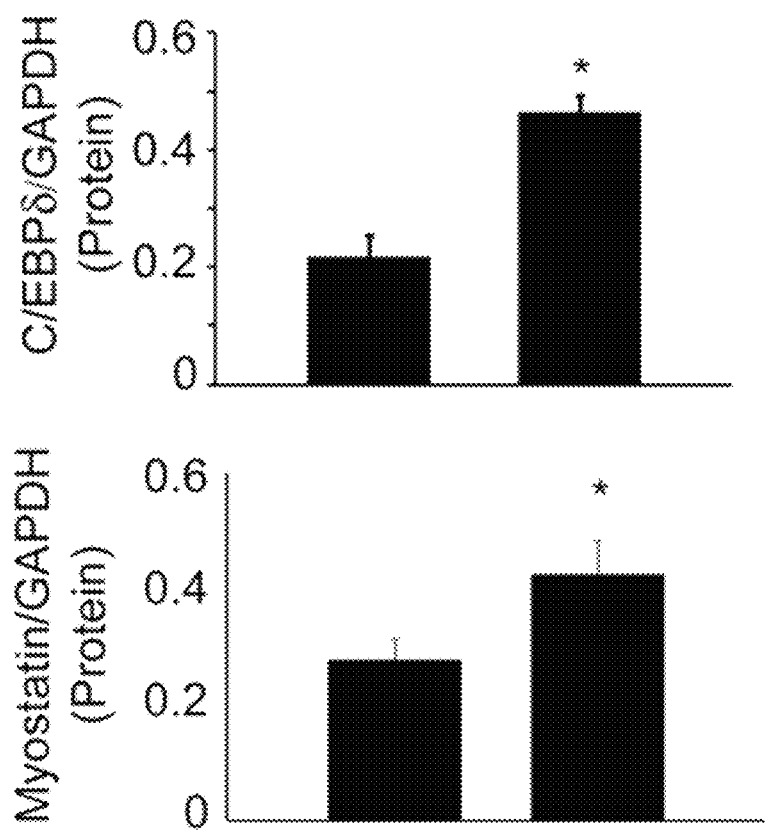

FIGS. 25A-25D shows evidence for a p-Stat3, C/EBPδ and myostatin pathway in muscles of patients with CKD FIG. 25A. Representative western blots of p-Akt from muscle biopsies of healthy control or CKD patients. Bar graph shows the densities of p-Akt corrected for GAPDH (lower panel; n=4 CKD patients and 3 healthy subjects). FIG. 25B. Levels of mRNAs of C/EBPδ or myostatin were analyzed by RT-PCR from muscle biopsies of healthy control or CKD patients (n=5 control subjects and 9 CKD patients). FIG. 25C. Representative western blots of the indicated proteins from muscle biopsies from healthy control or CKD patients. FIG. 25D. The band densities were quantified after correction for GAPDH (n=3 pairs for CEBPδ; n=8 pairs for myostatin). Values are means±SEM. *p<0.05 vs. healthy controls.

Figure 26:
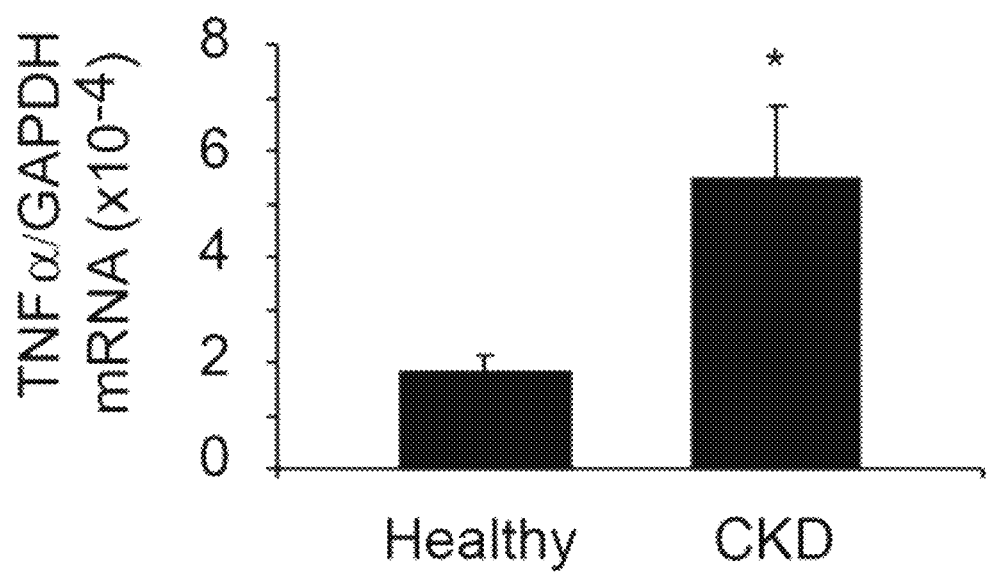

FIG. 26: Muscles of patients with CKD exhibited increased mRNA levels of TNFα. RT-PCR was used to assess TNFα mRNA levels corrected for GAPDH. The bar graph (mean±SEM) illustrates the difference found in samples of 9 patients with CKD and 5 healthy control (*, p<0.05 vs. healthy subjects).

Figure 27:
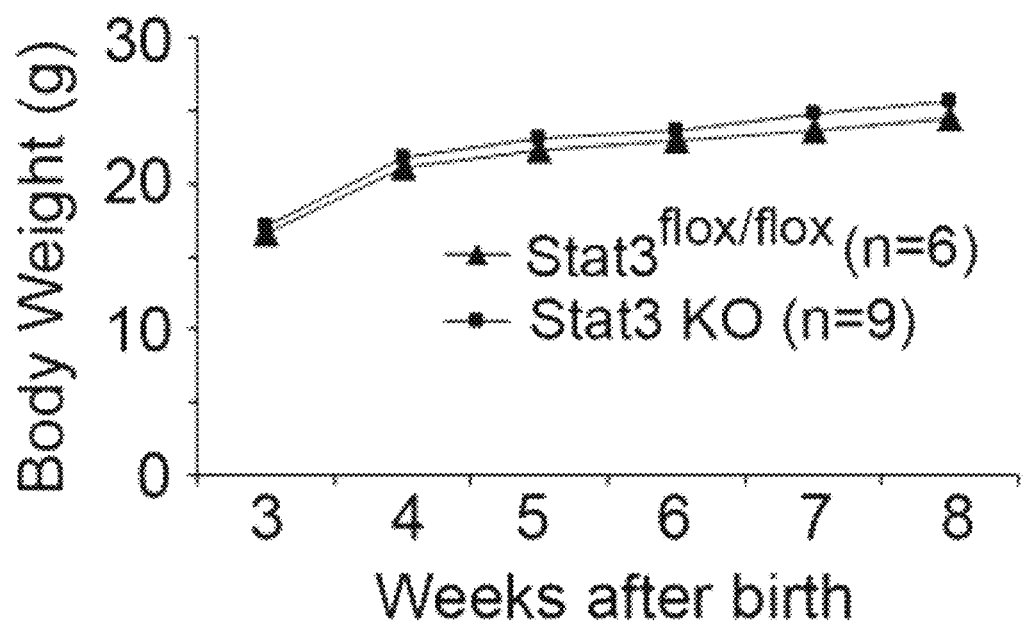

FIG. 27 shows the body weight changes in mice with Stat3 KO in muscle. Changes in body weights of Stat3 KO and Stat3flox/flox control mice measured from 3 to 8 weeks after birth. There were no significant differences in body weights of Stat3 KO vs. Stat3flox/flox mice without CKD (n=6 control; n=9 Stat3 KO).

Figure 28:
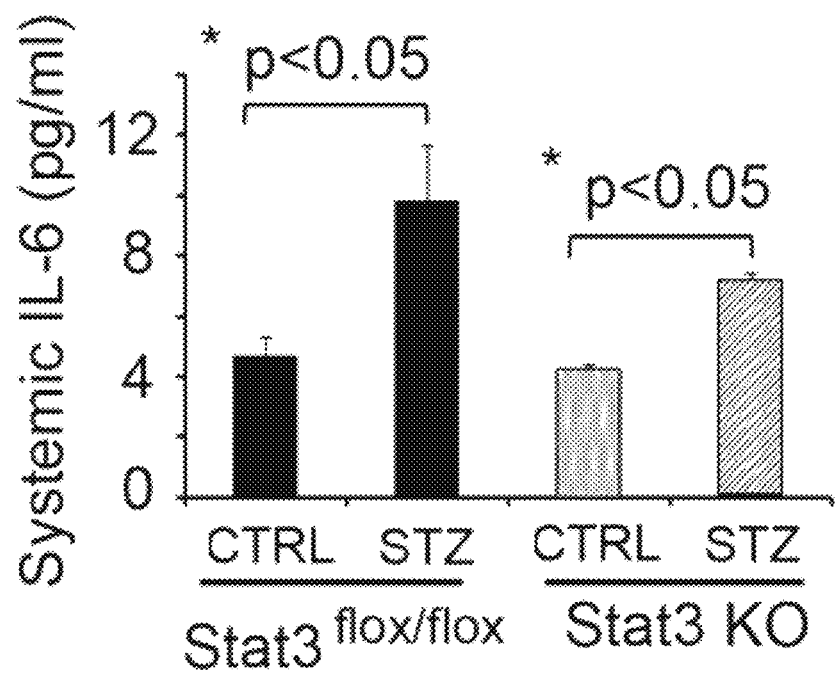

FIG. 28 provides serum levels of IL-6 from STZ mice was assessed by ELISA (n=4 mice/group).

Figure 29:
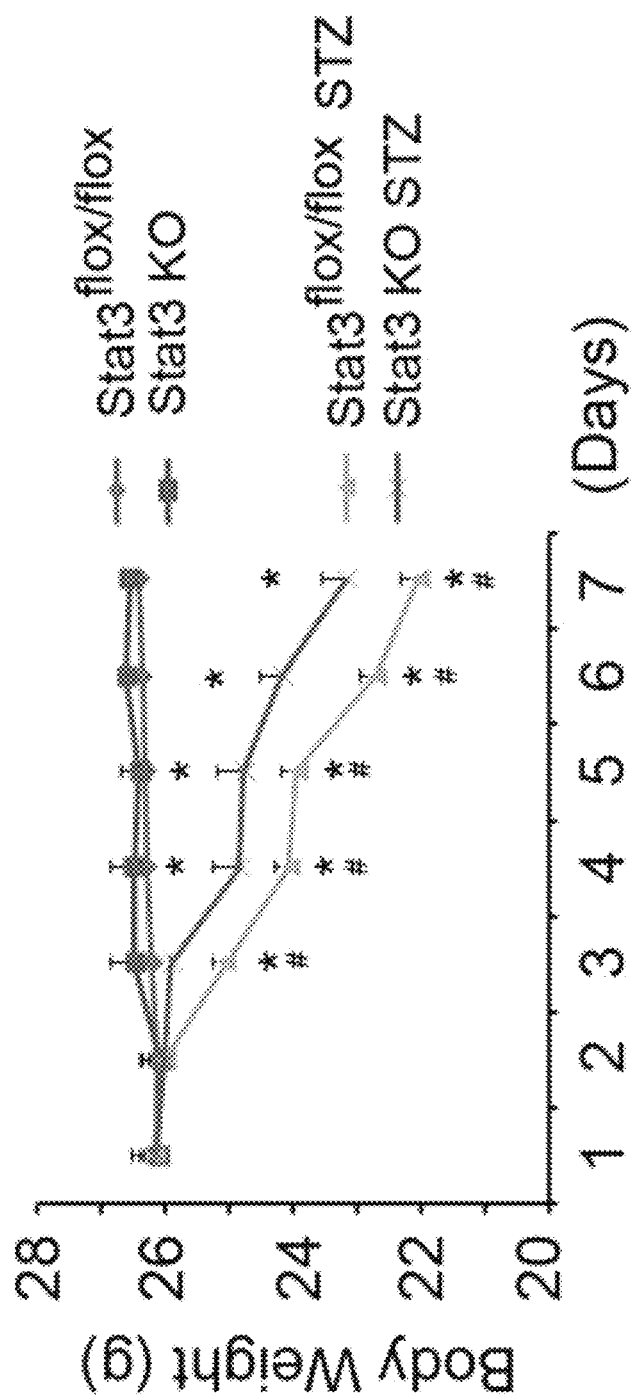

FIG. 29 shows changes in body weights of Stat3 KO or Stat3flox/flox mice with acute diabetes. During 9 days after streptozotocin injection, the daily body weight changes was shown (n=10 mice/group; *p<0.05 vs. Stat3flox/flox non-STZ; #p<0.05 vs. Stat3 KO STZ).

Figure 30:
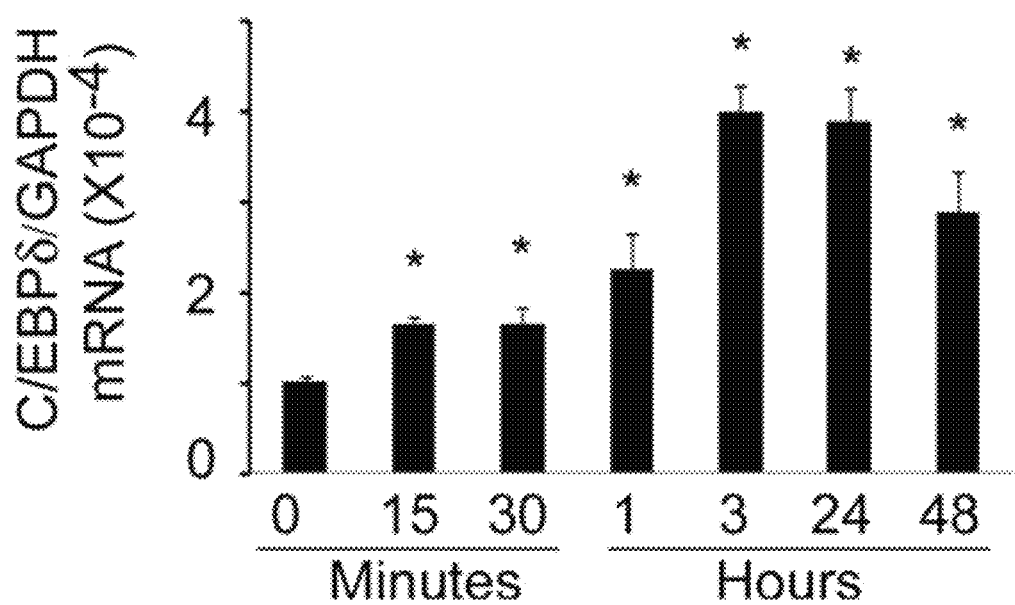

FIG. 30 demonstrates Stat3 activation in C2Cl2 myotubes increases the mRNA expression of C/EBPδ C2Cl2 myotubes were treated with IL-6 (100 ng/ml) for different times. RT-PCR was used to assess mRNA levels of C/EBPδ. Bar graphs show changes in mRNAs of C/EBP after correction for the mRNA of GAPDH. n=3 repeats; *p<0.05 vs. time zero.

Figure 31:
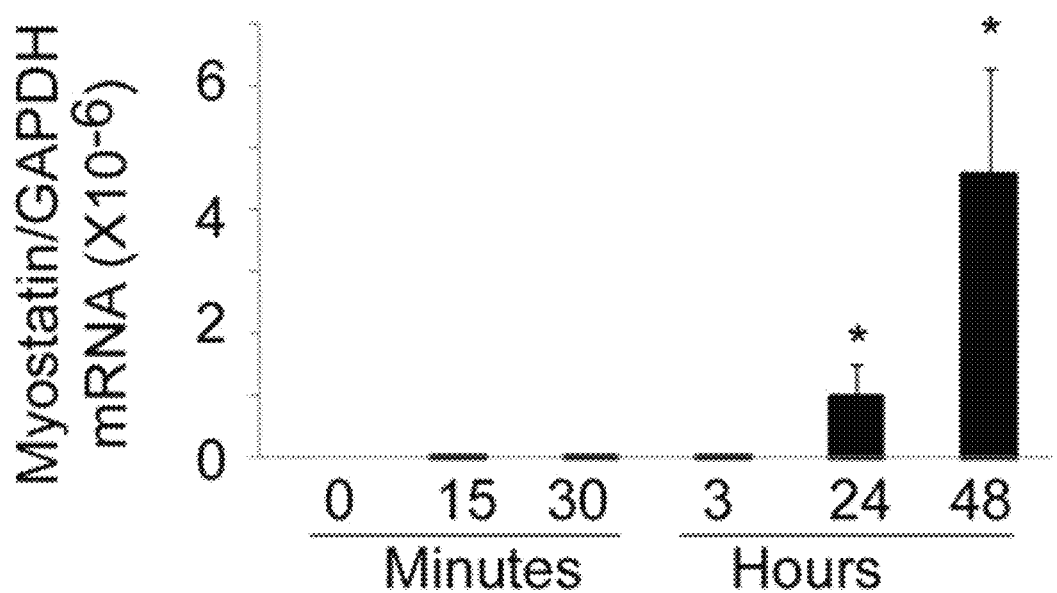

FIG. 31 provides Stat3 activation in C2Cl2 myotubes increases the mRNA expression of myostatin. C2Cl2 myotubes were treated with IL-6 (100 ng/ml) for different times. RT-PCR was used to assess mRNA levels of myostatin. Bar graphs show changes in mRNAs of myostatin after correction for the mRNA of GAPDH. n=3 repeats; *p<0.05 vs. time zero.

Figure 32:
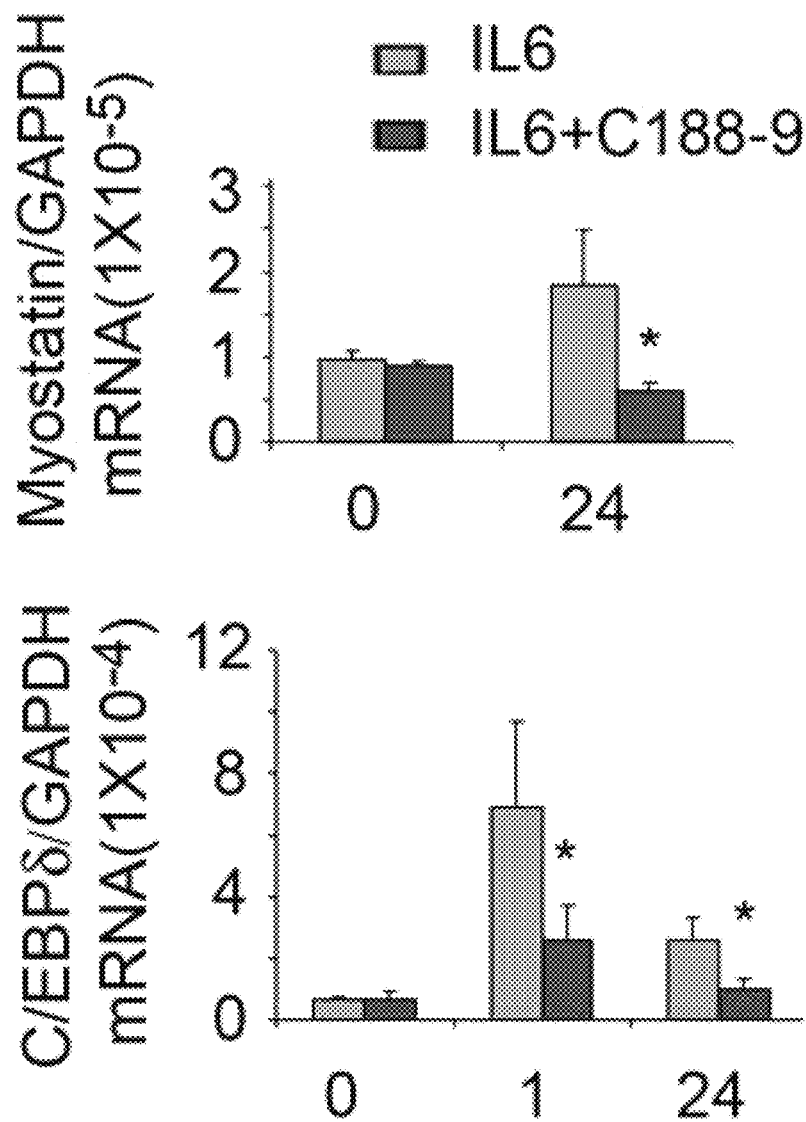

FIG. 32 demonstrates the mRNA expression of myostatin and C/EBPδ induced by IL-6 requires Stat3 activation. C2Cl2 myotubes were treated with or without C188-9 for 1 or 24 h and RT-PCR was used to assess mRNA levels. The bar graphs (mean±SEM) illustrate the mRNA levels corrected for GAPDH of myostatin (top), and C/EBPδ (bottom). N=3 independent experiments; *, p<0.05 vs. results without C188-9.

Figure 33:
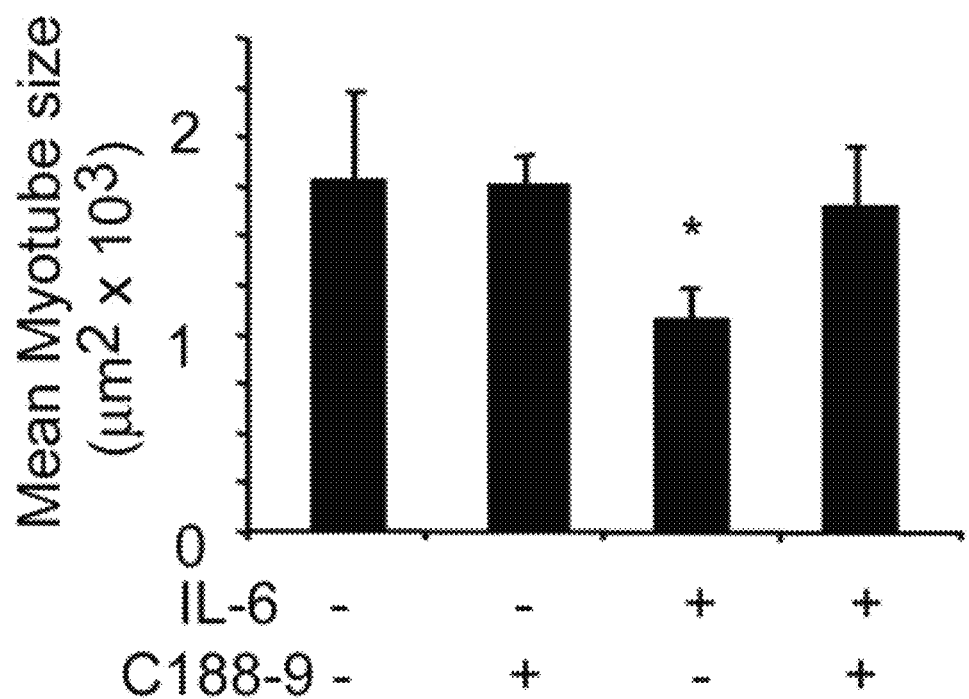

FIG. 33 demonstrates that C-188-9 suppresses IL-6 induced myotube wasting. C2Cl2 myotubes were treated with C188-9, a Stat3 inhibitor, for 2 h before adding IL-6 (100 ng/ml) for 24 h. Myotube sizes were measured (mean±SEM; n=3 independent experiments; *, p<0.05 vs. untreated myotubes).

Figure 34:
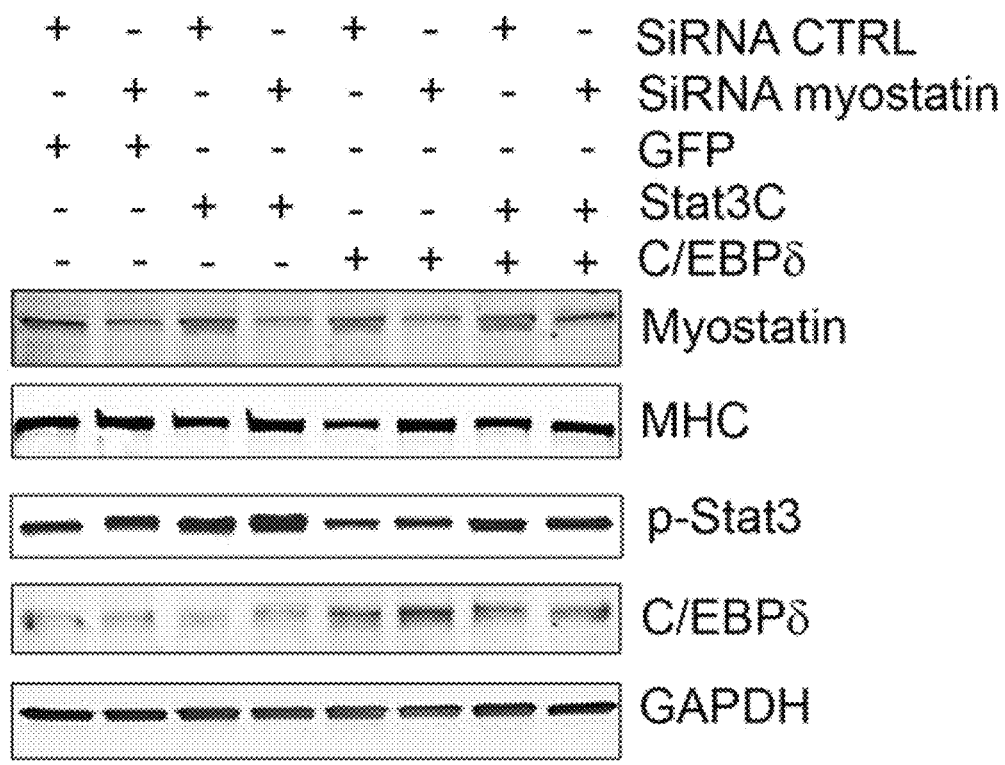

FIG. 34 shows protein levels were measured in C2Cl2 cells with myostatin knockdown and overexpress Stat3C or C/EBPδ. C2Cl2 myoblasts were transfected with lentivirus expressing a siRNA to myostatin. Myoblasts exhibiting suppression of myostatin were selected and then differentiated after they had been transfected with plasmids expressing Stat3C, C/EBPδ or Stat3C plus C/EBPδ. Western blots of proteins expressed in response to tranfections were shown.

Figure 35:
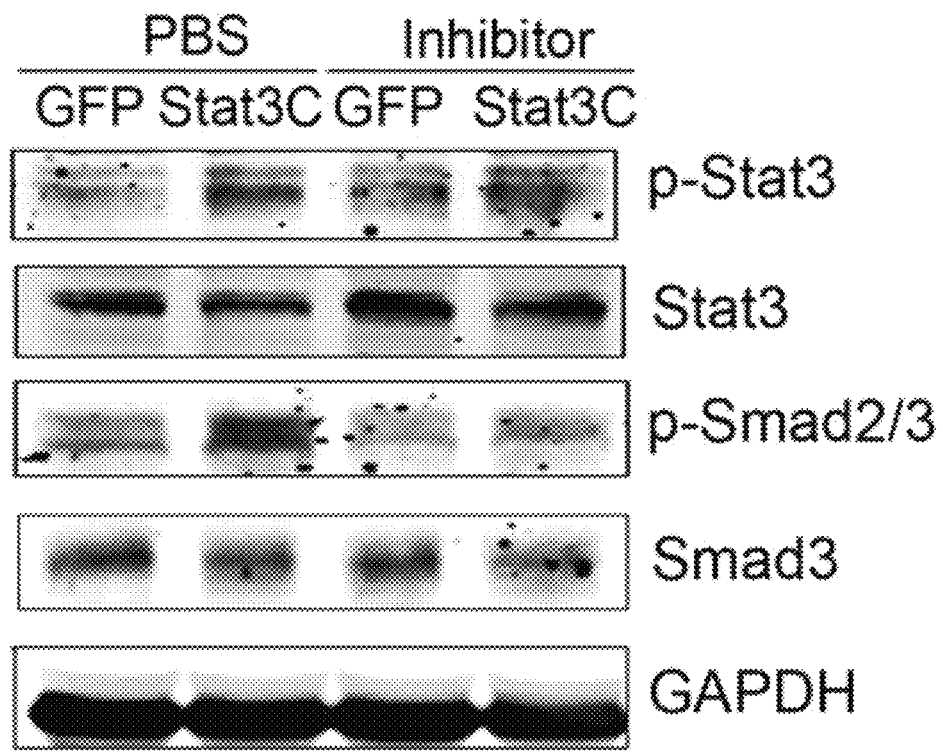

FIG. 35 shows that myostatin inhibition blocked Stat3C induced p-Smad2/3. The muscle lysates from muscle treafected with lentivirus expressing GFP or Stat3C and mice treated with anitmyostatin peptibody or PBS were subjected to western bloting to show the levels of p-stat3 and p-Smad2/3.

Figure 36A:
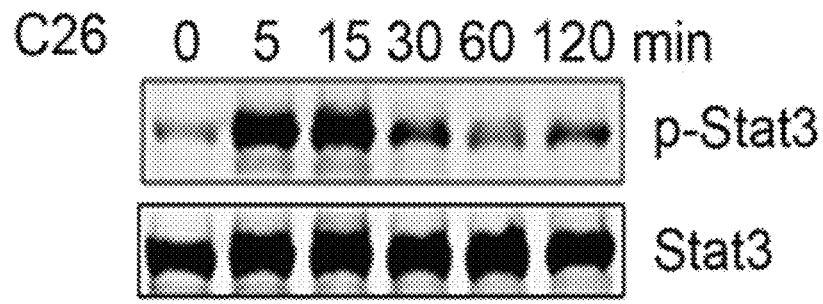
Figure 36B:
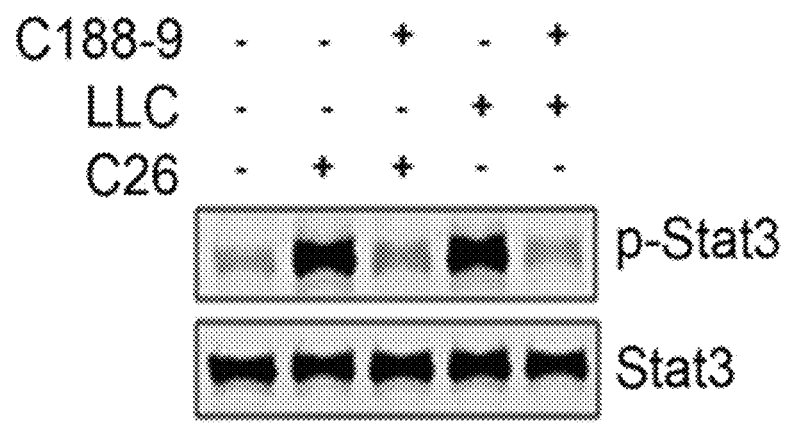
Figure 36C:
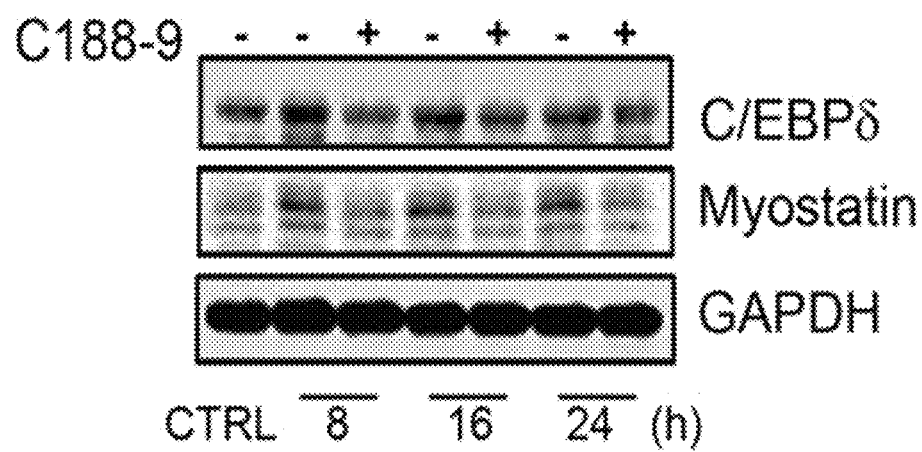
Figure 36D:
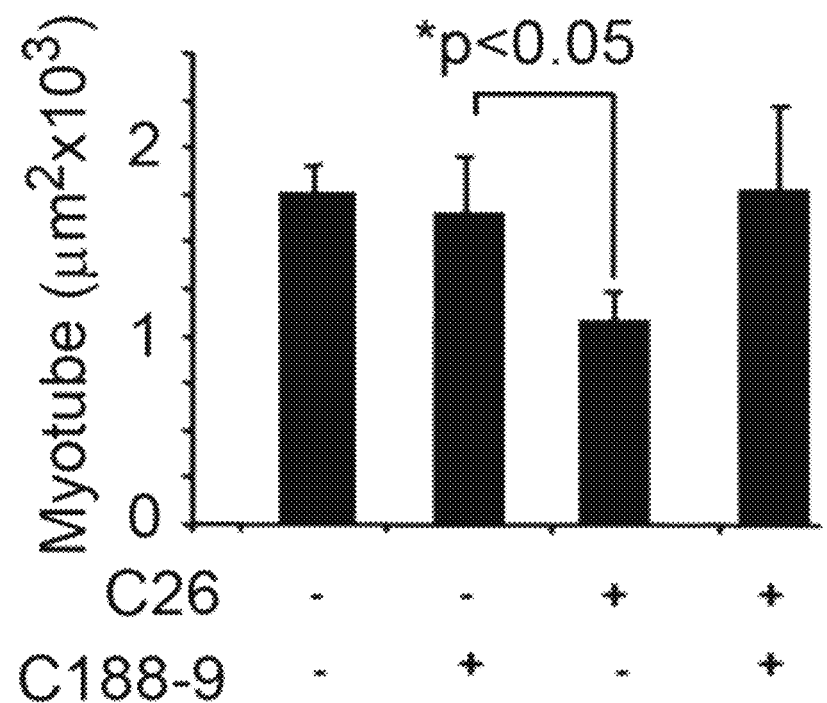

FIGS. 36A-36D shows that conditioned media from C26 or LLC-cancer cells activates p-Stat3 in C2Cl2 cells, a model of skeletal muscle. C2Cl2 myotubes. FIG. 36A. Representative western blots of p-Stat3 and Stat3 in C2Cl2 myotubes that were exposed for different times to conditioned media from C26 colon cancer cells. FIG. 36B. C2Cl2 myotubes were pretreated with the Stat3 inhibitor, C188-9, for 2 hours before they were exposed to conditioned media from C26 or LLC cancer cells. Representative western blots for p-Stat3 or Stat3 are shown. FIG. 36C. C2Cl2 myotubes were treated with C188-9 plus conditioned media from C26 cells for different times. Representative western blots for C/EBPδ and myostatin are shown. FIG. 36D. The average sizes of C2Cl2 myotubes was assessed following incubation with conditioned media of C26 cells with or without C188-9 for 72 hours (mean±SEM; p<0.05).

Figure 37A:
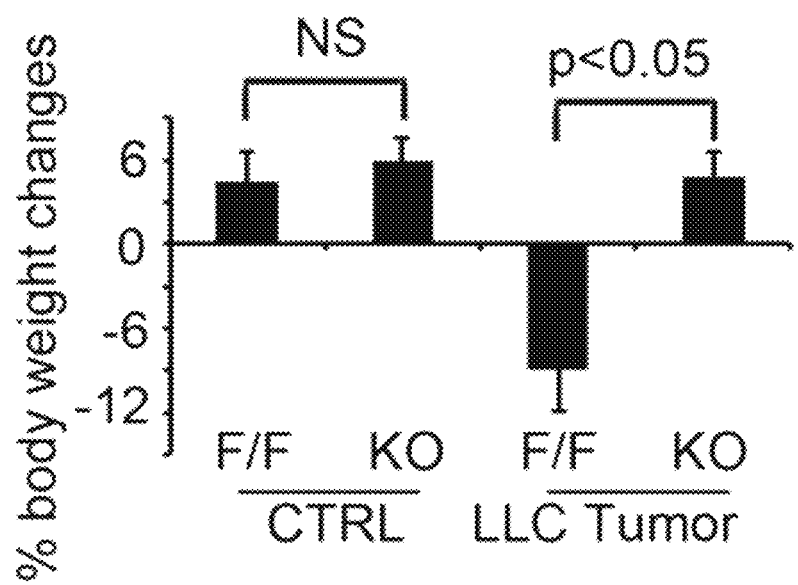
Figure 37B:
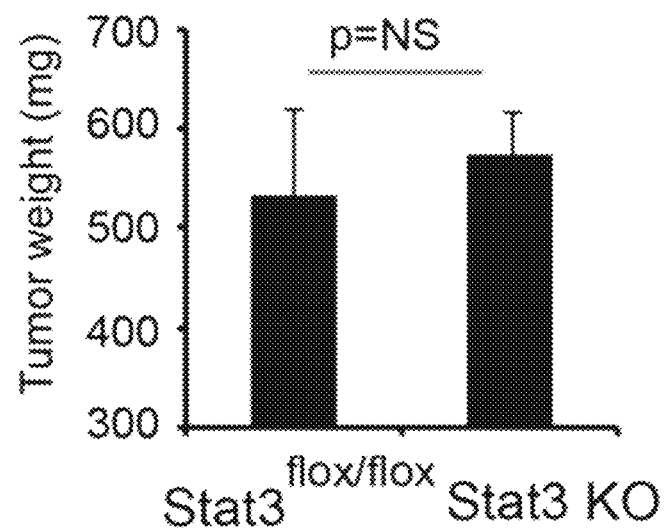
Figure 37C:
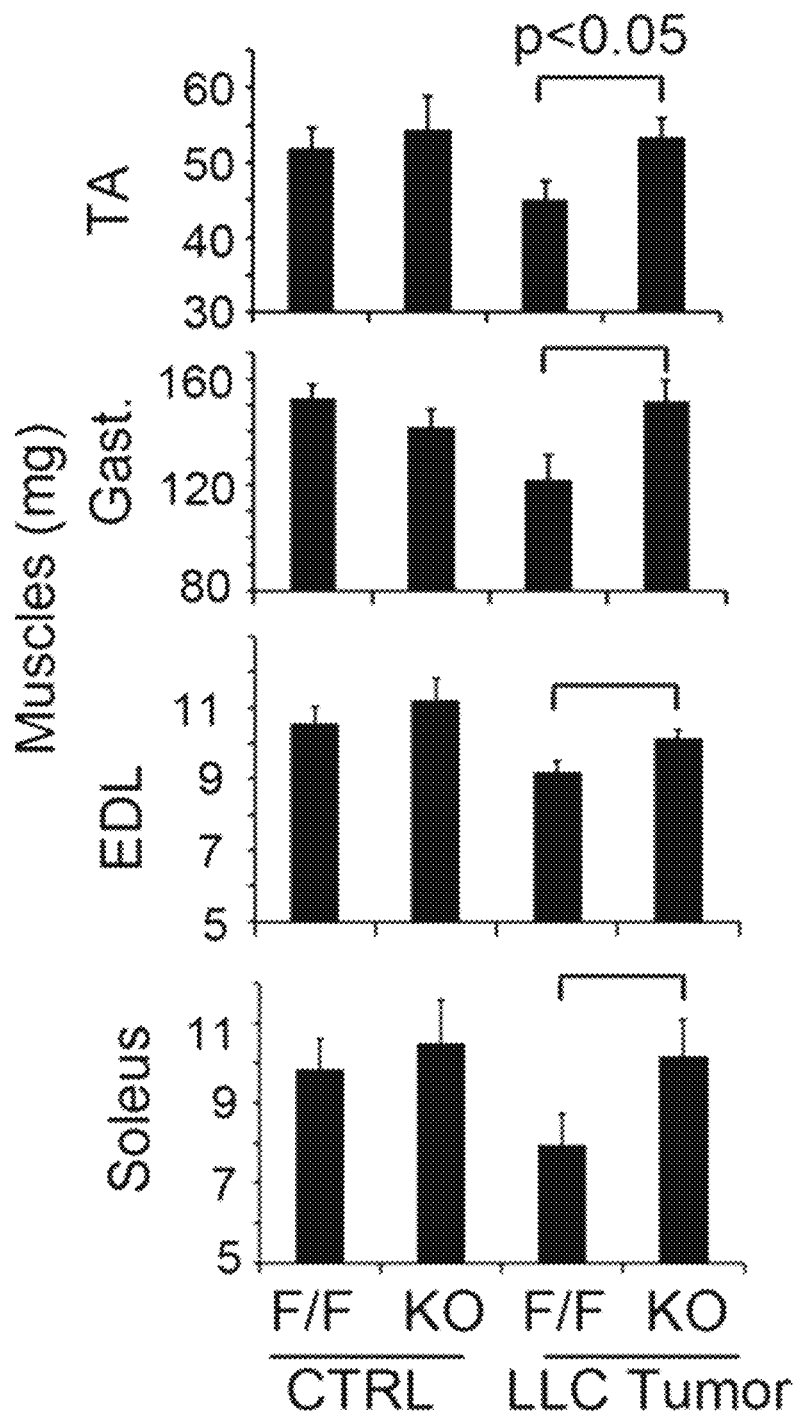
Figure 37D:
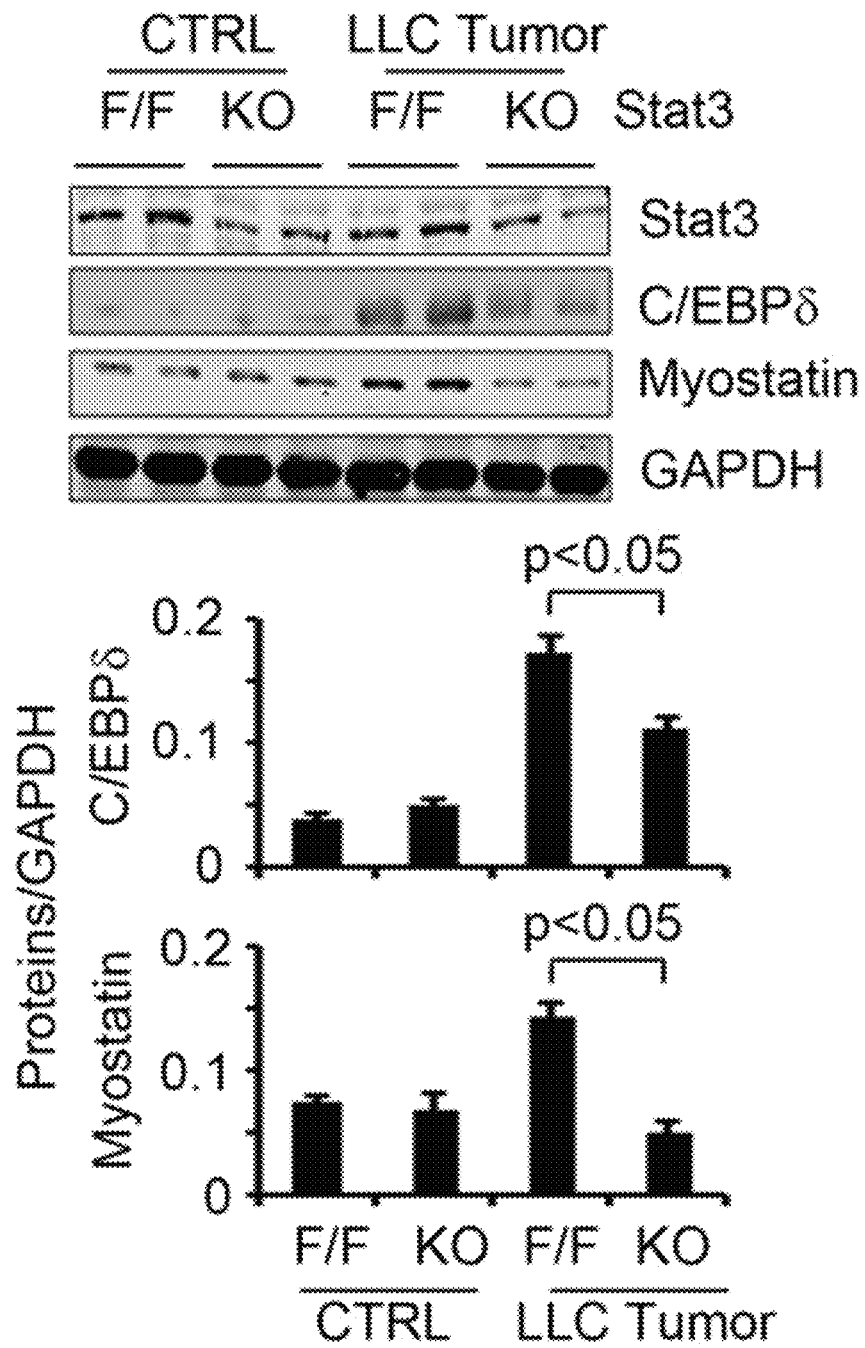
Figure 37E:
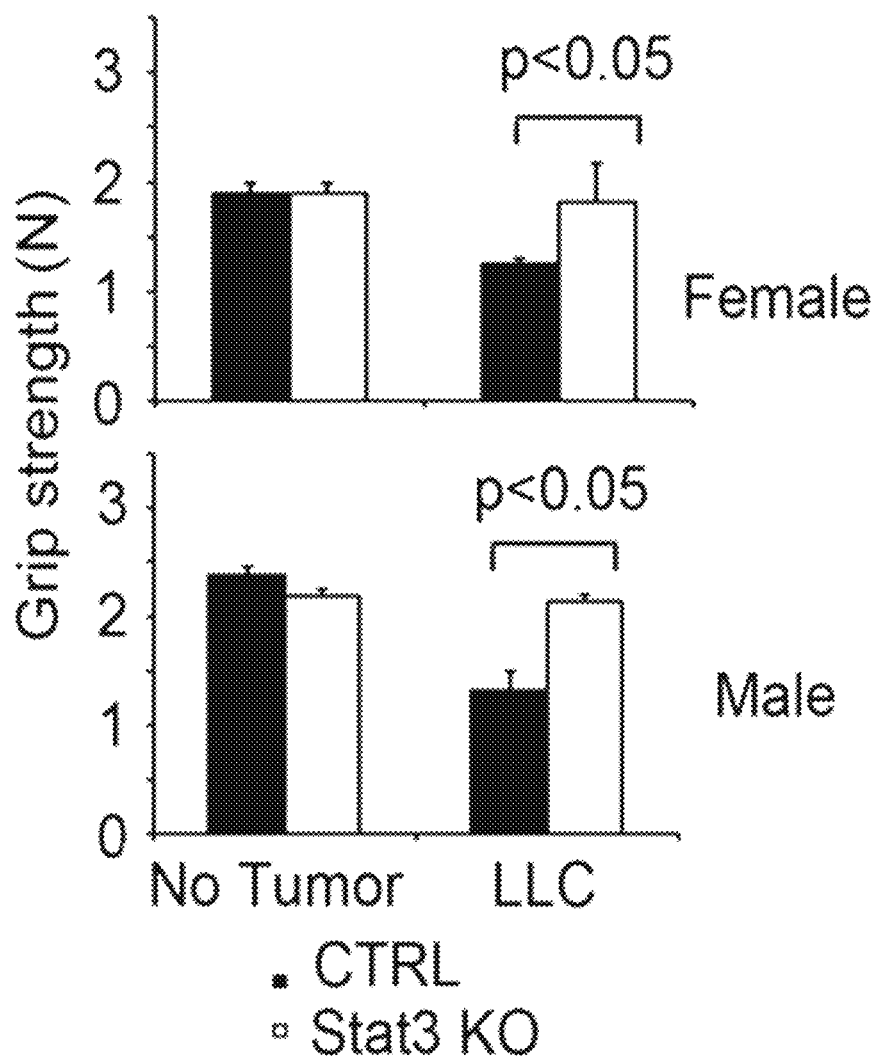

FIGS. 37A-37E shows that muscle-specific Stat3 KO in mice suppresses LLC-induced loss of muscle mass. Mice with muscle-specific Stat3 KO or control mice, Stat3$^{flox/flox}$, (10 mice in each group) were injected with LLC 18 days earlier. FIG. 37A. Changes in body weight are expressed as a percentage of the body weight measured before LLC was injected. FIG. 37B. Weights of tumor measured when mice were sacrificed. FIG. 37C. Weights of different muscles (TA, tibialis anterior; Gast, gastrocnemius; and EDL, extensor digitorum longus) measured at 18 days after injecting LLC. FIG. 37D. Representative western blotting of Stat3, C/EBPδ and myostatin from muscles of mice with muscle-specific KO of Stat3 or Stat3$^{flox/flox}$ mice. Mice with and without tumor were compared and densities of blots were quantified (lower panel). FIG. 37E. Muscle grip strength (n=5 mice in each group) was measured (mean±SEM).

Figure 38A:
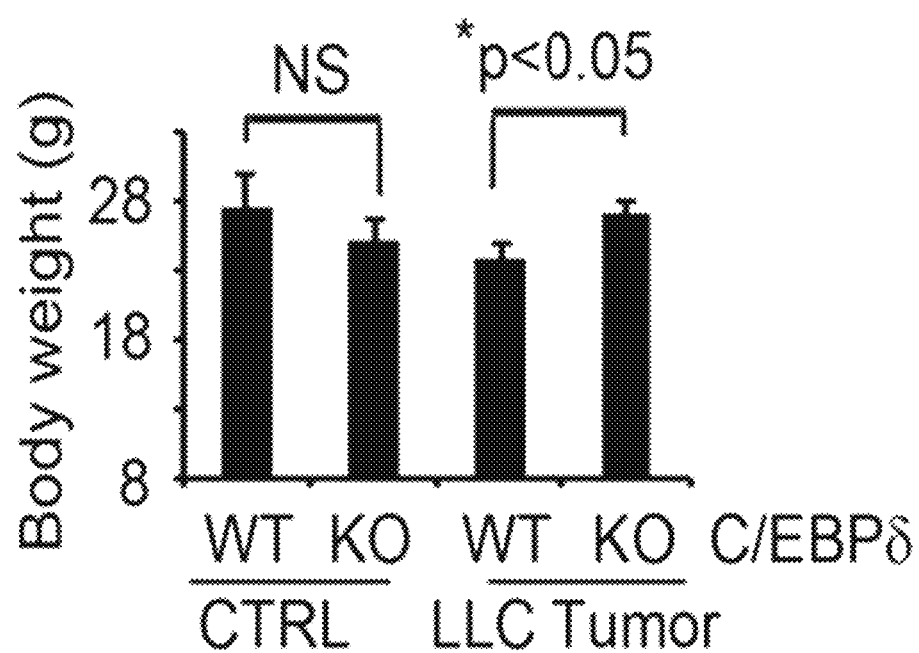
Figure 38B:
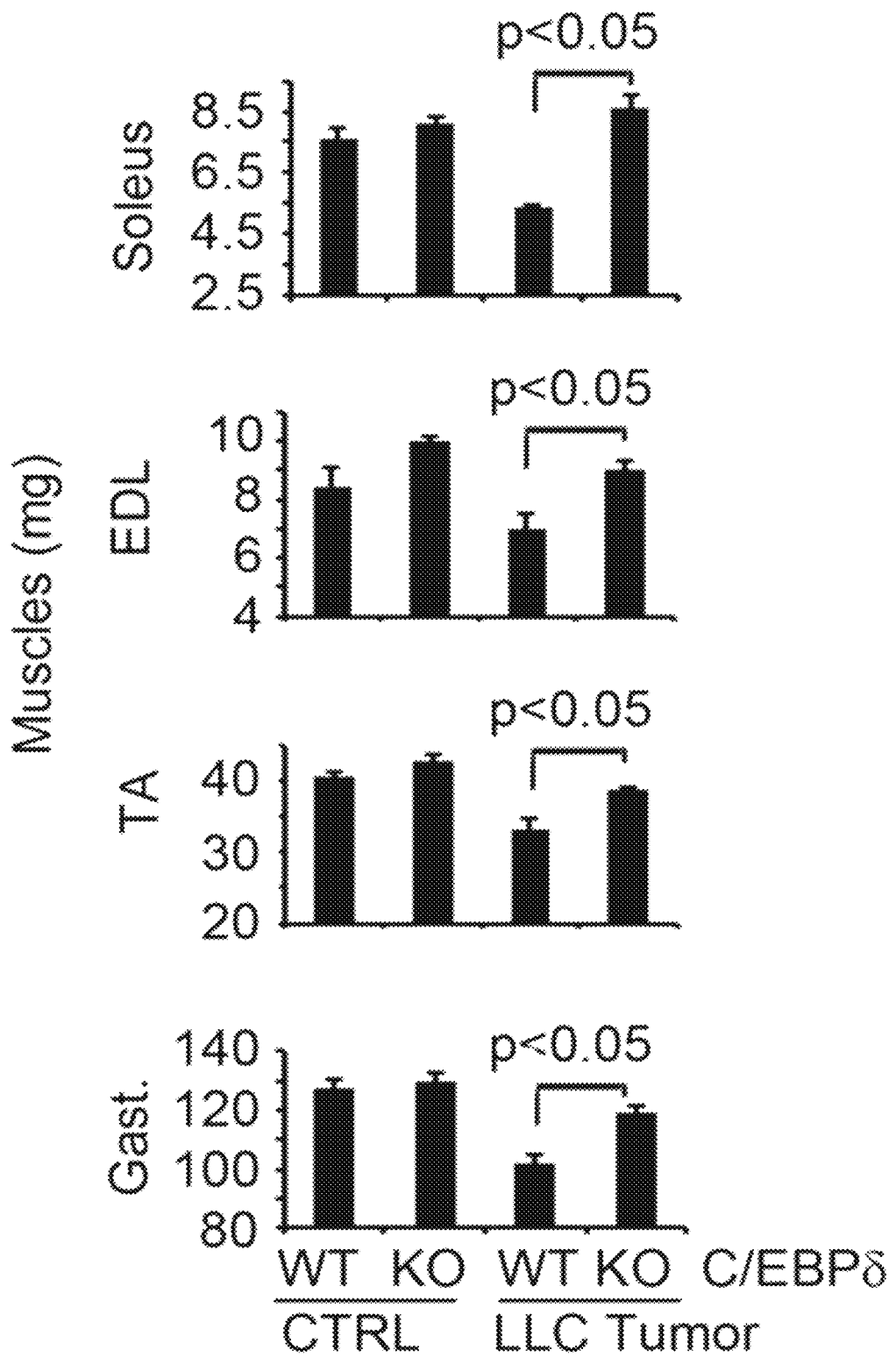
Figure 38C:
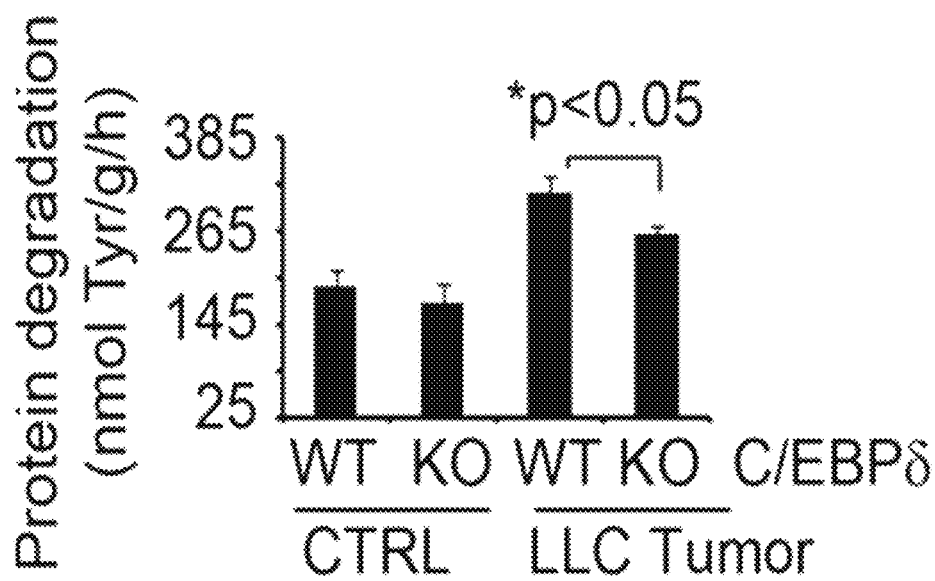
Figure 38D:
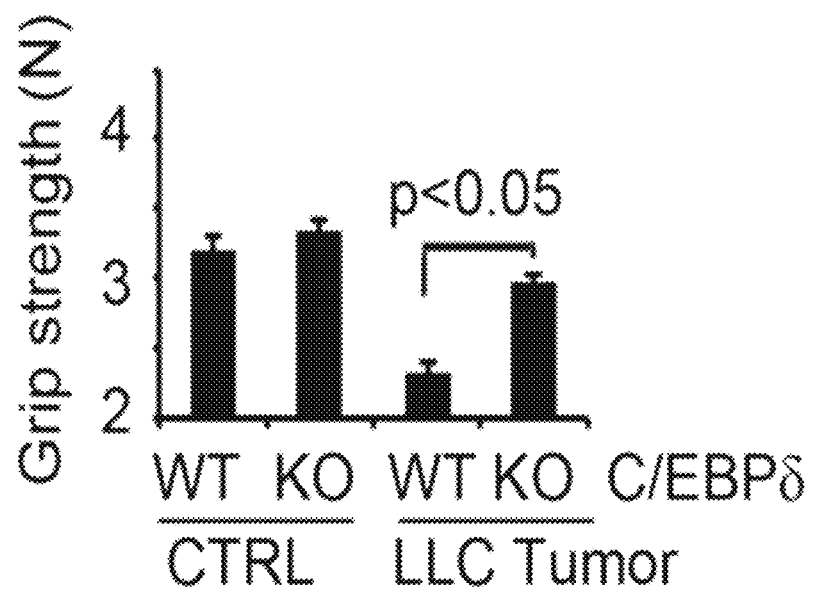
Figure 38E:
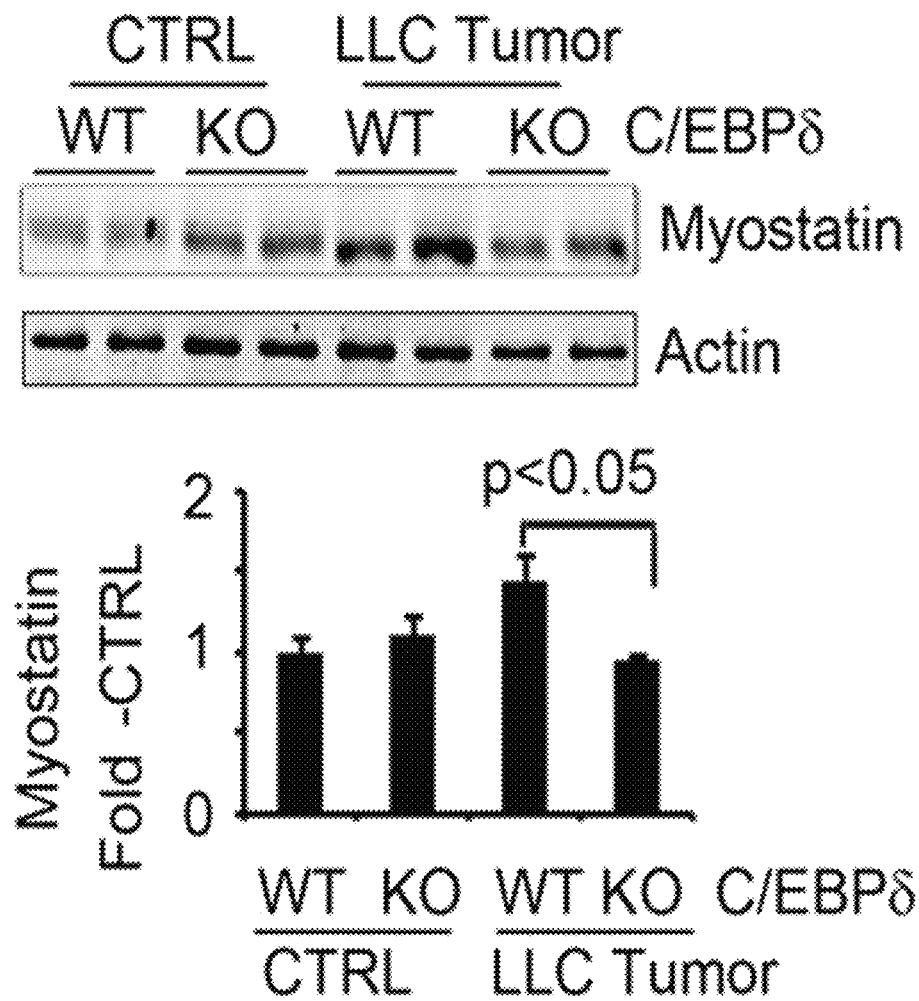

FIGS. 38A-38E demonstrates that elimination of C/EBPδ in mice suppresses LLC-induced cachexia. C/EBPδ KO and control mice were injected with LLC and 18 days later, there was measured: FIG. 38A. body weight; FIG. 38B. weights of different types of muscle based on fiber type; FIG. 38C. measured rates of muscle protein degradation; FIG. 38D. muscle grip strength; FIG. 38E. representative western blots of myostatin in muscles of m C/EBPδ or control mice treated with or without LLC (upper panel). The fold-increase in myostatin vs. results in control mice are shown in the lower panel. Results are reported as mean±SEM.

Figure 39A:
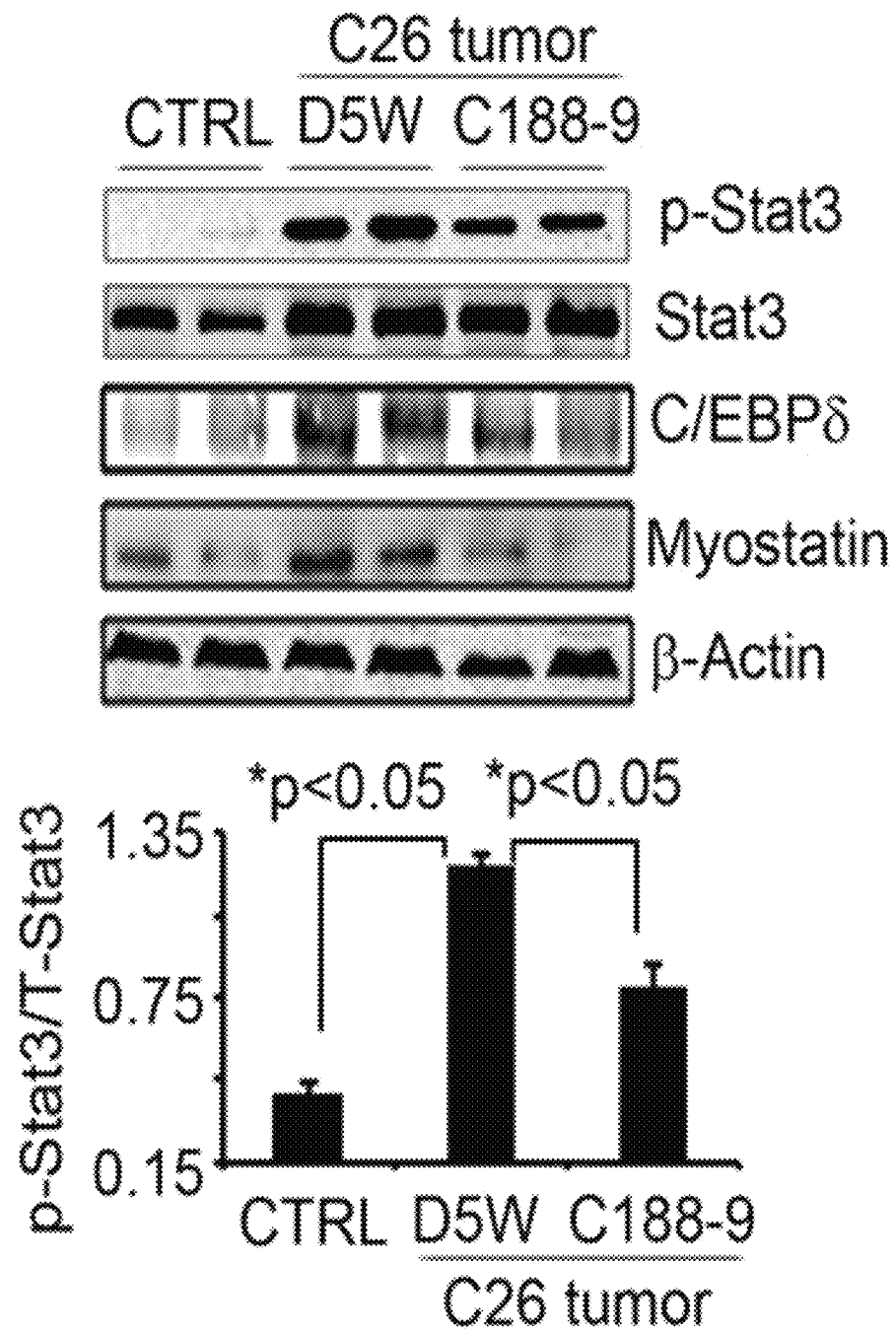
Figure 39B:
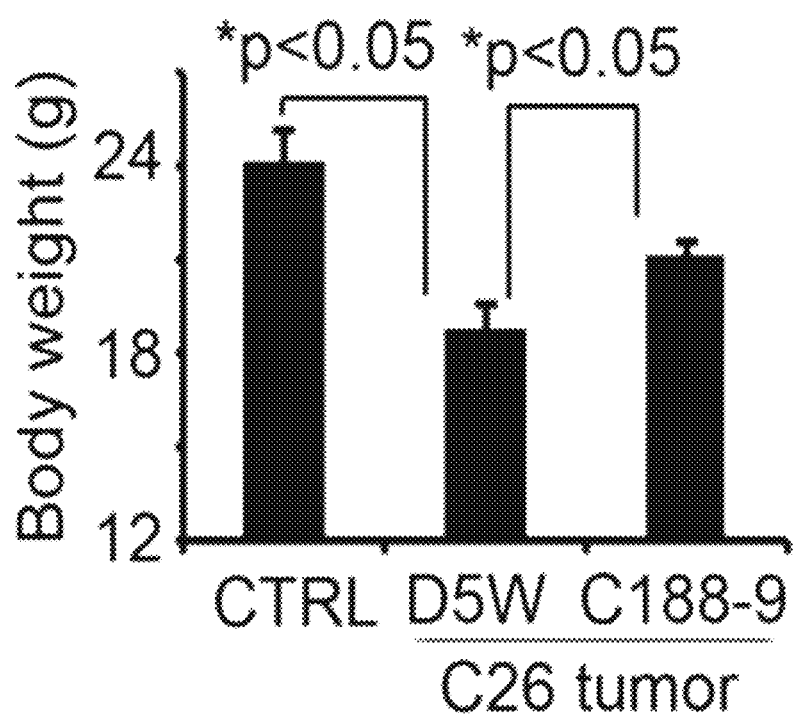
Figure 39C:
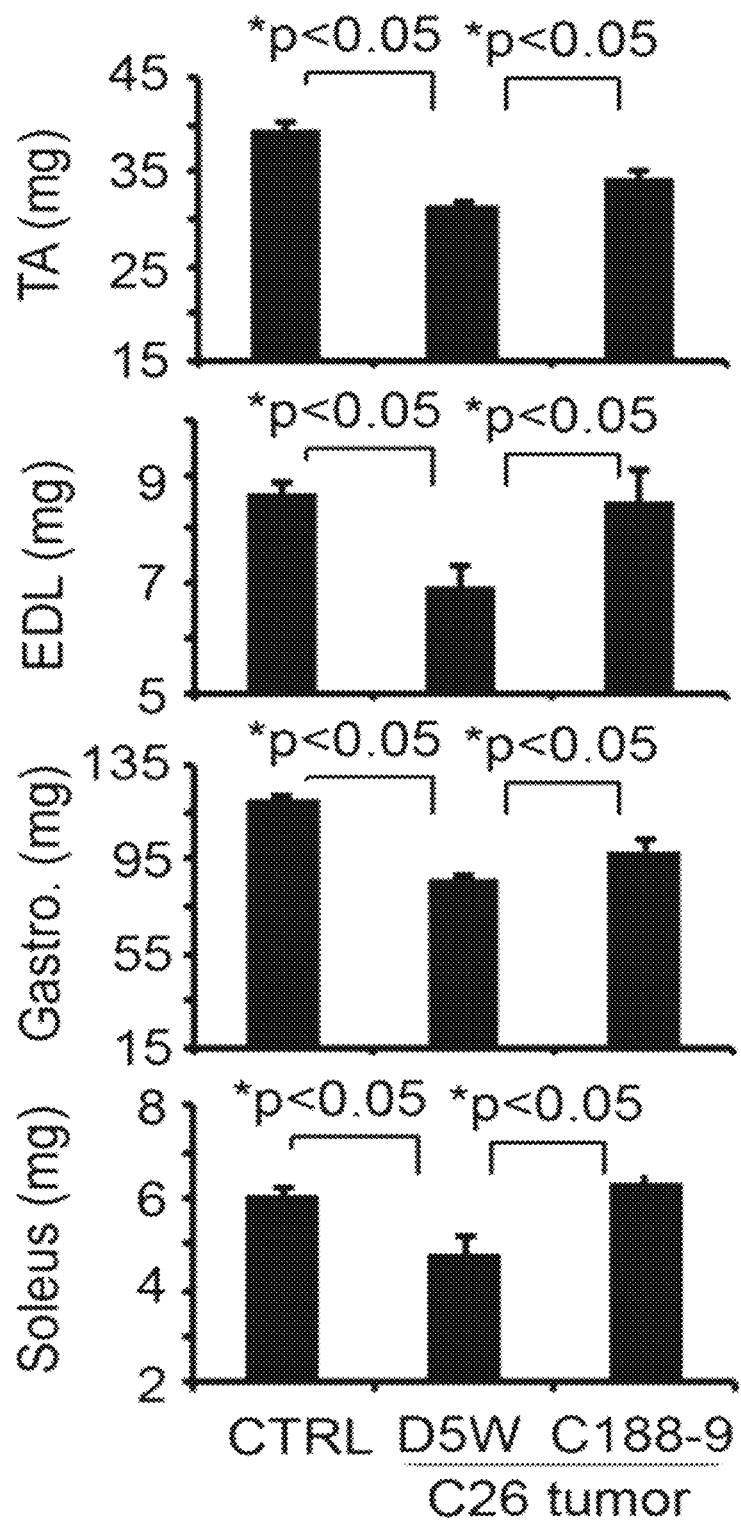
Figure 39D:
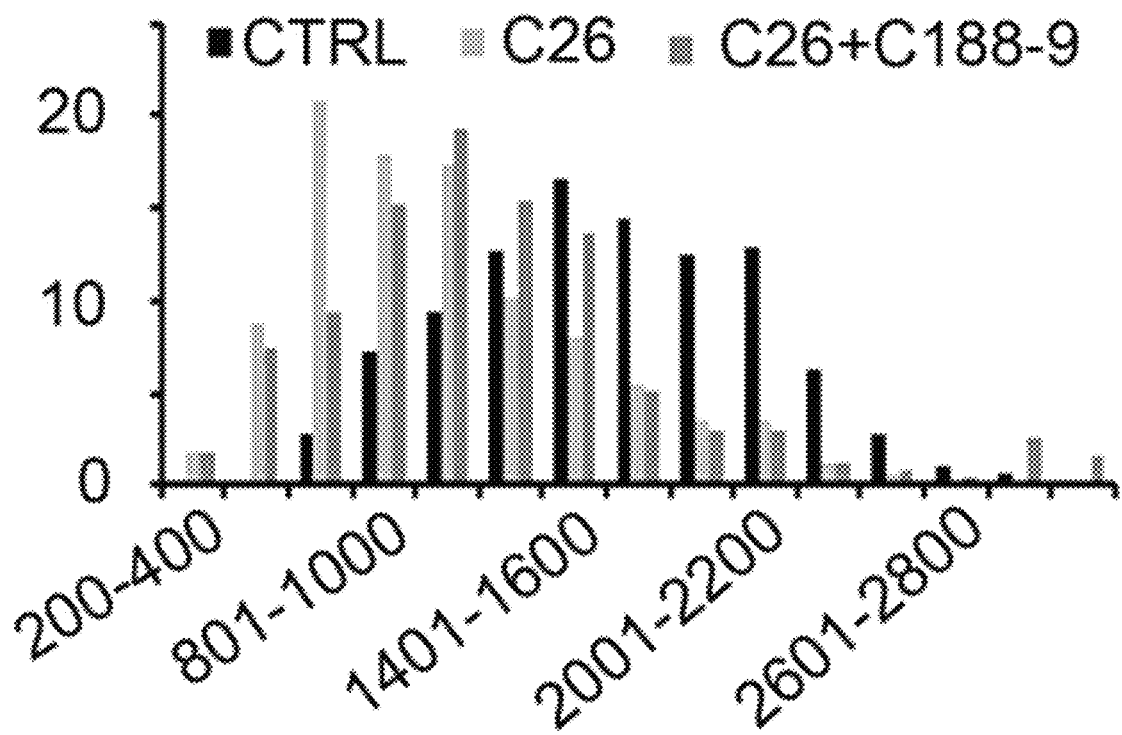
Figure 39E:
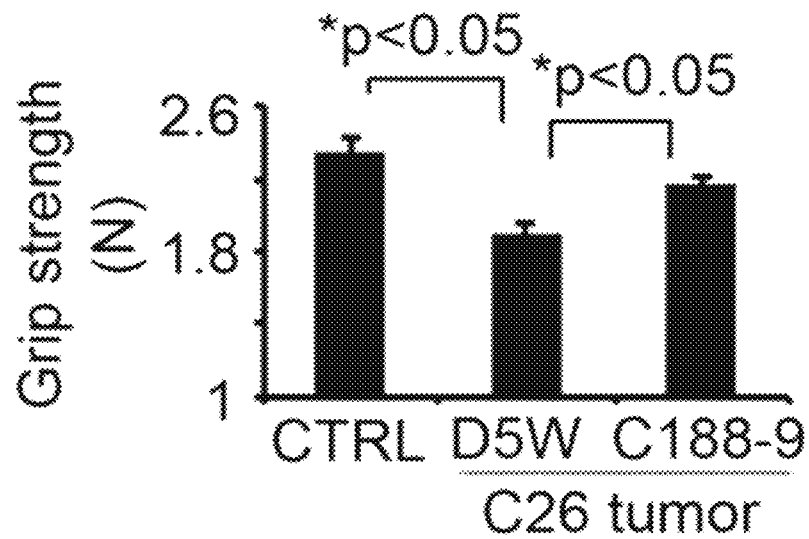
Figure 39F:
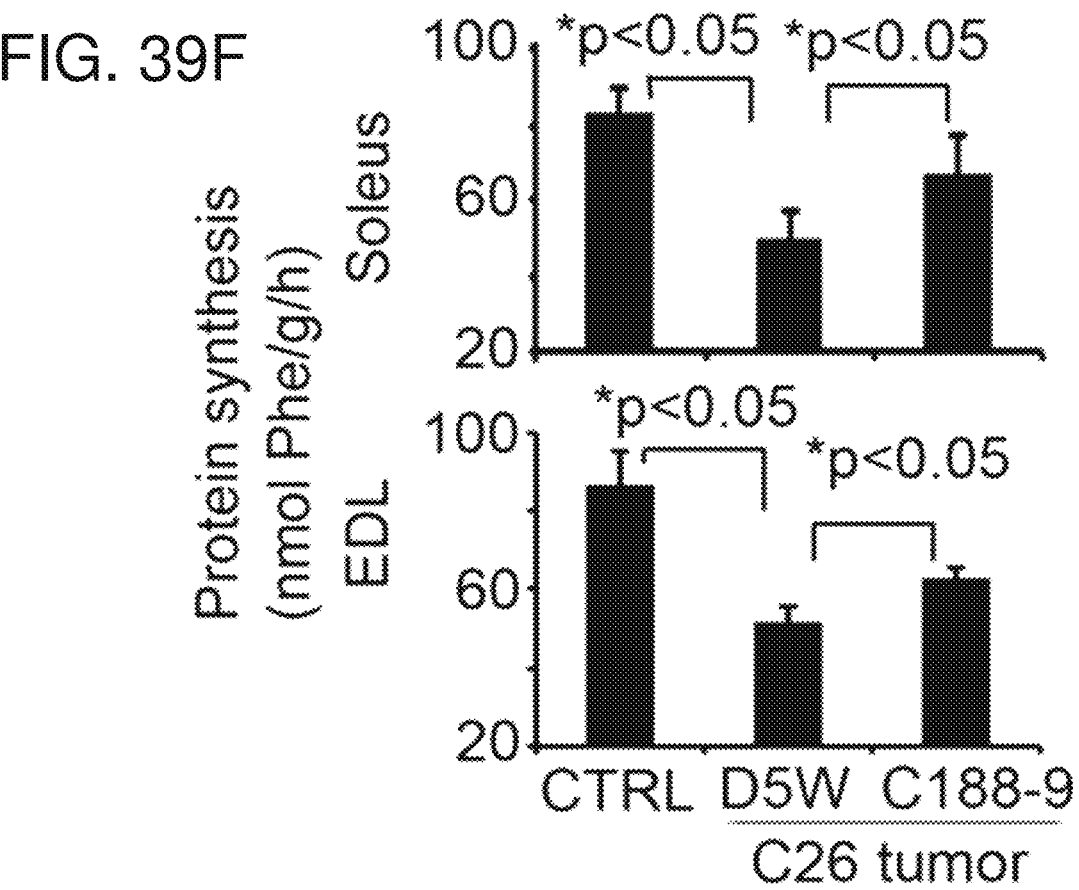
Figure 39G:
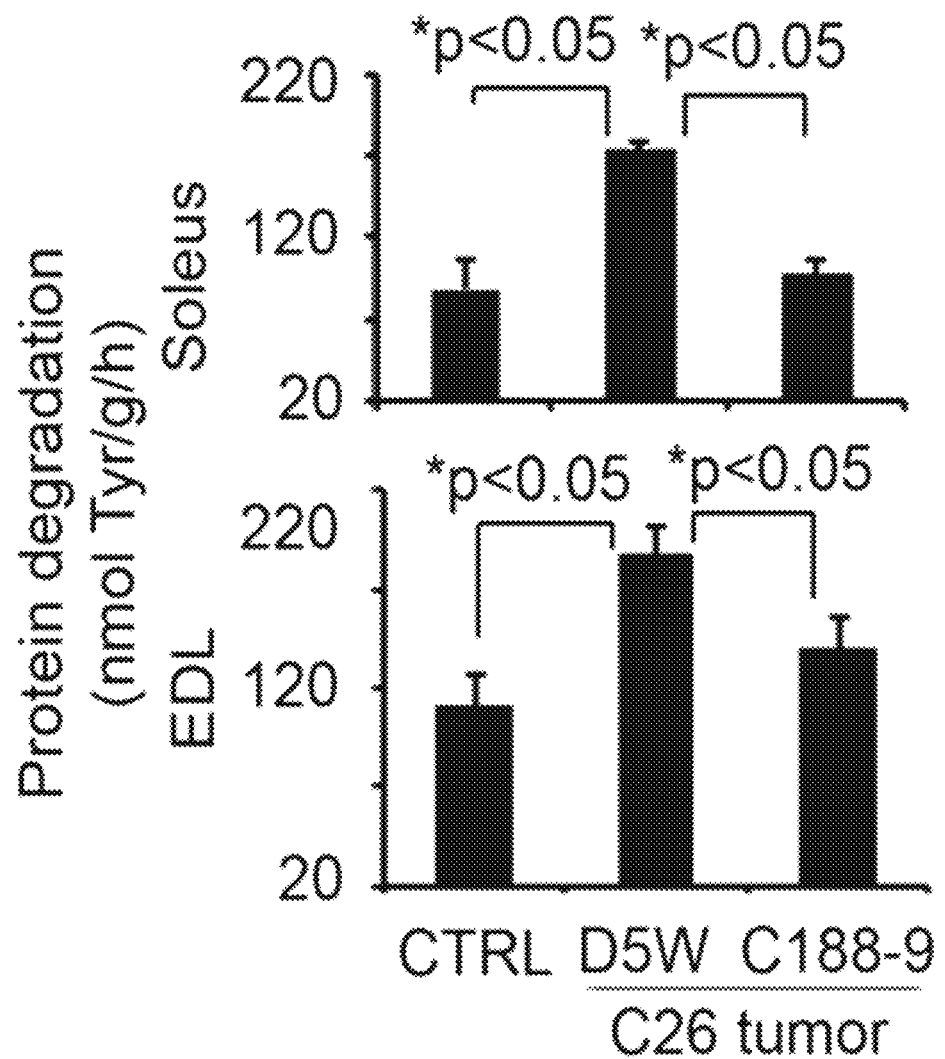

FIGS. 39A-39G provides that blocking Stat3 activation with C188-9, a Stat3 inhibitor, suppresses cancer cachexia. CD2F1 mice bearing C26 tumor for 5 days were treated with C188-9 twice daily for 14 days. Results from these mice were compared to those of CD2F1 mice bearing tumor and treated with the diluent, 5% dextose in water (D5W). CD2F1 mice without C26 tumors served as the control mice. There were 12 mice in each group. FIG. 39A. representative western blots of different proteins (upper panel) were quantified (lower panel). Results shown are: FIG. 39B. body weights; FIG. 39C. muscle weights; FIG. 39D. the distribution of myofiber sizes of in the 3 groups of mice; FIG. 39E. muscle grip strength; and FIGS. 39F & 39G are measured rates of protein synthesis and degradation. Results are mean±SEM.

Figure 40A:
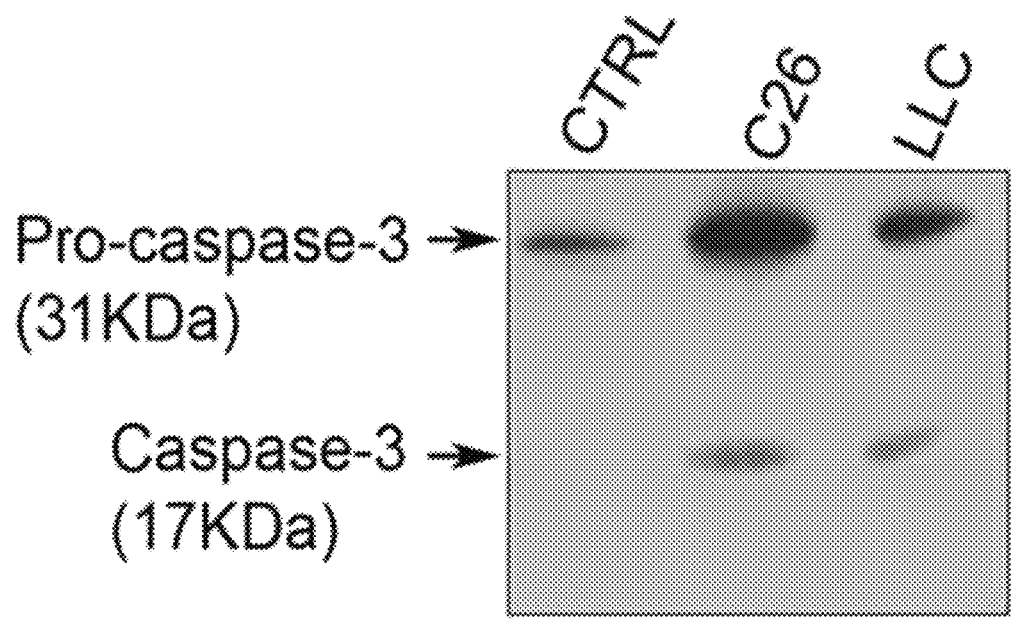
Figure 40B:
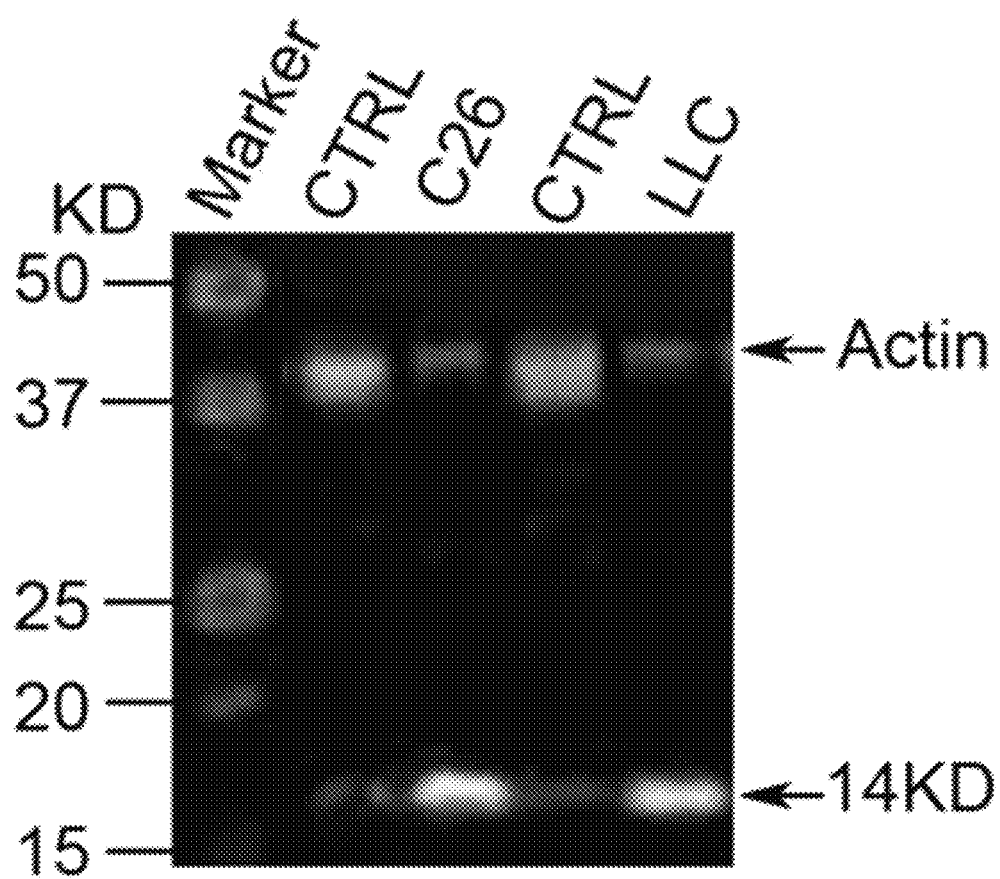
Figure 40C:
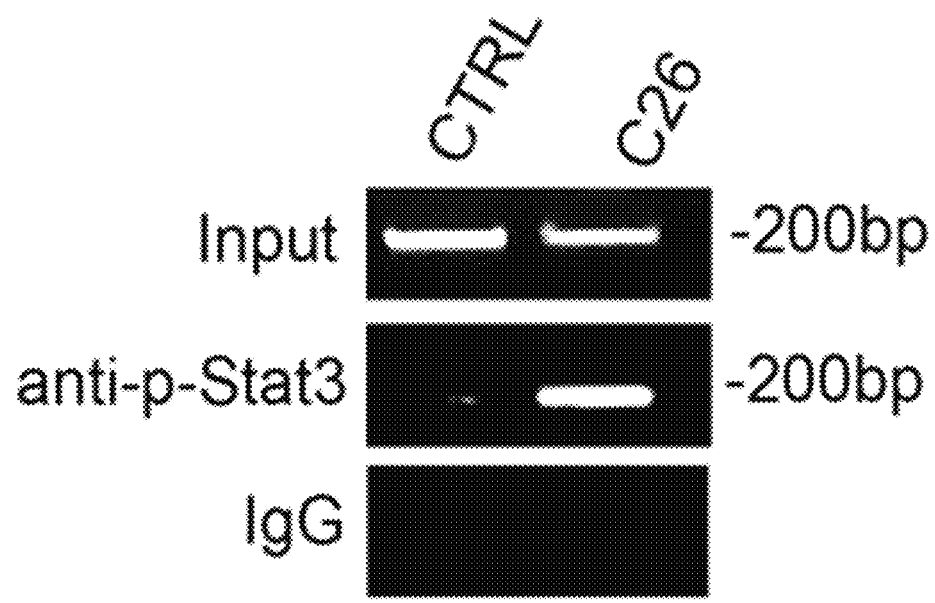
Figure 40D:
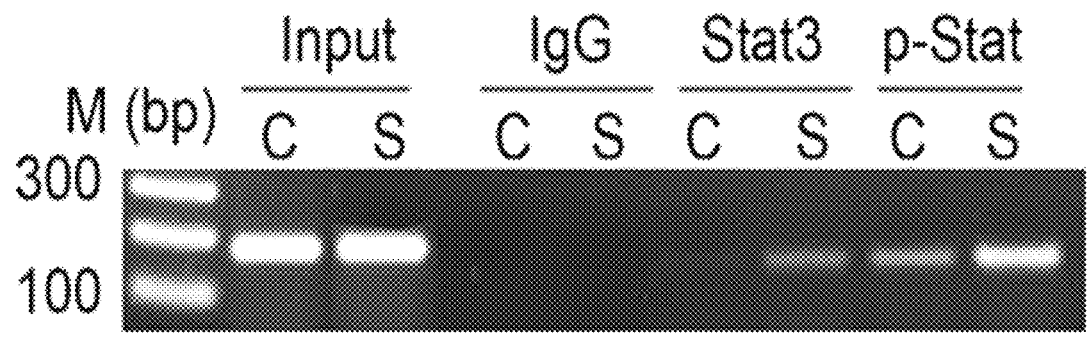
Figure 40E:
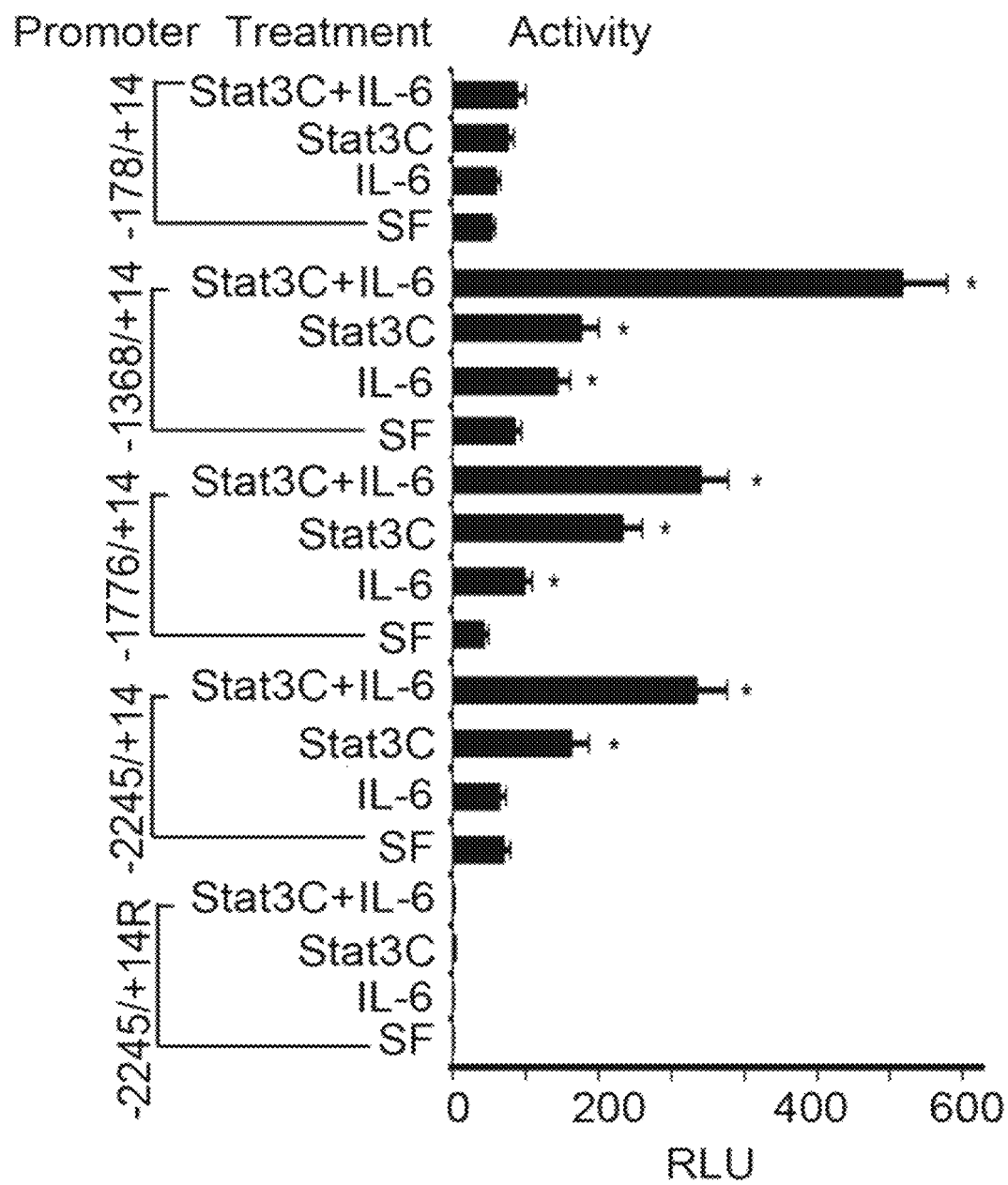

FIGS. 40A-40E shows that p-Stat3 stimulates the transcription of caspase-3, participating in the development of cancer cachexia. FIG. 40A. representative western blot reveals increased levels of procaspase-3 and caspase-3 in muscles of mice bearing C26 or LLC. FIG. 40B. representative western blot demonstrating increased caspase-3 activity measured as the cleavage of actin to produce the 14 kDa actin fragment, characteristic of catabolic conditions. FIG. 40C. C2Cl2 myotubes were treated for 24 hours with conditioned media from C26 cells. A ChiP assay shows that p-Stat3 binds to the caspase-3 promoter. FIG. 40D. C2Cl2 myotubes were infected with an adenovirus expressing GFP or Stat3. After 24 hours, cells expressing Stat3C were stimulated by IL-6. Results of a ChiP assay using anti-p-Stat3 or anti-Stat-3 revealed binding of Stat3 to the caspase-3 promoter. FIG. 40E. C2Cl2 cells were transfected with different segments of a caspase-3 promoter-luciferase construct plus a plasmid that expresses constitutively active Stat3. Subsequently, cells were treated with or without IL-6 for 6 h. and luciferase activity was used to assess caspase-3 promoter activity. Results are mean±SEM.

Figure 41A:
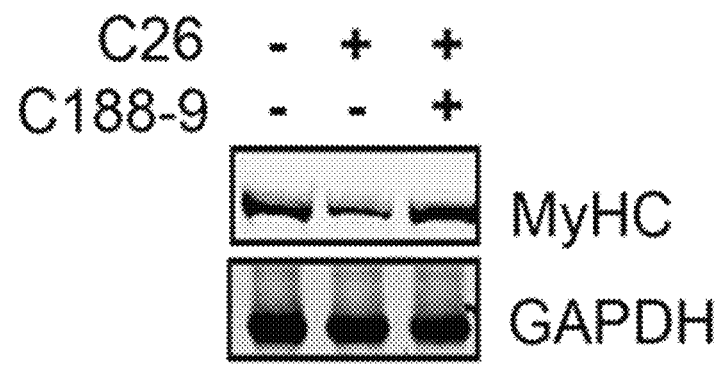
Figure 41B:
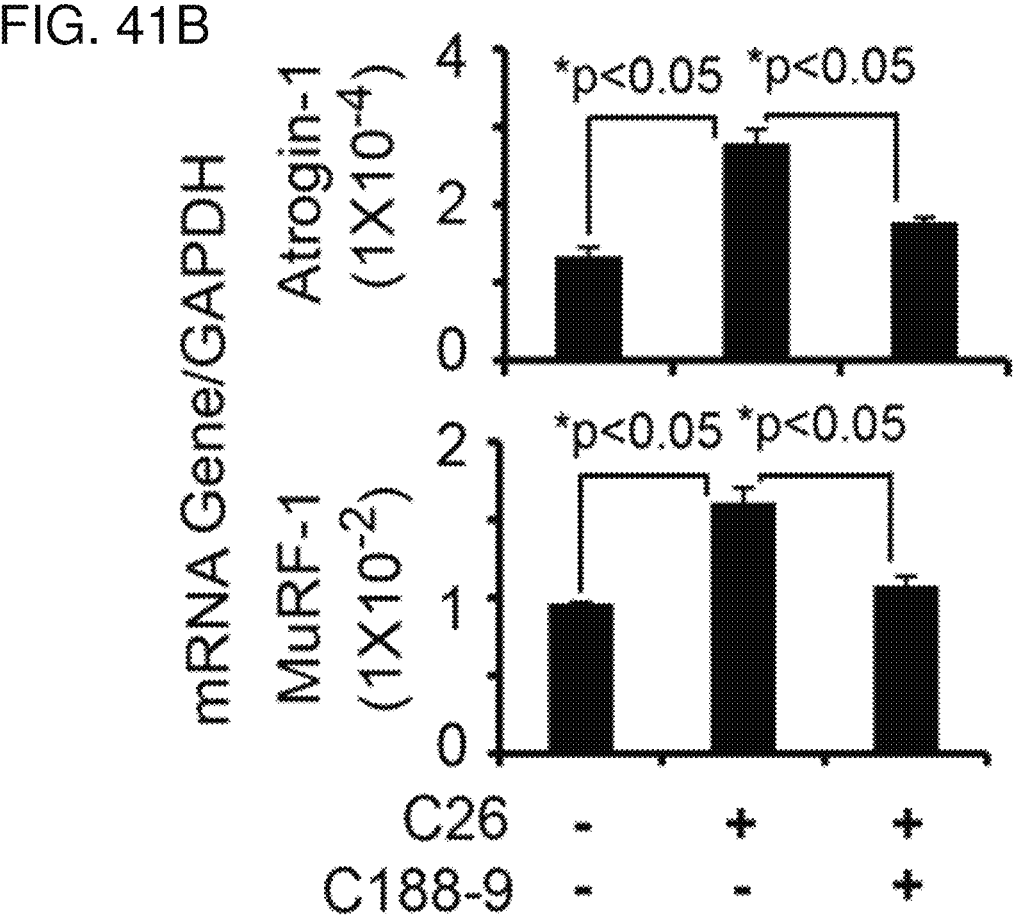
Figure 41C:
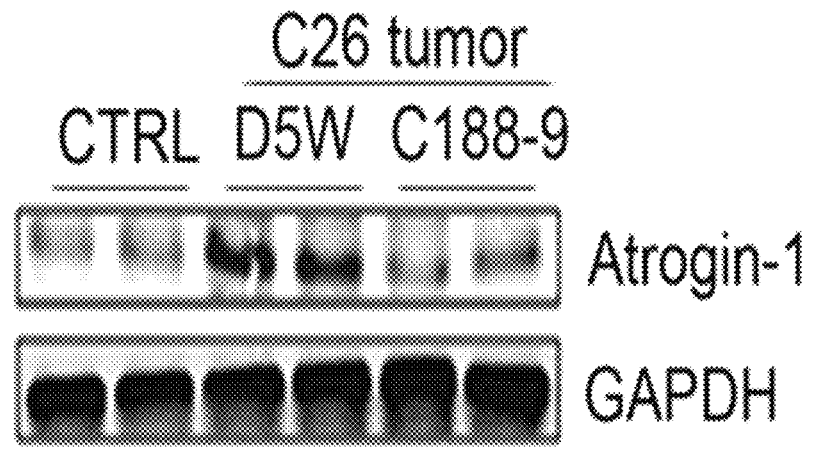
Figure 41D:
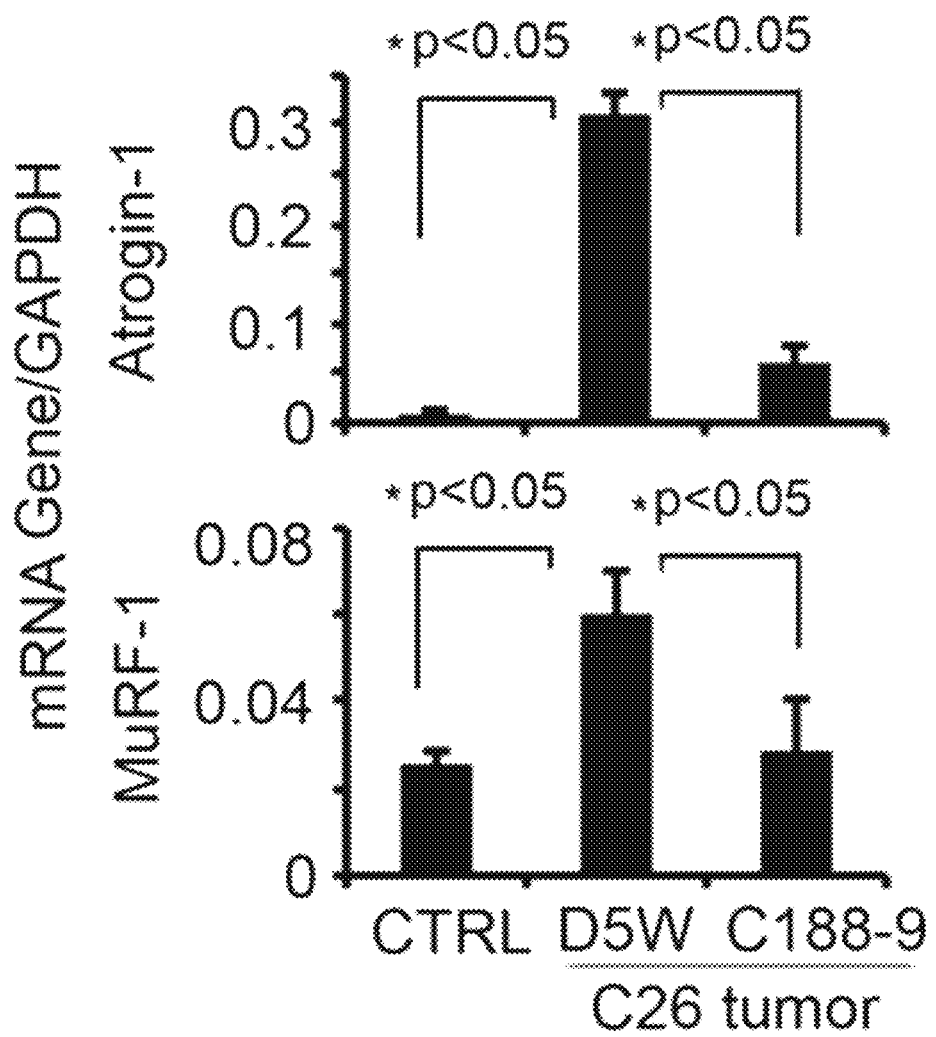
Figure 41E:
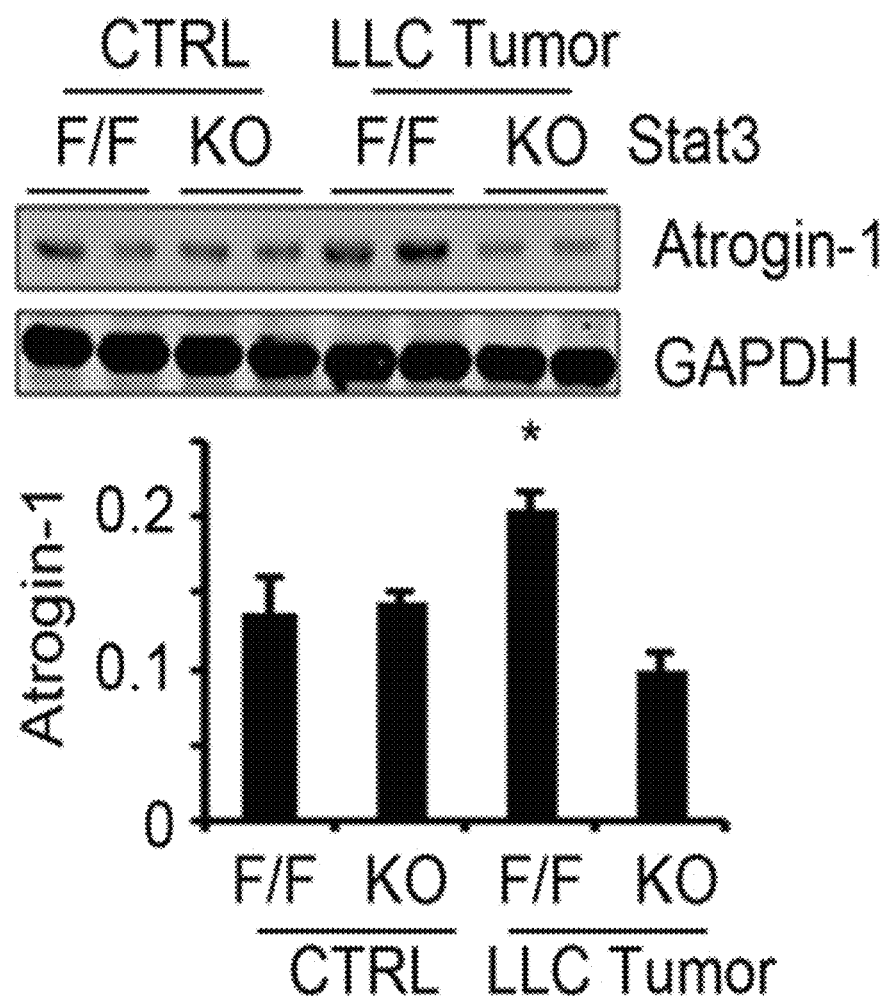
Figure 41F:
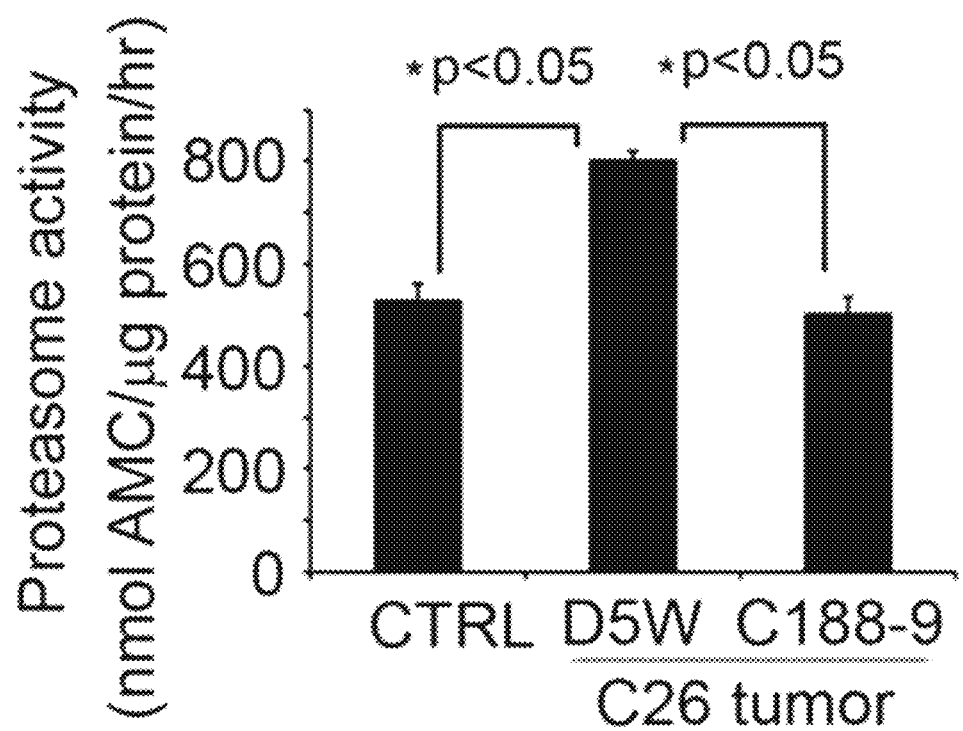

FIGS. 41A-41F shows activation of Stat3 induces ubiquitin-proteasome system in cancer-induced cachexia. FIG. 41A. C2Cl2 myotubes were treated with conditioned media from C26 cells with or without C188-9 for 72 hours. A representative western blot showing a decrease in the myosin heavy chain is blocked by C188-9. FIG. 41B. C2Cl2 myotubes were treated with conditioned media from C26 cells with or without C188-9 for 24 hours. Levels of mRNAs of MAFbx/Atrogin-1 and MuRF-1 are shown. FIGS. 41C & 41D. CD2F1 mice bearing C26 tumors were treated with C188-9 for 2 weeks. Representative western blots from lysates of gastrocnemius muscles show that C188-9 suppresses MAFbx/Atrogin-1 protein and mRNAs in mice bearing C26 tumors. FIG. 41E. LLC tumors in mice with muscle-specific KO of Stat3 or Stat3$^{flox/flox}$ and after 14 days, a representative western blot from muscle shows the protein level of MAFbx/Atrogin-1. Results are mean±SEM.

Figure 42:
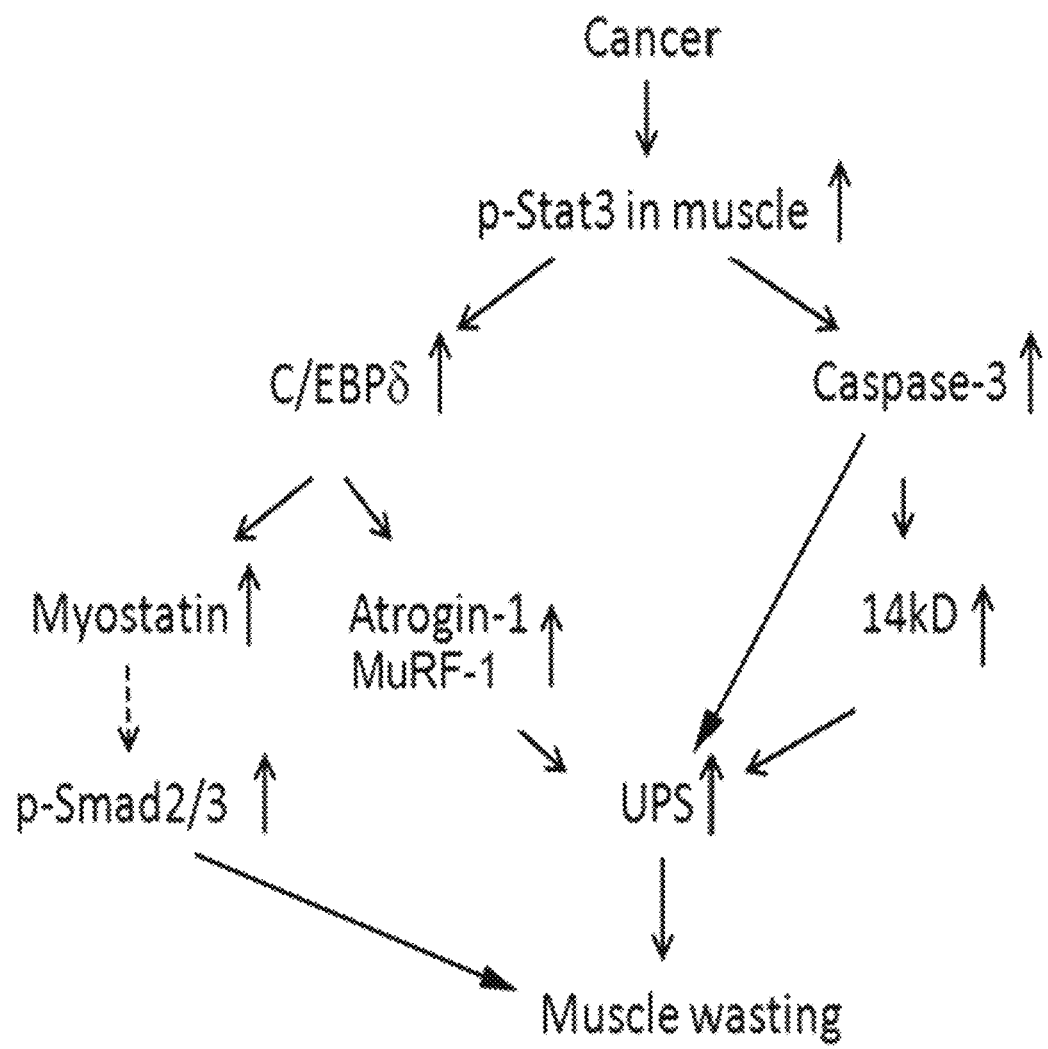

FIG. 42 illustrates a summary figure showing how cancer that activates p-Stat3 in muscle can stimulate loss of muscle mass. Stat3 activation stimulates expression of C/EBPδ which increases myostatin and MAFbx/Atrogin-1 and MuRF-1 to increase muscle wasting by the UPS. Stat3 activation also increases caspase-3 expression and activity to coordinate muscle proteolysis with the UPS.

DETAILED DESCRIPTION OF THE INVENTION

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

In some embodiments, there is a method of treating, preventing, and/or reducing the risk of a condition selected from muscle weakness, muscle wasting and cachexia or any combination thereof in an individual, comprising delivering to the individual one or more particular compounds. In some embodiments, the compound(s) is a STAT3 inhibitor. In certain embodiments the compound(s) is not a STAT3 inhibitor. In particular cases, the compound(s) is a STAT1 inhibitor, but in particular cases it is not a STAT1 inhibitor. In certain aspects, there are some compounds that are both STAT3 and STAT1 inhibitors or is neither a STAT3 or STAT1 inhibitor.

In certain embodiments of the invention, there is a compound for use in the prevention, treatment, and/or reduction in risk for a condition selected from muscle weakness, muscle wasting and cachexia or any combination thereof, wherein the compound is selected from the group consisting of N-(1',2-dihydroxy-1,2'-binaphthalen-4'-yl)-4-methoxy-benzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, or a combination thereof, a functionally active derivative, and a mixture thereof.

In certain embodiments of the invention, there is a compound for use in the prevention, treatment, and/or reduction in risk for a condition selected from muscle weakness, muscle wasting and cachexia or any combination thereof, wherein the compound is selected from the group consisting of 4-[3-(2,3-dihydro-1,4-benzodioxin-6-yl)-3-oxo-1-propen-1-yl] benzoic acid; 4{5-[(3-ethyl-4-oxo-2-thioxo-1,3-thiazolidin-5-ylidene)methyl]-2-furyl}benzoic acid; 4-[({3-

[(carboxymethyl)thio]-4-hydroxy-1-naphthyl}amino)sulfonyl] benzoic acid; 3-({2-chloro-4-[(1,3-dioxo-1,3-dihydro-2H-inden-2-ylidene)methyl]-6-ethoxyphenoxy}methyl) benzoic acid; methyl 4-({[3-(2-methyoxy-2-oxoethyl)-4,8-dimethyl-2-oxo-2H-chromen-7-yl]oxy}methyl)benzoate; 4-chloro-3-{5-[(1,3-diethyl-4,6-dioxo-2-thioxotetrahydro-5 (2H)-pyrimidinylidene)methyl]-2-furyl}benzoic acid; a functionally active derivative and a mixture thereof. In a specific embodiment of the invention, the composition is a Stat3 inhibitor but does not inhibit Stat1.

In a specific embodiment of the invention, the composition is delivered in vivo in a mammal. In another embodiment the mammal is a human. In another specific embodiment the human is known to have a condition selected from muscle weakness, muscle wasting and cachexia or any combination thereof, is suspected of having a condition selected from muscle weakness, muscle wasting and cachexia or any combination thereof, or is at risk for developing a condition selected from muscle weakness, muscle wasting and cachexia or any combination thereof. In another embodiment, the human is known to have a condition selected from muscle weakness, muscle wasting and cachexia or any combination thereof and is receiving an additional therapy for the a condition selected from muscle weakness, muscle wasting and cachexia or any combination thereof and/or an underlying condition that is related to a condition selected from muscle weakness, muscle wasting and cachexia or any combination thereof. Composition(s) of the disclosure treat, prevent, and/or reduce the risk of body weight loss and/or muscle weight loss, in particular embodiments.

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

The term "inhibitor" as used herein refers to one or more molecules that interfere at least in part with the activity of Stat3 to perform one or more activities, including the ability of Stat3 to bind to a molecule and/or the ability to be phosphorylated.

The phrase "therapeutically effective amount" as used herein means that amount of a compound, material, or composition comprising a compound of the present invention that is effective for producing some desired therapeutic effect, e.g., treating (i.e., preventing and/or ameliorating) cancer in a subject, or inhibiting protein-protein interactions mediated by an SH2 domain in a subject, at a reasonable benefit/risk ratio applicable to any medical treatment. In one embodiment, the therapeutically effective amount is enough to reduce or eliminate at least one symptom. One of skill in the art recognizes that an amount may be considered therapeutically effective even if the cancer is not totally eradicated but improved partially. For example, the spread of the cancer may be halted or reduced, a side effect from the cancer may be partially reduced or completed eliminated, life span of the subject may be increased, the subject may experience less pain, and so forth.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "at risk for having muscle wasting" as used herein refers to an individual that is at risk for having less than their normal level of strength or too little muscle or having loss in muscle, such as an individual that has an underlying medical condition with such a symptom or is elderly.

The phrase "at risk for having cachexia" is used herein to refer to individuals that have a chance to have cachexia because of past, present, or future factors. In particular embodiments, an individual at risk for having cachexia is one that has an underlying condition that is known to cause or be associated with cachexia as at least one symptom. The condition may or may not be chronic. In some embodiments, an underlying medical condition that is known to have cachexia as at least one symptom includes at least renal failure, cancer, AIDS, HIV infection, chronic obstructive lung disease (including emphysema), multiple sclerosis, congestive heart failure, tuberculosis, familial amyloid polyneuropahty, acrodynia, hormonal deficiency, metaoblic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, myositis, polymyositis, dematomyosytis, rheumatological diseases, autoimmune disease, collogen-vascular disease, visceral leishmaniasis, prolonged bed rest, and/or addiction to drugs, such as amphetamine, opiates, or barbitutates.

As used herein, "binding affinity" refers to the strength of an interaction between two entities, such as a protein-protein interaction. Binding affinity is sometimes referred to as the $K_a$, or association constant, which describes the likelihood of the two separate entities to be in the bound state. Generally, the association constant is determined by a variety of methods in which two separate entities are mixed together, the unbound portion is separated from the bound portion, and concentrations of unbound and bound are measured. One of skill in the art realizes that there are a variety of methods for measuring association constants. For example, the unbound and bound portions may be separated from one another through adsorption, precipitation, gel filtration, dialysis, or centrifugation, for example. The measurement of the concentrations of bound and unbound portions may be accomplished, for example, by measuring radioactivity or fluorescence, for example. $K_a$ also can be inferred indirectly through determination of the $K_i$ or inhibitory constant. Determination of the $K_i$ can be made several ways for example by measuring the $K_a$ of STAT3 binding to its phosphopeptide ligand within the EGFR at position Y1068 and by measuring the concentration of a molecule that reduces binding of STAT3 by 50%. In certain embodiments of the invention, the binding affinity of a Stat3 inhibitor for the SH2 domain of Stat3 is similar to or greater than the affinity of the compounds listed herein.

The term "domain" as used herein refers to a subsection of a polypeptide that possesses a unique structural and/or functional characteristic; typically, this characteristic is similar across diverse polypeptides. The subsection typically comprises contiguous amino acids, although it may also comprise amino acids that act in concert or that are in close proximity due to folding or other configurations. An example of a protein domain is the Src homology 2 (SH2) domain of Stat3. The term "SH2 domain" is art-recognized, and, as used herein, refers to a protein domain involved in protein-protein interactions, such as a domain within the Src tyrosine kinase that regulates kinase activity. The invention contemplates modulation of activity, such as activity dependent upon protein-protein interactions, mediated by SH2 domains of proteins (e.g., tyrosine kinases such as Src) or proteins involved with transmission of a tyrosine kinase signal in organisms including mammals, such as humans.

As used herein, a "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, and chimpanzees. Mammals may be referred to as "patients" or "subjects" or "individuals".

II. General Embodiments

General embodiments include one or more compositions for the treatment and/or prevention and/or reduction in risk or severity of a condition selected from muscle weakness, muscle wasting and cachexia or any combination thereof and methods of use. The muscle weakness and/or muscle wasting and/or cachexia may have an unknown cause or it may be associated with an underlying condition. The underlying condition may be a catabolic condition. The underlying condition may be chronic kidney disease, diabetes, cancer, AIDS, and so forth.

In some cases an individual is suspected of having a condition selected from muscle weakness, muscle wasting and cachexia or any combination thereof; such suspicion may be because the individual has unintentional muscle and/or weight loss. In certain aspects, such suspicion may be because the individual has muscle loss. In some cases, an individual may have at least one symptom of a condition selected from muscle weakness, muscle wasting and cachexia or any combination thereof but may have other symptoms as well.

In certain cases, an individual is at risk of having a condition selected from muscle weakness, muscle wasting and cachexia or any combination thereof. In such cases, the individual has a medical condition that can be associated with muscle wasting and/or muscle weakness and/or cachexia and has not had enough progression of the medical condition to manifest muscle wasting and/or muscle weakness and/or cachexia or has not yet had a detectable symptom of muscle wasting and/or muscle weakness and/or cachexia.

In some embodiments, the individual is known to have an underlying condition that often has muscle wasting and/or muscle weakness and/or cachexia as at least one symptom, and that individual may or may have not shown a sign of having muscle wasting and/or muscle weakness and/or cachexia. In cases wherein an individual has an underlying condition that often has muscle wasting and/or muscle weakness and/or cachexia as at least one symptom, the individual may be provided with an effective amount of one or more compositions of the invention prior to and/or after the appearance of muscle wasting and/or muscle weakness and/or cachexia. When the individual is provided one of more compositions prior to the appearance of muscle wasting and/or muscle weakness and/or cachexia, the onset of muscle wasting and/or muscle weakness and/or cachexia may be delayed or completely inhibited and/or the severity of the muscle wasting and/or muscle weakness and/or cachexia may be reduced, compared to the condition of the individual without having received the composition(s), for example.

In particular embodiments, an individual has been diagnosed with an underlying condition known to have muscle wasting and/or muscle weakness and/or cachexia as at least one symptom, and methods of the invention may include steps of diagnosing of the muscle weakness and/or muscle wasting and/or cachexia and/or the underlying condition of the individual. An individual may be tested for muscle wasting by standard means in the art.

III. Muscle Wasting and/or Muscle Weakness and/or Cachexia

Embodiments of the invention concern methods of treatment and/or prevention of any kind of a condition selected from muscle weakness, muscle wasting, cachexia, and any combination thereof.

Muscle wasting and/or muscle weakness embodiments may arise in the context of the individual also having cachexia, or the individual may not also have cachexia. The muscle wasting and/or muscle weakness may be the result of age or it may be the result of an underlying medical condition. The muscle wasting and/or muscle weakness may manifest prior to or after the detection of other symptoms of the underlying medical condition. The muscle wasting may be completely prevented or reversed or there may be a delay in onset and/or severity upon use of one or more compositions of the invention.

Muscle wasting and/or muscle weakness may be tested for by a variety of ways, including physical examination; sitting and standing tests; walking tests; measurement of body mass index; reflex tests; blood tests for muscle enzymes; CT scan; measurement of total body nitrogen; muscle biopsy; and/or electromyogram, for example.

Cachexia, which may also be referred to as wasting syndrome, occurs when there is a loss of body mass that cannot be reversed by nutritional means. Examples of symptoms of cachexia include weight loss, muscle atrophy, fatigue, weakness, and/or considerable appetite loss in an individual that is not actively seeking to lose weight. In particular aspects, the cachexia is the result of a primary pathology, such as given that even if the affected individual consumes more calories, there is loss of body mass. In specific cases, skeletal muscle depletion is a prognostic factor.

In embodiments of the invention, the individual may be known to have the medical condition associated with the muscle wasting and/or muscle weakness and/or cachexia, although in some cases the individual is not known to have the medical condition. In particular cases, an individual has muscle wasting and/or muscle weakness and/or cachexia as a symptom of an underlying medical condition that is either known or not known. An individual may present with muscle wasting, muscle weakness and/or cachexia as the first symptom and the doctor may then look for an underlying condition. An individual may present with the underlying medical condition and the doctor may monitor the individual for the onset of muscle wasting and/or muscle weakness and/or cachexia or may recognize one or more symptoms of muscle wasting and/or muscle weakness and/or cachexia.

In embodiments of the invention, one or more of the compositions are provided to an individual with a condition selected from muscle weakness, muscle wasting and cachexia or any combination thereof in addition to another agent for muscle wasting and/or muscle weakness and/or cachexia treatment. Examples of cachexia treatment include anabolic steroids; drugs that mimic progesterone; BMS-945429 (also known as ALD518); Enobosarm; propranolol and etodolac; omega-3 fatty acids; medical marijuana, IGF-1; nutritional supplements and/or exercise.

In particular embodiments, the individual has cancer cachexia. Approximately half of all cancer patients have cachexia. Although cachexia can occur in any type of cancer, those individuals with upper gastrointestinal and pancreatic cancers have the highest frequency of developing a cachexic symptom. The individual may have terminal cancer. The individual may have metastatic cancer.

In some embodiments the individual has a severe case of cachexia, such as where the affected individual is so physically weak that the individual is in a state of immobility resulting from loss of appetite, asthenia, and/or anemia, for example.

IV. Compositions

Embodiments of the invention encompass compositions that are useful for treating, preventing, and/or reducing the risk of a condition selected from muscle weakness, muscle wasting and cachexia or any combination thereof. Specific compositions are disclosed herein, but one of skill in the art recognizes that functional derivatives of such compositions are also encompassed by the invention. The term "derivative" as used herein is a compound that is formed from a similar compound or a compound that can be considered to arise from another compound, if one atom is replaced with another atom or group of atoms. Derivative can also refer to compounds that at least theoretically can be formed from the precursor compound.

In particular embodiments, compositions and functionally active derivatives as described herein are utilized in treatment and/or prevention and/or reduction in the risk and/or severity of a condition selected from muscle weakness, muscle wasting and cachexia or any combination thereof. Specific but nonlimiting examples of different R groups for the compositions are provided in Tables 1, 2, and 3.

In particular embodiments, there are compositions selected from the group consisting of N-(3,1'-Dihydroxy-[1, 2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, and functional derivatives thereof.

The term "functionally active derivative" or "functional derivative" is a derivative as previously defined that retains the function of the compound from which it is derived. In one embodiment of the invention, a derivative of N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, 4-[3-(2,3-dihydro-1,4-benzodioxin-6-yl)-3-oxo-1-propen-1-yl] benzoic acid, 4{5-[(3-ethyl-4-oxo-2-thioxo-1,3-thiazolidin-5-ylidene)methyl]-2-furyl}benzoic acid, 4-[({3-[(carboxymethyl)thio]-4-hydroxy-1-naphthyl}amino)sulfonyl] benzoic acid, 3-({2-chloro-4-[(1,3-dioxo-1,3-dihydro-2H-inden-2-ylidene)methyl]-6-ethoxyphenoxy}methyl)benzoic acid, methyl 4-({[3-(2-methyoxy-2-oxoethyl)-4,8-dimethyl-2-oxo-2H-chromen-7-yl]oxy}methyl) benzoate, or 4-chloro-3-{5-[(1,3-diethyl-4,6-dioxo-2-thioxotetrahydro-5(2H)-pyrimidinylidene)methyl]-2-furyl}benzoic acid retains Stat3 inhibitory activity. In another embodiment of the invention, a derivative of 4-[3-(2,3-dihydro-1,4-benzodioxin-6-yl)-3-oxo-1-propen-1-yl] benzoic acid, 4{5-[(3-ethyl-4-oxo-2-thioxo-1,3-thiazolidin-5-ylidene) methyl]-2-furyl}benzoic acid, 4-[({3-[(carboxymethyl)thio]-4-hydroxy-1-naphthyl}amino)sulfonyl]benzoic acid, 3-({2-chloro-4-[(1,3-dioxo-1,3-dihydro-2H-inden-2-ylidene) methyl]-6-ethoxyphenoxy}methyl)benzoic acid, methyl 4-({[3-(2-methyoxy-2-oxoethyl)-4,8-dimethyl-2-oxo-2H-chromen-7-yl]oxy}methyl)benzoate, or 4-chloro-3-{5-[(1,3-diethyl-4,6-dioxo-2-thioxotetrahydro-5(2H)-pyrimidinylidene)methyl]-2-furyl}benzoic acid retains Stat3 inhibitory activity and, in specific embodiments, also retains non-inhibition of Stat1, although in some cases it may also inhibit Stat1.

In a specific embodiment of the invention, there is a method of treating and/or preventing and/or reducing the risk and/or severity of a condition selected from muscle weakness, muscle wasting and cachexia or any combination thereof in an individual comprising delivering to the individual a compound selected from the group consisting of N-(1',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, 4-Bromo-N-[4-hydroxy-3-(1H-[1,2,4]triazol-3-ylsulfanyl)-naphthalen-1-yl]-benzenesulfonamide, 4-[3-(2,3-dihydro-1,4-benzodioxin-6-yl)-3-oxo-1-propen-1-yl] benzoic acid 4{5-[(3-ethyl-4-oxo-2-thioxo-1,3-thiazolidin-5-ylidene)methyl]-2-furyl}benzoic acid, 4-[({3-[(carboxymethyl)thio]-4-hydroxy-1-naphthyl}amino)sulfonyl] benzoic acid, 3-({2-chloro-4-[(1,3-dioxo-1,3-dihydro-2H-inden-2-ylidene) methyl]-6-ethoxyphenoxy}methyl)benzoic acid, methyl 4-({[3-(2-methyoxy-2-oxoethyl)-4,8-dimethyl-2-oxo-2H- chromen-7-yl]oxy}methyl)benzoate, 4-chloro-3-{5-[(1,3-diethyl-4,6-dioxo-2-thioxotetrahydro-5(2H)-pyrimidinylidene)methyl]-2-furyl}benzoic acid, and a mixture thereof.

In another embodiment, the composition comprises the general formula:

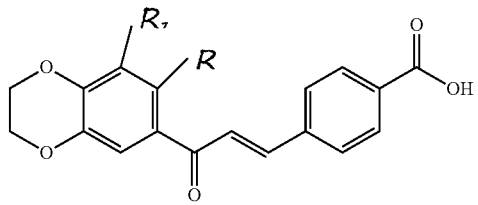

wherein $R_1$ and $R_2$ may be the same or different and are selected from the group consisting of hydrogen, carbon, sulfur, nitrogen, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the composition comprises the general formula:

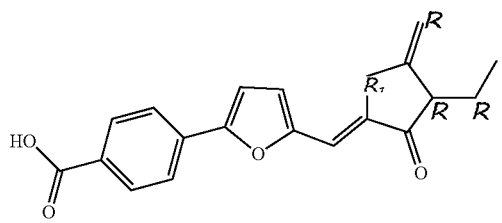

wherein $R_1$, and $R_3$ may be the same or different and are selected from the group consisting of hydrogen, carbon, nitrogen, sulfur, oxygen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives, and $R_2$ and $R_4$ may be the same or different and are selected from the group consisting of hydrogen, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

In another embodiment of the invention, the composition comprises the general formula:

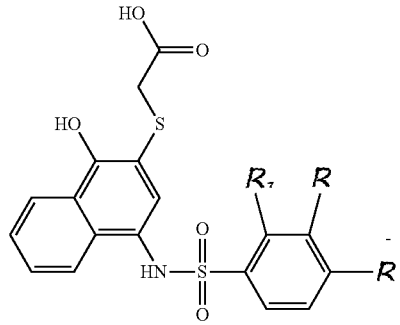

wherein $R_1$, $R_2$, and $R_3$ may be the same or different and are selected from the group consisting of hydrogen, carboxyl, alkanes. cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes. arene-based derivatives, heteroarene-based derivatives, phenols, phenol-based derivatives, benzoic acid, and benzoic acid-based derivatives.

An exemplary and illustrative list of alkanes, cyclic alkanes, and alkane-based derivates are described herein. Non-limiting examples of ketones, ketone-based derivatives, aldehydes, aldehyde-based derivatives; carboxylic acids, carboxylic acid-based derivatives, ethers, ether-based derivatives, esters, ester-based derivatives, amines, amino-based derivatives, amides, and amide-based derivatives are listed herein. Exemplary monocyclic or polycyclic arene, heteroarenes, arene-based or heteroarene-based derivatives, phenols, phenol-based derivatives, benzoic acid and benzoic acid-based derivatives are described herein.

TABLE 1

| Chemical names | Formulas |
| --- | --- |
| Methyl | $CH_3$ |
| Ethyl | $C_2H_5$ |
| Vinyl (ethenyl) | $C_2H_3$ |
| Ethynyl | $C_2H$ |
| Cyclopropyl | $C_3H_5$ |
| Cyclobutyl | $C_4H_7$ |
| Cyclopentyl | $C_5H_9$ |
| Cyclohexyl | $C_6H_{11}$ |

TABLE 2

| Chemical names | Chemical formulas |
| --- | --- |
| Acetonyl | $C_3H_5O$ |
| Methanal (formaldehyde) | $CH_2O$ |
| Paraldehyde | $C_6H_{12}O_3$ |
| Ethanoic acid | $CH_3COOH$ |
| Diethyl ether | $C_4H_{10}O$ |
| Trimethylamine | $C_3H_9N$ |
| Acetamide | $C_2H_5NO$ |

TABLE 2-continued

| Chemical names | Chemical formulas |
|---|---|
| Ethanol | $C_2H_5OH$ |
| Methanol | $CH_3OH$ |

TABLE 3

| Chemical names | Chemical formulas |
|---|---|
| Benzol | $C_6H_6$ |
| Phenol | $C_6H_6O$ |
| Benzoic acid | $C_7H_6O_2$ |
| Aniline | $C_6H_7N$ |
| Toluene | $C_7H_8$ |
| Pyridazine | $C_4H_4N_2$ |
| Pyrimidine | $C_4H_4N_2$ |
| Pyrazine | $C_4H_4N_2$ |
| Biphenyl | $C_{12}H_{10}$ |

The compositions of the present invention and any functionally active derivatives thereof may be obtained by any suitable means. In specific embodiments, the derivatives of the invention are provided commercially, although in alternate embodiments the derivatives are synthesized. The chemical synthesis of the derivatives may employ well known techniques from readily available starting materials. Such synthetic transformations may include, but are not limited to protection, de-protection, oxidation, reduction, metal catalyzed C—C cross coupling, Heck coupling or Suzuki coupling steps (see for example, March's Advanced Organic Chemistry: Reactions, Mechanisms, and Structures, 5' Edition John Wiley and Sons by Michael B. Smith and Jerry March, incorporated here in full by reference).

V. Embodiments for Targeting Stat3

STAT proteins, of which there are seven (1, 2, 3, 4, 5A, 5B and 6), transmit peptide hormone signals from the cell surface to the nucleus. Detailed structural information of STAT proteins currently is limited to Stat1 and Stat3. Stat1 was the first STAT to be discovered (Fu et al., 1992) and is required for signaling by the Type I and II IFNs (Meraz et al, 1996; Wiederkehr-Adam et al, 2003; Durbin et al, 1996; Haan et al., 1999). Studies in Stat1-deficient mice (Meraz et al, 1996; Durbin et al, 1996; Ryan et al., 1998) support an essential role for Stat1 in innate immunity, notably against viral pathogens. In addition, Stat1 is a potent inhibitor of growth and promoter of apoptosis (Bromberg and Darnell, 2000). Also, because tumors from carcinogen-treated wild-type animals grow more rapidly when transplanted into the Stat1-deficient animals than they do in a wild-type host, Stat1 contributes to tumor surveillance (Kaplan et al., 1998).

Stat3 was originally termed acute-phase response factor (APRF) because it was first identified as a transcription factor that bound to IL-6-response elements within the enhancer-promoter region of various acute-phase protein genes (Akira, 1997). In addition to receptors for the IL-6 cytokine family, other signaling pathways are linked to Stat3 activation include receptors for other type I and type II cytokine receptors, receptor tyrosine kinases, G-protein-coupled receptors and Src kinases (Schindler and Darnell, 1995; Turkson et al., 1998). Targeted disruption of the mouse Stat3 gene leads to embryonic lethality at 6.5 to 7.5 days (Takeda et al., 1997) indicating that Stat3 is essential for early embryonic development possibly gastrulation or visceral endoderm function (Akira, 2000). Tissue-specific deletion of Stat3 using Cre-lox technology has revealed decreased mammary epithelial cell apoptosis resulting in delayed breast involution during weaning (Chapman et al., 1999). Recent findings indicate that switching of the predominant STAT protein activated by a given receptor can occur when a STAT downstream of that receptor is genetically deleted (Costa-Pereira et al., 2002; Qing and Stark, 2004). These findings suggest the possibility that the effect of Stat3 deletion in breast tissue may be mediated indirectly by increased activation of other STAT proteins, especially Stat5.

Stat1 and Stat3 isoforms. Two isoforms of Stat1 and Stat3 have been identified—α (p91 and p92, respectively) and β (p84 and p83, respectively) (Schindler et al., 1992; Schaefer et al., 1995; Caldenhoven et al., 1996; Chakraborty et al., 1996)—that arise due to alternative mRNA splicing (FIG. 13). In contrast to Stat1β (712 aa), in which the C-terminal transactivation is simply deleted, the 55 amino acid residues of Stat3α are replaced in Stat3 β by 7 unique amino acid residues at its C-terminus. Unlike Stat1 β, Stat3 β is not simply a dominant-negative of Stat3α (Maritano et al., 2004) and regulates gene targets in a manner distinct from Stat3 β (Maritano et al., 2004; Yoo et al., 2002). Stat3α has been demonstrated to contribute to transformation in cell models and many human cancers including breast cancer. Stat3α was shown to be constitutively activated in fibroblasts transformed by oncoproteins such as v-Src (Yu et al., 1995; Garcia and Jove, 1998) and to be essential for v-Src-mediated transformation (Turkson et al., 1998; Costa-Pereira et al., 2002). In contrast to Stat3α, Stat3β antagonized v-Src transformation mediated through Stat3α (Turkson et al., 1998). Overexpression of a constitutively active form of Stat3α in immortalized rat or mouse fibroblasts induced their transformation and conferred the ability to form tumors in nude mice (Bromberg et al., 1999). Stat3 has been shown to be constitutively activated in a variety of hematological and solid tumors including breast cancer (Dong et al., 2003; Redell and Tweardy, 2003) as a result of either autocrine growth factor production or dysregulation of protein tyrosine kinases. In virtually all cases, the isoform demonstrating increased activity is Stat3α.

Targeting Stat3α while sparing Stat1. Given its multiple contributory roles to oncogenesis, Stat3 has recently gained attention as a potential target for cancer therapy (Bromberg, 2002; Turkson, 2004). While several methods of Stat3 inhibition have been employed successfully and have established proof-of-principle that targeting Stat3 is potentially beneficial in a variety of tumor systems including breast cancer in which Stat3 is constitutively activated (Epling-Burnette et al., 2001; Yoshikawa et al., 2001; Li and Shaw, 2002; Catlett-Falcone et al., 1999; Mora et al., 2002; Grandis et al., 2000; Leong et al., 2003; Jing et al., 2003; Jing et al., 2004; Turkson et al., 2001; Ren et al., 2003; Shao et al., 2003; Turkson et al., 2004; Uddin et al., 2005); all have potential limitations for translation to clinical use for cancer therapy related to issues regarding delivery, specificity or toxicity.

Specific strategies that target Stat3 by identifying inhibitors of Stat3 recruitment and/or dimerization have been pursued by several groups (Turkson et al., 2001; Ren et al., 2003; Shao et al., 2003; Uddin et al., 2005; Song et al., 2005; Schust et al., 2006). As outlined below, this strategy has the potential to achieve specificity based on the observation that the preferred pY peptide motif of each STAT protein is distinct. When coupled to a small molecule approach, this strategy has the potential to overcome issues of delivery and toxicity.

Targeting Stat3α while sparing Stat3β. Some of the distinct biochemical features of Stat3β vs. Stat3α, notably constitutive activation and a 10-to-20 fold increased DNA binding affinity, have been attributed to the absence of the C-terminal transactivation domain (TAD) resulting in increased Stat3β dimer stability (Park et al., 1996; Park et al., 2000). Increased dimer stability likely results from higher binding affinity of the SH2 domain to pY peptide motifs when in the context of Stat3β compared to Stat3α because of reduced steric hindrance conferred by removal of the TAD. These differential biochemical features between Stat3 α and Stat3β are exploited to develop a chemical compound that selectively targets Stat3 α, in some embodiments. This selectivity enhances the anti-tumor effect of such compounds, in certain cases, because they would spare Stat3β, which functions to antagonize the oncogenic functions of Stat3α.

In certain embodiments of the invention, specific therapies targeting Stat3 signaling are useful for treatment of cachexia.

VI. Combination Therapy

It is an aspect of this invention that a composition as disclosed herein is used in combination with another agent or therapy method, such as another muscle wasting and/or muscle weakness and/or cachexia treatment and/or a treatment for an underlying condition. The composition(s) (which may or may not be a Stat3 inhibitor) may precede or follow the other agent treatment by intervals ranging from minutes to weeks, for example. In embodiments where the other agent and the composition of the invention are applied separately to an individual with cachexia, such as upon delivery to an individual suspected of having cachexia, known to have cachexia, or at risk for having cachexia, one would generally ensure that a significant period of time did not expire between the time of each delivery, such that the agent and composition of the invention would still be able to exert an advantageously combined effect on the individual.

For example, in such instances, it is contemplated that one may contact the cell, tissue or organism with one, two, three, four or more modalities substantially simultaneously (i.e., within less than about a minute) with the composition of the invention. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the composition of the invention. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the composition of the invention, for example. In some situations, it may be desirable to extend the time period for treatment significantly, such as where several weeks (e.g., about 1, about 2, about 3, about 4, about 5, about 6, about 7 or about 8 weeks or more) lapse between the respective administrations. In some situations, it may be desirable to extend the time period for treatment significantly, such as where several months (e.g., about 1, about 2, about 3, about 4, about 5, about 6, about 7 or about 8 weeks or more) lapse between the respective administrations.

Various combinations may be employed, the composition of the invention is "A" and the secondary agent, which can be any other cancer therapeutic agent, is "B":

| A/B/A | B/A/B | B/B/A | A/A/B | A/B/B |
|-------|-------|-------|-------|-------|
| B/A/A | A/B/B/B | B/A/B/B | B/B/B/A | B/B/A/B |
| A/A/B/B | A/B/A/B | A/B/B/A | B/B/A/A | B/A/B/A |
| B/A/A/B | A/A/A/B | B/A/A/A | A/B/A/A | A/A/B/A |

Administration of the therapeutic compositions of the present invention to a patient will follow general protocols for the administration of drugs, taking into account the toxicity. It is expected that the treatment cycles would be repeated as necessary.

In embodiments wherein an individual has cachexia associated with cancer, the individual may also be receiving chemotherapy, immunotherapy, hormone therapy, radiation therapy and/or surgery.

VII. Pharmaceutical Compositions

Pharmaceutical compositions of the present invention comprise an effective amount of a composition as disclosed herein dissolved or dispersed in a pharmaceutically acceptable carrier. The phrases "pharmaceutical" or "pharmacologically acceptable" refer to molecular entities and compositions that do not produce an adverse, allergic or other untoward reaction when administered to an animal, such as, for example, a human, as appropriate. The preparation of a pharmaceutical composition that contains at least one Stat3 inhibitor of the invention, and in some cases an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition(s) may comprise different types of carriers depending on whether it is to be administered in solid, liquid or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), as an aerosol, or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an individual can be determined by physical and physiological factors such as body weight, severity of condition, the type of disease being treated, previous or concurrent therapeutic interventions, and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a composition. In other embodiments, the active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above. In certain embodiments of the invention, various dosing mechanisms are contemplated. For example, the composition may be given one or more times a day, one or more times a week, or one or more times a month, and so forth.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The composition may be formulated in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof such methods. In many cases, it will be preferable to include isotonic agents, such as, for example, sugars, sodium chloride or combinations thereof.

Sterile injectable solutions are prepared by incorporating the instant invention in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VIII. Kits of the Invention

Any of the compositions described herein may be comprised in a kit, and they are housed in a suitable container. The kits will thus comprise, in suitable container means, one or more compositions and, in some cases, an additional agent of the present invention. In some cases, there are one or more agents other than the composition of the disclosure that are included in the kit, such as one or more other agents for the treatment of muscle wasting and/or muscle weakness and/or cachexia and/or one or more agents for the treatment of an underlying condition associated with muscle wasting and/or muscle weakness and/or cachexia. In particular embodiments, there is an apparatus or any kind of means for the diagnosing of muscle wasting and/or muscle weakness and/or cachexia.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition, additional agent, and any other reagent containers in close confinement for commercial sale. Such containers may include injection or blow molded plastic containers into which the desired vials are retained.

Compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Virtual ligand screening. The inventors isolated the three-dimensional structure of the Stat3 SH2 domain from the core fragment structure of phosphorylated Stat3 homodimers bound to DNA (Becker et al., 1998) deposited in the RCSB Protein Data Bank (PDB) databank (PDB code 1BG1) and converted it to be an Internal Coordinate Mechanics (ICM)-compatible system by adding hydrogen atoms, modifying unusual amino acids, making charge adjustments and performing additional cleanup steps. In addition, the inventors retrieved the coordinates of the Stat1 SH2 domain from the PDB databank (PDB code 1BF5) for use in computational selectivity analysis (Chen et al., 1998). Commercial chemical databases (Chembridge, Asinex, ChemDiv, Enamine, Keyorganics and Life Chemicals) were chosen as sources of compounds for screening in silico. Selection was of the amide hydrogen of E638 within the site that binds the +3 residue (Q, C or T) within the pY-peptide ligand (Shao et al., 2006) as the central point of the binding pocket, which consisted of a cube with dimensions 16.0×16.9×13.7 angstrom. In addition to the +3 binding site, this cube contained the pY residue binding site consisting mainly of R609 and K591 (Shao et al., 2006) and a hydrophobic binding site consisting of $Loop_{\beta C-\beta D}$ and $Loop_{\alpha B-\alpha C}$. Sequence alignment and overlay of the Stat3 and Stat1 structures revealed substantial differences in sequence of these loops; lack of their superimposition indicated that this region might serve as a selectivity filter (Cohen et al., 2005). A flexible docking calculation (Totrov and Abagyan 1997) was performed in order to determine the global minimum energy score and thereby predict the optimum conformation of the compound within the pocket. A compound was selected for purchase and biochemical testing based on fulfilling the criteria of interaction analysis (CIA): 1) global minimum energy score 5-30, 2) formation of a salt-bridge and/or H-bond network within the pY-residue binding site and 3) formation of a H-bond with or blocking access to the amide hydrogen of E638. Most, but not all, compounds also interacted with the hydrophobic binding site.

Stat3 SH2/pY-peptide binding assay. Stat3 binding assays were performed at 25° C. with a BIAcore 3000 biosensor using 20 mM Tris buffer pH 8 containing 2 mM mercaptoethanol and 5% DMSO as the running buffer (Kim et al., 2005). Phosphorylated and control non-phosphorylated biotinylated EGFR derived dodecapeptides based on the sequence surrounding Y1068 (Shao et al., 2004) were immobilized on a streptavidin coated sensor chip (BIAcore inc., Picataway N.J.). The binding of Stat3 was conducted in 20 mM Tris buffer pH 8 containing 2 mM ß-mercaptoethanol at a flow rate of 10 uL/min for 1-2 minute. Aliquots of Stat3 at 500 nM were premixed with compound to achieve a final concentration of 1-1,000 uM and incubated at 4° C. prior to being injected onto the sensor chip. The chip was regenerated by injecting 10 uL of 100 mM glycine at pH 1.5 after each sample injection. A control (Stat3 with DMSO but without compound) was run at the beginning and the end of each cycle (40 sample injections) to ensure that the integrity of the sensor chip was maintained throughout the cycle run. The average of the two controls was normalized to 100% and used to evaluate the effect of each compound on Stat3 binding. Responses were normalized by dividing the value at 2 min by the response obtained in the absence of compounds at 2 min and multiplying by 100. $IC_{50}$ values were determined by plotting % maximum response as a function of log concentration of compound and fitting the experimental points to a competitive binding model using a four parameter logistic equation: $R=R_{high}-(R_{high}-R_{low})/(1+conc/A1)\hat{}A2$, where R=percent response at inhibitor concentration, $R_{high}$=percent response with no compound, $R_{low}$=percent response at highest compound concentration, A2=fitting parameter (slope) and A1=$IC_{50}$ (BIAevaluation Software version 4.1).

Immunoblot assay. The human hepatocellular carcinoma cell line (HepG2) was grown in 6-well plates under standard conditions. Cells were pretreated with compounds (0, 1, 3, 10, 30, 100 and 300 uM) for 1 hour then stimulated under optimal conditions with either interferon gamma (IFN-γ; 30 ng/ml for 30 min) to activate Stat1 or interleukin-6 (IL-6; 30 ng/ml for 30 min) to activate Stat3 (30-31). Cultures were then harvested and proteins extracted using high-salt buffer, as described (Shao et al., 2006). Briefly, extracts were mixed with 2× sodium dodecyl sulfate (SDS) sample buffer (125 mmol/L Tris-HCL pH 6.8; 4% SDS; 20% glycerol; 10%2-mercaptoethanol) at a 1:1 ratio and heated for 5 minutes at 100° C. Proteins (20 μg) were separated by 7.5% SDS-PAGE and transferred to polyvinylidene fluoride (PVDF) membrane (Millipore, Waltham, Mass.) and immunoblotted. Prestained molecular weight markers (Biorad, Hercules, Calif.) were included in each gel. Membranes were probed serially with antibody against Stat1 $pY^{701}$ or Stat3 $pY^{705}$ followed by antibody against Stat1 or Stat3 (Transduction labs, Lexington, Ky.) then antibody against β-actin (Abcam, Cambridge, Mass.). Membranes were stripped between antibody probing using Restore™ Western Blot Stripping Buffer (Thermo Fisher Scientific Inc., Waltham, Mass.) per the manufacturer's instructions. Horseradish peroxidase-conjugated goat-anti-mouse IgG was used as the secondary antibody (Invitrogen Carlsbad, Calif.) and the membranes were developed with enhanced chemiluminescence (ECL) detection system (Amersham Life Sciences Inc.; Arlington Heights, Ill.).

Similarity screen. Three compounds identified in the initial virtual ligand screening (VLS) Cpd3, Cpd30 and Cpd188 inhibited Stat3 SH2/pY-peptide binding and IL-6-mediated Stat3 phosphorylation and were chosen as reference molecules for similarity screening. A fingerprint similarity query for each reference compound was submitted to Molcart/ICM (Max Distance, 0.4). Similarity between each reference molecule and each database molecule was computed and the similarity results were ranked in decreasing order of ICM similarity score (Eckert and Bajorath 2007). The databases searched included ChemBridge, LifeChemicals, Enamine, ChemDiv, Asinex, AcbBlocks, KeyOrganics and PubChem for a total of 2.47 million compounds. All compounds identified were docked into the binding pocket of Stat3 SH2 domain in silico. Compounds that fulfilled CIA criteria were purchased and tested as described for compounds identified in the primary screen.

Electrophoretic Mobility Shift Assay (EMSA): EMSA was performed using the hSIE radiolabeled duplex oligonucleotide as a probe as described (Tweardy et al., 1995). Briefly, high salt extracts were prepared from HepG2 cells incubated without or with IL-6 (30 ng/ml) for 30 minutes. Protein concentration was determined by Bradford Assay and 20 ug of extract was incubated with compound (300 uM) for 60 minutes at 37° C. Bound and unbound hSIE probe was separated by polyacrylamide gel electrophoresis (4.5%). Gels were dried and autoradiographed.

Molecular modeling. All 3-D configurations of the Stat3 SH2 domain complexed with compounds were determined by global energy optimization that involves multiple steps: 1) location of organic molecules were adjusted as a whole in 2 Å amplitude by pseudo-Brownian random translations and rotations around the molecular center of gravity, 2) the internal variables of organic molecules were randomly changed. 3) coupled groups within the Stat3 SH2 domain side-chain torsion angles were sampled with biased probability shaking while the remaining variables of the protein were fixed, 4) local energy minimizations were performed using the Empirical Conformation Energy Program for Peptides type-3 (ECEPP3) in a vacuum (Nemethy et al., 1992) with distance-dependent dielectric constant ε=4r, surface-based solvent energy and entropic contributions from the protein side chains evaluated added and 5) conformations of the complex, which were determined by Metropolis criteria, were selected for the next conformation-scanning circle. The initial 3-dimensional configuration of the Stat1 SH2 domain in a complex with each compound was predicted and generated by superimposing, within the computational model, the 3-dimensional features of the Stat1 SH2 onto the 3-dimensional configuration of the Stat3 SH2 domain in a complex with each compound. The final computational model of Stat1 SH2 in a complex with each compound was determined by local minimization using Internal Coordinate Force Field (ICFF)-based molecular mechanics (Totrov and Abagyan 1997). The inventors computed the van der Waals energy of the complex of Stat1 or 3-SH2 bound with each compound using Lennard-Jones potential with ECEPP/3 force field (Nemethy et al., 1992).

Confocal and high-throughput fluorescence microscopy. Confocal and highthroughput fluorescence microscopy (HTFM) of MEF/GFP-Stat3c cells were performed as described (Huang et al., 2007). Briefly, for confocal fluorescence microscopy, cells were grown in 6-well plates containing a cover slip. For HTFM, cells were seeded into 96-well CC3 plates at a density of 5,000 cells/well using an automated plating system. Cells were cultured under standard conditions until 85-90% confluent. Cells were pretreated with compound for 1 hour at 37° C. then stimulated with IL-6 (200 ng/ml) and IL-6sR (250 ng/ml) for 30 minutes. Cells were fixed with 4% formaldehyde in PEM Buffer (80 mM Potassium PIPES, pH 6.8, 5 mM EGTA pH 7.0, 2 mM $MgCl_2$) for 30 minutes at 4° C., quenched in 1 mg/ml of NaBH4 (Sigma) in PEM buffer and counterstained for 1 min in 4,6-diamidino-2-phenylindole (DAPI; Sigma; 1 mg/ml) in PEM buffer. Cover slips were examined by confocal fluorescent microscopy. Plates were analyzed by automated HTFM using the Cell Lab IC Image Cytometer (IC100) platform and CytoshopVersion 2.1 analysis software (Beckman Coulter). Nuclear translocation is quantified by using the fraction localized in the nucleus (FLIN) measurement (Sharp et al., 2006).

Example 2

Identification by VLS of Compounds that Blocked Stat3 Binding to its Phosphopeptide Ligand and Inhibited IL-6-Mediated Phosphorylation of Stat3

The VLS protocol was used to evaluate a total of 920,000 drug-like compounds. Of these, 142 compounds fulfilled CIA criteria. These compounds were purchased and tested for their ability to block Stat3 binding to its phosphopeptide ligand in a surface plasmon resonance (SPR)-based binding assay and to inhibit IL-6-mediated phosphorylation of Stat3. SPR competition experiments showed that of the 142 compounds tested, 3 compounds Cpd3, Cpd30 and Cpd188-were able to directly compete with pY-peptide for binding to Stat3 with $IC_{50}$ values of 447, 30, and 20 μM, respectively (FIGS. 1 and 3; Table 4).

TABLE 4

$IC_{50}$ values (μM) of 6 active compounds

| Assay | Cpd3 | Cpd30 | Cpd188 | Cpd3-2 | Cpd3-7 | Cpd30-12 |
|---|---|---|---|---|---|---|
| SPR | 447[1] | 30 | 20 | 256 | 137 | 114 |
| pStat3 | 91 | 18 | 73 | 144 | 63 | 60 |
| HTM | 131 | 77 | 39 | 150 | 20 | >300 |

[1]Data presented are the mean or mean ± SD;
ND = not determined.

In addition, each compound inhibited IL-6-mediated phosphorylation of Stat3 with IC50 values of 91, 18 and 73 μM respectively (FIGS. 2A-2F; Table 4).

Similarity screening with Cpd3, Cpd30 and Cpd188 identified 4,302 additional compounds. VLS screening was performed with each of these compounds, which identified 41 compounds that fulfilled CIA criteria; these were purchased and tested. SPR competition experiments showed that of these 41 compounds, 3 compounds-Cpd3-2, Cpd3-7 and Cpd30-12-were able to directly compete with pY-peptide for binding to Stat3 with $IC_{50}$ values of 256, 137 and 114 μM, respectively (FIGS. 1 and 3; Table 4). In addition, each compound inhibited IL-6-mediated phosphorylation of Stat3 with IC50 values of 144, 63 and 60 μM, respectively (FIGS. 2A-2F; Table 4).

Example 3

Compound-Mediated Inhibition of Ligand-Stimulated Phosphorylation of Stat3 is Specific for Stat3 Vs. Stat1

While Stat3 contributes to oncogenesis, in part, through inhibition of apoptosis, Stat1 is anti-oncogenic; it mediates the apoptotic effects of interferons and contributes to tumor surveillance (Kaplan et al., 1998; Ramana et al., 2000). Consequently, compounds that target Stat3 while sparing Stat1, leaving its anti-oncogenic functions unopposed, may result in a synergistic anti-tumor effect. To assess the selectivity of the compounds for Stat3 vs. Stat1, HepG2 cells were incubated with Cpd3, Cpd30, Cpd188, Cpd3-2, Cpd3-7, and Cpd30-12 (300 µM) for 1 hour at 37° C. before IFN-γ stimulation (FIG. 4). Only treatment with Cpd30-12 blocked Stat1 phosphorylation while each of the other five compounds-Cpd3, Cpd30, Cpd188, Cpd3-2 and Cpd3-7-did not. Thus, five of the six exemplary compounds identified were selective and inhibited ligand-stimulated phosphorylation of Stat3 but not Stat1.

Example 4

Sequence Analysis and Molecular Modeling of the Interaction of Each Compound with the Stat3 Vs. Stat1 SH2 Domain To understand at the molecular level the basis for the selectivity of Cpds 3, 30, 188, 3-2 and 3-7 and the absence of selectivity in the case of Cpd 30-12, the amino acid sequence and available structures of the Stat1 and Stat3 SH2 domain were compared and also it was examined how each compound interacted with both. Sequence alignment revealed identity in the residues within Stat3 and Stat1 corresponding to the binding site for the pY residue and the +3 residue (FIG. 5A). In addition, overlay of the Stat3 and Stat1 SH2 structures revealed that the loops that contained these binding sites were superimposed (FIG. 5B). In contrast, sequence alignment revealed substantial differences in the sequence of the regions of the SH2 domain corresponding to the loops forming the hydrophobic binding site (FIG. 5A). In addition, review of the overlay of Stat3 and Stat1 SH2 domains revealed that, in contrast to the close apposition of the two loops of Stat3 that form the hydrophobic binding site, the corresponding two loops of Stat1 are not closely apposed to form a pocket (FIG. 5B).

Review of computational models of Cpd3, Cpd30, Cpd188, Cpd3-2 and Cpd3-7 in a complex with the Stat3 SH2 domain revealed that each has significant interactions with the Stat3 SH2 domain binding pocket at all three binding sites, the pY-residue binding site, the +3 residue binding site and the hydrophobic binding site (FIGS. 6A, B, C, D, and E). In contrast, Cpd30-12 interacts with the pY-residue binding site and blocks access to the +3 residue-binding site but does not interact with or block access to the hydrophobic binding site (FIG. 6F). In addition, van der Waals energies of the 5 selective compounds were much more favorable for their interaction with the loops of Stat3 forming the hydrophobic binding site than with corresponding loops of Stat1 (FIG. 5C). Thus, computer modeling indicated that activity of compounds against Stat3 derives from their ability to interact with the binding sites for the pY and the +3 residues within the binding pocket, while selectivity for Stat3 vs. Stat1 derives from the ability of compounds to interact with the hydrophobic binding site within the Stat3 SH2 binding pocket, which served as a selectivity filter.

Example 5

Inhibition of Nuclear Translocation of Phosphorylated Stat3 by Cpd3, Cpd30, Cpd188, Cpd3-2 and Cpd3-7 Assessed by HTFM Following its phosphorylation on Y705, Stat3 undergoes a change in conformation from head-to-head dimerization mediated through its N-terminal oligomerization domain to tail-to-tail dimerization mediated by reciprocal SH2/pY705-peptide ligand interactions. This conformational change is followed by nuclear accumulation. Compounds that targeted SH2/pY-peptide ligand interactions of Stat3 would be expected to inhibit nuclear accumulation of Stat3. To determine if this was the case with the compounds herein, a nuclear translocation assay (FIGS. 7A-7B) was employed using murine embryonic fibroblast (MEF) cells that are deficient in endogenous Stat3 but constitutively express GFP-tagged Stat3α at endogenous levels, MEF/GFP-Stat3 α (Huang et al., 2007). Preincubation of MEF/GFP-Stat3 α cells with Cpd3, Cpd30, Cpd188, Cpd3-2 and Cpd3-7, but not Cpd30-12, blocked ligand-mediated nuclear translocation of GFP-Stat3 α with $IC_{50}$ values of 131, 77, 39, 150 and 20 µM (FIGS. 7A-7B and Table 4).

Example 6

Destabilization of Stat3-DNA Complexes by Cpd3 and Cpd3-7

Once in the nucleus, Stat3 dimers bind to specific DNA elements to activate and, in some instances, repress gene transcription. Tyrosine-phosphorylated dodecapeptides based on motifs within receptors that recruit Stat3 have previously been shown to destabilize Stat3 (Chakraborty et al., 1999; Shao et al., 2003). Compounds that bind to the phosphopeptide-binding site of Stat3 might be expected to do the same. To determine if this was the case for any of the identified compounds, extracts of IL-6-stimulated HepG2 cells were incubated in binding reactions containing radiolabeled hSIE (FIG. 8) and each of the five selective compounds (300 M). Incubation with Cpd3 or Cpd3-7 reduced the amount of hSIE shifted by half or greater. The other compounds did not have a detectable effect on the Stat3: hSIE band intensity. Thus, 2 of the 5 selective compounds destabilized Stat3:hSIE complexes.

Example 7

Exemplary Approach for Stat3 Inhibitors for Cancer Stem Cells

In the field of Stat3 probe development the inventors have focused on small molecule Stat3 probes (Xu et al., 2009), and several features of the small molecule program are useful, including: 1) a clearly defined mode of action of these probes: they target the Stat3 Src-homology (SH) 2 domain that is involved in 2 steps in the Stat3 activation pathway; 2) their specificity of action; and 3) the potential for using lead probes identified so far to identify probes with 2-to-3 logs greater activity based on recent and exemplary SAR analysis and medicinal chemistry considerations outlined below.

In specific embodiments, compound affinity is improved upon gaining a log greater affinity upon moving from 1st generation to 2nd generation probes using 3-D pharmacophore analysis. In addition, selectivity is improved through modeling embodiments, in particular through identification of a distinct hydrophobic binding domain in the phosphopeptide binding pocket of Stat3 SH2 vs. the Stat1 SH2 (Xu et al., 2009).

Identification of 1st generation Stat3 chemical probes. To develop chemical probes that selectively target Stat3, the inventors virtually screened 920,000 small drug-like compounds by docking each into the peptide-binding pocket of the Stat3 SH2 domain, which consists of three sites—the pY-residue binding site, the +3 residue-binding site and a hydrophobic binding site, which served as a selectivity filter (Xu et al., 2009). Three compounds (Cpd3, Cpd30 and Cpd188) satisfied criteria of interaction analysis, competitively inhibited recombinant Stat3 binding to its immobilized pY-peptide ligand and inhibited IL-6-mediated tyrosine phosphorylation of Stat3. These compounds were used in a similarity screen of 2.47 million compounds, which identified 3 more compounds (Cpd3-2, Cpd3-7 and Cpd30-12) with similar activities. Examinations of the 6 active compounds for the ability to inhibit IFN-γ-mediated Stat1 phosphorylation revealed that all but Cpd30-12 were selective for Stat3. Molecular modeling of the SH2 domains of Stat3 and Stat1 bound to compound revealed that compound interaction with the hydrophobic binding site was the basis for selectivity. All 5 selective compounds inhibited nuclear-tocytoplasmic translocation of Stat3, while 3 of 5 compounds (Cpd3, Cpd30 and Cpd188) induced apoptosis preferentially of exemplary breast cancer cell lines with constitutive Stat3 activation.

Identification of 2nd generation Stat3 chemical probes. The similarity screening described above did not yield any hits using Cpd188, the most active of the 3 lead compounds, as the query compound. Consequently, the inventors repeated 2-D similarity screening using the scaffold of Cpd188 as the query structure and the Life Chemicals library, which yielded 207 hits. 3-D pharmacophore analysis was performed on these 207 compounds using Ligand Scout and the top 39 scoring compounds were purchased and tested for inhibition of Stat3 binding to its phosphopeptide ligand by SPR. All but six of these 39 compounds have measurable SPR IC50s, with 19 having IC50 values equal to or less than the parent compound and 2 (Cpd188-9 and Cpd188-15) having IC50 values one log lower. Examination of these 19 compounds has revealed a statistically significant correlation between 3-D pharmacophore scores and SPR IC50s and as well as 3-D pharmacophore score and IC50s for inhibition of ligand-mediated cytoplasmic-to-nuclear translocation. In addition, both Cpd188-9 and Cpd188-15 exhibited a log greater activity in inducing human leukemic cell line apoptosis than the parent Cpd188 (FIG. 15). In addition, Cpd188-38 exhibited a 2 logs greater activity than parent Cpd188 in inhibiting cytoplasmic-to-nuclear translocation in HTFM assay, while Cpd188-15 exhibited a 1 log greater activity than parent Cpd188 in decreasing MSFE (Table 5). Furthermore, several of the second-generation 188-like compounds represent a substantial improvement over Cpd188 from a medicinal chemistry, metabolism and bioavailability standpoint. In particular, Cpd188-9 lacked both carboxyl groups, which in particular cases improves cell permeability and/or the thioether group, which is subject to oxidation. R2=0.2 P=0.013 (M)

TABLE 5

Summary of Certain 2nd Generation 188-like Compounds

| Compound | SPR IC$_{50}$, µM* | HTFM IC$_{50}$, µM* | Mammosphere ~IC$_{50}$, µM*** |
|---|---|---|---|
| 188 | 20** | 32 ± 4 | 30-100 |
| 188-1 | 6 ± 2 | 26 ± 4 | 30 |
| 188-9 | 3 ± 2 | 47 ± 21 | 10 |
| 188-10 | 8 ± 3 | 22 ± 19 | 30 |
| 188-15 | 2 ± 1 | 49 | 3 |
| 188-16 | 4 ± 0 | 9 ± 5 | 30 |
| 188-17 | 4 ± 2 | 76 | 30 |
| 188-18 | 4 ± 1 | 27 ± 8 | 30 |
| 188-38 | 19 ± 9 | 0.4 ± 0.1 | 10-30 |

*mean ± SD
**Xu et al PLos ONE
***SUM159PT and HS578T cells plated (6 wells per test) without or with compound at 1, 10, or 100 µM, incubated 3 d; spheres counted on day 3

Structure-activity relationship (SAR) analysis of 2nd generation Stat3 probes. All of the 39 second generation compounds described above, plus Cpd188 itself, are derivatives of N-naphth-1-yl benzenesulfamide. Upon careful analysis of their structure-activity relationships (SAR), the inventors found that most of these Cpd188-like compounds (38 out of 40: the rest of 2 are weak and will be described below in EXP ID) can be divided into three structural groups in a general trend of decreased activity, as shown in FIG. 16. Five compounds in Group III are actually the parents of compounds in Groups I and II. Addition of a variety of groups (the —R group highlighted in red in the general structure of Group I in FIG. 16), such as a triazole-3-yl-mercapto (188-15) or a chloro (188-10) group, to the 3-position of the naphthylamine ring led to the Group I compounds, which are the most potent series of Stat3 probes. In a specific embodiment, this is the most important contributor to the inhibitory activity: a total of eight 3-substituents are found in Group I compounds, which invariably enhance the activity by several orders of magnitude.

Most Stat3 probes in Group II contain a 5-membered ring that combines the 3-R and 4-OR2 groups, such as a furan (188-11). However, the compounds in this group are, in average, ~5× less active than the Group I compounds, which indicates that in certain aspects the H atom of the 4-hydroxy group (highlighted in blue in the general structure of Group I in FIG. 16) is important, e.g., involved in a favorable H-bond with the protein. Lacking the ability to form the H-bond attributes to the weaker activities of Group II probes, in particular cases. These considerations underlie a medicinal chemistry approach outlined below.

Example 8

Medicinal Chemistry for Synthesis of 3$^{RD}$ Generation 188-Like Sulfamide Stat3 Probes The crystal structure of Stat3 shows that the SH2 domain has a large, widely dispersed and generally shallow binding area with several valleys and hills that recognize the pY-peptide ligand (FIG. 18). Structure-based molecular modeling (docking) was useful in identifying the contribution of the hydrophobic binding surface of the Stat3 SH2 domain as a selectivity filter (Xu et al., 2009). However, different docking programs gave distinct binding poses for the same probe over the binding surface with similar predicted binding affinities. The inventors therefore in particular embodiments, based on initial SAR results outlined above, use traditional medicinal chemistry to further carry out an exemplary comprehensive structure activity relationship study, to optimize the activity as well as the selectivity of this novel class of sulfamide probes of Stat3. Compound 188-15 serves as a scaffold for making the new generation compounds, as shown schematically (FIG. 16).

In addition, chemistry for making these compounds is straightforward with a good yield, involving the reaction of a sulfonyl chloride with an aniline/amine, which can be either obtained commercially or synthesized readily.

For the proposed modifications described below, one can consult FIG. 17. EXP IA. Modification 1. Since almost all of the $2^{nd}$ generation probes contain a phenylsulfonyl group, the first step towards activity optimization focuses on synthesizing a series of compounds that have a larger (e.g., bicyclic or tricyclic) or an alkyl sulfonyl group. The general synthetic route is shown as follows:

There are about 4,300 commercially available sulfonyl chlorides, among which 25, such as those shown above, are selected to make probes. Aniline 2, which is the amine component of compound 188-10 (FIG. 16), one the most active probes, is readily made in a simple two step reaction from nitro compound 1. One can first make 25 (for example) compounds and test their activities in an in vitro rapid throughput SPR and in vivo HTFM assays. Based on the outcomes of structure-activity relationship study, more compounds can be designed and synthesized and tested in an iterative manner until optimization of this modification.

EXP IB. Modification 2. Next, one can modify the 3-substituent of the naphthylamine ring, based on either the structure of compound 188-15, for example. Prior SAR studies demonstrated this substituent is useful to the activity of this class of probes, in certain embodiments. However, a total of 8 groups at this position with a huge difference in size, from a single atom Cl to a large, bicyclic benzothiazole-2-ylmercapto group, showed similar activities. This feature indicates that in certain embodiments modifications at this position should be more focused on other properties, such as electrostatic interactions with the protein, as exemplified below. In addition, many of these groups are thioethers, which may be subjected to oxidation/degradation in vivo and lead to an unfavorable pharmacokinetic profile, in particular aspects. The central —S— atom is changed to a more metabolically stable isosteres, such as —CH$_2$—, —NH—, and —O—, in certain cases. In certain aspects one can synthesize the following compounds to optimize the 3-substituent:

The synthesis is also started from 1, in certain cases. Regio-selective halogenation and formylation at the 3-position gives rise to two compounds, i.e., bromo- or iodo-compound 3 and aldehyde 4, which are versatile, common starting compounds for introducing a wide range of substituents at this position (e.g., those listed above).

Moreover, the crystal structure of Stat3 SH2 domain also provides strong evidence that more compounds with different electrostatic properties are useful for characterization. The electrostatic molecular surface of the protein shows two distinct features, as shown in FIG. 18. The first one is the negatively charged Glu638 surface stands out in the center. Next, of particular interest is a positively charged area, composed of Arg609 and Lys591 located in the edge of the domain, which is actually the pY (phosphorylated tyrosine) binding site of the receptor. The inventors also found that introducing a negatively charged group targeting the pY binding site leads to particularly active probes, in certain embodiments. For example, the docking study of the 3-phosphomethyl compound 5 (R=CH$_2$PO$_3^{2-}$) showed all of the phosphonate groups of the 20 docking poses are tightly clustered together and located in the pY binding site, indicating strong electrostatic and H-bond interactions with the residues Arg609 and Lys591 (FIG. 18).

EXP IC. Modifications 3 and 4. Collectively, Modifications 3 and 4 test the effects of changing the substituents at the 4, 5, and 6-positions. The —OH at 4-position may be superior to —OR, in certain aspects. One can test whether the H atom in —OH is responsible for a better activity by synthesizing compounds 6 (acylated or alkylated 5), as schematically shown below. In addition, dehydroxy compounds 7 may also be made, starting from 3-bromonaphthyl-1-amine.

Regarding the general synthetic methods for modifying positions 5 and 6, one can first synthesize about a dozen of these compounds in this category and if very active compounds emerge, one can make more compounds to optimize the activity for these two positions.

EXP ID. Modification 5. The only two compounds not included in the SAR analysis (due to a different 4-substituent) are shown here, as well as their inhibitory activities against Stat3:

Despite the weak activity, masking the polar H of the sulfamide for the second compound is favorable, in certain aspects, which provides an easy route to making more potent probes. One can therefore use the following method to make a series of N-acyl or N-alkyl sulfamides 5:

Example 9

Identification of Stat3-Selective Chemical Probes from Sulfamide Compounds Synthesized in Example 11

Each novel sulfamide compound is tested for the ability to inhibit Stat3 binding to its phosphopeptide ligand by SPR and the ability to block IL-6-stimulated cytoplasmic-to-nuclear translocation in the HTFM assay. Probes with activity in these assays equivalent to or greater than the most active 2nd generation compounds are tested for inhibition of IL-6-stimulated Stat3 phosphorylation and lack of ability to inhibit IFN-γ-stimulated Stat1 phosphorylation as outlined below.

EXP IIA. Stat3/pY-peptide SPR binding inhibition assay. Stat3 pY-peptide binding assays is performed at 25° C. using a BIAcore 3000 biosensor as described (Xu et al., 2009). Briefly, phosphorylated and control nonphosphorylated biotinylated EGFR derived dodecapeptides based on the sequence surrounding Y1068 are immobilized on a streptavidin coated sensor chip (BIAcore Inc., Piscataway N.J.). The binding of Stat3 is performed in 20 mM Tris buffer pH 8 containing 2 mM β-mercaptoethanol at a flow rate of 10 uL/min for 1-2 minute. Aliquots of Stat3 at 500 nM are premixed with compound to achieve a final concentration of 1-1,000 uM and incubated at 4° C. prior to being injected onto the sensor chip. The chip is regenerated by injecting 10 uL of 100 mM glycine at pH 1.5 after each sample injection. A control (Stat3 with DMSO but without compound) is run at the beginning and the end of each cycle (40 sample injections) to ensure that the integrity of the sensor chip is maintained throughout the cycle run. The average of the two controls is normalized to 100% and used to evaluate the effect of each compound on Stat3 binding. Responses are normalized by dividing the value at 2 min by the response obtained in the absence of compounds at 2 min and multiplying by 100. IC$_{50}$ values are determined by plotting % maximum response as a function of log concentration of compound and fitting the experimental points to a competitive binding model using a four parameter logistic equation: R=R$_{high}$−(R$_{high}$−R$_{low}$)/(1+conc/A1)$^{A2}$, where R=percent response at inhibitor concentration, R$_{high}$=percent response with no compound, R$_{low}$=percent response at highest compound concentration, A2=fitting parameter (slope) and A1=IC$_{50}$ (BIAevaluation Software version 4.1).

EXP IIB. High throughput fluorescence microscopy (HTFM), cytoplasm-to-nucleus translocation inhibition assays. HTFM of MEF/GFP-Stat3α cells is performed to assess the ability of probes to inhibit GFP-Stat3 cytoplasmic-to-nuclear translocation, as described (Xu et al., 2009), using the robotic system available as part of the John S.

Dunn Gulf Coast Consortium for Chemical Genomics at the University of Texas-Houston School of Medicine. Briefly, cells are seeded into 96-well CC3 plates at a density of 5,000 cells/well and cultured under standard conditions until 85-90% confluent. Cells are pre-treated with compound for 1 hour at 37° C. then stimulated with IL-6 (100 ng/ml) and IL-6sR (150 ng/ml) for 30 minutes. Cells are fixed with 4% formaldehyde in PEM Buffer (80 mM Potassium PIPES, pH 6.8, 5 mM EGTA pH 7.0, 2 mM $MgCl_2$) for 30 minutes at 4° C., quenched in 1 mg/ml of $NaBH_4$ (Sigma) in PEM buffer and counterstained for 1 min in 4,6-diamidino-2-phenylindole (DAPI; Sigma; 1 mg/ml) in PEM buffer. Plates are analyzed by automated HTFM using the Cell Lab IC Image Cytometer (IC100) platform and CytoshopVersion 2.1 analysis software (Beckman Coulter).

Nuclear translocation is quantified by using the fraction localized in the nucleus (FLIN) measurement. FLIN values are normalized by subtracting the FLIN for unstimulated cells then dividing this difference by the maximum difference (delta, A) in FLIN (FLIN in cells stimulated with IL-6/sIL-6R in the absence of compound minus FLIN of unstimulated cells). This ratio is multiplied by 100 to obtain the percentage of maximum difference in FLIN and is plotted as a function of the log compound concentration. The best-fitting curve and $IC_{50}$ value are determined using 4-Parameter LogisticModel/Dose Response/XLfit 4.2, IDBS software.

EXP IIC. Ligand-mediated pStat3 and pStat1 inhibition assays. Newly synthesized Stat3 probes with activity equivalent to or greater than parent compound 188 in the SPR and HTFM assays will be tested for the ability to selectively inhibit ligand-mediated phosphorylation of Stat3 as described (Xu et al., 2009). Briefly, human hepatocellular carcinoma cells (HepG2) are grown in 6-well plates and pretreated with compounds (0, 0.1, 0.3, 1, 3, 10, 30, 100 µM) for 1 hour then stimulated under optimal conditions with either interleukin-6 (IL-6; 30 ng/ml for 30 min) to activate Stat3 or interferon gamma (IFN-γ; 30 ng/ml for 30 min) to activate Stat1. Cells are harvested and proteins extracted using high-salt buffer, mixed with 2× sodium dodecyl sulfate (SDS) sample buffer (125 mmol/L Tris-HCL pH 6.8; 4% SDS; 20% glycerol; 10%2-mercaptoethanol) at a 1:1 ratio then heated for 5 minutes at 100° C. Proteins (20 µg) are separated by 7.5% SDS-PAGE and transferred to polyvinylidene fluoride (PVDF) membrane (Millipore, Waltham, Mass.) and immunoblotted. Membranes are probed serially with antibody against Stat1 pY701 or Stat3 pY705 followed by antibody against Stat1 or Stat3 (Transduction labs, Lexington, Ky.) then antibody against β-actin (Abcam, Cambridge, Mass.). Membranes are stripped between antibody probings using Restore™ Western Blot Stripping Buffer (Thermo Fisher Scientific Inc., Waltham, Mass.) per the manufacturer's instructions. Horseradish peroxidase-conjugated goat-anti-mouse IgG is used as the secondary antibody (Invitrogen Carlsbad, Calif.) and the membranes are developed with enhanced chemiluminescence (ECL) detection system (Amersham Life Sciences Inc.; Arlington Heights, Ill.). Band intensities are quantified by densitometry. The value of each pStat3 band is divided by its corresponding total Stat3 band intensity; the results are normalized to the DMSO-treated control value. This value was plotted as a function of the log compound concentration. The best-fitting curve is determined using 4-Parameter Logistic Model/Dose Response/XLfit 4.2, IDBS software and was used to calculate the $IC_{50}$ value.

EXP IID. Molecular modeling of probe-Stat3 interactions. The results of modeling of the binding of the first generation probe to the Stat3 vs. Stat1 SH2 domains suggested that the basis for experimental selectivity of probes for Stat3 vs. Stat1 rested on the ability of the probes to have greater interaction with the hydrophobic binding site within the pY-peptide binding pocket of Stat3 compared to Stat1. Thus, the hydrophobic binding site served as a selectivity filter. To test if this remains the case for newly synthesized 3rd generation probes, one can use 2 complementary docking programs GLIDE (Schrödinger) and ICM (MolSoft) to determine the lowest energy docking configuration of each probe within the pY-peptide binding domain of Stat3 and Stat1 SH2 domain. One can review the computational models of each probe in a complex with the Stat3 vs. Stat1 SH2 domain and, in particular, compare the van der Waals energies and determine if they are equivalent for their interaction with the Stat3 SH2 domain vs. the Stat1 SH2 domain. It was this calculation that determined the selectivity of 1st generation probes for Stat3 vs. Stat1. In particular, van der Waals energy calculations implicated residues that form the hydrophobic binding site (W623, Q635, V637, Y640 and Y657) as critical for this selectivity.

In specific embodiments of the invention, there is identification of probes with one log or greater activity than $2^{nd}$ generation probes in SPR, HTFM and pStat3 assays. Furthermore, in certain aspects some of the most active $3^{rd}$ generation probes that emerge from this analysis are selective for Stat3 vs. Stat1 based on their greater interaction with the hydrophobic binding site within the Stat3 vs. Stat1 SH2 pY-peptide binding pocket.

Example 10

Exemplary Compositions of the Disclosure

Exemplary composition(s) of the disclosure are provided in Tables 6-11 below.

TABLE 6

| IDNUMBER | Structure | Formula structure | MW | LogP |
| --- | --- | --- | --- | --- |
| F1566-0306 | 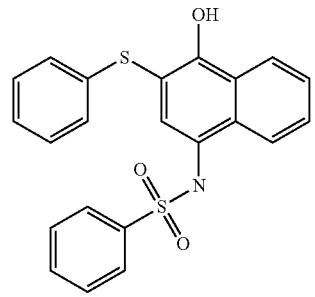 [SMILES: O=S(=O)(Nc1cc(Sc2ccccc2)c(O)c2ccccc12)c1ccccc1] | C22H17NO3S2 | 407.5137 | 5.846 |

TABLE 6-continued

| IDNUMBER | Structure | Formula structure | MW | LogP |
| --- | --- | --- | --- | --- |
| F1566-0318 | 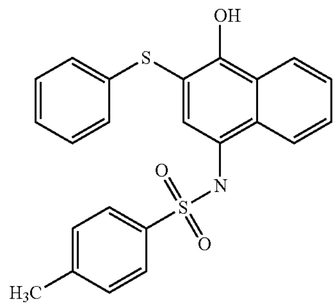 [SMILES: Cc1ccc(S(=O)(=O)Nc2cc(Sc3ccccc3)c(O)c3ccccc23)cc1] | C23H19NO3S2 | 421.5408 | 6.144 |
| F1566-0330 | 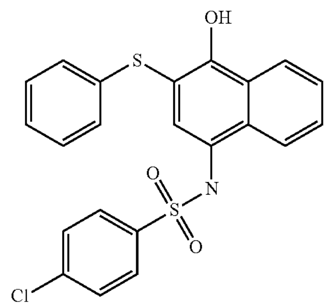 [SMILES: O=S(=O)(Nc1cc(Sc2ccccc2)c(O)c2ccccc12)c1ccc(Cl)cc1] | C22H16ClNO3S2 | 441.9587 | 6.438 |
| F1566-0342 | 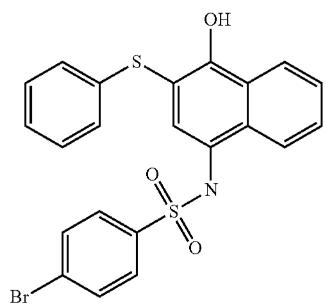 [SMILES: O=S(=O)(Nc1cc(Sc2ccccc2)c(O)c2ccccc12)c1ccc(Br)cc1] | C22H16BrNO3S2 | 486.4097 | 6.644 |
| F1566-0366 | 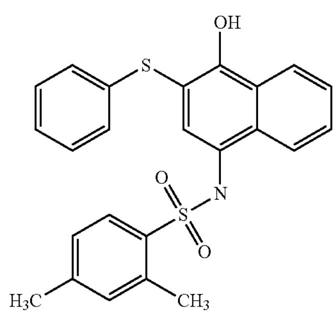 [SMILES: Cc1ccc(S(=O)(=O)Nc2cc(Sc3ccccc3)c(O)c3ccccc23)c(C)c1] | C24H21NO3S2 | 435.5679 | 6.477 |
| F1566-0414 | 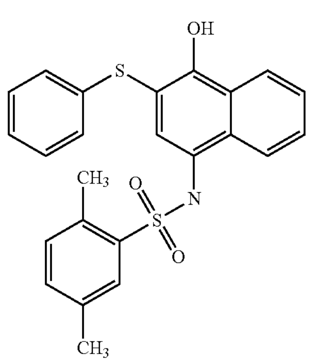 [SMILES: Cc1ccc(C)c(S(=O)(=O)Nc2cc(Sc3ccccc3)c(O)c3ccccc23)c1] | C24H21NO3S2 | 435.5679 | 6.477 |

TABLE 6-continued
| IDNUMBER | Structure | Formula structure | MW | LogP |
|---|---|---|---|---|
| F1566-0438 | 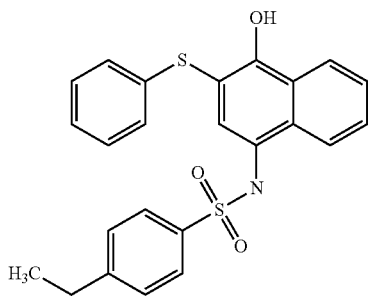 [SMILES: CCc1ccc(S(=O)(=O)Nc2cc(Sc3ccccc3)c(O)c3ccccc23)cc1] | C24H21NO3S2 | 435.5679 | 6.619 |
| F1566-0450 | 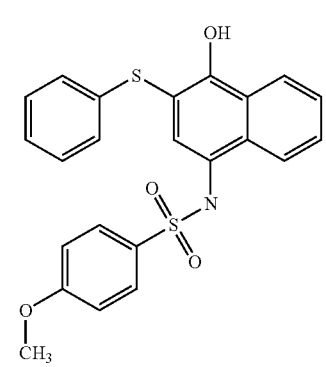 [SMILES: COc1ccc(S(=O)(=O)Nc2cc(Sc3ccccc3)c(O)c3ccccc23)cc1] | C23H19NO4S2 | 437.5402 | 5.802 |
| F1566-0462 | 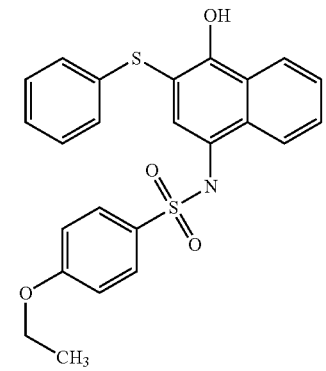 [SMILES: CCOc1ccc(S(=O)(=O)Nc2cc(Sc3ccccc3)c(O)c3ccccc23)cc1] | C24H21NO4S2 | 451.5673 | 6.143 |
| F1566-0486 | 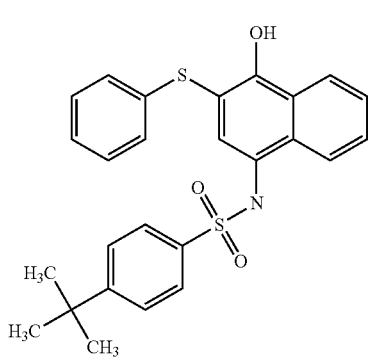 [SMILES: CC(C)(C)c1ccc(S(=O)(=O)Nc2cc(Sc3ccccc3)c(O)c3ccccc23)cc1] | C26H25NO3S2 | 463.6221 | 7.345 |

TABLE 6-continued
| IDNUMBER | Structure | Formula structure | MW | LogP |
|---|---|---|---|---|
| F1566-0510 | 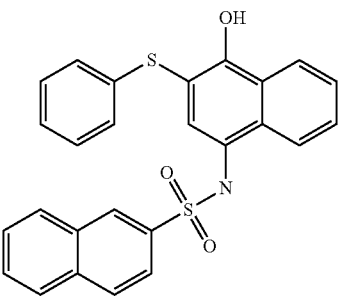 [SMILES: O=S(=O)(Nc1cc(Sc2ccccc2)c(O)c2ccccc12)c1ccc2ccccc2c1] | C26H19NO3S2 | 457.5742 | 7.105 |
| F1566-0546 | 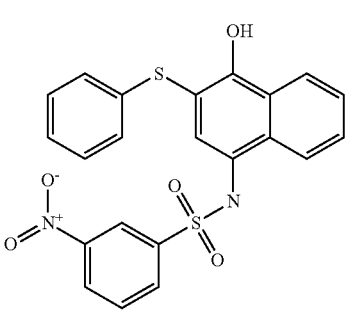 [SMILES: O=[N+]([O-])c1cccc(S(=O)(=O)Nc2cc(Sc3ccccc3)c(O)c3ccccc23)c1] | C22H16N2O5S2 | 452.5112 | 5.818 |
| F1566-0558 | 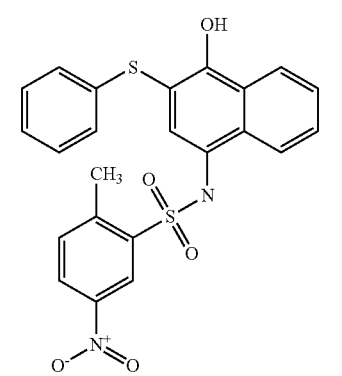 [SMILES: Cc1ccc([N+](=O)[O-])cc1S(=O)(=O)Nc1cc(Sc2ccccc2)c(O)c2ccccc12] | C23H18N2O5S2 | 466.5383 | 6.114 |
| F1566-0618 | 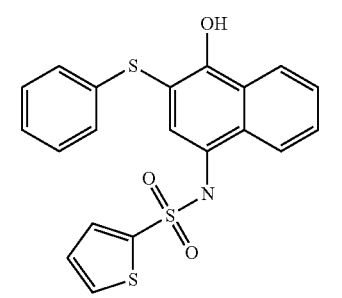 [SMILES: O=S(=O)(Nc1cc(Sc2ccccc2)c(O)c2ccccc12)c1cccs1] | C20H15NO3S3 | 413.5395 | 5.359 |

TABLE 6-continued
| IDNUMBER | Structure | Formula structure | MW | LogP |
|---|---|---|---|---|
| F1566-1606 | 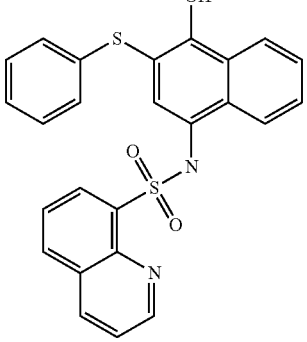 | C25H18N2O3S2 | 458.5618 | 6.046 |
| F1566-1818 | 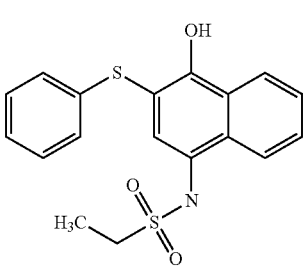 [SMILES: CCS(=O)(=O)Nc1cc(Sc2ccccc2)c(O)c2ccccc12] | C18H17NO3S2 | 359.4691 | 4.705 |
| F1566-1832 | 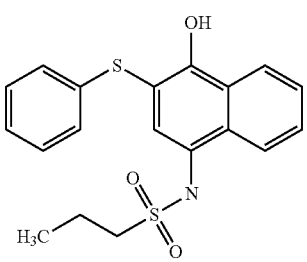 [SMILES: CCCS(=O)(=O)Nc1cc(Sc2ccccc2)c(O)c2ccccc12] | C19H19NO3S2 | 373.4962 | 5.147 |
| F1566-1846 | 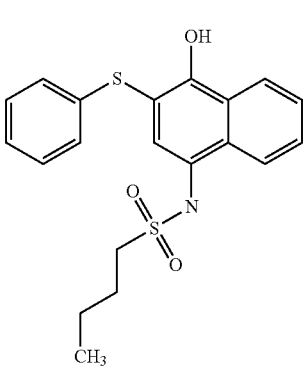 [SMILES: CCCCS(=O)(=O)Nc1cc(Sc2ccccc2)c(O)c2ccccc12] | C20H21NO3S2 | 387.5233 | 5.589 |
| F1566-1860 | 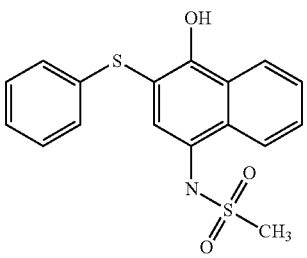 [SMILES: CS(=O)(=O)Nc1cc(Sc2ccccc2)c(O)c2ccccc12] | C17H15NO3S2 | 345.442 | 4.192 |

TABLE 6-continued

| IDNUMBER | Structure | Formula structure | MW | LogP |
| --- | --- | --- | --- | --- |
| F5749-0371 | 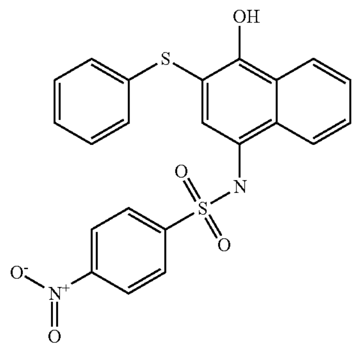 [SMILES: O=[N+]([O-])c1ccc(S(=O)(=O)Nc2cc(Sc3ccccc3)c(O)c3ccccc23)cc1] | C22H16N2O5S2 | 452.5112 | 5.781 |
| F5749-0372 | 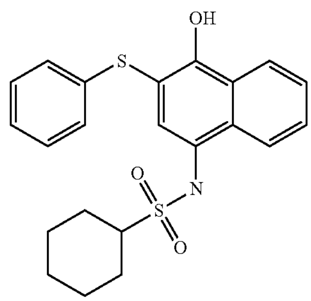 [SMILES: O=S(=O)(Nc1cc(Sc2ccccc2)c(O)c2ccccc12)C1CCCCC1] | C22H23NO3S2 | 413.5615 | 6.171 |
| F5749-0373 | 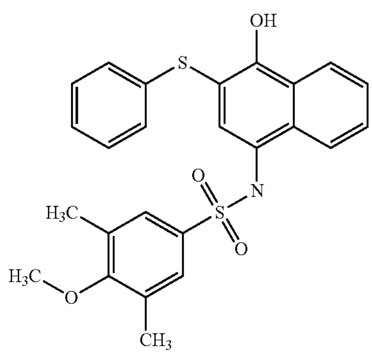 [SMILES: COc1c(C)cc(S(=O)(=O)Nc2cc(Sc3ccccc3)c(O)c3ccccc23)cc1C] | C25H23NO4S2 | 465.5944 | 6.468 |
| F5749-0374 | 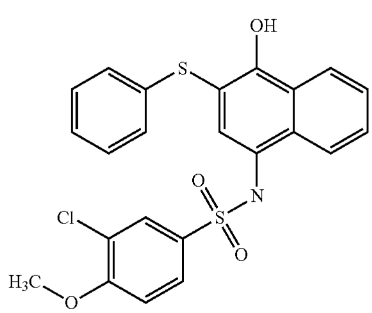 [SMILES: COc1ccc(S(=O)(=O)Nc2cc(Sc3ccccc3)c(O)c3ccccc23)cc1Cl] | C23H18ClNO4S2 | 471.9852 | 6.429 |

TABLE 6-continued
| IDNUMBER | Structure | Formula structure | MW | LogP |
|---|---|---|---|---|
| F5749-0375 | 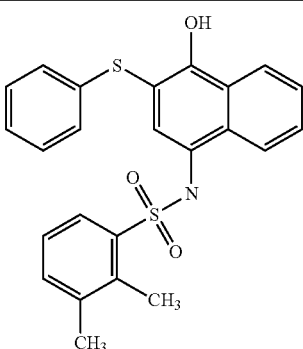 | C24H21NO3S2 | 435.5679 | 6.438 |
| F5749-0376 | 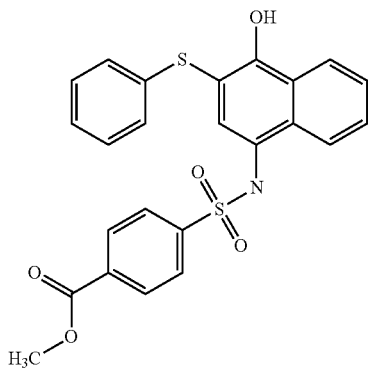 [SMILES: COC(=O)c1ccc(S(=O)(=O)Nc2cc(Sc3ccccc3)c(O)c3ccccc23)cc1] | C24H19NO5S2 | 465.5507 | 5.787 |
| F5749-0377 | 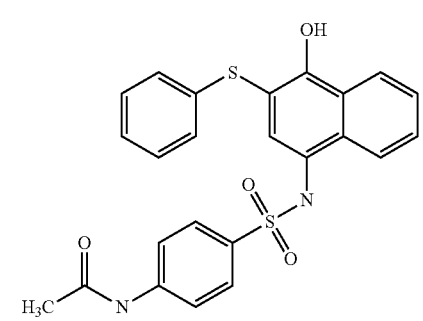 [SMILES: CC(=O)Nc1ccc(S(=O)(=O)Nc2cc(Sc3ccccc3)c(O)c3ccccc23)cc1] | C24H20N2O4S2 | 464.566 | 5.137 |
| F5749-0378 | 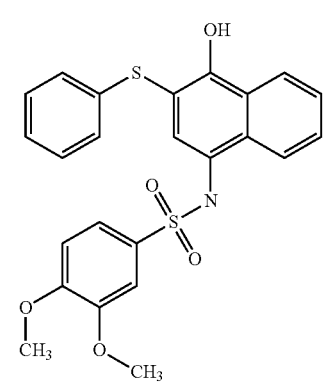 [SMILES: COc1ccc(S(=O)(=O)Nc2cc(Sc3ccccc3)c(O)c3ccccc23)cc1OC] | C24H21NO5S2 | 467.5667 | 5.54474 |

TABLE 6-continued
| IDNUMBER | Structure | Formula structure | MW | LogP |
|---|---|---|---|---|
| F5749-0379 | 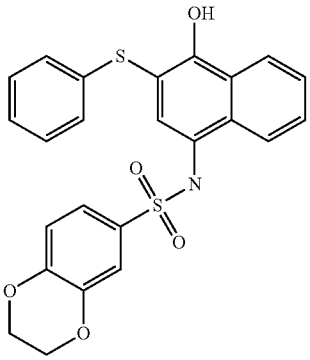 [SMILES: O=S(=O)(Nc1cc(Sc2ccccc2)c(O)c2ccccc12)c1ccc2c(c1)OCCO2] | C24H19NO5S2 | 465.5507 | 5.441 |
| F5749-0380 | 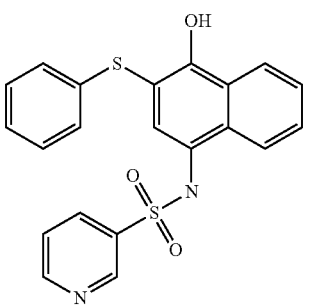 [SMILES: O=S(=O)(Nc1cc(Sc2ccccc2)c(O)c2ccccc12)c1cccnc1] | C21H16N2O3S2 | 408.5013 | 4.613 |
| F5749-0381 | 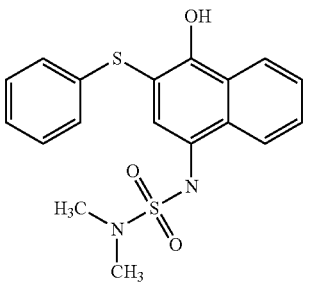 | C18H18N2O3S2 | 374.4838 | 3.74 |
| F5749-0382 | 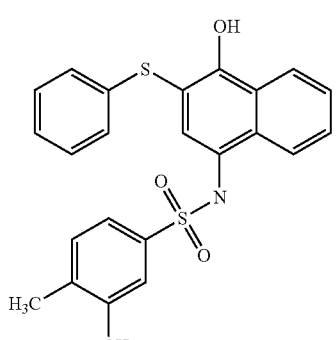 | C24H21NO3S2 | 435.5679 | 6.477 |

TABLE 6-continued
| IDNUMBER | Structure | Formula structure | MW | LogP |
|---|---|---|---|---|
| F5749-0383 | 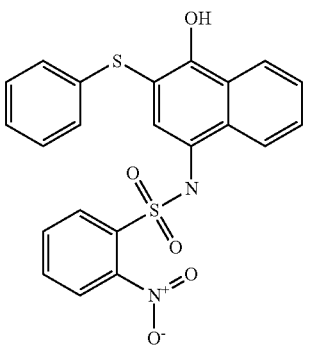 [SMILES: O=[N+]([O-])c1ccccc1S(=O)(=O)Nc1cc(Sc2ccccc2)c(O)c2ccccc12] | C22H16N2O5S2 | 452.5112 | 5.779 |
| F5749-0384 | 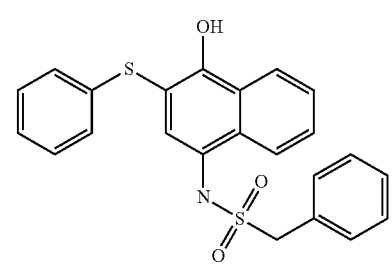 [SMILES: O=S(=O)(Cc1ccccc1)Nc1cc(Sc2ccccc2)c(O)c2ccccc12] | C23H19NO3S2 | 421.5408 | 5.98 |
| F5749-0385 | 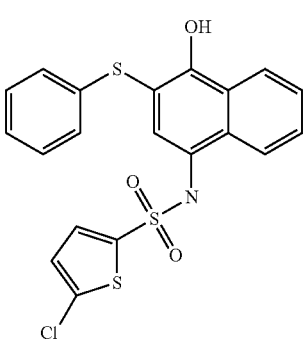 [SMILES: O=S(=O)(Nc1cc(Sc2ccccc2)c(O)c2ccccc12)c1ccc(Cl)s1] | C20H14ClNO3S3 | 447.9845 | 6.649 |
| F5749-0386 | 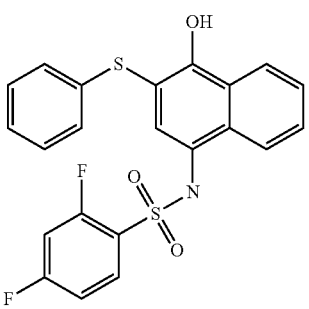 [SMILES: O=S(=O)(Nc1cc(Sc2ccccc2)c(O)c2ccccc12)c1ccc(F)cc1F] | C22H15F2NO3S2 | 443.4946 | 6.187 |
| F5749-0387 | 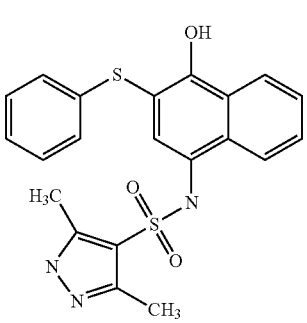 [SMILES: Cc1n[nH]c(C)c1S(=O)(=O)Nc1cc(Sc2ccccc2)c(O)c2ccccc12] | C21H19N3O3S2 | 425.5319 | 4.956 |

TABLE 6-continued
| IDNUMBER | Structure | Formula structure | MW | LogP |
|---|---|---|---|---|
| F5749-0388 | 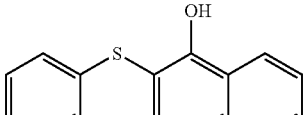 | C21H18N2O4S2 | 426.5166 | 4.99 |
| F5749-0389 | 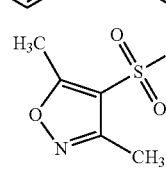 | C23H22N2O5S2 | 470.5702 | 3.633 |
| F5749-0390 | 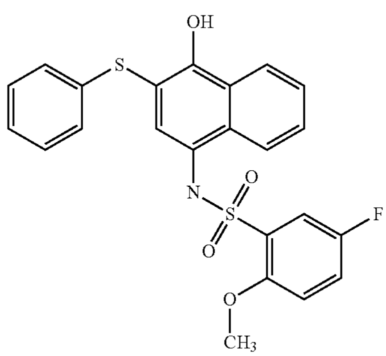 [SMILES: COc1ccc(F)cc1S(=O)(=O)Nc1cc(Sc2ccccc2)c(O)c2ccccc12] | C23H18FNO4S2 | 455.5306 | 5.99 |
| F5749-0391 | 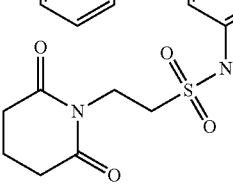 | C24H21NO4S2 | 451.5673 | 6.135 |

TABLE 6-continued
| IDNUMBER | Structure | Formula structure | MW | LogP |
|---|---|---|---|---|
| F5749-0392 | 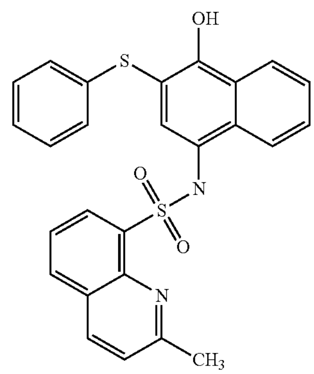 [SMILES: Cc1ccc2cccc(S(=O)(=O)Nc3cc(Sc4ccccc4)c(O)c4ccccc34)c2n1] | C26H20N2O3S2 | 472.5889 | 6.305 |
| F5749-0393 | 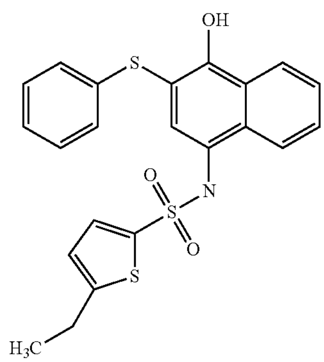 [SMILES: CCc1ccc(S(=O)(=O)Nc2cc(Sc3ccccc3)c(O)c3ccccc23)s1] | C22H19NO3S3 | 441.5936 | 6.497 |
| F5749-0394 | 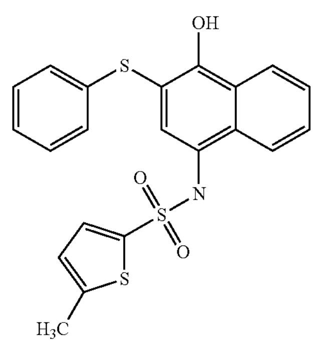 [SMILES: Cc1ccc(S(=O)(=O)Nc2cc(Sc3ccccc3)c(O)c3ccccc23)s1] | C21H17NO3S3 | 427.5665 | 6.022 |
| F5749-0395 | 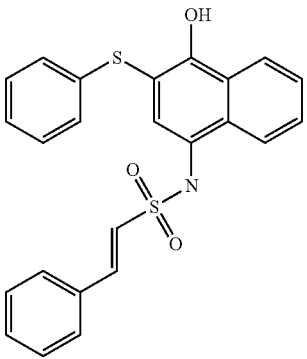 [SMILES: O=S(=O)(/C=C/c1ccccc1)Nc1cc(Sc2ccccc2)c(O)c2ccccc12] | C24H19NO3S2 | 433.5519 | 6.204 |

TABLE 6-continued
| IDNUMBER | Structure | Formula structure | MW | LogP |
|---|---|---|---|---|
| F5749-0396 | 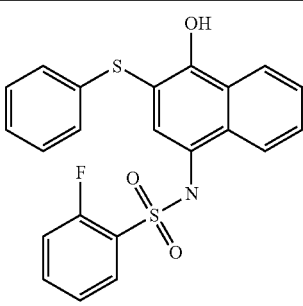 | C22H16FNO3S2 | 425.5041 | 5.997 |
| F5749-0397 | 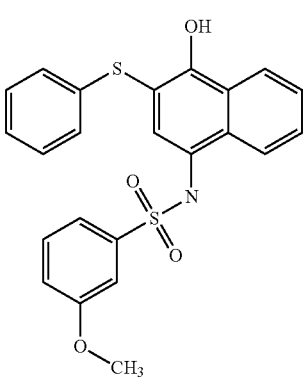 [SMILES: COc1cccc(S(=O)(=O)Nc2cc(Sc3ccccc3)c(O)c3ccccc23)c1] | C23H19NO4S2 | 437.5402 | 5.839 |
| F5749-0398 | 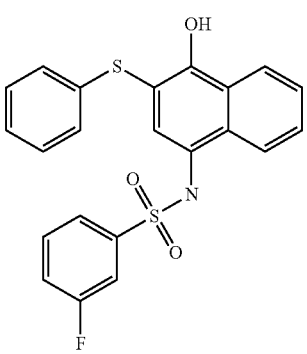 [SMILES: O=S(=O)(Nc1cc(Sc2ccccc2)c(O)c2ccccc12)c1cccc(F)c1] | C22H16FNO3S2 | 425.5041 | 6.036 |
| F5749-0399 | 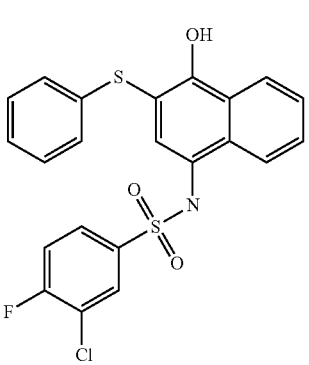 [SMILES: O=S(=O)(Nc1cc(Sc2ccccc2)c(O)c2ccccc12)c1ccc(F)c(Cl)c1] | C22H15ClFNO3S2 | 459.9492 | 6.626 |

TABLE 6-continued

| IDNUMBER | Structure | Formula structure | MW | LogP |
|---|---|---|---|---|
| F5749-0400 | 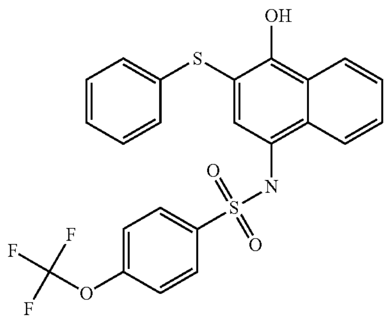 [SMILES: O=S(=O)(Nc1cc(Sc2ccccc2)c(O)c2ccccc12)c1ccc(OC(F)(F)F)cc1] | C23H16F3NO4S2 | 491.5115 | 7.24476 |
| F5749-0401 | 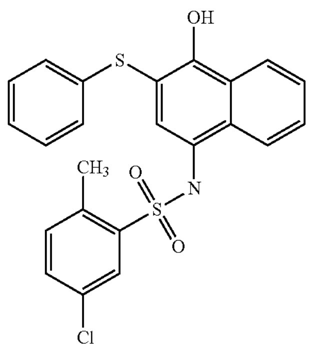 [SMILES: Cc1ccc(Cl)cc1S(=O)(=O)Nc1cc(Sc2ccccc2)c(O)c2ccccc12] | C23H18ClNO3S2 | 455.9858 | 6.771 |
| F5749-0402 | 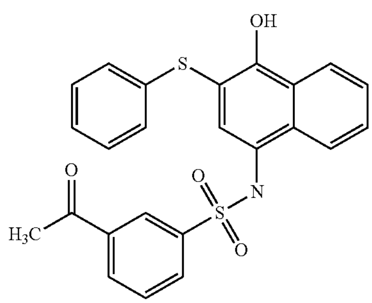 [SMILES: CC(=O)c1cccc(S(=O)(=O)Nc2cc(Sc3ccccc3)c(O)c3ccccc23)c1] | C24H19NO4S2 | 449.5513 | 5.736 |
| F5749-0403 | 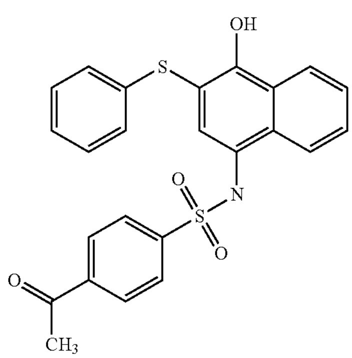 [SMILES: CC(=O)c1ccc(S(=O)(=O)Nc2cc(Sc3ccccc3)c(O)c3ccccc23)cc1] | C24H19NO4S2 | 449.5513 | 5.699 |

TABLE 6-continued
| IDNUMBER | Structure | Formula structure | MW | LogP |
| --- | --- | --- | --- | --- |
| F5749-0404 | 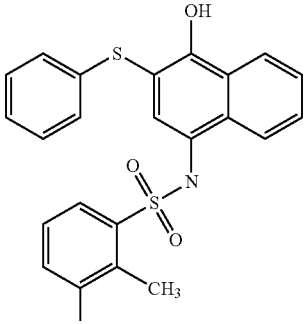 | C23H18ClNO3S2 | 455.9858 | 6.732 |
| F5749-0405 | 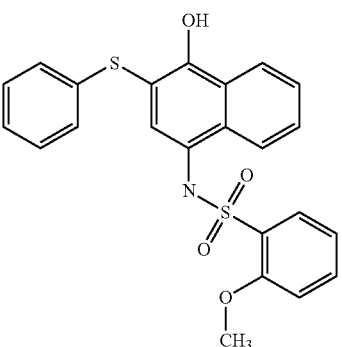 [SMILES: COc1ccccc1S(=O)(=O)Nc1cc(Sc2ccccc2)c(O)c2ccccc12] | C23H19NO4S2 | 437.5402 | 5.8 |
| F5749-0406 | 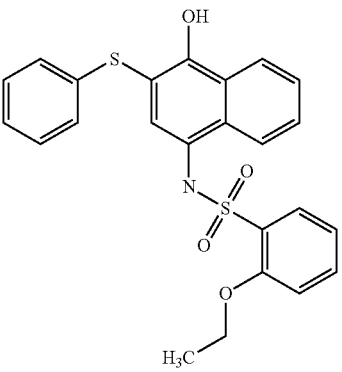 [SMILES: CCOc1ccccc1S(=O)(=O)Nc1cc(Sc2ccccc2)c(O)c2ccccc12] | C24H21NO4S2 | 451.5673 | 6.141 |
| F5749-0407 | 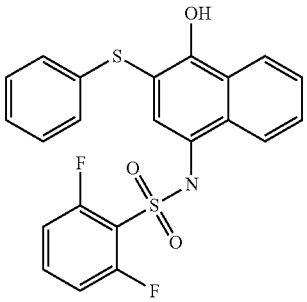 | C22H15F2NO3S2 | 443.4946 | 6.148 |

TABLE 6-continued
| IDNUMBER | Structure | Formula structure | MW | LogP |
|---|---|---|---|---|
| F5749-0408 | 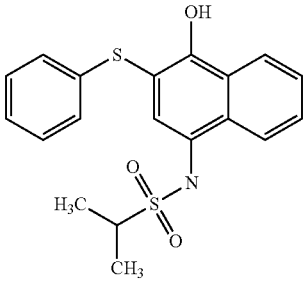 | C19H19NO3S2 | 373.4962 | 5.339 |
| F5749-0409 | 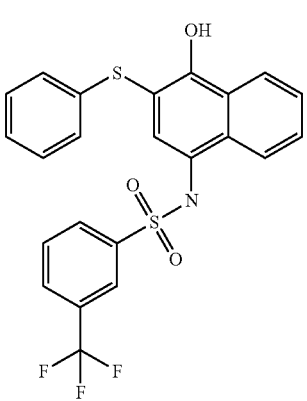 [SMILES: O=S(=O)(Nc1cc(Sc2ccccc2)c(O)c2ccccc12)c1cccc(C(F)(F)F)c1] | C23H16F3NO3S2 | 475.5121 | 6.81776 |
| F5749-0410 | 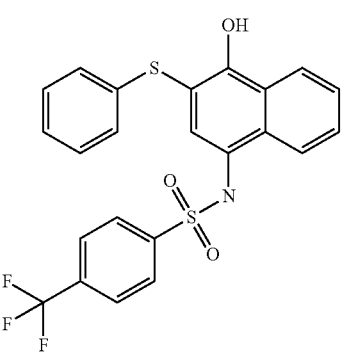 [SMILES: O=S(=O)(Nc1cc(Sc2ccccc2)c(O)c2ccccc12)c1ccc(C(F)(F)F)cc1] | C23H16F3NO3S2 | 475.5121 | 6.78076 |
| F5749-0411 | 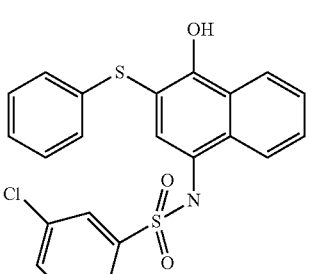 | C22H16ClNO3S2 | 441.9587 | 6.475 |

TABLE 6-continued
| IDNUMBER | Structure | Formula structure | MW | LogP |
|---|---|---|---|---|
| F5749-0412 | 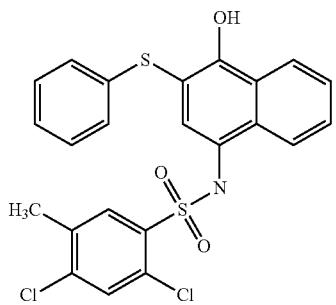 [SMILES: Cc1cc(S(=O)(=O)Nc2cc(Sc3ccccc3)c(O)c3ccccc23)c(Cl)cc1Cl] | C23H17Cl2NO3S2 | 490.4308 | 7.398 |
| F5749-0413 | 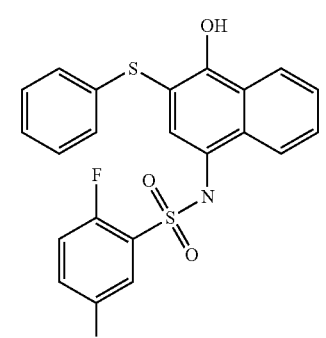 | C22H15F2NO3S2 | 443.4946 | 6.187 |
| F5749-0414 | 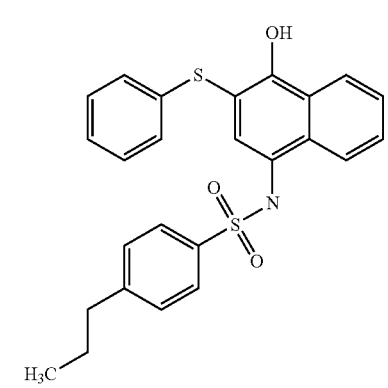 [SMILES: CCCc1ccc(S(=O)(=O)Nc2cc(Sc3ccccc3)c(O)c3ccccc23)cc1] | C25H23NO3S2 | 449.595 | 7.061 |
| F5749-0415 | 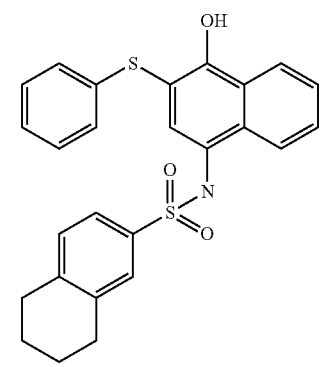 [SMILES: O=S(=O)(Nc1cc(Sc2ccccc2)c(O)c2ccccc12)c1ccc2c(c1)CCCC2] | C26H23NO3S2 | 461.6061 | 6.933 |

TABLE 6-continued

| IDNUMBER | Structure | Formula structure | MW | LogP |
|---|---|---|---|---|
| F5749-0416 | 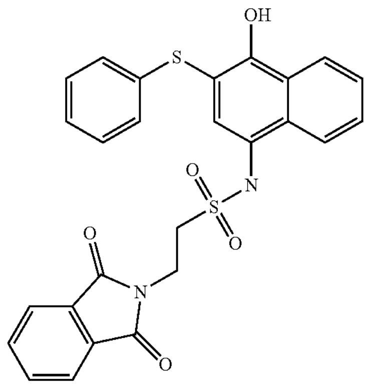 [SMILES: O=C1c2ccccc2C(=O)N1CCS(=O)(=O)Nc1cc(Sc2ccccc2)c(O)c2ccccc12] | C26H20N2O5S2 | 504.5877 | 4.973 |
| F5749-0417 | 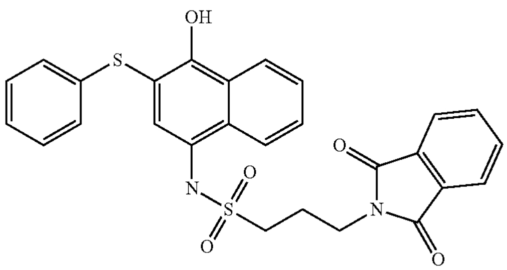 [SMILES: O=C1c2ccccc2C(=O)N1CCCS(=O)(=O)Nc1cc(Sc2ccccc2)c(O)c2ccccc12] | C27H22N2O5S2 | 518.6148 | 5.415 |
| F5749-0418 | 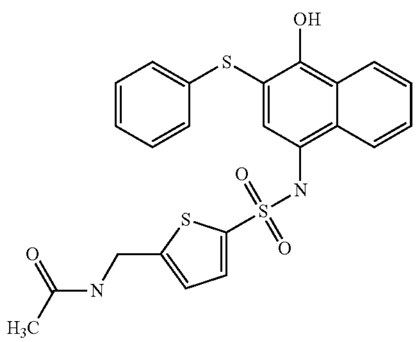 [SMILES: CC(=O)NCc1ccc(S(=O)(=O)Nc2cc(Sc3ccccc3)c(O)c3ccccc23)s1] | C23H20N2O4S3 | 484.6189 | 5.149 |
| F5749-0419 | 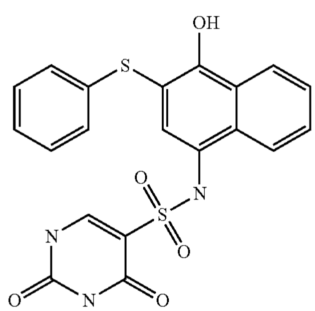 [SMILES: O=c1[nH]cc(S(=O)(=O)Nc2cc(Sc3ccccc3)c(O)c3ccccc23)c(=O)[nH]1] | C20H15N3O5S2 | 441.4877 | 2.891 |
| F5749-0420 | 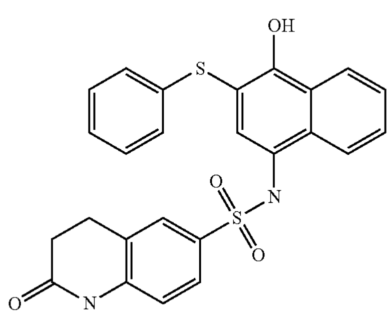 [SMILES: O=C1CCc2cc(S(=O)(=O)Nc3cc(Sc4ccccc4)c(O)c4ccccc34)ccc2N1] | C25H20N2O4S2 | 476.5772 | 5.042 |

TABLE 6-continued
| IDNUMBER | Structure | Formula structure | MW | LogP |
|---|---|---|---|---|
| F5749-0421 | 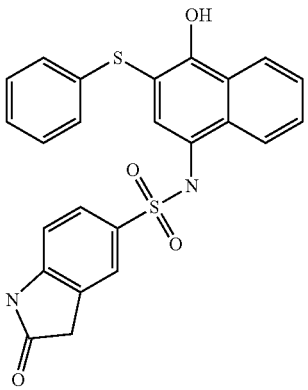 [SMILES: O=C1Cc2cc(S(=O)(=O)Nc3cc(Sc4ccccc4)c(O)c4ccccc34)ccc2N1] | C24H18N2O4S2 | 462.5501 | 4.954 |
| F5749-0422 | 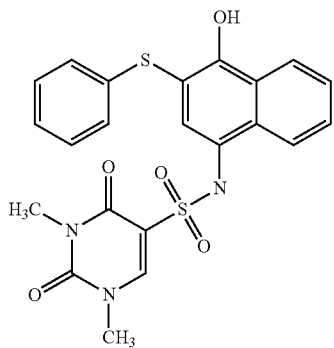 [SMILES: Cn1cc(S(=O)(=O)Nc2cc(Sc3ccccc3)c(O)c3ccccc23)c(=O)n(C)c1=O] | C22H19N3O5S2 | 469.5418 | 2.955 |
| F5749-0423 | 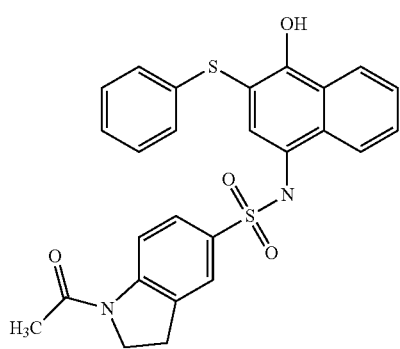 [SMILES: CC(=O)N1CCc2cc(S(=O)(=O)Nc3cc(Sc4ccccc4)c(O)c4ccccc34)ccc21] | C26H22N2O4S2 | 490.6042 | 5.277 |
| F5749-0424 | 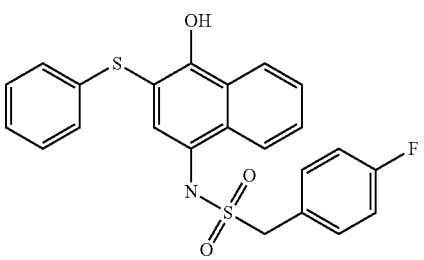 [SMILES: O=S(=O)(Cc1ccc(F)cc1)Nc1cc(Sc2ccccc2)c(O)c2ccccc12] | C23H18FNO3S2 | 439.5312 | 6.133 |

TABLE 6-continued

| IDNUMBER | Structure | Formula structure | MW | LogP |
|---|---|---|---|---|
| F5749-0425 | 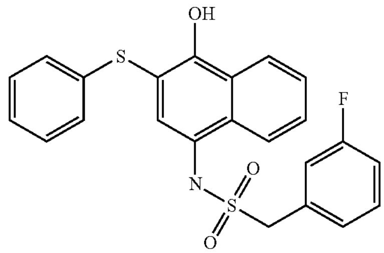 [SMILES: O=S(=O)(Cc1cccc(F)c1)Nc1cc(Sc2ccccc2)c(O)c2ccccc12] | C23H18FNO3S2 | 439.5312 | 6.17 |
| F5749-0426 | 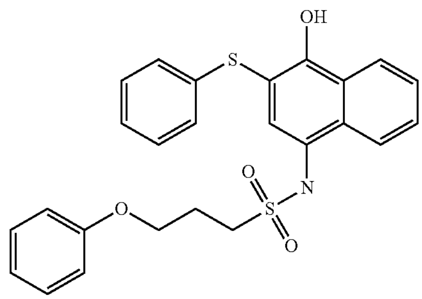 [SMILES: O=S(=O)(CCCOc1ccccc1)Nc1cc(Sc2ccccc2)c(O)c2ccccc12] | C25H23NO4S2 | 465.5944 | 6.206 |
| F5749-0427 | 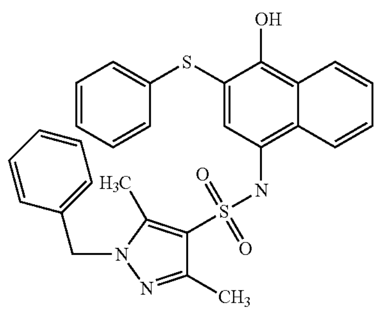 [SMILES: Cc1nn(Cc2ccccc2)c(C)c1S(=O)(=O)Nc1cc(Sc2ccccc2)c(O)c2ccccc12] | C28H25N3O3S2 | 515.6578 | 6.125 |
| F5749-0428 | 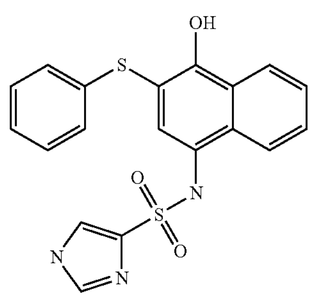 [SMILES: O=S(=O)(Nc1cc(Sc2ccccc2)c(O)c2ccccc12)c1c[nH]cn1] | C19H15N3O3S2 | 397.4777 | 3.986 |
| F5749-0429 | 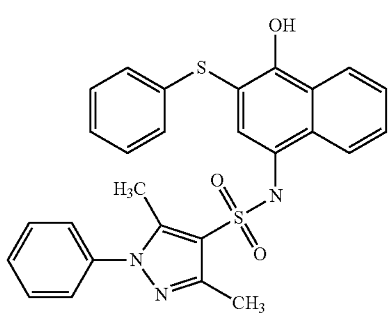 [SMILES: Cc1nn(-c2ccccc2)c(C)c1S(=O)(=O)Nc1cc(Sc2ccccc2)c(O)c2ccccc12] | C27H23N3O3S2 | 501.6307 | 5.991 |

TABLE 6-continued

| IDNUMBER | Structure | Formula structure | MW | LogP |
| --- | --- | --- | --- | --- |
| F5749-0430 | 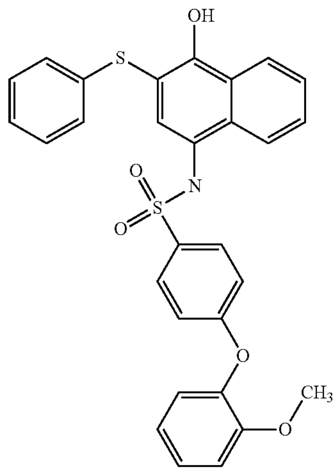 [SMILES: COc1ccccc1Oc1ccc(S(=O)(=O)Nc2cc(Sc3ccccc3)c(O)c3ccccc23)cc1] | C29H23NO5S2 | 529.6384 | 7.16174 |
| F5749-0431 | 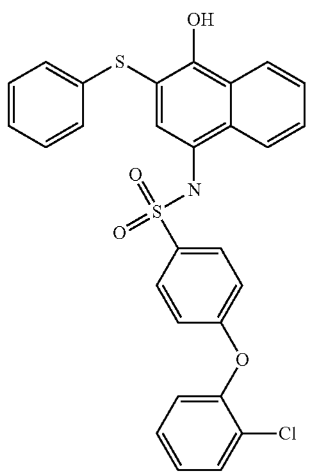 [SMILES: O=S(=O)(Nc1cc(Sc2ccccc2)c(O)c2ccccc12)c1ccc(Oc2ccccc2Cl)cc1] | C28H20ClNO4S2 | 534.0569 | 8.046 |
| F5749-0432 | 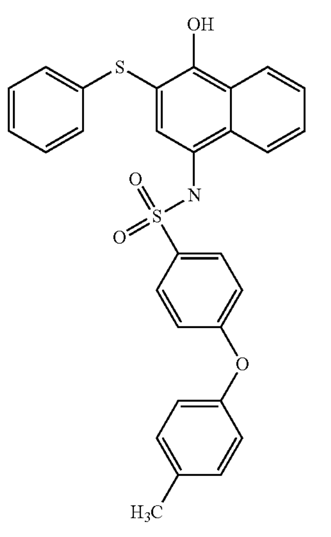 [SMILES: Cc1ccc(Oc2ccc(S(=O)(=O)Nc3cc(Sc4ccccc4)c(O)c4ccccc34)cc2)cc1] | C29H23NO4S2 | 513.639 | 7.754 |

| IDNUMBER | Structure | Formula structure | MW | LogP |
| --- | --- | --- | --- | --- |
| F5749-0433 | 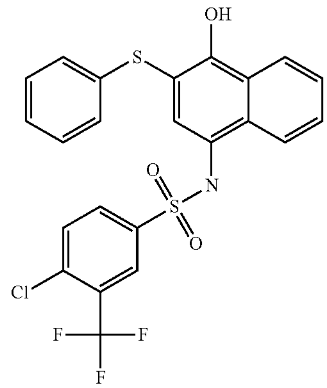 [SMILES: O=S(=O)(Nc1cc(Sc2ccccc2)c(O)c2ccccc12)c1ccc(Cl)c(C(F)(F)F)c1] | C23H15ClF3NO3S2 | 509.9571 | 7.40776 |
| F5749-0434 | 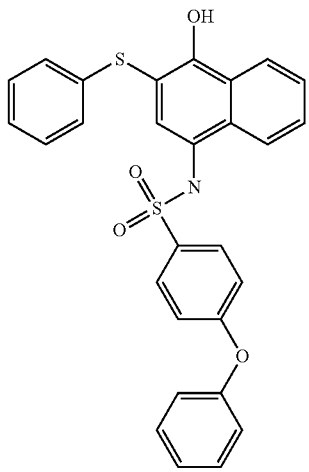 [SMILES: O=S(=O)(Nc1cc(Sc2ccccc2)c(O)c2ccccc12)c1ccc(Oc2ccccc2)cc1] | C28H21NO4S2 | 499.6119 | 7.456 |
| F5749-0435 | 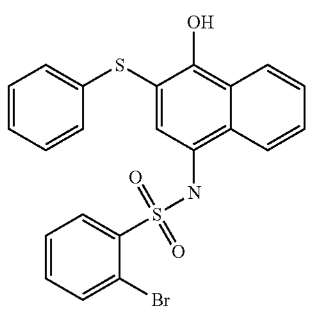 | C22H16BrNO3S2 | 486.4097 | 6.642 |
| F5749-0436 | 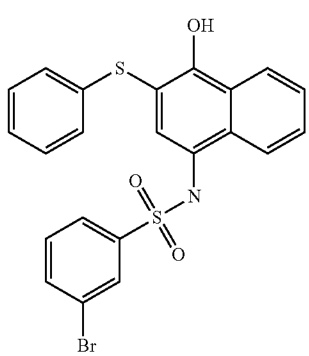 [SMILES: O=S(=O)(Nc1cc(Sc2ccccc2)c(O)c2ccccc12)c1cccc(Br)c1] | C22H16BrNO3S2 | 486.4097 | 6.681 |

TABLE 6-continued
| IDNUMBER | Structure | Formula structure | MW | LogP |
|---|---|---|---|---|
| F5749-0437 | 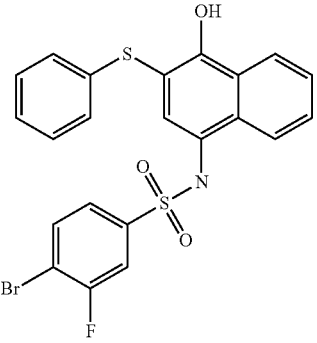 [SMILES: O=S(=O)(Nc1cc(Sc2ccccc2)c(O)c2ccccc12)c1ccc(Br)c(F)c1] | C22H15BrFNO3S2 | 504.4002 | 6.832 |
| F5749-0438 | 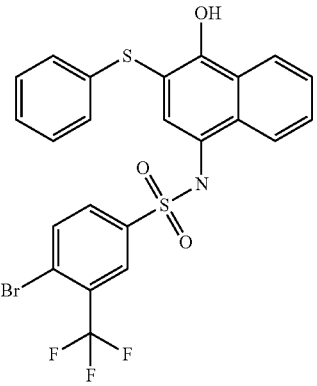 [SMILES: O=S(=O)(Nc1cc(Sc2ccccc2)c(O)c2ccccc12)c1ccc(Br)c(C(F)(F)F)c1] | C23H15BrF3NO3S2 | 554.4081 | 7.61376 |
| F5749-0439 | 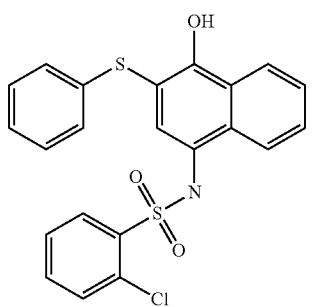 [SMILES: O=S(=O)(Nc1cc(Sc2ccccc2)c(O)c2ccccc12)c1ccccc1Cl] | C22H16ClNO3S2 | 441.9587 | 6.436 |
| F5749-0440 | 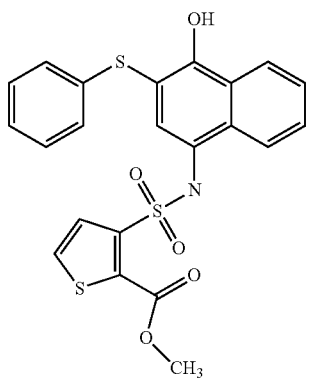 [SMILES: COC(=O)c1sccc1S(=O)(=O)Nc1cc(Sc2ccccc2)c(O)c2ccccc12] | C22H17NO5S3 | 471.5765 | 5.046 |

TABLE 6-continued
| IDNUMBER | Structure | Formula structure | MW | LogP |
| --- | --- | --- | --- | --- |
| F5749-0441 | 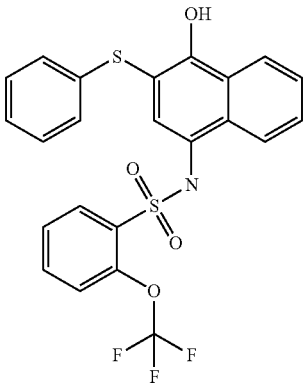 [SMILES: O=S(=O)(Nc1cc(Sc2ccccc2)c(O)c2ccccc12)c1ccccc1OC(F)(F)F] | C23H16F3NO4S2 | 491.5115 | 7.24276 |
TABLE 7
| IDNUMBER | Structure | Formula structure | MW | LogP |
| --- | --- | --- | --- | --- |
| F0808-0081 | 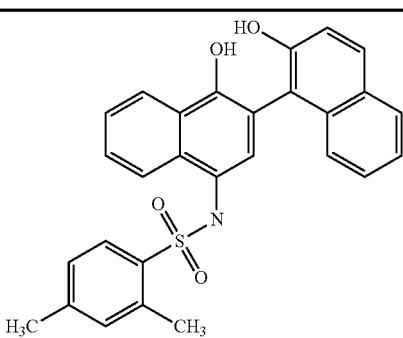 | C28H23NO4S | 469.5638 | 7.101 |
| F0808-0084 | 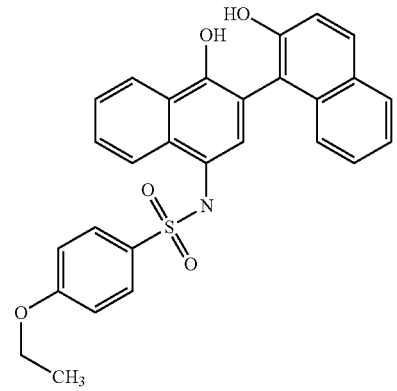 [SMILES: CCOc1ccc(S(=O)(=O)Nc2cc(-c3c(O)ccc4ccccc34)c(O)c3ccccc23)cc1] | C28H23NO5S | 485.5632 | 6.767 |
| F0808-0085 | 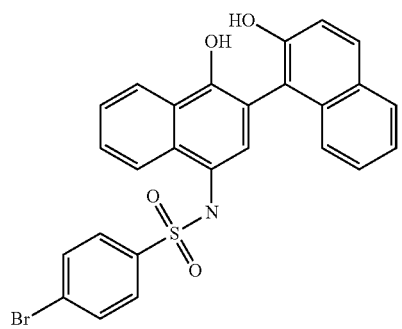 | C26H18BrNO4S | 520.4057 | 7.268 |

TABLE 7-continued

| IDNUMBER | Structure | Formula structure | MW | LogP |
|---|---|---|---|---|
| F0808-0086 | 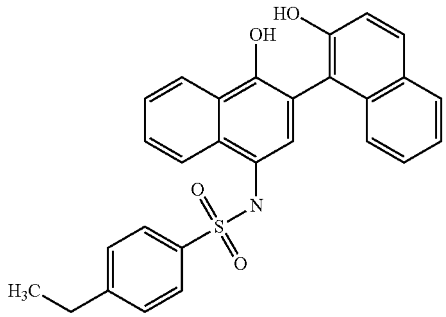 [SMILES: CCc1ccc(S(=O)(=O)Nc2cc(-c3c(O)ccc4ccccc34)c(O)c3ccccc23)cc1] | C28H23NO4S | 469.5638 | 7.243 |
| F0808-0089 | 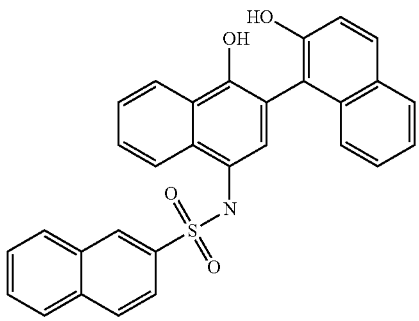 [SMILES: O=S(=O)(Nc1cc(-c2c(O)ccc3ccccc23)c(O)c2ccccc12)c1ccc2ccccc2c1] | C30H21NO4S | 491.5702 | 7.729 |
| F0808-0091 | 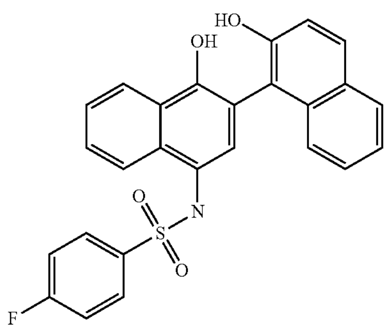 [SMILES: O=S(=O)(Nc1cc(-c2c(O)ccc3ccccc23)c(O)c2ccccc12)c1ccc(F)cc1] | C26H18FNO4S | 459.5001 | 6.623 |
| F0808-0092 | 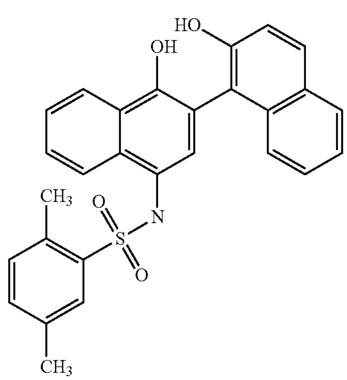 [SMILES: Cc1ccc(C)c(S(=O)(=O)Nc2cc(-c3c(O)ccc4ccccc34)c(O)c3ccccc23)c1] | C28H23NO4S | 469.5638 | 7.101 |

TABLE 7-continued
| IDNUMBER | Structure | Formula structure | MW | LogP |
|---|---|---|---|---|
| F0808-0094 | 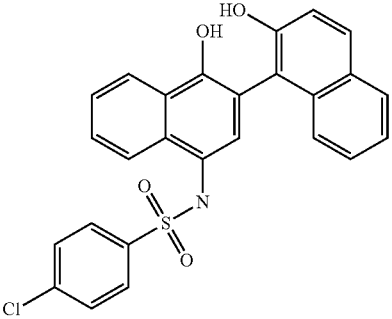 [SMILES: O=S(=O)(Nc1cc(-c2c(O)ccc3ccccc23)c(O)c2ccccc12)c1ccc(Cl)cc1] | C26H18ClNO4S | 475.9547 | 7.062 |
| F1269-0222 | 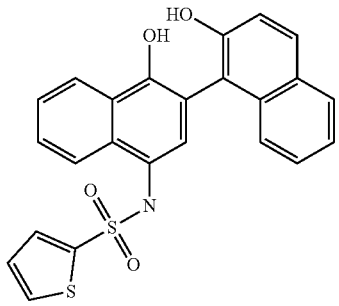 [SMILES: O=S(=O)(Nc1cc(-c2c(O)ccc3ccccc23)c(O)c2ccccc12)c1cccs1] | C24H17NO4S2 | 447.5354 | 5.983 |
| F1269-2003 | 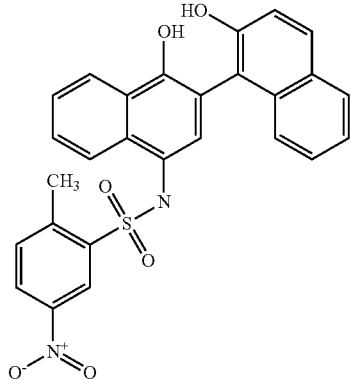 [SMILES: Cc1ccc([N+](=O)[O-])cc1S(=O)(=O)Nc1cc(-c2c(O)ccc3ccccc23)c(O)c2ccccc12] | C27H20N2O6S | 500.5343 | 6.738 |
| F1566-1138 | 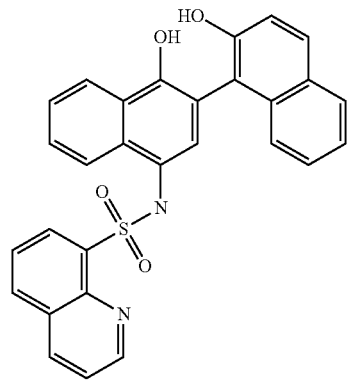 [SMILES: O=S(=O)(Nc1cc(-c2c(O)ccc3ccccc23)c(O)c2ccccc12)c1cccc2cccnc12] | C29H20N2O4S | 492.5578 | 6.67 |

TABLE 7-continued

| IDNUMBER | Structure | Formula structure | MW | LogP |
|---|---|---|---|---|
| F5749-0001 | 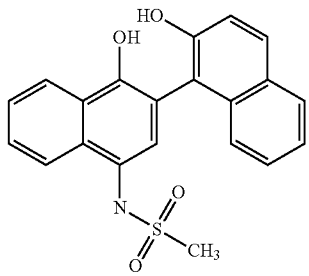 [SMILES: CS(=O)(=O)Nc1cc(-c2c(O)ccc3ccccc23)c(O)c2ccccc12] | C21H17NO4S | 379.4379 | 4.816 |
| F5749-0002 | 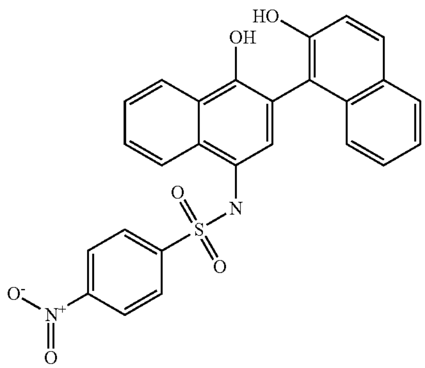 [SMILES: O=[N+]([O-])c1ccc(S(=O)(=O)Nc2cc(-c3c(O)ccc4ccccc34)c(O)c3ccccc23)cc1] | C26H18N2O6S | 486.5072 | 6.405 |
| F5749-0003 | 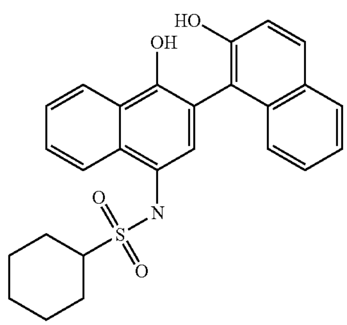 [SMILES: O=S(=O)(Nc1cc(-c2c(O)ccc3ccccc23)c(O)c2ccccc12)C1CCCCC1] | C26H25NO4S | 447.5575 | 6.795 |
| F5749-0004 | 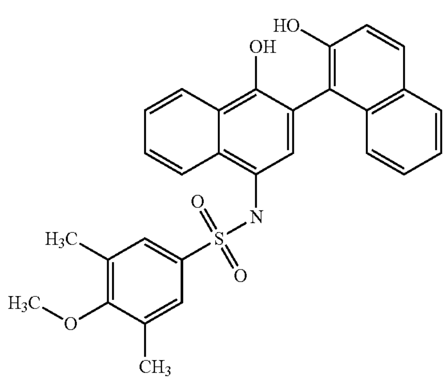 [SMILES: COc1c(C)cc(S(=O)(=O)Nc2cc(-c3c(O)ccc4ccccc34)c(O)c3ccccc23)cc1C] | C29H25NO5S | 499.5903 | 7.092 |

TABLE 7-continued

| IDNUMBER | Structure | Formula structure | MW | LogP |
| --- | --- | --- | --- | --- |
| F5749-0005 | 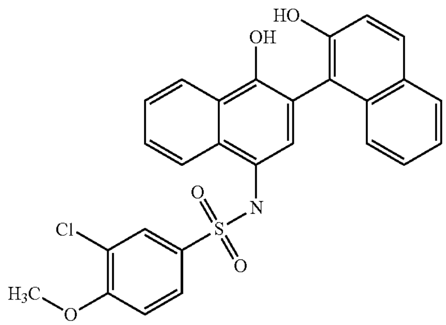 [SMILES: COc1ccc(S(=O)(=O)Nc2cc(-c3c(O)ccc4ccccc34)c(O)c3ccccc23)cc1Cl] | C27H20ClNO5S | 505.9812 | 7.053 |
| F5749-0006 | 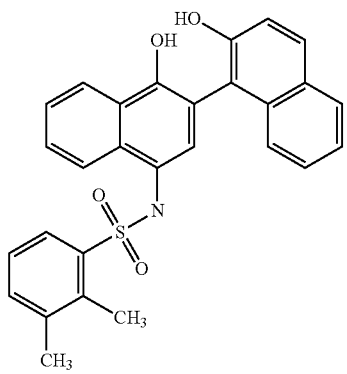 [SMILES: Cc1cccc(S(=O)(=O)Nc2cc(-c3c(O)ccc4ccccc34)c(O)c3ccccc23)c1C] | C28H23NO4S | 469.5638 | 7.062 |
| F5749-0007 | 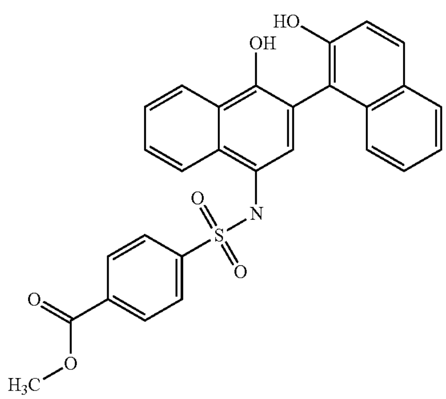 [SMILES: COC(=O)c1ccc(S(=O)(=O)Nc2cc(-c3c(O)ccc4ccccc34)c(O)c3ccccc23)cc1] | C28H21NO6S | 499.5467 | 6.411 |
| F5749-0008 | 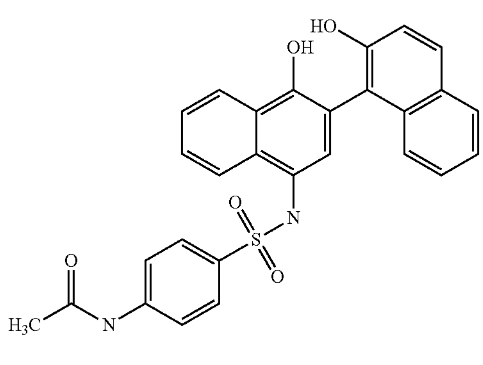 [SMILES: CC(=O)Nc1ccc(S(=O)(=O)Nc2cc(-c3c(O)ccc4ccccc34)c(O)c3ccccc23)cc1] | C28H22N2O5S | 498.5619 | 5.761 |

TABLE 7-continued

| IDNUMBER | Structure | Formula structure | MW | LogP |
|---|---|---|---|---|
| F5749-0009 | 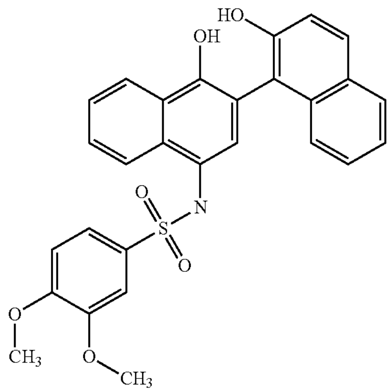 [SMILES: COc1ccc(S(=O)(=O)Nc2cc(-c3c(O)ccc4ccccc34)c(O)c3ccccc23)cc1OC] | C28H23NO6S | 501.5626 | 6.16874 |
| F5749-0010 | 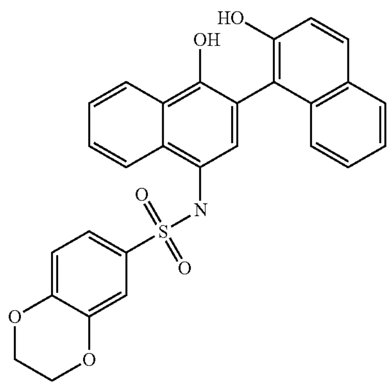 [SMILES: O=S(=O)(Nc1cc(-c2c(O)ccc3ccccc23)c(O)c2ccccc12)c1ccc2c(c1)OCCO2] | C28H21NO6S | 499.5467 | 6.065 |
| F5749-0011 | 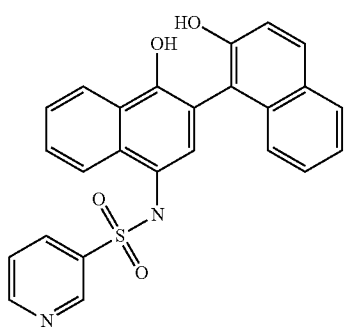 [SMILES: O=S(=O)(Nc1cc(-c2c(O)ccc3ccccc23)c(O)c2ccccc12)c1cccnc1] | C25H18N2O4S | 442.4972 | 5.237 |
| F5749-0012 | 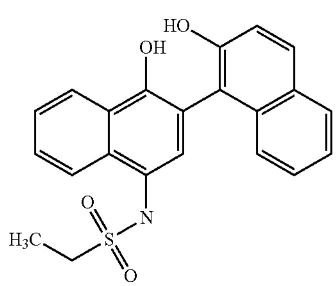 [SMILES: CCS(=O)(=O)Nc1cc(-c2c(O)ccc3ccccc23)c(O)c2ccccc12] | C22H19NO4S | 393.465 | 5.329 |

TABLE 7-continued
| IDNUMBER | Structure | Formula structure | MW | LogP |
|---|---|---|---|---|
| F5749-0013 | 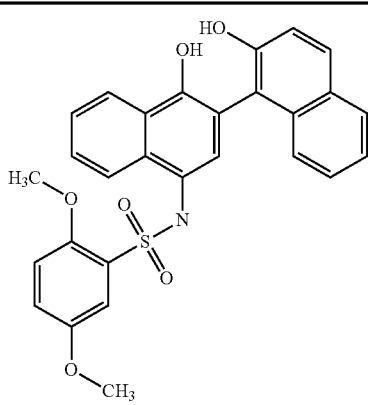 | C28H23NO6S | 501.5626 | 6.417 |
| F5749-0014 | 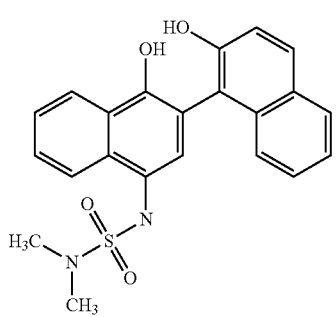 [SMILES: CN(C)S(=O)(=O)Nc1cc(-c2c(O)ccc3ccccc23)c(O)c2ccccc12] | C22H20N2O4S | 408.4797 | 4.364 |
| F5749-0015 | 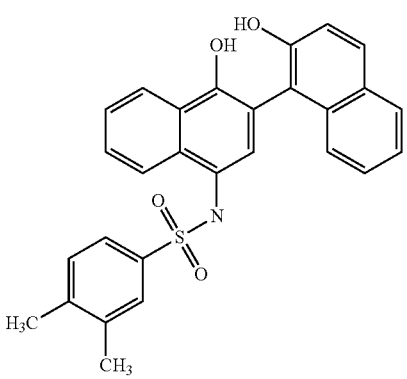 [SMILES: Cc1ccc(S(=O)(=O)Nc2cc(-c3c(O)ccc4ccccc34)c(O)c3ccccc23)cc1C] | C28H23NO4S | 469.5638 | 7.101 |
| F5749-0016 | 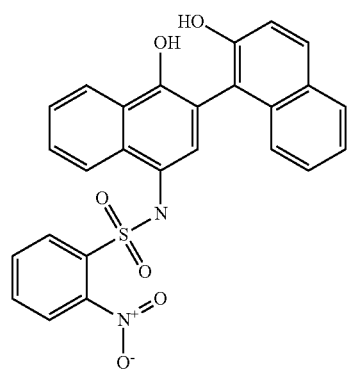 [SMILES: O=[N+]([O-])c1ccccc1S(=O)(=O)Nc1cc(-c2c(O)ccc3ccccc23)c(O)c2ccccc12] | C26H18N2O6S | 486.5072 | 6.403 |

TABLE 7-continued

| IDNUMBER | Structure | Formula structure | MW | LogP |
|---|---|---|---|---|
| F5749-0017 | 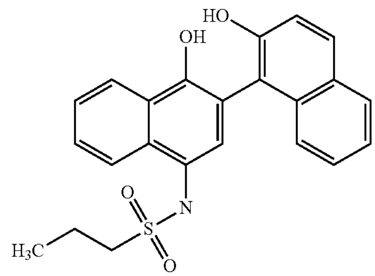 [SMILES: CCCS(=O)(=O)Nc1cc(-c2c(O)ccc3ccccc23)c(O)c2ccccc12] | C23H21NO4S | 407.4921 | 5.771 |
| F5749-0018 | 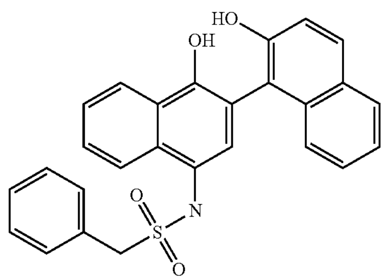 [SMILES: O=S(=O)(Cc1ccccc1)Nc1cc(-c2c(O)ccc3ccccc23)c(O)c2ccccc12] | C27H21NO4S | 455.5367 | 6.604 |
| F5749-0019 | 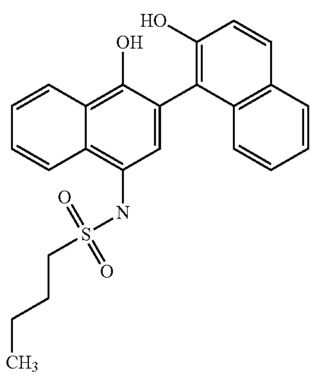 [SMILES: CCCCS(=O)(=O)Nc1cc(-c2c(O)ccc3ccccc23)c(O)c2ccccc12] | C24H23NO4S | 421.5192 | 6.213 |
| F5749-0020 | 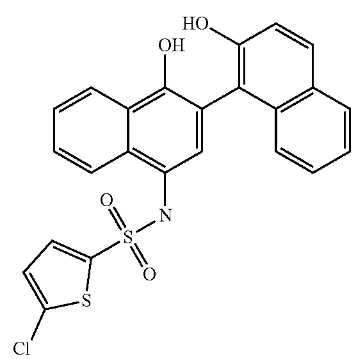 [SMILES: O=S(=O)(Nc1cc(-c2c(O)ccc3ccccc23)c(O)c2ccccc12)c1ccc(Cl)s1] | C24H16ClNO4S2 | 481.9804 | 7.273 |
| F5749-0021 | 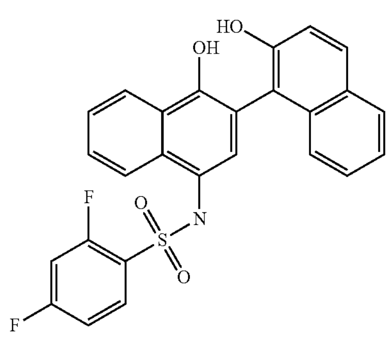 [SMILES: O=S(=O)(Nc1cc(-c2c(O)ccc3ccccc23)c(O)c2ccccc12)c1ccc(F)cc1F] | C26H17F2NO4S | 477.4905 | 6.811 |

TABLE 7-continued

| IDNUMBER | Structure | Formula structure | MW | LogP |
|---|---|---|---|---|
| F5749-0022 | 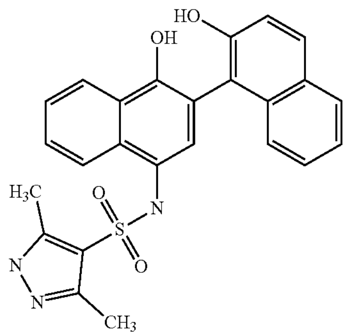 [SMILES: Cc1n[nH]c(C)c1S(=O)(=O)Nc1cc(-c2c(O)ccc3ccccc23)c(O)c2ccccc12] | C25H21N3O4S | 459.5278 | 5.58 |
| F5749-0023 | 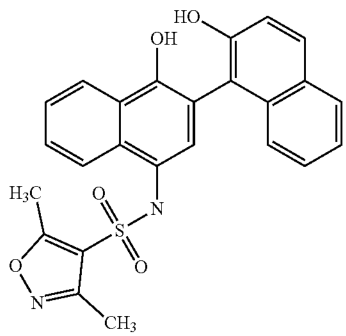 | C25H20N2O5S | 460.5126 | 5.614 |
| F5749-0024 | 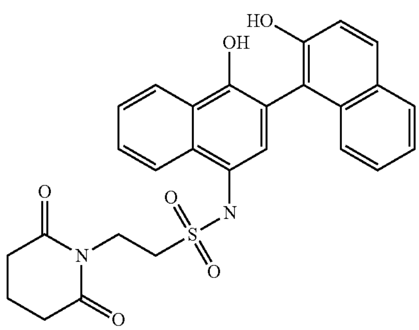 [SMILES: O=C1CCCC(=O)N1CCS(=O)(=O)Nc1cc(-c2c(O)ccc3ccccc23)c(O)c2ccccc12] | C27H24N2O6S | 504.5661 | 4.257 |
| F5749-0025 | 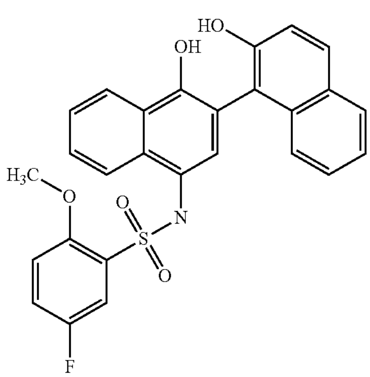 [SMILES: COc1ccc(F)cc1S(=O)(=O)Nc1cc(-c2c(O)ccc3ccccc23)c(O)c2ccccc12] | C27H20FNO5S | 489.5266 | 6.614 |

TABLE 7-continued

| IDNUMBER | Structure | Formula structure | MW | LogP |
| --- | --- | --- | --- | --- |
| F5749-0026 | 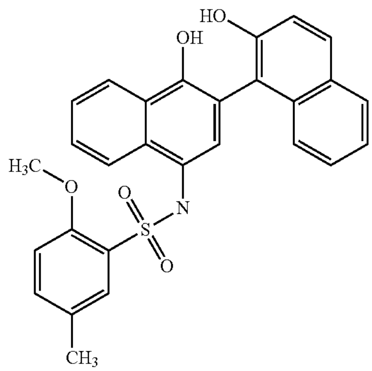 [SMILES: COc1ccc(C)cc1S(=O)(=O)Nc1cc(-c2c(O)ccc3ccccc23)c(O)c2ccccc12] | C28H23NO5S | 485.5632 | 6.759 |
| F5749-0027 | 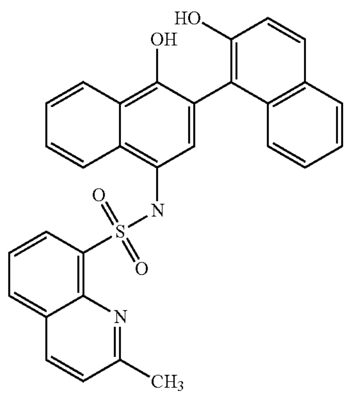 [SMILES: Cc1ccc2cccc(S(=O)(=O)Nc3cc(-c4c(O)ccc5ccccc45)c(O)c4ccccc34)c2n1] | C30H22N2O4S | 506.5848 | 6.929 |
| F5749-0028 | 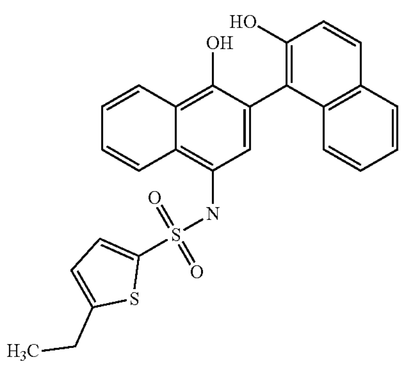 [SMILES: CCc1ccc(S(=O)(=O)Nc2cc(-c3c(O)ccc4ccccc34)c(O)c3ccccc23)s1] | C26H21NO4S2 | 475.5896 | 7.121 |
| F5749-0029 | 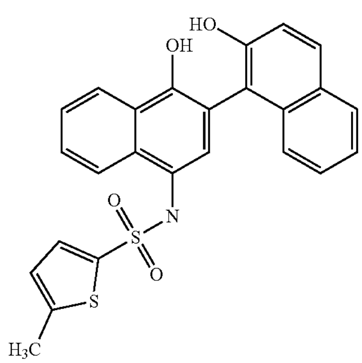 [SMILES: Cc1ccc(S(=O)(=O)Nc2cc(-c3c(O)ccc4ccccc34)c(O)c3ccccc23)s1] | C25H19NO4S2 | 461.5625 | 6.646 |

TABLE 7-continued

| IDNUMBER | Structure | Formula structure | MW | LogP |
| --- | --- | --- | --- | --- |
| F5749-0030 | 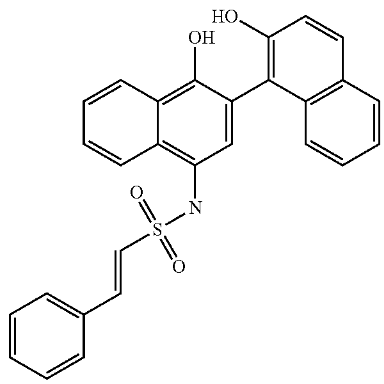 [SMILES: O=S(=O)(/C=C/c1ccccc1)Nc1cc(-c2c(O)ccc3ccccc23)c(O)c2ccccc12] | C28H21NO4S | 467.5479 | 6.828 |
| F5749-0031 | 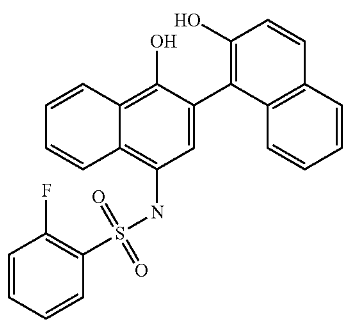 [SMILES: O=S(=O)(Nc1cc(-c2c(O)ccc3ccccc23)c(O)c2ccccc12)c1ccccc1F] | C26H18FNO4S | 459.5001 | 6.621 |
| F5749-0032 | 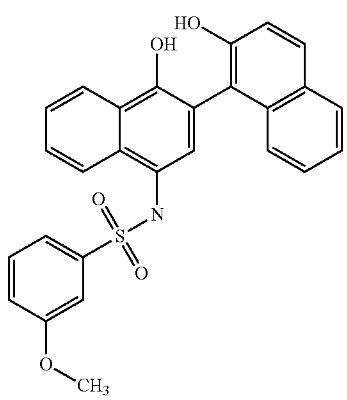 [SMILES: COc1cccc(S(=O)(=O)Nc2cc(-c3c(O)ccc4ccccc34)c(O)c3ccccc23)c1] | C27H21NO5S | 471.5361 | 6.463 |
| F5749-0033 | 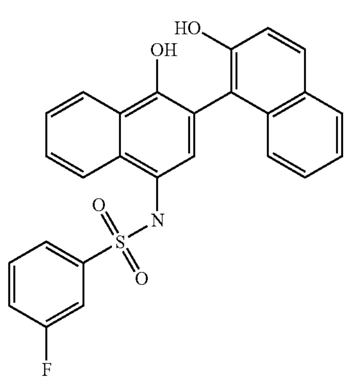 [SMILES: O=S(=O)(Nc1cc(-c2c(O)ccc3ccccc23)c(O)c2ccccc12)c1cccc(F)c1] | C26H18FNO4S | 459.5001 | 6.66 |

TABLE 7-continued

| IDNUMBER | Structure | Formula structure | MW | LogP |
|---|---|---|---|---|
| F5749-0034 | 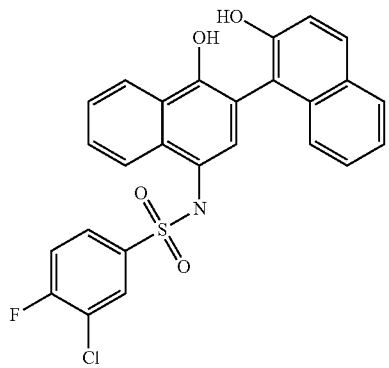 [SMILES: O=S(=O)(Nc1cc(-c2c(O)ccc3ccccc23)c(O)c2ccccc12)c1ccc(F)c(Cl)c1] | C26H17ClFNO4S | 493.9451 | 7.25 |
| F5749-0035 | 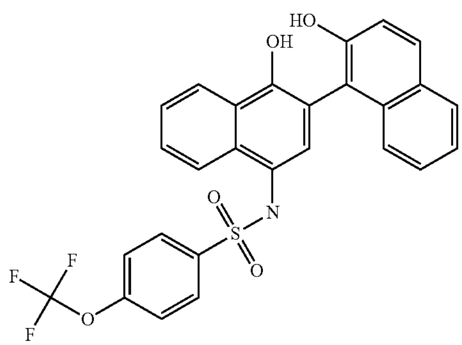 [SMILES: O=S(=O)(Nc1cc(-c2c(O)ccc3ccccc23)c(O)c2ccccc12)c1ccc(OC(F)(F)F)cc1] | C27H18F3NO5S | 525.5074 | 7.86876 |
| F5749-0036 | 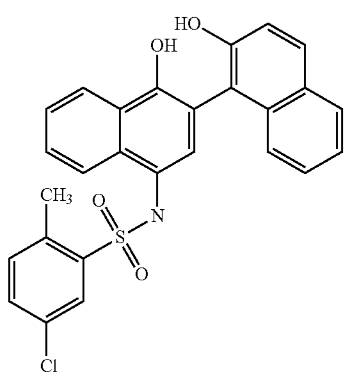 [SMILES: Cc1ccc(Cl)cc1S(=O)(=O)Nc1cc(-c2c(O)ccc3ccccc23)c(O)c2ccccc12] | C27H20ClNO4S | 489.9818 | 7.395 |
| F5749-0037 | 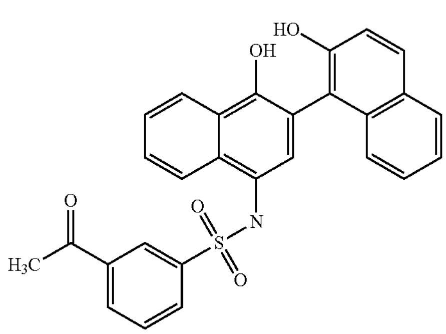 [SMILES: CC(=O)c1cccc(S(=O)(=O)Nc2cc(-c3c(O)ccc4ccccc34)c(O)c3ccccc23)c1] | C28H21NO5S | 483.5473 | 6.36 |

TABLE 7-continued
| IDNUMBER | Structure | Formula structure | MW | LogP |
|---|---|---|---|---|
| F5749-0038 | 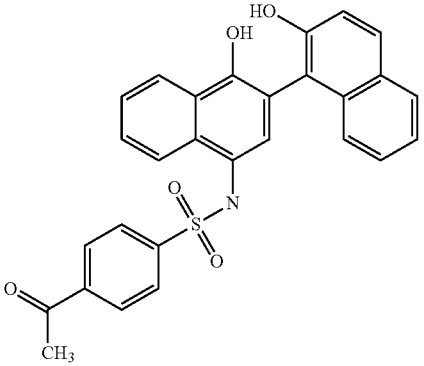 [SMILES: CC(=O)c1ccc(S(=O)(=O)Nc2cc(-c3c(O)ccc4ccccc34)c(O)c3ccccc23)cc1] | C28H21NO5S | 483.5473 | 6.323 |
| F5749-0039 | 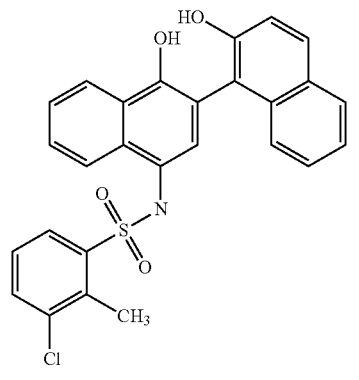 [SMILES: Cc1c(Cl)cccc1S(=O)(=O)Nc1cc(-c2c(O)ccc3ccccc23)c(O)c2ccccc12] | C27H20ClNO4S | 489.9818 | 7.356 |
| F5749-0040 | 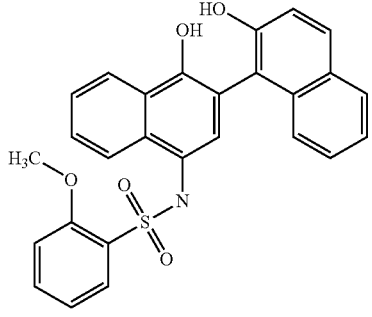 [SMILES: COc1ccccc1S(=O)(=O)Nc1cc(-c2c(O)ccc3ccccc23)c(O)c2ccccc12] | C27H21NO5S | 471.5361 | 6.424 |
| F5749-0041 | 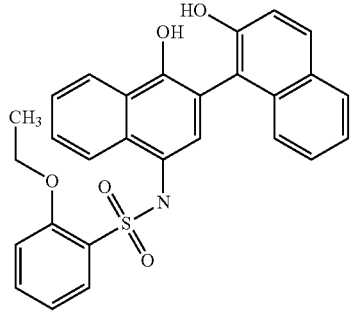 [SMILES: CCOc1ccccc1S(=O)(=O)Nc1cc(-c2c(O)ccc3ccccc23)c(O)c2ccccc12] | C28H23NO5S | 485.5632 | 6.765 |

TABLE 7-continued

| IDNUMBER | Structure | Formula structure | MW | LogP |
| --- | --- | --- | --- | --- |
| F5749-0042 | 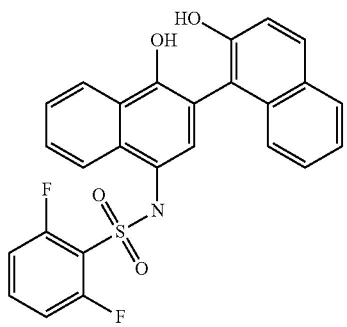 [SMILES: O=S(=O)(Nc1cc(-c2c(O)ccc3ccccc23)c(O)c2ccccc12)c1c(F)cccc1F] | C26H17F2NO4S | 477.4905 | 6.772 |
| F5749-0043 | 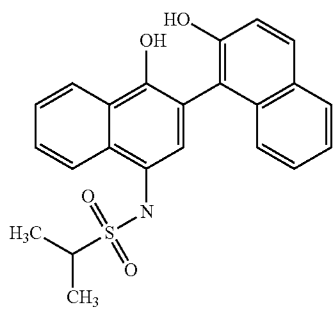 | C23H21NO4S | 407.4921 | 5.963 |
| F5749-0044 | 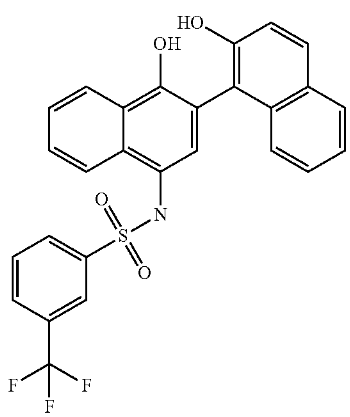 [SMILES: O=S(=O)(Nc1cc(-c2c(O)ccc3ccccc23)c(O)c2ccccc12)c1cccc(C(F)(F)F)c1] | C27H18F3NO4S | 509.508 | 7.44176 |
| F5749-0045 | 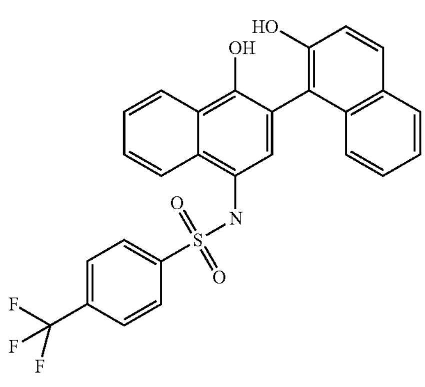 [SMILES: O=S(=O)(Nc1cc(-c2c(O)ccc3ccccc23)c(O)c2ccccc12)c1ccc(C(F)(F)F)cc1] | C27H18F3NO4S | 509.508 | 7.40476 |

TABLE 7-continued

| IDNUMBER | Structure | Formula structure | MW | LogP |
|---|---|---|---|---|
| F5749-0046 | 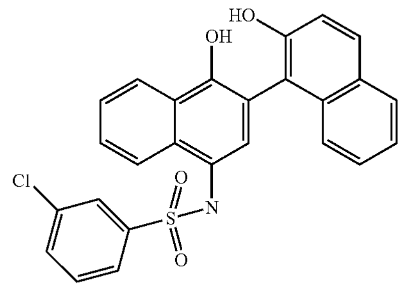 [SMILES: O=S(=O)(Nc1cc(-c2c(O)ccc3ccccc23)c(O)c2ccccc12)c1cccc(Cl)c1] | C26H18ClNO4S | 475.9547 | 7.099 |
| F5749-0047 | 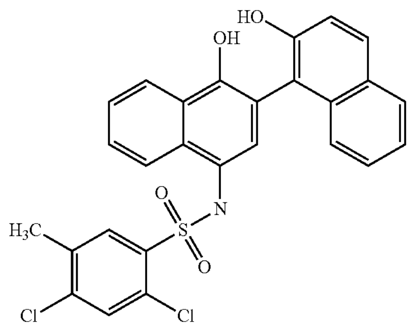 [SMILES: Cc1cc(S(=O)(=O)Nc2cc(-c3c(O)ccc4ccccc34)c(O)c3ccccc23)c(Cl)cc1Cl] | C27H19Cl2NO4S | 524.4268 | 8.022 |
| F5749-0048 | 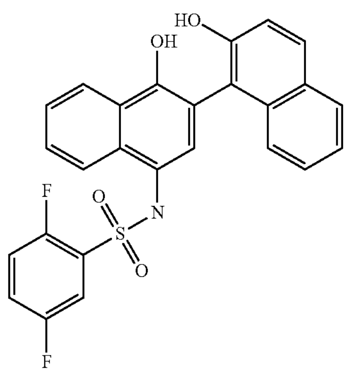 [SMILES: O=S(=O)(Nc1cc(-c2c(O)ccc3ccccc23)c(O)c2ccccc12)c1cc(F)ccc1F] | C26H17F2NO4S | 477.4905 | 6.811 |
| F5749-0049 | 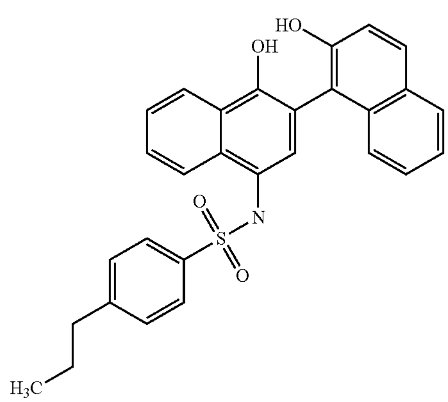 [SMILES: CCCc1ccc(S(=O)(=O)Nc2cc(-c3c(O)ccc4ccccc34)c(O)c3ccccc23)cc1] | C29H25NO4S | 483.5909 | 7.685 |

TABLE 7-continued

| IDNUMBER | Structure | Formula structure | MW | LogP |
|---|---|---|---|---|
| F5749-0050 | 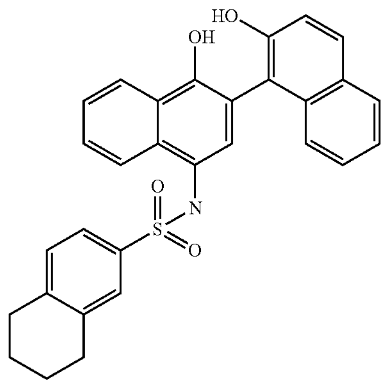 [SMILES: O=S(=O)(Nc1cc(-c2c(O)ccc3ccccc23)c(O)c2ccccc12)c1ccc2c(c1)CCCC2] | C30H25NO4S | 495.6021 | 7.557 |
| F5749-0051 | 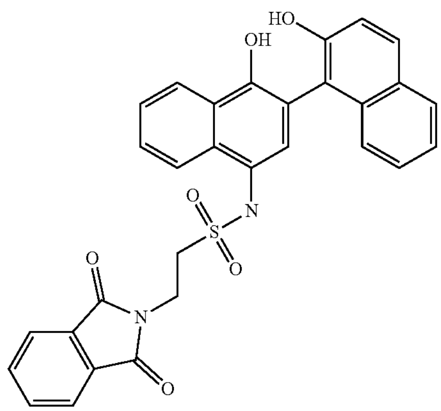 [SMILES: O=C1c2ccccc2C(=O)N1CCS(=O)(=O)Nc1cc(-c2c(O)ccc3ccccc23)c(O)c2ccccc12] | C30H22N2O6S | 538.5836 | 5.597 |
| F5749-0052 | 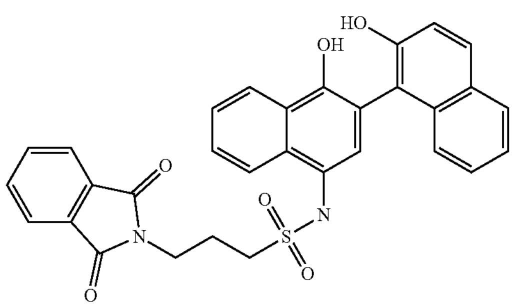 [SMILES: O=C1c2ccccc2C(=O)N1CCCS(=O)(=O)Nc1cc(-c2c(O)ccc3ccccc23)c(O)c2ccccc12] | C31H24N2O6S | 552.6107 | 6.039 |
| F5749-0053 | 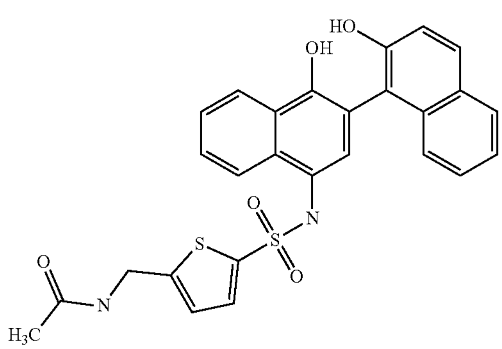 [SMILES: CC(=O)NCc1ccc(S(=O)(=O)Nc2cc(-c3c(O)ccc4ccccc34)c(O)c3ccccc23)s1] | C27H22N2O5S2 | 518.6148 | 5.773 |

TABLE 7-continued
| IDNUMBER | Structure | Formula structure | MW | LogP |
|---|---|---|---|---|
| F5749-0054 | 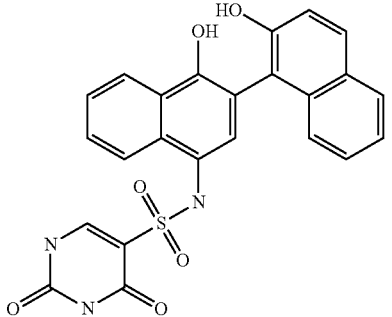 [SMILES: O=c1[nH]cc(S(=O)(=O)Nc2cc(-c3c(O)ccc4ccccc34)c(O)c3ccccc23)c(=O)[nH]1] | C24H17N3O6S | 475.4836 | 3.515 |
| F5749-0055 | 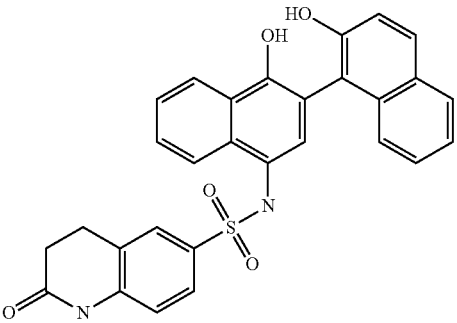 [SMILES: O=C1CCc2cc(S(=O)(=O)Nc3cc(-c4c(O)ccc5ccccc45)c(O)c4ccccc34)ccc2N1] | C29H22N2O5S | 510.5731 | 5.666 |
| F5749-0056 | 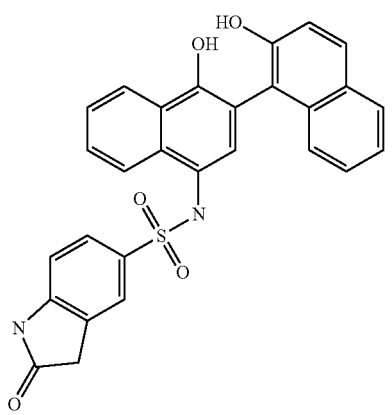 [SMILES: O=C1Cc2cc(S(=O)(=O)Nc3cc(-c4c(O)ccc5ccccc45)c(O)c4ccccc34)ccc2N1] | C28H20N2O5S | 496.546 | 5.578 |
| F5749-0057 | 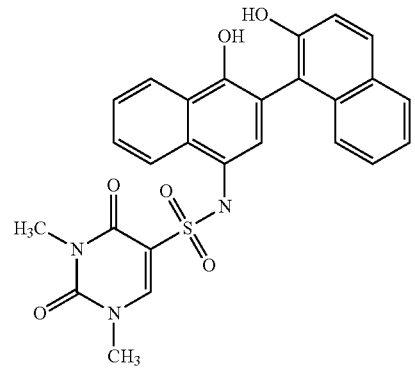 [SMILES: Cn1cc(S(=O)(=O)Nc2cc(-c3c(O)ccc4ccccc34)c(O)c3ccccc23)c(=O)n(C)c1=O] | C26H21N3O6S | 503.5378 | 3.579 |

TABLE 7-continued

| IDNUMBER | Structure | Formula structure | MW | LogP |
|---|---|---|---|---|
| F5749-0058 | 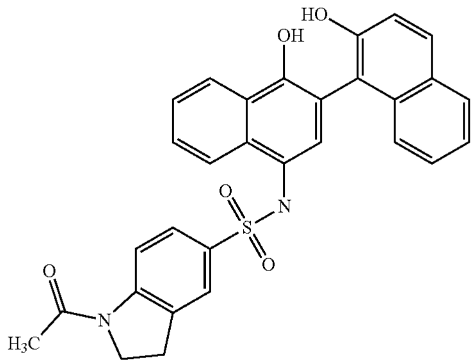 [SMILES: CC(=O)N1CCc2cc(S(=O)(=O)Nc3cc(-c4c(O)ccc5ccccc45)c(O)c4ccccc34)ccc21] | C30H24N2O5S | 524.6002 | 5.901 |
| F5749-0059 | 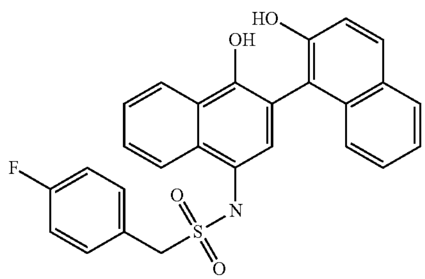 [SMILES: O=S(=O)(Cc1ccc(F)cc1)Nc1cc(-c2c(O)ccc3ccccc23)c(O)c2ccccc12] | C27H20FNO4S | 473.5272 | 6.757 |
| F5749-0060 | 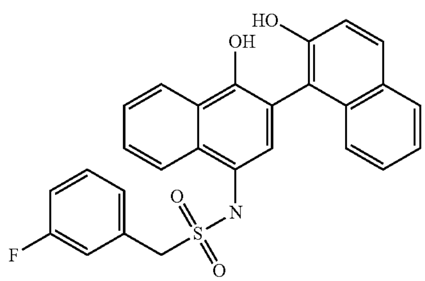 [SMILES: O=S(=O)(Cc1cccc(F)c1)Nc1cc(-c2c(O)ccc3ccccc23)c(O)c2ccccc12] | C27H20FNO4S | 473.5272 | 6.794 |
| F5749-0061 | 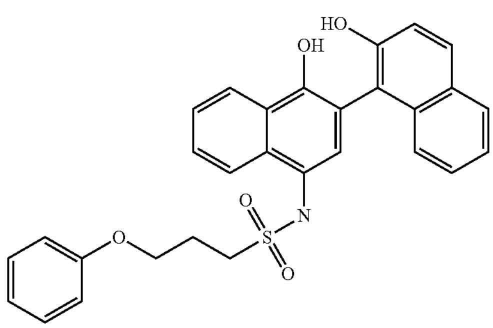 [SMILES: O=S(=O)(CCCOc1ccccc1)Nc1cc(-c2c(O)ccc3ccccc23)c(O)c2ccccc12] | C29H25NO5S | 499.5903 | 6.83 |
| F5749-0062 | 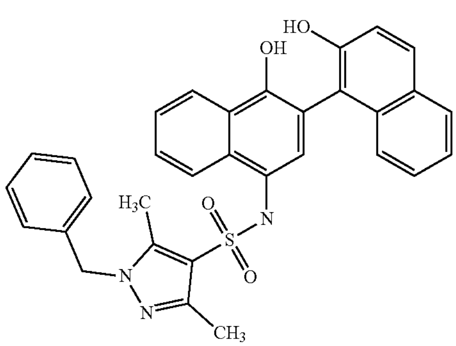 [SMILES: Cc1nn(Cc2ccccc2)c(C)c1S(=O)(=O)Nc1cc(-c2c(O)ccc3ccccc23)c(O)c2ccccc12] | C32H27N3O4S | 549.6537 | 6.749 |

TABLE 7-continued
| IDNUMBER | Structure | Formula structure | MW | LogP |
|---|---|---|---|---|
| F5749-0063 | 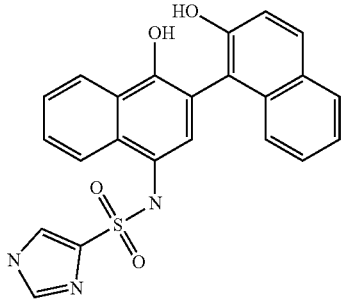 [SMILES: O=S(=O)(Nc1cc(-c2c(O)ccc3ccccc23)c(O)c2ccccc12)c1c[nH]cn1] | C23H17N3O4S | 431.4736 | 4.61 |
| F5749-0064 | 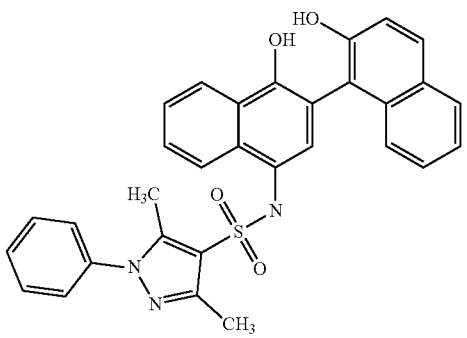 [SMILES: Cc1nn(-c2ccccc2)c(C)c1S(=O)(=O)Nc1cc(-c2c(O)ccc3ccccc23)c(O)c2ccccc12] | C31H25N3O4S | 535.6266 | 6.615 |
| F5749-0065 | 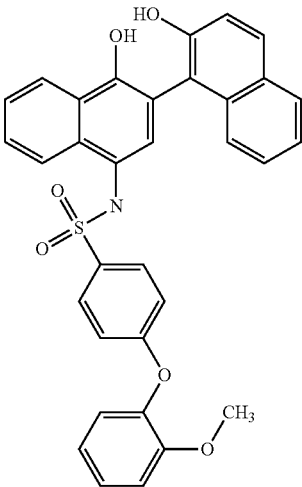 [SMILES: COc1ccccc1Oc1ccc(S(=O)(=O)Nc2cc(-c3c(O)ccc4ccccc34)c(O)c3ccccc23)cc1] | C33H25NO6S | 563.6343 | 7.78574 |

TABLE 7-continued

| IDNUMBER | Structure | Formula structure | MW | LogP |
| --- | --- | --- | --- | --- |
| F5749-0066 | 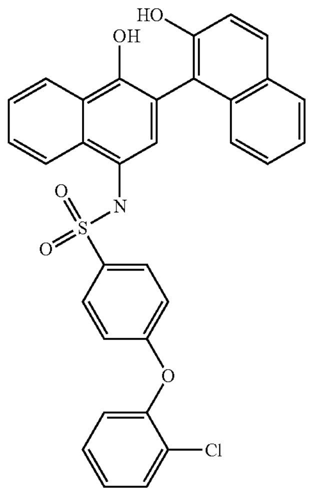 [SMILES: O=S(=O)(Nc1cc(-c2c(O)ccc3ccccc23)c(O)c2ccccc12)c1ccc(Oc2ccccc2Cl)cc1] | C32H22ClNO5S | 568.0528 | 8.67 |
| F5749-0067 | 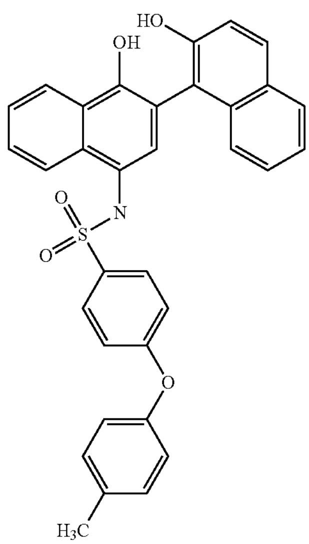 [SMILES: Cc1ccc(Oc2ccc(S(=O)(=O)Nc3cc(-c4c(O)ccc5ccccc45)c(O)c4ccccc34)cc2)cc1] | C33H25NO5S | 547.6349 | 8.378 |
| F5749-0068 | 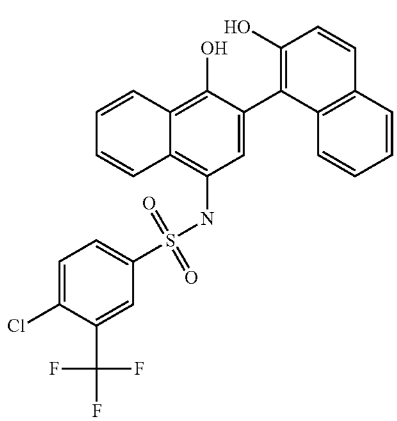 [SMILES: O=S(=O)(Nc1cc(-c2c(O)ccc3ccccc23)c(O)c2ccccc12)c1ccc(Cl)c(C(F)(F)F)c1] | C27H17ClF3NO4S | 543.953 | 8.03176 |

TABLE 7-continued

| IDNUMBER | Structure | Formula structure | MW | LogP |
| --- | --- | --- | --- | --- |
| F5749-0069 | 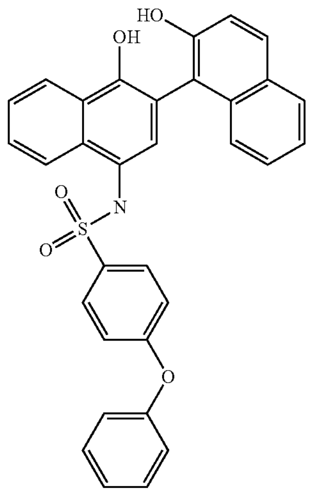 [SMILES: O=S(=O)(Nc1cc(-c2c(O)ccc3ccccc23)c(O)c2ccccc12)c1ccc(Oc2ccccc2)cc1] | C32H23NO5S | 533.6078 | 8.08 |
| F5749-0070 | 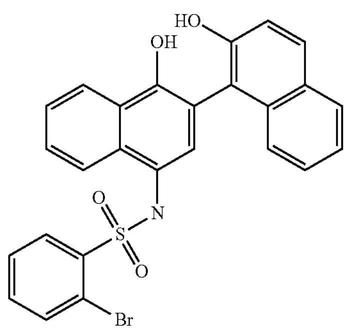 [SMILES: O=S(=O)(Nc1cc(-c2c(O)ccc3ccccc23)c(O)c2ccccc12)c1ccccc1Br] | C26H18BrNO4S | 520.4057 | 7.266 |
| F5749-0071 | 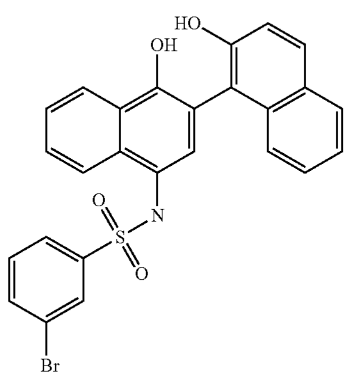 [SMILES: O=S(=O)(Nc1cc(-c2c(O)ccc3ccccc23)c(O)c2ccccc12)c1cccc(Br)c1] | C26H18BrNO4S | 520.4057 | 7.305 |
| F5749-0072 | 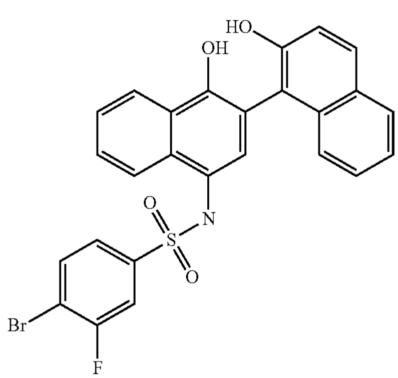 [SMILES: O=S(=O)(Nc1cc(-c2c(O)ccc3ccccc23)c(O)c2ccccc12)c1ccc(Br)c(F)c1] | C26H17BrFNO4S | 538.3961 | 7.456 |

TABLE 7-continued

| IDNUMBER | Structure | Formula structure | MW | LogP |
|---|---|---|---|---|
| F5749-0073 | 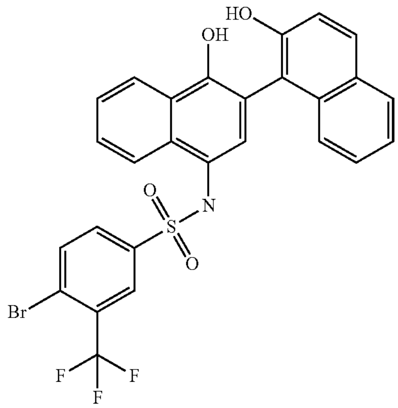 [SMILES: O=S(=O)(Nc1cc(-c2c(O)ccc3ccccc23)c(O)c2ccccc12)c1ccc(Br)c(C(F)(F)F)c1] | C27H17BrF3NO4S | 588.404 | 8.23776 |
| F5749-0074 | 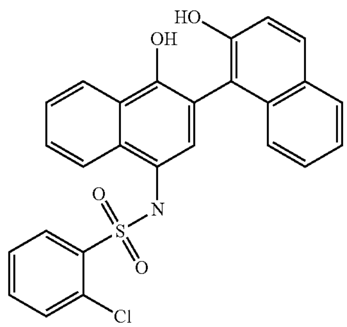 | C26H18ClNO4S | 475.9547 | 7.06 |
| F5749-0075 | 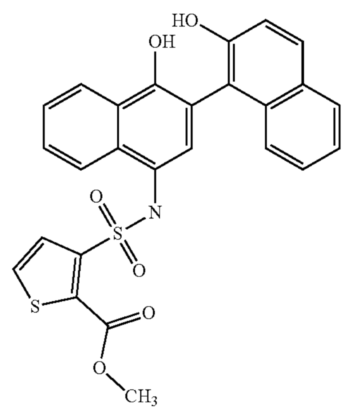 [SMILES: COC(=O)c1sccc1S(=O)(=O)Nc1cc(-c2c(O)ccc3ccccc23)c(O)c2ccccc12] | C26H19NO6S2 | 505.5724 | 5.67 |
| F5749-0076 | 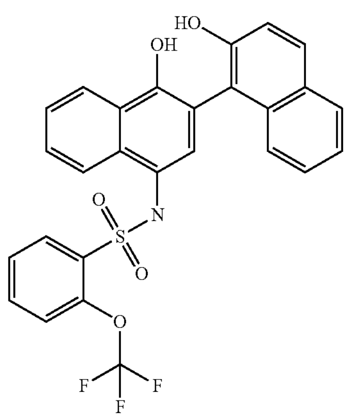 [SMILES: O=S(=O)(Nc1cc(-c2c(O)ccc3ccccc23)c(O)c2ccccc12)c1ccccc1OC(F)(F)F] | C27H18F3NO5S | 525.5074 | 7.86676 |

TABLE 8

| IDNUMBER | Structure | Formula structure | MW | LogP |
|---|---|---|---|---|
| F1566-0329 | 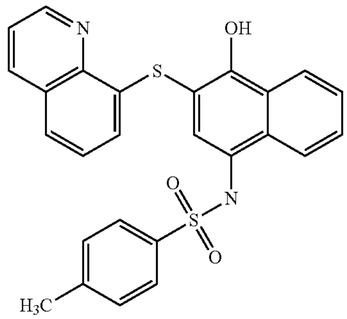 [SMILES: Cc1ccc(S(=O)(=O)Nc2cc(Sc3cccc4cccnc34)c(O)c3ccccc23)cc1] | C26H20N2O3S2 | 472.5889 | 6.344 |
| F1566-0341 | 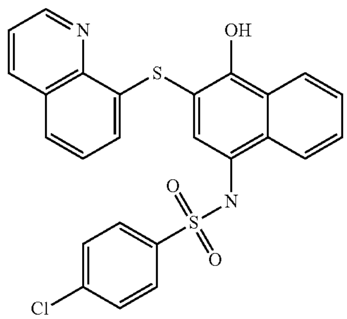 [SMILES: O=S(=O)(Nc1cc(Sc2cccc3cccnc23)c(O)c2ccccc12)c1ccc(Br)cc1] | C25H17ClN2O3S2 | 493.0068 | 6.638 |
| F1566-0353 | 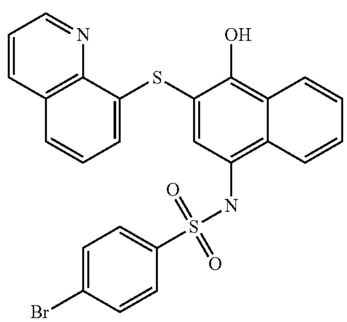 | C25H17BrN2O3S2 | 537.4578 | 6.844 |
| F1566-0377 | 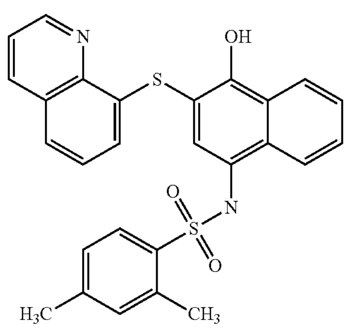 [SMILES: Cc1ccc(S(=O)(=O)Nc2cc(Sc3cccc4cccnc34)c(O)c3ccccc23)c(C)c1] | C27H22N2O3S2 | 486.616 | 6.677 |

TABLE 8-continued

| IDNUMBER | Structure | Formula structure | MW | LogP |
| --- | --- | --- | --- | --- |
| F1566-0425 | 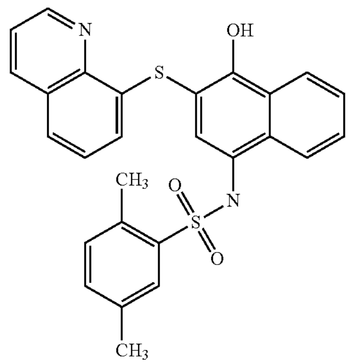 [SMILES: Cc1ccc(C)c(S(=O)(=O)Nc2cc(Sc3cccc4cccnc34)c(O)c3ccccc23)c1] | C27H22N2O3S2 | 486.616 | 6.677 |
| F1566-0449 | 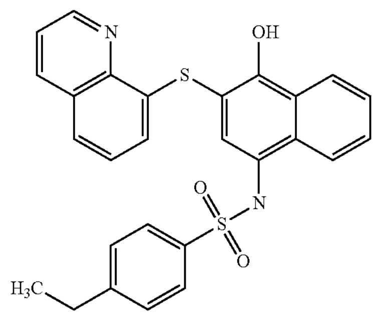 [SMILES: CCc1ccc(S(=O)(=O)Nc2cc(Sc3cccc4cccnc34)c(O)c3ccccc23)cc1] | C27H22N2O3S2 | 486.616 | 6.819 |
| F1566-0473 | 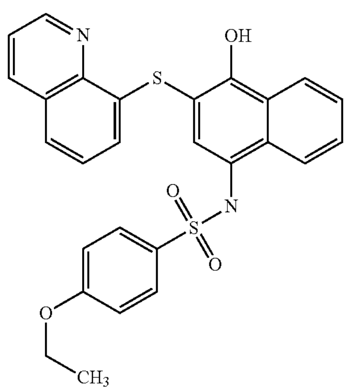 [SMILES: CCOc1ccc(S(=O)(=O)Nc2cc(Sc3cccc4cccnc34)c(O)c3ccccc23)cc1] | C27H22N2O4S2 | 502.6154 | 6.343 |
| F1566-0497 | 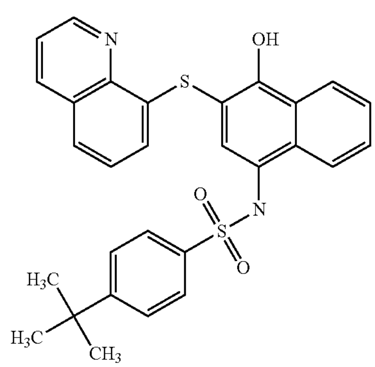 [SMILES: CC(C)(C)c1ccc(S(=O)(=O)Nc2cc(Sc3cccc4cccnc34)c(O)c3ccccc23)cc1] | C29H26N2O3S2 | 514.6702 | 7.545 |

TABLE 8-continued
| IDNUMBER | Structure | Formula structure | MW | LogP |
|---|---|---|---|---|
| F1566-0521 | 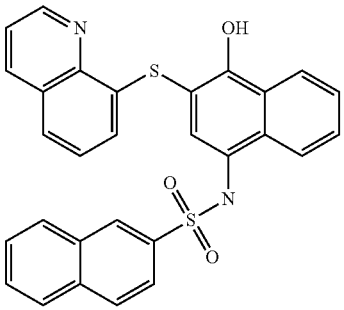 [SMILES: O=S(=O)(Nc1cc(Sc2cccc3cccnc23)c(O)c2ccccc12)c1ccc2ccccc2c1] | C29H20N2O3S2 | 508.6224 | 7.305 |
| F1566-0557 | 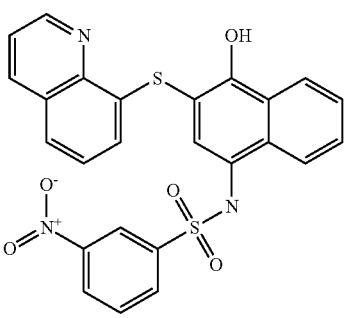 [SMILES: O=[N+]([O-])c1cccc(S(=O)(=O)Nc2cc(Sc3cccc4cccnc34)c(O)c3ccccc23)c1] | C25H17N3O5S2 | 503.5593 | 6.018 |
| F1566-0569 | 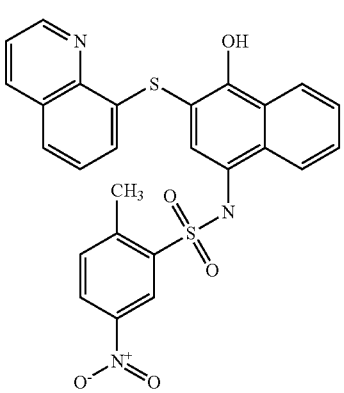 [SMILES: Cc1ccc([N+](=O)[O-])cc1S(=O)(=O)Nc1cc(Sc2cccc3cccnc23)c(O)c2ccccc12] | C26H19N3O5S2 | 517.5864 | 6.314 |
| F1566-0617 | 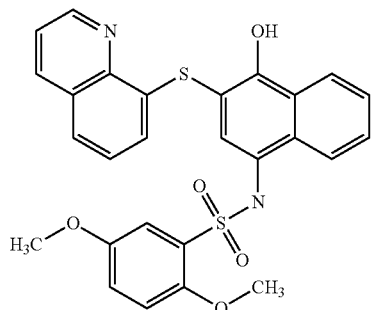 | C27H22N2O5S2 | 518.6148 | 5.993 |

TABLE 8-continued

| IDNUMBER | Structure | Formula structure | MW | LogP |
|---|---|---|---|---|
| F1566-0629 | 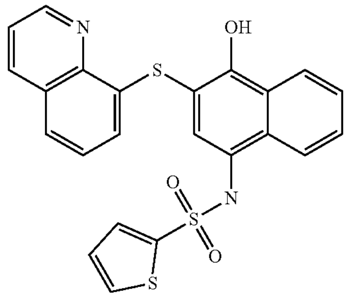 [SMILES: O=S(=O)(Nc1cc(Sc2cccc3cccnc23)c(O)c2ccccc12)c1cccs1] | C23H16N2O3S3 | 464.5876 | 5.559 |
| F1566-1608 | 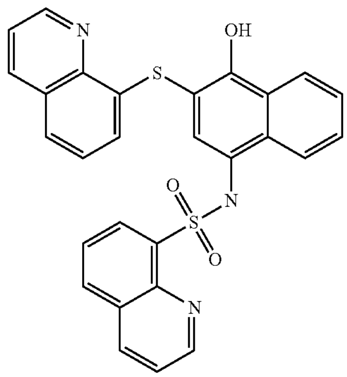 [SMILES: O=S(=O)(Nc1cc(Sc2cccc3cccnc23)c(O)c2ccccc12)c1cccc2cccnc12] | C28H19N3O3S2 | 509.6099 | 6.246 |
| F1566-1821 | 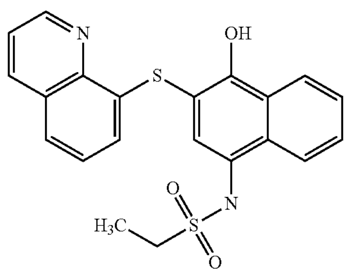 [SMILES: CCS(=O)(=O)Nc1cc(Sc2cccc3cccnc23)c(O)c2ccccc12] | C21H18N2O3S2 | 410.5172 | 4.905 |
| F1566-1835 | 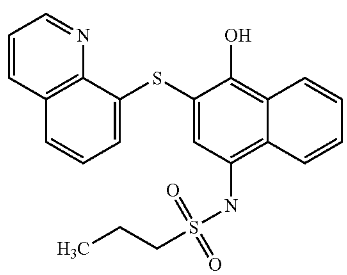 [SMILES: CCCS(=O)(=O)Nc1cc(Sc2cccc3cccnc23)c(O)c2ccccc12] | C22H20N2O3S2 | 424.5443 | 5.347 |
| F1566-1849 | 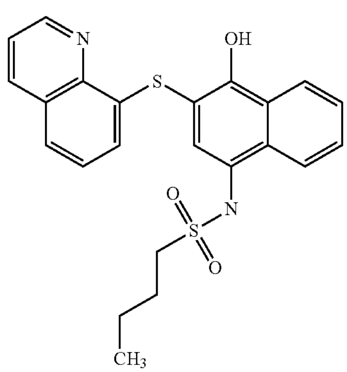 [SMILES: CCCCS(=O)(=O)Nc1cc(Sc2cccc3cccnc23)c(O)c2ccccc12] | C23H22N2O3S2 | 438.5714 | 5.789 |

TABLE 8-continued
| IDNUMBER | Structure | Formula structure | MW | LogP |
|---|---|---|---|---|
| F1566-1863 | 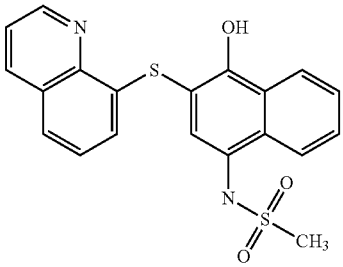 [SMILES: CS(=O)(=O)Nc1cc(Sc2cccc3cccnc23)c(O)c2ccccc12] | C20H16N2O3S2 | 396.4901 | 4.392 |
| F5749-0077 | 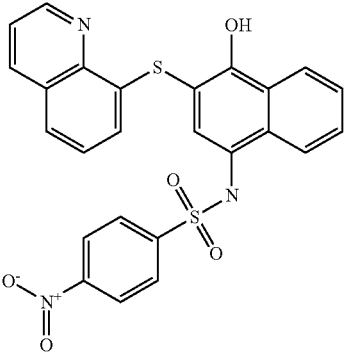 [SMILES: O=[N+]([O-])c1ccc(S(=O)(=O)Nc2cc(Sc3cccc4cccnc34)c(O)c3ccccc23)cc1] | C25H17N3O5S2 | 503.5593 | 5.981 |
| F5749-0078 | 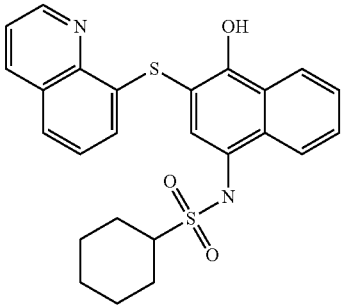 [SMILES: O=S(=O)(Nc1cc(Sc2cccc3cccnc23)c(O)c2ccccc12)C1CCCCC1] | C25H24N2O3S2 | 464.6096 | 6.371 |
| F5749-0079 | 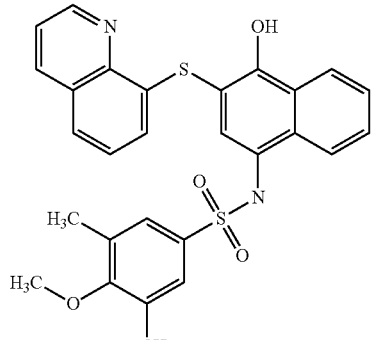 | C28H24N2O4S2 | 516.6425 | 6.668 |

TABLE 8-continued

| IDNUMBER | Structure | Formula structure | MW | LogP |
|---|---|---|---|---|
| F5749-0080 | 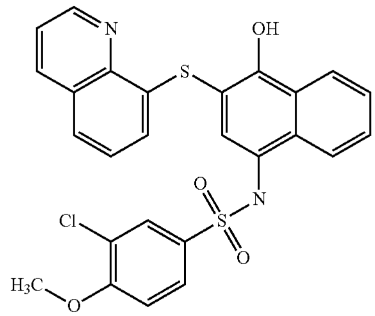 [SMILES: COc1ccc(S(=O)(=O)Nc2cc(Sc3cccc4cccnc34)c(O)c3ccccc23)cc1Cl] | C26H19ClN2O4S2 | 523.0333 | 6.629 |
| F5749-0081 | 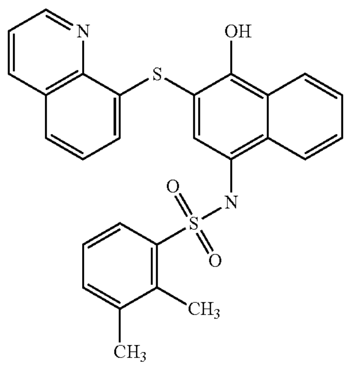 [SMILES: Cc1cccc(S(=O)(=O)Nc2cc(Sc3cccc4cccnc34)c(O)c3ccccc23)c1C] | C27H22N2O3S2 | 486.616 | 6.638 |
| F5749-0082 | 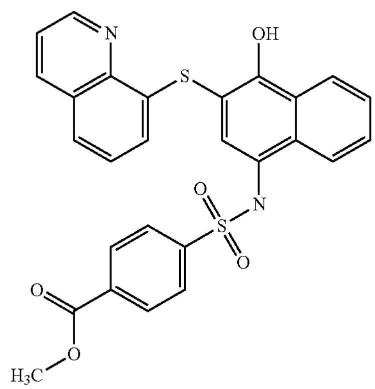 [SMILES: COC(=O)c1ccc(S(=O)(=O)Nc2cc(Sc3cccc4cccnc34)c(O)c3ccccc23)cc1] | C27H20N2O5S2 | 516.5989 | 5.987 |
| F5749-0083 | 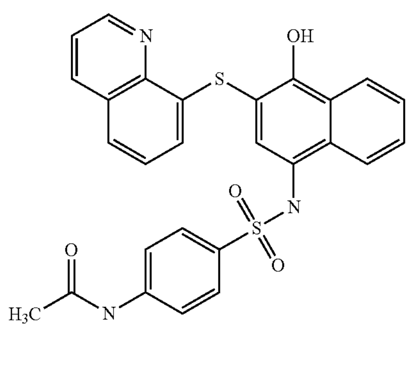 [SMILES: CC(=O)Nc1ccc(S(=O)(=O)Nc2cc(Sc3cccc4cccnc34)c(O)c3ccccc23)cc1] | C27H21N3O4S2 | 515.6141 | 5.337 |

TABLE 8-continued

| IDNUMBER | Structure | Formula structure | MW | LogP |
|---|---|---|---|---|
| F5749-0084 | 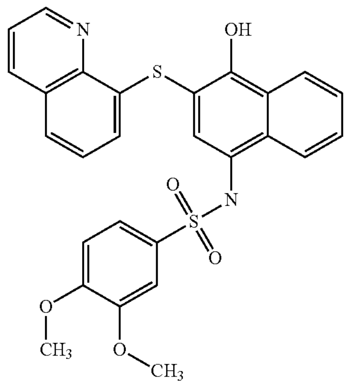 [SMILES: COc1ccc(S(=O)(=O)Nc2cc(Sc3cccc4cccnc34)c(O)c3ccccc23)cc1OC] | C27H22N2O5S2 | 518.6148 | 5.74474 |
| F5749-0085 | 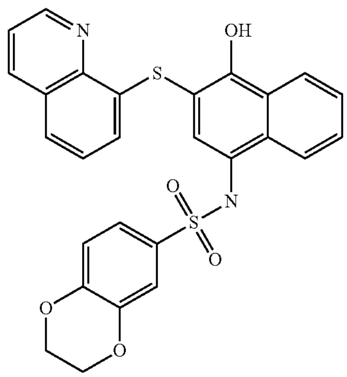 [SMILES: O=S(=O)(Nc1cc(Sc2cccc3cccnc23)c(O)c2ccccc12)c1ccc2c(c1)OCCO2] | C27H20N2O5S2 | 516.5989 | 5.641 |
| F5749-0086 | 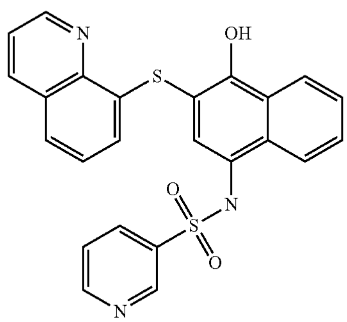 [SMILES: O=S(=O)(Nc1cc(Sc2cccc3cccnc23)c(O)c2ccccc12)c1cccnc1] | C24H17N3O3S2 | 459.5494 | 4.813 |
| F5749-0087 | 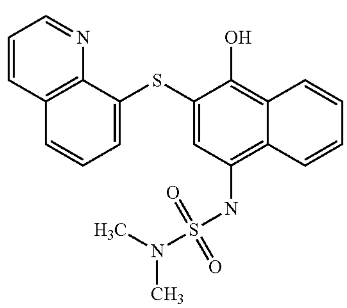 [SMILES: CN(C)S(=O)(=O)Nc1cc(Sc2cccc3cccnc23)c(O)c2ccccc12] | C21H19N3O3S2 | 425.5319 | 3.94 |

TABLE 8-continued

| IDNUMBER | Structure | Formula structure | MW | LogP |
|---|---|---|---|---|
| F5749-0088 | 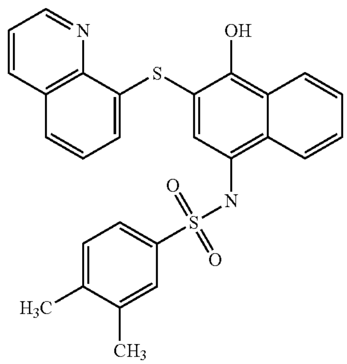 [SMILES: Cc1ccc(S(=O)(=O)Nc2cc(Sc3cccc4cccnc34)c(O)c3ccccc23)cc1C] | C27H22N2O3S2 | 486.616 | 6.677 |
| F5749-0089 | 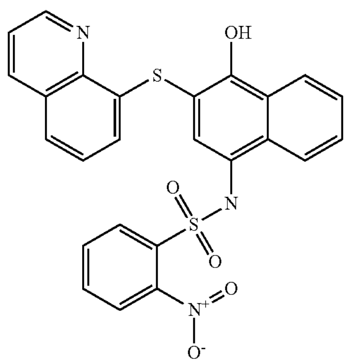 [SMILES: O=[N+]([O-])c1ccccc1S(=O)(=O)Nc1cc(Sc2cccc3cccnc23)c(O)c2ccccc12] | C25H17N3O5S2 | 503.5593 | 5.979 |
| F5749-0090 | 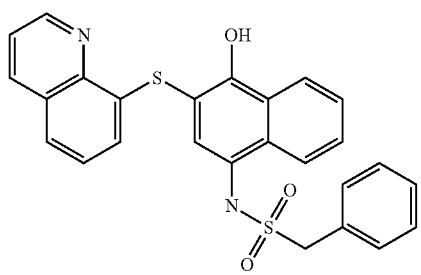 [SMILES: O=S(=O)(Cc1ccccc1)Nc1cc(Sc2cccc3cccnc23)c(O)c2ccccc12] | C26H20N2O3S2 | 472.5889 | 6.18 |
| F5749-0091 | 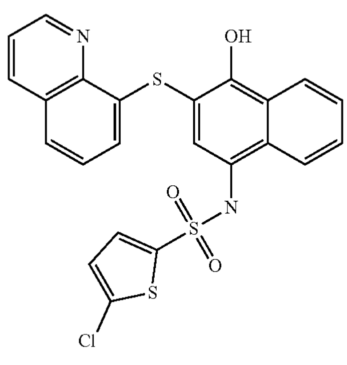 [SMILES: O=S(=O)(Nc1cc(Sc2cccc3cccnc23)c(O)c2ccccc12)c1ccc(Cl)s1] | C23H15ClN2O3S3 | 499.0326 | 6.849 |

TABLE 8-continued

| IDNUMBER | Structure | Formula structure | MW | LogP |
|---|---|---|---|---|
| F5749-0092 | 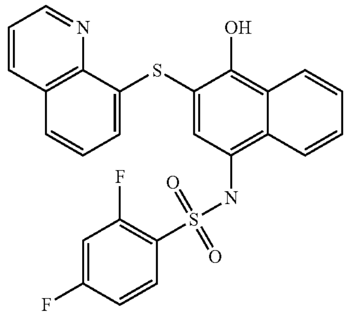 [SMILES: O=S(=O)(Nc1cc(Sc2cccc3cccnc23)c(O)c2ccccc12)c1ccc(F)cc1F] | C25H16F2N2O3S2 | 494.5427 | 6.387 |
| F5749-0093 | 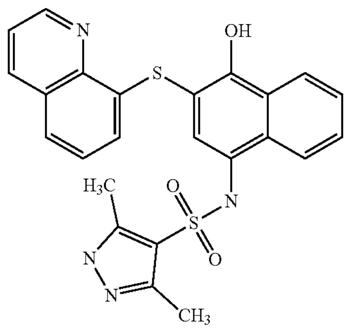 [SMILES: Cc1noc(C)c1S(=O)(=O)Nc1cc(Sc2cccc3cccnc23)c(O)c2ccccc12] | C24H20N4O3S2 | 476.58 | 5.156 |
| F5749-0094 | 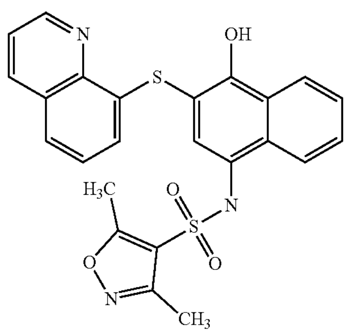 | C24H19N3O4S2 | 477.5647 | 5.19 |
| F5749-0095 | 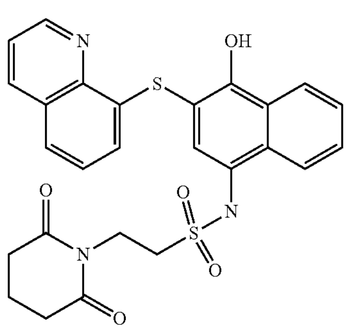 [SMILES: O=C1CCCC(=O)N1CCS(=O)(=O)Nc1cc(Sc2cccc3cccnc23)c(O)c2ccccc12] | C26H23N3O5S2 | 521.6183 | 3.833 |

TABLE 8-continued

| IDNUMBER | Structure | Formula structure | MW | LogP |
|---|---|---|---|---|
| F5749-0096 | 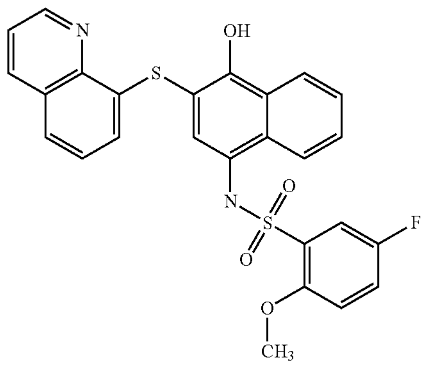 [SMILES: COc1ccc(F)cc1S(=O)(=O)Nc1cc(Sc2cccc3cccnc23)c(O)c2ccccc12] | C26H19FN2O4S2 | 506.5787 | 6.19 |
| F5749-0097 | 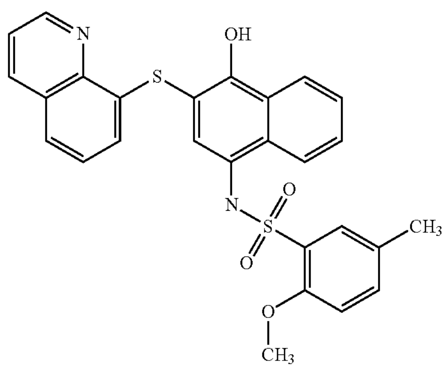 [SMILES: COc1ccc(C)cc1S(=O)(=O)Nc1cc(Sc2cccc3cccnc23)c(O)c2ccccc12] | C27H22N2O4S2 | 502.6154 | 6.335 |
| F5749-0098 | 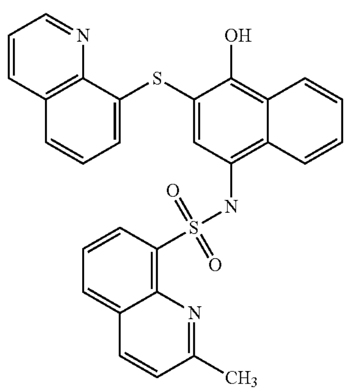 [SMILES: Cc1ccc2cccc(S(=O)(=O)Nc3cc(Sc4cccc5cccnc45)c(O)c4ccccc34)c2n1] | C29H21N3O3S2 | 523.637 | 6.505 |
| F5749-0099 | 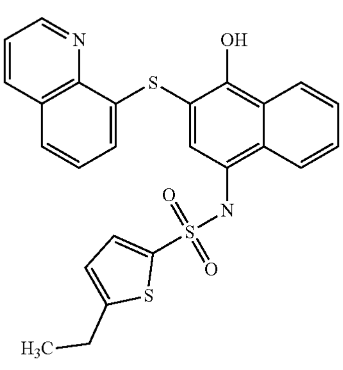 [SMILES: CCc1ccc(S(=O)(=O)Nc2cc(Sc3cccc4cccnc34)c(O)c3ccccc23)s1] | C25H20N2O3S3 | 492.6418 | 6.697 |

TABLE 8-continued

| IDNUMBER | Structure | Formula structure | MW | LogP |
|---|---|---|---|---|
| F5749-0100 | 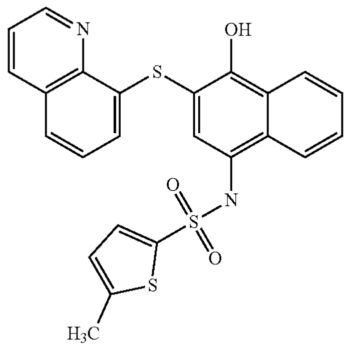 [SMILES: Cc1ccc(S(=O)(=O)Nc2cc(Sc3cccc4cccnc34)c(O)c3ccccc23)s1] | C24H18N2O3S3 | 478.6147 | 6.222 |
| F5749-0101 | 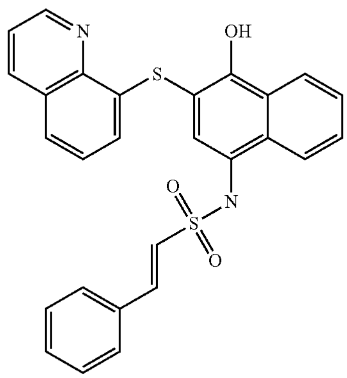 [SMILES: O=S(=O)(/C=C/c1ccccc1)Nc1cc(Sc2cccc3cccnc23)c(O)c2ccccc12] | C27H20N2O3S2 | 484.6001 | 6.404 |
| F5749-0102 | 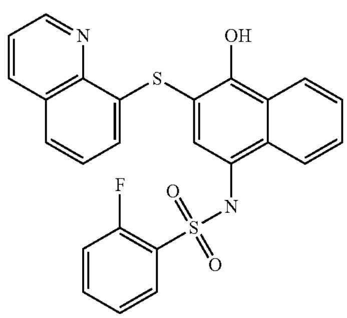 [SMILES: O=S(=O)(Nc1cc(Sc2cccc3cccnc23)c(O)c2ccccc12)c1ccccc1F] | C25H17FN2O3S2 | 476.5522 | 6.197 |
| F5749-0103 | 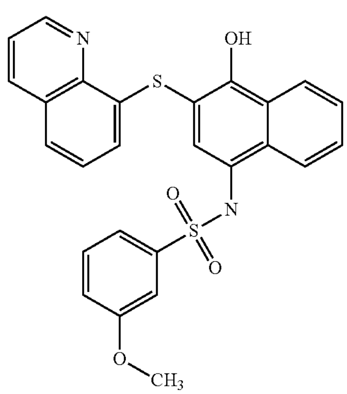 [SMILES: COc1cccc(S(=O)(=O)Nc2cc(Sc3cccc4cccnc34)c(O)c3ccccc23)c1] | C26H20N2O4S2 | 488.5883 | 6.039 |

TABLE 8-continued

| IDNUMBER | Structure | Formula structure | MW | LogP |
|---|---|---|---|---|
| F5749-0104 | 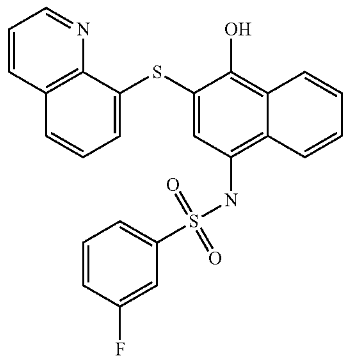 [SMILES: O=S(=O)(Nc1cc(Sc2cccc3cccnc23)c(O)c2ccccc12)c1cccc(F)c1] | C25H17FN2O3S2 | 476.5522 | 6.236 |
| F5749-0105 | 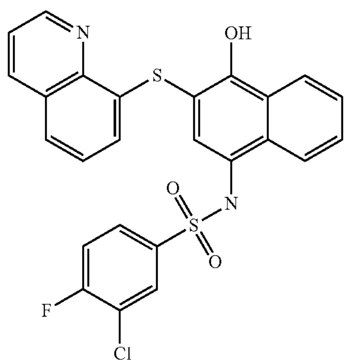 [SMILES: O=S(=O)(Nc1cc(Sc2cccc3cccnc23)c(O)c2ccccc12)c1ccc(F)c(Cl)c1] | C25H16ClFN2O3S2 | 510.9973 | 6.826 |
| F5749-0106 | 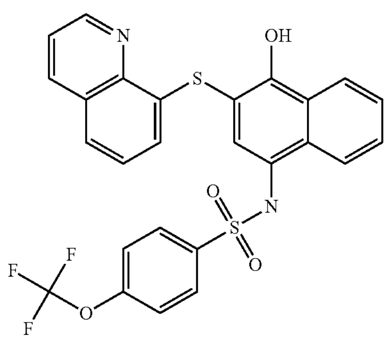 [SMILES: O=S(=O)(Nc1cc(Sc2cccc3cccnc23)c(O)c2ccccc12)c1ccc(OC(F)(F)F)cc1] | C26H17F3N2O4S2 | 542.5596 | 7.44476 |
| F5749-0107 | 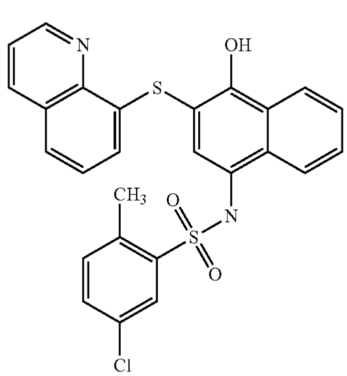 [SMILES: Cc1ccc(Cl)cc1S(=O)(=O)Nc1cc(Sc2cccc3cccnc23)c(O)c2ccccc12] | C26H19ClN2O3S2 | 507.0339 | 6.971 |

TABLE 8-continued
| IDNUMBER | Structure | Formula structure | MW | LogP |
|---|---|---|---|---|
| F5749-0108 | 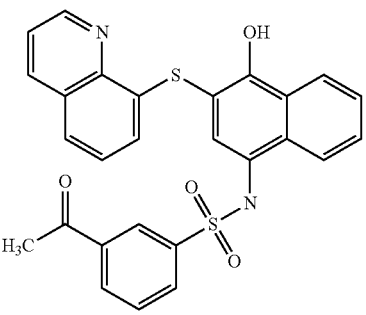 [SMILES: CC(=O)c1cccc(S(=O)(=O)Nc2cc(Sc3cccc4cccnc34)c(O)c3ccccc23)c1] | C27H20N2O4S2 | 500.5995 | 5.936 |
| F5749-0109 | 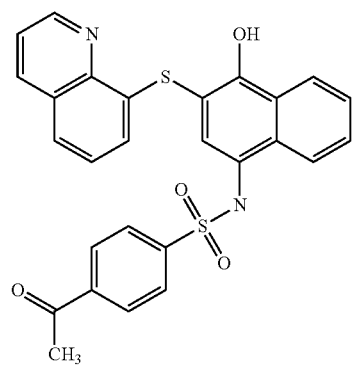 [SMILES: CC(=O)c1ccc(S(=O)(=O)Nc2cc(Sc3cccc4cccnc34)c(O)c3ccccc23)cc1] | C27H20N2O4S2 | 500.5995 | 5.899 |
| F5749-0110 | 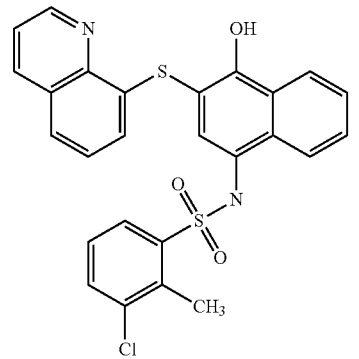 [SMILES: Cc1c(Cl)cccc1S(=O)(=O)Nc1cc(Sc2cccc3cccnc23)c(O)c2ccccc12] | C26H19ClN2O3S2 | 507.0339 | 6.932 |
| F5749-0111 | 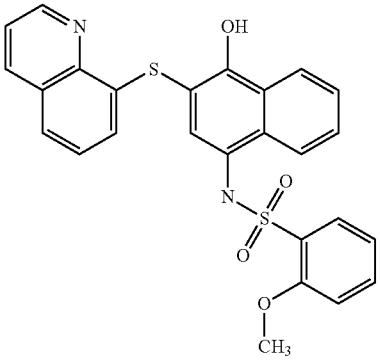 [SMILES: COc1ccccc1S(=O)(=O)Nc1cc(Sc2cccc3cccnc23)c(O)c2ccccc12] | C26H20N2O4S2 | 488.5883 | 6 |

TABLE 8-continued
| IDNUMBER | Structure | Formula structure | MW | LogP |
|---|---|---|---|---|
| F5749-0112 | 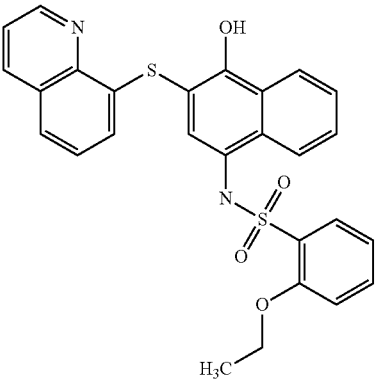 [SMILES: CCOc1ccccc1S(=O)(=O)Nc1cc(Sc2cccc3cccnc23)c(O)c2ccccc12] | C27H22N2O4S2 | 502.6154 | 6.341 |
| F5749-0113 | 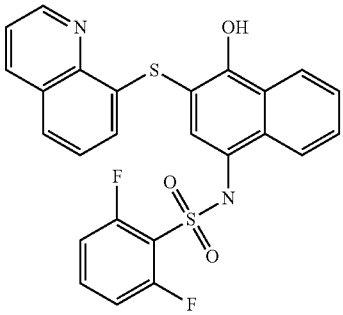 [SMILES: O=S(=O)(Nc1cc(Sc2cccc3cccnc23)c(O)c2ccccc12)c1c(F)cccc1F] | C25H16F2N2O3S2 | 494.5427 | 6.348 |
| F5749-0114 | 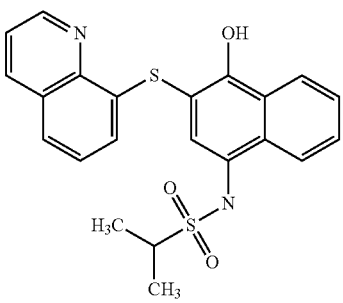 | C22H20N2O3S2 | 424.5443 | 5.539 |
| F5749-0115 | 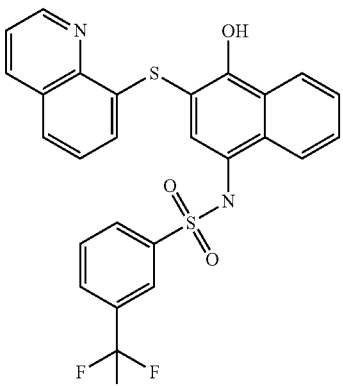 | C26H17F3N2O3S2 | 526.5602 | 7.01776 |

TABLE 8-continued

| IDNUMBER | Structure | Formula structure | MW | LogP |
|---|---|---|---|---|
| F5749-0116 | 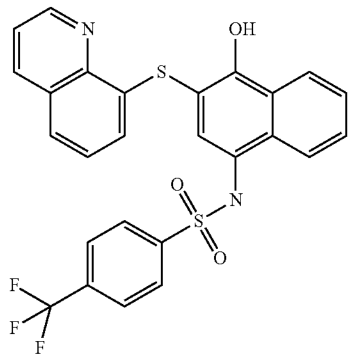 [SMILES: O=S(=O)(Nc1cc(Sc2cccc3cccnc23)c(O)c2ccccc12)c1ccc(C(F)(F)F)cc1] | C26H17F3N2O3S2 | 526.5602 | 6.98076 |
| F5749-0117 | 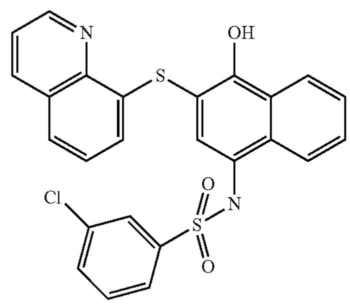 [SMILES: O=S(=O)(Nc1cc(Sc2cccc3cccnc23)c(O)c2ccccc12)c1cccc(Cl)c1] | C25H17ClN2O3S2 | 493.0068 | 6.675 |
| F5749-0118 | 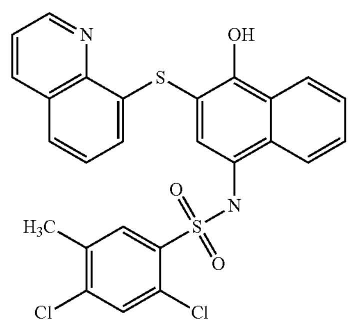 [SMILES: Cc1cc(S(=O)(=O)Nc2cc(Sc3cccc4cccnc34)c(O)c3ccccc23)c(Cl)cc1Cl] | C26H18Cl2N2O3S2 | 541.479 | 7.598 |
| F5749-0119 | 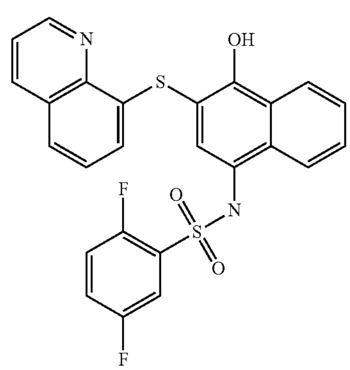 [SMILES: O=S(=O)(Nc1cc(Sc2cccc3cccnc23)c(O)c2ccccc12)c1cc(F)ccc1F] | C25H16F2N2O3S2 | 494.5427 | 6.387 |

TABLE 8-continued
| IDNUMBER | Structure | Formula structure | MW | LogP |
|---|---|---|---|---|
| F5749-0120 | 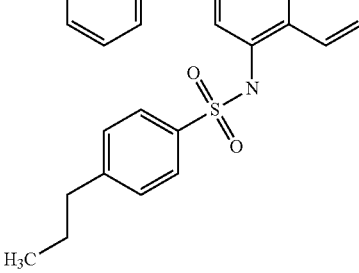 | C28H24N2O3S2 | 500.6431 | 7.261 |
| F5749-0121 | 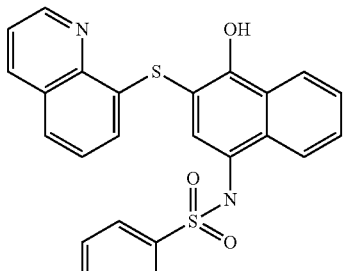 | C29H24N2O3S2 | 512.6542 | 7.133 |
| F5749-0122 | 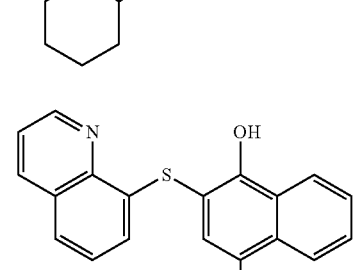 | C29H21N3O5S2 | 555.6358 | 5.173 |
| F5749-0123 | 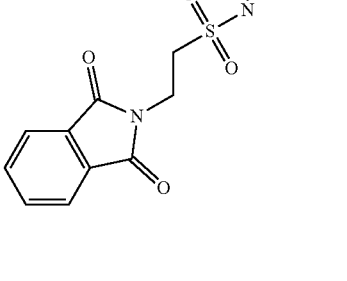 | C30H23N3O5S2 | 569.6629 | 5.615 |

TABLE 8-continued

| IDNUMBER | Structure | Formula structure | MW | LogP |
| --- | --- | --- | --- | --- |
| F5749-0124 | 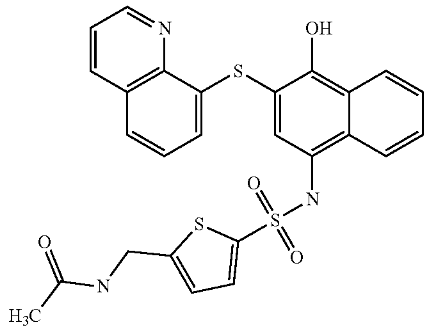 [SMILES: CC(=O)NCc1ccc(S(=O)(=O)Nc2cc(Sc3cccc4cccnc34)c(O)c3ccccc23)s1] | C26H21N3O4S3 | 535.667 | 5.349 |
| F5749-0125 | 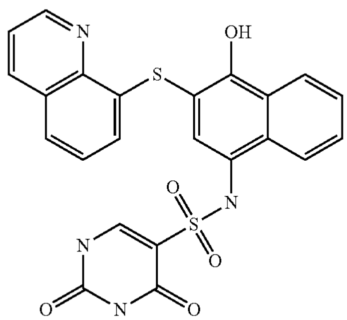 [SMILES: O=c1[nH]cc(S(=O)(=O)Nc2cc(Sc3cccc4cccnc34)c(O)c3ccccc23)c(=O)[nH]1] | C23H16N4O5S2 | 492.5358 | 3.091 |
| F5749-0126 | 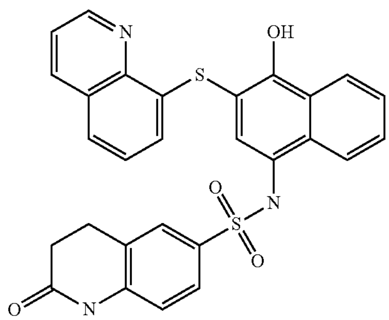 [SMILES: O=C1CCc2cc(S(=O)(=O)Nc3cc(Sc4cccc5cccnc45)c(O)c4ccccc34)ccc2N1] | C28H21N3O4S2 | 527.6253 | 5.242 |
| F5749-0127 | 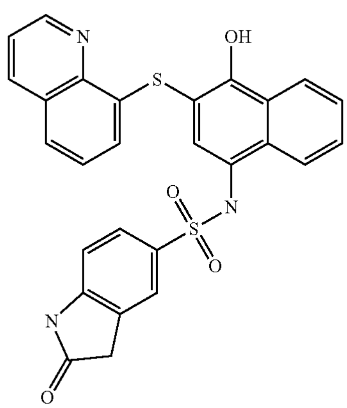 [SMILES: O=C1Cc2cc(S(=O)(=O)Nc3cc(Sc4cccc5cccnc45)c(O)c4ccccc34)ccc2N1] | C27H19N3O4S2 | 513.5982 | 5.154 |

TABLE 8-continued

| IDNUMBER | Structure | Formula structure | MW | LogP |
| --- | --- | --- | --- | --- |
| F5749-0128 | 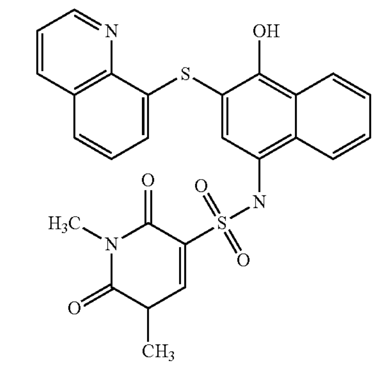 [SMILES: CC1C=C(S(=O)(=O)Nc2cc(Sc3cccc4cccnc34)c(O)c3ccccc23)C(=O)N(C)C1=O] | C25H20N4O5S2 | 520.59 | 3.155 |
| F5749-0129 | 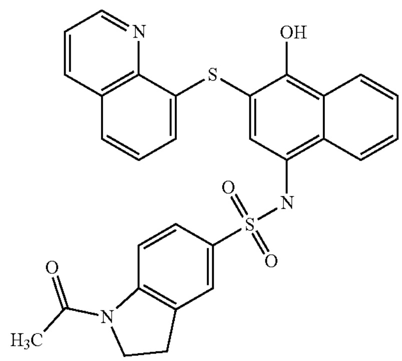 [SMILES: CC(=O)N1CCc2cc(S(=O)(=O)Nc3cc(Sc4cccc5cccnc45)c(O)c4ccccc34)ccc21] | C29H23N3O4S2 | 541.6524 | 5.477 |
| F5749-0130 | 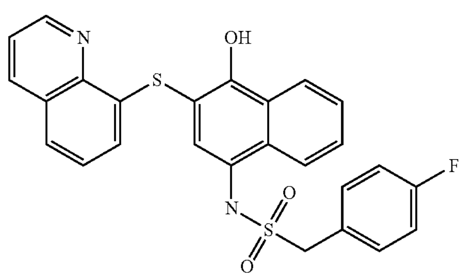 [SMILES: O=S(=O)(Cc1ccc(F)cc1)Nc1cc(Sc2cccc3cccnc23)c(O)c2ccccc12] | C26H19FN2O3S2 | 490.5793 | 6.333 |
| F5749-0131 | 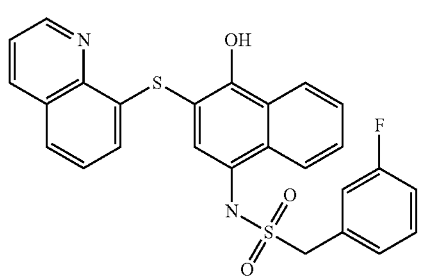 [SMILES: O=S(=O)(Cc1cccc(F)c1)Nc1cc(Sc2cccc3cccnc23)c(O)c2ccccc12] | C26H19FN2O3S2 | 490.5793 | 6.37 |
| F5749-0132 | 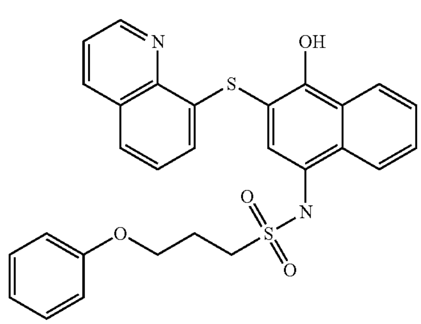 [SMILES: O=S(=O)(CCCOc1ccccc1)Nc1cc(Sc2cccc3cccnc23)c(O)c2ccccc12] | C28H24N2O4S2 | 516.6425 | 6.406 |

TABLE 8-continued

| IDNUMBER | Structure | Formula structure | MW | LogP |
|---|---|---|---|---|
| F5749-0133 | 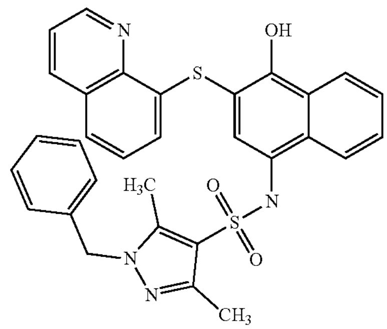 [SMILES: Cc1nn(Cc2ccccc2)c(C)c1S(=O)(=O)Nc1cc(Sc2cccc3cccnc23)c(O)c2ccccc12] | C31H26N4O3S2 | 566.7059 | 6.325 |
| F5749-0134 | 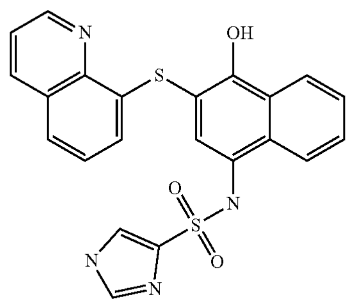 [SMILES: O=S(=O)(Nc1cc(Sc2cccc3cccnc23)c(O)c2ccccc12)c1c[nH]cn1] | C22H16N4O3S2 | 448.5258 | 4.186 |
| F5749-0135 | 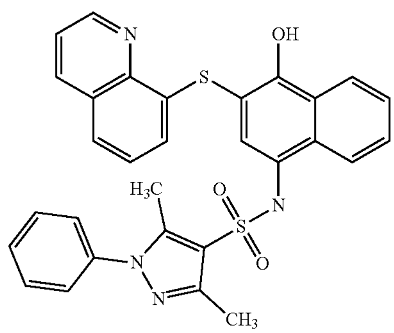 [SMILES: Cc1nn(-c2ccccc2)c(C)c1S(=O)(=O)Nc1cc(Sc2cccc3cccnc23)c(O)c2ccccc12] | C30H24N4O3S2 | 552.6788 | 6.191 |
| F5749-0136 | 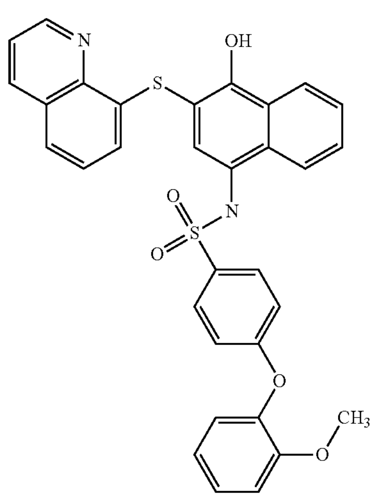 [SMILES: COc1ccccc1Oc1ccc(S(=O)(=O)Nc2cc(Sc3cccc4cccnc34)c(O)c3ccccc23)cc1] | C32H24N2O5S2 | 580.6865 | 7.36174 |

TABLE 8-continued

| IDNUMBER | Structure | Formula structure | MW | LogP |
| --- | --- | --- | --- | --- |
| F5749-0137 | 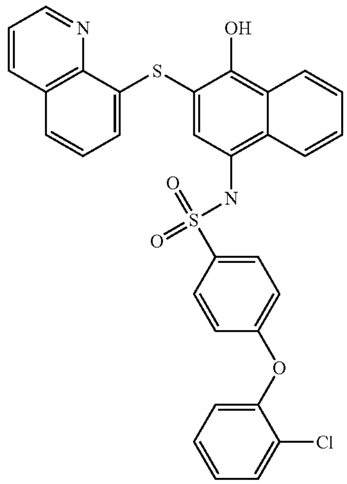 [SMILES: O=S(=O)(Nc1cc(Sc2cccc3cccnc23)c(O)c2ccccc12)c1ccc(Oc2ccccc2Cl)cc1] | C31H21ClN2O4S2 | 585.105 | 8.246 |
| F5749-0138 | 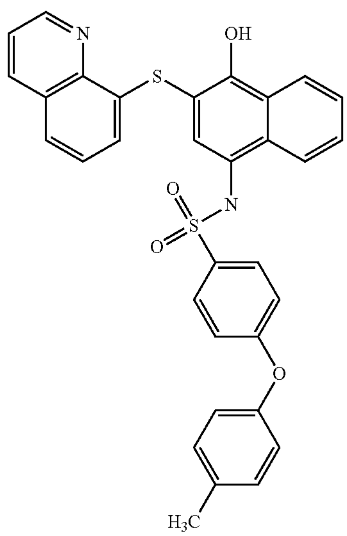 [SMILES: Cc1ccc(Oc2ccc(S(=O)(=O)Nc3cc(Sc4cccc5cccnc45)c(O)c4ccccc34)cc2)cc1] | C32H24N2O4S2 | 564.6871 | 7.954 |
| F5749-0139 | 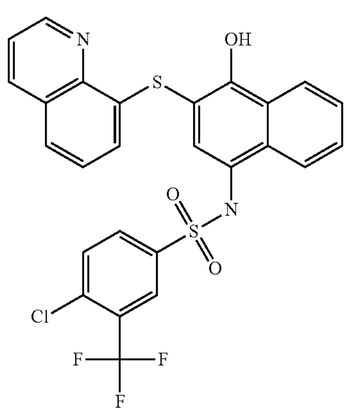 [SMILES: O=S(=O)(Nc1cc(Sc2cccc3cccnc23)c(O)c2ccccc12)c1ccc(Cl)c(C(F)(F)F)c1] | C26H16ClF3N2O3S2 | 561.0052 | 7.60776 |

TABLE 8-continued

| IDNUMBER | Structure | Formula structure | MW | LogP |
|---|---|---|---|---|
| F5749-0140 | 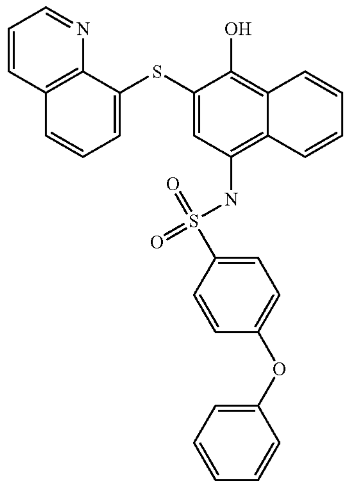 [SMILES: O=S(=O)(Nc1cc(Sc2cccc3cccnc23)c(O)c2ccccc12)c1ccc(Oc2ccccc2)cc1] | C31H22N2O4S2 | 550.66 | 7.656 |
| F5749-0141 | 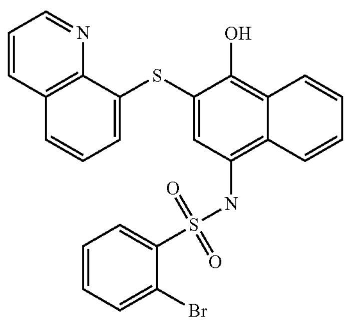 [SMILES: O=S(=O)(Nc1cc(Sc2cccc3cccnc23)c(O)c2ccccc12)c1ccccc1Br] | C25H17BrN2O3S2 | 537.4578 | 6.842 |
| F5749-0142 | 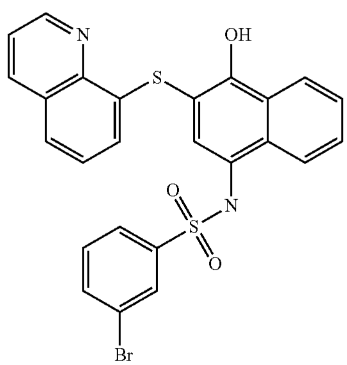 [SMILES: O=S(=O)(Nc1cc(Sc2cccc3cccnc23)c(O)c2ccccc12)c1cccc(Br)c1] | C25H17BrN2O3S2 | 537.4578 | 6.881 |
| F5749-0143 | 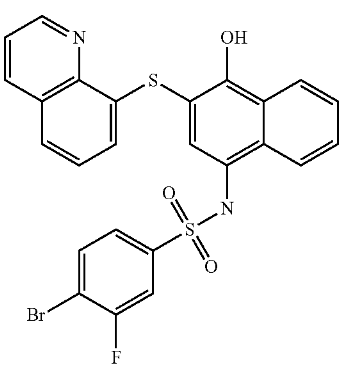 [SMILES: O=S(=O)(Nc1cc(Sc2cccc3cccnc23)c(O)c2ccccc12)c1ccc(Br)c(F)c1] | C25H16BrFN2O3S2 | 555.4483 | 7.032 |

TABLE 8-continued

| IDNUMBER | Structure | Formula structure | MW | LogP |
|---|---|---|---|---|
| F5749-0144 | 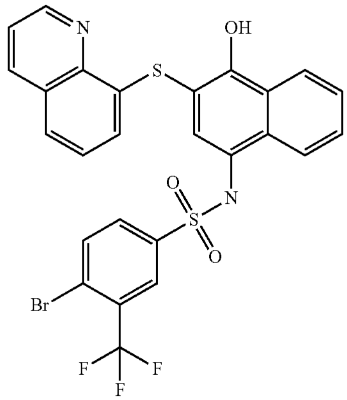 [SMILES: O=S(=O)(Nc1cc(Sc2cccc3cccnc23)c(O)c2ccccc12)c1ccc(Br)c(C(F)(F)F)c1] | C26H16BrF3N2O3S2 | 605.4562 | 7.81376 |
| F5749-0145 | 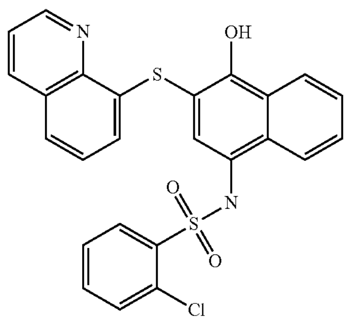 [SMILES: O=S(=O)(Nc1cc(Sc2cccc3cccnc23)c(O)c2ccccc12)c1ccccc1Cl] | C25H17ClN2O3S2 | 493.0068 | 6.636 |
| F5749-0146 | 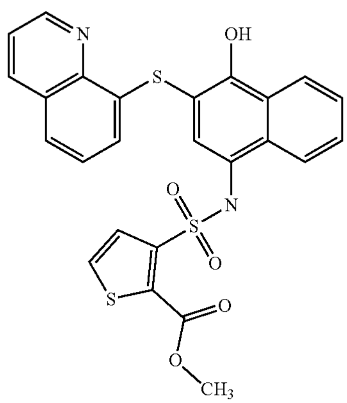 [SMILES: COC(=O)c1sccc1S(=O)(=O)Nc1cc(Sc2cccc3cccnc23)c(O)c2ccccc12] | C25H18N2O5S3 | 522.6246 | 5.246 |
| F5749-0147 | 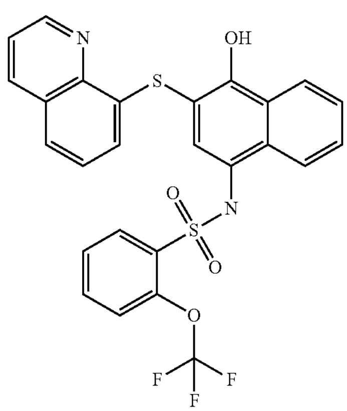 [SMILES: O=S(=O)(Nc1cc(Sc2cccc3cccnc23)c(O)c2ccccc12)c1ccccc1OC(F)(F)F] | C26H17F3N2O4S2 | 542.5596 | 7.44276 |

TABLE 9

| ID NUMBER | Structure | Formula structure | MW | Log P |
|---|---|---|---|---|
| F1565-0253 | 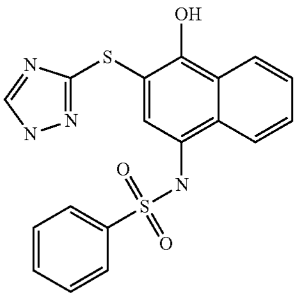 [SMILES: O=S(=O)(Nc1cc(Sc2nc[nH]n2)c(O)c2ccccc12)c1ccccc1] | C18H14N4O3S2 | 398.4653 | 3.698 |
| F1566-0328 | 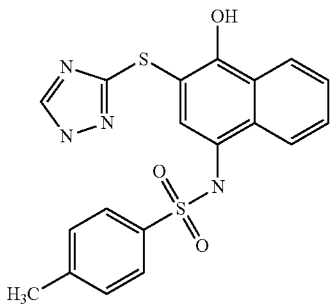 [SMILES: Cc1ccc(S(=O)(=O)Nc2cc(Sc3nc[nH]n3)c(O)c3ccccc23)cc1] | C19H16N4O3S2 | 412.4924 | 3.996 |
| F1566-0340 | 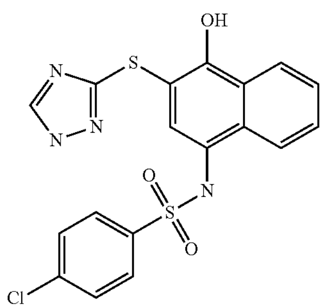 [SMILES: O=S(=O)(Nc1cc(Sc2nc[nH]n2)c(O)c2ccccc12)c1ccc(Cl)cc1] | C18H13ClN4O3S2 | 432.9103 | 4.29 |
| F1566-0520 | 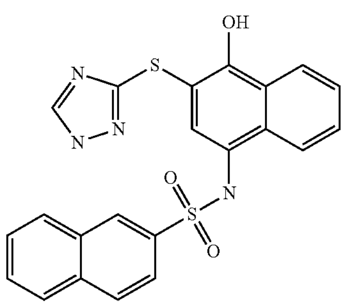 [SMILES: O=S(=O)(Nc1cc(Sc2nc[nH]n2)c(O)c2ccccc12)c1ccc2ccccc2c1] | C22H16N4O3S2 | 448.5258 | 4.957 |
| F1566-0556 | 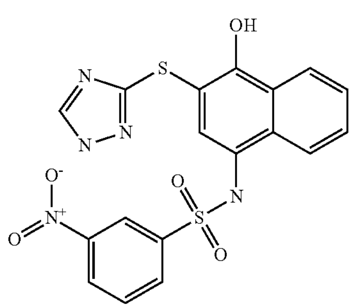 [SMILES: O=[N+]([O-])c1cccc(S(=O)(=O)Nc2cc(Sc3nc[nH]n3)c(O)c3ccccc23)c1] | C18H13N5O5S2 | 443.4628 | 3.67 |

TABLE 9-continued

| ID NUMBER | Structure | Formula structure | MW | Log P |
|---|---|---|---|---|
| F1566-0568 | 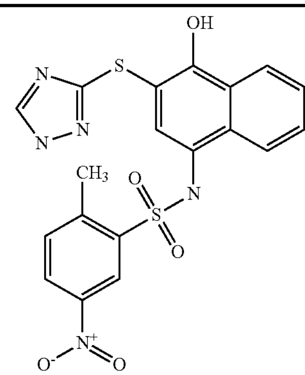 | C19H15N5O5S2 | 457.4899 | 3.966 |
| F1566-0616 | 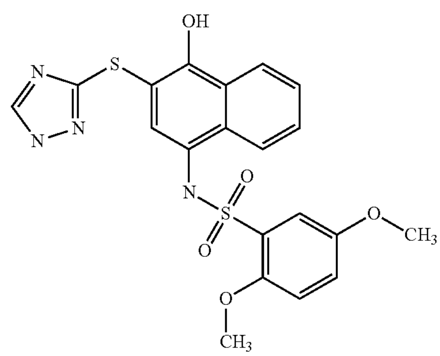 [SMILES: COc1ccc(OC)c(S(=O)(=O)Nc2cc(Sc3nc[nH]n3)c(O)c3ccccc23)c1] | C20H18N4O5S2 | 458.5183 | 3.645 |
| F1566-0628 | 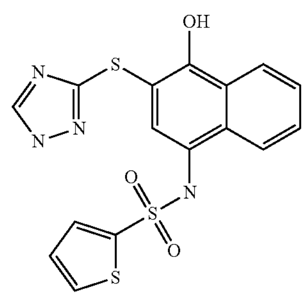 [SMILES: O=S(=O)(Nc1cc(Sc2nc[nH]n2)c(O)c2ccccc12)c1cccs1] | C16H12N4O3S3 | 404.491 | 3.211 |
| F5749-0148 | 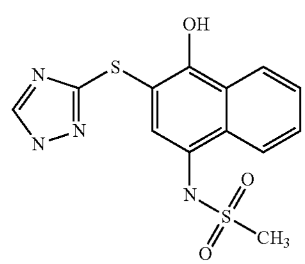 [SMILES: CS(=O)(=O)Nc1cc(Sc2nc[nH]n2)c(O)c2ccccc12] | C13H12N4O3S2 | 336.3936 | 2.044 |
| F5749-0149 | 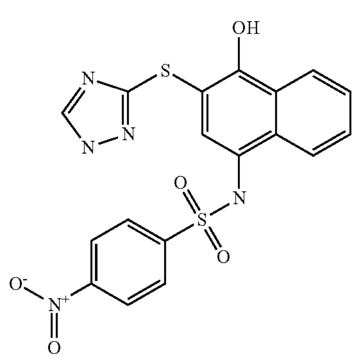 [SMILES: O=[N+]([O-])c1ccc(S(=O)(=O)Nc2cc(Sc3nc[nH]n3)c(O)c3ccccc23)cc1] | C18H13N5O5S2 | 443.4628 | 3.633 |

TABLE 9-continued
| ID NUMBER | Structure | Formula structure | MW | Log P |
|---|---|---|---|---|
| F5749-0150 | 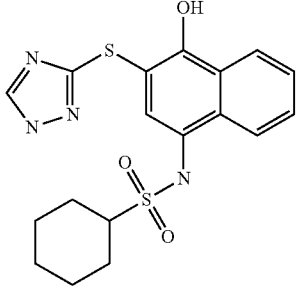 [SMILES: O=S(=O)(Nc1cc(Sc2nc[nH]n2)c(O)c2ccccc12)C1CCCCC1] | C18H20N4O3S2 | 404.5131 | 4.023 |
| F5749-0151 | 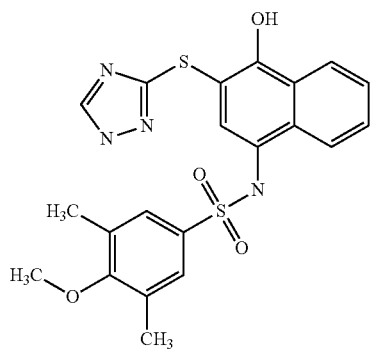 [SMILES: COc1c(C)cc(S(=O)(=O)Nc2cc(Sc3nc[nH]n3)c(O)c3ccccc23)cc1C] | C21H20N4O4S2 | 456.546 | 4.32 |
| F5749-0152 | 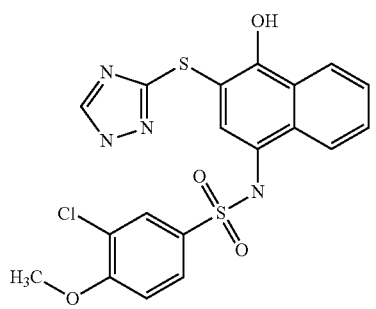 [SMILES: COc1ccc(S(=O)(=O)Nc2cc(Sc3nc[nH]n3)c(O)c3ccccc23)cc1Cl] | C19H15ClN4O4S2 | 462.9368 | 4.281 |
| F5749-0153 | 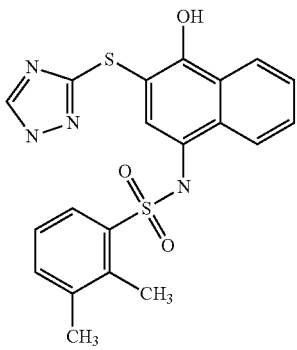 [SMILES: Cc1cccc(S(=O)(=O)Nc2cc(Sc3nc[nH]n3)c(O)c3ccccc23)c1C] | C20H18N4O3S2 | 426.5195 | 4.29 |

TABLE 9-continued

| ID NUMBER | Structure | Formula structure | MW | Log P |
|---|---|---|---|---|
| F5749-0154 | 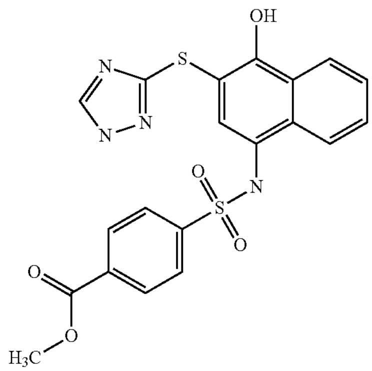 [SMILES: COC(=O)c1ccc(S(=O)(=O)Nc2cc(Sc3nc[nH]n3)c(O)c3ccccc23)cc1] | C20H16N4O5S2 | 456.5023 | 3.639 |
| F5749-0155 | 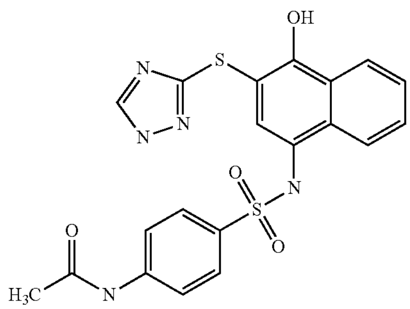 [SMILES: CC(=O)Nc1ccc(S(=O)(=O)Nc2cc(Sc3nc[nH]n3)c(O)c3ccccc23)cc1] | C20H17N5O4S2 | 455.5176 | 2.989 |
| F5749-0156 | 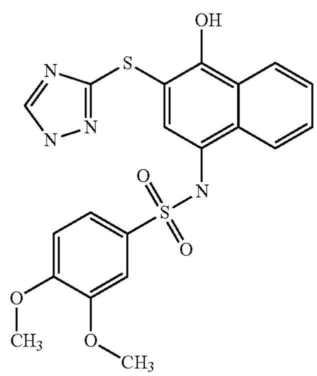 [SMILES: COc1ccc(S(=O)(=O)Nc2cc(Sc3nc[nH]n3)c(O)c3ccccc23)cc1OC] | C20H18N4O5S2 | 458.5183 | 3.39674 |
| F5749-0157 | 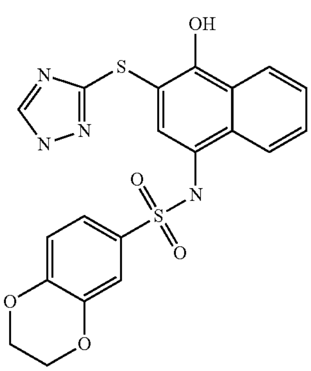 [SMILES: O=S(=O)(Nc1cc(Sc2nc[nH]n2)c(O)c2ccccc12)c1ccc2c(c1)OCCO2] | C20H16N4O5S2 | 456.5023 | 3.293 |

TABLE 9-continued
| ID NUMBER | Structure | Formula structure | MW | Log P |
|---|---|---|---|---|
| F5749-0158 | 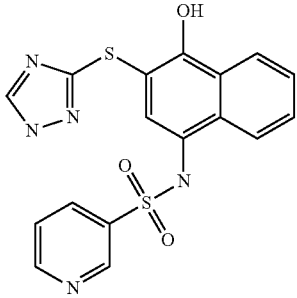 [SMILES: O=S(=O)(Nc1cc(Sc2nc[nH]n2)c(O)c2ccccc12)c1cccnc1] | C17H13N5O3S2 | 399.4529 | 2.465 |
| F5749-0159 | 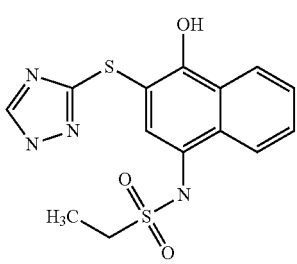 [SMILES: CCS(=O)(=O)Nc1cc(Sc2nc[nH]n2)c(O)c2ccccc12] | C14H14N4O3S2 | 350.4207 | 2.557 |
| F5749-0160 | 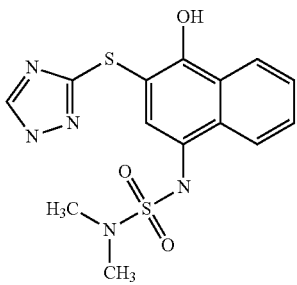 | C14H15N5O3S2 | 365.4354 | 1.592 |
| F5749-0161 | 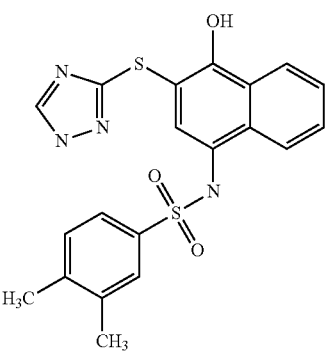 [SMILES: Cc1ccc(S(=O)(=O)Nc2cc(Sc3nc[nH]n3)c(O)c3ccccc23)cc1C] | C20H18N4O3S2 | 426.5195 | 4.329 |
| F5749-0162 | 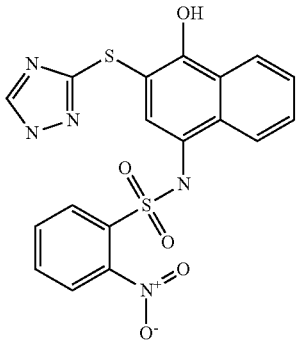 [SMILES: O=[N+]([O-])c1ccccc1S(=O)(=O)Nc1cc(Sc2nc[nH]n2)c(O)c2ccccc12] | C18H13N5O5S2 | 443.4628 | 3.631 |

TABLE 9-continued

| ID NUMBER | Structure | Formula structure | MW | Log P |
| --- | --- | --- | --- | --- |
| F5749-0163 | 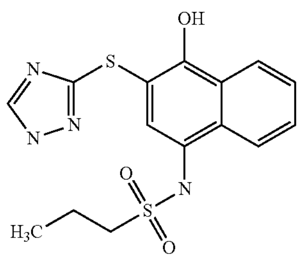 [SMILES: CCCS(=O)(=O)Nc1cc(Sc2nc[nH]n2)c(O)c2ccccc12] | C15H16N4O3S2 | 364.4478 | 2.999 |
| F5749-0164 | 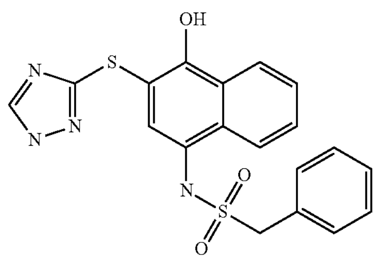 [SMILES: O=S(=O)(Cc1ccccc1)Nc1cc(Sc2nc[nH]n2)c(O)c2ccccc12] | C19H16N4O3S2 | 412.4924 | 3.832 |
| F5749-0165 | 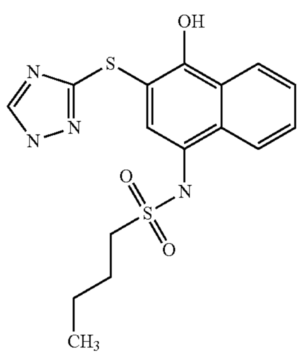 [SMILES: CCCCS(=O)(=O)Nc1cc(Sc2nc[nH]n2)c(O)c2ccccc12] | C16H18N4O3S2 | 378.4749 | 3.441 |
| F5749-0166 | 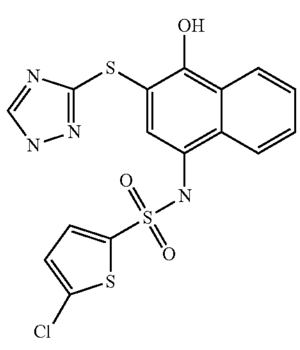 [SMILES: O=S(=O)(Nc1cc(Sc2nc[nH]n2)c(O)c2ccccc12)c1ccc(Cl)s1] | C16H11ClN4O3S3 | 438.9361 | 4.501 |
| F5749-0167 | 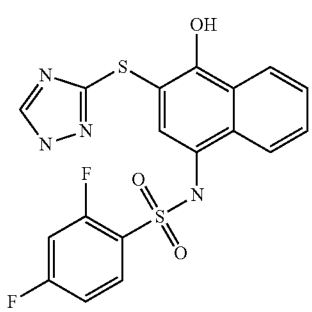 [SMILES: O=S(=O)(Nc1cc(Sc2nc[nH]n2)c(O)c2ccccc12)c1ccc(F)cc1F] | C18H12F2N4O3S2 | 434.4461 | 4.039 |

TABLE 9-continued

| ID NUMBER | Structure | Formula structure | MW | Log P |
|---|---|---|---|---|
| F5749-0168 | 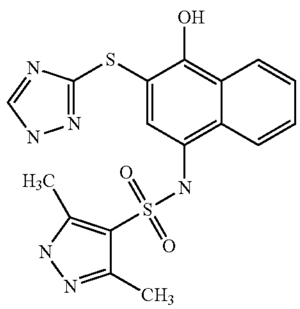 | C17H16N6O3S2 | 416.4835 | 2.808 |
| F5749-0169 | 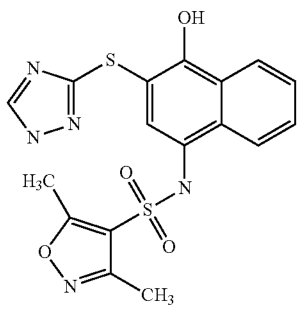 [SMILES: Cc1noc(C)c1S(=O)(=O)Nc1cc(Sc2nc[nH]n2)c(O)c2ccccc12] | C17H15N5O4S2 | 417.4682 | 2.842 |
| F5749-0170 | 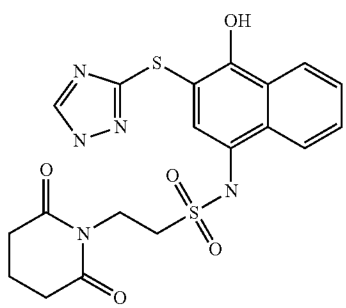 [SMILES: O=C1CCCC(=O)N1CCS(=O)(=O)Nc1cc(Sc2nc[nH]n2)c(O)c2ccccc12] | C19H19N5O5S2 | 461.5218 | 1.485 |
| F5749-0171 | 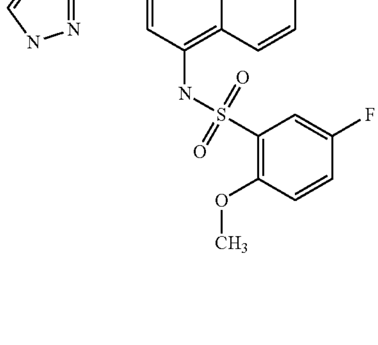 | C19H15FN4O4S2 | 446.4822 | 3.842 |

TABLE 9-continued

| ID NUMBER | Structure | Formula structure | MW | Log P |
| --- | --- | --- | --- | --- |
| F5749-0172 | 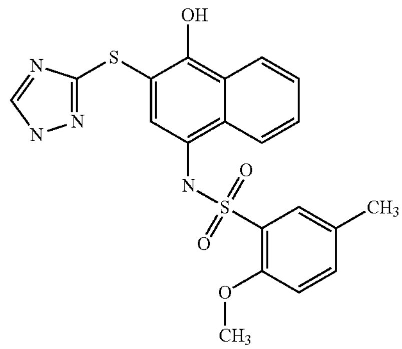 [SMILES: COc1ccc(C)cc1S(=O)(=O)Nc1cc(Sc2nc[nH]n2)c(O)c2ccccc12] | C20H18N4O4S2 | 442.5189 | 3.987 |
| F5749-0173 | 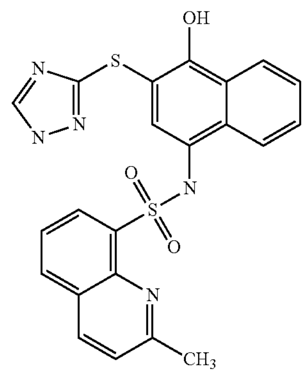 [SMILES: Cc1ccc2cccc(S(=O)(=O)Nc3cc(Sc4nc[nH]n4)c(O)c4ccccc34)c2n1] | C22H17N5O3S2 | 463.5405 | 4.157 |
| F5749-0174 | 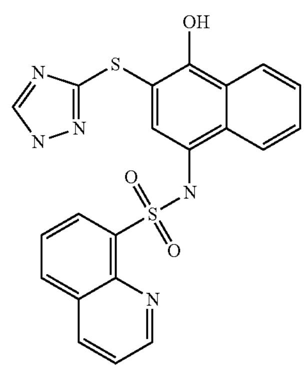 [SMILES: O=S(=O)(Nc1cc(Sc2nc[nH]n2)c(O)c2ccccc12)c1cccc2cccnc12] | C21H15N5O3S2 | 449.5134 | 3.898 |
| F5749-0175 | 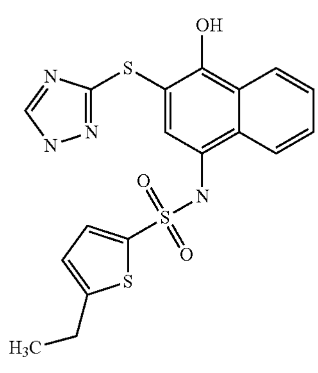 [SMILES: CCc1ccc(S(=O)(=O)Nc2cc(Sc3nc[nH]n3)c(O)c3ccccc23)s1] | C18H16N4O3S3 | 432.5452 | 4.349 |

TABLE 9-continued

| ID NUMBER | Structure | Formula structure | MW | Log P |
|---|---|---|---|---|
| F5749-0176 | 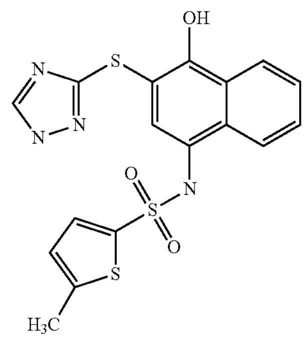 [SMILES: Cc1ccc(S(=O)(=O)Nc2cc(Sc3nc[nH]n3)c(O)c3ccccc23)s1] | C17H14N4O3S3 | 418.5181 | 3.874 |
| F5749-0177 | 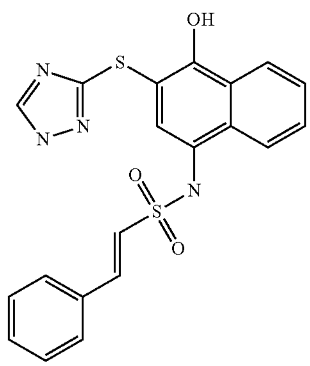 [SMILES: O=S(=O)(/C=C/c1ccccc1)Nc1cc(Sc2nc[nH]n2)c(O)c2ccccc12] | C20H16N4O3S2 | 424.5035 | 4.056 |
| F5749-0178 | 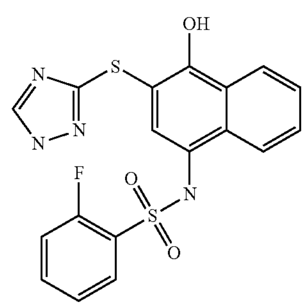 [SMILES: O=S(=O)(Nc1cc(Sc2nc[nH]n2)c(O)c2ccccc12)c1ccccc1F] | C18H13FN4O3S2 | 416.4557 | 3.849 |
| F5749-0179 | 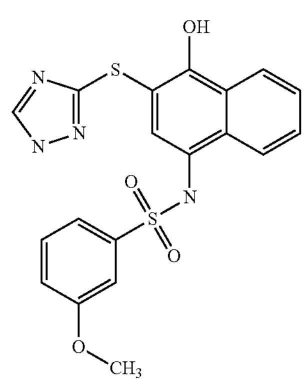 [SMILES: COc1cccc(S(=O)(=O)Nc2cc(Sc3nc[nH]n3)c(O)c3ccccc23)c1] | C19H16N4O4S2 | 428.4918 | 3.691 |

| ID NUMBER | Structure | Formula structure | MW | Log P |
|---|---|---|---|---|
| F5749-0180 | 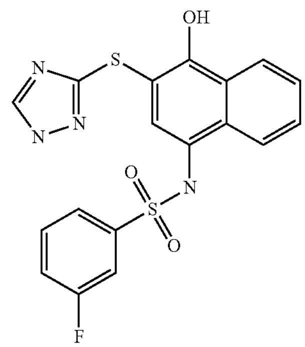 [SMILES: O=S(=O)(Nc1cc(Sc2nc[nH]n2)c(O)c2ccccc12)c1cccc(F)c1] | C18H13FN4O3S2 | 416.4557 | 3.888 |
| F5749-0181 | 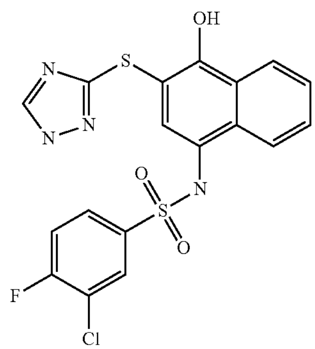 [SMILES: O=S(=O)(Nc1cc(Sc2nc[nH]n2)c(O)c2ccccc12)c1ccc(F)c(Cl)c1] | C18H12ClFN4O3S2 | 450.9007 | 4.478 |
| F5749-0182 | 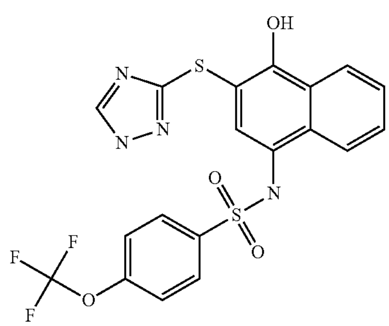 [SMILES: O=S(=O)(Nc1cc(Sc2nc[nH]n2)c(O)c2ccccc12)c1ccc(OC(F)(F)F)cc1] | C19H13F3N4O4S2 | 482.4631 | 5.09676 |
| F5749-0183 | 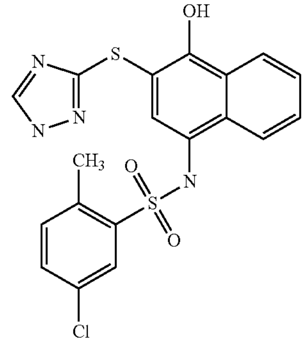 [SMILES: Cc1ccc(Cl)cc1S(=O)(=O)Nc1cc(Sc2nc[nH]n2)c(O)c2ccccc12] | C19H15ClN4O3S2 | 446.9374 | 4.623 |

TABLE 9-continued

| ID NUMBER | Structure | Formula structure | MW | Log P |
|---|---|---|---|---|
| F5749-0184 | 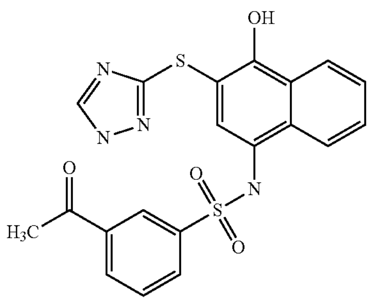 [SMILES: CC(=O)c1cccc(S(=O)(=O)Nc2cc(Sc3nc[nH]n3)c(O)c3ccccc23)c1] | C20H16N4O4S2 | 440.5029 | 3.588 |
| F5749-0185 | 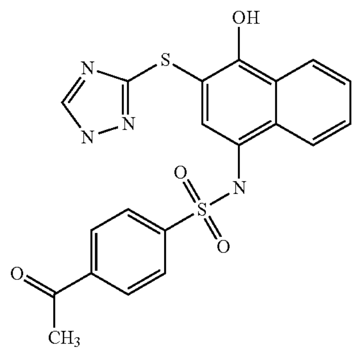 [SMILES: CC(=O)c1ccc(S(=O)(=O)Nc2cc(Sc3nc[nH]n3)c(O)c3ccccc23)cc1] | C20H16N4O4S2 | 440.5029 | 3.551 |
| F5749-0186 | 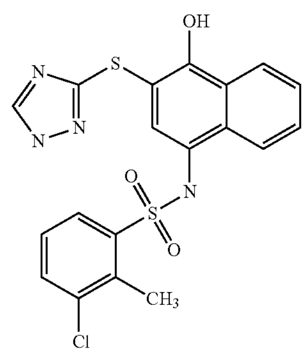 [SMILES: Cc1c(Cl)cccc1S(=O)(=O)Nc1cc(Sc2nc[nH]n2)c(O)c2ccccc12] | C19H15ClN4O3S2 | 446.9374 | 4.584 |
| F5749-0187 | 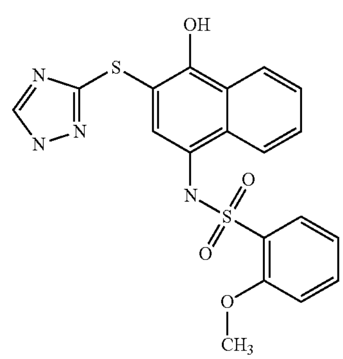 [SMILES: COc1ccccc1S(=O)(=O)Nc1cc(Sc2nc[nH]n2)c(O)c2ccccc12] | C19H16N4O4S2 | 428.4918 | 3.652 |

TABLE 9-continued

| ID NUMBER | Structure | Formula structure | MW | Log P |
|---|---|---|---|---|
| F5749-0188 | 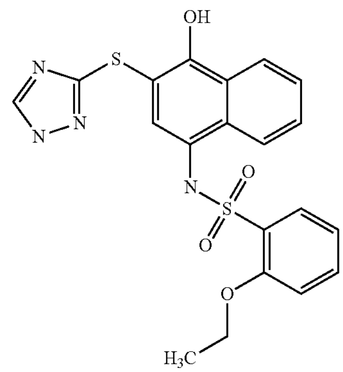 [SMILES: CCOc1ccccc1S(=O)(=O)Nc1cc(Sc2nc[nH]n2)c(O)c2ccccc12] | C20H18N4O4S2 | 442.5189 | 3.993 |
| F5749-0189 | 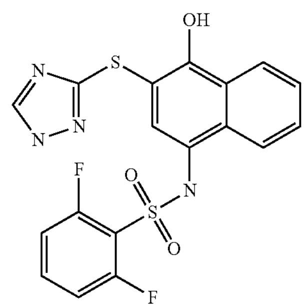 [SMILES: O=S(=O)(Nc1cc(Sc2nc[nH]n2)c(O)c2ccccc12)c1c(F)cccc1F] | C18H12F2N4O3S2 | 434.4461 | 4 |
| F5749-0190 | 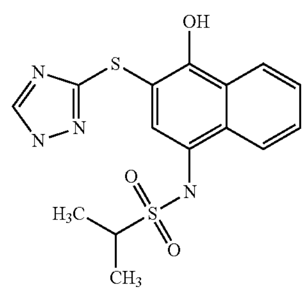 [SMILES: CC(C)S(=O)(=O)Nc1cc(Sc2nc[nH]n2)c(O)c2ccccc12] | C15H16N4O3S2 | 364.4478 | 3.191 |
| F5749-0191 | 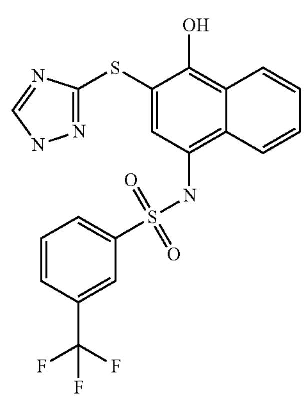 [SMILES: O=S(=O)(Nc1cc(Sc2nc[nH]n2)c(O)c2ccccc12)c1cccc(C(F)(F)F)c1] | C19H13F3N4O3S2 | 466.4637 | 4.66976 |

TABLE 9-continued
| ID NUMBER | Structure | Formula structure | MW | Log P |
|---|---|---|---|---|
| F5749-0192 | 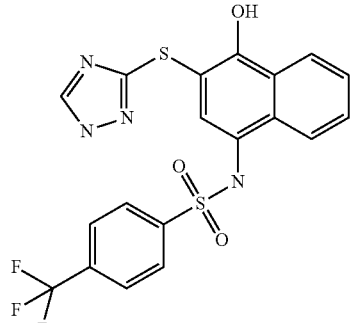 | C19H13F3N4O3S2 | 466.4637 | 4.63276 |
| F5749-0193 | 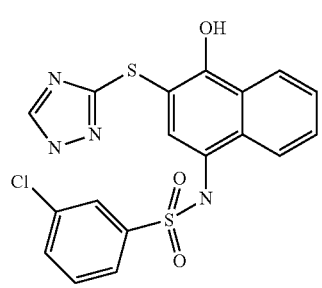 [SMILES: O=S(=O)(Nc1cc(Sc2nc[nH]n2)c(O)c2ccccc12)c1cccc(Cl)c1] | C18H13ClN4O3S2 | 432.9103 | 4.327 |
| F5749-0194 | 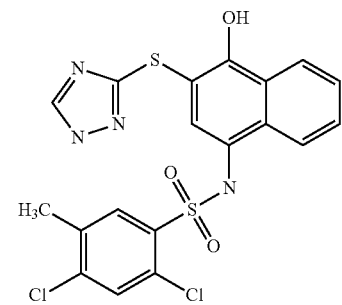 [SMILES: Cc1cc(S(=O)(=O)Nc2cc(Sc3nc[nH]n3)c(O)c3ccccc23)c(Cl)cc1Cl] | C19H14Cl2N4O3S2 | 481.3824 | 5.25 |
| F5749-0195 | 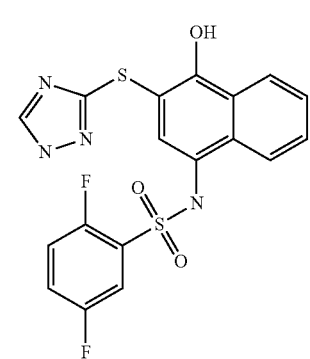 [SMILES: O=S(=O)(Nc1cc(Sc2nc[nH]n2)c(O)c2ccccc12)c1cc(F)ccc1F] | C18H12F2N4O3S2 | 434.4461 | 4.039 |

TABLE 9-continued

| ID NUMBER | Structure | Formula structure | MW | Log P |
|---|---|---|---|---|
| F5749-0196 | 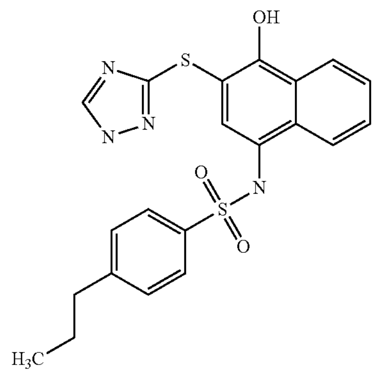 [SMILES: CCCc1ccc(S(=O)(=O)Nc2cc(Sc3nc[nH]n3)c(O)c3ccccc23)cc1] | C21H20N4O3S2 | 440.5466 | 4.913 |
| F5749-0197 | 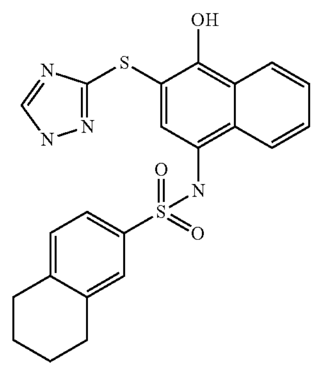 [SMILES: O=S(=O)(Nc1cc(Sc2nc[nH]n2)c(O)c2ccccc12)c1ccc2c(c1)CCCC2] | C22H20N4O3S2 | 452.5577 | 4.785 |
| F5749-0198 | 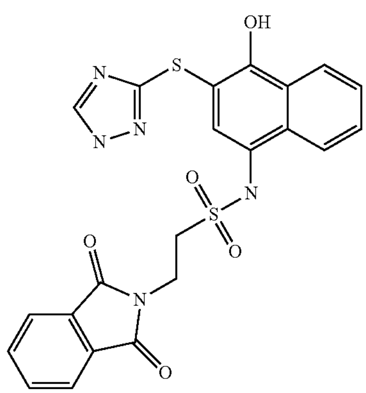 [SMILES: O=C1c2ccccc2C(=O)N1CCS(=O)(=O)Nc1cc(Sc2nc[nH]n2)c(O)c2ccccc12] | C22H17N5O5S2 | 495.5393 | 2.825 |
| F5749-0199 | 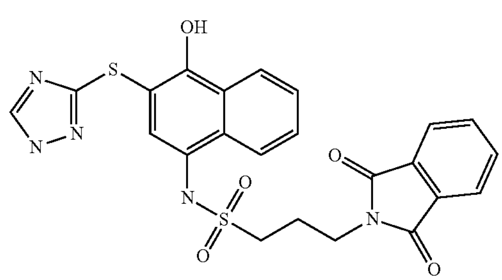 [SMILES: O=C1c2ccccc2C(=O)N1CCCS(=O)(=O)Nc1cc(Sc2nc[nH]n2)c(O)c2ccccc12] | C23H19N5O5S2 | 509.5664 | 3.267 |

TABLE 9-continued
| ID NUMBER | Structure | Formula structure | MW | Log P |
|---|---|---|---|---|
| F5749-0200 | 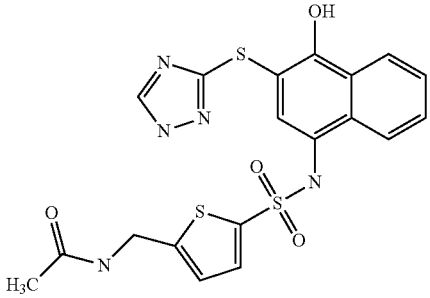 [SMILES: CC(=O)NCc1ccc(S(=O)(=O)Nc2cc(Sc3nc[nH]n3)c(O)c3ccccc23)s1] | C19H17N5O4S3 | 475.5704 | 3.001 |
| F5749-0201 | 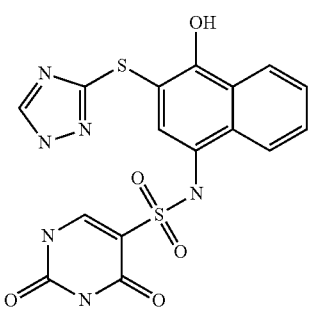 [SMILES: O=c1[nH]cc(S(=O)(=O)Nc2cc(Sc3nc[nH]n3)c(O)c3ccccc23)c(=O)[nH]1] | C16H12N6O5S2 | 432.4392 | 0.743 |
| F5749-0202 | 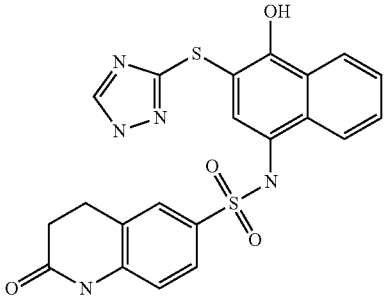 [SMILES: O=C1CCc2cc(S(=O)(=O)Nc3cc(Sc4nc[nH]n4)c(O)c4ccccc34)ccc2N1] | C21H17N5O4S2 | 467.5287 | 2.894 |
| F5749-0203 | 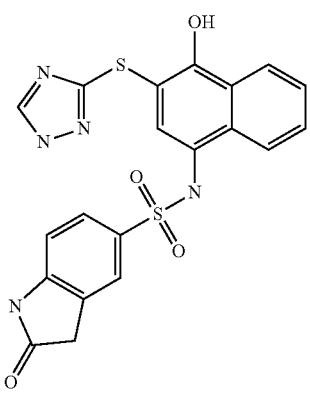 [SMILES: O=C1Cc2cc(S(=O)(=O)Nc3cc(Sc4nc[nH]n4)c(O)c4ccccc34)ccc2N1] | C20H15N5O4S2 | 453.5017 | 2.806 |

TABLE 9-continued

| ID NUMBER | Structure | Formula structure | MW | Log P |
|---|---|---|---|---|
| F5749-0204 | 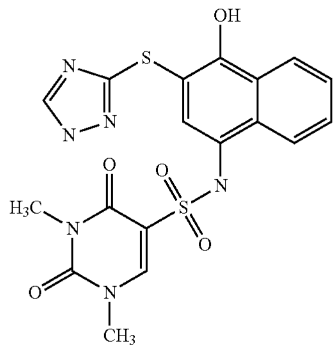 [SMILES: Cn1cc(S(=O)(=O)Nc2cc(Sc3nc[nH]n3)c(O)c3ccccc23)c(=O)n(C)c1=O] | C18H16N6O5S2 | 460.4934 | 0.807 |
| F5749-0205 | 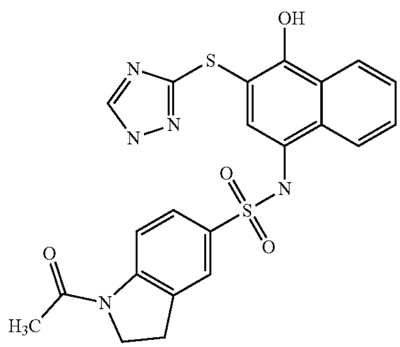 [SMILES: CC(=O)N1CCc2cc(S(=O)(=O)Nc3cc(Sc4nc[nH]n4)c(O)c4ccccc34)ccc21] | C22H19N5O4S2 | 481.5558 | 3.129 |
| F5749-0206 | 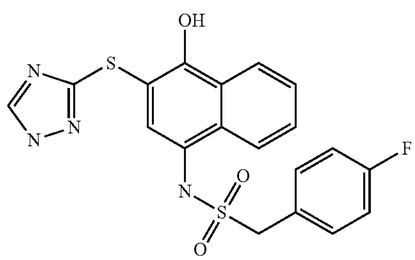 [SMILES: O=S(=O)(Cc1ccc(F)cc1)Nc1cc(Sc2nc[nH]n2)c(O)c2ccccc12] | C19H15FN4O3S2 | 430.4828 | 3.985 |
| F5749-0207 | 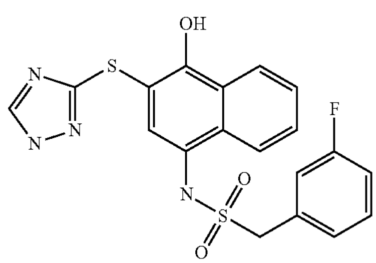 [SMILES: O=S(=O)(Cc1cccc(F)c1)Nc1cc(Sc2nc[nH]n2)c(O)c2ccccc12] | C19H15FN4O3S2 | 430.4828 | 4.022 |
| F5749-0208 | 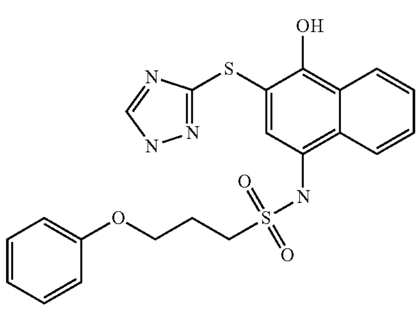 [SMILES: O=S(=O)(CCCOc1ccccc1)Nc1cc(Sc2nc[nH]n2)c(O)c2ccccc12] | C21H20N4O4S2 | 456.546 | 4.058 |

TABLE 9-continued

| ID NUMBER | Structure | Formula structure | MW | Log P |
|---|---|---|---|---|
| F5749-0209 | 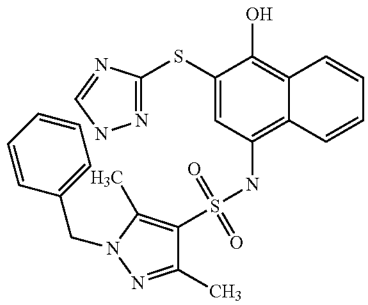 [SMILES: Cc1nn(Cc2ccccc2)c(C)c1S(=O)(=O)Nc1cc(Sc2nc[nH]n2)c(O)c2ccccc12] | C24H22N6O3S2 | 506.6093 | 3.977 |
| F5749-0210 | 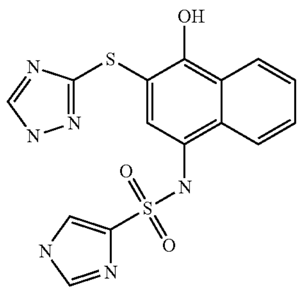 [SMILES: O=S(=O)(Nc1cc(Sc2nc[nH]n2)c(O)c2ccccc12)c1c[nH]cn1] | C15H12N6O3S2 | 388.4293 | 1.838 |
| F5749-0211 | 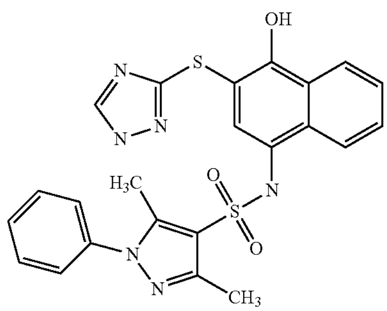 [SMILES: Cc1nn(-c2ccccc2)c(C)c1S(=O)(=O)Nc1cc(Sc2nc[nH]n2)c(O)c2ccccc12] | C23H20N6O3S2 | 492.5823 | 3.843 |
| F5749-0212 | 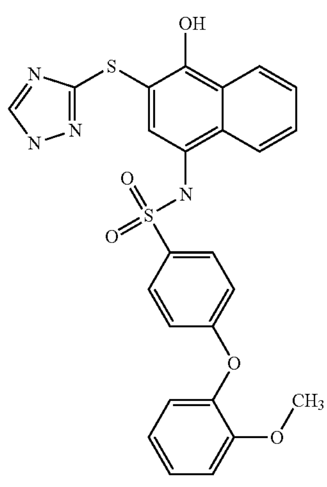 [SMILES: COc1ccccc1Oc1ccc(S(=O)(=O)Nc2cc(Sc3nc[nH]n3)c(O)c3ccccc23)cc1] | C25H20N4O5S2 | 520.59 | 5.01374 |

TABLE 9-continued
| ID NUMBER | Structure | Formula structure | MW | Log P |
|---|---|---|---|---|
| F5749-0213 | 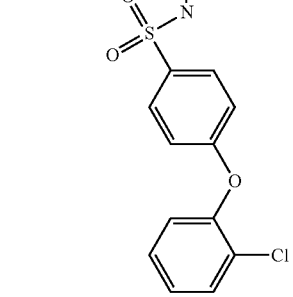 | C24H17ClN4O4S2 | 525.0085 | 5.898 |
| F5749-0214 | 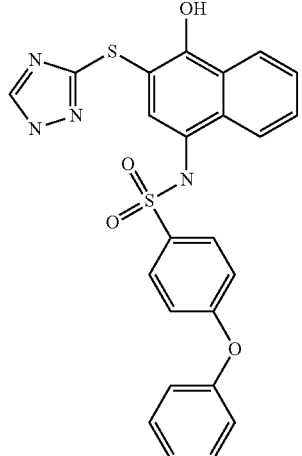 | C25H20N4O4S2 | 504.5906 | 5.606 |
| F5749-0215 | 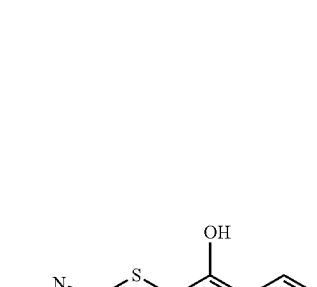 | C19H12ClF3N4O3S2 | 500.9087 | 5.25976 |

TABLE 9-continued
| ID NUMBER | Structure | Formula structure | MW | Log P |
|---|---|---|---|---|
| F5749-0216 | 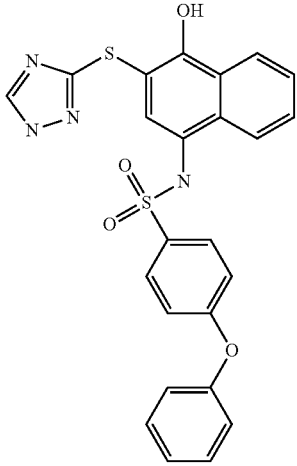 [SMILES: O=S(=O)(Nc1cc(Sc2nc[nH]n2)c(O)c2ccccc12)c1ccc(Oc2ccccc2)cc1] | C24H18N4O4S2 | 490.5635 | 5.308 |
| F5749-0217 | 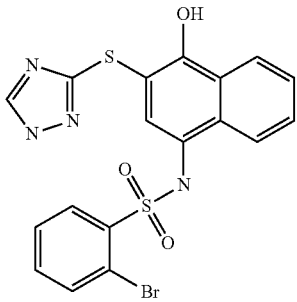 [SMILES: O=S(=O)(Nc1cc(Sc2nc[nH]n2)c(O)c2ccccc12)c1ccccc1Br] | C18H13BrN4O3S2 | 477.3613 | 4.494 |
| F5749-0218 | 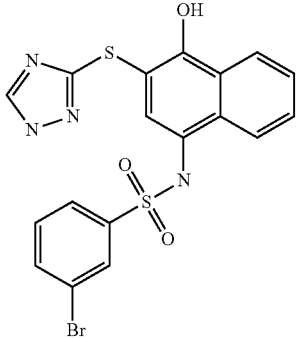 [SMILES: O=S(=O)(Nc1cc(Sc2nc[nH]n2)c(O)c2ccccc12)c1cccc(Br)c1] | C18H13BrN4O3S2 | 477.3613 | 4.533 |
| F5749-0219 | 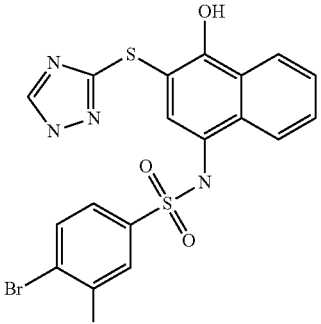 | C18H12BrFN4O3S2 | 495.3517 | 4.684 |

TABLE 9-continued
| ID NUMBER | Structure | Formula structure | MW | Log P |
|---|---|---|---|---|
| F5749-0220 | 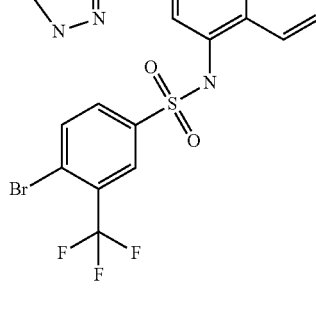 | C19H12BrF3N4O3S2 | 545.3597 | 5.46576 |
| F5749-0221 | 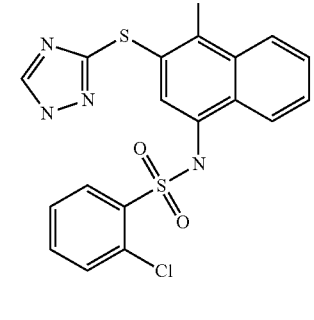 | C18H13ClN4O3S2 | 432.9103 | 4.288 |
| F5749-0222 | 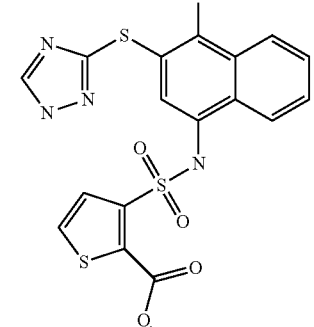 | C18H14N4O5S3 | 462.5281 | 2.898 |
| F5749-0223 | 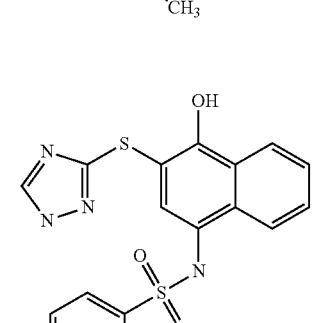 | C19H13F3N4O4S2 | 482.4631 | 5.09476 |

TABLE 10

| ID NUMBER | Structure | Formula structure | MW | LogP |
|---|---|---|---|---|
| F0808-0128 | 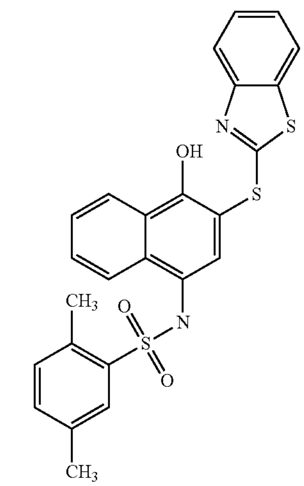 [SMILES: Cc1ccc(C)c(S(=O)(=O)Nc2cc(Sc3nc4ccccc4s3)c(O)c3ccccc23)c1] | C25H20N2O3S3 | 492.6418 | 6.892 |
| F0808-0132 | 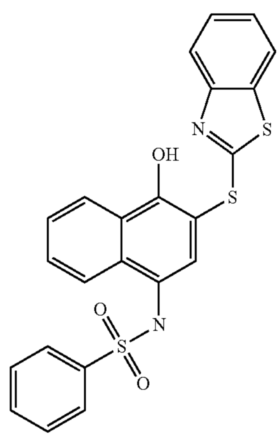 [SMILES: O=S(=O)(Nc1cc(Sc2nc3ccccc3s2)c(O)c2ccccc12)c1ccccc1] | C23H16N2O3S3 | 464.5876 | 6.261 |
| F0808-0133 | 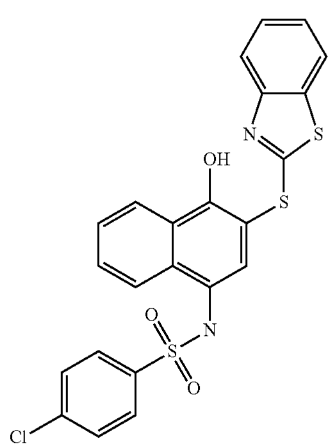 [SMILES: O=S(=O)(Nc1cc(Sc2nc3ccccc3s2)c(O)c2ccccc12)c1ccc(Cl)cc1] | C23H15ClN2O3S3 | 499.0326 | 6.853 |

TABLE 10-continued

| ID NUMBER | Structure | Formula structure | MW | LogP |
|---|---|---|---|---|
| F0808-0134 | 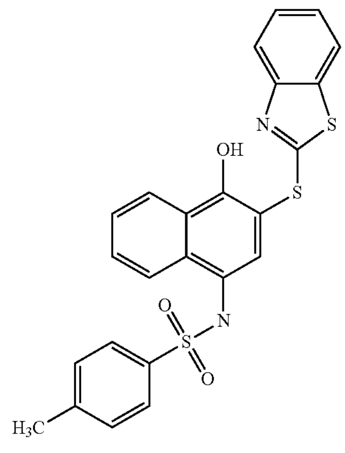 [SMILES: Cc1ccc(S(=O)(=O)Nc2cc(Sc3nc4ccccc4s3)c(O)c3ccccc23)cc1] | C24H18N2O3S3 | 478.6147 | 6.559 |
| F0808-0136 | 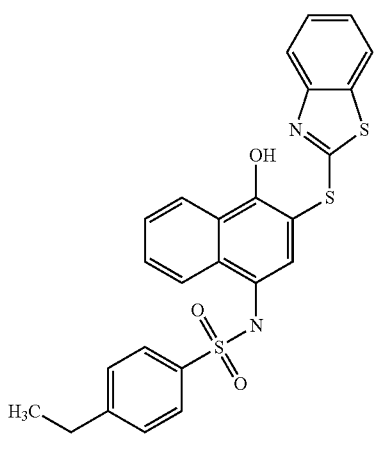 [SMILES: CCc1ccc(S(=O)(=O)Nc2cc(Sc3nc4ccccc4s3)c(O)c3ccccc23)cc1] | C25H20N2O3S3 | 492.6418 | 7.034 |
| F0808-0137 | 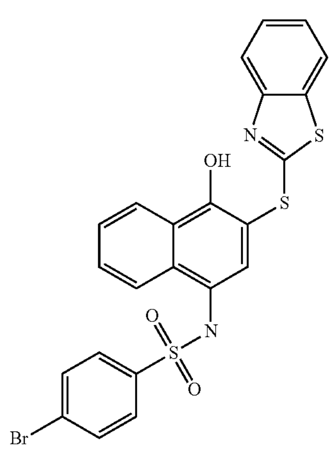 | C23H15BrN2O3S3 | 543.4836 | 7.059 |

TABLE 10-continued

| ID NUMBER | Structure | Formula structure | MW | LogP |
|---|---|---|---|---|
| F1269-0225 | 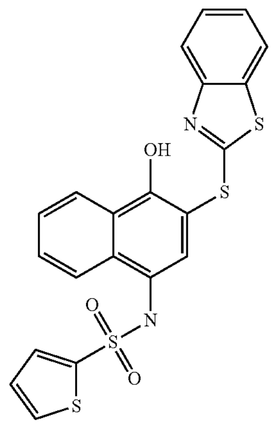 [SMILES: O=S(=O)(Nc1cc(Sc2nc3ccccc3s2)c(O)c2ccccc12)c1cccs1] | C21H14N2O3S4 | 470.6133 | 5.774 |
| F1269-1420 | 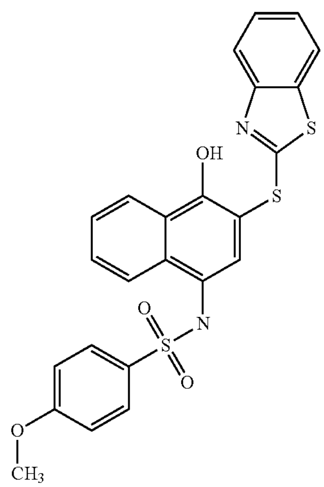 [SMILES: COc1ccc(S(=O)(=O)Nc2cc(Sc3nc4ccccc4s3)c(O)c3ccccc23)cc1] | C24H18N2O4S3 | 494.6141 | 6.217 |
| F1566-1144 | 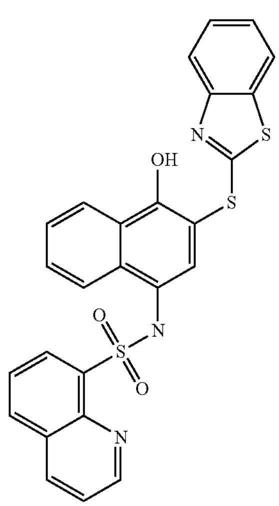 [SMILES: O=S(=O)(Nc1cc(Sc2nc3ccccc3s2)c(O)c2ccccc12)c1cccc2cccnc12] | C26H17N3O3S3 | 515.6357 | 6.461 |

TABLE 10-continued

| ID NUMBER | Structure | Formula structure | MW | LogP |
|---|---|---|---|---|
| F1566-1584 | 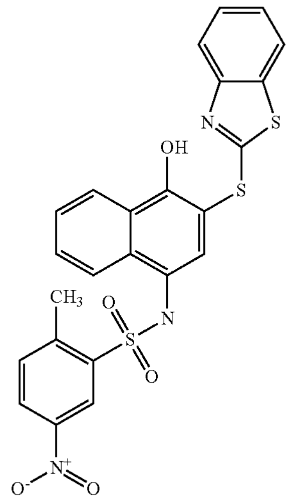 [SMILES: Cc1ccc([N+](=O)[O-])cc1S(=O)(=O)Nc1cc(Sc2nc3ccccc3s2)c(O)c2ccccc12] | C24H17N3O5S3 | 523.6122 | 6.529 |
| F1566-1596 | 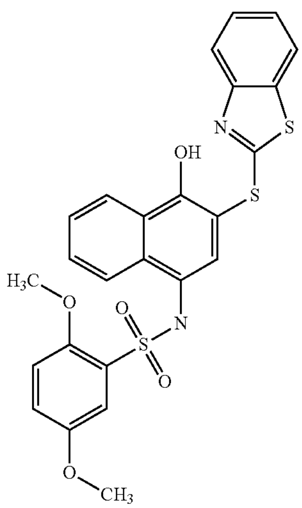 [SMILES: COc1ccc(OC)c(S(=O)(=O)Nc2cc(Sc3nc4ccccc4s3)c(O)c3ccccc23)c1] | C25H20N2O5S3 | 524.6406 | 6.208 |
| F1566-1816 | 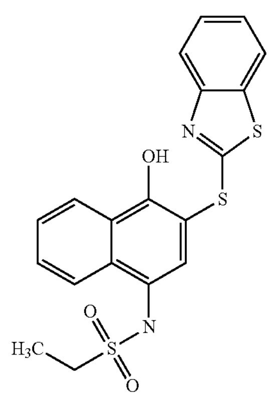 [SMILES: CCS(=O)(=O)Nc1cc(Sc2nc3ccccc3s2)c(O)c2ccccc12] | C19H16N2O3S3 | 416.543 | 5.12 |

TABLE 10-continued

| ID NUMBER | Structure | Formula structure | MW | LogP |
|---|---|---|---|---|
| F1566-1830 | 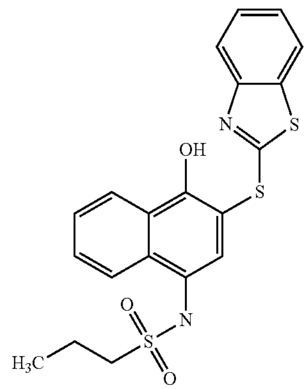 [SMILES: CCCS(=O)(=O)Nc1cc(Sc2nc3ccccc3s2)c(O)c2ccccc12] | C20H18N2O3S3 | 430.5701 | 5.562 |
| F1566-1844 | 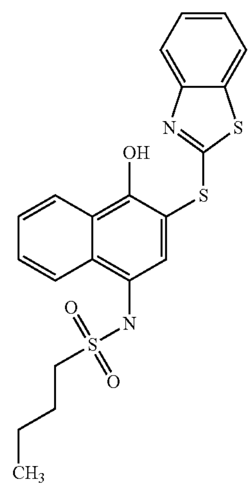 [SMILES: CCCCS(=O)(=O)Nc1cc(Sc2nc3ccccc3s2)c(O)c2ccccc12] | C21H20N2O3S3 | 444.5972 | 6.004 |
| F1566-1858 | 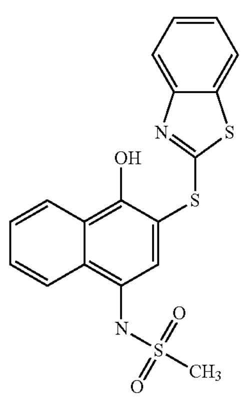 [SMILES: CS(=O)(=O)Nc1cc(Sc2nc3ccccc3s2)c(O)c2ccccc12] | C18H14N2O3S3 | 402.5159 | 4.607 |

TABLE 10-continued

| ID NUMBER | Structure | Formula structure | MW | LogP |
|---|---|---|---|---|
| F5749-0224 | 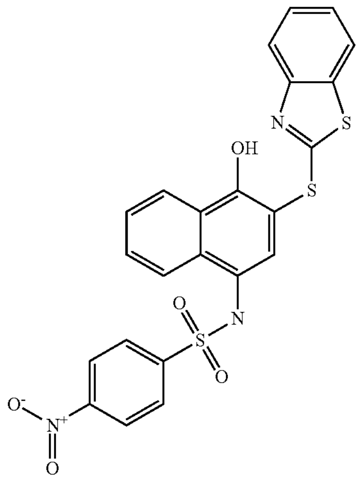 [SMILES: O=[N+]([O-])c1ccc(S(=O)(=O)Nc2cc(Sc3nc4ccccc4s3)c(O)c3ccccc23)cc1] | C23H15N3O5S3 | 509.5851 | 6.196 |
| F5749-0225 | 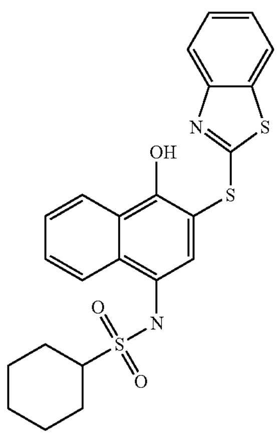 [SMILES: O=S(=O)(Nc1cc(Sc2nc3ccccc3s2)c(O)c2ccccc12)C1CCCCC1] | C23H22N2O3S3 | 470.6354 | 6.586 |
| F5749-0226 | 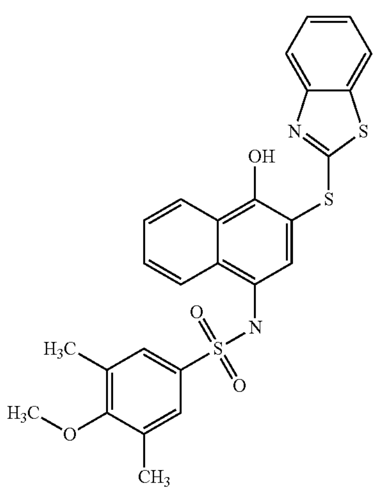 [SMILES: COc1c(C)cc(S(=O)(=O)Nc2cc(Sc3nc4ccccc4s3)c(O)c3ccccc23)cc1C] | C26H22N2O4S3 | 522.6682 | 6.883 |

TABLE 10-continued
| ID NUMBER | Structure | Formula structure | MW | LogP |
|---|---|---|---|---|
| F5749-0227 | 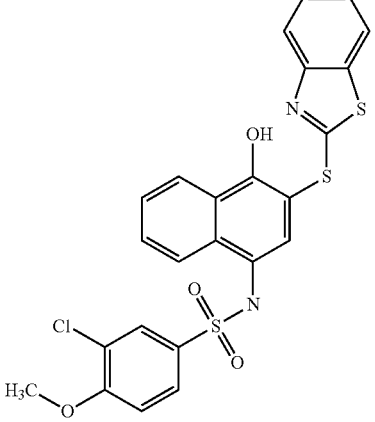 | C24H17ClN2O4S3 | 529.0591 | 6.844 |
| F5749-0228 | 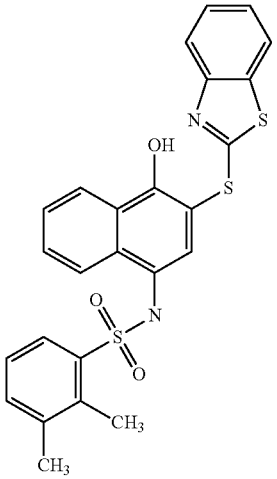 [SMILES: Cc1cccc(S(=O)(=O)Nc2cc(Sc3nc4ccccc4s3)c(O)c3ccccc23)c1C] | C25H20N2O3S3 | 492.6418 | 6.853 |
| F5749-0229 | 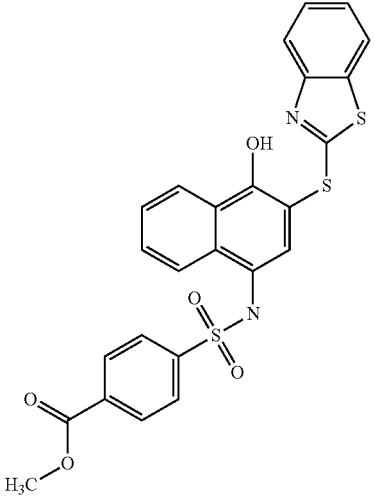 [SMILES: COC(=O)c1ccc(S(=O)(=O)Nc2cc(Sc3nc4ccccc4s3)c(O)c3ccccc23)cc1] | C25H18N2O5S3 | 522.6246 | 6.202 |

TABLE 10-continued

| ID NUMBER | Structure | Formula structure | MW | LogP |
|---|---|---|---|---|
| F5749-0230 | 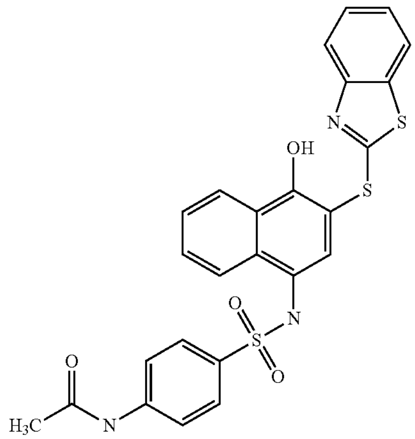 [SMILES: CC(=O)Nc1ccc(S(=O)(=O)Nc2cc(Sc3nc4ccccc4s3)c(O)c3ccccc23)cc1] | C25H19N3O4S3 | 521.6399 | 5.552 |
| F5749-0231 | 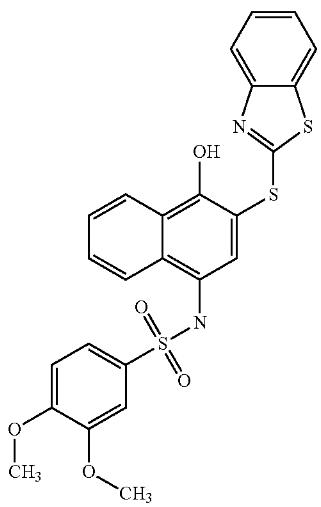 [SMILES: COc1ccc(S(=O)(=O)Nc2cc(Sc3nc4ccccc4s3)c(O)c3ccccc23)cc1OC] | C25H20N2O5S3 | 524.6406 | 5.95974 |
| F5749-0232 | 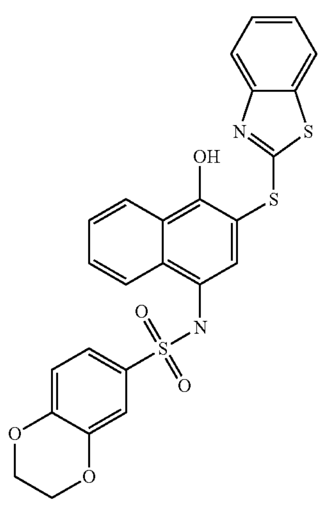 [SMILES: O=S(=O)(Nc1cc(Sc2nc3ccccc3s2)c(O)c2ccccc12)c1ccc2c(c1)OCCO2] | C25H18N2O5S3 | 522.6246 | 5.856 |

TABLE 10-continued
| ID NUMBER | Structure | Formula structure | MW | LogP |
|---|---|---|---|---|
| F5749-0233 | 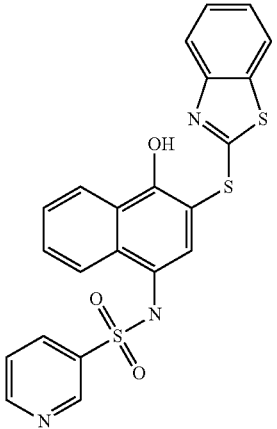 [SMILES: O=S(=O)(Nc1cc(Sc2nc3ccccc3s2)c(O)c2ccccc12)c1cccnc1] | C22H15N3O3S3 | 465.5752 | 5.028 |
| F5749-0234 | 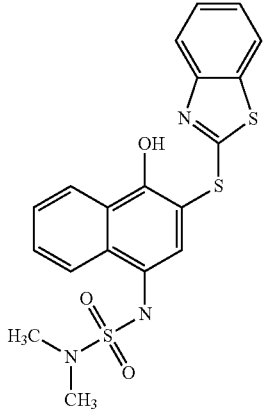 [SMILES: CN(C)S(=O)(=O)Nc1cc(Sc2nc3ccccc3s2)c(O)c2ccccc12] | C19H17N3O3S3 | 431.5576 | 4.155 |
| F5749-0235 | 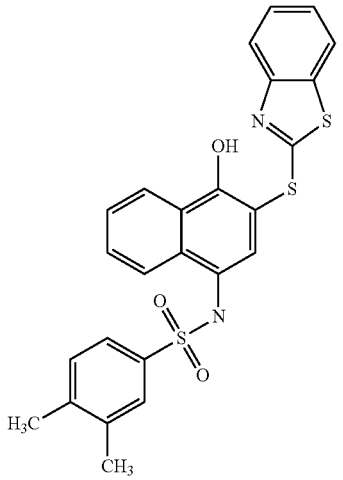 [SMILES: Cc1ccc(S(=O)(=O)Nc2cc(Sc3nc4ccccc4s3)c(O)c3ccccc23)cc1C] | C25H20N2O3S3 | 492.6418 | 6.892 |

TABLE 10-continued
| ID NUMBER | Structure | Formula structure | MW | LogP |
|---|---|---|---|---|
| F5749-0236 | 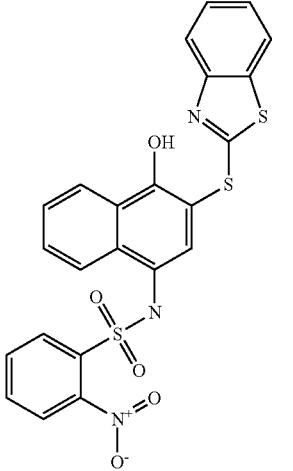 [SMILES: O=[N+]([O-])c1ccccc1S(=O)(=O)Nc1cc(Sc2nc3ccccc3s2)c(O)c2ccccc12] | C23H15N3O5S3 | 509.5851 | 6.194 |
| F5749-0237 | 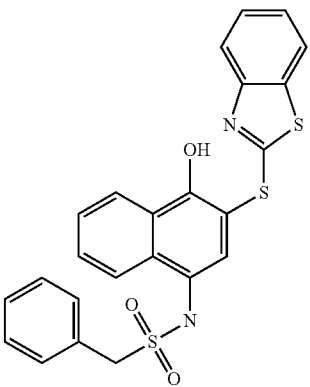 [SMILES: O=S(=O)(Cc1ccccc1)Nc1cc(Sc2nc3ccccc3s2)c(O)c2ccccc12] | C24H18N2O3S3 | 478.6147 | 6.395 |
| F5749-0238 | 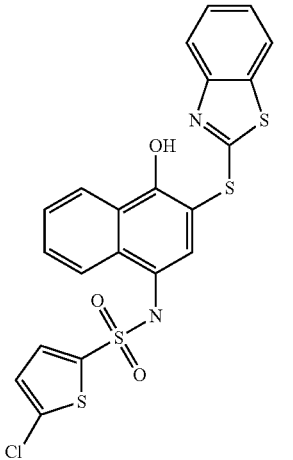 [SMILES: O=S(=O)(Nc1cc(Sc2nc3ccccc3s2)c(O)c2ccccc12)c1ccc(Cl)s1] | C21H13ClN2O3S4 | 505.0584 | 7.064 |

TABLE 10-continued

| ID NUMBER | Structure | Formula structure | MW | LogP |
|---|---|---|---|---|
| F5749-0239 | 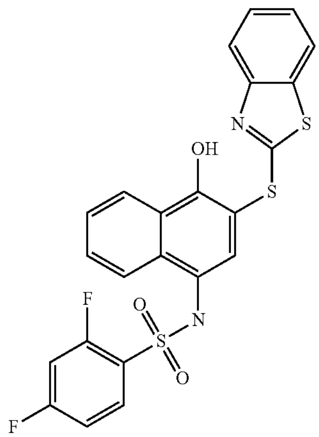 [SMILES: O=S(=O)(Nc1cc(Sc2nc3ccccc3s2)c(O)c2ccccc12)c1ccc(F)cc1F] | C23H14F2N2O3S3 | 500.5684 | 6.602 |
| F5749-0240 | 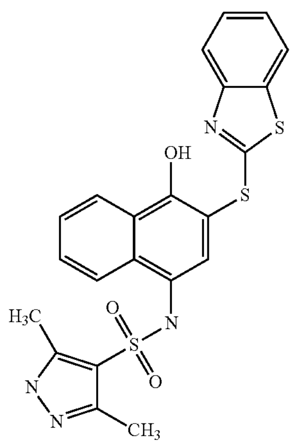 [SMILES: Cc1n[nH]c(C)c1S(=O)(=O)Nc1cc(Sc2nc3ccccc3s2)c(O)c2ccccc12] | C22H18N4O3S3 | 482.6058 | 5.371 |
| F5749-0241 | 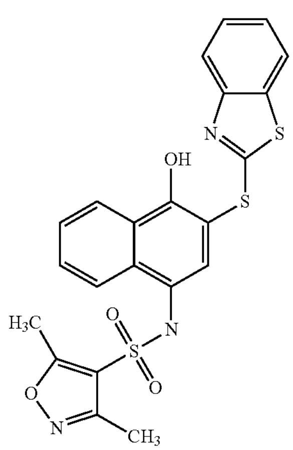 | C22H17N3O4S3 | 483.5905 | 5.405 |

TABLE 10-continued

| ID NUMBER | Structure | Formula structure | MW | LogP |
|---|---|---|---|---|
| F5749-0242 | 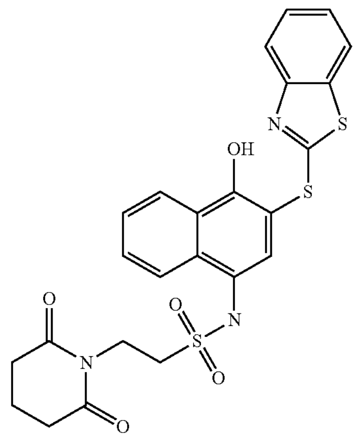 [SMILES: O=C1CCCC(=O)N1CCS(=O)(=O)Nc1cc(Sc2nc3ccccc3s2)c(O)c2ccccc12] | C24H21N3O5S3 | 527.6441 | 4.048 |
| F5749-0243 | 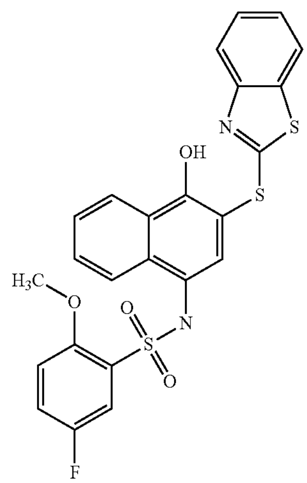 [SMILES: COc1ccc(F)cc1S(=O)(=O)Nc1cc(Sc2nc3ccccc3s2)c(O)c2ccccc12] | C24H17FN2O4S3 | 512.6045 | 6.405 |
| F5749-0244 | 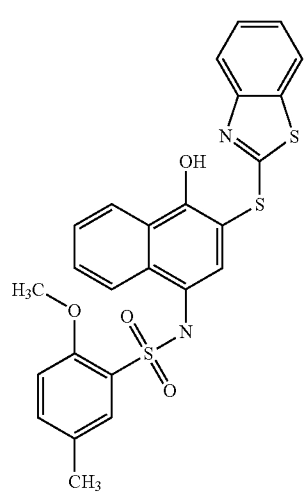 [SMILES: COc1ccc(C)cc1S(=O)(=O)Nc1cc(Sc2nc3ccccc3s2)c(O)c2ccccc12] | C25H20N2O4S3 | 508.6412 | 6.55 |

TABLE 10-continued

| ID NUMBER | Structure | Formula structure | MW | LogP |
| --- | --- | --- | --- | --- |
| F5749-0245 | 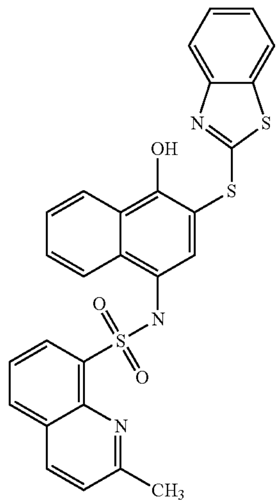 [SMILES: Cc1ccc2cccc(S(=O)(=O)Nc3cc(Sc4nc5ccccc5s4)c(O)c4ccccc34)c2n1] | C27H19N3O3S3 | 529.6628 | 6.72 |
| F5749-0246 | 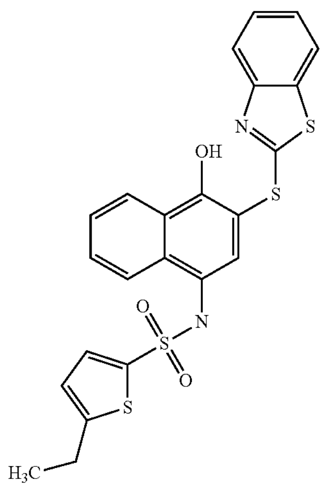 [SMILES: CCc1ccc(S(=O)(=O)Nc2cc(Sc3nc4ccccc4s3)c(O)c3ccccc23)s1] | C23H18N2O3S4 | 498.6675 | 6.912 |
| F5749-0247 | 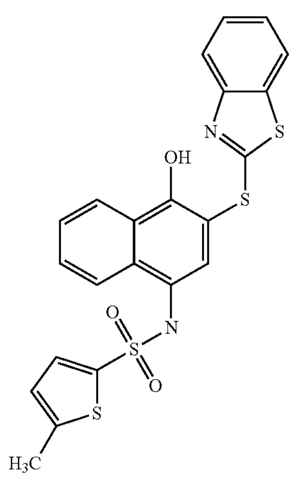 [SMILES: Cc1ccc(S(=O)(=O)Nc2cc(Sc3nc4ccccc4s3)c(O)c3ccccc23)s1] | C22H16N2O3S4 | 484.6404 | 6.437 |

TABLE 10-continued

| ID NUMBER | Structure | Formula structure | MW | LogP |
|---|---|---|---|---|
| F5749-0248 | 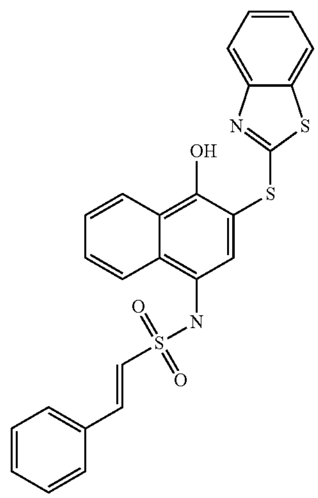 [SMILES: O=S(=O)(/C=C/c1ccccc1)Nc1cc(Sc2nc3ccccc3s2)c(O)c2ccccc12] | C25H18N2O3S3 | 490.6258 | 6.619 |
| F5749-0249 | 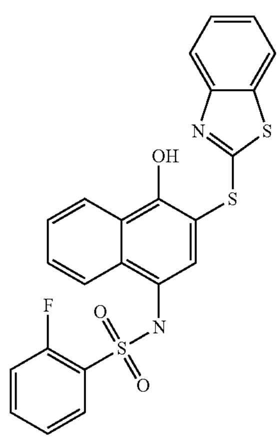 [SMILES: O=S(=O)(Nc1cc(Sc2nc3ccccc3s2)c(O)c2ccccc12)c1ccccc1F] | C23H15FN2O3S3 | 482.578 | 6.412 |
| F5749-0250 | 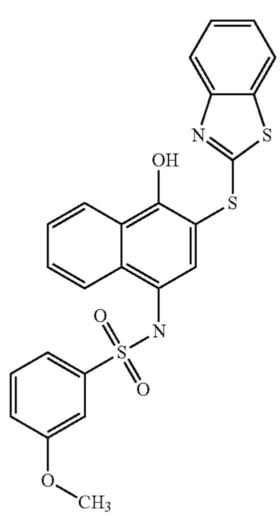 [SMILES: COc1cccc(S(=O)(=O)Nc2cc(Sc3nc4ccccc4s3)c(O)c3ccccc23)c1] | C24H18N2O4S3 | 494.6141 | 6.254 |

TABLE 10-continued

| ID NUMBER | Structure | Formula structure | MW | LogP |
|---|---|---|---|---|
| F5749-0251 | 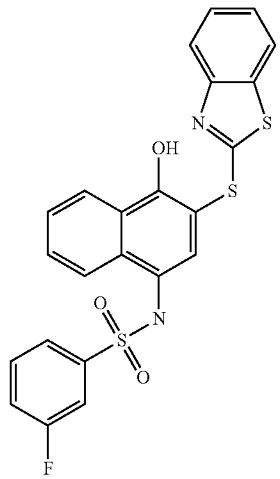 [SMILES: O=S(=O)(Nc1cc(Sc2nc3ccccc3s2)c(O)c2ccccc12)c1cccc(F)c1] | C23H15FN2O3S3 | 482.578 | 6.451 |
| F5749-0252 | 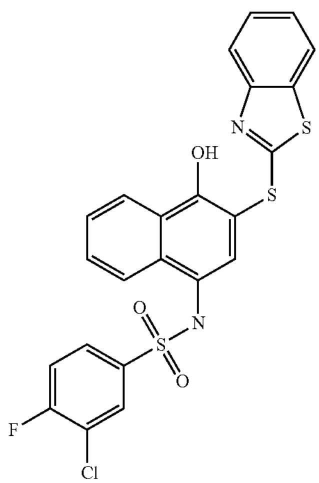 [SMILES: O=S(=O)(Nc1cc(Sc2nc3ccccc3s2)c(O)c2ccccc12)c1ccc(F)c(Cl)c1] | C23H14ClFN2O3S3 | 517.023 | 7.041 |
| F5749-0253 | 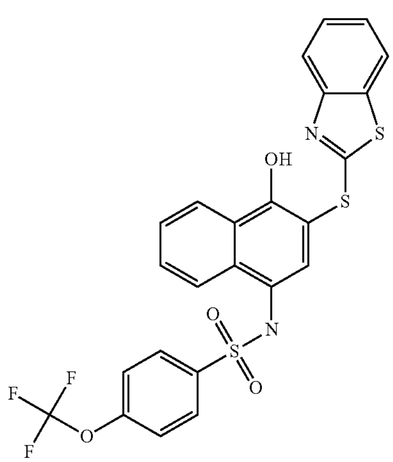 [SMILES: O=S(=O)(Nc1cc(Sc2nc3ccccc3s2)c(O)c2ccccc12)c1ccc(OC(F)(F)F)cc1] | C24H15F3N2O4S3 | 548.5854 | 7.65976 |

TABLE 10-continued

| ID NUMBER | Structure | Formula structure | MW | LogP |
|---|---|---|---|---|
| F5749-0254 | 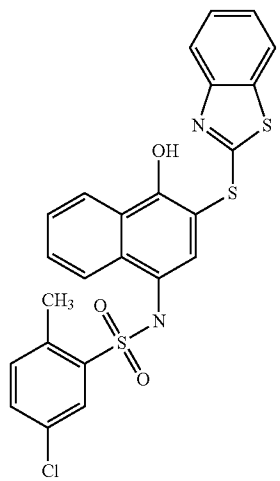 [SMILES: Cc1ccc(Cl)cc1S(=O)(=O)Nc1cc(Sc2nc3ccccc3s2)c(O)c2ccccc12] | C24H17ClN2O3S3 | 513.0597 | 7.186 |
| F5749-0255 | 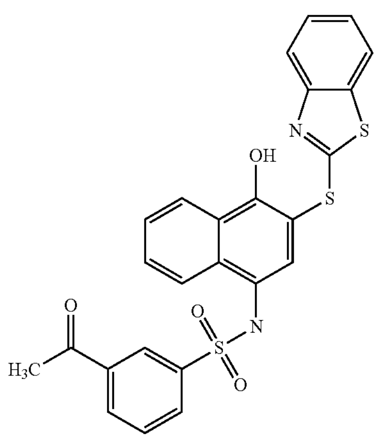 [SMILES: CC(=O)c1cccc(S(=O)(=O)Nc2cc(Sc3nc4ccccc4s3)c(O)c3ccccc23)c1] | C25H18N2O4S3 | 506.6252 | 6.151 |
| F5749-0256 | 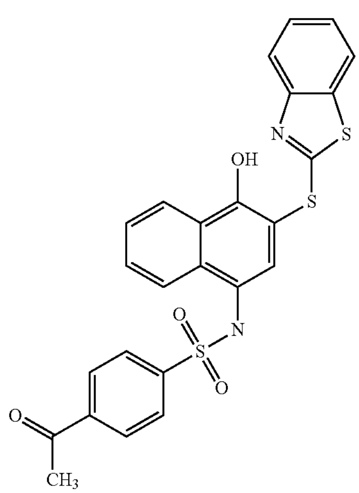 [SMILES: CC(=O)c1ccc(S(=O)(=O)Nc2cc(Sc3nc4ccccc4s3)c(O)c3ccccc23)cc1] | C25H18N2O4S3 | 506.6252 | 6.114 |

TABLE 10-continued

| ID NUMBER | Structure | Formula structure | MW | LogP |
|---|---|---|---|---|
| F5749-0257 | 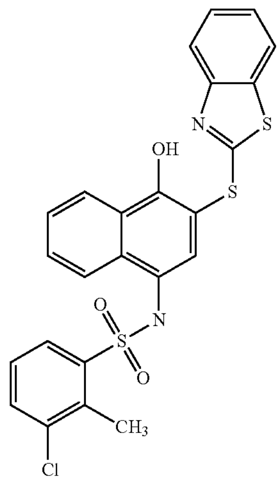 [SMILES: Cc1c(Cl)cccc1S(=O)(=O)Nc1cc(Sc2nc3ccccc3s2)c(O)c2ccccc12] | C24H17ClN2O3S3 | 513.0597 | 7.147 |
| F5749-0258 | 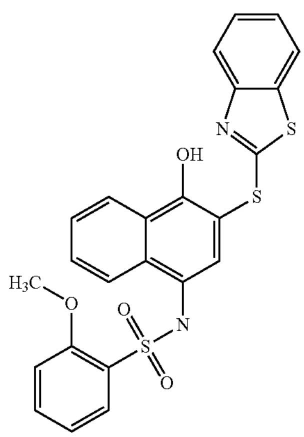 [SMILES: COc1ccccc1S(=O)(=O)Nc1cc(Sc2nc3ccccc3s2)c(O)c2ccccc12] | C24H18N2O4S3 | 494.6141 | 6.215 |
| F5749-0259 | 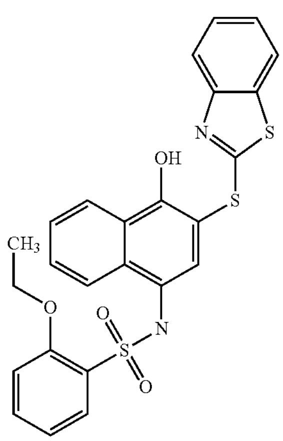 [SMILES: CCOc1ccccc1S(=O)(=O)Nc1cc(Sc2nc3ccccc3s2)c(O)c2ccccc12] | C25H20N2O4S3 | 508.6412 | 6.556 |

TABLE 10-continued

| ID NUMBER | Structure | Formula structure | MW | LogP |
|---|---|---|---|---|
| F5749-0260 | 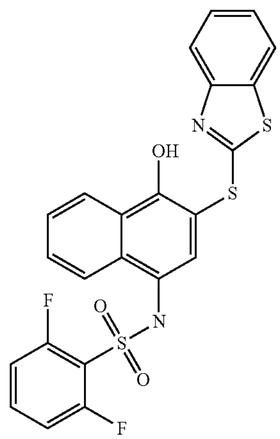 [SMILES: O=S(=O)(Nc1cc(Sc2nc3ccccc3s2)c(O)c2ccccc12)c1c(F)cccc1F] | C23H14F2N2O3S3 | 500.5684 | 6.563 |
| F5749-0261 | 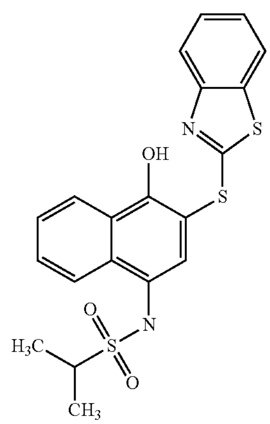 | C20H18N2O3S3 | 430.5701 | 5.754 |
| F5749-0262 | 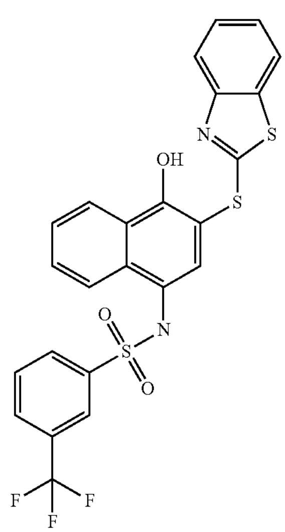 [SMILES: O=S(=O)(Nc1cc(Sc2nc3ccccc3s2)c(O)c2ccccc12)c1cccc(C(F)(F)F)c1] | C24H15F3N2O3S3 | 532.586 | 7.23276 |

TABLE 10-continued

| ID NUMBER | Structure | Formula structure | MW | LogP |
|---|---|---|---|---|
| F5749-0263 | 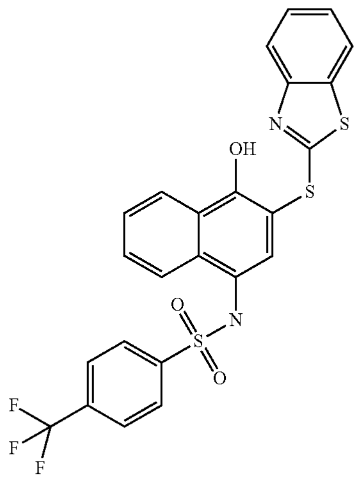 [SMILES: O=S(=O)(Nc1cc(Sc2nc3ccccc3s2)c(O)c2ccccc12)c1ccc(C(F)(F)F)cc1] | C24H15F3N2O3S3 | 532.586 | 7.19576 |
| F5749-0264 | 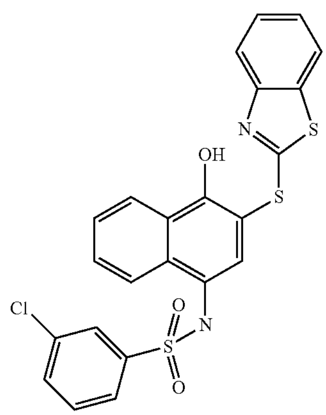 [SMILES: O=S(=O)(Nc1cc(Sc2nc3ccccc3s2)c(O)c2ccccc12)c1cccc(Cl)c1] | C23H15ClN2O3S3 | 499.0326 | 6.89 |
| F5749-0265 | 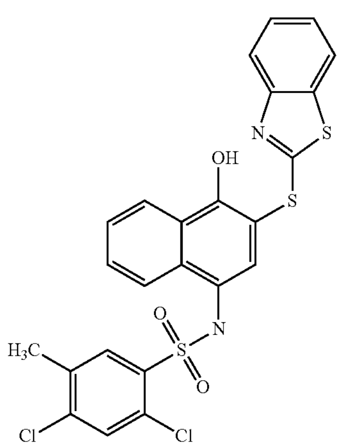 [SMILES: Cc1cc(S(=O)(=O)Nc2cc(Sc3nc4ccccc4s3)c(O)c3ccccc23)c(Cl)cc1Cl] | C24H16Cl2N2O3S3 | 547.5047 | 7.813 |

TABLE 10-continued
| ID NUMBER | Structure | Formula structure | MW | LogP |
|---|---|---|---|---|
| F5749-0266 | 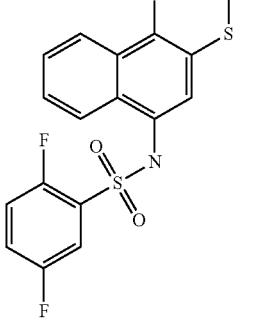 | C23H14F2N2O3S3 | 500.5684 | 6.602 |
| F5749-0267 | 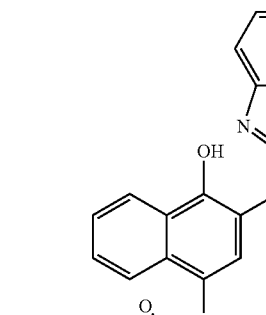 | C26H22N2O3S3 | 506.6688 | 7.476 |
| F5749-0268 | 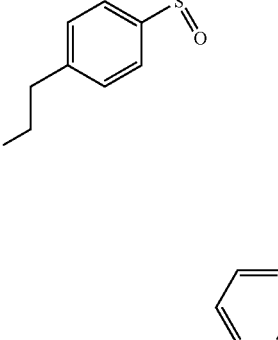 | C27H22N2O3S3 | 518.68 | 7.348 |

TABLE 10-continued

| ID NUMBER | Structure | Formula structure | MW | LogP |
|---|---|---|---|---|
| F5749-0269 | 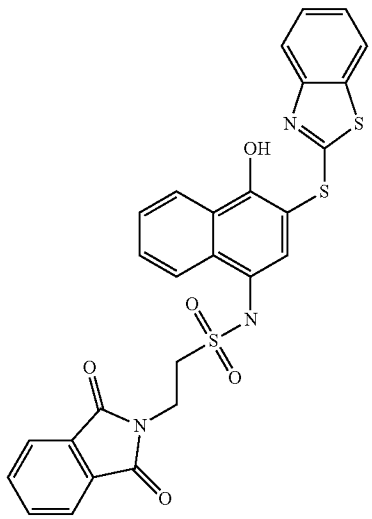 [SMILES: O=C1c2ccccc2C(=O)N1CCS(=O)(=O)Nc1cc(Sc2nc3ccccc3s2)c(O)c2ccccc12] | C27H19N3O5S3 | 561.6616 | 5.388 |
| F5749-0270 | 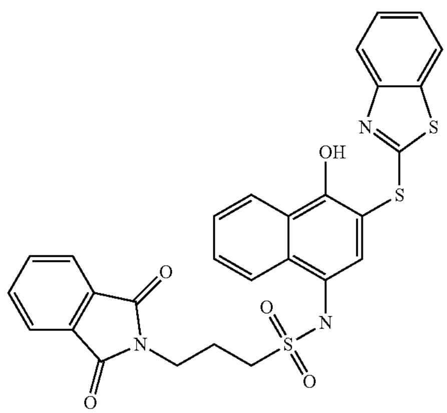 [SMILES: O=C1c2ccccc2C(=O)N1CCCS(=O)(=O)Nc1cc(Sc2nc3ccccc3s2)c(O)c2ccccc12] | C28H21N3O5S3 | 575.6887 | 5.83 |
| F5749-0271 | 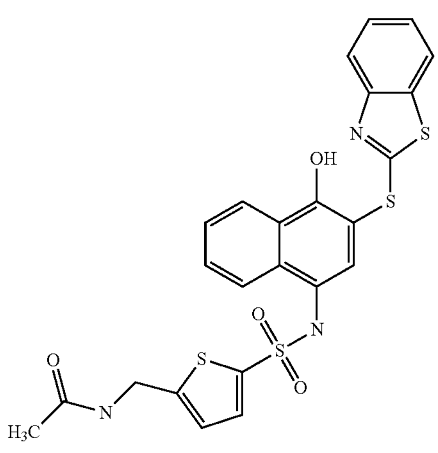 [SMILES: CC(=O)NCc1ccc(S(=O)(=O)Nc2cc(Sc3nc4ccccc4s3)c(O)c3ccccc23)s1] | C24H19N3O4S4 | 541.6927 | 5.564 |

TABLE 10-continued

| ID NUMBER | Structure | Formula structure | MW | LogP |
|---|---|---|---|---|
| F5749-0272 | 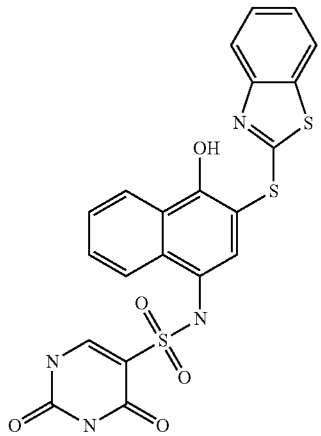 [SMILES: O=c1[nH]cc(S(=O)(=O)Nc2cc(Sc3nc4ccccc4s3)c(O)c3ccccc23)c(=O)[nH]1] | C21H14N4O5S3 | 498.5615 | 3.306 |
| F5749-0273 | 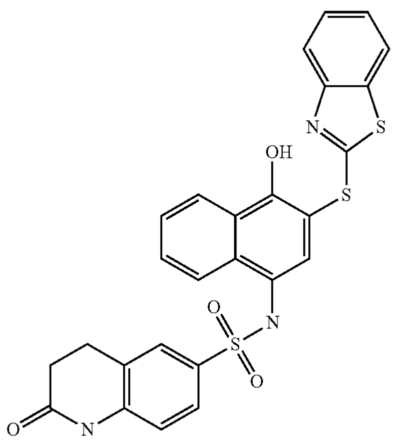 [SMILES: O=C1CCc2cc(S(=O)(=O)Nc3cc(Sc4nc5ccccc5s4)c(O)c4ccccc34)ccc2N1] | C26H19N3O4S3 | 533.651 | 5.457 |
| F5749-0274 | 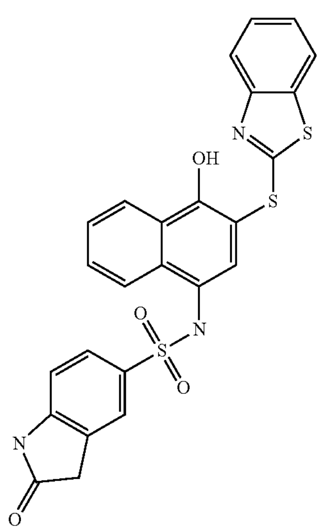 [SMILES: O=C1Cc2cc(S(=O)(=O)Nc3cc(Sc4nc5ccccc5s4)c(O)c4ccccc34)ccc2N1] | C25H17N3O4S3 | 519.6239 | 5.369 |

TABLE 10-continued

| ID NUMBER | Structure | Formula structure | MW | LogP |
|---|---|---|---|---|
| F5749-0275 | 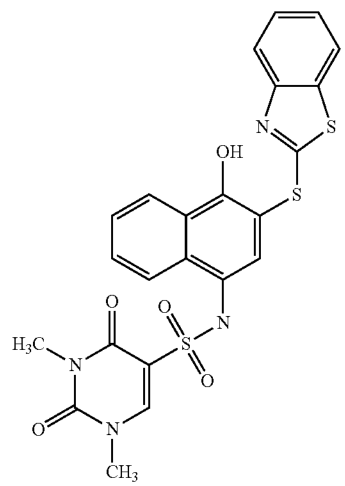 [SMILES: Cn1cc(S(=O)(=O)Nc2cc(Sc3nc4ccccc4s3)c(O)c3ccccc23)c(=O)n(C)c1=O] | C23H18N4O5S3 | 526.6157 | 3.37 |
| F5749-0276 | 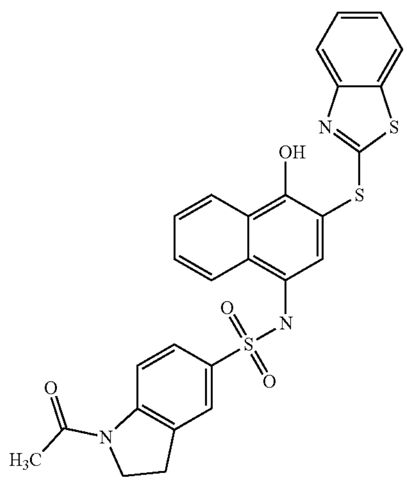 [SMILES: CC(=O)N1CCc2cc(S(=O)(=O)Nc3cc(Sc4nc5ccccc5s4)c(O)c4ccccc34)ccc21] | C27H21N3O4S3 | 547.6781 | 5.692 |
| F5749-0277 | 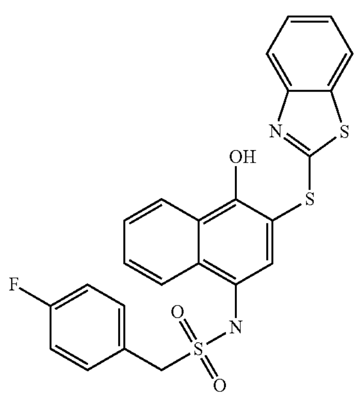 [SMILES: O=S(=O)(Cc1ccc(F)cc1)Nc1cc(Sc2nc3ccccc3s2)c(O)c2ccccc12] | C24H17FN2O3S3 | 496.6051 | 6.548 |

TABLE 10-continued
| ID NUMBER | Structure | Formula structure | MW | LogP |
|---|---|---|---|---|
| F5749-0278 | 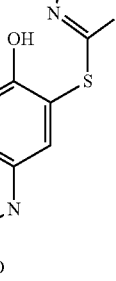 | C24H17FN2O3S3 | 496.6051 | 6.585 |
| F5749-0279 | 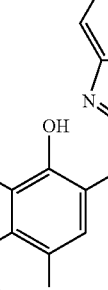 | C26H22N2O4S3 | 522.6682 | 6.621 |
| F5749-0280 | 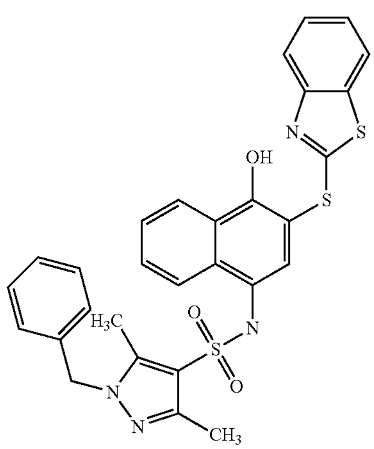 [SMILES: Cc1nn(Cc2ccccc2)c(C)c1S(=O)(=O)Nc1cc(Sc2nc3ccccc3s2)c(O)c2ccccc12] | C29H24N4O3S3 | 572.7316 | 6.54 |

TABLE 10-continued
| ID NUMBER | Structure | Formula structure | MW | LogP |
|---|---|---|---|---|
| F5749-0281 | 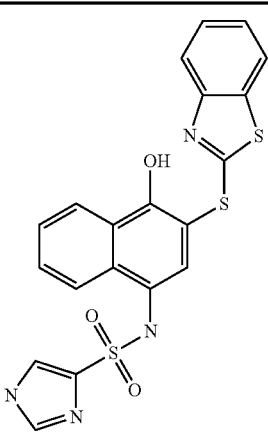 | C20H14N4O3S3 | 454.5516 | 4.401 |
| F5749-0282 | 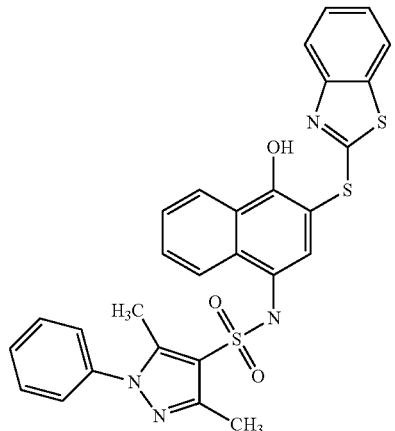 | C28H22N4O3S3 | 558.7045 | 6.406 |
| F5749-0283 | 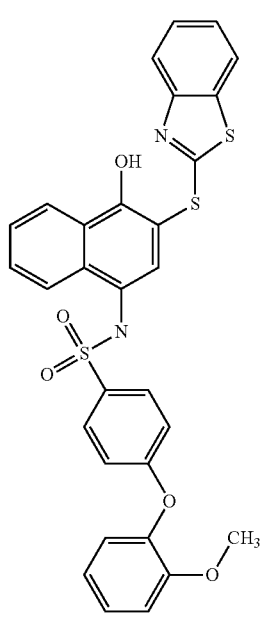 [SMILES: COc1ccccc1Oc1ccc(S(=O)(=O)Nc2cc(Sc3nc4ccccc4s3)c(O)c3ccccc23)cc1] | C30H22N2O5S3 | 586.7122 | 7.57674 |

TABLE 10-continued
| ID NUMBER | Structure | Formula structure | MW | LogP |
|---|---|---|---|---|
| F5749-0284 | 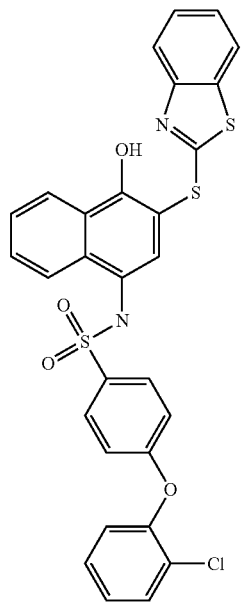 [SMILES: O=S(=O)(Nc1cc(Sc2nc3ccccc3s2)c(O)c2ccccc12)c1ccc(Oc2ccccc2Cl)cc1] | C29H19ClN2O4S3 | 591.1308 | 8.461 |
| F5749-0285 | 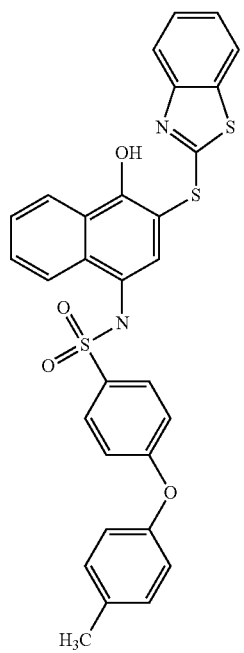 [SMILES: Cc1ccc(Oc2ccc(S(=O)(=O)Nc3cc(Sc4nc5ccccc5s4)c(O)c4ccccc34)cc2)cc1] | C30H22N2O4S3 | 570.7128 | 8.169 |

TABLE 10-continued
| ID NUMBER | Structure | Formula structure | MW | LogP |
|---|---|---|---|---|
| F5749-0286 | 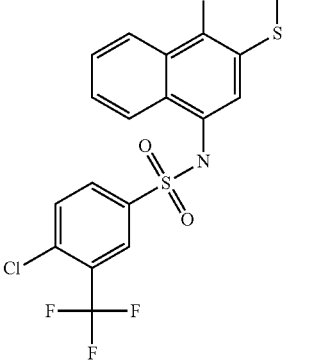 | C24H14ClF3N2O3S3 | 567.031 | 7.82276 |
| F5749-0287 | 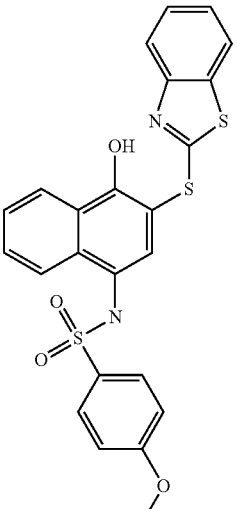 | C29H20N2O4S3 | 556.6858 | 7.871 |
| F5749-0288 | 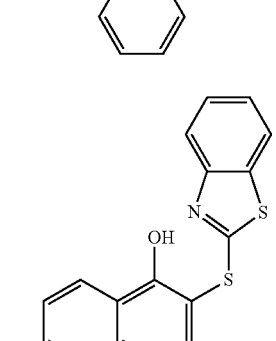 | C23H15BrN2O3S3 | 543.4836 | 7.057 |

TABLE 10-continued

| ID NUMBER | Structure | Formula structure | MW | LogP |
|---|---|---|---|---|
| F5749-0289 | 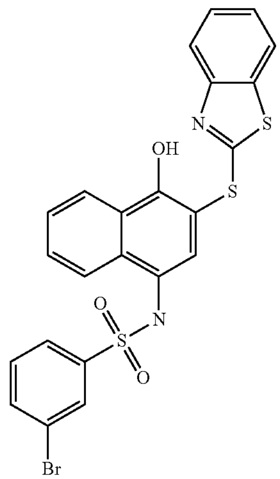 [SMILES: O=S(=O)(Nc1cc(Sc2nc3ccccc3s2)c(O)c2ccccc12)c1cccc(Br)c1] | C23H15BrN2O3S3 | 543.4836 | 7.096 |
| F5749-0290 | 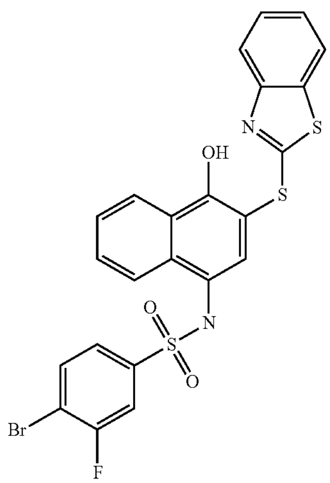 [SMILES: O=S(=O)(Nc1cc(Sc2nc3ccccc3s2)c(O)c2ccccc12)c1ccc(Br)c(F)c1] | C23H14BrFN2O3S3 | 561.474 | 7.247 |
| F5749-0291 | 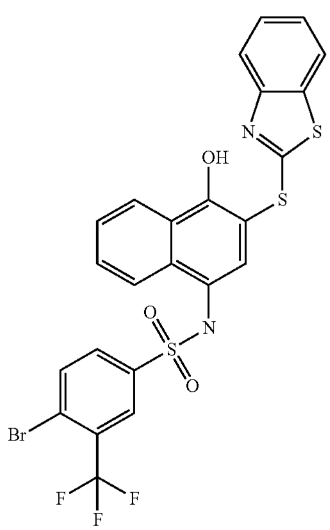 [SMILES: O=S(=O)(Nc1cc(Sc2nc3ccccc3s2)c(O)c2ccccc12)c1ccc(Br)c(C(F)(F)F)c1] | C24H14BrF3N2O3S3 | 611.482 | 8.02876 |

TABLE 10-continued

| ID NUMBER | Structure | Formula structure | MW | LogP |
|---|---|---|---|---|
| F5749-0292 | 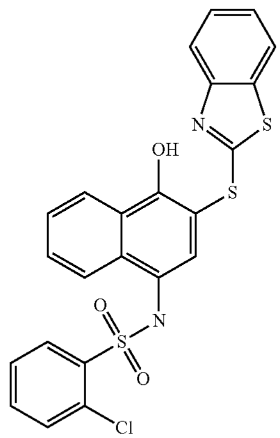 [SMILES: O=S(=O)(Nc1cc(Sc2nc3ccccc3s2)c(O)c2ccccc12)c1ccccc1Cl] | C23H15ClN2O3S3 | 499.0326 | 6.851 |
| F5749-0293 | 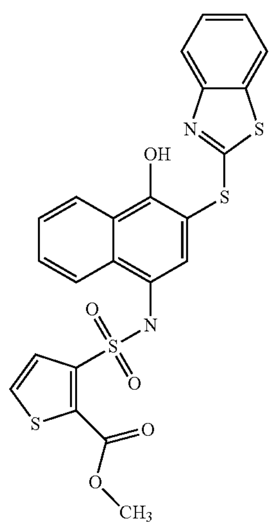 [SMILES: COC(=O)c1sccc1S(=O)(=O)Nc1cc(Sc2nc3ccccc3s2)c(O)c2ccccc12] | C23H16N2O5S4 | 528.6504 | 5.461 |
| F5749-0294 | 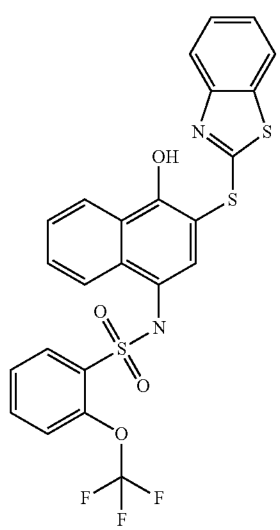 [SMILES: O=S(=O)(Nc1cc(Sc2nc3ccccc3s2)c(O)c2ccccc12)c1ccccc1OC(F)(F)F] | C24H15F3N2O4S3 | 548.5854 | 7.65776 |

TABLE 11

| ID NUMBER | Structure | Formula structure | MW | Log P |
|---|---|---|---|---|
| F0433-0038 | 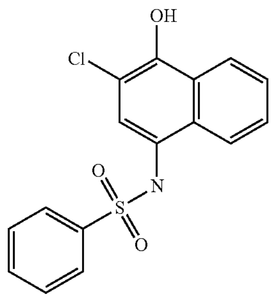 [SMILES: O=S(=O)(Nc1cc(Cl)c(O)c2ccccc12)c1ccccc1] | C16H12ClNO3S | 333.7959 | 4.192 |
| F0433-0041 | 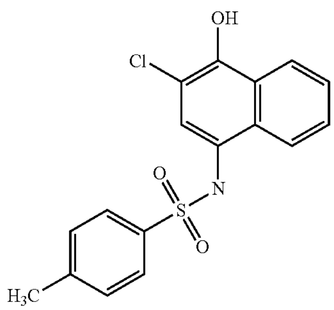 [SMILES: Cc1ccc(S(=O)(=O)Nc2cc(Cl)c(O)c3ccccc23)cc1] | C17H14ClNO3S | 347.823 | 4.49 |
| F0433-0044 | 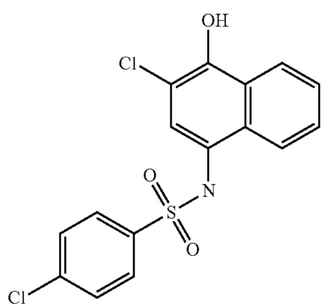 [SMILES: O=S(=O)(Nc1cc(Cl)c(O)c2ccccc12)c1ccc(Cl)cc1] | C16H11Cl2NO3S | 368.241 | 4.784 |
| F0433-0047 | 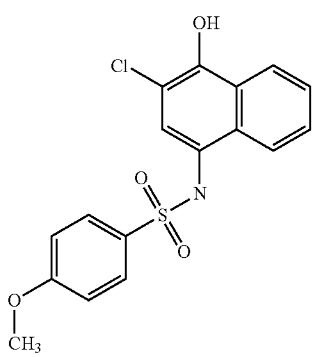 [SMILES: COc1ccc(S(=O)(=O)Nc2cc(Cl)c(O)c3ccccc23)cc1] | C17H14ClNO4S | 363.8224 | 4.148 |
| F0433-0050 | 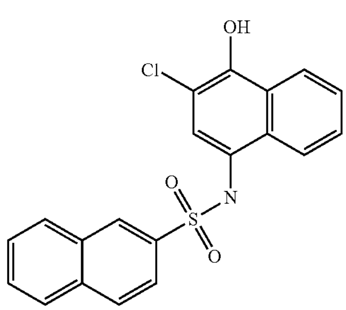 [SMILES: O=S(=O)(Nc1cc(Cl)c(O)c2ccccc12)c1ccc2ccccc2c1] | C20H14ClNO3S | 383.8565 | 5.451 |

TABLE 11-continued

| ID NUMBER | Structure | Formula structure | MW | Log P |
|---|---|---|---|---|
| F0808-1895 | 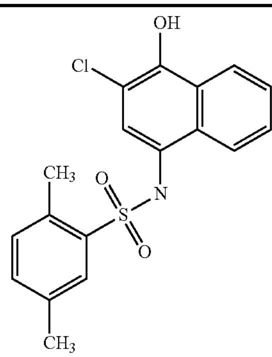 | C18H16ClNO3S | 361.8501 | 4.823 |
| F0808-1902 | 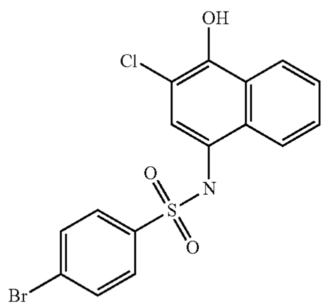 | C16H11BrClNO3S | 412.692 | 4.99 |
| F0808-1909 | 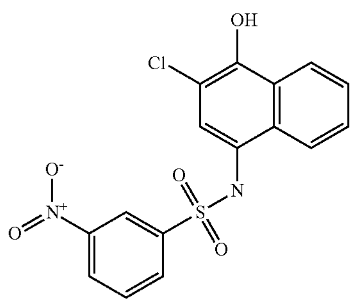 [SMILES: O=[N+]([O-])c1cccc(S(=O)(=O)Nc2cc(Cl)c(O)c3ccccc23)c1] | C16H11ClN2O5S | 378.7935 | 4.164 |
| F0808-1913 | 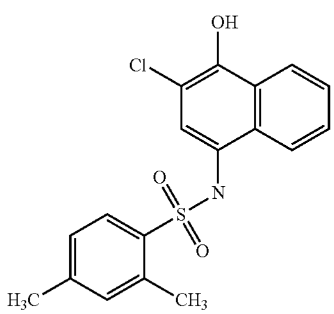 [SMILES: Cc1ccc(S(=O)(=O)Nc2cc(Cl)c(O)c3ccccc23)c(C)c1] | C18H16ClNO3S | 361.8501 | 4.823 |
| F0808-1914 | 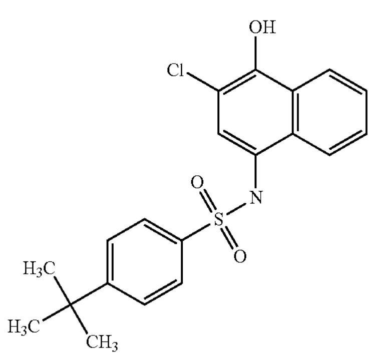 [SMILES: CC(C)(C)c1ccc(S(=O)(=O)Nc2cc(Cl)c(O)c3ccccc23)cc1] | C20H20ClNO3S | 389.9043 | 5.691 |

TABLE 11-continued

| ID NUMBER | Structure | Formula structure | MW | Log P |
|---|---|---|---|---|
| F1269-0272 | 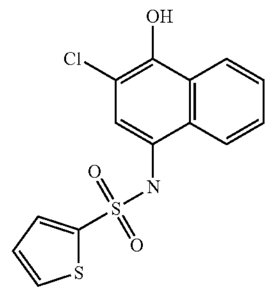 [SMILES: O=S(=O)(Nc1cc(Cl)c(O)c2ccccc12)c1cccs1] | C14H10ClNO3S2 | 339.8217 | 3.705 |
| F1269-1995 | 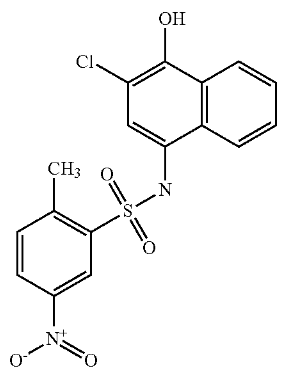 [SMILES: Cc1ccc([N+](=O)[O-])cc1S(=O)(=O)Nc1cc(Cl)c(O)c2ccccc12] | C17H13ClN2O5S | 392.8206 | 4.46 |
| F1566-1223 | 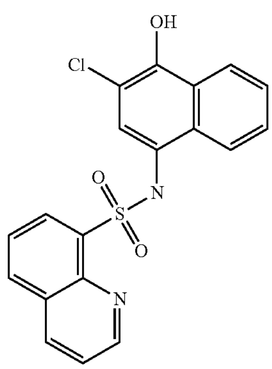 [SMILES: O=S(=O)(Nc1cc(Cl)c(O)c2ccccc12)c1cccc2cccnc12] | C19H13ClN2O3S | 384.8441 | 4.392 |
| F5749-0295 | 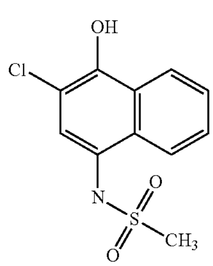 [SMILES: CS(=O)(=O)Nc1cc(Cl)c(O)c2ccccc12] | C11H10ClNO3S | 271.7243 | 2.538 |

TABLE 11-continued

| ID NUMBER | Structure | Formula structure | MW | Log P |
|---|---|---|---|---|
| F5749-0296 | 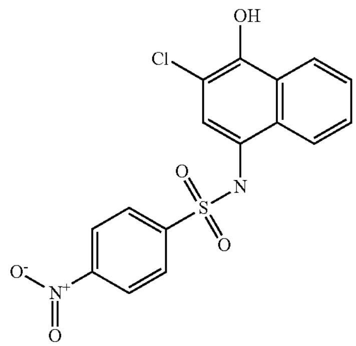 [SMILES: O=[N+]([O-])c1ccc(S(=O)(=O)Nc2cc(Cl)c(O)c3ccccc23)cc1] | C16H11ClN2O5S | 378.7935 | 4.127 |
| F5749-0297 | 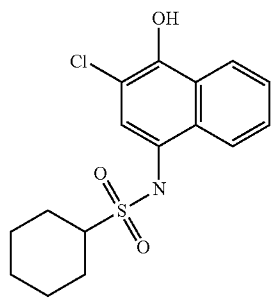 [SMILES: O=S(=O)(Nc1cc(Cl)c(O)c2ccccc12)C1CCCCC1] | C16H18ClNO3S | 339.8438 | 4.517 |
| F5749-0298 | 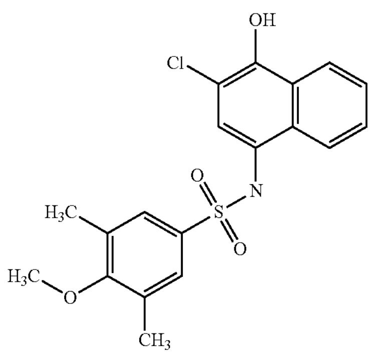 [SMILES: COc1c(C)cc(S(=O)(=O)Nc2cc(Cl)c(O)c3ccccc23)cc1C] | C19H18ClNO4S | 391.8766 | 4.814 |
| F5749-0299 | 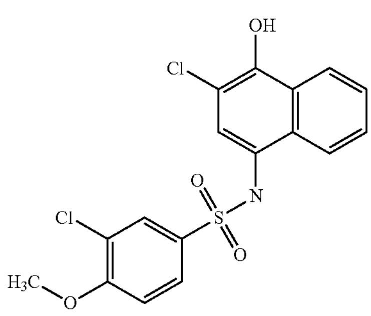 [SMILES: COc1ccc(S(=O)(=O)Nc2cc(Cl)c(O)c3ccccc23)cc1Cl] | C17H13Cl2NO4S | 398.2675 | 4.775 |

TABLE 11-continued
| ID NUMBER | Structure | Formula structure | MW | Log P |
|---|---|---|---|---|
| F5749-0300 | 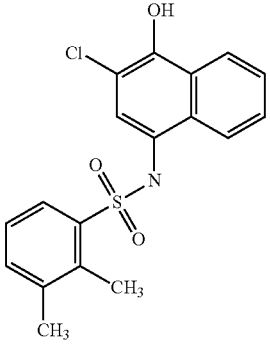 [SMILES: Cc1cccc(S(=O)(=O)Nc2cc(Cl)c(O)c3ccccc23)c1C] | C18H16ClNO3S | 361.8501 | 4.784 |
| F5749-0301 | 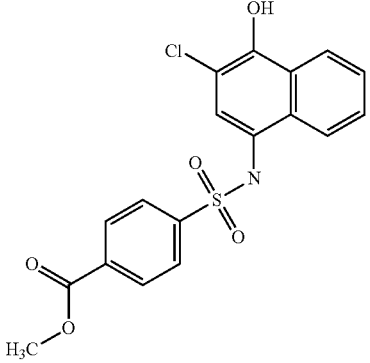 [SMILES: COC(=O)c1ccc(S(=O)(=O)Nc2cc(Cl)c(O)c3ccccc23)cc1] | C18H14ClNO5S | 391.833 | 4.133 |
| F5749-0302 | 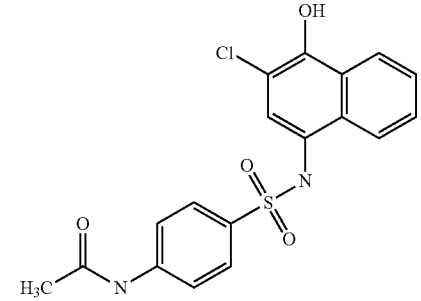 [SMILES: CC(=O)Nc1ccc(S(=O)(=O)Nc2cc(Cl)c(O)c3ccccc23)cc1] | C18H15ClN2O4S | 390.8483 | 3.483 |
| F5749-0303 | 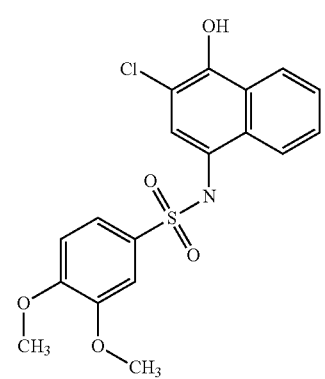 [SMILES: COc1ccc(S(=O)(=O)Nc2cc(Cl)c(O)c3ccccc23)cc1OC] | C18H16ClNO5S | 393.8489 | 3.89074 |

TABLE 11-continued

| ID NUMBER | Structure | Formula structure | MW | Log P |
|---|---|---|---|---|
| F5749-0304 | 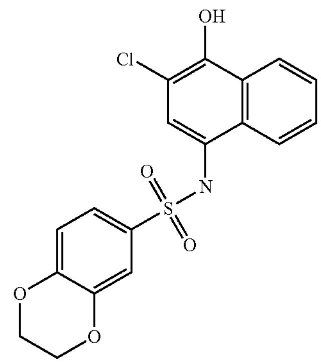 [SMILES: O=S(=O)(Nc1cc(Cl)c(O)c2ccccc12)c1ccc2c(c1)OCCO2] | C18H14ClNO5S | 391.833 | 3.787 |
| F5749-0305 | 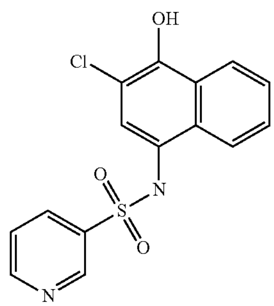 [SMILES: O=S(=O)(Nc1cc(Cl)c(O)c2ccccc12)c1cccnc1] | C15H11ClN2O3S | 334.7835 | 2.959 |
| F5749-0306 | 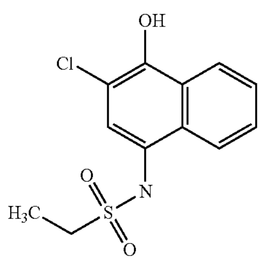 [SMILES: CCS(=O)(=O)Nc1cc(Cl)c(O)c2ccccc12] | C12H12ClNO3S | 285.7513 | 3.051 |
| F5749-0307 | 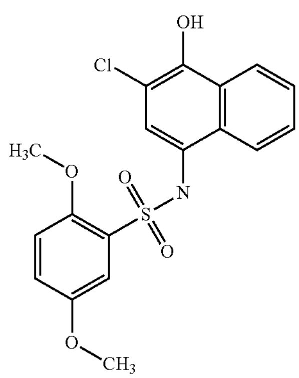 [SMILES: COc1ccc(OC)c(S(=O)(=O)Nc2cc(Cl)c(O)c3ccccc23)c1] | C18H16ClNO5S | 393.8489 | 4.139 |
| F5749-0308 | 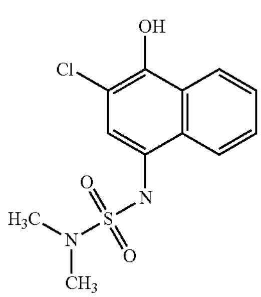 [SMILES: CN(C)S(=O)(=O)Nc1cc(Cl)c(O)c2ccccc12] | C12H13ClN2O3S | 300.766 | 2.086 |

TABLE 11-continued
| ID NUMBER | Structure | Formula structure | MW | Log P |
|---|---|---|---|---|
| F5749-0309 | 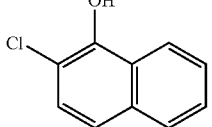 | C18H16ClNO3S | 361.8501 | 4.823 |
| F5749-0310 | 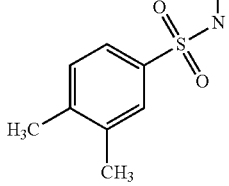 | C16H11ClN2O5S | 378.7935 | 4.125 |
| F5749-0311 | 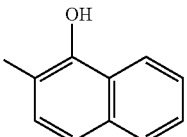 | C13H14ClNO3S | 299.7784 | 3.493 |
| F5749-0312 | 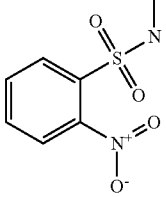 | C17H14ClNO3S | 347.823 | 4.326 |
| F5749-0313 | 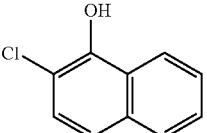 | C14H16ClNO3S | 313.8055 | 3.935 |

TABLE 11-continued

| ID NUMBER | Structure | Formula structure | MW | Log P |
|---|---|---|---|---|
| F5749-0314 | 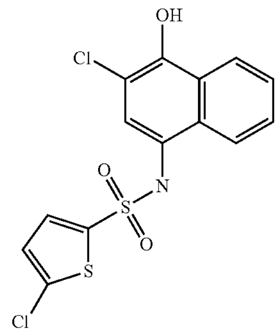 [SMILES: O=S(=O)(Nc1cc(Cl)c(O)c2ccccc12)c1ccc(Cl)s1] | C14H9Cl2NO3S2 | 374.2667 | 4.995 |
| F5749-0315 | 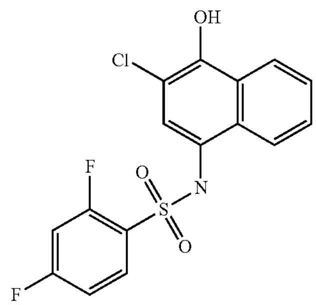 [SMILES: O=S(=O)(Nc1cc(Cl)c(O)c2ccccc12)c1ccc(F)cc1F] | C16H10ClF2NO3S | 369.7768 | 4.533 |
| F5749-0316 | 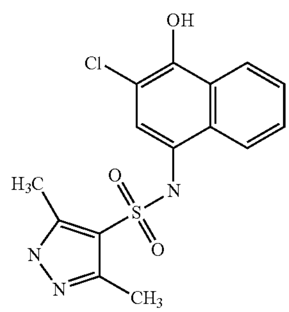 [SMILES: Cc1n[nH]c(C)c1S(=O)(=O)Nc1cc(Cl)c(O)c2ccccc12] | C15H14ClN3O3S | 351.8141 | 3.302 |
| F5749-0317 | 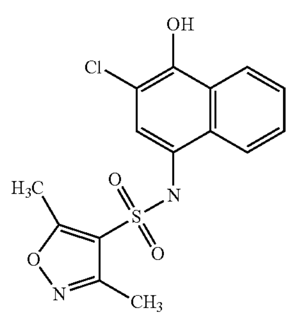 [SMILES: Cc1noc(C)c1S(=O)(=O)Nc1cc(Cl)c(O)c2ccccc12] | C15H13ClN2O4S | 352.7989 | 3.336 |
| F5749-0318 | 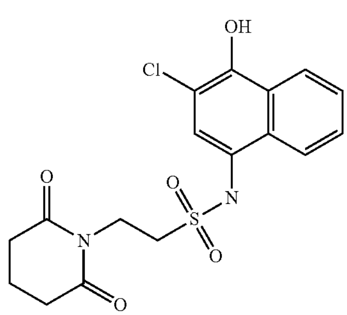 [SMILES: O=C1CCCC(=O)N1CCS(=O)(=O)Nc1cc(Cl)c(O)c2ccccc12] | C17H17ClN2O5S | 396.8524 | 1.979 |

TABLE 11-continued

| ID NUMBER | Structure | Formula structure | MW | Log P |
|---|---|---|---|---|
| F5749-0319 | 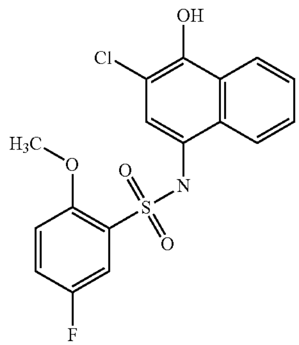 [SMILES: COc1ccc(F)cc1S(=O)(=O)Nc1cc(Cl)c(O)c2ccccc12] | C17H13ClFNO4S | 381.8129 | 4.336 |
| F5749-0320 | 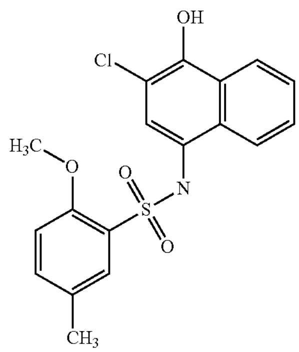 [SMILES: COc1ccc(C)cc1S(=O)(=O)Nc1cc(Cl)c(O)c2ccccc12] | C18H16ClNO4S | 377.8495 | 4.481 |
| F5749-0321 | 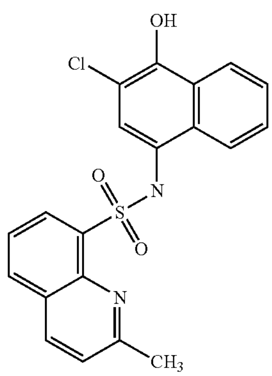 [SMILES: Cc1ccc2cccc(S(=O)(=O)Nc3cc(Cl)c(O)c4ccccc34)c2n1] | C20H15ClN2O3S | 398.8712 | 4.651 |
| F5749-0322 | 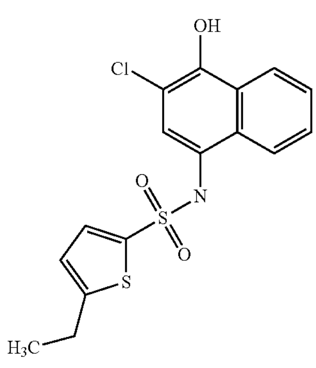 [SMILES: CCc1ccc(S(=O)(=O)Nc2cc(Cl)c(O)c3ccccc23)s1] | C16H14ClNO3S2 | 367.8759 | 4.843 |

| ID NUMBER | Structure | Formula structure | MW | Log P |
|---|---|---|---|---|
| F5749-0323 | 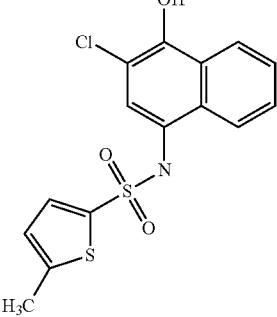 | C15H12ClNO3S2 | 353.8488 | 4.368 |
| F5749-0324 | 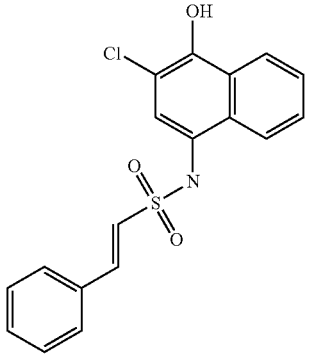 [SMILES: O=S(=O)(/C=C/c1ccccc1)Nc1cc(Cl)c(O)c2ccccc12] | C18H14ClNO3S | 359.8342 | 4.55 |
| F5749-0325 | 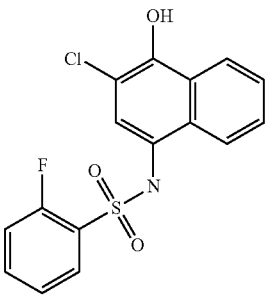 [SMILES: O=S(=O)(Nc1cc(Cl)c(O)c2ccccc12)c1ccccc1F] | C16H11ClFNO3S | 351.7864 | 4.343 |
| F5749-0326 | 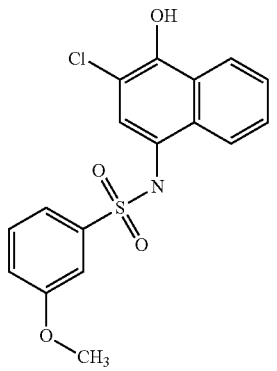 [SMILES: COc1cccc(S(=O)(=O)Nc2cc(Cl)c(O)c3ccccc23)c1] | C17H14ClNO4S | 363.8224 | 4.185 |

TABLE 11-continued

| ID NUMBER | Structure | Formula structure | MW | Log P |
|---|---|---|---|---|
| F5749-0327 | 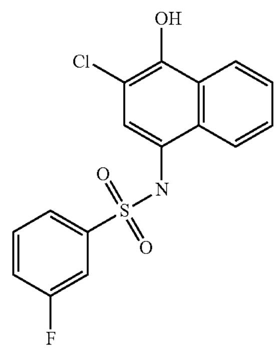 [SMILES: O=S(=O)(Nc1cc(Cl)c(O)c2ccccc12)c1cccc(F)c1] | C16H11ClFNO3S | 351.7864 | 4.382 |
| F5749-0328 | 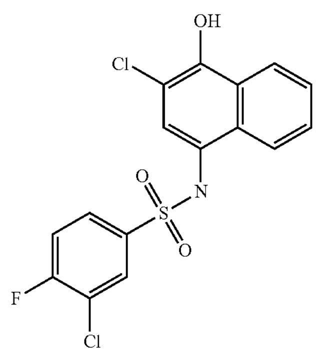 [SMILES: O=S(=O)(Nc1cc(Cl)c(O)c2ccccc12)c1ccc(F)c(Cl)c1] | C16H10Cl2FNO3S | 386.2314 | 4.972 |
| F5749-0329 | 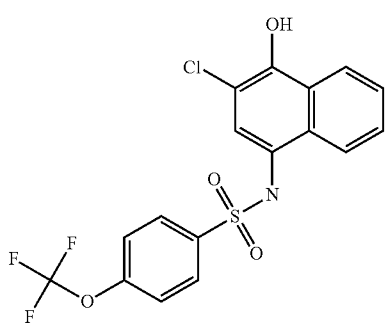 [SMILES: O=S(=O)(Nc1cc(Cl)c(O)c2ccccc12)c1ccc(OC(F)(F)F)cc1] | C17H11ClF3NO4S | 417.7937 | 5.59076 |
| F5749-0330 | 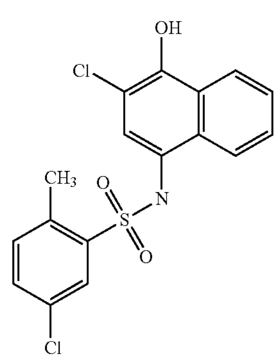 [SMILES: Cc1ccc(Cl)cc1S(=O)(=O)Nc1cc(Cl)c(O)c2ccccc12] | C17H13Cl2NO3S | 382.2681 | 5.117 |

TABLE 11-continued

| ID NUMBER | Structure | Formula structure | MW | Log P |
|---|---|---|---|---|
| F5749-0331 | 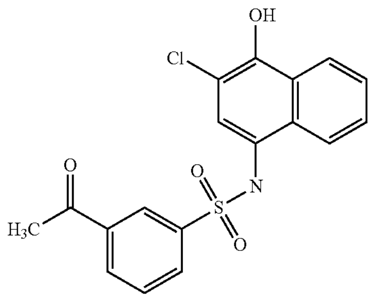 [SMILES: CC(=O)c1cccc(S(=O)(=O)Nc2cc(Cl)c(O)c3ccccc23)c1] | C18H14ClNO4S | 375.8336 | 4.082 |
| F5749-0332 | 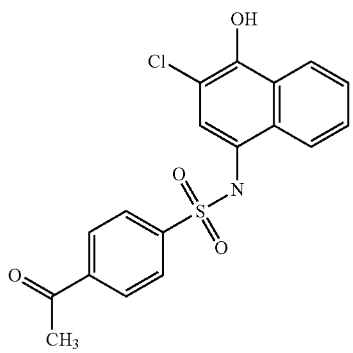 [SMILES: CC(=O)c1ccc(S(=O)(=O)Nc2cc(Cl)c(O)c3ccccc23)cc1] | C18H14ClNO4S | 375.8336 | 4.045 |
| F5749-0333 | 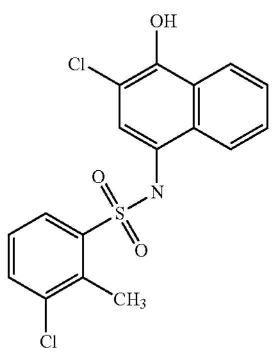 [SMILES: Cc1c(Cl)cccc1S(=O)(=O)Nc1cc(Cl)c(O)c2ccccc12] | C17H13Cl2NO3S | 382.2681 | 5.078 |
| F5749-0334 | 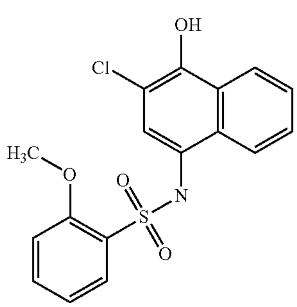 [SMILES: COc1ccccc1S(=O)(=O)Nc1cc(Cl)c(O)c2ccccc12] | C17H14ClNO4S | 363.8224 | 4.146 |
| F5749-0335 | 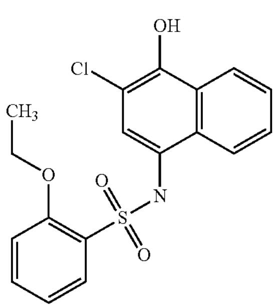 [SMILES: CCOc1ccccc1S(=O)(=O)Nc1cc(Cl)c(O)c2ccccc12] | C18H16ClNO4S | 377.8495 | 4.487 |

TABLE 11-continued
| ID NUMBER | Structure | Formula structure | MW | Log P |
|---|---|---|---|---|
| F5749-0336 | 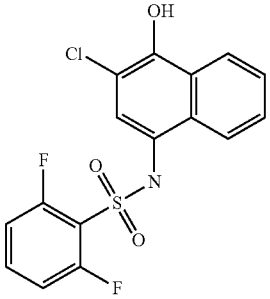 [SMILES: O=S(=O)(Nc1cc(Cl)c(O)c2ccccc12)c1c(F)cccc1F] | C16H10ClF2NO3S | 369.7768 | 4.494 |
| F5749-0337 | 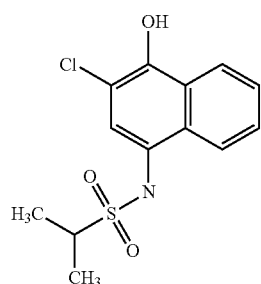 | C13H14ClNO3S | 299.7784 | 3.685 |
| F5749-0338 | 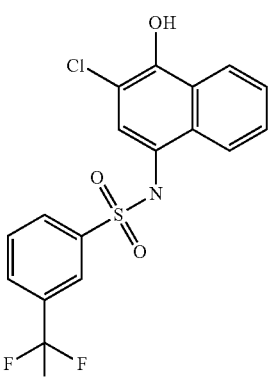 | C17H11ClF3NO3S | 401.7943 | 5.16376 |
| F5749-0339 | 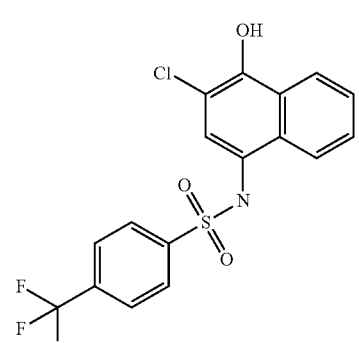 | C17H11ClF3NO3S | 401.7943 | 5.12676 |

TABLE 11-continued

| ID NUMBER | Structure | Formula structure | MW | Log P |
|---|---|---|---|---|
| F5749-0340 | 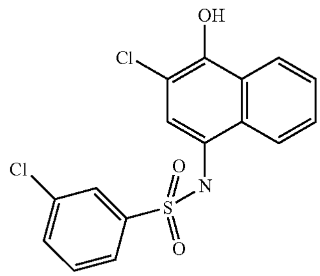 [SMILES: O=S(=O)(Nc1cc(Cl)c(O)c2ccccc12)c1cccc(Cl)c1] | C16H11Cl2NO3S | 368.241 | 4.821 |
| F5749-0341 | 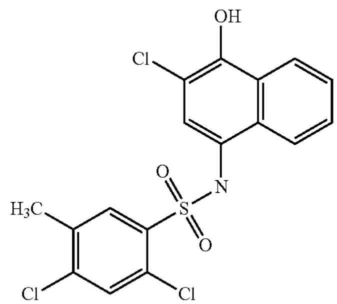 [SMILES: Cc1cc(S(=O)(=O)Nc2cc(Cl)c(O)c3ccccc23)c(Cl)cc1Cl] | C17H12Cl3NO3S | 416.7131 | 5.744 |
| F5749-0342 | 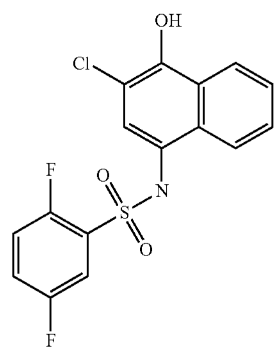 [SMILES: O=S(=O)(Nc1cc(Cl)c(O)c2ccccc12)c1cc(F)ccc1F] | C16H10ClF2NO3S | 369.7768 | 4.533 |
| F5749-0343 | 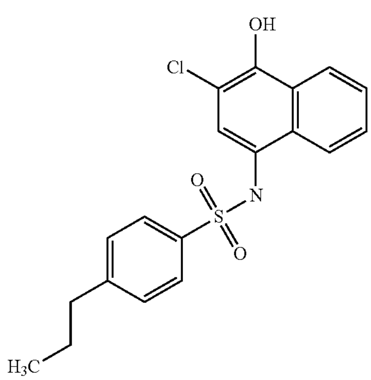 [SMILES: CCCc1ccc(S(=O)(=O)Nc2cc(Cl)c(O)c3ccccc23)cc1] | C19H18ClNO3S | 375.8772 | 5.407 |

TABLE 11-continued

| ID NUMBER | Structure | Formula structure | MW | Log P |
|---|---|---|---|---|
| F5749-0344 | 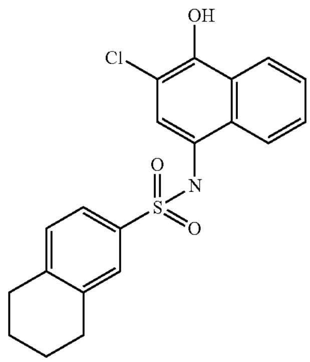 [SMILES: O=S(=O)(Nc1cc(Cl)c(O)c2ccccc12)c1ccc2c(c1)CCCC2] | C20H18ClNO3S | 387.8884 | 5.279 |
| F5749-0345 | 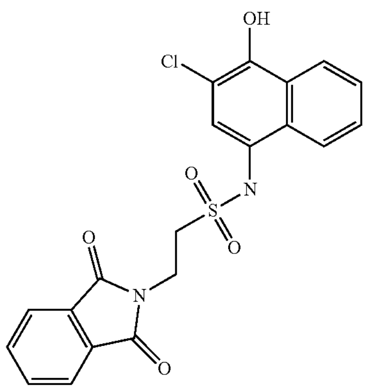 [SMILES: O=C1c2ccccc2C(=O)N1CCS(=O)(=O)Nc1cc(Cl)c(O)c2ccccc12] | C20H15ClN2O5S | 430.87 | 3.319 |
| F5749-0346 | 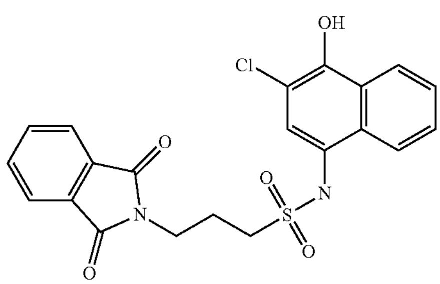 [SMILES: O=C1c2ccccc2C(=O)N1CCCS(=O)(=O)Nc1cc(Cl)c(O)c2ccccc12] | C21H17ClN2O5S | 444.897 | 3.761 |
| F5749-0347 | 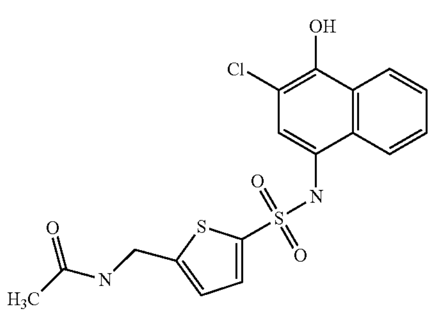 [SMILES: CC(=O)NCc1ccc(S(=O)(=O)Nc2cc(Cl)c(O)c3ccccc23)s1] | C17H15ClN2O4S2 | 410.9011 | 3.495 |

TABLE 11-continued
| ID NUMBER | Structure | Formula structure | MW | Log P |
|---|---|---|---|---|
| F5749-0348 | 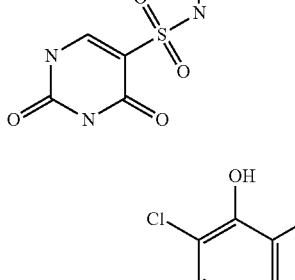 | C14H10ClN3O5S | 367.7699 | 1.237 |
| F5749-0349 | 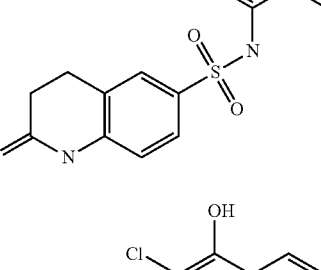 | C19H15ClN2O4S | 402.8594 | 3.388 |
| F5749-0350 | 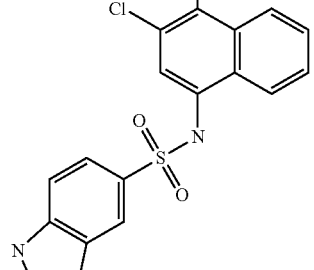 | C18H13ClN2O4S | 388.8323 | 3.3 |
| F5749-0351 | 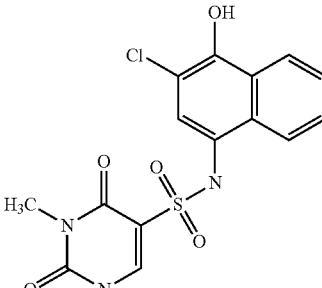 | C16H14ClN3O5S | 395.8241 | 1.301 |

TABLE 11-continued

| ID NUMBER | Structure | Formula structure | MW | Log P |
| --- | --- | --- | --- | --- |
| F5749-0352 | 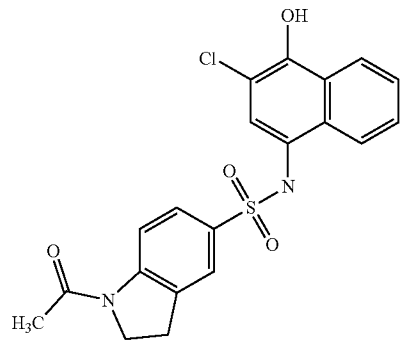 [SMILES: CC(=O)N1CCc2cc(S(=O)(=O)Nc3cc(Cl)c(O)c4ccccc34)ccc21] | C20H17ClN2O4S | 416.8865 | 3.623 |
| F5749-0353 | 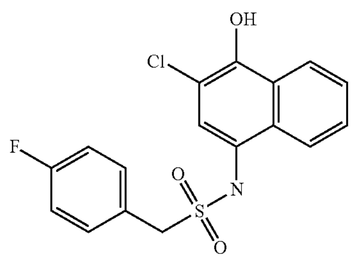 [SMILES: O=S(=O)(Cc1ccc(F)cc1)Nc1cc(Cl)c(O)c2ccccc12] | C17H13ClFNO3S | 365.8135 | 4.479 |
| F5749-0354 | 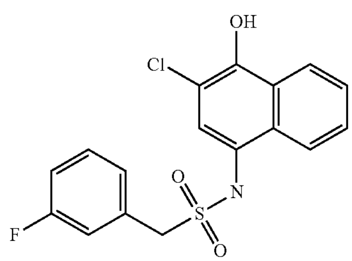 [SMILES: O=S(=O)(Cc1cccc(F)c1)Nc1cc(Cl)c(O)c2ccccc12] | C17H13ClFNO3S | 365.8135 | 4.516 |
| F5749-0355 | 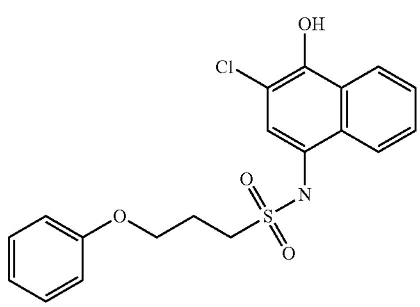 [SMILES: O=S(=O)(CCCOc1ccccc1)Nc1cc(Cl)c(O)c2ccccc12] | C19H18ClNO4S | 391.8766 | 4.552 |
| F5749-0356 | 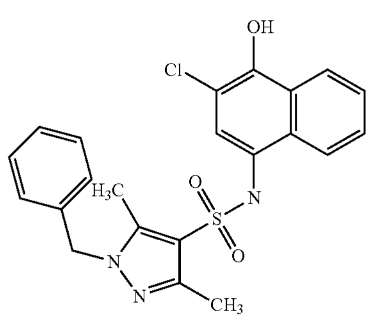 [SMILES: Cc1nn(Cc2ccccc2)c(C)c1S(=O)(=O)Nc1cc(Cl)c(O)c2ccccc12] | C22H20ClN3O3S | 441.94 | 4.471 |

TABLE 11-continued

| ID NUMBER | Structure | Formula structure | MW | Log P |
|---|---|---|---|---|
| F5749-0357 | 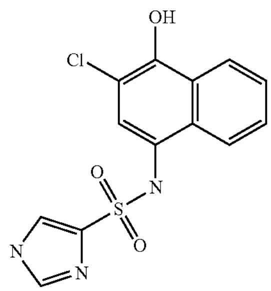 [SMILES: O=S(=O)(Nc1cc(Cl)c(O)c2ccccc12)c1c[nH]cn1] | C13H10ClN3O3S | 323.76 | 2.332 |
| F5749-0358 | 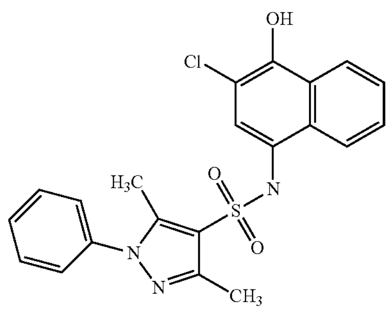 [SMILES: Cc1nn(-c2ccccc2)c(C)c1S(=O)(=O)Nc1cc(Cl)c(O)c2ccccc12] | C21H18ClN3O3S | 427.9129 | 4.337 |
| F5749-0359 | 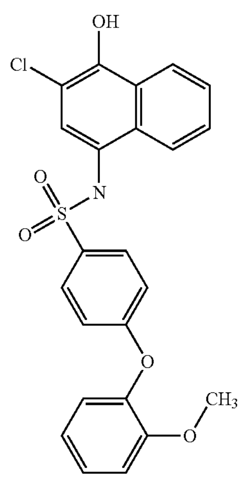 [SMILES: COc1ccccc1Oc1ccc(S(=O)(=O)Nc2cc(Cl)c(O)c3ccccc23)cc1] | C23H18ClNO5S | 455.9206 | 5.50774 |
| F5749-0360 | 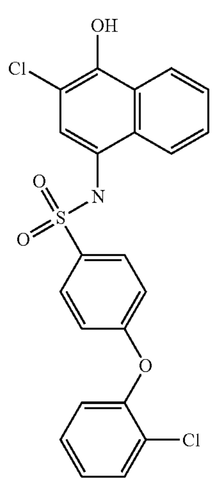 [SMILES: O=S(=O)(Nc1cc(Cl)c(O)c2ccccc12)c1ccc(Oc2ccccc2Cl)cc1] | C22H15Cl2NO4S | 460.3392 | 6.392 |

| ID NUMBER | Structure | Formula structure | MW | Log P |
|---|---|---|---|---|
| F5749-0361 | 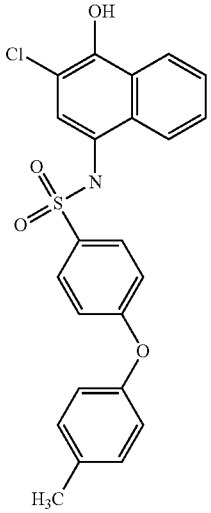 [SMILES: Cc1ccc(Oc2ccc(S(=O)(=O)Nc3cc(Cl)c(O)c4ccccc34)cc2)cc1] | C23H18ClNO4S | 439.9212 | 6.1 |
| F5749-0362 | 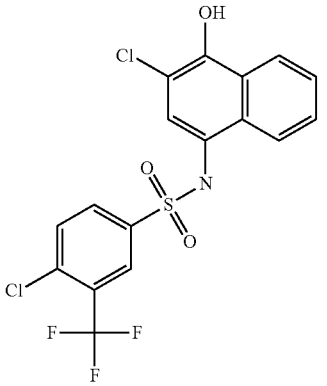 [SMILES: O=S(=O)(Nc1cc(Cl)c(O)c2ccccc12)c1ccc(Cl)c(C(F)(F)F)c1] | C17H10Cl2F3NO3S | 436.2394 | 5.75376 |
| F5749-0363 | 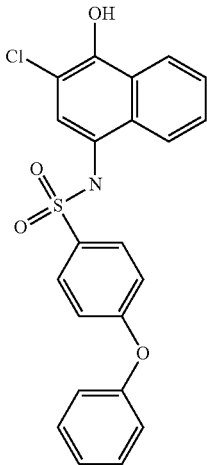 [SMILES: O=S(=O)(Nc1cc(Cl)c(O)c2ccccc12)c1ccc(Oc2ccccc2)cc1] | C22H16ClNO4S | 425.8941 | 5.802 |

TABLE 11-continued
| ID NUMBER | Structure | Formula structure | MW | Log P |
|---|---|---|---|---|
| F5749-0364 | 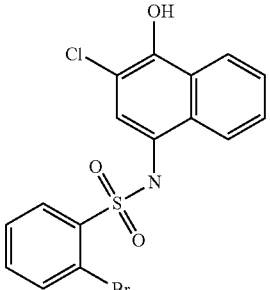 | C16H11BrClNO3S | 412.692 | 4.988 |
| F5749-0365 | 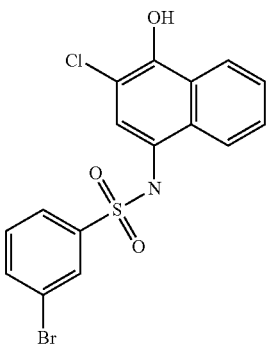 [SMILES: O=S(=O)(Nc1cc(Cl)c(O)c2ccccc12)c1cccc(Br)c1] | C16H11BrClNO3S | 412.692 | 5.027 |
| F5749-0366 | 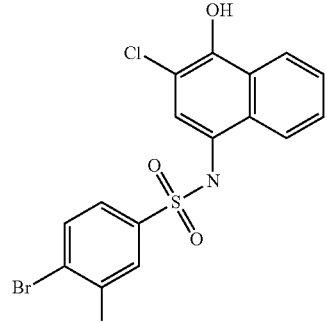 | C16H10BrClFNO3S | 430.6824 | 5.178 |
| F5749-0367 | 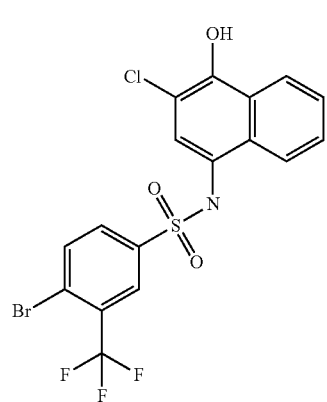 [SMILES: O=S(=O)(Nc1cc(Cl)c(O)c2ccccc12)c1ccc(Br)c(C(F)(F)F)c1] | C17H10BrClF3NO3S | 480.6904 | 5.95976 |

TABLE 11-continued

| ID NUMBER | Structure | Formula structure | MW | Log P |
|---|---|---|---|---|
| F5749-0368 | 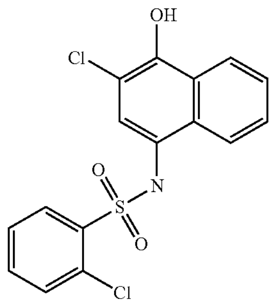 [SMILES: O=S(=O)(Nc1cc(Cl)c(O)c2ccccc12)c1ccccc1Cl] | C16H11Cl2NO3S | 368.241 | 4.782 |
| F5749-0369 | 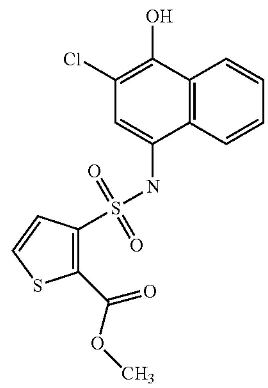 [SMILES: COC(=O)c1sccc1S(=O)(=O)Nc1cc(Cl)c(O)c2ccccc12] | C16H12ClNO5S2 | 397.8587 | 3.392 |
| F5749-0370 | 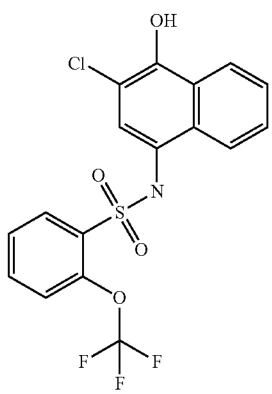 [SMILES: O=S(=O)(Nc1cc(Cl)c(O)c2ccccc12)c1ccccc1OC(F)(F)F] | C17H11ClF3NO4S | 417.7937 | 5.58876 |

Example 11

Stat3 Activation Initiates a C/EBPδ to Myostatin Pathway that Stimulates Loss of Muscle Mass As addressed herein, catabolic conditions like chronic kidney disease (CKD) cause loss of muscle mass by unclear mechanisms. In muscle biopsies from CKD patients, activated Stat3 (p-Stat3) was found and it was considered that p-Stat3 initiates muscle wasting. Mice were generated with muscle-specific knockout (KO) that prevents activation of Stat3. In these mice, losses of body and muscle weights were suppressed in models of CKD or acute diabetes. A small molecule that inhibits Stat3 activation, produced similar responses suggesting a potential for translation strategies. Using C/EBPδ KO mice and C2Cl2 myotubes with knockdown of C/EBPδ or myostatin, it was determined that p-Stat3 initiates muscle wasting via C/EBPδ, stimulating myostatin, a negative muscle growth regulator. C/EBPδ KO also improved survival of CKD mice. It was verified that p-Stat3, C/EBPδ and myostatin were increased in muscles of CKD patients. The pathway from p-Stat3 to C/EBPδ to myostatin and muscle wasting provides a route for therapeutic targets that prevent muscle wasting.

Muscle Biopsies of Patients with CKD Reveal Inflammation and Stat3 Activation

To address the mechanisms underlying muscle wasting, 18 CKD patients scheduled for peritoneal dialysis catheter insertion and a control group of 16 age- and gender-matched healthy subjects were studied. All subjects led a sedentary lifestyle. In the 18 CKD patients, the BUN and serum creatinine were increased 4- and ~8-fold respectively over control subjects (Table 12).

TABLE 12

Clinical characteristics of patients with chronic kidney disease (CKD) and controls

|  | Controls | CKD patients | p-value |
|---|---|---|---|
| Number of subjects | 16 | 18 |  |
| Age (years) | 63 (46-77) | 67 (36-79) | 0.15 |
| Diabetes | 0/16 | 4/18 |  |
| Hypertension | 0/16 | 17/18 |  |
| Atherosclerosis | 0/16 | 14/18 |  |
| Gender (M:F) | 13:3 | 11:7 |  |
| BMI (kg/m$^2$) | 25.4 ± 0.5 | 27.4 ± 1.2 | 0.07 |
| BUN (mg/dl) | 20.6 ± 1.3 | 89.8 ± 4.6 | <0.05 |
| SCr (mg/dL) | 0.96 ± 0.04 | 7.6 ± 1.8 | <0.05 |
| eGFR (ml/min/1.73 m2) | 76.7 ± 3.7 | 9.1 ± 0.8 | <0.05 |
| CSA 0.1 m2) | 1873 (1100-3389) | 1003 (717-1601) | <0.003 |
| CRP (mg/dl) | 3.21 ± 0.22 | 10.46 ± 2.98 | <0.05 |
| Fibrinogen (mg/dl) | 291.7 ± 31.7 | 579 ± 37.5 | <0.005 |

All CKD patients experienced unintentional weight loss in the 3 months before muscle biopsies were obtained. In CKD patients, the mean estimated protein and calorie intakes were 0.9 g/Kg and 28 Kcal/Kg respectively, compared to ~1 g/Kg and 30-32 Kcal/Kg respectively, in control healthy subjects (from diet diaries). Even though these intakes of protein and calorie exceed the recommended daily allowance (RDA), 13 of the 18 patients were malnourished signified by a the subjective global assessment level of >2, and serum albumin was low in 11 patients (<3.8 g/100 ml) (Fouque et al., 2008). Even though the body mass index was low (<23 Kg/m$^2$) in only 4 subjects, all patients had evidence of protein losses: there was a marked reduction in muscle-fiber cross-sectional area (CSA) (CKD patients median=1003 µm$^2$, range 717-1601; controls median=1873 µm$^2$, range 1100-3389; p<0.003 Mann-Whitney). The fat free mass (FFM) from skin fold thickness (Avesani et al., 2004) was calculated. Over 3 months, the FFM in CKD patients declined from 45.9±2 to 44.1±2 kg (p<0.05). Regarding drugs that might influence muscle metabolism, no patient was receiving steroids but 14 patients were treated with statins; these patients did not have signs of myopathy. Characteristics of the CKD patients and control subjects are shown in Table 12. All patients were treated with diuretic (furosemide) at different dosages, lisinopril or doxazosin (17 patients), proton pump inhibitors (14 patients), platelet aggregation inhibitors (14 patients), insulin therapy (4 patients), oral anticoagulant therapy (1 patient) and erythropoietin (10 patients). Diabetes was well controlled with hemoglobin A1c values <6.5% and fasting plasma glucose levels <110 mg/dL. There were increased levels of inflammatory markers in CKD patients, including circulating C-reactive protein (control; 3.21±0.22 vs. CKD; 10.46±2.98 mg/dL; p<0.05) and fibrinogen (control; 291±31.7 vs. CKD; 579±37.5 mg/dL; p<0.005) (Table 12). There also were increased levels of IL-6 and TNFα in muscle biopsies compared to results from control subjects (FIG. 19A). Finally, TNFα mRNA was increased (FIG. 26) and as noted previously, so was IL-6 mRNA (Verzola et al., 2011).

Activated Stat3 protein was significantly increased in muscles of CKD patients vs. healthy subjects (FIG. 19B). p-Stat3 was principally located in nuclei of biopsies as ~40% of nuclei in muscle biopsies of CKD patients were positive for p-Stat3 vs. ~20% in healthy subjects (FIG. 19C). Thus, significant increases in the expressions of inflammatory cytokines, IL-6 and TNFα, were associated with Stat3 activation in muscles of CKD patients who expressed evidence of muscle wasting.

Muscle-Specific Stat3 KO Suppresses Loss of Muscle Despite CKD or Type 1 Diabetes In gastrocnemius muscles of mice with CKD, the level of p-Stat3 was increased compared to results in muscles of pair-fed, sham-operated, control mice (FIG. 20A). To explore if the activation of Stat3 triggers muscle wasting in vivo, mice with muscle-specific deletion of the Stat3 tyrosine phosphorylation site (Stat3 KO) were studied, compared to results in control, Stat3$^{flox/flox}$ mice (Takeda et al., 1998). Mice with muscle-specific Stat3 KO did not differ from control mice in terms of development, food intake and body weight (FIG. 27). But with CKD, body weights of Stat3 KO mice increased vs. results in pair-fed Stat3$^{flox/flox}$ mice with CKD (FIG. 20B). The gain in weight was due in part to increased muscle mass: after 5 weeks of CKD, the weights of gastrocnemius and tibialis anterior muscles were significantly greater than muscles from Stat3$^{flox/flox}$ mice (FIGS. 20C, D). To determine why loss of muscle mass was blunted in Stat3 KO mice with CKD, rates of muscle protein synthesis and degradation were measured and there was a significant improvement in both indices of protein metabolism in Stat3 KO mice with CKD (FIGS. 20E, F). Likewise, there was an increase in grip strength of Stat3 KO mice vs. Stat3$^{flox/flox}$ mice (FIG. 20G).

Muscle atrophy in several catabolic conditions is characterized as an increase in circulating inflammatory cytokines, impaired insulin/IGF-1 signaling and an increase in muscle protein degradation via the ubiquitin-proteasome system (UPS) (Zhang et al., 2011; Lecker et al., 2004). To determine if results present in mice with CKD occur in another model of muscle wasting, streptozotocin-treated, acutely diabetic mice (Price et al., 1996) were studied. There was an increase in p-Stat3 plus high circulating and muscle levels of IL-6 in acutely diabetic mice (FIG. 20H, FIG. 28). IL-6 mRNA in muscles of STZ-treated mice was increased 2-fold over control mice. Stat3 KO mice expressed a slower decrease in body weight vs. results in acutely diabetic, Stat3$^{flox/flox}$ mice (FIG. 29). The slower loss of body weight in acutely diabetic Stat3 KO mice was associated with a greater mass of gastrocnemius and tibialis anterior muscles vs. results in Stat3$^{flox/flox}$ mice (FIGS. 20, J). In the absence of CKD- or diabetes-induced catabolism, muscle-specific Stat3 KO did not significantly affect body weight, muscle mass, protein metabolism or grip strength compared to results in Stat3$^{flox/flox}$ mice (FIGS. 20A-20J). Thus, p-Stat3 can trigger muscle wasting in certain catabolic conditions.

Inhibition of Stat3 Activation Blocks CKD-Induced Muscle Wasting

Figure 21G:
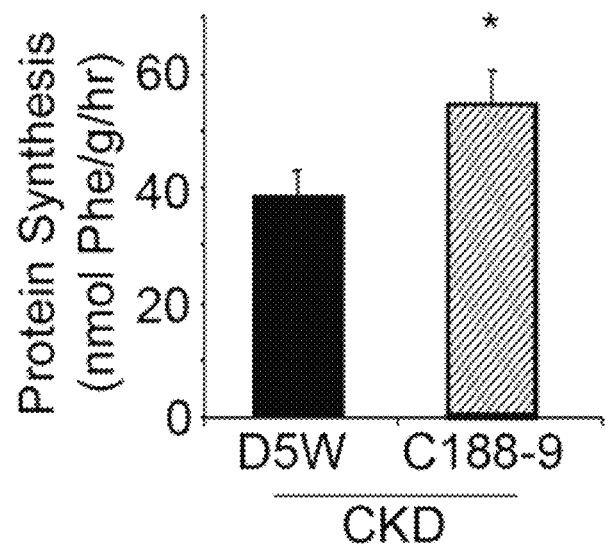
Figure 21H:
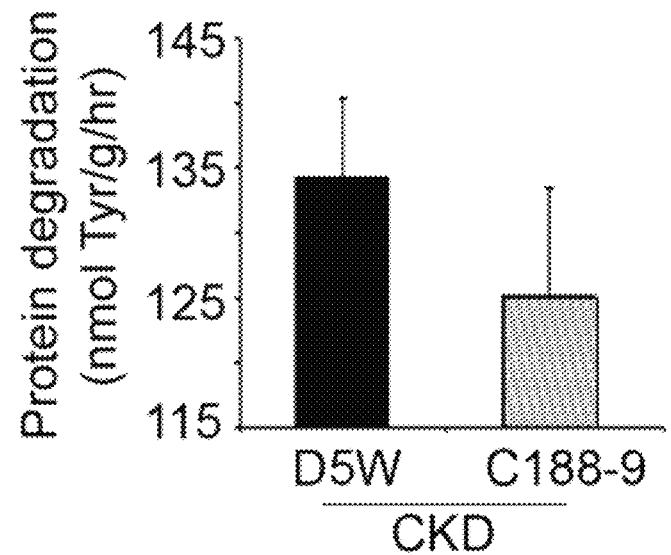

To determine if a translational strategy might be developed to interfere with muscle wasting when Stat3 is activated, C188-9, a small molecule inhibitor of Stat3 phosphorylation, was evaluated. C188-9 has a potency in the low micromolar range and can be administered for prolonged periods (Xu et al., 2009; Redell et al., 2011). After 2 weeks of CKD, mice were paired for their BUN and body weights and injected with either C188-9 or the diluent, 5% dextrose in water (D5W). C188-9 treatment decreased the level of p-Stat3 in muscle without affecting the Stat3 level (FIG. 21A). Consistent with results from Stat3 KO mice with CKD, the body weights of CKD mice treated with the Stat3 inhibitor were significantly greater than weights of the control, CKD mice (FIG. 21B). After 14 days of C188-9, it was found that the increase in body weight included more muscle as the weights of gastrocnemius and tibialis anterior muscles were greater (FIGS. 21C, 21D). The increase in muscle mass was confirmed by an analysis of the size distribution of myofibers in muscles of CKD mice treated with C188-9 (FIG. 21E). This improvement in muscle mass was accompanied by improved grip strength in CKD mice treated with C188-9 (FIG. 21F). Consistent with results from the Stat3 KO mice, blocking Stat3 with C188-9 in control, wild type mice did not significantly affect their food intake, body weight, muscle mass or grip strength (FIGS. 21B-D, F). The mechanism underlying the C188-9-induced increase in muscle weight included improved muscle protein synthesis and decreased protein degradation (FIGS. 21G, H). Inhibiting Stat3 activation suppresses CKD-induced loss of both muscle mass and strength.

In C2C12 Myotubes, Stat3 Activation Increases the Expression of C/EBPδ and Myostatin The signaling pathway from activated Stat3 to muscle wasting was evaluated. Myostatin was studied because its expression is increased in muscles of CKD mice and myostatin inhibition overcomes the decrease in protein synthesis and the increase in protein degradation stimulated by CKD (Zhang et al., 2011). To determine how CKD leads to myostatin expression, C/EBPδ was evaluated because the myostatin promoter has several C/EBP recognition sites (Ma et al., 2001) and Stat3 can regulate C/EBPδ at least in epithelial cells (Zhang et al., 2007). First, C2C12 myotubes were treated with IL-6 to activate Stat3. After 3 h, there was an increase in the C/EBPδ protein in myotubes responding to activated Stat3. After 24 h, myostatin protein was increased and changes in mRNAs were consistent with the western blotting results (FIG. 22A, FIG. 30, 31). These results show that p-Stat3, C/EBPδ and myostatin were activated sequentially.

Next, C2C12 myotubes were infected with a lentivirus which expresses a constitutively active Stat3-GFP (Stat3C-GFP). The higher level of p-Stat3 expression resulted in an increase in C/EBPδ and myostatin plus a decrease in p-Akt and myosin heavy chain (MHC) vs. results from myotubes expressing GFP alone (FIG. 22B). Other evidence that Stat3 activation stimulates myostatin expression was uncovered when the inhibitor of Stat3 (C188-9) was used to block p-Stat3 in C2C12 myotubes. After 24 h of exposure to IL-6, there was an increase in p-Stat3, C/EBPδ and myostatin and C188-9 blocked these responses. The inhibitor also increased p-Akt (FIG. 22C) and suppressed C/EBPδ and myostatin mRNAs in IL-6-treated C2C12 myotubes (FIG. 32). Notably, C188-9 not only suppressed p-Stat3 but also prevented the decrease in myotubes size induced by exposure to IL-6 (FIG. 33).

To assess whether Stat3 affects C/EBPδ expression, C2C12 myoblasts were co-transfected with a plasmid expressing a C/EBPδ promoter-driven luciferase plus a lentivirus expressing the constitutively active Stat3C-GFP. Overexpression of Stat3C increased C/EBPδ promoter activity compared to that in lentivirus expressing GFP control; addition of IL-6 stimulated C/EBPδ promoter activity in myoblasts (FIG. 22D).

To identify whether p-Stat3 acts through C/EBPδ to stimulate myostatin, C/EBPδ was knocked down using siRNA. In this case, the IL-6-induced increase in myostatin expression was blocked when C/EBPδ was suppressed even though p-Stat3 was increased (FIG. 22E). Next, C2C12 myoblasts were co-transfected with a plasmid expressing myostatin promoter driven luciferase plus one of the following: 1) a plasmid expressing Stat3C; 2) a plasmid expressing C/EBPδ; 3) C/EBPδ siRNA oligonucleotide; or 4) a plasmid expressing Stat3C and the C/EBPδ siRNA. Constitutively active Stat3C moderately increased myostatin promoter activity while transfection with C/EBPδ alone significantly increased myostatin promoter activity. Knockdown of C/EBPδ blocked myostatin promoter activity that was stimulated by IL6 or Stat3C (FIG. 22F).

C2C12 myoblasts were also transfected with a lentivirus that expresses myostatin siRNA; it decreased myostatin expression and reduced protein degradation even in cells expressing Stat3C or C/EBPδ (FIG. 22G, FIG. 34). Thus, the Stat3 to C/EBPδ to myostatin pathway provides a mechanism causing loss of muscle mass.

CKD-Induced Muscle Wasting In Vivo is Mediated by a Pathway from p-Stat3 to C/EBPδ to Myostatin In muscles of CKD or acutely diabetic mice, there were increases in the expression of p-Stat3, C/EBPδ and myostatin (FIG. 23A, D). The C/EBPδ and myostatin proteins in muscles of Stat3 KO mice with CKD were significantly below responses in muscles of Stat3$^{flox/flox}$ mice with CKD. p-Smad2/3, the down stream signal of myostatin, expression was also increased in muscles of CKD mice consistent with reports that p-Smad2/3 mediates myostatin-induced muscle atrophy (Trendelenburg et al., 2009). The increase in p-Smad2/3 in muscle of mice with CKD was sharply decreased in muscles of Stat3 KO mice with CKD. This suggests that in CKD, Stat3 activation results in myostatin expression and activation of its downstream signaling pathway (FIG. 23A). Similar results were found when C/EBPδ and myostatin mRNAs were examined in muscles of the Stat3 KO mice with CKD; levels in Stat3 KO mice with CKD were below those of control, Stat3$^{flox/flox}$ mice with CKD (FIG. 23B, C). Activated Stat3 in muscles of CKD mice was not completely blocked by muscle-specific KO of Stat3 when compared to p-Stat3 in muscles of non-CKD mice. Possibly, the remaining p-Stat3 in muscle lysates of Stat3 KO mice could reflect p-Stat3 in blood cells, blood vessels or the interstitium since the results were obtained from western blots of gastrocnemius muscle lysates.

When mice were treated with CKD using the inhibitor of Stat3, both C/EBPδ and myostatin proteins were decreased and the CKD-induced phosphorylation of p-Smad2/3 was blocked. In this case, the Akt phosphorylation was higher (FIG. 23E). Notably, C188-9 suppressed the CKD-stimulated mRNA expressions of C/EBPδ and myostatin (FIG. 23F, G). In control mice without CKD, muscle-specific Stat3 KO or C188-9 treatment did not change either C/EBPδ or myostatin mRNAs or proteins in muscle.

To demonstrate a link from Stat3 to C/EBPδ to myostatin in vivo, C/EBPδ deficient mice were studied that have normal embryonic development, are fertile and do not display overt developmental or physiological defects (Sterneck et al., 1998). CKD was created in heterozygous and homozygous C/EBPδ KO and wild type mice and fed the different groups the same amount of chow as eaten by wild type mice with CKD. In homozygous C/EBPδ KO mice with CKD, the loss of body and muscle weights were prevented. There also was improved survival in pair fed, homozygous C/EBPδ KO mice with CKD (FIGS. 24A-C). Despite the increase in p-Stat3 in muscles of homo- and heterozygous C/EBPδ KO or wild type mice with CKD, there was no increase in expression of myostatin in mice with homozygous C/EBPδ KO (FIG. 24D). The degree of survival and myostatin expression in muscles of heterozygous C/EBPδ KO mice were intermediate between homozygous KO and wild type mice.

To examine whether Stat3-induced muscle wasting in vivo is mediated by myostatin, a lentivirus expressing constitutively active Stat3-GFP (Stat3C-GFP) was injected into the right hindlimb of newborn mice. The injection was repeated 2 weeks later. At the same time, lentivirus expressing GFP was injected into the left hindlimb (Control). Two weeks later, one group of mice was injected with anti-myostatin peptibody for two weeks; the other group was injected with PBS. Overexpression of Stat3C induced a significant reduction in myofiber sizes compared to results in the contralateral hindlimb treated with the GFP. Notably, myostatin inhibition eliminated these responses. Next, muscle cross sections were immunostained with p-Smad2/3 and it was found that there was high levels p-Smad2/3 in myofibers overexpressing Stat3C-GFP. Similar to results in CKD mice with muscle-specific Stat3 KO or following treatment with the Stat3 inhibitor, the increase in p-Smad2/3 was blocked by the anti-myostatin peptibody (FIGS. 24E, F, FIG. 35), consistent with a catabolic pathway from p-Stat3 to C/EBPδ to myostatin-induced muscle protein loss.

In CKD Patients, there is Evidence for the p-Stat3, C/EBPδ to Myostatin Pathway in Muscle Muscle biopsies from patients with advanced CKD had significantly decreased sizes of myofibers and levels of p-Akt (Table 12, FIG. 25A). There was, however, increased mRNA and protein levels of p-Stat3, C/EBPδ and myostatin in muscles of CKD patients (FIGS. 25B-D).

Many catabolic conditions including CKD, diabetes, cancer and serious infections are complicated by progressive muscle wasting which decreases the quality of life and raises the risk of morbidity and mortality. The complications of CKD (excess angiotensin II, glucocorticoids, acidosis and impaired insulin/IGF-1 signaling) stimulate protein degradation and loss of muscle mass. CKD also increases inflammatory markers including IL-6, TNF-α and CRP et al which can activate p-Stat3 (Zhang et al., 2009; May et al., 1987; Hu et al., 2009; Zhang et al., 2011). Still, the molecular mechanisms causing muscle loss are poorly understood which hampers the development of drug or other treatment strategies. In the present studies, it is identified that activated Stat3 triggers a pathway from p-Stat3 to myostatin which causes the progressive muscle wasting that is induced by CKD or acute diabetes.

Evidence for the p-Stat3-dependent pathway that initiates loss of muscle mass was obtained in five experimental models: cultured C2Cl2 myotubes; muscle-specific p-Stat3 KO mice; mice treated with a small molecule that inhibits Stat3 activation; C/EBPδ KO mice; and muscle biopsies of patients with CKD. The results show that CKD activates Stat3 leading to increased expression of C/EBPδ and transcriptional regulation of myostatin expression. When this pathway is activated, there is a decrease in p-Akt which is shown will activate caspase-3 and the ubiquitin-proteasome system (UPS) to degrade muscle protein (Zhang et al., 2011; Du et al., 2004; Wang et al., 2010). The results demonstrate that: 1) CKD or acute diabetes activates Stat3 in muscle causing loss of muscle mass; 2) targeted knockout of Stat3 in muscle or pharmacologic inhibition of Stat3 suppresses the muscle wasting that is induced by CKD or acute diabetes. This leads to an increase in muscle protein synthesis and a decrease in protein degradation with improvement in muscle mass and grip strength; 3) C/EBPδ is a mediator of the pathway from p-Stat3 to myostatin because its KO inhibits myostatin expression and suppresses muscle wasting. In addition, C/EBPδ KO was associated with an improvement in survival. In muscle biopsies of patients with CKD, there are similar changes in the levels of the same mediators suggesting the results could form the basis for developing translation strategies to suppress muscle wasting in CKD.

Presently, there are no clinically available drugs that directly target Stat3. Small molecule, drug development programs are initiated that target either the Stat3 homodimer interface or the Stat3 SH2 domain; the latter is required for Stat3 binding to phosphotyrosylpeptide ligands located within activated receptor complexes and within the Stat3 homodimer itself. Three candidate compounds (C3, C30 and C188) were identified; some identified single compounds including static (Schust et al., 2006), STA-21 (Song et al., 2005), S31-201 (Siddiquee et al., 2007) or LLL12 (Lin et al., 2010). Regarding LLL12, the evidence for direct inhibition of Stat3 vs. an upstream kinase was not presented. In contrast, C188-9, does not inhibit upstream JAK or Src kinases (Redell et al., 2011). Regarding potency, neither the parent compounds identified by others nor derivatives of them are as potent as C188-9 (Bhasin et al., 2008; Zhang et al., 2010). In addition, compounds identified by others that have been tested in mice are not as well tolerated as C188-9 (Lin et al., 2009; Zhang et al., 2010); those compounds have a maximum tolerated dose of 5 mg/kg every 2 or 3 days compared to 100 mg/kg/day over 14 days for C188-9 (Tweardy et al, unpublished data). Thus, C188-9 has promise as a lead for development into a drug that could be administered safely to patients.

How does C188-9 influence muscle protein wasting? One possibility is that injection of IL-6 into rodents activates Stat3 and stimulates muscle proteolysis (Goodman, 1994). Indeed, there was increased IL-6 in muscles of CKD patients and in STZ-induced acute diabetes in mice. The latter is consistent with reports from type 1 diabetic patients (Mysliwiec et al., 2006; Mysliwiec et al., 2008; Shelbaya et al., 2012). The potential origin of IL-6 in type 1 diabetes includes peripheral blood mononuclear cells and/or Th17 T cells (Bradshaw et al., 2009; Foss-Freitas et al., 2006; Ryba-Stanislawowska et al., 2013). However, others find that IL-6 does not stimulate muscle loss in the absence of another illness such as cancer (Baltgalvis et al., 2008). Thus, it is unclear how cytokines cause muscle proteolysis. In specific embodiments, the increase in IL-6 stimulated by CKD (Kimmel et al., 1998) and possibly other cytokines, activates p-Stat3 which triggers muscle wasting. Indeed, when Stat3 was deleted from muscle or when the Stat3 inhibitor was studied, C188-9, CKD-induced muscle wasting was inhibited. How could p-Stat3 stimulate muscle wasting? p-Stat3 upregulates C/EBPδ and increases the transcription of myostatin, a potent negative regulator of muscle mass. Others have implicated C/EBPδ in the pathogenesis of catabolic disorders. For example, based on microarray analyses, there was upregulation of multiple genes including C/EBPδ in muscles of mice with cancer cachexia or in muscle biopsies of hemodialysis patients (Bonetto et al., 2011; Gutierrez et al., 2008). In addition, there are reports that p-Stat3 stimulates C/EBPδ expression in cancer, immune or liver cells. This is relevant because the C/EBPδ promoter contains a Stat3 binding site making it a likely participant in the pathway (Zhang et al., 2007; Sanford and DeWille, 2005). Indeed, exposure of C2Cl2 myotubes to IL-6 stimulates p-Stat3 and sequentially increases the expression of C/EBPδ. Likewise, expression of constitutively active Stat3 in myotubes increased the C/EBPδ promoter activity and the expression of the C/EBPδ protein. Contrariwise, Stat3 inhibition in C2Cl2 myotubes or in CKD mice suppressed the expression of C/EBPδ. A likely target of C/EBPδ is myostatin. For example, when the siRNA to C/EBPδ was expressed in myotubes, the increase in myostatin stimulated by IL-6 was blocked. In addition, C/EBPδ KO in mice with CKD prevented their loss of muscle mass and expression of myostatin. Conclusions from these results are consistent with reports that myostatin is expressed in a wide variety of catabolic conditions associated with muscle wasting, including cancer, CKD, diabetes or weightlessness (spaceflight) (Zhou et al., 2010; Zhang et al., 2011; Feldman et al., 2006; Lalani et al., 2000). In mice with CKD, the activation of Stat3 leads to expression of myostatin and its downstream signals, p-Smad2/3, plus accelerated protein degradation. Overexpression of Stat3C in muscle of mice causes decreased myofiber sizes and knocking down myostatin resolves the phenotype of Stat3 activation: myofiber sizes are increased and p-Smad2/3 levels are reduced. Moreover, inhibition of myostatin suppresses the muscle wasting caused by CKD (Zhang et al., 2011). Finally, Zhou et al., reported that a soluble, actRIIB receptor inhibited myostatin and the UPS, blocking losses of muscle mass in several models of cancer (Zhou et al., 2010).

The mechanism by which an increase in myostatin leads to loss of muscle mass could be a decrease in p-Akt in muscle. A decrease in p-Akt activates caspase-3 leading to cleavage of the complex structure of muscle proteins and activation of proteolysis by the 26S proteasome (Du et al., 2004; Wang et al., 2010). In addition, a low p-Akt level would reduce phosphorylation of forkhead transcription factors which stimulate the expression of the muscle-specific E3 ubiquitin ligases, Atrogin-1/MAFbx or MuRF-1 and accelerate proteolysis in the UPS (Sandri et al., 2004; Lee et al., 2004; Stitt et al., 2004; Lecker et al., 2006). In the present experiments, inhibition of p-Stat3 with C188-9 decreased myostatin expression and the activation of its downstream signaling mediators, p-Smad2/3; there also was an increase in p-Akt. In muscle of CKD patients, as well, there was a sharp decrease in p-Akt with increased mRNA and protein expressions of C/EBPδ and myostatin.

In summary, the results have uncovered a new pathway that stimulates muscle wasting in response to activation of Stat3. The pathway is activated by CKD or acute diabetes and provides new insights into the relationships among the signaling molecules, Stat3, C/EBPδ, and myostatin. Results from studies of cultured skeletal muscle cells or mice are consistent with changes in the levels of the same signaling molecules in muscle biopsies of CKD patients. Consequently, these results are translatable into treatment strategies for catabolic conditions like CKD that causes muscle wasting. Development of a safe and potent small molecule Stat3 inhibitor is a useful therapeutic approach to muscle wasting in catabolic conditions.

Experimental Procedures

Mouse Models

All animal experiments and procedures were approved by the Baylor College of Medicine Institutional Animal Care and Use Committee (IACUC). Subtotal nephrectomy was used to create CKD in mice (Zhang et al., 2011; May et al., 1987). To induce diabetes, 12-week-old Stat3$^{flox/flox}$ and Stat3 KO mice were injected intraperitoneally with 2 doses of 150 mg/kg/d STZ (Sigma-Aldrich) in 0.1 M citrate buffer (pH 4). Control mice were injected with the citrate buffer. Mice were housed in individual cages and the diabetic Stat3$^{flox/flox}$ mice were pair-fed with diabetic Stat3 KO mice for 9 days.

Muscle Biopsies

During placement of a peritoneal dialysis catheter in CKD patients, the rectus abdominis muscle was biopsied, frozen at −80° C. and stored until analyzed. Biopsy of this muscle was obtained from healthy subjects during abdominal hernia surgeries. The procedures were approved by the Ethical Committee of the Department of Internal Medicine of the University, Genoa, Italy, in accordance with the Helsinki declaration regarding ethics of human research.

mRNA Analyses mRNAs were analyzed by RT-PCR as described (Takeda et al., 1998). Primers are listed in Table 13. Relative mRNA levels were calculated from cycle threshold (Ct) values using GAPDH as the internal control [relative expression=$2^{(sample\ Ct-GAPDH\ Ct)}$].

TABLE 13

Exemplary primer sequences for RT-PCR

| Gene | Accession | forward primers (5'-3') | reverse primer (5'-3') |
| --- | --- | --- | --- |
| C/EBP δ | NM_005195 | TCTACATCTTACTCCTGTTGAT (SEQ ID NO: 1) | CAAATGCTGCTTTATTCTTACAA (SEQ ID NO: 2) |
| Myostatin | NM_005259 | CAACCTGAATCCAACTTA (SEQ ID NO: 3) | TGTTACCTTGACCTCTAA (SEQ ID NO: 4) |
| SOCS3 | NM_003955 | TTACAATCTGCCTCAATC (SEQ ID NO: 5) | ATCTCCTAATAGCCTCAA (SEQ ID NO: 6) |
| GAPDH | NM_002046 | CTCTGGTAAAGTGGATATTGT (SEQ ID NO: 7) | GGTGGAATCATATTGGAACA (SEQ ID NO: 8) |
| TNF-a | NM_000594 | CAACCTCTTCTGGCTCAA (SEQ ID NO: 9) | TGGTGGTCTTGTTGCTTA (SEQ ID NO: 10) |
| C/EBP δ | NM_007679 | CTCCAGGGTCTAAATACATAGC (SEQ ID NO: 11) | CTCACAGCAGTCCACAAG (SEQ ID NO: 12) |
| SOCS3 | NM_007707 | CACAGCAAGTTTCCCGCCGCC (SEQ ID NO: 13) | GTGCACCAGCTTGAGTACACA (SEQ ID NO: 14) |
| Myostatin | NM_010834 | CTCCAGAATAGAAGCCATA (SEQ ID NO: 15) | GCAGAAGTTGTCTTATAGC (SEQ ID NO: 16) |

TABLE 13-continued

Exemplary primer sequences for RT-PCR

| Gene | Accession | forward primers (5'-3') | reverse primer (5'-3') |
|---|---|---|---|
| Atrogin-1 | AF441120 | GAGGCAGATTCGCAAGCGTTTGAT (SEQ ID NO: 17) | TCCAGGAGAGAATGTGGCAGTGTT (SEQ ID NO: 18) |
| MuRF-1 | NM_001039048.2 | AGTGTCCATGTCTGGAGGTCGTTT (SEQ ID NO: 19) | ACTGGAGCACTCCTGCTTGTAGAT (SEQ ID NO: 20) |
| GAPDH | NM008084 | ACCACCATGGAGAAGGCCGG (SEQ ID NO: 21) | CTCAGTGTAGCCCAAGATGC (SEQ ID NO: 22) |

Muscle Force Measurement

Mouse grip strength was measured daily for 4 consecutive days using a Grip Strength Meter (Columbus Instrument Co., Columbus, Ohio). Each day, 5 grip strengths were assessed at 1 min intervals and the average grip strength over 4 days was calculated.

Statistical Analysis

Data were expressed as the Mean±SEM. Differences between two groups were analyzed by the t test; multiple comparisons were analyzed by ANOVA with a post hoc analysis by the Student-Newman-Keuls test for multiple comparisons. Results were considered statistically significant at $p<0.05$.

Reagents

Antibodies against p-Akt (Ser473), Akt, p-Stat3 (Tyr705), Stat3, P-Smad2 (Ser465/467)/Smad3 (Ser423/425), p-IRS1 (Ser307) and IRS1 were from Cell Signaling Technology (Beverly, Mass.); C/EBPδ were from ACRIS (San Diego, Calif.); Smad3, myostatin, IL-6 and TNFα were from Abcam (Cambridge, Mass.); while those against laminin and MHC were from Sigma-Aldrich (St. Louis, Mo.). The GAPDH antibody was from Chemicon (Temecula, Calif.). IL-6 recombinant protein was from R&D Systems (Minneapolis, Minn.).

p-Stat3 Inhibitor

Three small-molecule probes (C3, C30 and C188) that target the phosphotyrosyl (pY) peptide binding site within the Stat3 SH2 domain were identified using virtual ligand screening (Xu et al., 2009). Each compound competitively inhibited Stat3 binding to its pY-peptide ligand and ligand-induced Stat3 phosphorylation. C188 was the most potent of the three compounds identified. Similarity screening using the naphthalenyl-benzenesulfamide scaffold of C188 followed by 3-D pharmacophore analysis identified C188-9, which potently inhibited both Stat3 binding to its pY-peptide ligand ($K_i=136$ nM) and G-CSF-induced Stat3 phosphorylation (IC50=3±2 µM). Importantly, C188-9 at 10 µM concentration did not inhibit upstream tyrosine kinases known to activate Stat3, including Janus kinases (Jak1, Jak2) or Src family kinases (Hck, Lyn or Srms) as determined in a phosphoprotein array (RayBiotech, Norcross, Ga.) (Xu et al., 2009; Redell et al., 2011).

Cell Culture

C2C12 myoblasts (ATCC, Manassas, Va.) were grown in high glucose Dulbecco's Modified Eagle's Medium (DMEM) supplemented with 10% FBS, 100 U/ml penicillin, 100 mg/ml streptomycin, 100 mg/ml sodium pyruvate and 2 mM L-glutamine. To obtain myotubes, myoblasts were cultured to 80-95% confluence and the media was changed to DMEM supplemented with 2% horse serum (Sigma-Aldrich). Myotubes were incubated in serum-free media before being treated for different times with recombinant IL-6 with/without the Stat3 inhibitor, C188-9. Myotube sizes were evaluated by NIS-element software. Cell transfection was achieved by electroporation with Amaxa Nucleofector (Lonza, Allendale, N.J.). C2Cl2 myoblasts (106) were electroporated with 0.5 µg control or C/EBPδ siRNAs. Alternatively, 2 µg plasmids expressing Stat3C or C/EBPδ or C/EBPδ promoter- or myostatin promoter-reporter luciferase construct were trasfected (control, Renilla) and luciferase activities was measured using the Promega assay (Madison, Wis.).

Western Blotting

Muscle samples (1 mg per 10 µl of RIPA buffer) or C2Cl2 myotubes were homogenized in RIPA buffer containing Complete Mini Protease Inhibitor and PhosStop Phosphatase Inhibitor (Roche Applied Science, Indianapolis, Ind.). Lysates were centrifuged for 5 min at 16,200×g at 4° C. and equal amounts of protein from the supernatant were separated on SDS-polyacrylamide gels in Tris/SDS buffer, transferred onto nitrocellulose membranes and incubated with primary antibodies overnight at 4° C. After washing with TBST, the membrane was incubated with secondary antibodies conjugated to IRDye (Cell Signaling, Beverly, Mass.) at room temperature for 1 h. Protein bands were scanned using the Odyssey system (LI-COR, Lincoln, Nebr.). The band density of target proteins was quantified using NIH ImageJ Software.

Immunohistochemical Staining

Cryo-sections (10 µm) of the midbelly region of tibialis anterior (TA) muscles were fixed in 4% paraformaldehyde and incubated with anti-laminin before exposing them to an Alexa Fluor 488-conjugated mouse IgG secondary antibody (Invitrogen, Grand Island, N.Y.). Nuclei were stained with DAPI. Myofiber sizes were measured using NIS-Elements Br 3.0 software (Nikon) and the size distribution was calculated from 2000 myofibers by observers blinded to treatments. Paraffin sections (5 mm) of human muscles were immunohistochemically stained for the expression of p-Stat3, IL-6 and TNFα by incubating them with the primary antibody for 1 h at room temperature followed by incubation for 30 min with biotinylated antibodies. IL-6 and TNFα expression in 3 representative areas of the muscle sections was analyzed and expressed as the percentage of the myofiber area that stained positively. Stat3 in nuclei was expressed as the percent of nuclei positive for p-Stat3 in a total of 550 nuclei; the observer was blinded to patient vs. healthy subject.

Mouse Models

Transgenic mice expressing muscle creatine kinase-Cre (Mck-Cre) from Jackson Laboratory (Bar Harbor, Me.) were cross-bred with Stat3flox/flox mice with loxP sites flanking portions of exons 21 and 22 of the Stat3 gene. This site encodes a tyrosine residue (Tyr705) that is essential for Stat3 activation (Takeda et al., 1998). Mice expressing both Mck-Cre and Stat3flox/flox (i.e., Stat3 KO) were identified by genotyping and Western blotting. Heterozygous, C/EBPδ deficient mice were a gift from Dr. E. Sterneck (NIH—NCI, Frederick, Md.). Homozygous, C/EBPδ KO mice were developed by cross breeding of C/EBPδ heterozygous mice and PCR-genotyping. Subtotal nephrectomy was used to create CKD in wild type, Stat3flox/flox, Stat3 KO and C/EBPδ deficient mice (Zhang et al., 2011; May et al., 1987). Briefly, anesthetized mice underwent subtotal nephrectomy in two stages followed by a weeklong recovery while they were eating a 6% protein diet to reduce mortality from uremia. Subsequently, uremia was induced by feeding these and control mice a 40% protein diet. Mice were housed in 12-h light-dark cycles and body weights and food eaten were assessed daily. The influence of the Stat3 inhibitor, C188-9, was tested in CKD mice paired for BUN, body weights and chow intake; one mouse was injected subcutaneously with 6.25 mg/kg of C188-9 in D5W daily for 14 days while the paired CKD mouse was injected with an equal amount of D5W. Stat3 KO mice with CKD were fed the same amount of chow as the wild type mice with CKD. Homozygous and heterozygous C/EBPδ KO mice with CKD were fed the same amount of food as eaten by wild type mice with CKD for 14 days.

Lentivirus Production and Transfection

To produce lentiviruses to express Stat3C-GFP or GFP, 5×106 293T cells were cotransfected with 2 μg EF.STAT3C.Ubc.GFP or GFP (Addgene Cambridge, Mass.) plus 1 μg HIV-1 packaging vector 68.1 plus 0.4 μg VSVG envelope using Lipofectamine 2000. After 48 h, the virus pellet was collected by centrifugation (50,000×g for 2 h), re-suspended in Tris-NaCl-EDTA buffer and stored at −80° C. C2Cl2 myotubes were transfected with 107 virus particles/ml of DMEM plus 10% FBS and 5 μg/ml polybrene and 48 h later, proteins were evaluated by western blot.

For in vivo transfection, 10 μl of $10^7$ virus particles/ml of Stat3C-GFP was slowly injected into right hindlimb of newborn C57/BL6 mice; GFP was injected into the left hindlimb as a control. Two weeks later, the lentivirus injections were repeated. Mice were divided into two groups: 1) anti-myostatin peptibody treatment for two weeks as described (Zhang et al., 2011); or 2) an equal volume of PBS. At 6 weeks after the initial injection, sizes of myofibers expressing GFP were measured. Myostatin- and control-shRNAs lentivirus particles were from Santa Cruz Technology; ~50% confluent C2Cl2 myoblasts were transfected with 105 virus units in 8 μg/ml polybrene and selected by 5 μg/ml puromycin. Selected clones were tranfected with Stat3C or C/EBPδ and used to measure protein degradation after differentiation into myotubes.

Protein Synthesis and Degradation

Extensor digitorum longus (EDL) muscles were maintained at resting length and incubated in Krebs-Henseleit bicarbonate buffer with 10 mM glucose as described (Zhang et al., 2011). L-[U-$^{14}$C] phenylalanine incorporation into muscle protein and tyrosine release were measured as rates of protein synthesis and degradation (Clark and Mitch, 1983). In cultured C2Cl2 myotubes treated to knockdown myostatin or overexpress Stat3C or C/EBPδ, protein degradation in cells prelabeled with L-[U-$^{14}$C] phenylalanine was calculated from radiolabeled phenylalanine release (Zhang et al., 2009). The measurements were repeated six times.

Example 12

Inhibiting Stat3 Activation Suppresses Cancer-Induced Muscle Wasting

As described in this example, while evaluating cachexia it was found that conditioned media from C26 colon carcinoma or Lewis lung carcinoma (LLC) cells, activated p-Stat3 in C2Cl2 myotubes, followed by expression of C/EBPδ and myostatin with reduced myotube mass. In mice, LLC caused muscle wasting via a pathway from p-Stat3 to C/EBPδ to myostatin and activation of proteolysis by caspase-3 and the ubiquitin-proteasome system. Muscle-specific Stat3 KO suppressed cancer cachexia without reducing tumor growth. In mice with LLC, C/EBPδ KO blocked myostatin and the loss of body and muscle weights with improved grip strength. Since p-Stat3 initiates muscle wasting, it was evaluated whether a small molecule inhibitor of p-Stat3, C188-9, blocks cancer cachexia. In mice with C26 cancer, C188-9 blocked Stat3 activation, increased body and muscle weights while improving grip strength. C188-9 improved the synthesis and degradation of muscle proteins resulting in increased myofiber sizes. Thus, p-Stat3 inhibition genetically or chemically suppresses a pathway causing muscle wasting in these cancer models. Blocking the pathway could lead to novel therapeutic strategies to prevent cancer-induced muscle atrophy.

Material and Methods

Animals

All animal experiments and procedures were approved by the Baylor College of Medicine Institutional Animal Care and Use Committee (IACUC). CD2F1 mice (Charles River; Houston, Tex.) were studied at 8-10 weeks of age following subcutaneous injection of C26 tumor cells (5×$10^6$ cells in 500 μL medium) in the right flank. After 5 days, tumor bearing mice were treated with daily injections of the diluent, D5W (control), or C188-9 (12.5 mg Stat3 inhibitor/kg body weight). Control and cancer bearing mice were pair-fed for 14 days and growth was measured. For pair-feeding, the amount eaten by the cancer-bearing mouse was fed to the paired, control mouse the following day.

Mice were studied with muscle-specific knockout of Stat3 (Stat3 KO) or C/EBPδ KO mice. Stat3 KO mice were created by breeding transgenic mice expressing Stat3$^{flox/flox}$ with mice expressing muscle creatine kinase Cre (MCK-Cre) (Zhang et al., 2013). The Stat3 KO or C/EBPδ KO mice were implanted with 5×$10^6$ LLC cancer cells and body weights were measured during 12-14 days of pair feeding. Subsequently, mixed fiber tibialis anterior (TA) and gastrocnemius muscles, the predominately red myofiber, soleus muscle, and the white myofiber extensor digitorum longus (EDL) muscles were dissected, weighed, immediately frozen in liquid nitrogen and stored at −80° C.

Reagents

Antibodies against total-Stat3 and phospho-Stat3 were purchased from Cell Signaling Technology (Beverly, Mass.). Antibodies against C/EBPδ were from Acris Antibodies (San Diego, Calif.), against Atrogin1/MAFbx and MuRF1 from Santa Cruz Biotechnology (Santa Cruz, Calif.), against myostatin from Abcam (Cambridge, Mass.) and against glyceraldehyde-3-phosphate dehydrogenase (GAPDH) from Milipore (Temecula, Calif.).

Cell Culture Studies

Mouse C2Cl2 myoblasts (ATCC, Manassas, Va.) and LLC cells (Dr. Yi-Ping Li; University of Texas Health Sciences Center, Houston, Tex.) were cultured in DMEM (Cellgro Mediatech, Manassas, Va.), supplemented with 10% FBS (Invitrogen, Carlsbad, Calif.) plus 100 U/ml penicillin and 100 g/ml streptomycin. C26 cells (a gift from Dr. Vickie Baracos, University of Alberta, Edmonton, Alberta, Canada) were cultured in RPMI 1640 medium (Sigma-Aldrich), supplemented with 10% FBS (Invitrogen, Carlsbad, Calif.), 100 U/ml penicillin, and 100 g/ml streptomycin.

At >80% confluence, the media was changed to DMEM supplemented with 2% horse serum (Sigma-Aldrich) to induce myoblasts to differentiate into myotubes (Zhang et al., 2011). After 36 h, conditioned media (CM) from cultured C26 or LLC cells was collected and centrifuged (450×g, 5 min, 4° C.); media was diluted 1:5 with 2% horse serum before adding cultured C2Cl2 myotubes (Zhang et al., 2011).

Real-Time PCR

RNA from gastrocnemius muscles was obtained using RNeasy (Qiagen, Valencia, Calif.). cDNAs were synthesized using the iScript advanced cDNA synthesis kit (Bio-Rad Laboratories, Hercules, Calif.). Real-time PCR was performed with a CFX96 RT-PCR machine and SYBR Green (Bio-Rad Laboratories). The relative mRNA expression levels were calculated from cycle threshold (Ct) values using glyceraldehyde 3-phosphate dehydrogenase (GAPDH) as the internal control (relative expression= $2^{(sample\ Ct-GAPDH\ Ct)}$) Primer sequences have been described (Zhang et al., 2013).

Protein Synthesis and Degradation

As described Soleus and EDL muscles were rapidly removed from mice (Zhang et al., 2011; Clark and Mitch, 1983). The muscles were maintained at resting length during incubation in Krebs-Henseleit bicarbonate buffer with 10 mM glucose and L-[U-$^{14}$C]phenylalanine. Protein synthesis was measured as the rate of incorporation of L-[U-$^{14}$C] phenylalanine in muscle protein while protein degradation was assessed as the release of tyrosine from muscle proteins undergoing degradation. Phenylalanine and tyrosine were studied because they are neither synthesized nor degraded by muscle and they rapidly equilibrate with the intracellular free amino acid pool in muscle.

Caspase-3 Promoter Assay

Using the MI Inspector program, 3 putative STAT3 binding sites were identified in the caspase-3 promoter. Dr. Sabbagh (Montreal, Quebec, Canada) kindly provided us with a series of deletions of the caspase-3 promoter in a luciferase reporter construct. Different constructs contained zero, 1,2 or 3 putative Stat3 binding sites while a reverse caspase-3 promoter sequence was used as a negative control. Each caspase-3 promoter-luciferase reporter construct was electroporated into C2Cl2 cells. Cells containing the different constructs were treated by 100 ng/ml IL-6 or a plasmid expressing constitutively active Stat3 or both. Luciferase activity in these cells was compared to luciferase activity in cells incubated in serum free media. Luciferase activity in cell lysates was measured using the dual-luciferase reporter-assay system.

ChIP Assay:

C2Cl2 myoblasts were infected with an adenovirus expressing Stat3 and then treated with or without IL-6. Myoblasts were crosslinked with 1% formadehyde for 15 min at RT and washed 3× with ice-cold PBS containing a protease inhibitor (Roche). Myoblasts were lysed in lysis buffer, vortexed and sonicated for 10 sec at power setting 4; this was repeated 4× (VibraCell Sonicator). The average lengths of DNA fragments ranged between 300 and 800 bp. After centrifugation, the protein-DNA lysate was diluted 10-fold in ChIP buffer (15 mM Tris (pH 8.0), 1% Triton X-100, 0.01% SDS, 1 mM EDTA, 150 mM NaCl, 1 mM PMSF, and 1/100 protease inhibitor cocktail). the samples were precleared using salmon sperm DNA and protein A/G Agarose beads for 1 h at 4° C. Each 100 µL of protein-DNA lysate was used as an input control.

Samples were immunoprecipitated with antibodies to Stat3, p-Stat3 or Rabbit IgG (Santa Cruz Biotechnology) overnight at 4° C. followed by incubation with protein A/G Agarose beads for 1 h at 4° C. The immune complexes were washed as described by the manufacturer. Immunoprecipitated DNA was reverse crosslinked at 65° C. for 4 h in the presence of 0.2 M NaCl and purified using phenol/chloroform/isoamylalcohol. A total of 5 µl of the purified DNA was subjected to PCR amplification of a 190-bp fragment using specific primers that were derived from the promoter region of the caspase-3 gene.

Proteasome Activity

Proteasomes were partially purified by differential centrifugation; equal amounts of protein from the preparations of proteasomes were used to measure proteasome activity as the release of 7-amino-4-methylcoumarin (AMC) from the fluorogenic peptide substrate LLVY-AMC (N-Suc-Leu-Leu-Val-Tyr-AMC). AMC fluorescence was measured using 380 nm excitation and 460 nm emission wavelengths. The difference between the fluorescence measured in the presence and absence of 100 µm lactacystin was used to calculate proteasome activity.

Muscle Force

Mouse grip strength was measured as described (Zhang et al., 2013). Briefly, 5 grip strengths were assessed at 1 min intervals using the Grip Strength Meter (Columbus Instrument Co., Columbus, Ohio). The average grip strength over 4 days was calculated.

Statistical Analysis

Student's t test was used when 2 experimental groups were compared and ANOVA when data from 3 or 4 groups were studied. After ANOVA analyses, pairwise comparisons were made by the Student-Newman-Keuls test. The data are presented as means±SEM.

Conditioned Media from Cultured C26 or LLC Cancer Cells Stimulates C2Cl2 Myotube Atrophy Via a Pathway from p-Stat3 to C/EBPδ to Myostatin.

The presence of cancer cachexia in patients or rodent models suggests that cancer cells release a factor(s) that stimulates the loss of muscle mass (Todorov et al., 1996). In exploring potential mediators of cachexia, conditioned media was added from cultures of C26 to C2Cl2 myotubes. Within 5 minutes, the conditioned media stimulated myotube responses that included a >10-fold increase in activated (phosphorylated) Stat3 (p-Stat3) (FIG. 36A). However, when the Stat3 inhibitor C188-9 was added to C2Cl2 myotubes 2 h before adding the C26 or LLC conditioned media, the increases in p-Stat3 (15 min for conditioned media) were blocked (FIG. 36B). The conditioned media also increased the expressions of C/EBPδ and myostatin in cultured C2Cl2 myotubes and they were suppressed by C188-9 (FIG. 36C). These results are relevant to the development of cachexia because the conditioned media reduced the sizes of myotubes and treatment with the Stat3 inhibitor, C188-9, prevented the decrease in sizes of myotubes (FIG. 36D).

Muscle-Specific Stat3 KO in Mice with LLC Tumors Improves Skeletal Muscle Metabolism The finding that media from cultured cancer cells activates Stat3, increases the expression of C/EBPδ and myostatin and causes atrophy of myotubes suggests that C/EBPδ and myostatin are "downstream" from Stat3 activation (FIG. 36) (Zhang et al., 2013). Because the increases in C/EBPδ and myostatin levels in C2Cl2 myotubes are suppressed by the C188-9 inhibitor of p-Stat3, in another embodiment it would be that C188-9 is not specific but also inhibits C/EBPδ and myostatin resulting in improvements in muscle metabolism (Zhang et al., 2013). To evaluate the latter consideration, mice were generated with muscle-specific Stat3 KO. These Stat3 KO mice are fertile and develop normally (Zhang et al., 2013). These KO mice and control, Stat3$^{flox/flox}$ mice were injected subcutaneously with LLC and then pairfed for 18 days. During the pair-feeding, the genetically altered mice were injected with LLC and given the same amount of food as that eaten on the prior day by the LCC tumor bearing, Stat3$^{flox/flox}$ mice. In the Stat3$^{flox/flox}$ mice, the LLC tumor caused a significant decrease in the body weight (FIG. 37A). In contrast, mice with muscle-specific, Stat3 KO had an improvement in their growth, reaching a level that was indistinguishable from that of control mice without the LLC cancer (FIG. 37A). Stat3 KO bearing tumor had higher body weight maybe due to increased amount of muscle mass vs. control mice bearing tumor (FIG. 37C). When the mice were examined in the absence of the LLC tumor, it was found that mice with muscle-specific Stat3 KO mice had the same growth as Stat3$^{flox/flox}$ mice. This result indicates that muscle-specific KO of Stat3 did not interfere with the growth of the genetically altered mouse. In addition, the responses were independent of changes in tumor mass (FIG. 37B). Both C/EBPδ and myostatin expressions in mice with muscle-specific Stat3 KO, were decreased similarly to the responses noted when the Stat3 inhibitor, C188-9, was added to C2Cl2 myotubes being treated with conditioned media from cancer cells (FIGS. 37D; 36C). in consistent with increased muscle mass, Stat3 KO mice bearing tumor showed higher muscle grip strength vs. constol Stat3$^{flox/flox}$ bearing tumor (FIG. 37E). Thus, in vivo genetic inhibition of p-Stat3 produces results like those achieved by suppressing p-Stat3 with C188-9 in vitro, consistent with the conclusion that C188-9 functions as an inhibitor of p-Stat3.

C/EBPδ KO in Mice Suppresses LLC Tumor-Induced Cachexia

Because LLC or C26 cancers increase the expressions of p-Stat3, C/EBPδ plus myostatin in muscle plus inhibition of myostatin blocks muscle wasting (Han et al., 2013), it was examined whether C/EBPδ also is necessary for the muscle wasting that follows activation of p-Stat3. Mice with whole body, homozygous C/EBPδ KO were created from C57BL6 mice; the mice are fertile and develop normally and they respond adversely to cancer. When LLC cancer cells were injected subcutaneously in the genetically altered and control mice, the absence of C/EBPδ did not affect the growth of LLC tumors. The weights of body and muscles of C/EBPδ KO mice were preserved but in WT mice bearing LLC, there was loss of body and muscle weights (FIGS. 38A, B). Notably, LLC caused a decrease in weights of the different types of muscles including the mixed-fiber gastrocnemius and tibialis anterior muscles as well as the red-fiber (soleus) and white fiber (extensor digitorum longus) muscles.

A mechanism that contributes to the loss of muscle mass in WT mice with LLC is an increase in protein degradation in muscles. This response was significantly reduced in C/EBPδ KO mice (FIG. 38C). The improvements in muscle mass and metabolism were associated with an increase in grip strength in C/EBPδ KO mice (FIG. 38D). Consistent with the proposed signaling pathway, C/EBPδ KO suppressed tumor induced myostatin level in muscle of mice (FIG. 38E). Taken together, the results demonstrate that C/EBPδ is required for the pathway that links p-Stat3 to loss of muscle mass.

Inhibition of Stat3 Activation Improves Cancer-Induced Muscle Wasting

To examine potential mechanisms causing cancer-induced loss of muscle mass, C26 cancer cells were injected into CD2F1 mice. As reported by others (Aulino et al., 2010), implantation of C26 tumors in mice causes a pronounced loss of body weights (FIG. 39B). Besides loss of muscle mass, there was a significant increase in pStat3 in muscles of mice bearing C26 tumors (FIG. 39A). To investigate whether body weight loss depended on Stat3 activation, mice bearing C26-tumor cells were treated with a small molecule inhibitor of p-Stat3, C188-9, for 14 days beginning at 5 days after tumor implantation. In tumor-bearing mice treated with C188-9, Stat3 activation was suppressed.

There also was a significant increase in body weight even though the C26 tumor had been in place for 19 days. The ability of C188-9 to improve body weight included blockade of muscle wasting since the weights of the mixed fiber tibialis anterior (TA) and gastrocnemius muscles as well as the predominately red fiber soleus and white fiber EDL muscles were significantly greater than the weights of pair-fed, tumor bearing mice that were treated with D5W (FIG. 39C). The myofiber sizes are consistent with muscle mass (FIGS. 39D&E). Notably, the increase in muscle mass in tumor bearing mice led to improved grip strength, a measure of muscle function (FIG. 37G). The mechanisms underlying for improvements in muscle mass included an increase in protein synthesis plus a decrease in protein degradation resulting in an improvement in the sizes of myofibers (FIGS. 39F&G). There was an increased rate of protein synthesis and degradation in both white (EDL) and red (soleus) fibers.

p-Stat3 Stimulates the Transcription of Caspase-3, Participating in the Development of Cancer Cachexia.

Caspase-3 is an initial step for muscle wasting, because caspase-3 plays two roles in promoting muscle proteolysis: first, caspase-3 cleaves the complex structure of muscle proteins to provide substrates for the UPS (Du et al., 2004; Song et al., 2005; Zhang et al., 2009). Second, caspase-3 cleaves specific subunits of the 19S proteasome particle that stimulates proteolytic activity of the 26S proteasome (Wang et al., 2010). Besides these properties, caspase-3 activation can be recognized by the presence of a 14 kD actin fragment that is left in the insoluble fraction of muscle biopsies (Du et al., 2004; Workeneh et al., 2006). To evaluate whether there is tumor induce caspase-3 expression and activation in muscle mass loss, procaspase-3 and cleaved caspase-3 were measured in muscle of mice bearing C26 or LLC tumor; both tumors stimulated pro-caspase-3 and cleaved caspase-3 level in muscle (FIG. 40A). The caspase-3 activity also increased, because in muscle of mice bearing either tumor, there was an increased 14 kD actin fragment (FIG. 40B).

Next, it was measured whether the increased caspase-3 expression is linked to tumor induced p-Stat3 in muscle. Using MatInspector program, there were three putative Stat3 binding sites in the 3 kb promoter region of caspse-3. To test if cancer cell media induced p-Stat3 stimulate it binding with caspase-3 promoter, C2Cl2 cells were treated with C26 conditioned media for 24 h and subjected to ChIP assay using anti-p-Stat3, the DNA associated with p-Stat3 was amplified using primers from caspase-3 promoter, there was DNA fragment from PCR amplification in C2Cl2 myotubes treated with C26 conditined media, but not in control cells (C2Cl2 myotubes in serum free media) (FIG. 40C). To further determine that Stat3 could binding with caspase-3 promoter to stimulate caspase-3 transcription, C2Cl2 myotubes were infected with adenovirus expressing Stat3. The control cells infected adenovirus expressing GFP. These cells treated with or without IL-6 (100 ng/ml) for 24 h. CHIP assay using anti-Stat3 indicate that cells without either overexpressing Stat3 or IL-6 treatment does not show Stat3 binding with caspase-3. Stat3 do binding with caspase-3 in cells overexpressing Stat3 and treated with IL-6. P-Stat3 binding with caspase-3 in any donsitions and there was a strong interaction between caspase-3 and p-Stat3 in cells onverexpressing Stat3 and stimulated with IL-6 (FIG. 40D). To test whether p-Stat3 binding with caspse-3 promoter to stimulates caspase-3 transcription, C2Cl2 myoblast was transfected with plasmid of caspase-3 promoter in luciferase construct and plasmid to express constitutively active Stat3 (Stat3C). Control cells transfected with cDNA3. Cells were treated with or without IL-6 for 6 h. There was IL-6 or StatC stimulated caspase-3 promoter activity, but cells stimulated both IL-6 and overexpressing Stat3 stimulated the highest caspase-3 promoter activity. When all three Stat3 binding site were deleted in caspase-3 promoter (−178/+14), there is no stimulated caspase-3 promoter activity found even with IL-6 or Stat3C or both (FIG. 40E). These results indicate that p-Stat3 binding with caspase-3 to stimulate its expression.

Activation of Stat3 Induces Ubiquitin-Proteasome System in Cancer-Induced Cachexia.

When C2Cl2 myotubes were treated with conditioned media from C26 cells with or without C188-9 for 72 hours, there was decreased protein level of myosin heavy chain, and this response is blocked by C188-9 (FIG. 41A). To test if this proteolysis involved UPS, Atrogin and MuRF-1 mRNA expression were measured in these cells; there was significantly increased expression of both muscle specific ubiquitin E3 lygases, and this response is suppressed by C188-9 (FIG. 41A). To test whether this is the case in muscle of mice, Atrogin-1 and MuRF-1 expression levels were measured in Stat3 KO or C188-9 treatment muscle of mice bearing tumor, and these results are consistent with results in cell culture. Finally, there was increased proteasome activity in muscle of mice bearing C26 tumor and it was suppressed by C188-9 (FIG. 41D). Therefore, Stat3 activation occurs in muscle of mice bearing tumor stimulated UPS to induce muscle wasting.

As an example, FIG. 42 exemplifies how in one embodiment cancer that activates p-Stat3 in muscle can stimulate loss of muscle mass. Stat3 activation stimulates expression of C/EBPδ that then increases myostatin and MAFbx/Atrogin-1 and MuRF-1 to increase muscle wasting by the UPS. Stat3 activation also increases caspase-3 expression and activity to coordinate muscle proteolysis with the UPS.

REFERENCES

All patents and publications cited herein are hereby incorporated by reference in their entirety herein. Full citations for the references cited herein are provided in the following list.

PUBLICATIONS

Akira, S., 2000. Roles of STAT3 defined by tissue-specific gene targeting. Oncogene 19:2607-2611.

Akira, S., 1997, IL-6-regulated transcription factors. Int J Biochem Cell Biol 29:1401-1418.

Akira, S., Isshiki, H., Sugita, T., Tanabe, O., Kinoshita, S., Nishio, Y., Nakajima, T., Hirano, T., and Kishimoto, T. (1990). A nuclear factor for IL-6 expression (NF-IL6) is a member of a C/EBP family. EMBO J. 9, 1897-1906.

Al-Hajj, M., Wicha, M. S., Benito-Hernandez, A., Morrison, S. J., and Clarke, M. F. 2003. Prospective identification of tumorigenic breast cancer cells. Proc Natl Acad Sci USA 100:3983-3988.

Allen, D. L. and Unterman, T. G. (2007). Regulation of myostatin expression and myoblast differentiation by FoxO and SMAD transcription factors. Am. J. Physiol Cell Physiol 292, C188-C199.

Alonzi, T., Gorgoni, B., Screpanti, I., Gulino, A., and Poli, V. (1997). Interleukin-6 and CAAT/enhancer binding protein beta-deficient mice act as tools to dissect the IL-6 signalling pathway and IL-6 regulation. Immunobiology 198, 144-156.

Baltgalvis, K. A., Berger, F. G., Pena, M. M., Davis, J. M., Muga, S. J., and Carson, J. A. (2008). Interleukin-6 and cachexia in ApcMin/+ mice. Am. J. Physiol Regul. Integr. Comp Physiol 294, R393-R401.

Becker, S., Groner B, Muller C W (1998) Three-dimensional structure of the Stat3[beta] homodimer bound to DNA. Nature 394(6689): 145-151.

Bhasin, D., Cisek, K., Pandharkar, T., Regan, N., Li, C., Pandit, B., Lin, J., and Li, P. K. (2008). Design, synthesis, and studies of small molecule STAT3 inhibitors. Bioorg. Med. Chem. Lett. 18, 391-395.

Bonetto, A., Aydogdu, T., Kunzevitzky, N., Guttridge, D. C., Khuri, S., Koniaris, L. G., and Zimmers, T. A. (2011). STAT3 activation in skeletal muscle links muscle wasting and the acute phase response in cancer cachexia. PLoS. One. 6, e22538.

Brinkley, B R, Beall P T, Wible L J, Mace M L, Turner D S et al. (1980) Variations in Cell Form and Cytoskeleton in Human Breast Carcinoma Cells in vitro. Cancer Res 40(9): 3118-3129.

Bromberg, J., 2002. Stat proteins and oncogenesis. J Clin Invest 109:1139-1142.

Bromberg, J., and Darnell, J. E., Jr. 2000. The role of STATs in transcriptional control and their impact on cellular function. Oncogene 19:2468-2473.

Bromberg, J. F., Horvath, C. M., Besser, D., Lathem, W. W., and Darnell, J. E., Jr. 1998. Stat3 activation is required for cellular transformation by v-src. Mol Cell Biol 18:2553-2558.

Bromberg, J. F., Wrzeszczynska, M. H., Devgan, G., Zhao, Y., Pestell, R. G., Albanese, C., and Darnell, J. E., Jr. 1999. Stat3 as an oncogene [published erratum appears in Cell 1999 Oct. 15; 99(2):239]. Cell 98:295-303.

Cailleau R O M, Crueiger Q V J. (1978) Long term human breast carcinoma cell lines of metastatic origin: preliminary characterization. In vitro 14: 911-915.

Caldenhoven, E., van, D. T. B., Solari, R., Armstrong, J., Raaijmakers, J. A. M., Lammers, J. W. J., Koenderman, L., and de, G. R. P. 1996. STAT3beta, a splice variant of transcription factor STAT3, is a dominant negative regulator of transcription. Journal of Biological Chemistry 271:13221-13227.

Carrero, J. J., Chmielewski, M., Axelsson, J., Snaedal, S., Heimburger, O., Barany, P., Suliman, M. E., Lindholm, B., Stenvinkel, P., and Qureshi, A. R. (2008). Muscle atrophy, inflammation and clinical outcome in incident and prevalent dialysis patients. Clin. Nutr. 27, 557-564.

Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., et al. 1999. Constitutive activation of Stat3 signaling confers resistance to apoptosis in human U266 myeloma cells. Immunity 10:105-115.

Chakraborty, A., Dyer K F, Cascio M, Mietzner T A, Tweardy D J (1999) Identification of a Novel Stat3 Recruitment and Activation Motif Within the Granulocyte Colony-Stimulating Factor Receptor. Blood 93(1): 15-24.

Chakraborty, A., White, S. M., Schaefer, T. S., Ball, E. D., Dyer, K. F., and Tweardy, D. J. 1996. Granulocyte colony-stimulating factor activation of Stat3 alpha and Stat3 beta in immature normal and leukemic human myeloid cells. Blood 88:2442-2449.

Chapman, R. S., Lourenco, P. C., Tonner, E., Flint, D. J., Selbert, S., Takeda, K., Akira, S., Clarke, A. R., and Watson, C. J. 1999. Suppression of epithelial apoptosis and delayed mammary gland involution in mice with a conditional knockout of Stat3. Genes Dev 13:2604-2616.

Chen, X., Vinkemeier U, Zhao Y, Jeruzalmi D, Darnell J E et al. (1998) Crystal Structure of a Tyrosine Phosphorylated STAT-1 Dimer Bound to DNA. Cell 93(5): 827-839.

Cheung, W. W., Paik, K. H., and Mak, R. H. (2010). Inflammation and cachexia in chronic kidney disease. Pediatr. Nephrol. 25, 711-724.

Cohen, M. S., Zhang C, Shokat K M, Taunton J (2005) Structural Bioinformatics-Based Design of Selective, Irreversible Kinase Inhibitors. Science 308(5726): 1318-1321.

Coleman, D R, Ren Z, Mandal P K, Cameron A G, Dyer G A et al. (2005) Investigation of the Binding Determinants of Phosphopeptides Targeted to the Src Homology 2 Domain of the Signal Transducer and Activator of Transcription 3. Development of a High-Affinity Peptide Inhibitor. J Med Chem 48(21): 6661-6670.

Costa-Pereira, A. P., Tininini, S., Strobl, B., Alonzi, T., Schlaak, J. F., Is'harc, H., Gesualdo, I., Newman, S. J., Kerr, I. M., and Poli, V. 2002. Mutational switch of an IL-6 response to an interferon-gamma-like response. Proc Natl Acad Sci USA 99:8043-8047.

Daling, J. R., and Malone, K. E. 2003. Incidence of invasive breast cancer by hormone receptor status from 1992 to 1998. J Clin Oncol 21:28-34.

Darnell J E (2005), Validating Stat3 in cancer therapy. Nat Med 11(6): 595-596.

Dave, B., and Chang, J. 2009. Treatment resistance in stem cells and breast cancer. J Mammary Gland Biol Neoplasia 14:79-82.

Diaz, N., Minton, S., Cox, C., Bowman, T., Gritsko, T., Garcia, R., Eweis, I., Wloch, M., Livingston, S., Seijo, E., et al. 2006. Activation of stat3 in primary tumors from high-risk breast cancer patients is associated with elevated levels of activated SRC and survivin expression. Clin Cancer Res 12:20-28.

Dong, S., Chen S-J, Tweardy D J (2003) Cross-talk between Retinoic Acid and Stat3 Signaling Pathways in Acute Promyelocytic Leukemia. Leuk Lymphoma 44: 2023-2029.

Du, J., Wang, X., Meireles, C. L., Bailey, J. L., Debigare, R., Zheng, B., Price, S. R., and Mitch, W. E. (2004). Activation of caspase 3 is an initial step triggering muscle proteolysis in catabolic conditions. J. Clin. Invest 113, 115-123.

Dunn, G P, Bruce A T, Ikeda H, Old L J, Schreiber R D (2002) Cancer immunoediting: from immunosurveillance to tumor escape. Nat Immunol 3(11): 991-998.

Durbin, J. E., Hackenmiller, R., Simon, M. C., and Levy, D. E. 1996. Targeted disruption of the mouse Stat1 gene results in compromised innate immunity to viral disease. Cell 84:443-450.

Eckert, H., Bajorath J (2007) Molecular similarity analysis in virtual screening: foundations, limitations and novel approaches. Drug discovery today 12(5-6): 225-233.

Epling-Burnette, P. K., Liu, J. H., Catlett-Falcone, R., Turkson, J., Oshiro, M., Kothapalli, R., Li, Y., Wang, J. M., Yang-Yen, H. F., Karras, J., et al. 2001. Inhibition of STAT3 signaling leads to apoptosis of leukemic large granular lymphocytes and decreased Mcl-1 expression. J Clin Invest 107:351-362.

Feldman, B. J., Streeper, R. S., Farese, R. V., Jr., and Yamamoto, K. R. (2006). Myostatin modulates adipogenesis to generate adipocytes with favorable metabolic effects. Proc. Natl. Acad. Sci. U.S.A 103, 15675-15680.

Fiala, S., 1968. The cancer cell as a stem cell unable to differentiate. A theory of carcinogenesis. Neoplasma 15:607-622.

Fouque, D., Kalantar-Zadeh, K., Kopple, J. D., Cano, N., Chauveau, P., Cuppari, L., Franch, H. A., Guarnieri, G., Ikizler, T. A., Kaysen, G. A., Lindholm, B., Massy, Z., Mitch, W. E., Pineda, E., Stenvinkel, P., Trevinho-Becerra, T., and Wanner, C. (2008). A proposed nomenclature and diagnostic criteria for protein-energy wasting in acute and chronic kidney disease. Kidney Int. 73, 391-398.

Fu, X.-Y., Schindler, C, Improta, T., Aebersold, R., and Darnell, J. E., Jr. 1992. The proteins of ISGF-3, the interferon alpha-induced transcriptional activator, define a gene family involved in signal transduction. Proceedings of the National Academy of Sciences of the United States of America 89:7840-7843.

Garcia, R., and, Jove, R. 1998. Activation of STAT transcription factors in oncogenic tyrosine kinase signaling. Journal of Biomedical Science In press.

Garcia R, Yu C L, Hudnall A, Catlett R, Nelson K L et al. (1997) Constitutive activation of Stat3 in fibroblasts transformed by diverse oncoproteins and in breast carcinoma cells. Cell Growth Differ 8(12): 1267-1276.

Garcia R, Bowman T L, Niu G, Yu H, Minton S et al. (2001) Constitutive activation of Stat3 by the Src and Jak tyrosine kinases participates in growth regulation of human breast carcinoma cells. Oncogene 20: 2499-2513.

Goodman, M. N. (1991). Tumor necrosis factor induces skeletal muscle protein breakdown in rats. Am. J. Physiol. 260, E727-E730.

Goodman, M. N. (1994). Interleukin-6 induces skeletal muscle protein breakdown in rats. Proc. Soc. Exp. Biol. Med. 205, 182-185.

Grandis, J. R., Drenning, S. D., Zeng, Q., Watkins, S. C., Melhem, M. F., Endo, S., Johnson, D. E., Huang, L., He, Y., and Kim, J. D. 2000. Constitutive activation of Stat3 signaling abrogates apoptosis in squamous cell carcinogenesis in vivo. Proc Natl Acad Sci USA 97:4227-4232.

Gritsko, T., Williams, A., Turkson, J., Kaneko, S., Bowman, T., Huang, M., Nam, S., Eweis, I., Diaz, N., Sullivan, D., et al. 2006. Persistent activation of stat3 signaling induces survivin gene expression and confers resistance to apoptosis in human breast cancer cells. Clin Cancer Res 12:11-19.

Haan, S., Hemmann, U., Hassiepen, U., Schaper, F., Schneider-Mergener, J., Wollmer, A., Heinrich, P. C., and Grotzinger, J. 1999. Characterization and binding specificity of the monomeric STAT3-SH2 domain. J Biol Chem 274: 1342-1348.

Hirano, T., Nakajima, K., and Hibi, M. (1997). Signaling mechanisms through gp130: a model of the cytokine system. Cytokine Growth Factor Rev. 8, 241-252.

Horvath, C. M. (2004). The Jak-STAT pathway stimulated by interleukin 6. Sci. STKE. 2004, tr9.

Hu, Z., Wang, H., Lee, I. H., Du, J., and Mitch, W. E. (2009). Endogenous glucocorticoids and impaired insulin signaling are both required to stimulate muscle wasting under pathophysiological conditions in mice. J. Clin. Invest. 119, 7650-7659.

Huang, Y., Qiu J, Dong S, Redell M S, Poli V et al. (2007) Stat3 Isoforms, {alpha} and, Demonstrate Distinct Intracellular Dynamics with Prolonged Nuclear Retention of Stat3 Mapping to Its Unique C-terminal End. J Biol Chem 282(48): 34958-34967.

Hung, A. M., Ellis, C. D., Shintani, A., Booker, C., and Ikizler, T. A. (2011). IL-1beta receptor antagonist reduces inflammation in hemodialysis patients. J. Am. Soc. Nephrol. 22, 437-442.

Jemal, A., Siegel, R., Ward, E., Murray, T., Xu, J., Smigal, C., and Thun, M. J. 2006. Cancer statistics, 2006. CA Cancer J Clin 56:106-130.

Jing, N., Tweardy D J (2005) Targeting Stat3 in cancer therapy. anticancer Drugs 16(6): 601-607.

Jing, N., Zhu Q, Yuan P, Li Y, Mao L et al. (2006) Targeting signal transducer and activator of transcription 3 with G-quartet oligonucleotides: a potential novel therapy for head and neck cancer. Mol Cancer Ther 5(2): 279-286.

Jing, N., Li Y, Xu X, Sha W, Li P et al. (2003) Targeting Stat3 with G-quartet oligodeoxynucleotides in human cancer cells. DNA Cell Biol 22(11): 685-696.

Jing, N., Li, Y., Xiong, W., Sha, W., Jing, L., and Tweardy, D. J. 2004. G-quartet oligonucleotides: a new class of signal transducer and activator of transcription 3 inhibitors that suppresses growth of prostate and breast tumors through induction of apoptosis. Cancer Res 64:6603-6609.

Kaplan, D. H., Shankaran, V., Dighe, A. S., Stockert, E., Aguet, M., Old, L. J., and Schreiber, R. D. 1998. Demonstration of an interferon gamma-dependent tumor surveillance system in immunocompetent mice. Proc Natl Acad Sci USA 95:7556-7561.

Kato, T., Sakamoto E, Kutsuna H, Kimura-Eto A, Hato F et al. (2004) Proteolytic Conversion of STAT3{alpha} to STAT3{gamma} in Human Neutrophils: ROLE OF GRANULE-DERIVED SERINE PROTEASES. J Biol Chem 279(30): 31076-31080.

Kim, J. K., Xu Y, Xu X, Keene D R, Gurusiddappa S et al. (2005) A Novel Binding Site in Collagen Type III for Integrins {alpha}1{beta}1 and {alpha}2{beta}1. J Biol Chem 280(37): 32512-32520.

Kimmel, P. L., Phillips, T. M., Simmens, S. J., Peterson, R. A., Weihs, K. L., Alleyne, S., Cruz, I., Yanovski, J. A., and Veis, J. H. (1998). Immunologic function and survival in hemodialysis patients. Kidney Int. 54, 236-244.

Kishimoto, T., Taga, T., and Akira, S. (1994). Cytokine signal transduction. Cell 76, 253-262.

Kortylewski, M., Kujawski M, Wang T, Wei S, Zhang S et al. (2005) Inhibiting Stat3 signaling in the hematopoietic system elicits multicomponent antitumor immunity. Nat Med 11(12): 1314-1321.

Lalani, R., Bhasin, S., Byhower, F., Tarnuzzer, R., Grant, M., Shen, R., Asa, S., Ezzat, S., and Gonzalez-Cadavid, N. F. (2000). Myostatin and insulin-like growth factor-I and -II expression in the muscle of rats exposed to the microgravity environment of the NeuroLab space shuttle flight. J Endocrinol. 167, 417-428.

Lecker, S. H., Goldberg, A. L., and Mitch, W. E. (2006). Protein degradation by the ubiquitin-proteasome pathway in normal and disease states. J. Am. Soc. Nephrol. 17, 1807-1819.

Lecker, S. H., Jagoe, R. T., Gomes, M., Baracos, V., Bailey, J. L., Price, S. R., Mitch, W. E., and Goldberg, A. L. (2004). Multiple types of skeletal muscle atrophy involve a common program of changes in gene expression. FASEB J. 18, 39-51.

Lee, S. W., Dai, G., Hu, Z., Wang, X., Du, J., and Mitch, W. E. (2004). Regulation of muscle protein degradation: coordinated control of apoptotic and ubiquitin-proteasome systems by phosphatidylinositol 3 kinase. J. Am. Soc. Nephrol. 15, 1537-1545.

Leong, P. L., Andrews, G. A., Johnson, D. E., Dyer, K. F., Xi, S., Mai, J. C., Robbins, P. D., Gadiparthi, S., Burke, N. A., Watkins, S. F., et al. 2003. Targeted inhibition of Stat3 with a decoy oligonucleotide abrogates head and neck cancer cell growth. Proc Natl Acad Sci USA 100:4138-4143.

Li, C. I., Daling, J. R., and Malone, K. E. 2003. Incidence of invasive breast cancer by hormone receptor status from 1992 to 1998. J Clin Oncol 21:28-34.

Li, L., and Shaw, P. E. 2002. Autocrine-mediated activation of STAT3 correlates with cell proliferation in breast carcinoma lines. J Biol Chem 277:17397-17405.

Li, X., Lewis, M. T., Huang, J., Gutierrez, C., Osborne, C. K., Wu, M. F., Hilsenbeck, S. G., Pavlick, A., Zhang, X., Chamness, G. C., et al. 2008. Intrinsic resistance of tumorigenic breast cancer cells to chemotherapy. J Natl Cancer Inst 100:672-679.

Lin, Q., Lai R, Chirieac L R, Li C, Thomazy V A et al. (2005) Constitutive Activation of JAK3/STAT3 in Colon Carcinoma Tumors and Cell Lines: Inhibition of JAK3/STAT3 Signaling Induces Apoptosis and Cell Cycle Arrest of Colon Carcinoma Cells. Am J Pathol 167(4): 969-980.

Lin, L., Amin, R., Gallicano, G. I., Glasgow, E., Jogunoori, W., Jessup, J. M., Zasloff, M., Marshall, J. L., Shetty, K., Johnson, L., Mishra, L., and He, A. R. (2009). The STAT3 inhibitor NSC 74859 is effective in hepatocellular cancers with disrupted TGF-beta signaling. Oncogene 28, 961-972.

Lin, L., Hutzen, B., Li, P. K., Ball, S., Zuo, M., Deangelis, S., Foust, E., Sobo, M., Friedman, L., Bhasin, D., Cen, L., Li, C., and Lin, J. (2010). A novel small molecule, LLL12, inhibits STAT3 phosphorylation and activities and exhibits potent growth-suppressive activity in human cancer cells. Neoplasia. 12, 39-50.

Ma, K., Mallidis, C., Artaza, J., Taylor, W., Gonzalez-Cadavid, N., and Bhasin, S. (2001). Characterization of 5'-regulatory region of human myostatin gene: regulation by dexamethasone in vitro. Am J Physiol Endocrinol. Metab 281, E1128-E1136.

Ma, K., Mallidis, C., Bhasin, S., Mahabadi, V., Artaza, J., Gonzalez-Cadavid, N., Arias, J., and Salehian, B. (2003). Glucocorticoid-induced skeletal muscle atrophy is associated with upregulation of myostatin gene expression. Am. J. Physiol 285, E363-E371.

Maritano, D., Sugrue, M. L., Tininini, S., Dewilde, S., Strobl, B., Fu, X., Murray-Tait, V., Chiarle, R., and Poli, V. 2004. The STAT3 isoforms alpha and beta have unique and specific functions. Nat Immunol 5:401-409.

May, R. C., Kelly, R. A., and Mitch, W. E. (1987). Mechanisms for defects in muscle protein metabolism in rats with chronic uremia: The influence of metabolic acidosis. J. Clin. Invest. 79, 1099-1103.

McMurray J S (2006), A New Small-Molecule Stat3 Inhibitor. Chemistry & Biology 13(11): 1123-1124.

Meraz, M. A., White, J. M., Sheehan, K. C., Bach, E. A., Rodig, S. J., Dighe, A. S., Kaplan, D. H., Riley, J. K., Greenlund, A. C., Campbell, D., et al. 1996. Targeted disruption of the Stat1 gene in mice reveals unexpected physiologic specificity in the JAK-STAT signaling pathway. Cell 84:431-442.

Minino, A. M., Heron, M. P., Murphy, S. L., and Kochanek, K. D. 2007. Deaths: final data for 2004. Natl Vital Stat Rep 55:1-119.

Mora, L. B., Buettner, R., Seigne, J., Diaz, J., Ahmad, N., Garcia, R., Bowman, T., Falcone, R., Fairclough, R., Cantor, A., et al. 2002. Constitutive activation of Stat3 in human prostate tumors and cell lines: direct inhibition of Stat3 signaling induces apoptosis of prostate cancer cells. Cancer Res 62:6659-6666.

Neculai, D., Neculai A M, Verrier S, Straub K, Klumpp K et al. (2005) Structure of the Unphosphorylated STAT5a Dimer. J Biol Chem 280(49): 40782-40787.

Nemethy, G., Gibson K D, Palmer K A, Yoon C N, Paterlini G et al. (1992) Energy Parameters in Polypeptides. 10. Improved Geometrical Parameters and Nonbonded Interactions for Use in the ECEPP/3 Algorithm, with Application to Proline-Containing Peptides. JPhys Chem 96: 6472-6484.

Park, O. K., Schaefer, T. S., and Nathans, D. 1996. In vitro activation of Stat3 by epidermal growth factor receptor kinase. Proceedings of the National Academy of Sciences of the United States of America 93:13704-13708.

Park, O. K., Schaefer, L. K., Wang, W., and Schaefer, T. S. 2000. Dimer stability as a determinant of differential DNA binding activity of Stat3 isoforms. J Biol Chem 275:32244-32249.

Penner, G., Gang, G., Sun, X., Wray, C., and Hasselgren, P. O. (2002). C/EBP DNA-binding activity is upregulated by a glucocorticoid-dependent mechanism in septic muscle. Am. J. Physiol Regul. Integr. Comp Physiol 282, R439-R444.

Poli, V. (1998). The role of C/EBP isoforms in the control of inflammatory and native immunity functions. J. Biol. Chem. 273, 29279-29282.

Price, S. R., Bailey, J. L., Wang, X., Jurkovitz, C., England, B. K., Ding, X., Phillips, L. S., and Mitch, W. E. (1996). Muscle wasting in insulinopenic rats results from activation of the ATP-dependent, ubiquitin-proteasome pathway by a mechanism including gene transcription. J. Clin. Invest. 98, 1703-1708.

Qing, Y., and Stark, G. R. 2004. Alternative activation of STAT1 and STAT3 in response to interferon-gamma. J Biol Chem 279:41679-41685.

Ramana, C., Chatterjee-Kishore M, Nguyen H, Stark G (2000) Complex roles of Stat1 in regulating gene expression. Oncogene 19(21): 2619-2627.

Ramji, D. P. and Foka, P. (2002). CCAAT/enhancer-binding proteins: structure, function and regulation. Biochem. J. 365, 561-575.

Real, P. J., Sierra, A., De Juan, A., Segovia, J. C., Lopez-Vega, J. M., and Fernandez-Luna, J. L. 2002. Resistance to chemotherapy via Stat3-dependent overexpression of Bcl-2 in metastatic breast cancer cells. Oncogene 21:7611-7618.

Redell, M S, Tweardy D J (2006) Targeting transcription factors in cancer: Challenges and evolving strategies. Drug Discovery Today: Technologies 3(3): 261-267.

Redell, M. S., and Tweardy, D. J. 2005. Targeting transcription factors for cancer therapy. Curr Pharm Des 11:2873-2887.

Redell, M. S., Ruiz, M. J., Alonzo, T. A., Gerbing, R. B., and Tweardy, D. J. (2011). Stat3 signaling in acute myeloid leukemia: ligand-dependent and -independent activation and induction of apoptosis by a novel small-molecule Stat3 inhibitor. Blood 117, 5701-5709.

Ren, Z., Cabell, L. A., Schaefer, T. S., and McMurray, J. S. 2003. Identification of a high-affinity phosphopeptide inhibitor of stat3. Bioorg Med Chem Lett 13:633-636.

Rui, L., Fisher, T. L., Thomas, J., and White, M. F. (2004). Regulation of insulin/insulin-like growth factor-1 signaling by proteasome-mediated degradation of insulin receptor substrate-1. J. Biol. Chem. 276, 40362-40367.

Rui, L., Yuan, M., Frantz, D., Shoelson, S., and White, M. F. (2002). SOCS-1 and SOCS-3 block insulin signaling by ubiquitin-mediated degradation of IRS1 and IRS2. J Biol. Chem. 277, 42394-42398.

Ryan, J. J., McReynolds, L. J., Huang, H., Nelms, K., and Paul, W. E. 1998. Characterization of a mobile Stat6 activation motif in the human IL-4 receptor. J Immunol 161:1811-1821.

Sandri, M., Sandri, C., Gilbert, A., Skuck, C., Calabria, E., Picard, A., Walsh, K., Schiaffino, S., Lecker, S. H., and Goldberg, A. L. (2004). Foxo transcription factors induce the atrophy-related ubiquitin ligase atrogin-1 and cause skeletal muscle atrophy. Cell 117, 399-412.

Sanford, D. C. and DeWille, J. W. (2005). C/EBPdelta is a downstream mediator of IL-6 induced growth inhibition of prostate cancer cells. Prostate 63, 143-154.

Satya-Prakash K L P S, Hsu T C, Olive M, Cailleau R (1981) Cytogenetic analysis on eight human breast tumor cell lines: high frequencies of 1q, 11q, and HeLa-like marker chromosomes. Cancer GenetCytogenet 3: 61-73.

Schaefer, T. S., Sanders, L. K., and Nathans, D. 1995. Cooperative transcriptional activity of Jun and Stat3 beta, a short form of Stat3. Proceedings of the National Academy of Sciences of the United States of America 92:9097-9101.

Schindler, C., and Darnell, J. E., Jr. 1995. Transcriptional responses to polypeptide ligands: the JAK-STAT pathway. [Review]. Annual Review of Biochemistry 64:621-651.

Schindler, C., Fu, X. Y., Improta, T., Aebersold, R., and Darnell, J. E., Jr. 1992. Proteins of transcription factor ISGF-3: one gene encodes the 91- and 84-kDa ISGF-3 proteins that are activated by interferon alpha. Proceedings of the National Academy of Sciences of the United States of America 89:7836-7839.

Schust, J., Sperl, B., Hollis, A., Mayer, T. U., and Berg, T. (2006). Stattic: a small-molecule inhibitor of STAT3 activation and dimerization. Chem. Biol. 13, 1235-1242.

Shah, V. O., Dominic, E. A., Moseley, P., Pickett, G., Fleet, M., Ness, S., and Raj, D. S. (2006). Hemodialysis modulates gene expression profile in skeletal muscle. Am. J. Kidney Dis. 48, 616-628.

Shao, H., Cheng H Y, Cook R G, Tweardy D J (2003) Identification and Characterization of Signal Transducer and Activator of Transcription 3 Recruitment Sites within the Epidermal Growth Factor Receptor. Cancer Res 63(14): 3923-3930.

Shao, H., Xu X, Jing N, Tweardy D J (2006) Unique Structural Determinants for Stat3 Recruitment and Activation by the Granulocyte Colony-Stimulating Factor Receptor at Phosphotyrosine Ligands 704 and 744. J Immunol 176(5): 2933-2941.

Shao, H., Xu X, Mastrangelo M-A A, Jing N, Cook R G et al. (2004) Structural Requirements for Signal Transducer and Activator of Transcription 3 Binding to Phosphotyrosine Ligands Containing the YXXQ Motif. J Biol Chem 279(18): 18967-18973.

Sharp, Z. D., Mancini M G, Hinojos C A, Dai F, Berno V et al. (2006) Estrogen-receptor-{alpha} exchange and chromatin dynamics are ligand- and domain-dependent. J Cell Sci 119(19): 4101-4116.

Siddiquee, K., Zhang S, Guida W C, Blaskovich M A, Greedy B et al. (2007) Selective chemical probe inhibitor of Stat3, identified through structure-based virtual screening, induces antitumor activity. Proceedings of the National Academy of Sciences 104(18): 7391-7396.

Song, H., Wang R, Wang S, Lin J (2005) A low-molecular-weight compound discovered through virtual database screening inhibits Stat3 function in breast cancer cells. Proceedings of the National Academy of Sciences 102 (13): 4700-4705.

Sterneck, E., Paylor, R., Jackson-Lewis, V., Libbey, M., Przedborski, S., Tessarollo, L., Crawley, J. N., and Johnson, P. F. (1998). Selectively enhanced contextual fear conditioning in mice lacking the transcriptional regulator CCAAT/enhancer binding protein delta. Proc. Natl. Acad. Sci. U.S.A 95, 10908-10913.

Stitt, T. N., Drujan, D., Clarke, B. A., Panaro, F., Timofeyva, Y., Klinenber, J. R., Gonzalez, M., Yancopoulos, G. D., and Glass, D. J. (2004). The IGF-1/PI3K/Akt pathway prevents expression of muscle atrophy-induced ubiquitin ligases by inhibiting FOXO transcription factors. Mol. Cell 14, 395-403.

Strecker, T. E., Shen, Q., Zhang, Y., Hill, J. L., Li, Y., Wang, C., Kim, H. T., Gilmer, T. M., Sexton, K. R., Hilsenbeck, S. G., et al. 2009. Effect of lapatinib on the development of estrogen receptor-negative mammary tumors in mice. J Natl Cancer Inst 101:107-113.

Takeda, K., Noguchi, K., Shi, W., Tanaka, T., Matsumoto, M., Yoshida, N., Kishimoto, T., and Akira, S. 1997. Targeted disruption of the mouse Stat3 gene leads to early embryonic lethality. Proc Natl Acad Sci USA 94:3801-3804.

Takeda, K., Kaisho, T., Yoshida, N., Takeda, J., Kishimoto, T., and Akira, S. (1998). Stat3 activation is responsible for IL-6-dependent T cell proliferation through preventing apoptosis: generation and characterization of T cell-specific Stat3-deficient mice. J. Immunol. 161, 4652-4660.

Totrov, M., Abagyan R (1997) Proteins 1: 215-220.

Turkson, J., 2004. STAT proteins as novel targets for cancer drug discovery. Expert Opin Ther Targets 8:409-422.

Turkson, J., Bowman, T., Garcia, R., Caldenhoven, E., De Groot, R. P., and Jove, R. 1998. Stat3 activation by Src induces specific gene regulation and is required for cell transformation. Mol Cell Biol 18:2545-2552.

Turkson, J., Jove R (2000) STAT proteins: novel molecular targets for cancer drug discovery. Oncogene 19: 6613-6626.

Turkson, J., Ryan, D., Kim, J. S., Zhang, Y., Chen, Z., Haura, E., Laudano, A., Sebti, S., Hamilton, A. D., and Jove, R. 2001. Phosphotyrosyl peptides block Stat3-mediated DNA binding activity, gene regulation, and cell transformation. J Biol Chem 276:45443-45455.

Turkson, J., Zhang, S., Palmer, J., Kay, H., Stanko, J., Mora, L. B., Sebti, S., Yu, H., and Jove, R. 2004. Inhibition of constitutive signal transducer and activator of transcription 3 activation by novel platinum complexes with potent antitumor activity. Mol Cancer Ther 3:1533-1542.

Tweardy, D J, Redell M S (2005) Targeting Transcription Factors for Cancer Therapy. Curr Pharm Des 11: 2873-2887.

Tweardy, D J, Wright T M, Ziegler S F, Baumann H, Chakraborty A et al. (1995) Granulocyte colony-stimulating factor rapidly activates a distinct STAT-like protein in normal myeloid cells. Blood 86(12): 4409-4416.

Uddin, S., Hussain, A. R., Manogaran, P. S., Al-Hussein, K., Platanias, L. C., Gutierrez, M. I., and Bhatia, K. G. 2005. Curcumin suppresses growth and induces apoptosis in primary effusion lymphoma. Oncogene 24:7022-7030.

Verzola, D., Procopio, V., Sofia, A., Villaggio, B., Tarroni, A., Bonanni, A., Mannucci, I, De, C. F., Gianetta, E., Saffioti, S., and Garibotto, G. (2011). Apoptosis and myostatin mRNA are upregulated in the skeletal muscle of patients with chronic kidney disease. Kidney Int. 79, 773-782.

Wang, X. H., Zhang, L., Mitch, W. E., LeDoux, J. M., Hu, J., and Du, J. (2010). Caspase-3 Cleaves Specific 19 S Proteasome Subunits in Skeletal Muscle Stimulating Proteasome Activity. J. Biol. Chem. 285, 21249-21257.

Wiederkehr-Adam, M., Ernst, P., Muller, K., Bieck, E., Gombert, F. O., Ottl, J., Graff, P., Grossmuller, F., and Heim, M. H. 2003. Characterization of phosphopeptide motifs specific for the Src homology 2 domains of signal transducer and activator of transcription 1 (STAT1) and STAT3. J Biol Chem 278:16117-16128.

Xu, X., Kasembeli, M. M., Jiang, X., Tweardy, B. J., and Tweardy, D. J. 2009. Chemical probes that competitively and selectively inhibit Stat3 activation. PLoS ONE 4:e4783.

Yang, H., Mammen, J., Wei, W., Menconi, M., Evenson, A., Fareed, M., Petkova, V., and Hasselgren, P. O. (2005). Expression and activity of C/EBPbeta and delta are upregulated by dexamethasone in skeletal muscle. J. Cell Physiol 204, 219-226.

Yoo, J. Y., Huso, D. L., Nathans, D., and Desiderio, S. 2002. Specific ablation of Stat3beta distorts the pattern of Stat3-responsive gene expression and impairs recovery from endotoxic shock. Cell 108:331-344.

Yoshikawa, H., Matsubara, K., Qian, G. S., Jackson, P., Groopman, J. D., Manning, J. E., Harris, C. C., and Herman, J. G. 2001. SOCS-1, a negative regulator of the JAK/STAT pathway, is silenced by methylation in human hepatocellular carcinoma and shows growth-suppression activity. Nat Genet 28:29-35.

Yu, C. L., Meyer, D. J., Campbell, G. S., Larner, A. C., Carter-Su, C., Schwartz, J., and Jove, R. 1995. Enhanced DNA-binding activity of a Stat3-related protein in cells transformed by the Src oncoprotein. Science 269:81-83.

Yu, H., Jove R (2004) The STATs of cancer-new molecular targets come of age. Nature Reviews Cancer 4(2): 97-105.

Zhang, L., Dong, Y., Dong, Y., Cheng, J., and Du, J. (2012). Role of integrin-beta3 protein in macrophage polarization and regeneration of injured muscle. J. Biol. Chem. 287, 6177-6186.

Zhang, L., Du, J., Hu, Z., Han, G., Delafontaine, P., Garcia, G., and Mitch, W. E. (2009). IL-6 and serum amyloid A synergy mediates angiotensin II-induced muscle wasting. J. Am. Soc. Nephrol. 20, 604-612.

Zhang, L., Rajan, V., Lin, E., Hu, Z., Han, H. Q., Zhou, X., Song, Y., Min, H., Wang, X., Du, J., and Mitch, W. E. (2011a). Pharmacological inhibition of myostatin suppresses systemic inflammation and muscle atrophy in mice with chronic kidney disease. FASEB J. 25, 1653-1663.

Zhang, X., Yue, P., Fletcher, S., Zhao, W., Gunning, P. T., and Turkson, J. (2010). A novel small-molecule disrupts Stat3 SH2 domain-phosphotyrosine interactions and Stat3-dependent tumor processes. Biochem. Pharmacol. 79, 1398-1409.

Zhang, Y., Sif, S., and DeWille, J. (2007). The mouse C/EBPdelta gene promoter is regulated by STAT3 and Sp1 transcriptional activators, chromatin remodeling and c-Myc repression. J. Cell Biochem. 102, 1256-1270.

Zhang R D F I, Price J E (1991) Relative malignant potential of human breast carcinoma cell lines established from pleural effusions and brain metastasis. Invasion Metastasis 11: 204-215.

Zhou, X., Wang, J. L., Lu, J., Song, Y., Kwak, K. S., Jiao, Q., Rosenfeld, R., Chen, Q., Boone, T., Simonet, W. S., Lacey, D. L., Goldberg, A. L., and Han, H. Q. (2010). Reversal of Cancer Cachexia and Muscle Wasting by ActRIIB Antagonism Leads to Prolonged Survival. Cell 142, 531-543.

Zhu, Q., Jing N (2007) Computational study on mechanism of G-quartet oligonucleotide T40214 selectively targeting Stat3. Journal of Computer-Aided Molecular Design 21(10): 641-648.

What is claimed is:

1. A method of treating muscle wasting, muscle weakness, or cachexia, or a combination thereof, in an individual in need thereof, comprising administering to the individual an effective amount of a compound selected from the group consisting of N-(1 ',2-dihydroxy-1,2'-binaphthalen-4'-yl)-4-methoxybenzenesulfonamide, N-(3,1'-Dihydroxy-[1,2']binaphthalenyl-4'-yl)-4-methoxy-benzenesulfonamide, N-(4,1'-Dihydroxy-[1,2']binaphthalenyl-4'-yl)-4-methoxy-benzenesulfonamide, N-(5,1'-Dihydroxy-[1,2']binaphthalenyl-4'-yl)-4-methoxy-benzenesulfonamide, N-(6,1'-Dihydroxy-[1,2']binaphthalenyl-4'-yl)-4-methoxy-benzenesulfonamide, N-(7,1'-Dihydroxy-[1,2']binaphthalenyl-4'-yl)-4-methoxy-benzenesulfonamide, N-(8,1'-Dihydroxy-[1,2']binaphthalenyl-4'-yl)-4-methoxy-benzenesulfonamide, 4-Bromo-N-(1,6'-dihydroxy-[2,2']binaphthalenyl-4-yl)-benzenesulfonamide, and 4-Bromo-N-[4-hydroxy-3-(1H-[1,2,4]triazol-3-yl-sulfanyl)-naphthalen-1-yl]-benzenesulfonamide, or a pharmaceutically acceptable salt thereof, wherein the muscle wasting, muscle weakness, or cachexia is not associated with cancer.

2. The method of claim 1, wherein muscle wasting or muscle weakness is associated with cachexia.

3. The method of claim 1, wherein the muscle wasting, muscle weakness, or cachexia, or a combination thereof, is associated with an underlying medical condition.

4. The method of claim 3, wherein the underlying medical condition is chronic.

5. The method of claim 3, wherein the underlying medical condition is selected from the group consisting of chronic kidney disease, diabetes, renal failure, AIDS, HIV infection, chronic obstructive lung disease, multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis *nodosa*, sarcoidosis, systemic lupus erythematosus, visceral leishmaniasis, prolonged bed rest, and drug addiction.

6. The method of claim 3, wherein the individual is administered a therapy for the underlying medical condition.

7. The method of claim 3, wherein the individual is administered an additional therapy for muscle wasting, muscle weakness, or cachexia, or a combination thereof, and the individual is administered a therapy for the underlying medical condition.

8. The method of claim 3, further comprising the step of diagnosing the underlying medical condition.

9. The method of claim 1, wherein the individual is administered the compound, or a pharmaceutically acceptable salt thereof, in multiple doses.

10. The method of claim 9, wherein the multiple doses are separated by hours, days, or weeks.

11. The method of claim 1, wherein the individual is administered an additional therapy for muscle wasting, muscle weakness, or cachexia, or a combination thereof.

12. The method of claim 1, wherein the compound is N-(1',2-dihydroxy-1,2'-binaphthalen-4'-yl)-4-methoxybenzenesulfonamide, or a pharmaceutically acceptable salt thereof.

13. The method of claim 1, wherein the compound inhibits signal transducer and activator of transcription 3 (Stat3), signal transducer and activator of transcription 1 (Stat1), or both.

14. The method of claim 1, further comprising the step of diagnosing muscle wasting, muscle weakness, or cachexia, or a combination thereof.

15. The method of claim 1, wherein the compound is delivered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularly, orally, topically, locally, injection, infusion, continuous infusion, localized perfusion, via a catheter, via a lavage, in lipid compositions, in liposome compositions, or as an aerosol.

* * * * *

UNITED STATES PATENT AND TRADEMARK OFFICE
CERTIFICATE OF CORRECTION

PATENT NO. : 11,161,831 B2  
APPLICATION NO. : 16/848661  
DATED : November 2, 2021  
INVENTOR(S) : David J. Tweardy et al.

Page 1 of 1

It is certified that error appears in the above-identified patent and that said Letters Patent is hereby corrected as shown below:

In the Claims

At Column 346, Line number 52, Claim 5: delete "bums" and replace with "burns"

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*